(12) United States Patent
Shen et al.

(10) Patent No.: US 11,332,465 B2
(45) Date of Patent: May 17, 2022

(54) DIARYLTHIOHYDANTOIN COMPOUND AS ANDROGEN RECEPTOR ANTAGONIST

(71) Applicant: CHIA TAI TIANQING PHARMACEUTICAL GROUP CO., LTD., Jiangsu (CN)

(72) Inventors: Chunli Shen, Jiangsu (CN); Chengde Wu, Jiangsu (CN); Shenglin Chen, Jiangsu (CN); Shuhui Chen, Jiangsu (CN); Xiquan Zhang, Jiangsu (CN); Xin Tian, Jiangsu (CN)

(73) Assignee: CHIA TAI TIANQING PHARMACEUTICAL GROUP CO., LTD., Jiangsu (CN)

( * ) Notice: Subject to any disclaimer, the term of this patent is extended or adjusted under 35 U.S.C. 154(b) by 0 days.

(21) Appl. No.: 16/637,236

(22) PCT Filed: Aug. 7, 2018

(86) PCT No.: PCT/CN2018/099161
§ 371 (c)(1),
(2) Date: Feb. 6, 2020

(87) PCT Pub. No.: WO2019/029521
PCT Pub. Date: Feb. 14, 2019

(65) Prior Publication Data
US 2020/0277290 A1 Sep. 3, 2020

(30) Foreign Application Priority Data

Aug. 7, 2017 (CN) .......................... 201710667860.4
Apr. 13, 2018 (CN) .......................... 201810333652.5

(51) Int. Cl.
| C07D 471/04 | (2006.01) |
| C07D 401/14 | (2006.01) |
| C07D 403/10 | (2006.01) |
| C07D 405/14 | (2006.01) |
| C07D 413/10 | (2006.01) |

(52) U.S. Cl.
CPC ......... *C07D 471/04* (2013.01); *C07D 401/14* (2013.01); *C07D 403/10* (2013.01); *C07D 405/14* (2013.01); *C07D 413/10* (2013.01)

(58) Field of Classification Search
CPC .................................................... C07D 471/04
See application file for complete search history.

(56) References Cited

U.S. PATENT DOCUMENTS

2014/0309262 A1   10/2014   Jung et al.

FOREIGN PATENT DOCUMENTS

| CN | 101817787 | | 9/2010 |
| CN | 103804358 | A | 5/2014 |
| CN | 104105690 | | 10/2014 |
| CN | 104341352 | | 2/2015 |
| CN | 104341396 | A | 2/2015 |
| CN | 106146474 | A | 11/2016 |
| EA | 201270720 | | 3/2013 |
| WO | WO 2011/103202 | | 8/2011 |
| WO | WO 2015/018356 | | 2/2015 |
| WO | WO 2018/009678 | | 1/2018 |

OTHER PUBLICATIONS

Translation of International Search Report for corresponding PCT Appl No. PCT/CN2018/099161, dated Oct. 26, 2018.
Greene's Protective Groups in Organic Synthesis, 4th ed., Wuts and Greene (eds)., Apr. 2006, Chapter 2, 351 pages.
International Search Report and Written Opinion in International Appln. No. PCT/CN2020/073821, dated Apr. 22, 2020, 16 pages.
Co-pending U.S. Appl. No. 17/427,496, filed Jul. 30, 2021, entitled "Crystal of Diarylthiohydantoin Compound".
Search Report in Chinese Appln. No. CN202110900404 dated Mar. 3, 2022, 2 pages, (without English translation).
Ivachtchenko et al., "Design synthesis and biological evaluation of novel 5-oxo-2-thioxoimidazolidine derivatives as potent androgen receptor antagonists," European Journal of Medicinal Chemistry, Jun. 2015, 99:51-66.

*Primary Examiner* — Patricia L Morris
(74) *Attorney, Agent, or Firm* — Fish & Richardson P.C.

(57) ABSTRACT

The present application belongs to the field of medicine. In particular, the present application relates to a diarylthiohydantoin compound as an androgen receptor antagonist or a pharmaceutically acceptable salt thereof, a preparation method of the same, a pharmaceutical composition comprising the compound, and a use thereof in treating a cell proliferative disease mediated by androgen. The compound of the present application has good antagonistic effect on androgen receptor and exhibits excellent antitumor effect.

20 Claims, No Drawings

DIARYLTHIOHYDANTOIN COMPOUND AS ANDROGEN RECEPTOR ANTAGONIST

CROSS-REFERENCE TO RELATED APPLICATIONS

The present application claims the priorities to and benefits of the Chinese Invention Patent Application No. 201710667860.4 filed with the China National Intellectual Property Administration on Aug. 7, 2017 and the Chinese Invention Patent Application No. 201810333652.5 filed with the China National Intellectual Property Administration on Apr. 13, 2018. The entire contents of these patent applications are incorporated herein by reference.

TECHNICAL FIELD

The present application belongs to the field of medicine, and specifically relates to a compound of Formula (I) or a pharmaceutically acceptable salt thereof, a preparation method thereof, a pharmaceutical composition comprising the compound, and use thereof in the preparation of a medicament for the treatment of androgen-mediated related diseases.

BACKGROUND

An androgen receptor (AR) belongs to a steroid receptor of the nuclear receptor 20 superfamily. When bound to androgen (such as testosterone and dihydrotestosterone), the AR is released from a complex formed by heat shock proteins, undergoes a phosphorylation reaction to form a dimer, which is transferred into a nucleus, and is bound to a DNA fragment associated with it, thereby stimulating the transcription of its target gene. The transcriptional activity of the androgen receptor activated by ligand binding is accomplished by the protein coordination of 25 co-activators. The main role of AR antagonists is to directly prevent testosterone or dihydrotestosterone from binding to the androgen receptors, block the effect of the androgens on cells, play a role of an antiandrogen, inhibit cell growth, and ultimately promote apoptosis and achieve an important role in treating prostatic cancer. Enzalutamide, an androgen receptor antagonist developed by Medivation & Astell as, has been marketed.

In view of the important role of androgen receptor antagonists, it is particularly important to develop androgen receptor antagonists suitable as therapeutic drugs. In general, a compound as a pharmaceutical active ingredient need to have excellent properties in the following aspects: bioactivity, safety, bioavailability, stability, and the like. The present invention provides a diarylthiohydantoin compound having a novel structure for use as an androgen receptor antagonist, and finds that a compound having such a structure exhibits excellent antitumor effects and has the above-mentioned excellent properties.

SUMMARY OF THE INVENTION

In one aspect, the present application relates to a compound of Formula (I) or a pharmaceutically acceptable salt thereof,

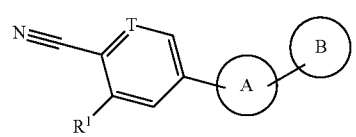

Formula (I)

wherein,

T is selected from the group consisting of CH and N;

$R^1$ is selected from the group consisting of hydrogen, halogen, $C_{1-12}$ alkyl, and halogen-substituted $C_{1-12}$ alkyl;

the ring A is selected from the group consisting of

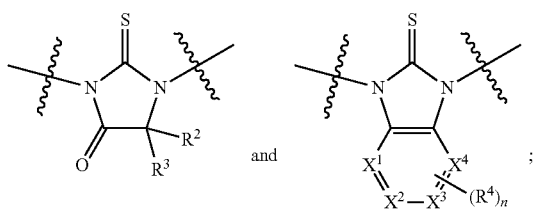

$R^2$ and $R^3$ are each independently selected from $C_{1-12}$ alkyl, or $R^2$ and $R^3$ are connected to each other to form a 3- to 6-membered cycloalkyl together;

$X^1$, $X^2$, $X^3$, and $X^4$ are each independently selected from the group consisting of CH and N, and at least one of them is N;

n is 0, 1, 2, or 3;

each $R^4$ is independently selected from $C_{1-12}$ alkyl;

the ring B is

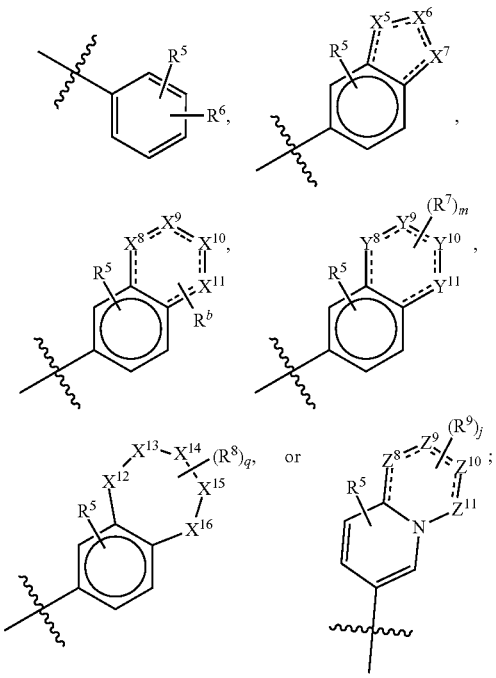

$R^5$ is selected from the group consisting of hydrogen, $C_{1-12}$ alkyl, $C_{1-12}$ alkoxy, and halogen;

$R^6$ is selected from $C_{1-12}$ alkylaminocarbonyl;

one of $X^5$, $X^6$, and $X^7$ is N(—$R^a$), and the others are CH or N;

$R^a$ is selected from 5-membered heterocycloalkyl, wherein the heterocycloalkyl is optionally substituted by halogen, $C_{1-4}$ alkyl, $C_{2-4}$ alkenyl, $C_{2-4}$ alkynyl, 3- to 6-membered cycloalkyl, 3- to 6-membered heterocycloalkyl, $C_{1-4}$ alkoxy, hydroxyl, or amino;

$X^8$, $X^9$, $X^{10}$, and $X^{11}$ are each independently selected from the group consisting of CH, C(=O), N, and NH, and three of $X^8$, $X^9$, $X^{10}$, and $X^{11}$ are C(=O), N, and NH, respectively;

$R^b$ is selected from $C_{1-12}$ alkyl, wherein the $C_{1-12}$ alkyl is optionally substituted by halogen;

$Y^8$, $Y^9$, $Y^{10}$, and $Y^{11}$ are each independently selected from the group consisting of CH and N, and at least two of $Y^8$, $Y^9$, $Y^{10}$, and $Y^{11}$ are N;

m is 0, 1, or 2;

each $R^7$ is independently selected from the group consisting of halogen, $C_{1-12}$ alkyl, hydroxyl, $C_{1-12}$ alkoxy, amino, 3- to 10-membered cycloalkyl, 3- to 10-membered heterocycloalkyl, 5- to 10-membered heteroaryl, and $C_{1-12}$ alkylamino, wherein the $C_{1-12}$ alkyl, 3- to 10-membered cycloalkyl, 3- to 10-membered heterocycloalkyl, 5- to 10-membered heteroaryl, or $C_{1-12}$ alkylamino is optionally substituted by halogen, and wherein the hydroxyl is substituted by: —$C_{1-12}$ alkyl-OH, —$C_{1-12}$ alkyl-(3- to 10-membered heterocycloalkyl), —$C_{1-12}$ alkyl-S(=O)$_2$R$^c$, —$C_{1-12}$ alkyl-NR$^d$R$^e$, —$C_{1-12}$ alkyl-C(=O)NR$^f$R$^g$, —$C_{1-12}$ alkyl-(3- to 10-membered cycloalkyl) optionally substituted by halogen or hydroxyl, or 3- to 10-membered heterocycloalkyl optionally substituted by halogen or hydroxyl;

$Z^8$, $Z^9$, $Z^{10}$, and $Z^{11}$ are each independently selected from the group consisting of CH, C(=O), and N;

j is 0, 1, or 2;

each $R^9$ is independently selected from the group consisting of halogen, $C_{1-12}$ alkyl, $C_{1-12}$ alkoxy, and hydroxyl, wherein the $C_{1-12}$ alkyl is optionally substituted by halogen or $C_{1-12}$ alkoxy, and wherein the hydroxyl is optionally substituted by: —$C_{1-12}$ alkyl-O—$C_{1-12}$ alkyl, —$C_{1-12}$ alkyl-OH, or —$C_{1-12}$ alkyl-C(=O)NR$^f$R$^g$;

$R^c$, $R^d$, $R^e$, $R^f$, and $R^g$ are each independently selected from the group consisting of hydrogen, $C_{1-12}$ alkyl, 3- to 10-membered cycloalkyl, 3- to 10-membered heterocycloalkyl, $C_{1-12}$ alkoxy, hydroxyl, and amino;

two of $X^{12}$, $X^{13}$, $X^{14}$, $X^{15}$, and $X^{16}$ are NH and C(=O), respectively, and the others are CH$_2$, O, or S;

q is 0, 1, 2, 3, or 4; and each $R^8$ is independently selected from the group consisting of halogen, $C_{1-12}$ alkyl, hydroxyl, amino, 3- to 10-membered cycloalkyl, $C_{1-12}$ alkoxy, 3- to 10-membered heterocycloalkyl, and $C_{1-12}$ alkylamino;

provided that: when the ring A is selected from

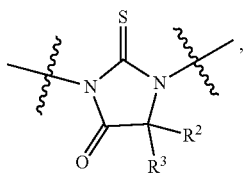

the ring B is not

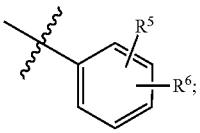

and when $R^7$ is selected from $C_{1-12}$ alkoxy, $R^7$ substitutes the hydrogen on $Y^9$, $Y^{10}$, or $Y^{11}$.

In another aspect, the present application relates to a pharmaceutical composition, comprising the compound of Formula (I) or a pharmaceutically acceptable salt thereof of the present application. In some embodiments, the pharmaceutical composition of the present application further comprises a pharmaceutically acceptable excipient.

In still another aspect, the present application relates to a method for treating an androgen-mediated disease in a mammal, comprising administering to a mammal, preferably a human, in need of the treatment a therapeutically effective amount of the compound of Formula (I) or a pharmaceutically acceptable salt thereof or the pharmaceutical composition thereof; and the disease includes, but is not limited to, cell proliferative diseases (e.g., cancer).

In yet another aspect, the present application relates to use of the compound of Formula (I) or a pharmaceutically acceptable salt thereof or the pharmaceutical composition thereof in the preparation of a medicament for the treatment of an androgen-mediated disease, and the disease includes, but is not limited to, cell proliferative diseases (e.g., cancer).

In still yet another aspect, the present application relates to use of the compound of Formula (I) or a pharmaceutically acceptable salt thereof or the pharmaceutical composition in the treatment of an androgen-mediated disease, and the disease includes, but is not limited to, cell proliferative diseases (e.g., cancer).

In a further aspect, the present application relates to the compound of Formula (I) or a pharmaceutically acceptable salt thereof or the pharmaceutical composition for use in preventing or treating an androgen-mediated disease, and the disease includes, but is not limited to, a cell proliferative disease (e.g., a cancer).

DETAILED DESCRIPTION OF THE INVENTION

In one aspect, the present application relates to a compound of Formula (I) or a pharmaceutically acceptable salt thereof, Formula (I)

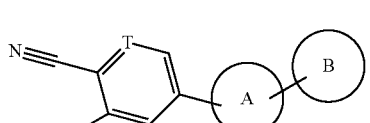

wherein,

T is selected from the group consisting of CH and N;

$R^1$ is selected from the group consisting of hydrogen, halogen, $C_{1-12}$ alkyl, and halogen-substituted $C_{1-12}$ alkyl;

the ring A is selected from the group consisting of

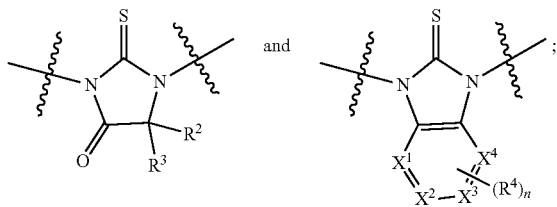

$R^2$ and $R^3$ are each independently selected from $C_{1-12}$ alkyl, or $R^2$ and $R^3$ are connected to each other to form a 3- to 6-membered cycloalkyl together;

$X^1$, $X^2$, $X^3$, and $X^4$ are each independently selected from the group consisting of CH and N, and at least one of them is N;

n is 0, 1, 2, or 3;

each $R^4$ is independently selected from $C_{1-12}$ alkyl;

the ring B is

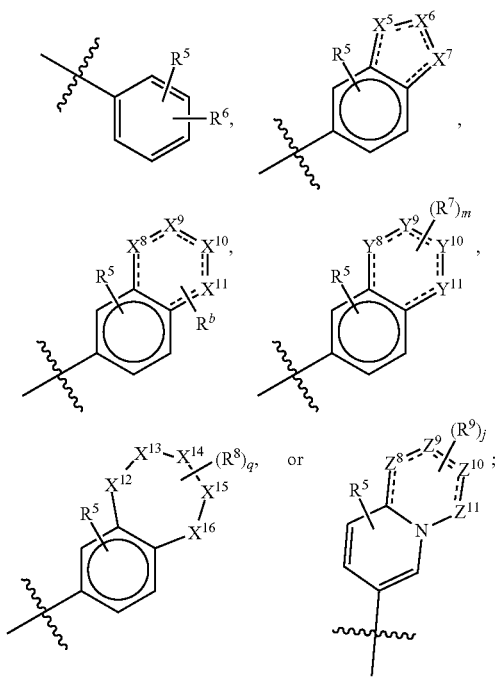

$R^5$ is selected from the group consisting of hydrogen, $C_{1-12}$ alkyl, $C_{1-12}$ alkoxy, and halogen;

$R^6$ is selected from $C_{1-12}$ alkylaminocarbonyl;

one of $X^5$, $X^6$, and $X^7$ is N(—$R^a$), and the others are CH or N;

$R^a$ is selected from 3- to 10-membered heterocycloalkyl, wherein the heterocycloalkyl is optionally substituted by halogen, $C_{1-12}$ alkyl, $C_{2-12}$ alkenyl, $C_{2-12}$ alkynyl, 3- to 10-membered cycloalkyl, 3- to 10-membered heterocycloalkyl, $C_{1-12}$ alkoxy, hydroxyl, or amino;

$X^8$, $X^9$, $X^{10}$, and $X^{11}$ are each independently selected from the group consisting of CH, C(=O), N, and NH, and three of $X^8$, $X^9$, $X^{10}$, and $X^{11}$ are C(=O), N, and NH, respectively;

$R^b$ is selected from $C_{1-12}$ alkyl, wherein the $C_{1-12}$ alkyl is optionally substituted by halogen;

$Y^8$, $Y^9$, $Y^{10}$, and $Y^{11}$ are each independently selected from the group consisting of CH and N, and at least two of $Y^8$, $Y^9$, $Y^{10}$, and $Y^{11}$ are N;

m is 0, 1, or 2;

each $R^7$ is independently selected from the group consisting of halogen, $C_{1-12}$ alkyl, hydroxyl, $C_{1-12}$ alkoxy, amino, 3- to 10-membered cycloalkyl, 3- to 10-membered heterocycloalkyl, 5- to 10-membered heteroaryl, and $C_{1-12}$ alkylamino, wherein the $C_{1-12}$ alkyl, 3- to 10-membered cycloalkyl, 3- to 10-membered heterocycloalkyl, 5- to 10-membered heteroaryl, or $C_{1-12}$ alkylamino is optionally substituted by halogen, and wherein the hydroxyl is optionally substituted by: —$C_{1-12}$ alkyl-OH, —$C_{1-12}$ alkyl-(3- to 10-membered heterocycloalkyl), —$C_{1-12}$ alkyl-S(=O)$_2$R$^c$, —$C_{1-12}$ alkyl-NR$^d$R$^e$, —$C_{1-12}$ alkyl-C(=O)NR$^f$R$^g$, —$C_{1-12}$ alkyl-(3- to 10-membered cycloalkyl) optionally substituted by halogen or hydroxyl, or 3- to 10-membered heterocycloalkyl optionally substituted by halogen or hydroxyl;

$Z^8$, $Z^9$, $Z^{10}$, and $Z^{11}$ are each independently selected from the group consisting of CH, C(=O), and N;

j is 0, 1, or 2;

each $R^9$ is independently selected from the group consisting of halogen, $C_{1-12}$ alkyl, $C_{1-12}$ alkoxy, and hydroxyl, wherein the $C_{1-12}$ alkyl is optionally substituted by halogen or $C_{1-12}$ alkoxy, and wherein the hydroxyl is optionally substituted by: —$C_{1-12}$ alkyl-O—$C_{1-2}$ alkyl, —$C_{1-12}$ alkyl-OH, or —$C_{1-12}$ alkyl-C(=O)NR$^f$R$^g$;

$R^c$, $R^d$, $R^e$, $R^f$, and $R^g$ are each independently selected from the group consisting of hydrogen, $C_{1-12}$ alkyl, 3- to 10-membered cycloalkyl, 3- to 10-membered heterocycloalkyl, $C_{1-12}$ alkoxy, hydroxyl, and amino;

two of $X^{12}$, $X^{13}$, $X^{14}$, $X^{15}$, and $X^{16}$ are NH and C(=O), respectively, and the others are CH$_2$, O, or S;

q is 0, 1, 2, 3, or 4; and each $R^8$ is independently selected from the group consisting of halogen, $C_{1-12}$ alkyl, hydroxyl, amino, 3- to 10-membered cycloalkyl, $C_{1-12}$ alkoxy, 3- to 10-membered heterocycloalkyl, and $C_{1-12}$ alkylamino;

provided that: when the ring A is selected from

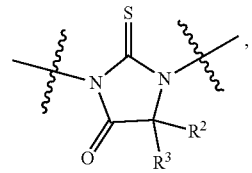

the ring B is not

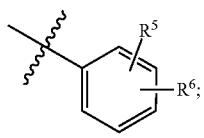

and when $R^7$ is selected from $C_{1-12}$ alkoxy, $R^7$ substitutes the hydrogen on $Y^9$, $Y^{10}$, or $Y^{11}$.

The heteroatom(s) in the heterocycloalkyl or heteroaryl described herein is(are) usually 1, 2, or 3 heteroatoms independently selected from the group consisting of sulfur, oxygen, and/or nitrogen; and in some embodiments, the heterocycloalkyl contains 1 or 2 O atoms, and the heteroaryl contains 1 or 2 N atoms.

In some embodiments, $R^1$ is selected from the group consisting of hydrogen, halogen, $C_{1-6}$ alkyl, and halogen-substituted $C_{1-6}$ alkyl; in some embodiments, $R^1$ is selected from the group consisting of halogen and halogen-substituted $C_{1-4}$ alkyl; in some embodiments, $R^1$ is selected from the group consisting of fluoro, chloro, bromo, and fluoro-substituted $C_{1-4}$ alkyl, in some embodiments, $R^1$ is selected from the group consisting of fluoro, chloro, and fluoro-substituted methyl; and in some embodiments, $R^1$ is selected from the group consisting of fluoro, chloro, difluoromethyl, and trifluoromethyl.

In some embodiments, $R^1$ is selected from halogen-substituted $C_{1-4}$ alkyl; in some embodiments, $R^1$ is selected from fluoro-substituted $C_{1-4}$ alkyl; in some embodiments, $R^1$ is selected from fluoro-substituted methyl; and in some embodiments, $R^1$ is selected from trifluoromethyl.

In some embodiments, $X^1$, $X^2$, $X^3$, and $X^4$ are each independently selected from the group consisting of CH and N, and one or two of $X^1$, $X^2$, $X^3$, and $X^4$ are N, and the others are CH.

In some embodiments, $X^1$, $X^2$, $X^3$, and $X^4$ are each independently selected from the group consisting of CH and N, and one of $X^1$, $X^2$, $X^3$, and $X^4$ is N, and the others are CH.

In some embodiments, the ring A is selected from the group consisting of

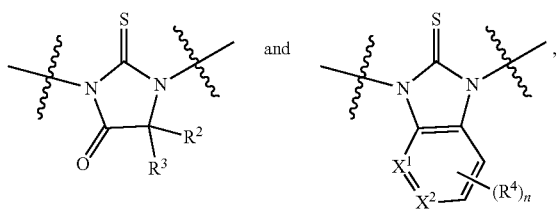

wherein $X^1$ and $X^2$ are each independently selected from the group consisting of CH and N, and at least one of them is N, and n is 0, 1, 2, or 3.

In some embodiments, the ring A is selected from the group consisting of

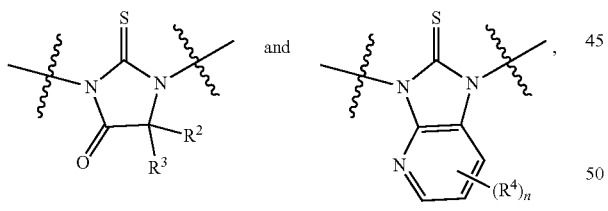

and n is 0 or 1.

In some embodiments, the ring A is selected from the group consisting of

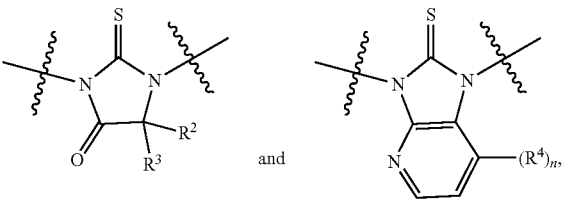

and n is 0 or 1.

In some embodiments, $R^2$ and $R^3$ are each independently selected from $C_{1-6}$ alkyl, or $R^2$ and $R^3$ are connected to each other to form a 3- to 6-membered cycloalkyl together, in some embodiments, $R^2$ and $R^3$ are each independently selected from $C_{1-4}$ alkyl, or $R^2$ and $R^3$ are connected to each other to form a 3- to 4-membered cycloalkyl together; in some embodiments, $R^2$ and $R^3$ are each independently selected from the group consisting of methyl and ethyl, or $R^2$ and $R^3$ are connected to each other to form a 3- to 4-membered cycloalkyl together, and in some embodiments, $R^2$ and $R^3$ are selected from methyl, or $R^2$ and $R^3$ are connected to each other to form cyclobutyl together.

In some specific embodiments, the ring A is selected from the group consisting of

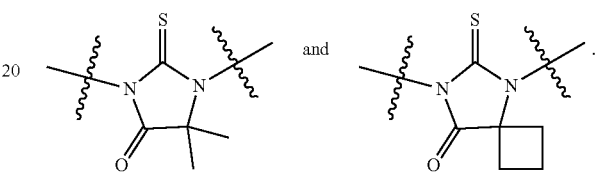

In some embodiments, each $R^4$ is independently selected from $C_{1-6}$ alkyl; in some embodiments, each $R^4$ is independently selected from $C_{1-4}$ alkyl; and in some embodiments, each $R^4$ is independently selected from methyl.

In some specific embodiments, the ring A is selected from the group consisting of

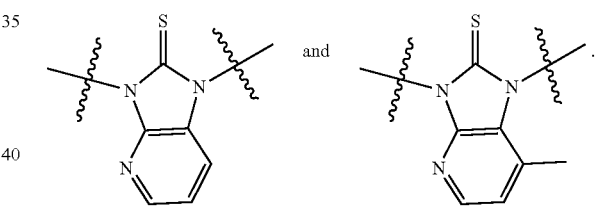

In some embodiments, the ring B is

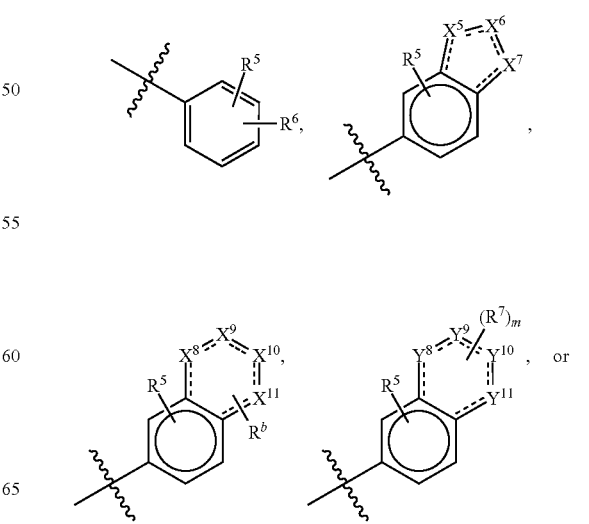

-continued

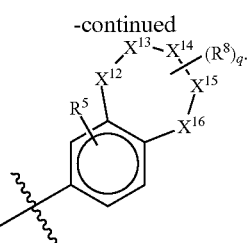

In some embodiments, $R^5$ is selected from the group consisting of hydrogen, $C_{1-6}$ alkyl, $C_{1-6}$ alkoxy, and halogen; in some embodiments, $R^5$ is selected from the group consisting of hydrogen, $C_{1-4}$ alkyl, $C_{1-4}$ alkoxy, and halogen; in some embodiments, $R^5$ is selected from the group consisting of hydrogen, methyl, methoxy, fluoro, chloro, bromo, and iodo, and in some embodiments, $R^5$ is selected from the group consisting of hydrogen, methyl, methoxy, fluoro, and chloro.

In some embodiments, $R^5$ is selected from the group consisting of hydrogen and halogen.

In some other embodiments, $R^5$ is selected from the group consisting of hydrogen and fluoro.

In some embodiments, the structural unit

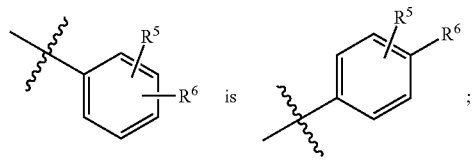

is

;

and in some embodiments, the structural unit

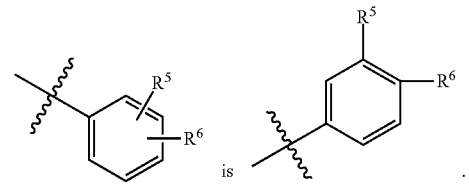

is

.

In some embodiments, $R^6$ is selected from $C_{1-6}$ alkylaminocarbonyl; in some embodiments, $R^6$ is selected from $C_{1-4}$ alkylaminocarbonyl; and in some embodiments, $R^6$ is selected from methylaminocarbonyl.

In some specific embodiments, the structural unit

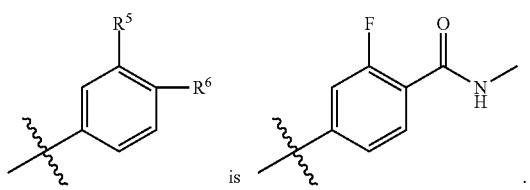

is

.

In some embodiments, $X^5$, $X^6$, and $X^7$ are each independently selected from the group consisting of CH, N, and N(—$R^a$), and at least two of $X^5$, $X^6$, and $X^7$ are N and N(—$R^a$), respectively, and the other is CH or N.

In some embodiments, $X^5$, $X^6$, and $X^7$ are each independently selected from the group consisting of CH, N, and N(—$R^a$), and two of $X^5$, $X^6$, and $X^7$ are N and N(—$R^a$), respectively, and the other is CH or N.

In some embodiments, $X^5$, $X^6$, and $X^7$ are each independently selected from the group consisting of CH, N, and N(—$R^a$), and are different from each other.

In some embodiments, the structural unit

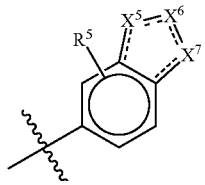

is selected from the group consisting of

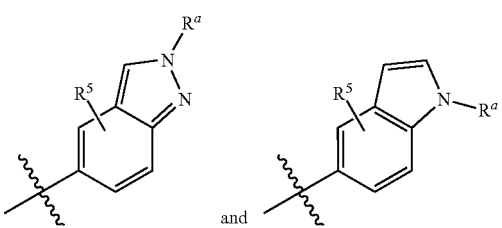

and

;

in some embodiments, the structural unit

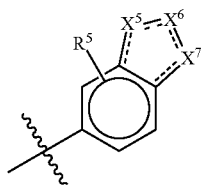

is selected from the group consisting of

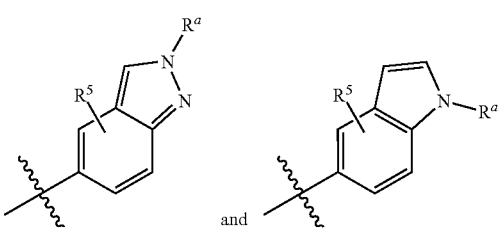

and

;

and in some embodiments, the structural unit

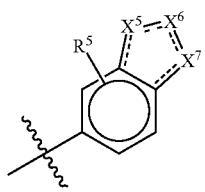

is selected from the group consisting of

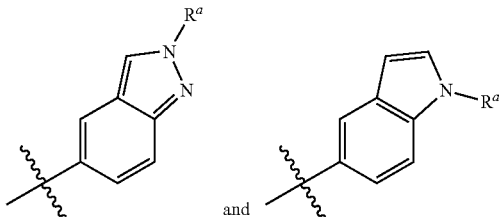

and

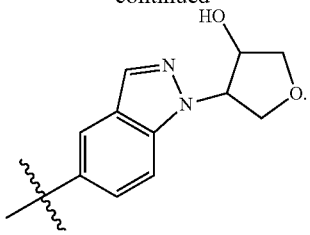

.

In some embodiments, $R^a$ is selected from 3- to 7-membered heterocycloalkyl, wherein the heterocycloalkyl is optionally substituted by halogen, $C_{1-6}$ alkyl, $C_{2-6}$ alkenyl, $C_{2-6}$ alkynyl, 3- to 6-membered cycloalkyl, 3- to 6-membered heterocycloalkyl, $C_{1-6}$alkoxy, hydroxyl, or amino; in some embodiments, $R^a$ is selected from 5-membered heterocycloalkyl, wherein the heterocycloalkyl is optionally substituted by halogen, $C_{1-4}$ alkyl, $C_{2-4}$ alkenyl, $C_{2-4}$ alkynyl, 3- to 6-membered cycloalkyl, 3- to 6-membered heterocycloalkyl, $C_{1-4}$ alkoxy, hydroxyl, or amino; in some embodiments, $R^a$ is selected from 5-membered oxacycloalkyl, wherein the oxacycloalkyl is substituted by hydroxyl; and in some embodiments, $R^a$ is selected from

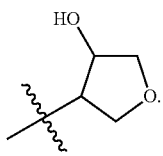 [SMILES: *C1COCC1O]

In some specific embodiments, the structural unit

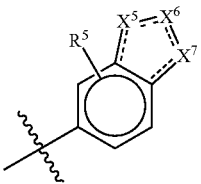

is selected from the group consisting of

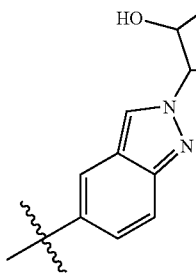

and

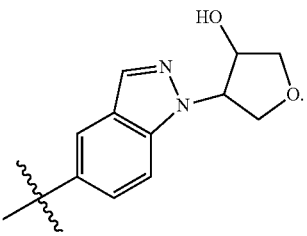

In some specific embodiments, the structural unit

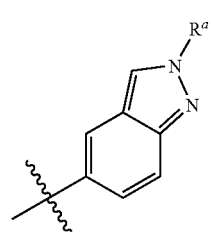 is 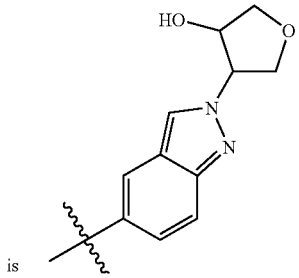, and the structural unit

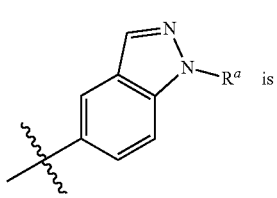 is

In some embodiments, $X^8$, $X^9$, $X^{10}$, and $X^{11}$ are each independently selected from the group consisting of CH, C(=O), N, and NH, and they are different from each other.

In some embodiments, the $R^b$ substitutes the hydrogen on NH or CH.

In some embodiments, the $R^b$ substitutes the hydrogen on NH.

In some embodiments, the structural unit

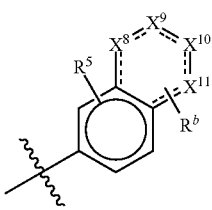

is selected from the group consisting of

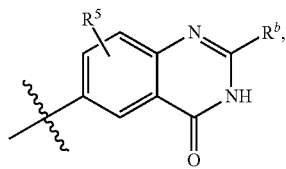

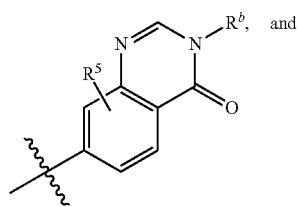

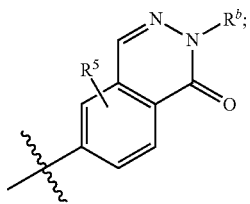

and in some embodiments, the structural unit

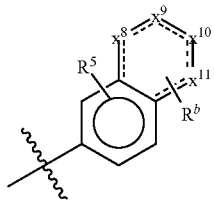

is selected from the group consisting of

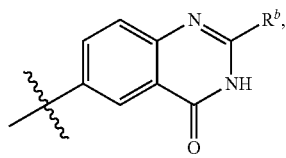

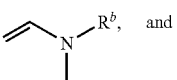 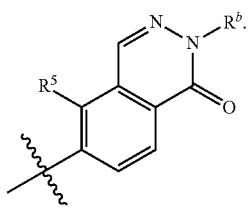

In some embodiments, the structural unit

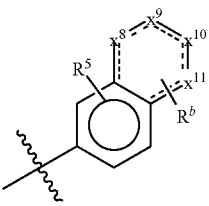

is selected from the group consisting of

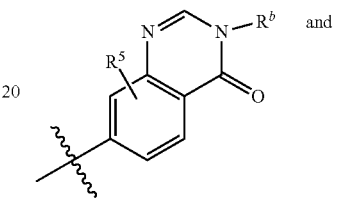 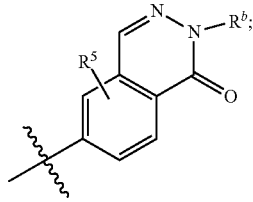

and in some embodiments, the structured unit

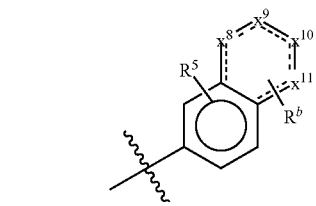

is selected from the group consisting of

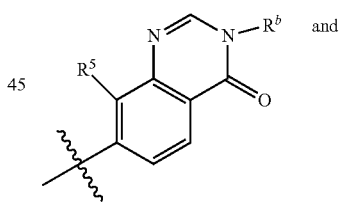 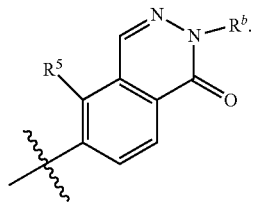

In some embodiments, $R^b$ is selected from $C_{1-6}$ alkyl, wherein the $C_{1-6}$ alkyl is optionally substituted by fluoro or chloro; in some embodiments, $R^b$ is selected from $C_{1-4}$ alkyl, wherein the $C_{1-4}$ alkyl is optionally substituted by fluoro; in some embodiments, $R^b$ is selected from ethyl, wherein the ethyl is optionally substituted by fluoro; and in some embodiments, $R^b$ is selected from the group consisting of —$CH_2CH_3$ and —$CH_2CF_3$.

In some embodiments, $R^b$ is selected from $C_{1-6}$ alkyl, wherein the $C_{1-6}$ alkyl is substituted by fluoro or chloro; in some embodiments, $R^b$ is selected from $C_{1-4}$ alkyl, wherein the $C_{1-4}$ alkyl is substituted by fluoro; in some embodiments, $R^b$ is selected from ethyl, wherein the ethyl is substituted by fluoro; and in some embodiments, $R^b$ is selected from —$CH_2CF_3$.

In some specific embodiments, the structural unit

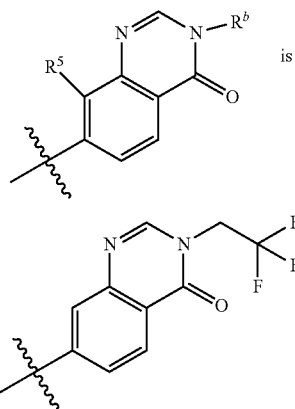

is the structural unit

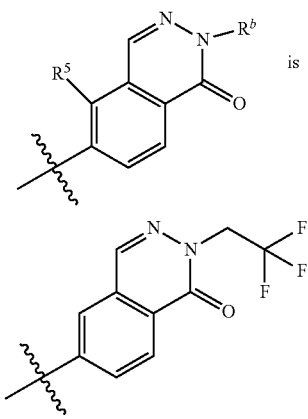

and the structural unit

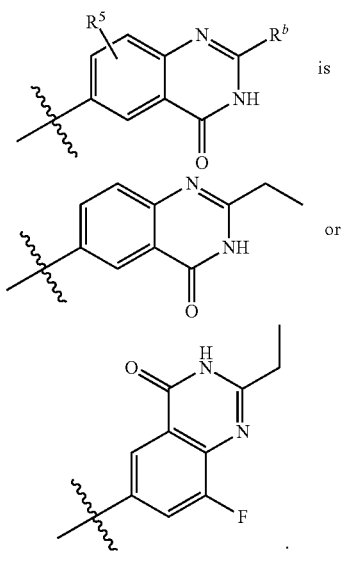

is or

In some specific embodiments, the structural unit

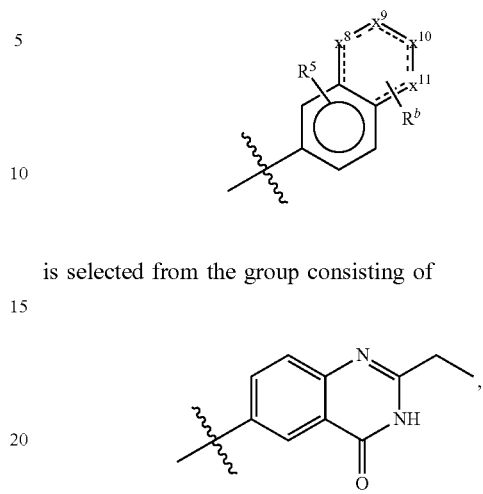

is selected from the group consisting of

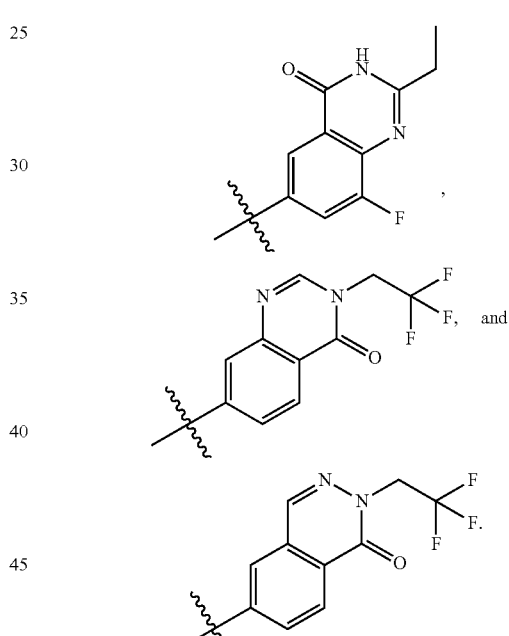

In some embodiments, $Y^8$, $Y^9$, $Y^{10}$, and $Y^{11}$ are each independently selected from the group consisting of CH and N, and two of $Y^8$, $Y^9$, $Y^{10}$, and $Y^{11}$ are N, and the others are CH.

In some embodiments, the structural unit

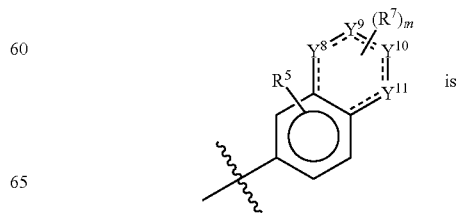

is

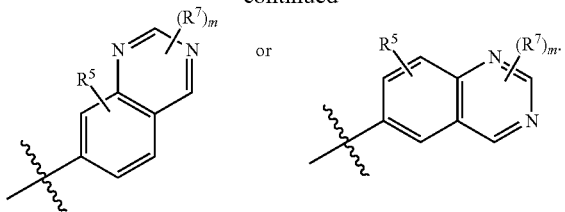

In some embodiments, the structural unit

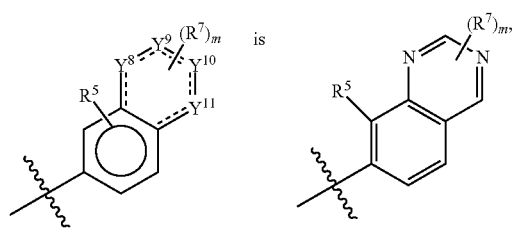

and in some embodiments, the structural unit

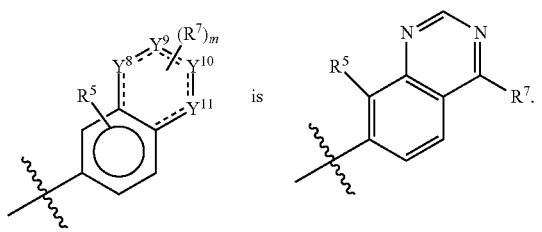

In some embodiments, the structural unit

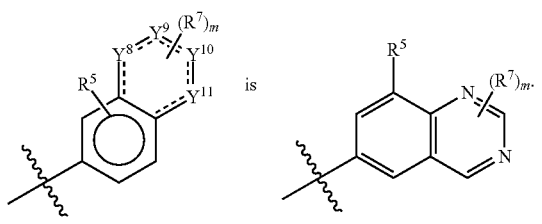

In some embodiments, $R^c$, $R^d$, and $R^e$ are each independently selected from the group consisting of hydrogen, $C_{1-12}$ alkyl, 3- to 10-membered cycloalkyl, 3- to 10-membered heterocycloalkyl, $C_{1-12}$ alkoxy, hydroxyl, and amino. In some embodiments, $R^c$, $R^d$, and $R^e$ are each independently selected from the group consisting of hydrogen, $C_{1-6}$ alkyl, 3- to 6-membered cycloalkyl, 3- to 6-membered heterocycloalkyl, $C_{1-6}$ alkoxy, hydroxyl, and amino; in some embodiments, $R^c$, $R^d$, and $R^e$ are each independently selected from $C_{1-4}$ alkyl; and in some embodiments, $R^c$, $R^d$ and $R^e$ are each independently selected from methyl.

In some embodiments, $R^c$, $R^d$, $R^e$, $R^f$, and $R^g$ are each independently selected from the group consisting of hydrogen, $C_{1-6}$ alkyl, 3- to 6-membered cycloalkyl, 3- to 6-membered heterocycloalkyl, $C_{1-6}$ alkoxy, hydroxyl, and amino; in some embodiments, $R^c$, $R^d$, $R^e$, $R^f$, and $R^g$ are each independently selected from the group consisting of hydrogen and $C_{1-4}$ alkyl; and in some embodiments, $R^c$, $R^d$, $R^e$, $R^f$, and $R^g$ are each independently selected from the group consisting of hydrogen and methyl.

In some embodiments, m is 1 or 2.

In some embodiments, the $R^7$ substitutes the hydrogen on CH.

In some embodiments, each $R^7$ is independently selected from the group consisting of halogen, $C_{1-6}$ alkyl, hydroxyl, $C_{1-6}$ alkoxy, amino, 3- to 6-membered cycloalkyl, 3- to 6-membered heterocycloalkyl, 5- to 6-membered heteroaryl, and $C_{1-6}$ alkylamino, wherein the $C_{1-6}$ alkyl, 3- to 6-membered cycloalkyl, 3- to 6-membered heterocycloalkyl, 5- to 6-membered heteroaryl, or $C_{1-6}$ alkylamino is optionally substituted by halogen, and wherein the hydroxyl is optionally substituted by: —$C_{1-6}$ alkyl-OH, —$C_{1-6}$ alkyl-(3- to 6-membered heterocycloalkyl), —$C_{1-6}$ alkyl-S(=O)$_2$R$^c$, —$C_{1-6}$ alkyl-NR$^d$R$^e$, —$C_{1-6}$ alkyl-C(=O)NR$^f$R$^g$, —$C_{1-6}$ alkyl-(3- to 6-membered cycloalkyl) optionally substituted by halogen or hydroxyl, or 3- to 6-membered heterocycloalkyl optionally substituted by halogen or hydroxyl, provided that: when $R^7$ is selected from $C_{1-6}$ alkoxy, $R^7$ substitutes the hydrogen on $Y^9$, $Y^{10}$, or $Y^{11}$. In some embodiments, each $R^7$ is independently selected from the group consisting of halogen, $C_{1-4}$ alkyl, hydroxyl, $C_{1-4}$ alkoxy, amino, 3- to 6-membered cycloalkyl, 5- to 6-membered heteroaryl, and $C_{1-4}$ alkylamino, wherein the $C_{1-4}$ alkyl, 3- to 6-membered cycloalkyl, or $C_{1-4}$ alkylamino is optionally substituted by halogen, and wherein the hydroxyl is optionally substituted by: —$C_{1-4}$ alkyl-OH, —$C_{1-4}$ alkyl-(3- to 6-membered heterocycloalkyl), —$C_{1-4}$ alkyl-S(=O)$_2$R$^c$, —$C_{1-4}$ alkyl-NR$^d$R$^e$, —$C_{1-4}$ alkyl-C(=O)NR$^f$R$^g$, —$C_{1-4}$ alkyl-(3- to 6-membered cycloalkyl) optionally substituted by halogen or hydroxyl, or 5- to 6-membered heterocycloalkyl optionally substituted by halogen or hydroxyl, provided that: when $R^7$ is selected from $C_{1-4}$ alkoxy, $R^7$ substitutes the hydrogen on $Y^9$, $Y^{10}$, or $Y^{11}$. In some embodiments, each $R^7$ is independently selected from the group consisting of methyl, ethyl, hydroxyl, methoxy, ethoxy, cyclopropyl, pyrazolyl, imidazolyl, and methylamino, wherein the methyl, ethyl, or cyclopropyl is optionally substituted by fluoro, and wherein the hydroxyl is optionally substituted by: -ethyl-OH, tetrahydropyranyl, -methyl-(oxetane), -propyl-S(=O)$_2$R$^c$, -ethyl-NR$^d$R$^e$, -methyl-C(=O)NR$^f$R$^g$, cyclopropylmethyl-optionally substituted by hydroxyl, or tetrahydrofuranyl optionally substituted by hydroxyl, provided that: when $R^7$ is selected from methoxy or ethoxy, $R^7$ substitutes the hydrogen on $Y^9$, $Y^{10}$, or $Y^{11}$. In some embodiments, each $R^7$ is independently selected from the group consisting of methyl, ethyl, hydroxyl, methoxy, ethoxy, cyclopropyl, pyrazolyl, imidazolyl, and methylamino, wherein the methyl or ethyl is optionally substituted by fluoro, and wherein the hydroxyl is optionally substituted by: -ethyl-OH,

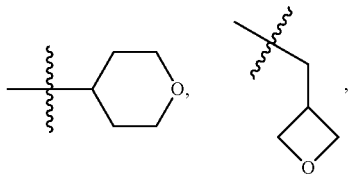 [SMILES: *C1CCOCC1 ; *CC1COC1 ; ","]

-propyl-S(=O)$_2$CH$_3$, —CH$_2$C(=O)NHCH$_3$, —CH$_2$C(=O)NH$_2$, -ethyl-N(CH$_3$)$_2$,

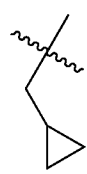 [SMILES: *CC1CC1]

optionally substituted by hydroxyl, or

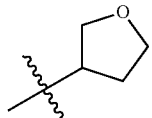

optionally substituted by hydroxyl, provided that: when $R^7$ is selected from the group consisting of methoxy and ethoxy, $R^7$ substitutes the hydrogen on $Y^9$, $Y^{10}$, or $Y^{11}$. In some embodiments, each $R^7$ is independently selected from the group consisting of methyl, ethyl, cyclopropyl, hydroxyl, methoxy, ethoxy, pyrazolyl, imidazolyl, difluoromethyl, difluoroethyl, and methylamino, wherein the hydroxyl is optionally substituted by: -ethyl-OH,

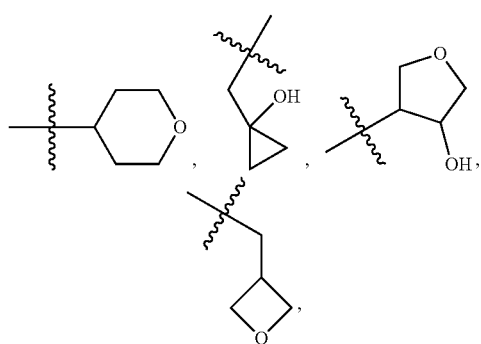

-propyl-S(=O)$_2$CH$_3$, —CH$_2$C(=O)NHCH$_3$, —CH$_2$C(=O)NH$_2$, or -ethyl-N(CH$_3$)$_2$, provided that: when $R^7$ is selected from the group consisting of methoxy and ethoxy, $R^7$ substitutes the hydrogen on $Y^9$, $Y^{10}$, or $Y^{11}$.

In some specific embodiments, each $R^7$ is independently selected from the group consisting of methyl, ethyl, cyclopropyl, difluoromethyl,

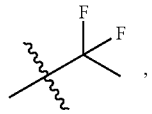 [SMILES: *C(C)(F)F]

methylamino,

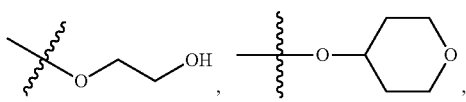

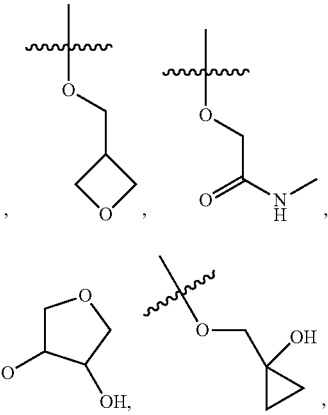

methoxy, ethoxy,

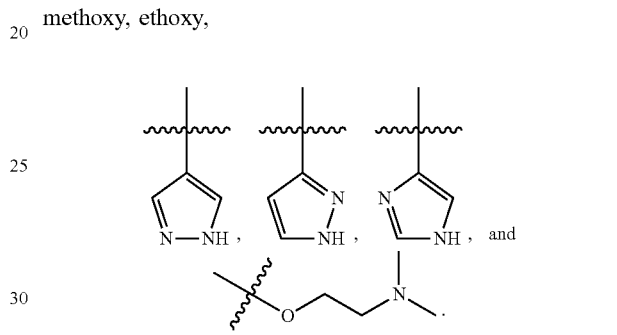

In some more specific embodiments, each $R^7$ is independently selected from the group consisting of methyl, ethyl, cyclopropyl, difluoromethyl,

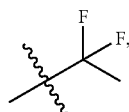

methylamino,

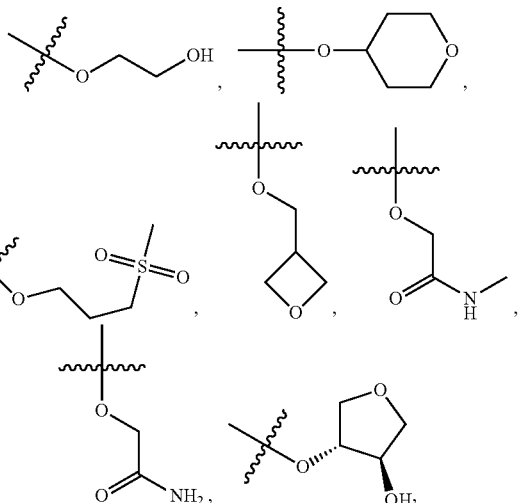

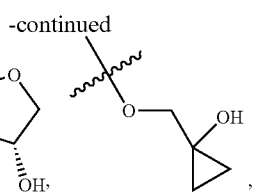

methoxy, ethoxy,

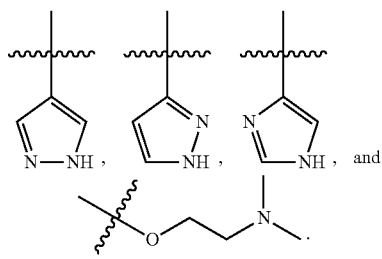

In some embodiments, each $R^7$ is independently selected from the group consisting of halogen, $C_{1-12}$ alkyl, hydroxyl, amino, 3- to 10-membered cycloalkyl, 3- to 10-membered heterocycloalkyl, and $C_{1-12}$ alkylamino, wherein the hydroxyl is substituted by: —$C_{1-12}$ alkyl-OH, 3- to 10-membered heterocycloalkyl, —$C_{1-12}$ alkyl-S(=O)$_2$R$^c$, or —$C_{1-12}$ alkyl-NR$^d$R$^e$, wherein the $C_{1-12}$ alkyl, 3- to 10-membered cycloalkyl, 3- to 10-membered heterocycloalkyl, or $C_{1-12}$ alkylamino is optionally substituted by halogen.

In some embodiments, each $R^7$ is independently selected from the group consisting of halogen, $C_{1-6}$ alkyl, hydroxyl, amino, 3- to 6-membered cycloalkyl, 3- to 6-membered heterocycloalkyl, and $C_{1-6}$ alkylamino, wherein the hydroxyl is substituted by: —$C_{1-6}$ alkyl-OH, 3- to 6-membered heterocycloalkyl, —$C_{1-6}$ alkyl-S(=O)$_2$R$^c$, or —$C_{1-6}$ alkyl-NR$^d$R$^e$, wherein the $C_{1-6}$ alkyl, 3- to 6-membered cycloalkyl, 3- to 6-membered heterocycloalkyl, or $C_{1-6}$ alkylamino is optionally substituted by halogen. In some embodiments, each $R^7$ is independently selected from the group consisting of halogen, $C_{1-4}$ alkyl, hydroxyl, amino, 3- to 6-membered cycloalkyl, and $C_{1-4}$ alkylamino, wherein the hydroxyl is substituted by: —$C_{1-4}$ alkyl-OH, 5- to 6-membered heterocycloalkyl, —$C_{1-4}$ alkyl-S(=O)$_2$R$^c$, or —$C_{1-4}$ alkyl-NR$^d$R$^e$, wherein the $C_{1-4}$ alkyl, 3- to 6-membered cycloalkyl, or $C_{1-4}$ alkylamino is optionally substituted by halogen. In some embodiments, each $R^7$ is independently selected from the group consisting of methyl, ethyl, hydroxyl, cyclopropyl, and methylamino, wherein the hydroxyl is substituted by: -ethyl-OH, tetrahydropyranyl, -propyl-S(=O)$_2$R$^c$, or -ethyl-NR$^d$R$^e$, wherein the methyl, ethyl, cyclopropyl or methylamino is optionally substituted by fluoro. In some embodiments, each $R^7$ is independently selected from the group consisting of methyl, ethyl, hydroxyl, cyclopropyl, and methylamino, wherein the hydroxyl is substituted by: -ethyl-OH,

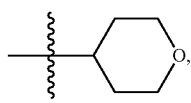 [SMILES: *C1CCOCC1]

-propyl-S(=O)$_2$CH$_3$, or -ethyl-N(CH$_3$)$_2$, wherein the methyl, ethyl, cyclopropyl or methylamino is optionally substituted by fluoro. In some embodiments, each $R^7$ is independently selected from the group consisting of methyl, ethyl, cyclopropyl, hydroxyl, difluoromethyl, and methylamino, wherein the hydroxyl is substituted by: -ethyl-OH,

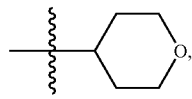

-propyl-S(=O)$_2$CH$_3$, or -ethyl-N(CH$_3$)$_2$.

In some specific embodiments, each $R^7$ is independently selected from the group consisting of methyl, ethyl, cyclopropyl, hydroxyl, difluoromethyl, methylamino,

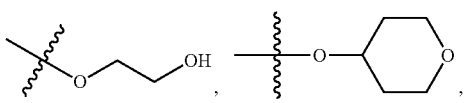

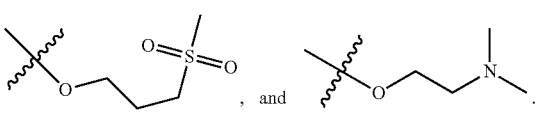

In some specific embodiments, the structural unit

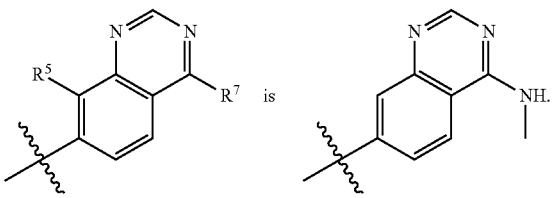

In some more specific embodiments, the structural unit

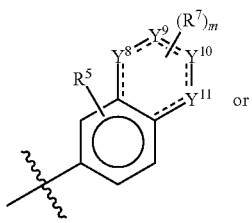

or

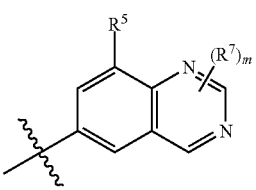

is selected from the group consisting of

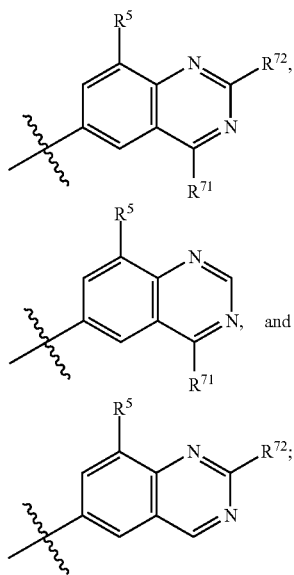

the group consisting of hydroxyl, pyrazolyl, and imidazolyl, wherein the hydroxyl is optionally substituted by: -ethyl-OH,

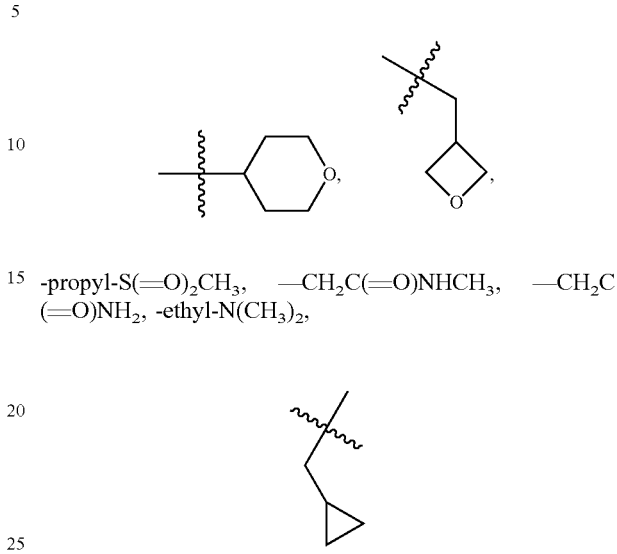

-propyl-S(=O)₂CH₃, —CH₂C(=O)NHCH₃, —CH₂C(=O)NH₂, -ethyl-N(CH₃)₂,

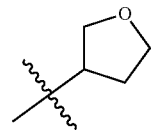 [SMILES: *C1CCOC1]

optionally substituted by hydroxyl, or

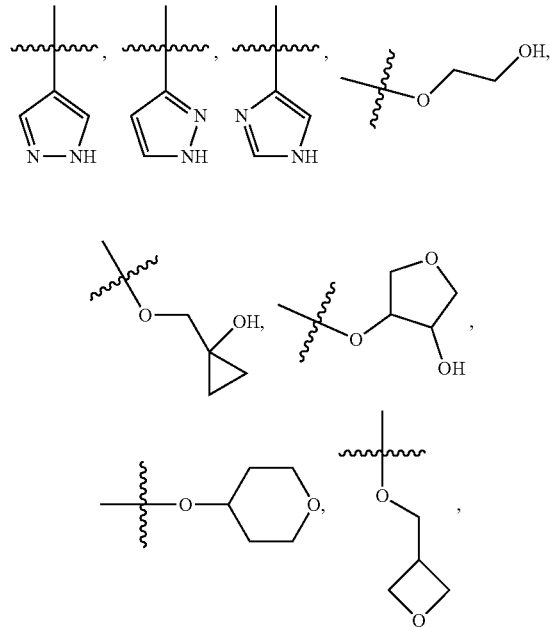

optionally substituted by hydroxyl.

wherein each R⁷¹ is independently selected from the group consisting of hydroxyl and 5- to 10-membered heteroaryl, the hydroxyl is optionally substituted by: —C$_{1-12}$ alkyl-OH, —C$_{1-12}$ alkyl-(3- to 10-membered heterocycloalkyl), —C$_{1-12}$ alkyl-S(=O)₂R$^c$, —C$_{1-12}$ alkyl-NR$^d$R$^e$, —C$_{1-12}$ alkyl-C(=O)NR$^f$R$^g$, —C$_{1-12}$ alkyl-(3- to 10-membered cycloalkyl) optionally substituted by halogen or hydroxyl, or 3- to 10-membered heterocycloalkyl optionally substituted by halogen or hydroxyl; and each R⁷² is independently selected from the group consisting of C$_{1-12}$ alkyl, hydroxyl, C$_{1-12}$ alkoxy, 3- to 10-membered cycloalkyl, and C$_{1-12}$ alkylamino, wherein the C$_{1-12}$ alkyl, 3- to 10-membered cycloalkyl, or C$_{1-12}$ alkylamino is optionally substituted by halogen, and wherein the hydroxyl is substituted by: —C$_{1-12}$ alkyl-OH, 3- to 10-membered heterocycloalkyl, —C$_{1-12}$ alkyl-S(=O)₂R$^c$, or —C$_{1-12}$ alkyl-NR$^d$R$^e$.

In some embodiments, each R⁷¹ is independently selected from the group consisting of hydroxyl and 5- to 6-membered heteroaryl, the hydroxyl is optionally substituted by: —C$_{1-6}$ alkyl-OH, —C$_{1-6}$ alkyl-(3- to 6-membered heterocycloalkyl), —C$_{1-6}$ alkyl-S(=O)₂R$^c$, —C$_{1-6}$ alkyl-NR$^d$R$^e$, —C$_{1-6}$ alkyl-C(=O)NR$^f$R$^g$, —C$_{1-6}$ alkyl-(3- to 6-membered cycloalkyl) optionally substituted by halogen or hydroxyl, or 3- to 6-membered heterocycloalkyl optionally substituted by halogen or hydroxyl. In some embodiments, each R⁷¹ is independently selected from the group consisting of hydroxyl and 5- to 6-membered heteroaryl, wherein the hydroxyl is optionally substituted by: —C$_{1-4}$ alkyl-OH, —C$_{1-4}$ alkyl-(3- to 6-membered heterocycloalkyl), —C$_{1-4}$ alkyl-S(=O)₂R$^c$, —C$_{1-4}$ alkyl-NR$^d$R$^e$, —C$_{1-4}$ alkyl-C(=O)NR$^f$R$^g$, —C$_{1-4}$ alkyl-(3- to 6-membered cycloalkyl) optionally substituted by halogen or hydroxyl, or 5- to 6-membered heterocycloalkyl optionally substituted by halogen or hydroxyl. In some embodiments, each R⁷¹ is independently selected from the group consisting of hydroxyl, pyrazolyl, and imidazolyl, wherein the hydroxyl is optionally substituted by: -ethyl-OH, tetrahydropyranyl, -methyl-(oxetane), -propyl-S(=O)₂R$^c$, -ethyl-NR$^d$R$^e$, -methyl-C(=O)NR$^f$R$^g$, cyclopropylmethyl- optionally substituted by hydroxyl, or tetrahydrofuranyl optionally substituted by hydroxyl. In some embodiments, each R⁷¹ is independently selected from In some specific embodiments, each R⁷¹ is independently selected from the group consisting of -continued

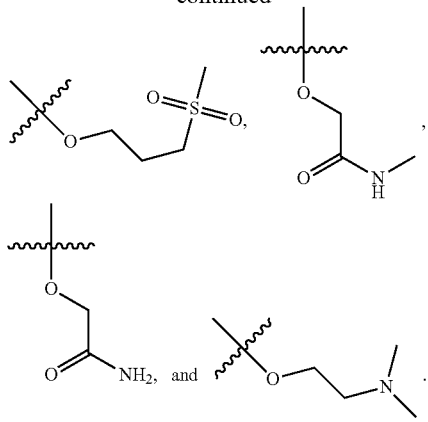

In some more specific embodiments, each $R^{71}$ is independently selected from the group consisting of hydroxyl,

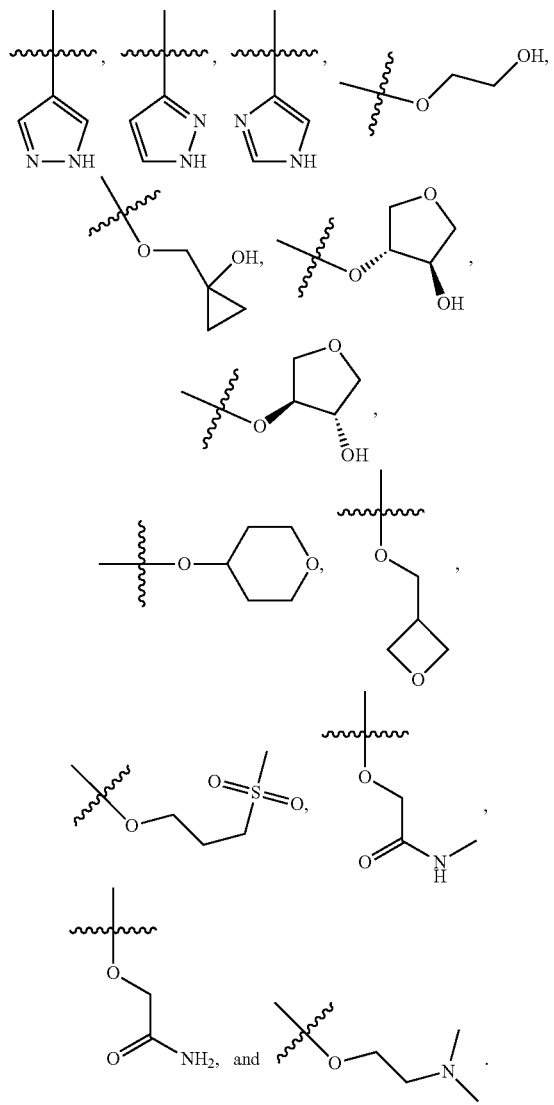

In some embodiments, each $R^{72}$ is independently selected from the group consisting of $C_{1-6}$ alkyl, hydroxyl, $C_{1-6}$ alkoxy, 3- to 6-membered cycloalkyl, and $C_{1-6}$ alkylamino, wherein the $C_{1-6}$ alkyl, 3- to 6-membered cycloalkyl, or $C_{1-6}$ alkylamino is optionally substituted by halogen, and wherein the hydroxyl is substituted by: —$C_{1-6}$ alkyl-OH, 5- to 6-membered heterocycloalkyl, —$C_{1-6}$ alkyl-S(=O)$_2$R$^c$, or —$C_{1-6}$ alkyl-NR$^d$R$^e$. In some embodiments, each $R^{72}$ is independently selected from the group consisting of $C_{1-4}$ alkyl, hydroxyl, $C_{1-4}$ alkoxy, 3- to 6-membered cycloalkyl, and $C_{1-4}$ alkylamino, wherein the $C_{1-4}$ alkyl, 3- to 6-membered cycloalkyl, or $C_{1-4}$ alkylamino is optionally substituted by halogen, and wherein the hydroxyl is substituted by: —$C_{1-4}$ alkyl-OH. In some embodiments, each $R^{72}$ is independently selected from the group consisting of methyl, ethyl, hydroxyl, methoxy, ethoxy, cyclopropyl, and methylamino, wherein the methyl, ethyl, or cyclopropyl is optionally substituted by fluoro; wherein the hydroxyl is substituted by: -ethyl-OH. In some embodiments, each $R^{72}$ is independently selected from the group consisting of methyl, ethyl, cyclopropyl, hydroxyl, methoxy, ethoxy, difluoromethyl, difluoroethyl, and methylamino, wherein the hydroxyl is substituted by: -ethyl-OH.

In some specific embodiments, each $R^{72}$ is independently selected from the group consisting of methyl, ethyl, cyclopropyl, difluoromethyl,

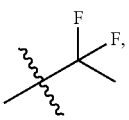 [SMILES: *C(C)(F)F]

methoxy, ethoxy, methylamino, and

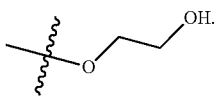 [SMILES: *OCCO]

In some embodiments, the structural unit

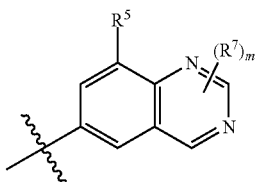

is selected from the group consisting of

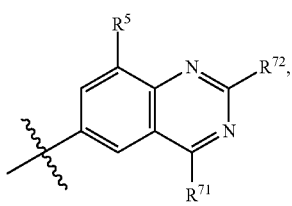

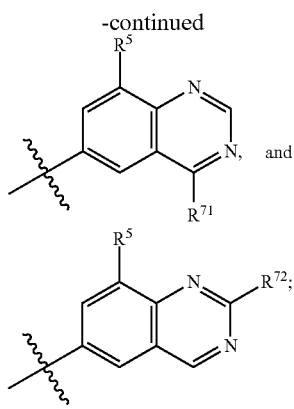

wherein each $R^{71}$ is independently selected from hydroxyl, and the hydroxyl is substituted by: —$C_{1-12}$ alkyl-OH, 3- to 10-membered heterocycloalkyl, —$C_{1-12}$ alkyl-S(=O)$_2$R$^c$, or —$C_{1-12}$ alkyl-NR$^d$R$^e$; and each $R^{72}$ is independently selected from the group consisting of $C_{1-12}$ alkyl, hydroxyl, 3- to 10-membered cycloalkyl, and $C_{1-12}$ alkylamino, wherein the hydroxyl is substituted by: —$C_{1-12}$ alkyl-OH, 3- to 10-membered heterocycloalkyl, —$C_{1-12}$ alkyl-S(=O)$_2$R$^c$, or —$C_{1-12}$ alkyl-NR$^d$R$^e$, wherein the $C_{1-12}$ alkyl, 3- to 10-membered cycloalkyl, or $C_{1-12}$ alkylamino is optionally substituted by halogen.

In some embodiments, each $R^{71}$ is independently selected from hydroxyl, and the hydroxyl is substituted by: —$C_{1-6}$ alkyl-OH, 3- to 6-membered heterocycloalkyl, —$C_{1-6}$ alkyl-S(=O)$_2$R$^c$, or —$C_{1-6}$ alkyl-NR$^d$R$^e$. In some embodiments, each $R^{71}$ is independently selected from hydroxyl, wherein the hydroxyl is substituted by: —$C_{1-4}$ alkyl-OH, 5- to 6-membered heterocycloalkyl, —$C_{1-4}$ alkyl-S(=O)$_2$R$^c$, or —$C_{1-4}$ alkyl-NR$^d$R$^e$. In some embodiments, each $R^{71}$ is independently selected from hydroxyl, wherein the hydroxyl is substituted by: -ethyl-OH, epoxyhexyl, -propyl-S(=O)$_2$R$^c$, or -ethyl-NR$^d$R$^e$. In some embodiments, each $R^{71}$ is independently selected from hydroxyl, wherein the hydroxyl is substituted by: -ethyl-OH,

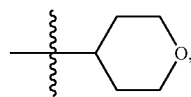 [SMILES: *C1CCOCC1]

-propyl-S(=O)$_2$CH$_3$, or -ethyl-N(CH$_3$)$_2$.

In some specific embodiments, each $R^{71}$ is independently selected from the group consisting of

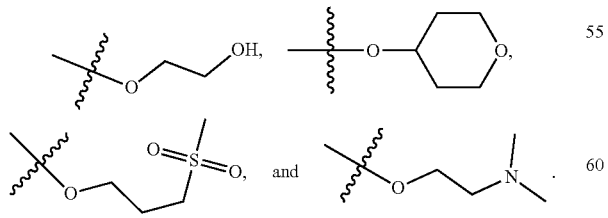

In some embodiments, each $R^{72}$ is independently selected from the group consisting of $C_{1-6}$ alkyl, hydroxyl, 3- to 6-membered cycloalkyl, and $C_{1-6}$ alkylamino, wherein the $C_{1-6}$ alkyl, 3- to 6-membered cycloalkyl, or $C_{1-6}$ alkylamino is optionally substituted by halogen, and wherein the hydroxyl is substituted by: —$C_{1-6}$ alkyl-OH, 5- to 6-membered heterocycloalkyl, —$C_{1-6}$ alkyl-S(=O)$_2$R$^c$, or —$C_{1-6}$ alkyl-NR$^d$R$^e$. In some embodiments, each $R^{72}$ is independently selected from the group consisting of $C_{1-4}$ alkyl, hydroxyl, 3- to 6-membered cycloalkyl, and $C_{1-4}$ alkylamino, wherein the $C_{1-4}$ alkyl, 3- to 6-membered cycloalkyl, or $C_{1-44}$ alkylamino is optionally substituted by halogen, wherein the hydroxyl is substituted by: —$C_{1-4}$ alkyl-OH. In some embodiments, each $R^{72}$ is independently selected from the group consisting of methyl, ethyl, hydroxyl, cyclopropyl, and methylamino, wherein the methyl, ethyl, or cyclopropyl is optionally substituted by fluoro; and wherein the hydroxyl is substituted by: -ethyl-OH. In some embodiments, each $R^{72}$ is independently selected from the group consisting of methyl, ethyl, cyclopropyl, hydroxyl, difluoromethyl, and methylamino, wherein the hydroxyl is substituted by: -ethyl-OH.

In some specific embodiments, each $R^{72}$ is independently selected from the group consisting of methyl, ethyl, cyclopropyl, hydroxyl, difluoromethyl, methylamino, and

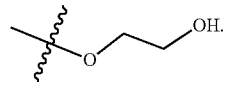 [SMILES: *OCCO]

In some specific embodiments, the structural unit

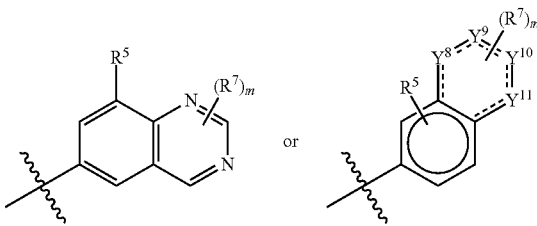

is selected from the group consisting of

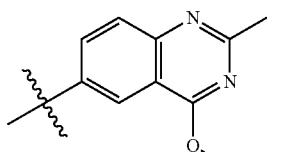

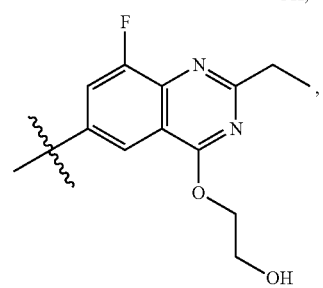

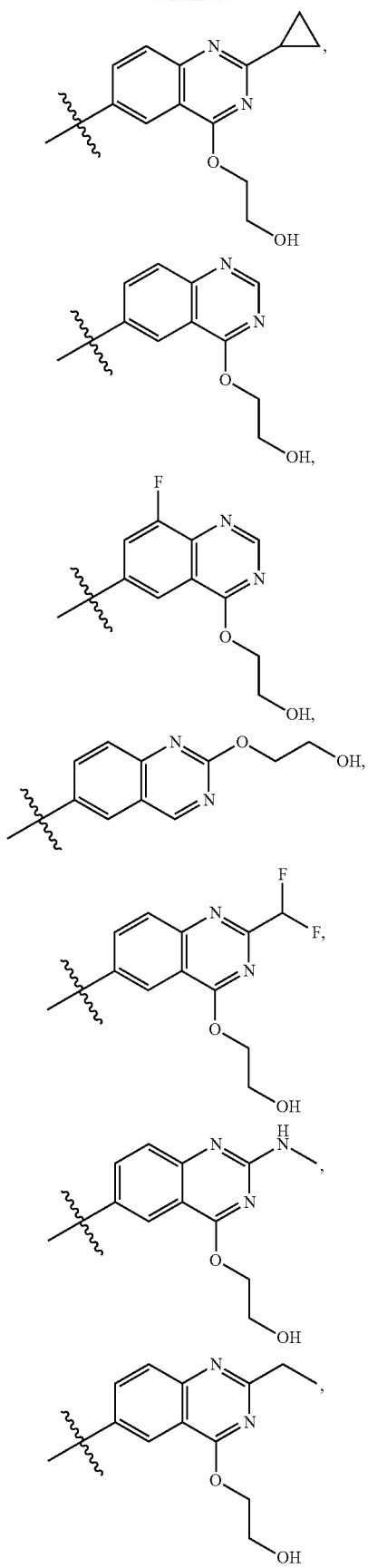
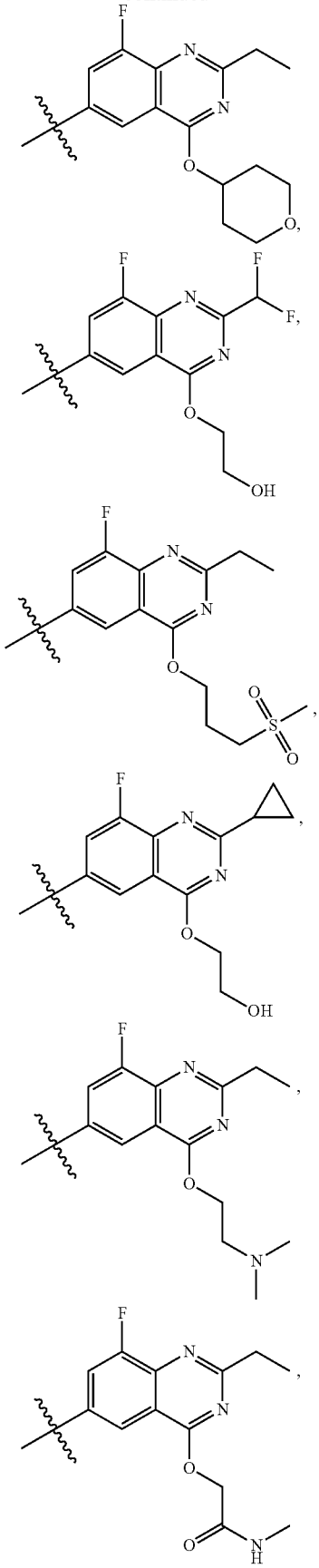

31
-continued
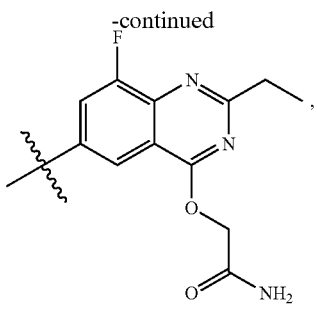
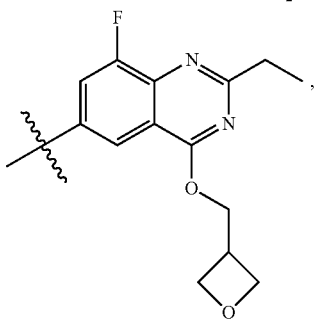
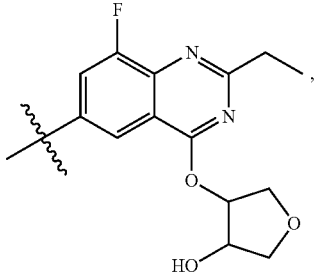
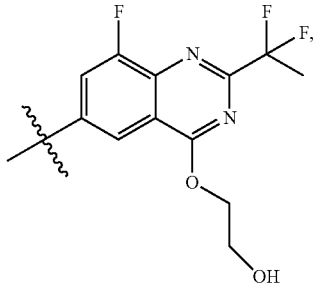
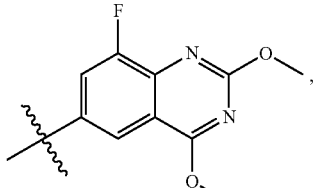
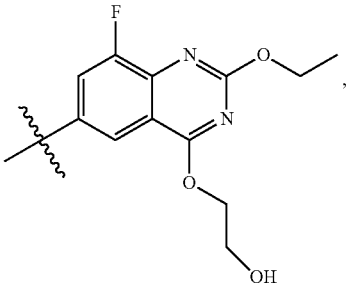
32
-continued
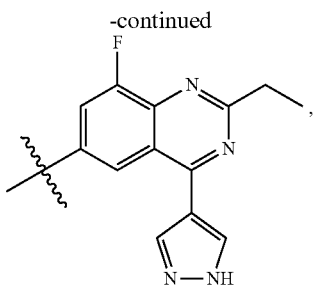
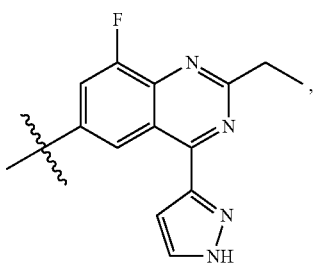
, and
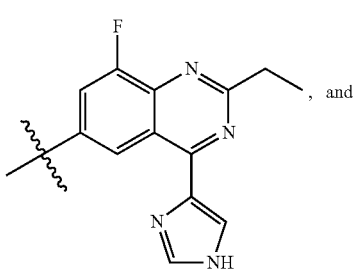
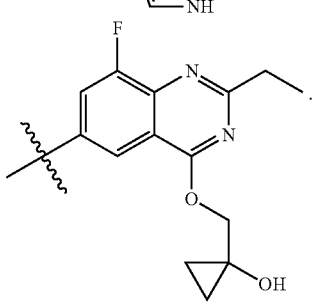
In some specific embodiments,
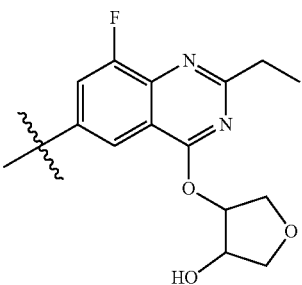 [SMILES: *c1cc(F)c2nc(CC)nc(OC3COCC3O)c2c1]

is selected from the group consisting of
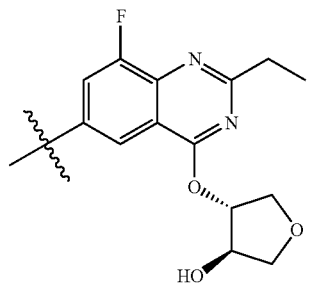
and
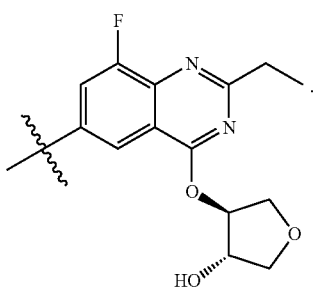
.
In some specific embodiments, the structural unit
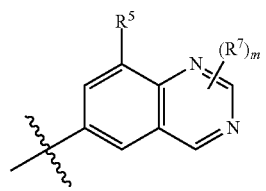
is selected from the group consisting of
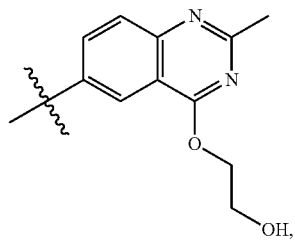,
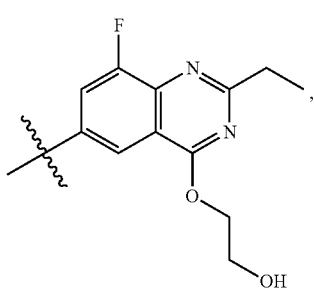,
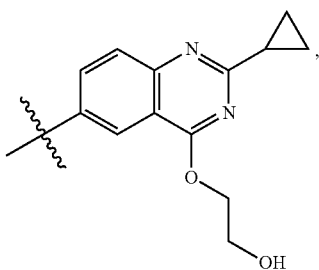,
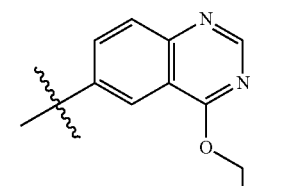,
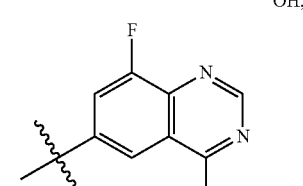,
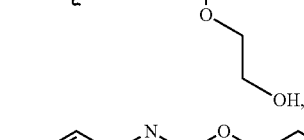,
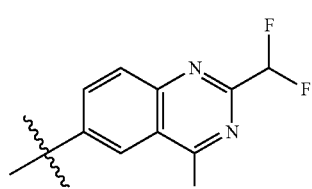,
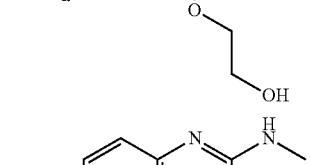,
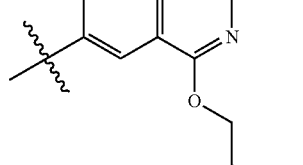,
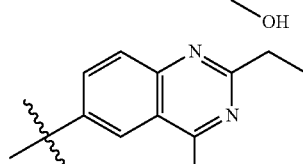,
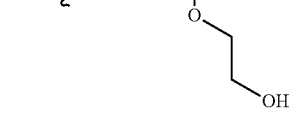

-continued

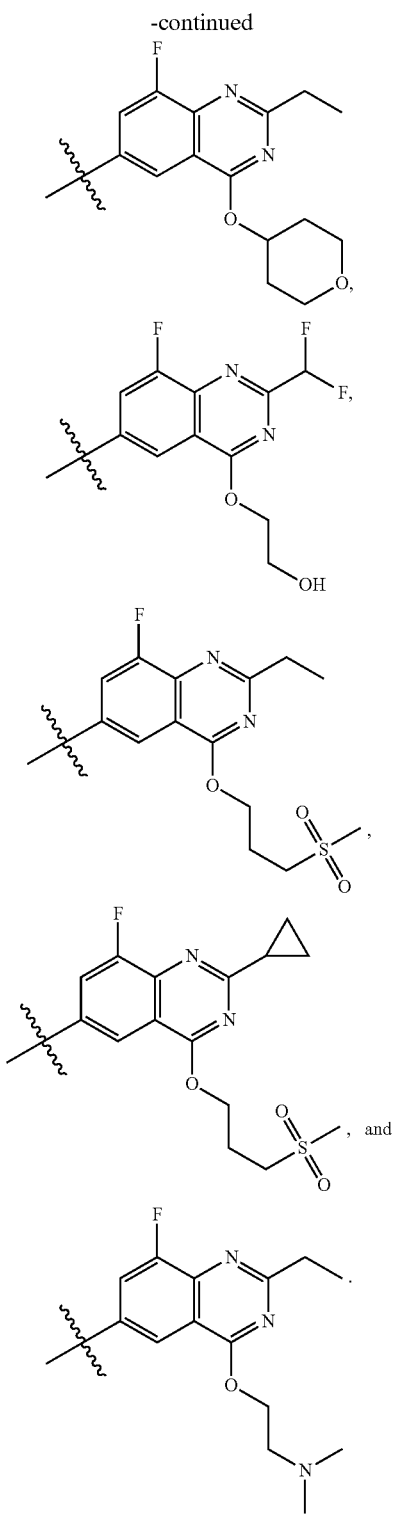

In some embodiments, $Z^8$, $Z^9$, $Z^{10}$, and $Z^{11}$ are each independently selected from the group consisting of CH, C(=O), and N, and at least one of them is selected from N; in some embodiments, at least one of them is selected from C(=O), and at least one of them is selected from N; and in some embodiments, one of them is selected from C(=O), another one of them is selected from N, and the other two are each CH.

In some embodiments, the structural unit

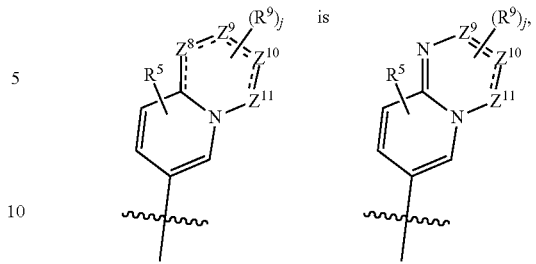

wherein $Z^9$, $Z^{10}$, and $Z^{11}$ are each independently selected from the group consisting of CH, C(=O), and N; in some embodiments, the structural unit

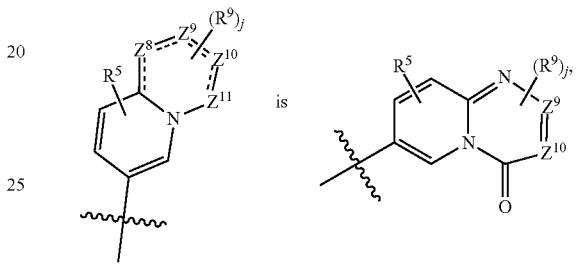

wherein $Z^9$ and $Z^{10}$ are each independently selected from the group consisting of CH and N; in some embodiments, the structural unit

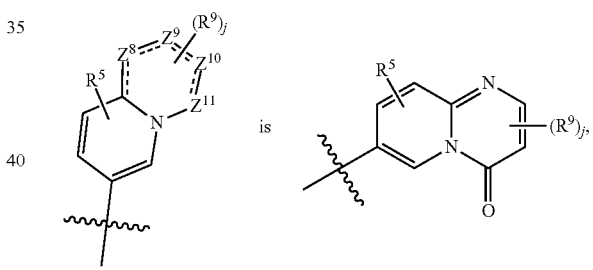

and in some embodiments, the structural unit

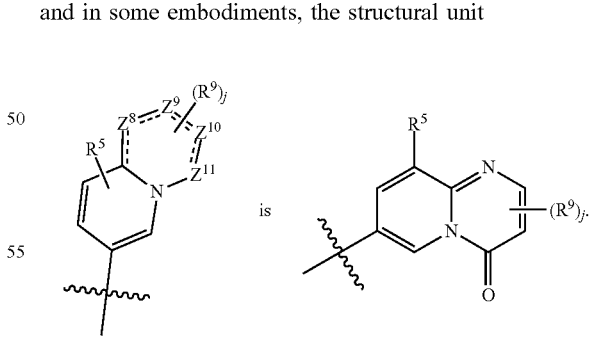

In some embodiments, j is 1 or 2.

In some embodiments, each $R^9$ is independently selected from the group consisting of halogen, $C_{1-6}$ alkyl, $C_{1-6}$ alkoxy, and hydroxyl, wherein the $C_{1-6}$ alkyl is optionally substituted by halogen or $C_{1-6}$ alkoxy, and wherein the hydroxyl is optionally substituted by: —$C_{1-6}$ alkyl-O—$C_{1-6}$ alkyl, —$C_{1-6}$ alkyl-OH, or —$C_{1-6}$ alkyl-C(=O)NR$^f$R$^g$. In some embodiments, each $R^9$ is independently selected from the group consisting of halogen, $C_{1-4}$ alkyl, $C_{1-4}$ alkoxy, and hydroxyl, wherein the $C_{1-4}$ alkyl is optionally substituted by halogen or $C_{1-4}$ alkoxy, and wherein the hydroxyl is optionally substituted by: —$C_{1-4}$ alkyl-O—$C_{1-4}$ alkyl, —$C_{1-4}$ alkyl-OH, or —$C_{1-4}$ alkyl-C(=O)NR$^f$R$^g$. In some embodiments, each R$^9$ is independently selected from the group consisting of halogen, methyl, ethyl, methoxy, ethoxy, and hydroxyl, wherein the methyl or ethyl is optionally substituted by halogen or methoxy, and wherein the hydroxyl is optionally substituted by: -ethyl-O-methyl, -ethyl-OH, or -methyl-C(=O)NR$^f$R$^g$. In some embodiments, each R$^9$ is independently selected from the group consisting of halogen, methyl, ethyl, methoxy, ethoxy, and hydroxyl, wherein the methyl or ethyl is optionally substituted by fluoro or methoxy, and wherein the hydroxyl is optionally substituted by: -ethyl-O-methyl, -ethyl-OH, —CH$_2$C(=O)NHCH$_3$, or —CH$_2$C(=O)NH$_2$.

In some specific embodiments, each R$^9$ is independently selected from the group consisting of ethyl, hydroxyl, methoxy,

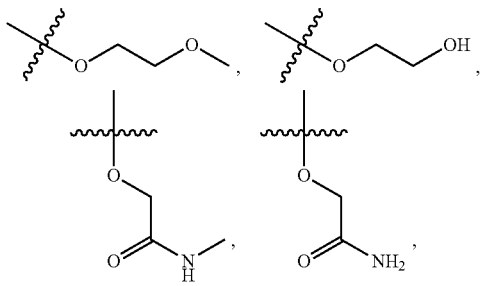

fluoro, ethoxy, difluoromethyl, and

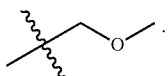

In some embodiments, the structural unit

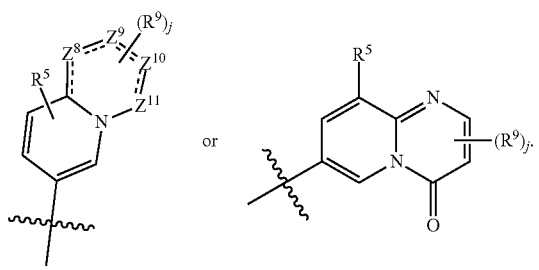

selected from the group consisting of

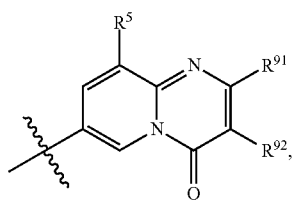

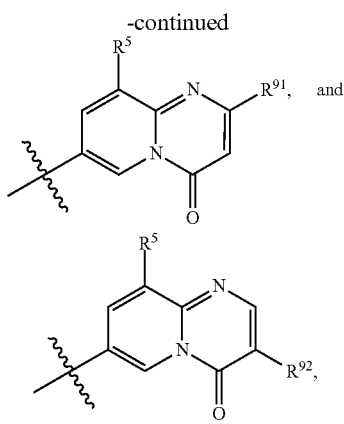

wherein R$^{91}$ is selected from the group consisting of $C_{1-12}$ alkyl, $C_{1-12}$ alkoxy, and hydroxyl, wherein the $C_{1-12}$ alkyl is optionally substituted by $C_{1-12}$ alkoxy or halogen, and wherein the hydroxyl is optionally substituted by —$C_{1-12}$ alkyl-OH, or —$C_{1-12}$ alkyl-O—$C_{1-12}$ alkyl; wherein R$^{92}$ is selected from the group consisting of hydroxyl, —$C_{1-12}$ alkoxy, and halogen, wherein the hydroxyl is optionally substituted by —$C_{1-12}$ alkyl-OH, —$C_{1-12}$ alkyl-O—$C_{1-12}$ alkyl, or —$C_{1-12}$ alkyl-C(=O)NR$^f$R$^g$.

In some embodiments, R$^{91}$ is selected from the group consisting of $C_{1-6}$ alkyl, $C_{1-6}$ alkoxy, and hydroxyl, wherein the $C_{1-6}$ alkyl is optionally substituted by $C_{1-6}$ alkoxy or halogen, and wherein the hydroxyl is optionally substituted by —$C_{1-6}$ alkyl-OH or —$C_{1-6}$ alkyl-O—$C_{1-6}$ alkyl. In some embodiments, R$^{91}$ is selected from the group consisting of $C_{1-4}$ alkyl, $C_{1-4}$ alkoxy, and hydroxyl, wherein the $C_{1-4}$ alkyl is optionally substituted by $C_{1-4}$ alkoxy or halogen, and wherein the hydroxyl is optionally substituted by —$C_{1-4}$ alkyl-OH or —$C_{1-4}$ alkyl-O—$C_{1-4}$ alkyl. In some embodiments, R$^{91}$ is selected from the group consisting of methyl, ethyl, methoxy, ethoxy, and hydroxyl, wherein the methyl or ethyl is optionally substituted by halogen or methoxy, and wherein the hydroxyl is optionally substituted by -ethyl-O-methyl or -ethyl-OH. In some embodiments, R$^{91}$ is selected from the group consisting of methyl, ethyl, methoxy, ethoxy, and hydroxyl, wherein the methyl or ethyl is optionally substituted by fluoro or methoxy, and wherein the hydroxyl is optionally substituted by -ethyl-O-methyl or -ethyl-OH.

In some specific embodiments, R$^{91}$ is selected from the group consisting of ethyl, methoxy, ethoxy, difluoromethyl,

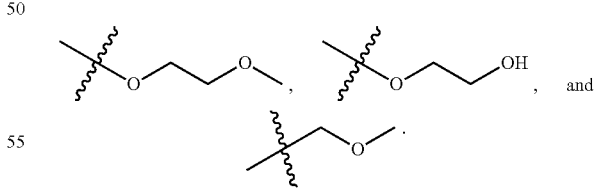

In some embodiments, R$^{92}$ is selected from the group consisting of hydroxyl, $C_{1-6}$ alkoxy, and halogen, wherein the hydroxyl is optionally substituted by —$C_{1-6}$ alkyl-OH, —$C_{1-6}$ alkyl-O—$C_{1-6}$ alkyl, or —$C_{1-6}$ alkyl-C(=O)NR$^f$R$^g$. In some embodiments, R$^{92}$ is selected from the group consisting of hydroxyl, $C_{1-4}$ alkoxy, and halogen, wherein the hydroxyl is optionally substituted by —$C_{1-4}$ alkyl-OH, —$C_{1-4}$ alkyl-O—$C_{1-4}$ alkyl, or —$C_{1-4}$ alkyl-C(=O)NR$^f$R$^g$. In some embodiments, R$^{92}$ is selected from the group consisting of hydroxyl, methoxy, and halogen, wherein the hydroxyl is optionally substituted by -ethyl-OH, -ethyl-O-methyl, or -methyl-C(=O)NR$^f$R$^g$. In some embodiments, R$^{92}$ is selected from the group consisting of hydroxyl, methoxy, and halogen, wherein the hydroxyl is optionally substituted by -ethyl-OH, -ethyl-O-methyl, —CH$_2$C(=O)NHCH$_3$, or —CH$_2$C(=O)NH$_2$.

In some specific embodiments, R$^{92}$ is selected from the group consisting of hydroxyl, methoxy,

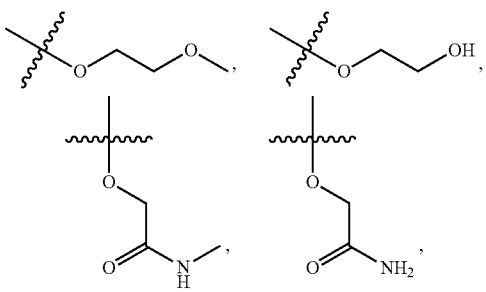

and fluoro.

In some specific embodiments, the structural unit

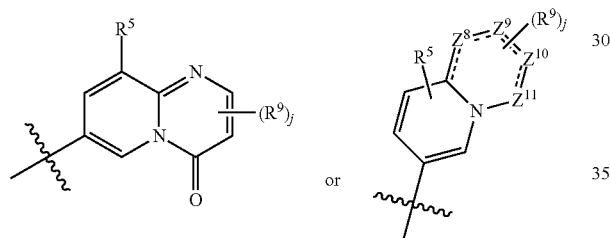

is selected from the group consisting of

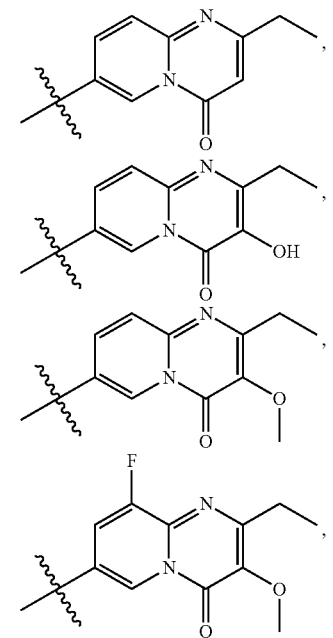

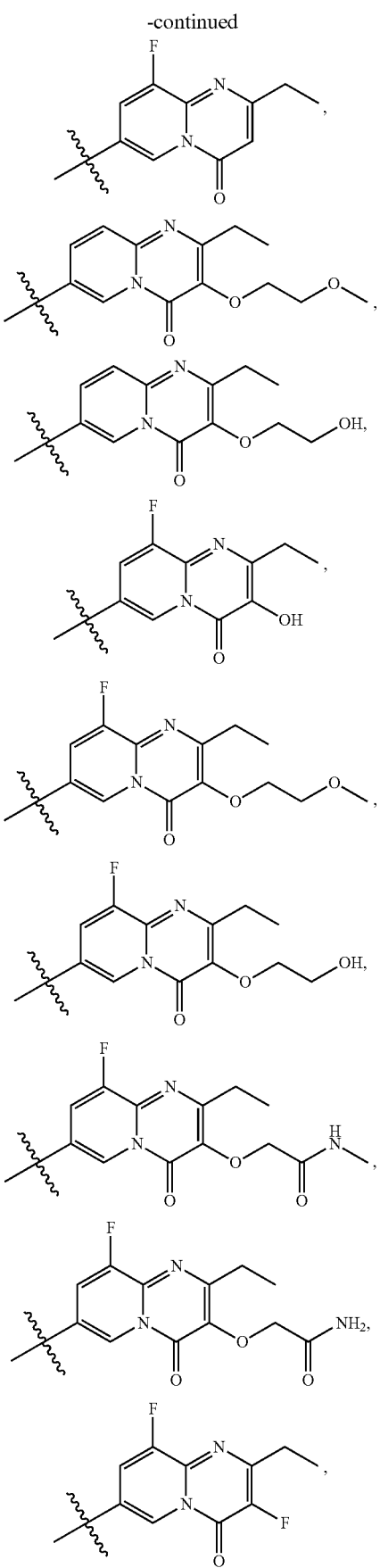

-continued

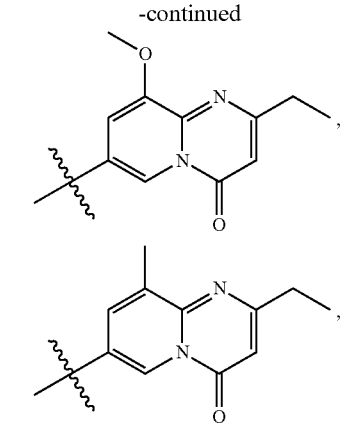

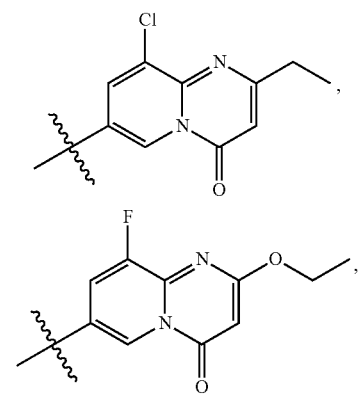

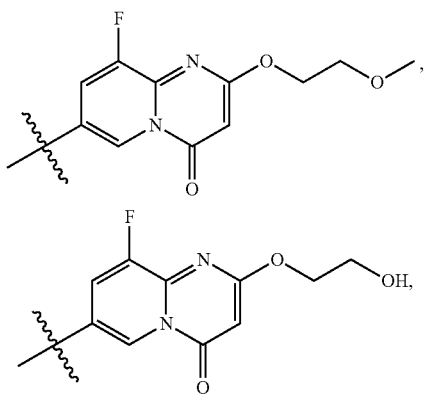

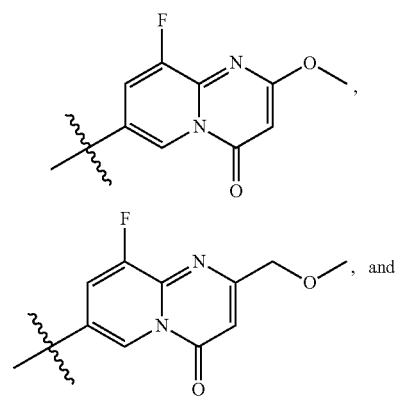, and

-continued

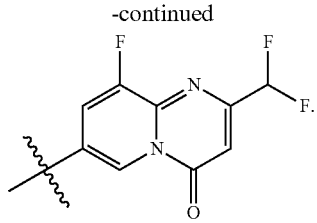

In some embodiments, two of $X^{12}$, $X^{13}$, $X^{14}$, $X^{15}$, and $X^{16}$ are NH and C(=O), respectively, and the others are $CH_2$ or O.

In some embodiments, the structural unit

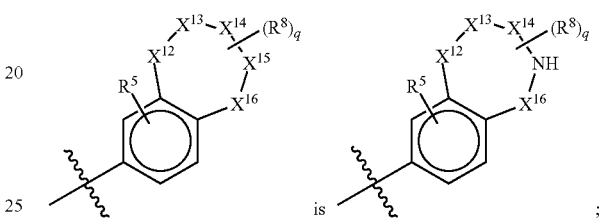

is ;

and in some embodiments, the structural unit

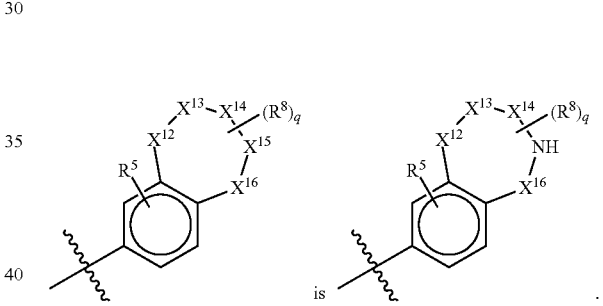

is .

In some embodiments, each $R^8$ is independently selected from the group consisting of hydrogen, $C_{1-6}$ alkyl, hydroxyl, amino, 3- to 6-membered cycloalkyl, $C_{1-6}$ alkoxy, 3- to 6-membered heterocycloalkyl, and $C_{1-6}$ alkylamino; in some embodiments, each $R^8$ is independently selected from $C_{1-4}$ alkyl; and in some embodiments, each $R^8$ is independently selected from ethyl.

In some embodiments, q is 0, 1, or 2; in some embodiments, q is 1 or 2; and in some embodiments, q is 1.

In some embodiments, the structural unit

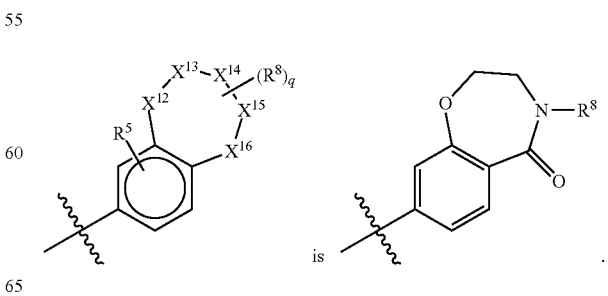

is .

In some specific embodiments, the structural unit

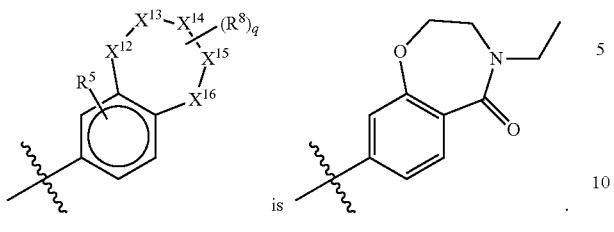

is

In another aspect, the present application provides a compound of Formula (II) or a pharmaceutically acceptable salt thereof:

Formula (II)

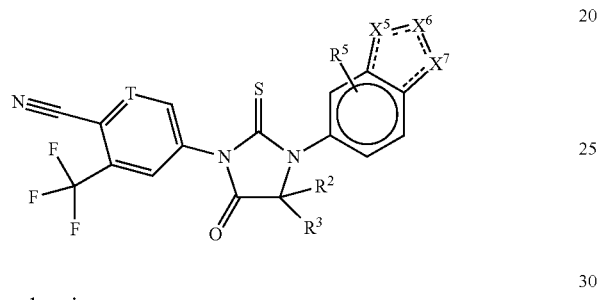

wherein,

R² and R³ are selected from methyl, or R² and R³ are connected to each other to form cyclobutyl together; and the structural unit

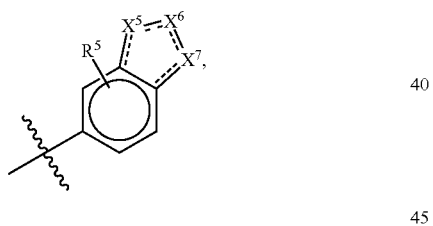

and $X^5$, $X^6$, $X^7$, T, and $R^5$ are as defined in the compound of Formula (I).

In some embodiments of the present invention, T is selected from CH.

In still another aspect, the present application provides a compound of Formula (III-1) or a compound of Formula (III-2) or a pharmaceutically acceptable salt thereof:

Formula (III-1)

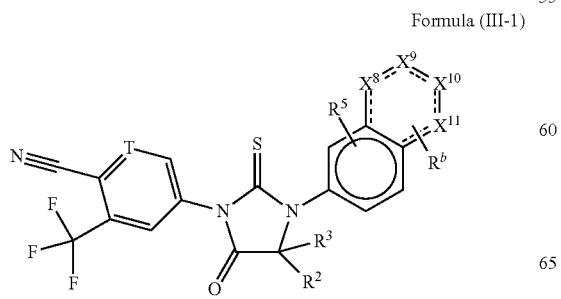

Formula (III-2)

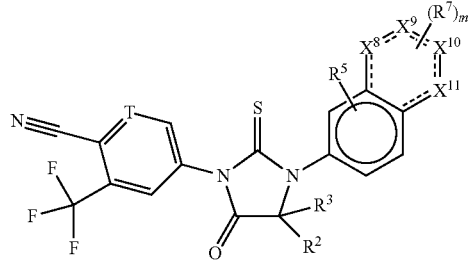

wherein,

R² and R³ are selected from methyl, or R² and R³ are connected to each other to form cyclobutyl together; and the structural units

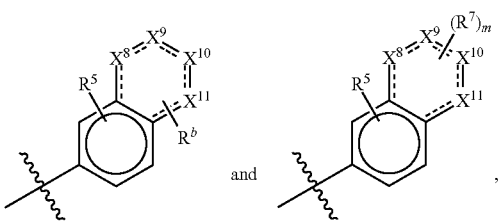

and $X^8$, $X^9$, $X^{10}$, $X^{11}$, $Y^8$, $Y^9$, $Y^{10}$, $Y^{11}$, T, $R^5$, $R^b$, $R^7$, and m are as defined in the compound of Formula (I).

In yet another aspect, the present application provides a compound of Formula (III-21) or a compound of Formula (III-22) or a pharmaceutically acceptable salt thereof:

Formula (III-21)

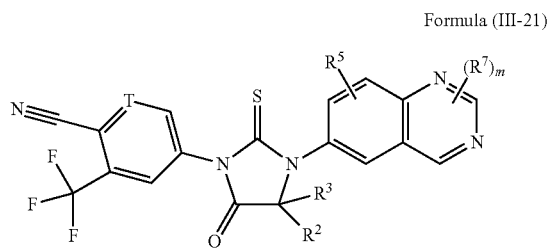

Formula (III-22)

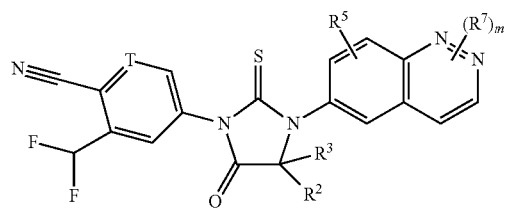

wherein, m is 1 or 2; R² and R³ are selected from methyl, or R² and R³ are connected to each other to form cyclobutyl together; and the structural unit

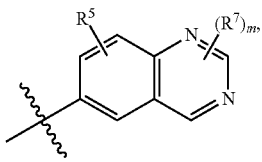

and T, $R^5$, and $R^7$ are as defined in the compound of Formula (I).

In some embodiments, the structural unit

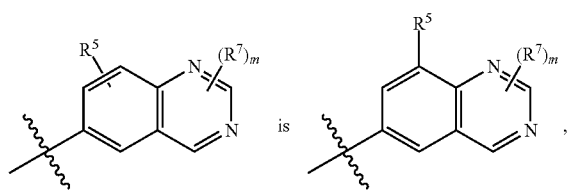

wherein the definition of the structural unit

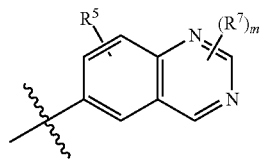

is as mentioned above.

In still yet another aspect, the present application provides a compound of Formula (IV) or a pharmaceutically acceptable salt thereof:

Formula (IV)

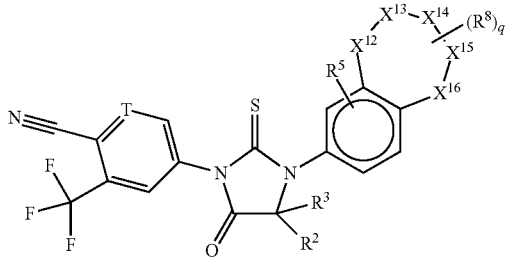

wherein, q is 1 or 2; $R^2$ and $R^3$ are selected from methyl, or $R^2$ and $R^3$ are connected to each other to form cyclobutyl together; and the structural unit

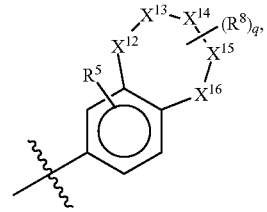

and T, $X^{12}$, $X^{13}$, $X^{14}$, $X^{15}$, $X^{16}$, $R^5$, and $R^8$ are as defined in the compound of Formula (I).

In some embodiments of the present application, T is selected from CH.

In a further aspect, the present application provides a compound of Formula (V) or a pharmaceutically acceptable salt thereof:

Formula (V)

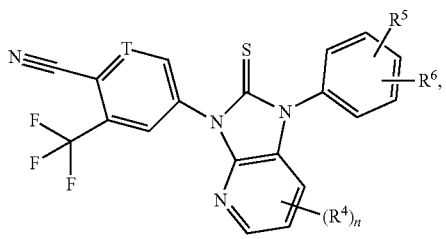

wherein the structural units

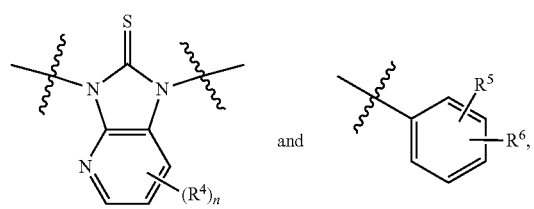

and T, $R^4$, n, $R^5$, and $R^6$ are as defined in the compound of Formula (I).

In some embodiments of the present application, T is selected from CH.

Preferably, the present application provides a compound of Formula (VI) or a pharmaceutically acceptable salt thereof:

Formula (VI)

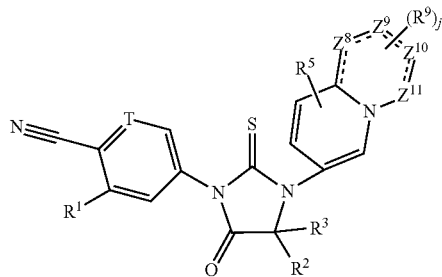

wherein,
the structural unit

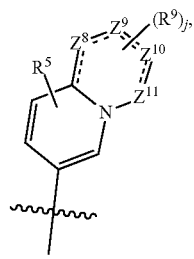

and T, R$^1$, R$^5$, R$^9$, Z$^8$, Z$^9$, Z$^{10}$, Z$^{11}$, and j are as defined in the compound of Formula (I); and R$^2$ and R$^3$ are selected from methyl, or R$^2$ and R$^3$ are connected to each other to form cyclobutyl together.

In some specific embodiments, R$^1$ is selected from the group consisting of fluoro, chloro, and trifluoromethyl.

Preferably, the present application provides a compound of Formula (VI-1) or a pharmaceutically acceptable salt thereof:

Formula (VI-I)

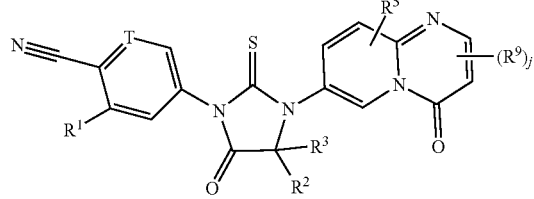

wherein,
T, R$^1$, R$^5$, R$^9$, and j are as defined in the compound of Formula (I); and R$^2$ and R$^3$ are selected from methyl, or R$^2$ and R$^3$ are connected to each other to form cyclobutyl together.

In some embodiments, the structural unit

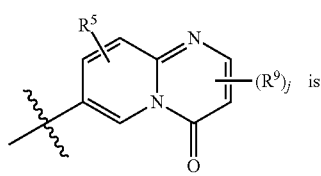 is

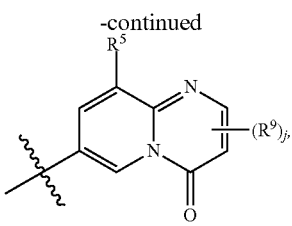

wherein the definition of the structural unit,

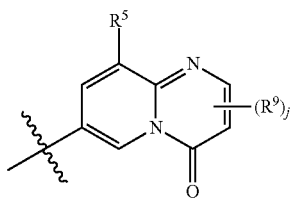

is as mentioned above.

In some specific embodiments, R$^1$ is selected from the group consisting of fluoro, chloro, and trifluoromethyl.

In another aspect, the present application provides a compound of Formula (VII) or a pharmaceutically acceptable salt thereof:

Formula (VII)

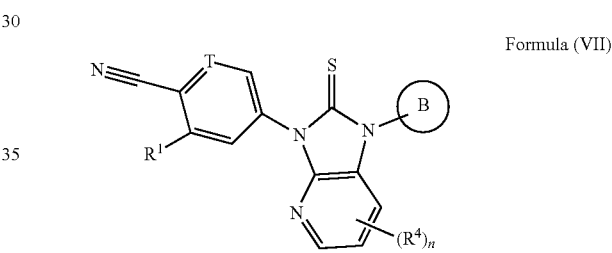

wherein,
T, R$^1$, R$^4$, and n are as defined in the compound of Formula (I); and
the ring B is selected from the group consisting of

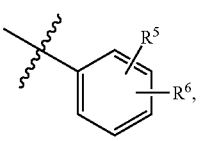

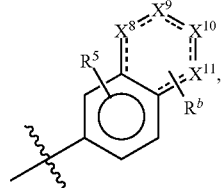

and

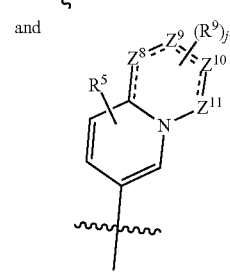

wherein X$^8$, X$^9$, X$^{10}$, X$^{11}$, Y$^8$, Y$^9$, Y$^{10}$, Y$^{11}$, Z$^8$, Z$^9$, Z$^{10}$, Z$^{11}$, R$^5$, R$^6$, R$^b$, R$^7$, R$^9$, m, j, and the structural units

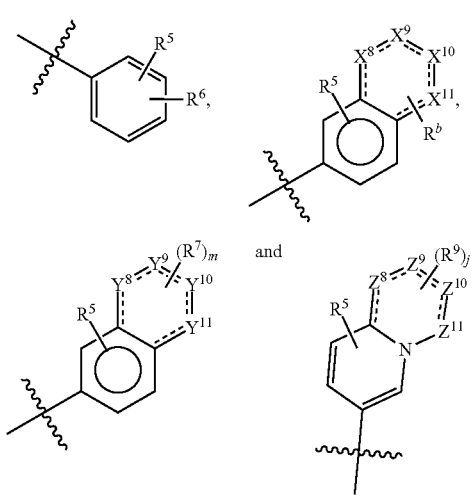
and
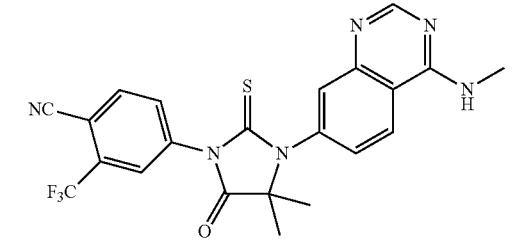
are as defined in the compound of Formula (I).
In still another aspect, the present application provides the following compounds or a pharmaceutically acceptable salt thereof:
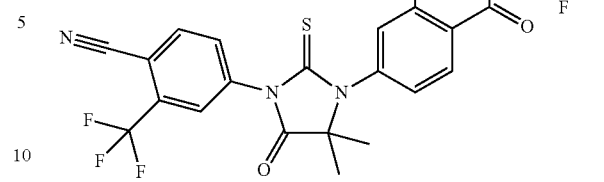
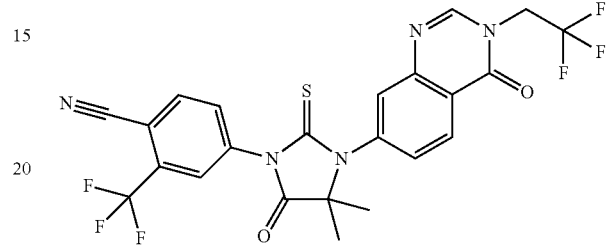
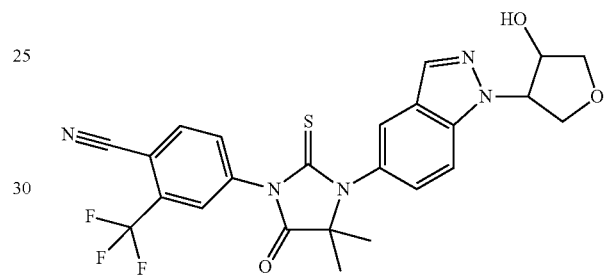
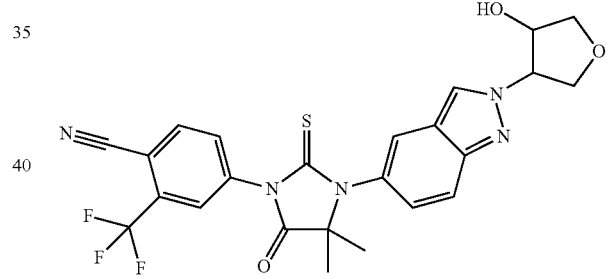
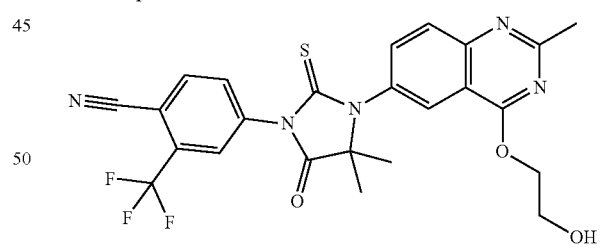
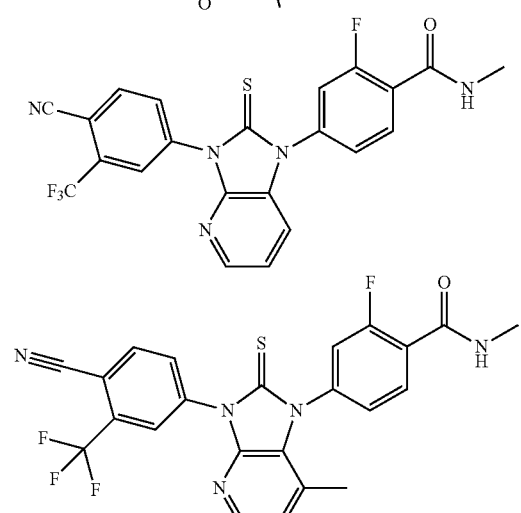
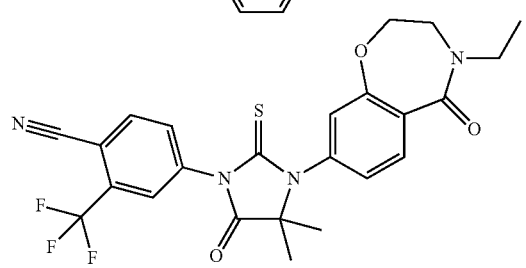
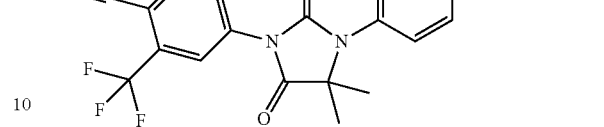
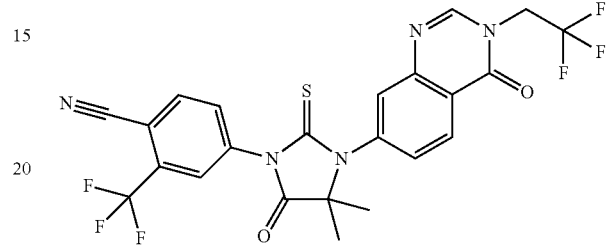
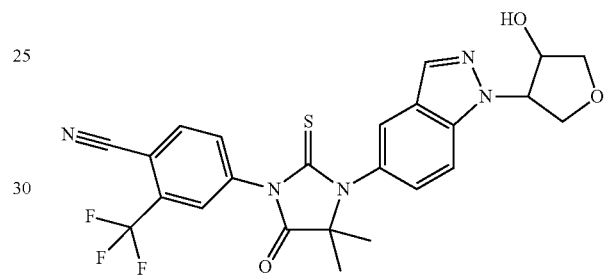
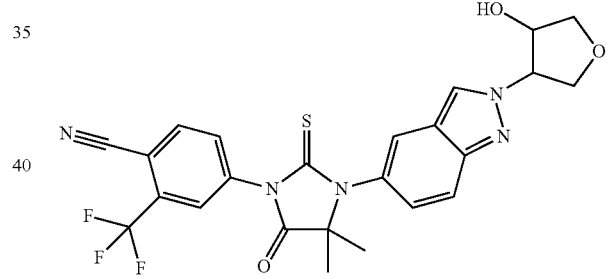
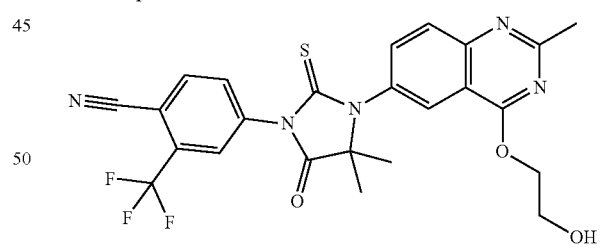
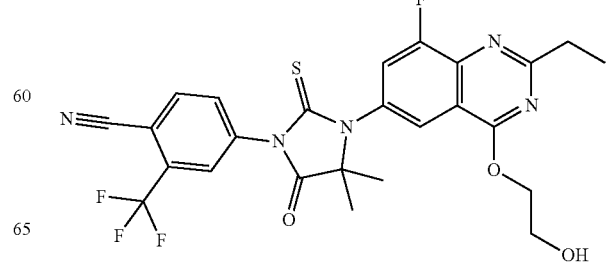

-continued
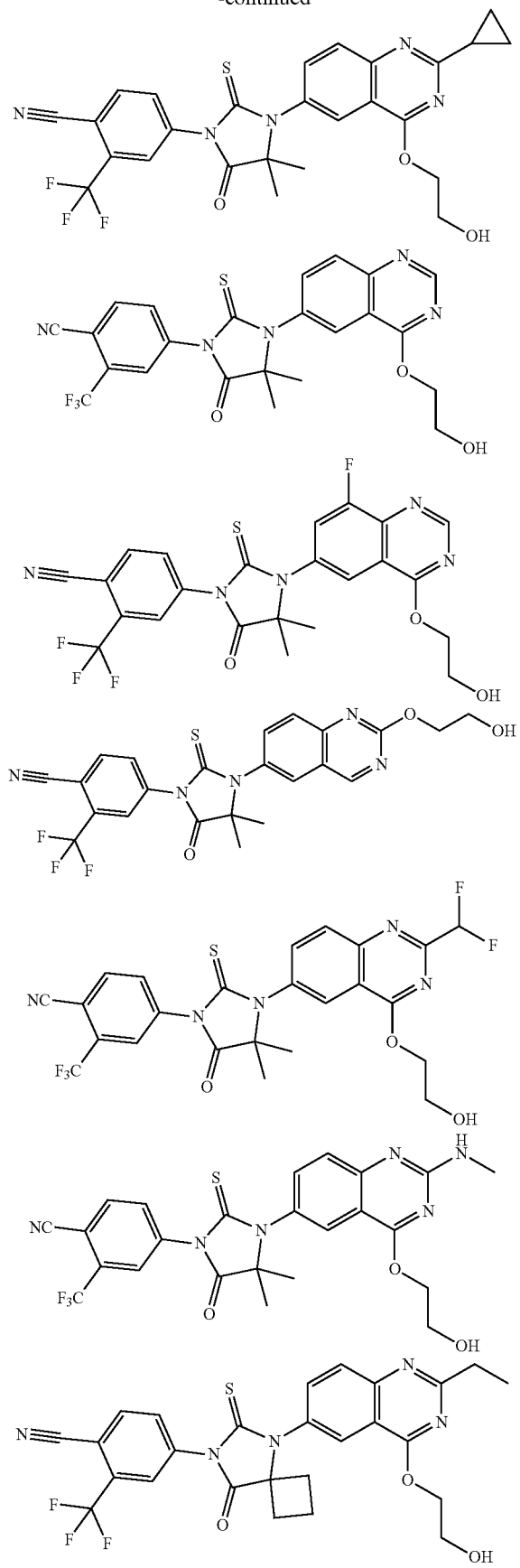
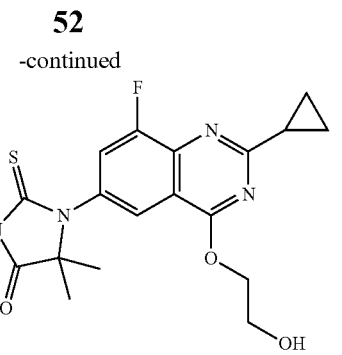

53
-continued
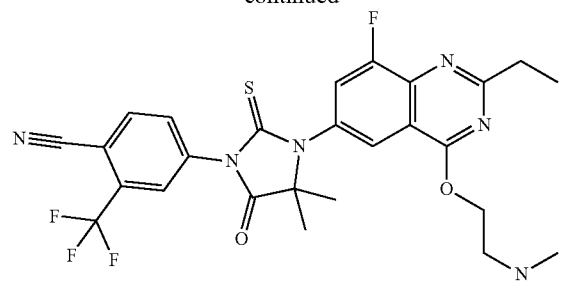
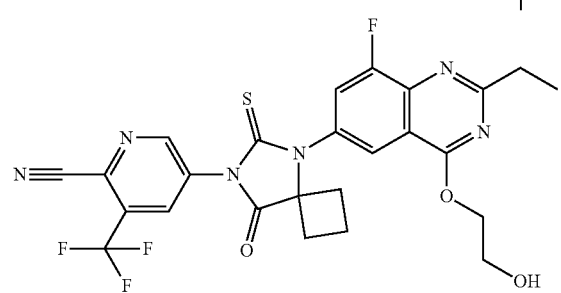
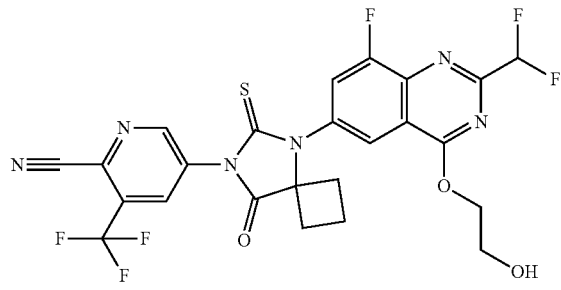
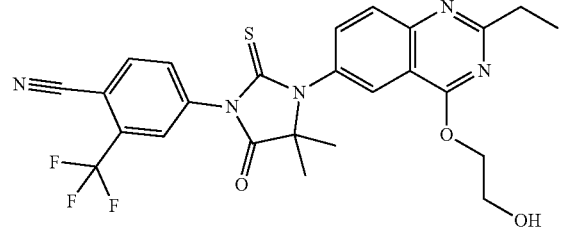
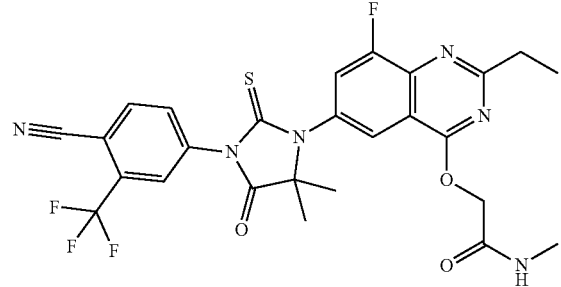
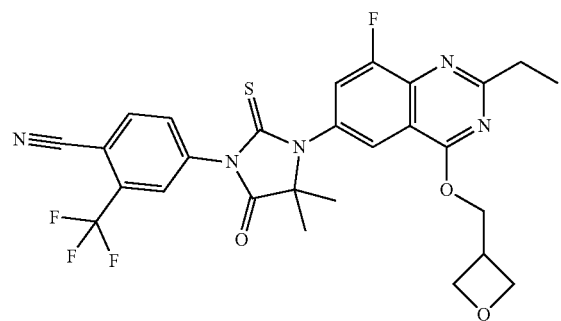
54
-continued
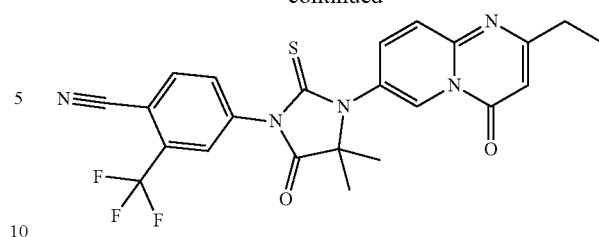
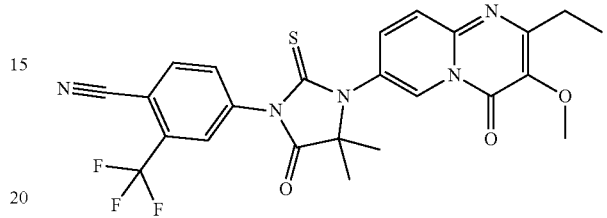
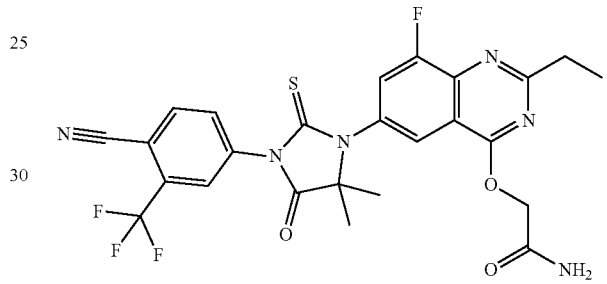
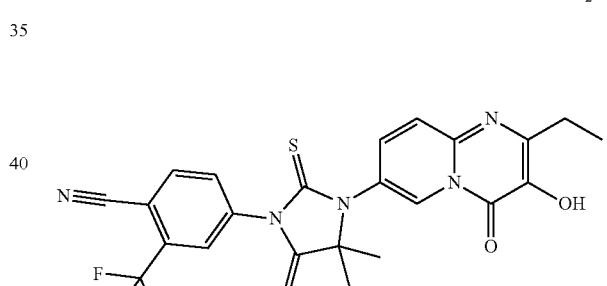
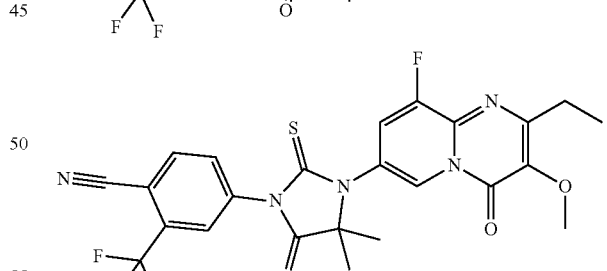
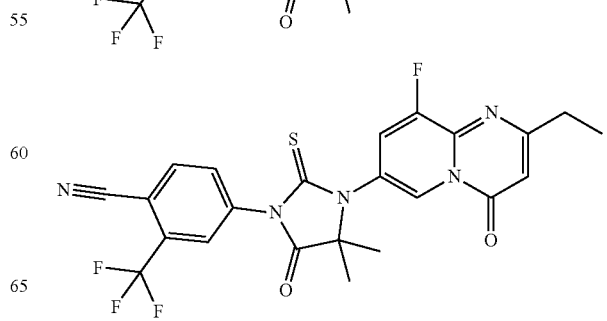

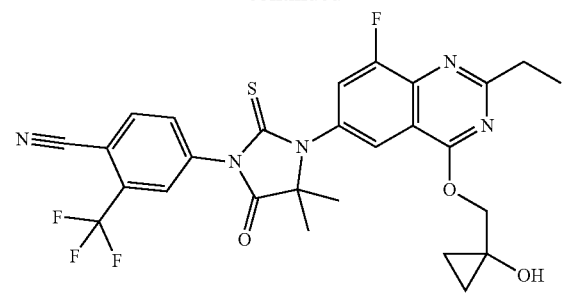
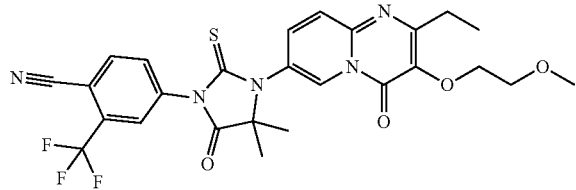
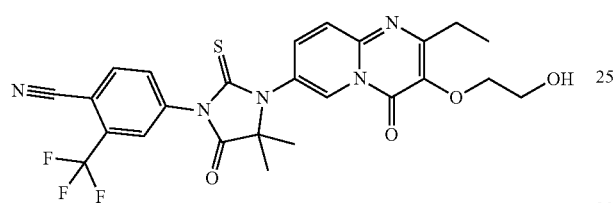
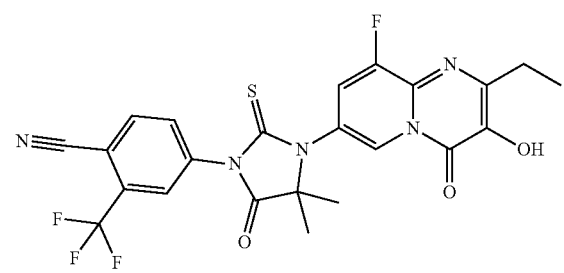
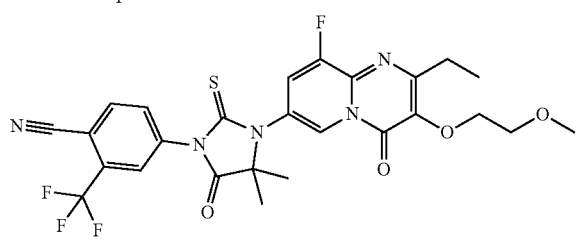
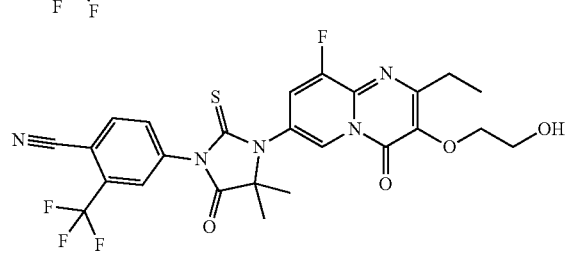
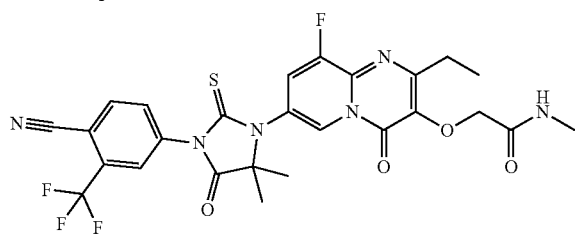
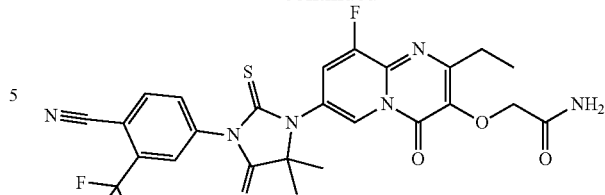
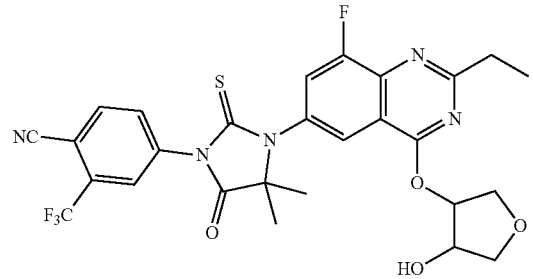
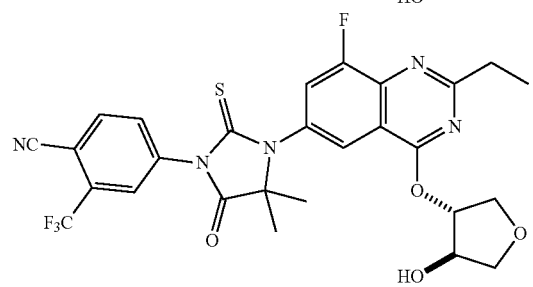
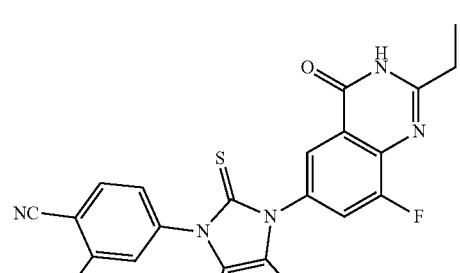
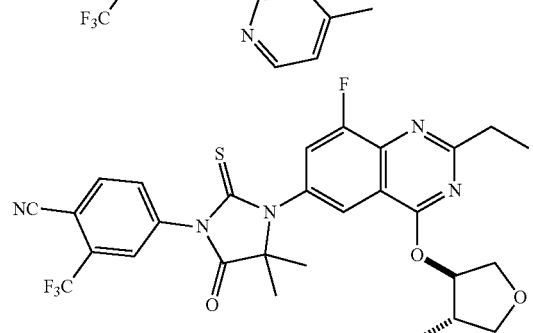
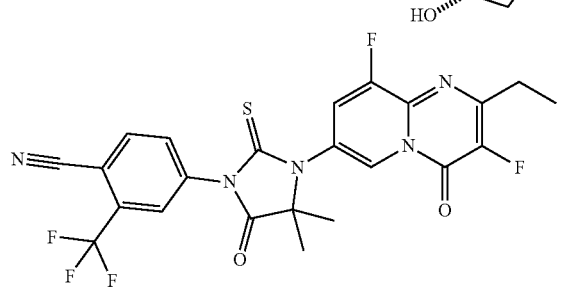

57
-continued
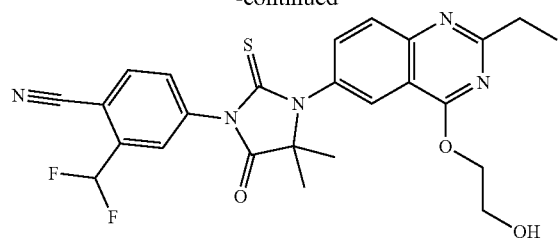
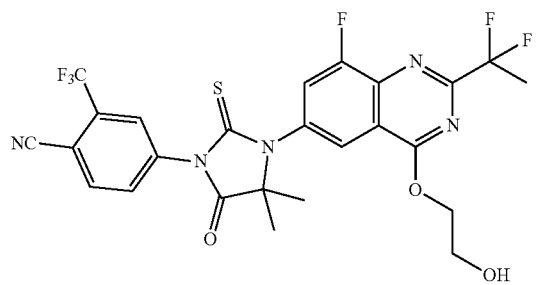
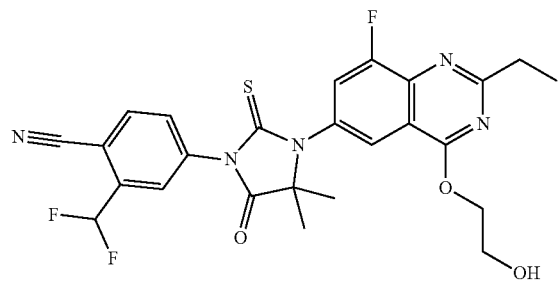
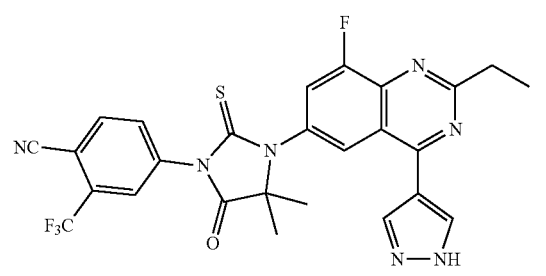
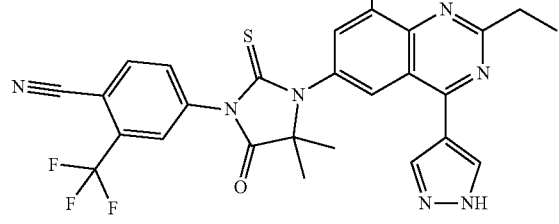
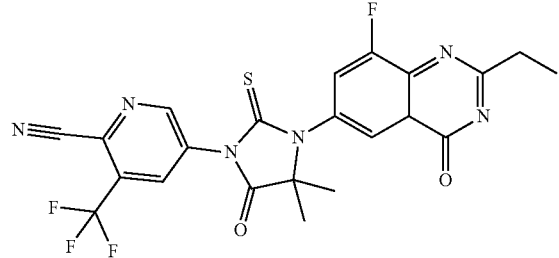
58
-continued
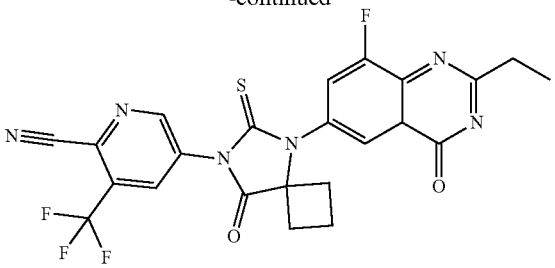
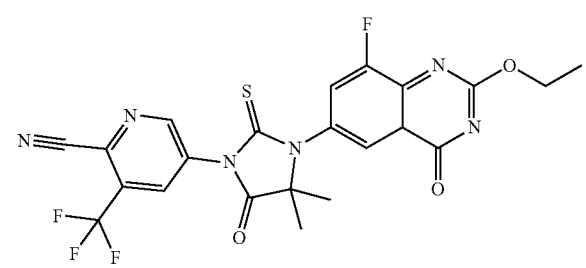
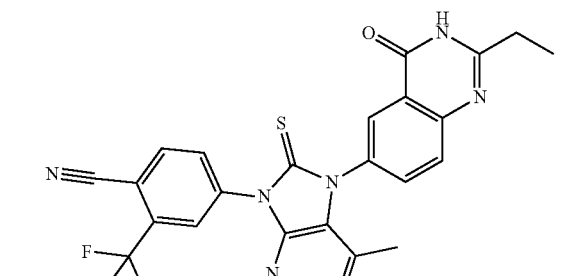
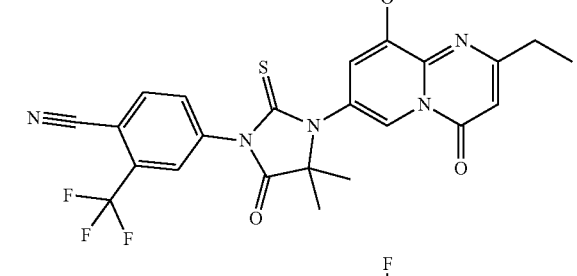
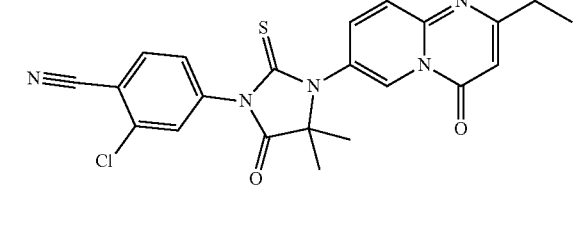
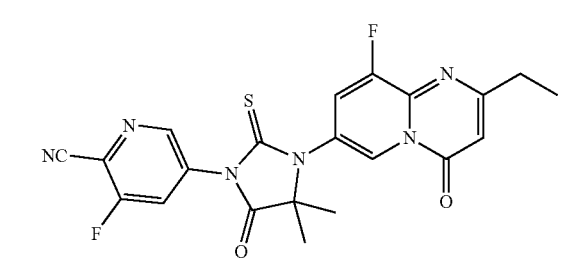

59
-continued

60
-continued

-continued

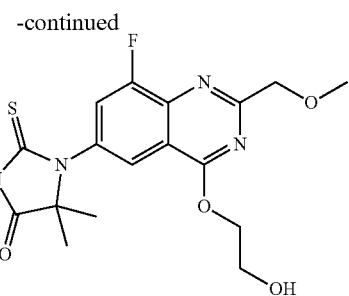

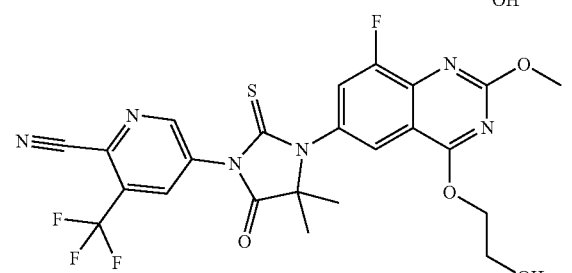

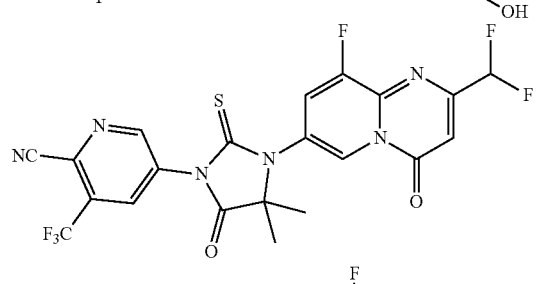

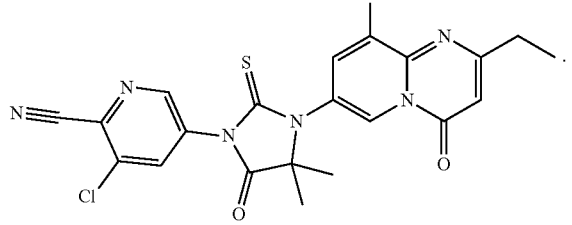

In yet another aspect, the present application relates to a pharmaceutical composition, comprising the compound of Formula (I), Formula (II), Formula (III-1), Formula (III-2), Formula (III-21), Formula (III-22), Formula (IV), Formula (V), Formula (VI), Formula (VI-1), or Formula (VII), or a pharmaceutically acceptable salt thereof according to the present application. In some embodiments, the pharmaceutical composition of the present application further comprises a pharmaceutically acceptable excipient.

In still yet another aspect, the present application relates to a method for treating an androgen-mediated disease in a mammal, comprising administering to a mammal, preferably a human, in need of the treatment a therapeutically effective amount of the compound of Formula (I), Formula (II), Formula (III-1), Formula (III-2), Formula (III-21), Formula (III-22), Formula (IV), Formula (V), Formula (VI), Formula (VI-1), or Formula (VII), or a pharmaceutically acceptable salt thereof, or the pharmaceutical composition thereof; and the disease includes, but is not limited to, cell proliferative diseases (e.g., cancer).

In a further aspect, the present application relates to use of the compound of Formula (I), Formula (II), Formula (III-1), Formula (III-2), Formula (III-21), Formula (III-22), Formula (IV), Formula (V), Formula (VI), Formula (VI-1), or Formula (VII), or a pharmaceutically acceptable salt thereof, or the pharmaceutical composition thereof in the preparation of a medicament for the treatment of an androgen-mediated disease, and the disease includes, but is not limited to, cell proliferative diseases (e.g., cancer).

In still a further aspect, the present application relates to use of the compound of Formula (I), Formula (II), Formula (III-1), Formula (III-2), Formula (III-21), Formula (III-22), Formula (IV), Formula (V), Formula (VI), Formula (VI-1), or Formula (VII), or a pharmaceutically acceptable salt thereof, or the pharmaceutical composition in the treatment of an androgen-mediated disease, and the disease includes, but is not limited to, cell proliferative diseases (e.g., cancer).

In yet a further aspect, the present application relates to the compound of Formula (I), Formula (II), Formula (III-1), Formula (III-2), Formula (III-21), Formula (III-22), Formula (IV), Formula (V), Formula (VI), Formula (VI-1), or Formula (VII), or a pharmaceutically acceptable salt thereof, or the pharmaceutical composition thereof for use in preventing or treating an androgen-mediated disease, and the disease includes, but is not limited to, cell proliferative diseases (e.g., cancer).

Definitions

Unless specified otherwise, the following terms used herein have the following meanings. If a particular term is not specifically defined, it cannot be considered to be indefinite or unclear, and shall be understood according to the ordinary meaning in the art. Where a trade name is cited herein, it is intended to indicate the corresponding product or its active ingredient.

The term "substituted" means that any one or more hydrogen atoms on a specific atom are replaced by substituents, as long as the valence of the specific atom is normal and the substituted compound is stable. When the substituent is oxo or keto (i.e., =O), it means that two hydrogen atoms are substituted.

The term "optional" or "optionally" is intended to mean that the subsequently described event or circumstance may or may not occur, and that the description includes instances where said event or circumstance occurs and instances where said event or circumstance does not occur. For example, when ethyl is "optionally" substituted with fluoro or chloro, it is intended to mean that the ethyl may be unsubstituted (e.g., —CH$_2$CH$_3$), monosubstituted (e.g., —CH$_2$CH$_2$F, —CHFCH$_3$), polysubstituted (e.g., —CHFCH$_2$F, —CHClCH$_2$F, —CH$_2$CHCl$_2$, —CH$_2$CHF$_2$ and the like), or completely substituted (—CFClCF$_3$, —CF$_2$CF$_3$). It will be understood by those skilled in the art, with respect to any groups containing one or more substituents, that such groups are not intended to introduce any substitutions or substitution patterns which are sterically impractical and/or synthetically non-feasible. Unless otherwise specified, the kinds and numbers of substituents may be arbitrary on the basis that they are chemically achievable.

When a substituent may be connected to more than one atom on a ring, such a substituent may be bound to any atom on the ring, for example, the structural unit

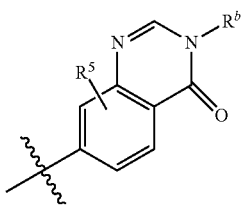

includes

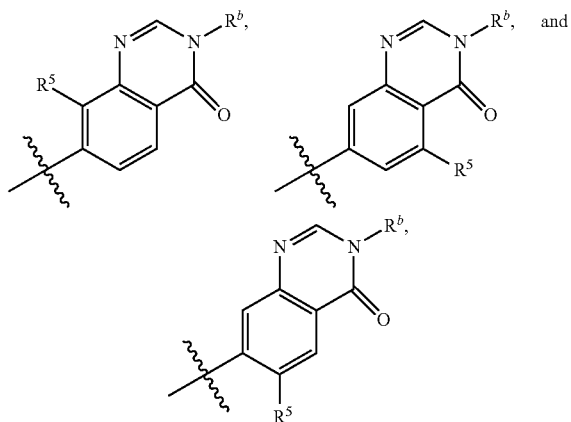

but does not include

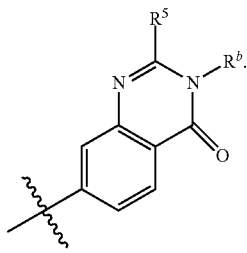

"$C_{m-n}$" as used herein means that this moiety has an integer number of carbon atoms in the given range. For example, "$C_{1-6}$" means that the group may have 1 carbon atom, 2 carbon atoms, 3 carbon atoms, 4 carbon atoms, 5 carbon atoms, or 6 carbon atoms; and "$C_{3-6}$" means that the group may have 3 carbon atoms, 4 carbon atoms, 5 carbon atoms, or 6 carbon atoms.

When any variable (e.g., $R^7$) occurs in the composition or structure of a compound more than once, the variable at each occurrence is independent defined. Therefore, for example, $(R^7)_m$ represents a group substituted by m $R^7$, and each $R^7$ has independent options; and specifically, for example, when m=2, one group is substituted by 2 $R^7$, and each $R^7$ has independent options.

The term "halo" or "halogen" refers to fluoro, chloro, bromo, and iodo.

The term "hydroxyl" refers to —OH group.

The term "amino" refers to —NH$_2$ group.

The term "trifluoromethyl" refers to —CF$_3$ group.

The term "alkyl" refers to a hydrocarbyl having a general formula $C_nH_{2n+1}$. The alkyl may be straight or branched. For example, the term "$C_{1-6}$ alkyl" "refers to an alkyl containing 1 to 6 carbon atoms (e.g., methyl, ethyl, n-propyl, isopropyl, n-butyl, isobutyl, sec-butyl, tert-butyl, n-pentyl, 1-methylbutyl, 2-methylbutyl, 3-methylbutyl, neopentyl, hexyl, 2-methylpentyl and the like). Similarly, the alkyl moiety (i.e., an alkyl) of an alkoxy has the same definition as above; and the term "$C_{1-3}$ alkyl" refers to an alkyl containing 1 to 3 carbon atoms (e.g., methyl, ethyl, n-propyl, or isopropyl).

The term "alkoxy" refers to —O-alkyl.

The term "alkylamino" refers to —NH-alkyl.

The term "alkylaminocarbonyl" refers to —C(=O)—NH-alkyl.

The term "alkenyl" refers to a straight or branched unsaturated aliphatic hydrocarbonyl consisting of carbon atoms and hydrogen atoms and having at least one double bond. Non-limiting examples of the alkenyl include, but are not limited to, ethenyl, 1-propenyl, 2-propenyl, 1-butenyl, isobutenyl, 1,3-butadienyl, and the like. For example, the term "$C_{2-6}$ alkenyl" refers to an alkenyl containing 2 to 6 carbon atoms; and the term $C_2$-$C_3$ alkenyl refers to an alkenyl containing 2 to 3 carbon atoms (e.g., ethenyl, 1-propenyl, or 2-propenyl).

The term "alkynyl" refers to a straight or branched unsaturated aliphatic hydrocarbonyl consisting of carbon atoms and hydrogen atoms and having at least one triple bond. Non-limiting examples of the alkynyl include, but are not limited to, ethynyl (—C≡CH), 1-propynyl (—C≡C—CH$_3$), 2-propynyl (—CH$_2$—C≡CH), 1,3-butadiynyl (—C≡CC≡CH), and the like.

The term "cycloalkyl" refers to a fully saturated carbon ring that may exist as a monocyclic ring, a bridged ring, or a spiro ring. Unless otherwise specified, the carbon ring is usually a 3- to 10-membered ring. Non-limiting examples of the cycloalkyl include, but are not limited to, cyclopropyl, cyclobutyl, cyclopentyl, cyclohexyl, norbornyl (bicyclo[2.2.1]heptyl), bicyclo[2.2.2]octyl, adamantyl, and the like. The cycloalkyl is preferably a monocyclic cycloalkyl having 3 to 6 ring atoms.

The term "heterocycloalkyl" refers to a fully saturated cyclic group that may exist as a monocyclic ring, a bicyclic ring, or a spiro ring. Unless otherwise indicated, the heterocyclic ring is usually a 3- to 7-membered ring containing 1 to 3 heteroatoms (preferably 1 or 2 heteroatoms) independently selected from the group consisting of sulfur, oxygen, and/or nitrogen.

Examples of a 3-membered heterocycloalkyl include, but are not limited to, epoxyethyl, cyclothioethyl, and azirdinyl; non-limiting examples of a 4-membered heterocycloalkyl include, but are not limited to, azetidinyl, oxetanyl, and thietanyl; examples of a 5-membered heterocycloalkyl include, but are not limited to, tetrahydrofuranyl, tetrahydrothienyl, pyrrolidinyl, isooxazolidinyl, oxazolidinyl, isothiazolidinyl, thiazolidinyl, imidazolidinyl, tetrahydropyrazolyl, and pyrrolinyl; examples of a 6-membered heterocycloalkyl include, but are not limited to, piperidinyl, tetrahydropyranyl, tetrahydrothiopyranyl, morpholinyl, piperazinyl, 1,4-thioxanyl, 1,4-dioxanyl, thiomorpholinyl, 1,2-dithioalkyl, 1,4-dithioalkyl, and tetrahydropyranyl; and examples of a 7-membered heterocycloalkyl include, but are not limited to, azacycloheptyl, oxacycloheptyl, and thiacycloheptyl. The heterocycloalkyl is preferably a monocyclic heterocycloalkyl having 5 to 6 ring atoms.

The term "heteroaryl" refers to a monocyclic or fused polycyclic ring system containing at least one ring atom selected from the group consisting of N, O, and S, the other ring atoms being C, and having at least one aromatic ring. A preferable heteroaryl has a single 4- to 8-membered ring, and particularly a 5- to 8-membered ring, or a plurality of fused rings containing 6 to 14, and particularly 6 to 10, ring atoms. Non-limiting examples of the heteroaryl include, but are not limited to, pyrrolyl, furanyl, thienyl, imidazolyl, oxazolyl, pyrazolyl, pyridinyl, pyrimidinyl, pyrazinyl, quinolyl, isoquinolyl, tetrazolyl, triazolyl, triazinyl, benzofuranyl, benzothienyl, indolyl, isoindolyl, and the like.

The "—$C_{1-12}$ alkyl-(3- to 10-membered cycloalkyl)" herein represents a $C_{1-12}$ alkyl substituted by a 3- to 10-membered cycloalkyl, and other similar expressions should be understood similarly.

Herein, the "—$C_{1-12}$ alkyl-(3- to 10-membered cycloalkyl) optionally substituted by halogen or hydroxyl" means that any hydrogen atom of the —$C_{1-12}$ alkyl-(3- to 10-membered cycloalkyl) may be substituted by halogen or hydroxyl, and other similar expressions should be understood similarly.

The structural unit

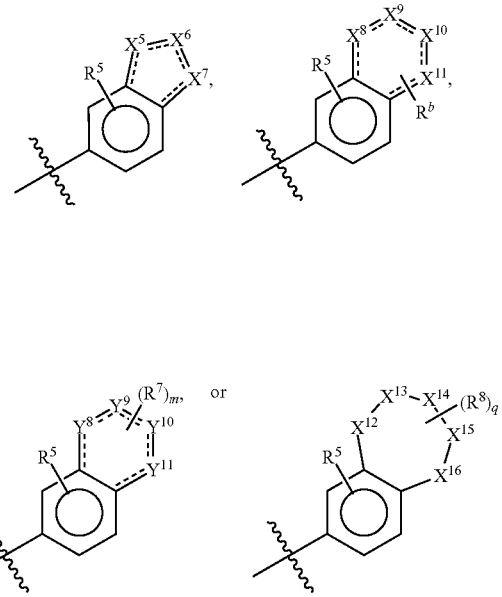

represents a benzoheterocyclic ring system. The bond "====" correspondingly represents a single bond or a double bond according to a specific option of $X^5$, $X^6$, $X^7$, $X^8$, $X^9$, $X^{10}$, $X^{11}$, $Y^8$, $Y^9$, $Y^{10}$, or $Y^{11}$ in the present application, and will not violate the valence bond theory. For example, when $X^5$ is CH, $X^6$ is N (—$R^a$), and $X^7$ is N, the structural unit

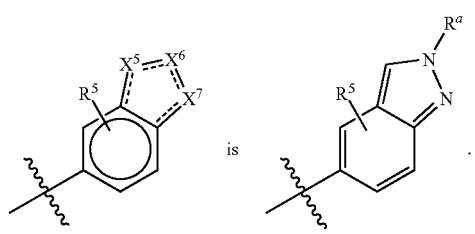

For example, when $X^5$ is CH, $X^6$ is N, and $X^7$ is N(—$R^a$), the structural unit

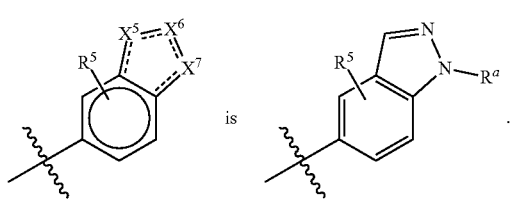

For example, when $X^8$ is N, $X^9$ is CH, $X^{10}$ is NH, and $X^{11}$ is C(=O), the structural unit

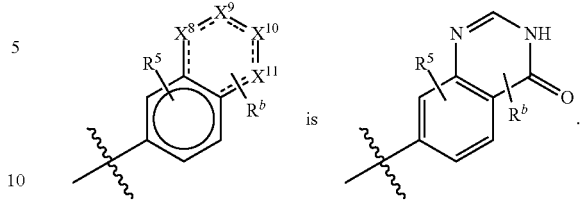

For example, when $Y^8$ is N, $Y^9$ is CH, $Y^{10}$ is N, and $Y^{11}$ is CH, the structural unit

The structural unit

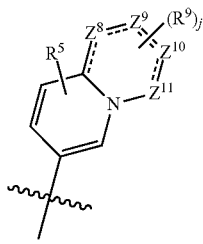

represents a pyridinoheterocyclic ring system. The bond "====" correspondingly represents a single bond or a double bond according to a specific option of $Z^8$, $Z^9$, $Z^{10}$, or $Z^{11}$ in the present application, and will not violate the valence bond theory.

Unless otherwise indicated, a wedge-shaped bond and a dotted bond ( ⟋ ⋯ ) denote an absolute configuration of a stereocenter, while a wavy line ⌇ denotes one of the absolute configurations of a stereocenter (e.g., one of ⟋ or ⋯ ), and ⋯ and ⟋ denote a relative configuration of a stereocenter. When the compounds of the present application contain olefinic double bonds or other geometrically asymmetric centers, they include E and Z geometric isomers, unless otherwise specified. Likewise, all tautomeric forms are included within the scope of the present application.

The compounds of the present application may exist in specific geometrical isomers or stereoisomeric forms. All such compounds are contemplated in the present application, including tautomers, cis- and trans-isomers, (−)- and (+)-enantiomers, (R)- and (S)-enantiomers, diastereomers, (D)-isomers, (L)-isomers, and their racemic mixtures and other mixtures, such as enantiomer or diastereomer enriched mixtures. All such mixtures are included in the scope of the present application. Substituents such as an alkyl group may have additional unsymmetrical carbon atoms. All such isomers and mixtures thereof are included within the scope of the present application.

The term "treating" or "treatment" means administering the compounds or preparations according to the present application to prevent, ameliorate, or eliminate a disease or one or more symptoms associated with the disease, and includes:

(i) preventing the occurrence of a disease or condition in a mammal, particularly when such an mammal is susceptible to the condition, but has not yet been diagnosed as having the condition;

(ii) inhibiting a disease or condition, i.e., arresting its development; and (iii) alleviating a disease or condition, i.e., causing regression of the disease or condition.

The term "therapeutically effective amount" is intended to refer to an amount of the compound of the present application for (i) treating or preventing a particular disease, condition, or disorder, (ii) relieving, ameliorating, or eliminating one or more symptoms of the particular disease, condition, or disorder, or (iii) preventing or delaying onset of one or more symptoms of the particular disease, condition, or disorder described herein. The amount of the compound of the present application constituting the "therapeutically effective amount" will vary depending on the compound, the disease condition and its severity, the administration method, and the age of the mammal to be treated, but may be routinely determined by those skilled in the art based on their own knowledge and the present disclosure.

The term "pharmaceutically acceptable" refers to those compounds, materials, compositions and/or dosage forms that are, within the scope of sound medical judgment, suitable for use in contact with the tissues of human being and animals without excessive toxicity, irritation, allergic response or other problems or complications, commensurate with a reasonable benefit/risk ratio.

As the pharmaceutically acceptable salts, for example, metal salts, ammonium salts, salts of organic bases, salts of inorganic acids, salts of organic acids, salts of alkaline or acidic amino acids may be mentioned.

The term "pharmaceutical composition" refers to a mixture of one or more of the compounds or salts thereof of the present application and a pharmaceutically acceptable excipient. An object of the pharmaceutical composition is to facilitate administering the compound of the present application to an organism.

The term "pharmaceutically acceptable excipient" refer to the excipients that neither have obvious irritation effects on an organism, nor will impair the bioactivity and properties of the active compound. Appropriate excipients are well known to those skilled in the art, such as carbohydrates, waxes, water-soluble and/or water-swellable polymers, hydrophilic or hydrophobic materials, gelatin, oils, solvents, water and the like.

The wording "comprise" and English variations thereof (such as "comprises" and "comprising") should be understood as open and non-exclusive meanings, i.e. "include but not limited to".

The intermediates and compounds according to the present application may also exist in the form of different tautomers, and all such forms are included in the scope of the present application. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of proton tautomers is an imidazole moiety, wherein a proton can migrate between the two nitrogen atoms of the ring. Valence tautomers include interconversions by reorganization of some of the bond-forming electrons.

The present application also includes isotopically-labeled compounds of the present application that are identical to those described herein, but in which one or more atoms are replaced with atoms having an atomic weight or mass number different from that normally found in nature. Examples of the isotopes that can be incorporated into the compounds of the present application include isotopes of hydrogen, carbon, nitrogen, oxygen, phosphorus, sulfur, fluorine, iodine, and chlorine. For example, the isotopes are $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I, and $^{36}$Cl, respectively.

Certain isotopically-labeled compounds of the present application (e.g., those labeled with $^3$H and $^{14}$C) can be used in compound and/or substrate tissue distribution assays. Tritium (i.e., $^3$H) and carbon-14 (i.e., $^{14}$C) isotopes are particularly preferred due to their ease of preparation and detectability. Positron emitting isotopes, such as $^{15}$O, $^{13}$N, $^{11}$C, and $^{18}$F, can be used in Positron Emission Topography (PET) studies to determine substrate occupancy. Isotopically-labeled compounds of the present application can generally be prepared by the procedures similar to those disclosed in the schemes and/or examples below, by replacing non-isotopically-labeled reagents with isotopically-labeled reagents.

Furthermore, the substitution with heavier isotopes (such as deuterium, i.e. $^2$H) may afford certain therapeutic advantages resulting from greater metabolic stability, for example, increased in vivo half-life or reduced dosage requirements, and thus may be preferable in some circumstances, wherein the deuterium substitution may be partial or complete, and the partial deuterium substitution means that at least one hydrogen is substituted with at least one deuterium.

The compounds of the present application may be asymmetric, for example, having one or more stereoisomers. Unless otherwise stated, all the stereoisomers are included, such as enantiomers and diastereoisomers. The compounds containing asymmetric carbon atoms of the present application can be isolated in optically active pure forms or racemic forms. Optically active pure forms can be resolved from racemic mixtures or synthesized by using chiral starting materials or chiral reagents.

The pharmaceutical composition of the present application can be prepared by combining the compound of the present application with a suitable pharmaceutically acceptable excipient, and for example, it can be formulated into solid, semi-solid, liquid or gaseous preparations, such as tablets, pills, capsules, powders, granules, ointments, emulsions, suspensions, suppositories, injections, inhalants, gels, microparticles, aerosols and the like.

Typical routes for administering the compound or a pharmaceutically acceptable salt thereof, or the pharmaceutical composition thereof of the present application include, but are not limited to, oral, rectal, topical, inhalational, parenteral, sublingual, intravaginal, intranasal, intraocular, intraperitoneal, intramuscular, subcutaneous, and intravenous administration.

The pharmaceutical composition of the present application can be manufactured by using well-known methods in the art, such as a conventional mixing method, a dissolution method, a granulation method, a method for preparing sugar-coated pills, a grinding method, a emulsification method, lyophilization and the like.

In some embodiments, the pharmaceutical composition is in an oral form. For the oral administration, the pharmaceutical composition can be formulated by mixing an active compound with a pharmaceutically acceptable excipient well known in the art. These excipients enable the compound of the present application to be formulated into tablets, pills, pastilles, dragees, capsules, liquids, gels, slurries, suspensions, and the like, for oral administration to a patient.

A solid oral composition can be prepared by conventional mixing, filling or tableting methods. For example, it can be obtained by the following method: mixing the active compound with a solid excipient, optionally grinding the resulting mixture, adding other suitable excipients, if necessary, and then processing the mixture into granules to obtain a core of a tablet or a dragee. Suitable excipients include, but are not limited to: binders, diluents, disintegrants, lubricants, glidants, sweeteners, or flavoring agents.

The pharmaceutical composition may also be suitable for parenteral administration, such as sterile solutions, suspensions or lyophilized products in suitable unit dosage forms.

In all the administration methods for the compounds of Formula (I), Formula (II), Formula (III-1), Formula (III-2), Formula (III-21), Formula (III-22), Formula (IV), Formula (V), Formula (VI), Formula (VI-1), or Formula (VII) according to the present application, the daily dose is 0.01 to 200 mg/kg body weight, in the form of separate or divided doses.

The compounds of the present application can be prepared by a variety of synthetic methods well known to those skilled in the art, including the specific embodiments listed below, the embodiments obtained by combining the specific embodiments listed below with other chemical synthesis methods, and equivalents well known to those skilled in the art. The preferred embodiments include, but are not limited to, the examples of the present application.

The chemical reactions in the specific embodiments of the present application are carried out in suitable solvents which are suitable for the chemical changes of the present application and the required reagents and materials thereof. In order to obtain the compounds of the present application, it is sometimes necessary for those skilled in the art to modify or select the synthetic steps or reaction schemes based on the existing embodiments.

It is one important consideration factor for planning a synthesis scheme in the art to select appropriate protecting groups for the reactive functional groups (such as the hydroxyl group in the present application). For example, reference may be made to Greene's Protective Groups in Organic Synthesis (4th Ed). Hoboken, N.J.: John Wiley & Sons, Inc. All references cited in the present application are incorporated herein by reference in their entirety.

In some embodiments, the compounds of Formula (I) of the present application may be prepared by those skilled in the field of organic synthesis through the following steps and routes:

Intermediate Synthesis (I):
Step 1:

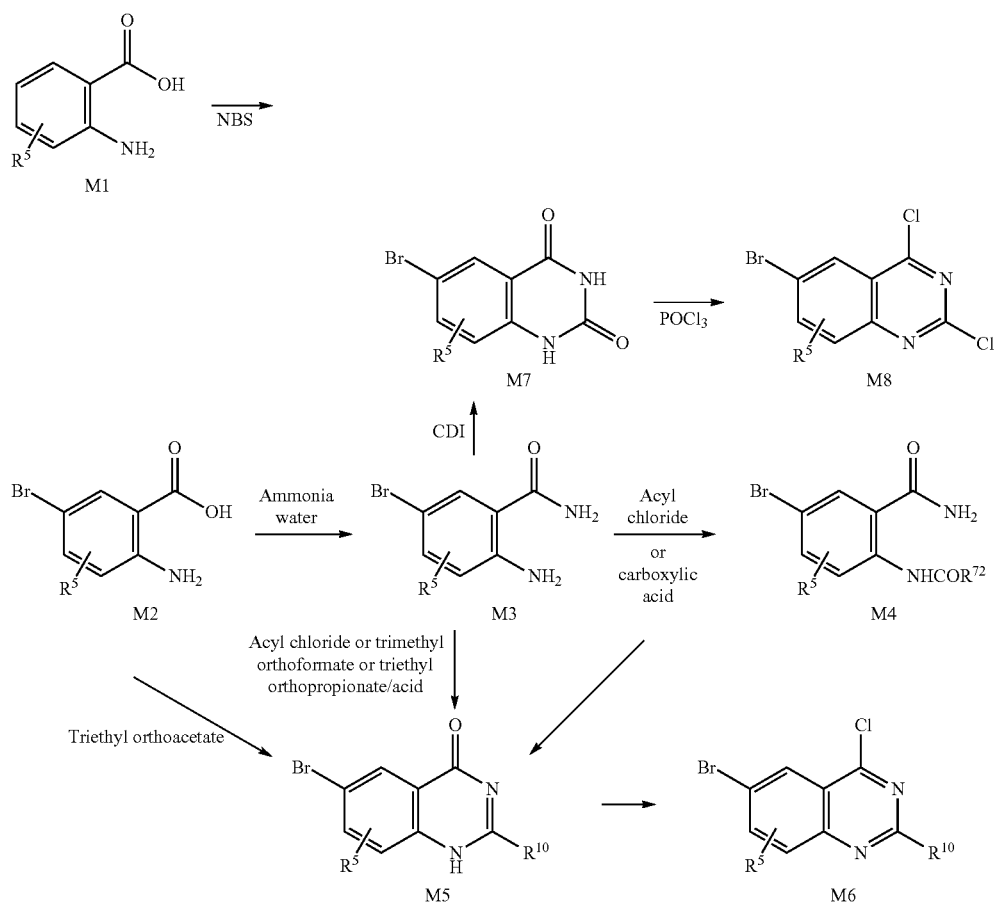

Step 2:
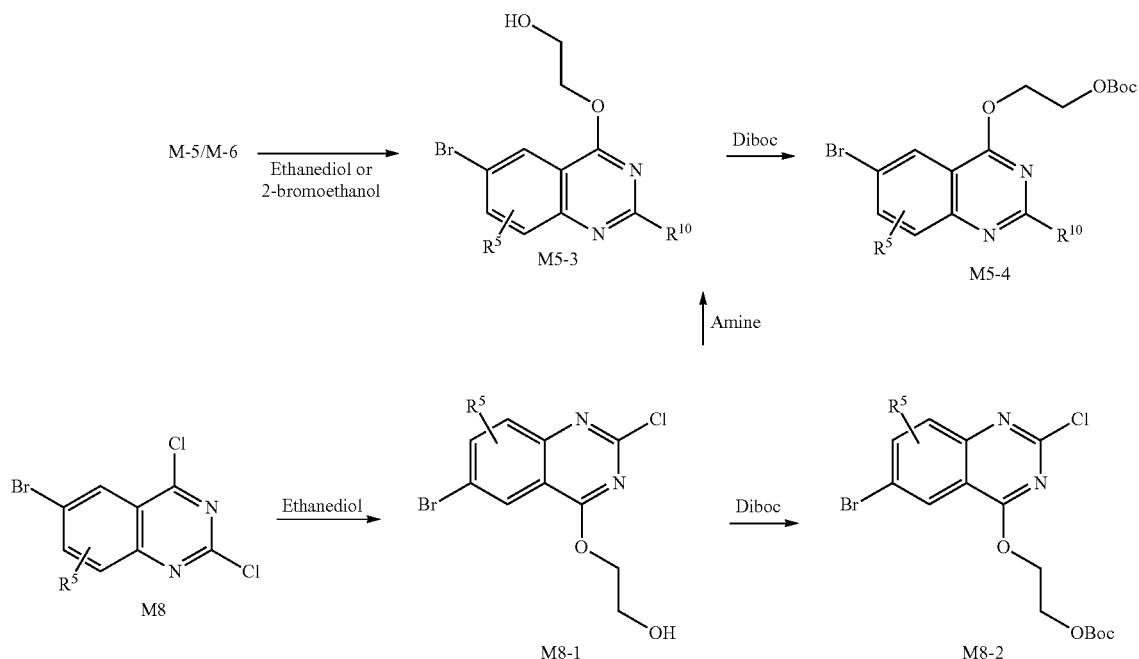
Scheme I of Step 3:
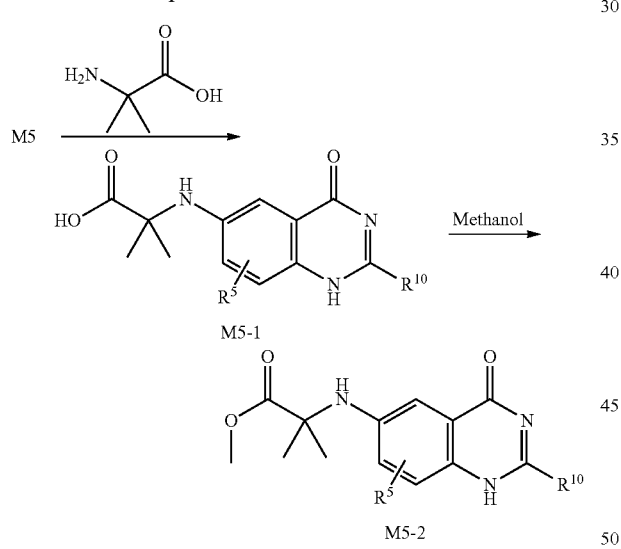
Scheme II of Step 3:
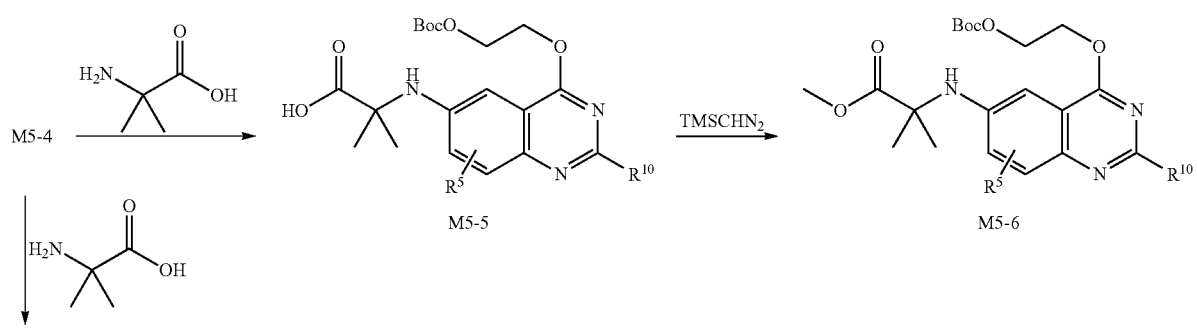

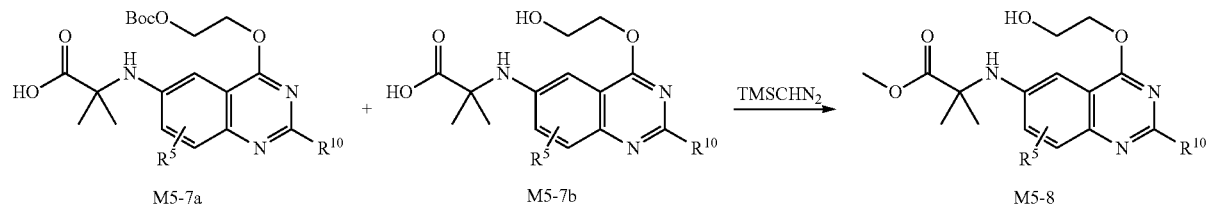
Scheme III of Step 3:
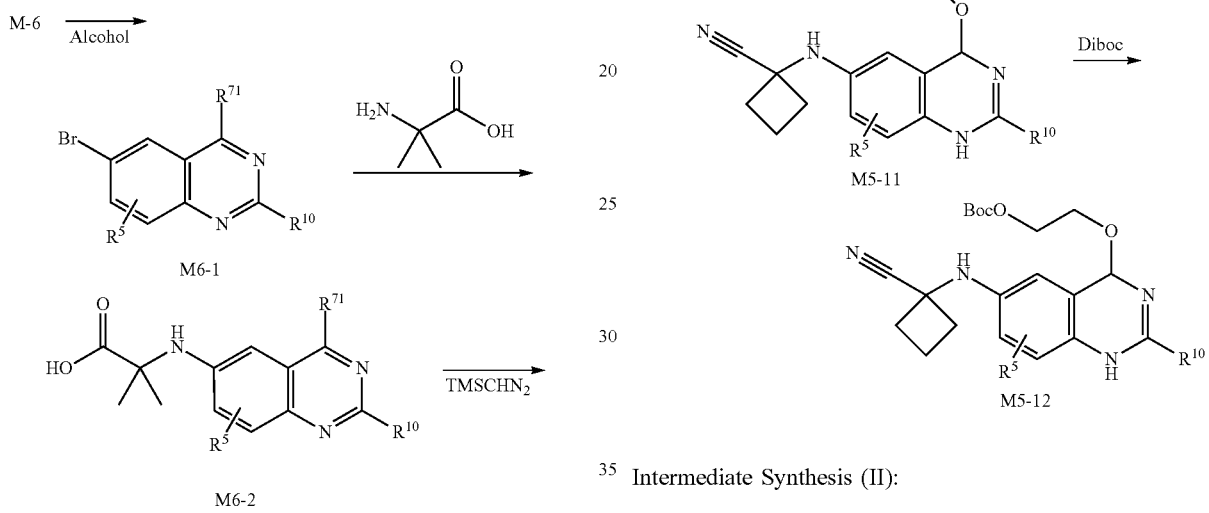
Scheme IV of Step 3:
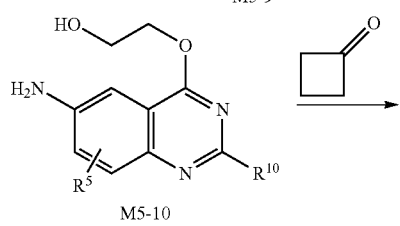
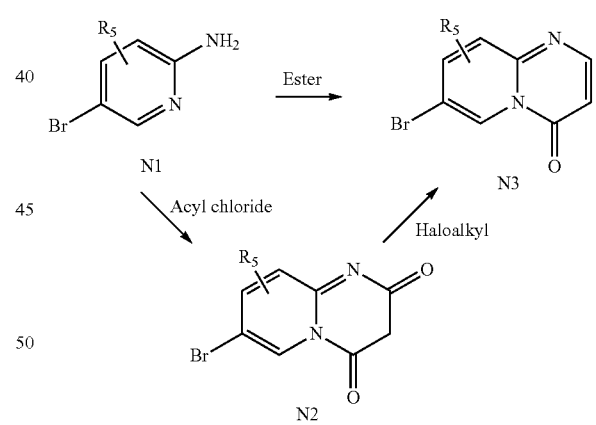
Intermediate Synthesis (II):
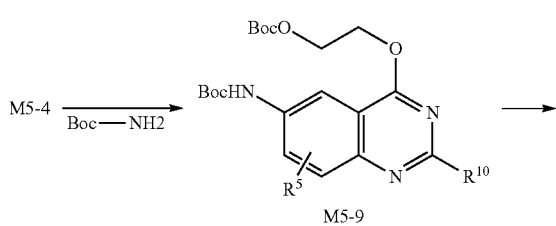
Scheme I of Step 2:
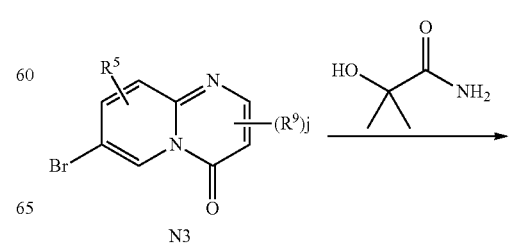

75
-continued
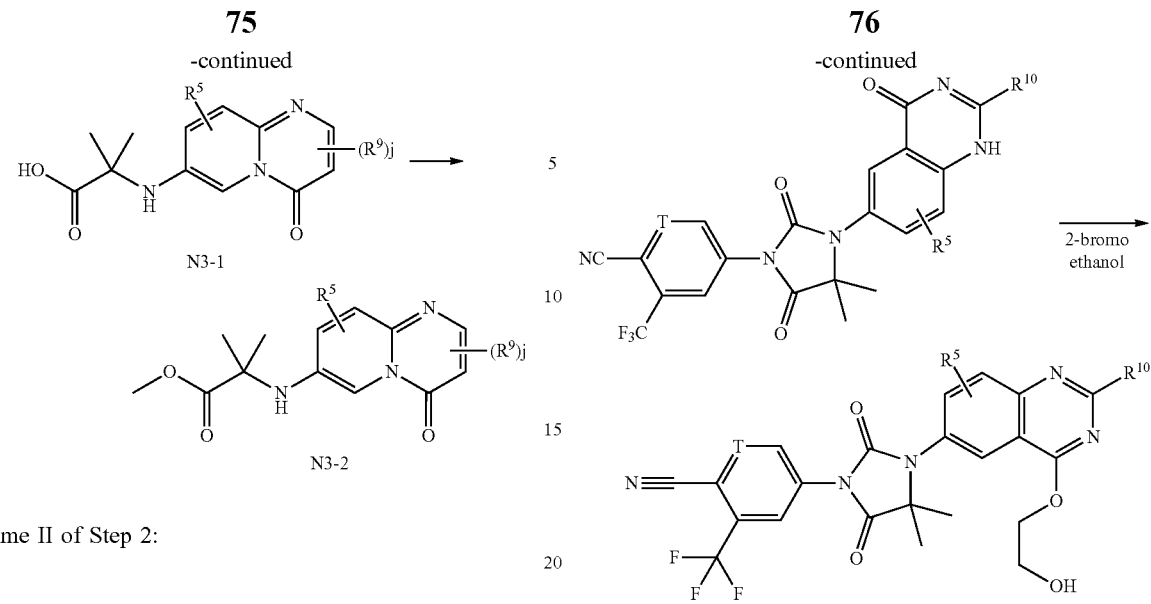
Scheme II of Step 2:
Preparation for the Target Compound (I)
Route I:
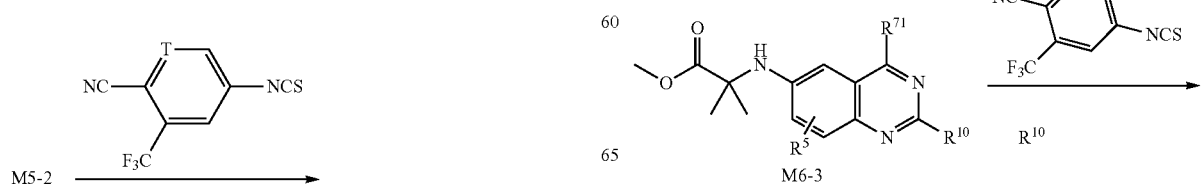
76
-continued
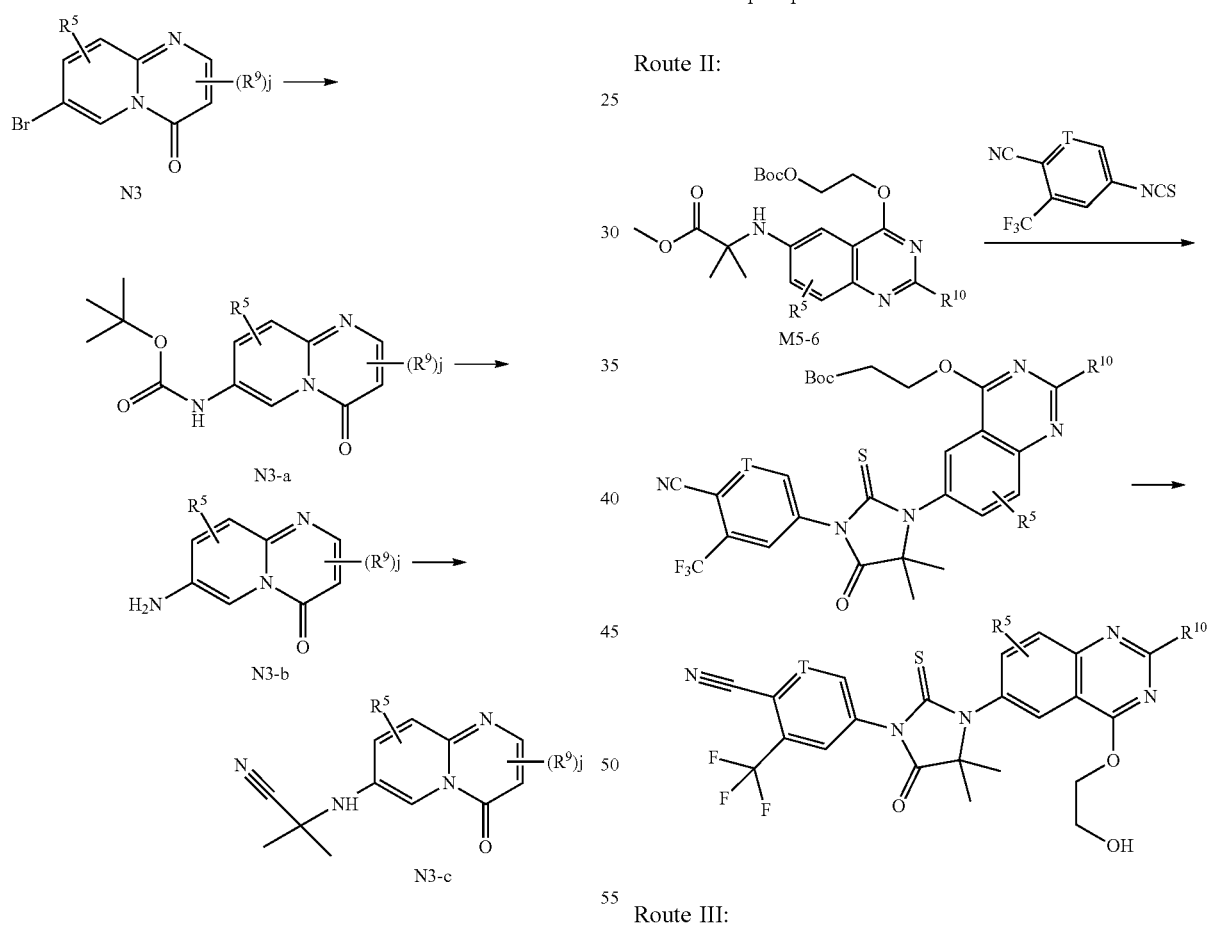
Route II:
Route III:

77
-continued
78
-continued
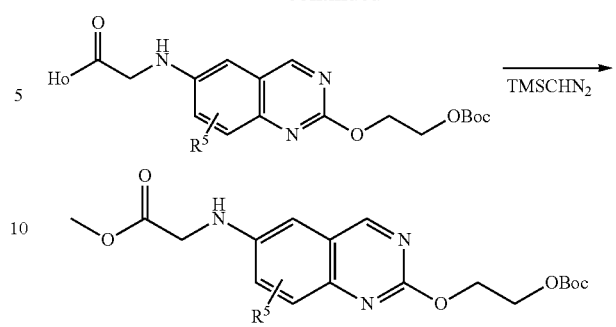
Route IV:
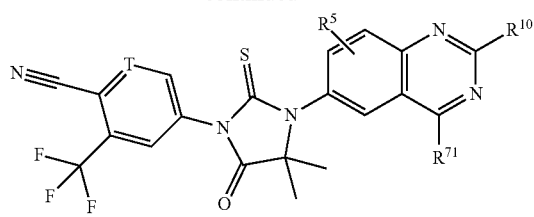
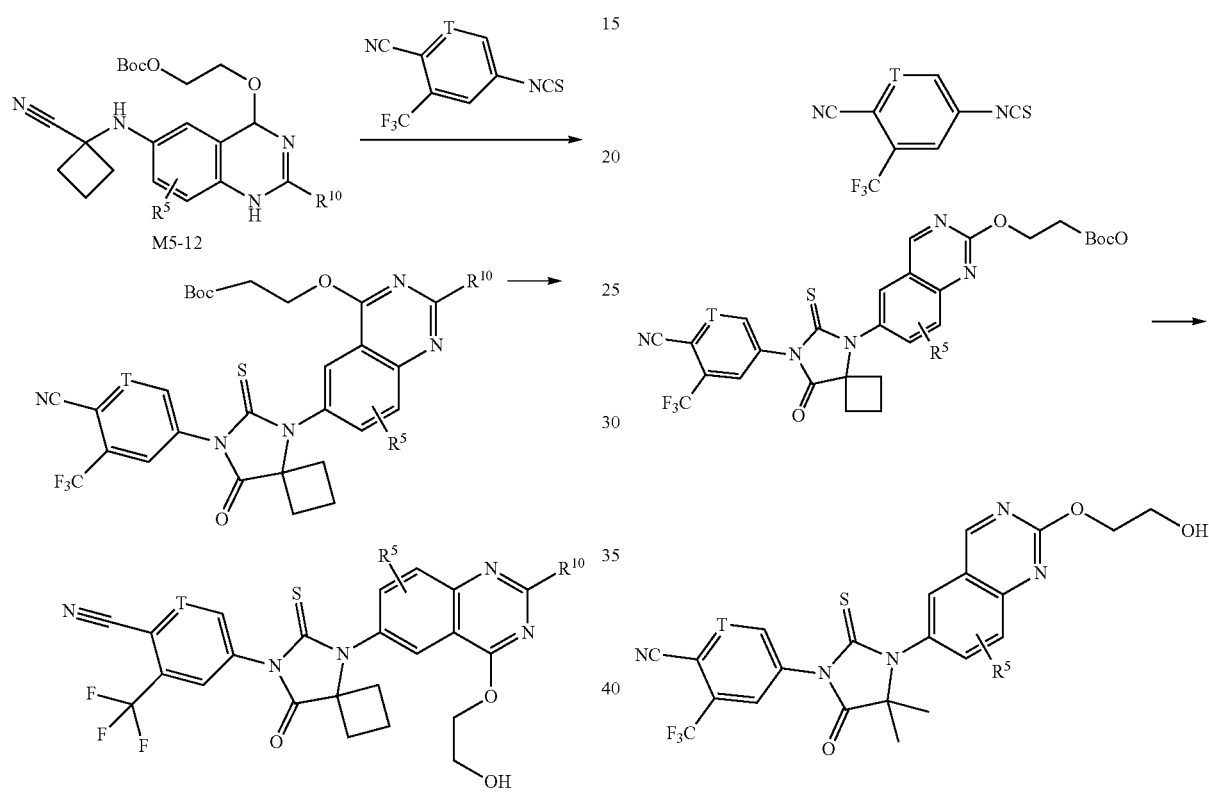
Route V:
Preparation for the Target Compound (II)
Route I:
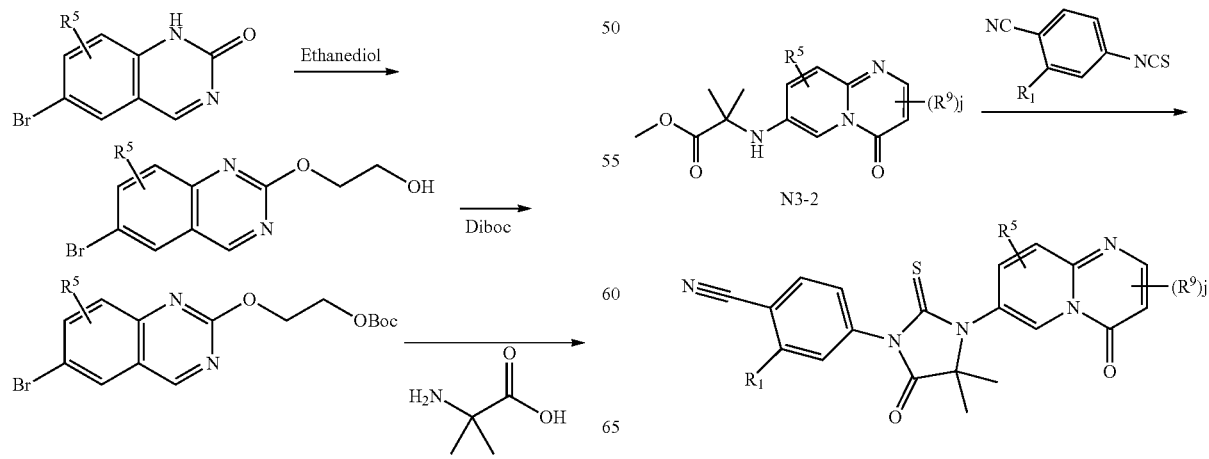

Route II:

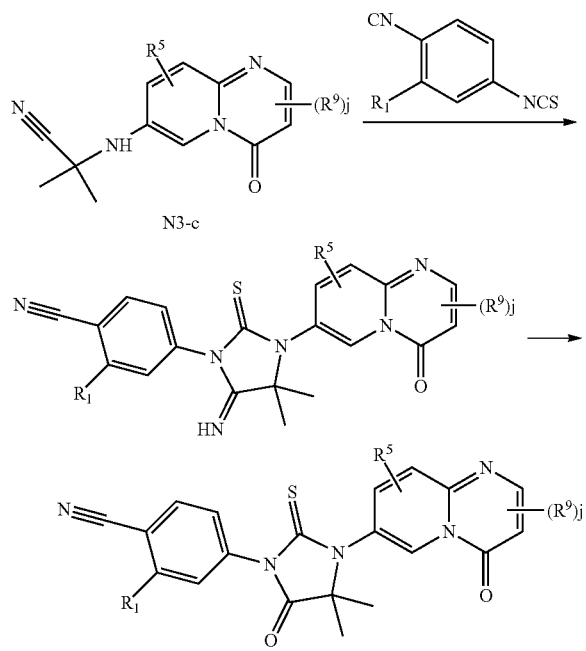

In the above routes, each $R^{71}$ is independently selected from the group consisting of hydroxyl and 5- to 10-membered heteroaryl, and the hydroxyl is optionally substituted by: —$C_{1-12}$ alkyl-(3- to 10-membered heterocycloalkyl), —$C_{1-12}$ alkyl-S(=O)$_2$ $R^c$, —$C_{1-12}$ alkyl-NR$^d$R$^e$, —$C_{1-12}$ alkyl-C(=O)NR$^f$R$^g$, —$C_{1-12}$ alkyl-(3- to 10-membered cycloalkyl) optionally substituted by halogen or hydroxyl, or 3- to 10-membered heterocycloalkyl optionally substituted by halogen or hydroxyl; or each $R^{71}$ is independently selected from hydroxyl, and the hydroxyl is optionally substituted by: heterocycloalkyl, -alkyl-S(=O)$_2$R$^c$, or -alkyl-NR$^d$R$^e$, wherein $R^c$, $R^d$ and $R^e$ are as defined in the present application; and $R^{10}$ is selected from the group consisting of $R^{72}$ and H, and j, T, $R^1$, $R^5$, $R^9$, and $R^{72}$ are as defined in the present application.

The following abbreviations are used in the present application:

DMF represents N,N-dimethylformamide, DMSO represents dimethyl sulfoxide, LCMS represents liquid chromatography-mass spectrometry, TLC represents thin layer chromatography, HPLC represents high performance liquid chromatography, Boc represents tert-butoxycarbonyl, TMSCHN$_2$ represents trimethylsilyldiazomethane, TMSCN represents trimethylsilyl cyanide, diBoc represents di-tert-butyl dicarbonate, NBS represents N-bromosuccinimide, CDI represents 1,1'-carbonyldiimidazole, Boc-NH$_2$ represents tert-butyl carbamate, Boc$_2$O represents di-tert-butyl dicarbonate, EDTA-K$_2$ represents dipotassium ethylenediamine tetraacetate, DAST represents diethylaminosulfur trifluoride, NMP represents 1-methyl-2-pyrrolidone, CMC represents carboxymethyl cellulose, HATU represents 2-(7-azabenzotriazol-1-yl)-N,N,N',N'-tetramethyluronium hexafluorophosphate; v/v represents a volume ratio; RLU represents a relative luminous intensity; Solutol represents polyethylene glycol-15 hydroxystearate; PEG400 represents polyethylene glycol 400; PO represents oral administration; QD represents the frequency of administration; PMB represents p-methoxybenzyl; and DPPF represents 1,1'-bis(diphenylphosphino)ferrocene.

Detailed Description of Embodiments

The present application will be described below in detail in conjunction with examples, but it is not intended to impose any unfavorable limitation to the present invention. The present application has been described in detail herein, and specific embodiments thereof are also disclosed. It will be apparent for those skilled in the art to make various modifications and improvements of the specific embodiments of the present application without departing from the spirit and scope of the present application. All solvents used in the present application are commercially available, and can be used without further purification. The starting compound materials used for synthesis in the present application are commercially available, or may be prepared by methods in the prior art.

The nuclear magnetic resonance chromatography (NMR) in the present application is determined by using BRUKER 400 nuclear magnetic resonance spectrometer with tetramethylsilane (TMS=δ 0.00) as the internal standard of the chemical shift. The nuclear magnetic resonance hydrogen spectrum data are recorded in the format of: peak pattern (s: singlet; d: doublet; t: triplet; q: quartet; m: multiplet), coupling constant (unit: Hertz Hz), and the number of protons. SHIMADUZU LCMS-2010 is used as the instrument for mass spectrometry.

Example 1 Synthesis of Compound 1

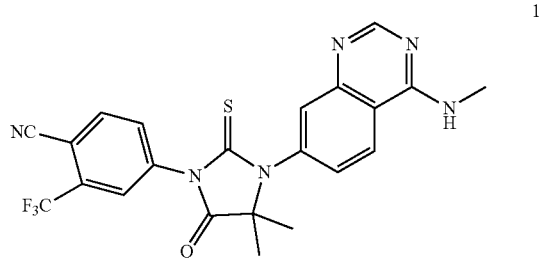 [SMILES: CNc1ncnc2cc(N3C(=S)N(c4ccc(C#N)c(C(F)(F)F)c4)C(=O)C3(C)C)ccc12]

1) Synthesis of Compound 1-2

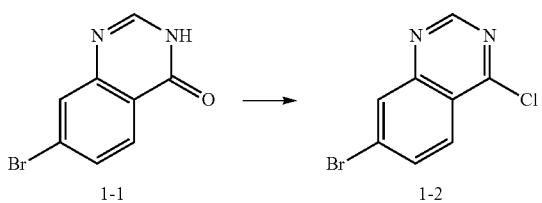 [SMILES: O=c1[nH]cnc2cc(Br)ccc12 ; Clc1ncnc2cc(Br)ccc12]

0.5 mL of dichlorosulfoxide was added dropwise to a solution of Compound 1-1 (300 mg, 1.33 mmol) in 5 mL of DMF. The reaction mixture was heated to 80° C., and stirred at this temperature for 6 h. The reaction mixture was spin-dried under reduced pressure. The resulting solid was dissolved in 30 mL of ethyl acetate, washed with 20 mL of water and 20 mL of saturated brine respectively, dried over anhydrous sodium sulfate, filtered, and concentrated, to obtain Compound 1-2. LCMS (ESI) m/z: 245 (M+3).

2) Synthesis of Compound 1-3

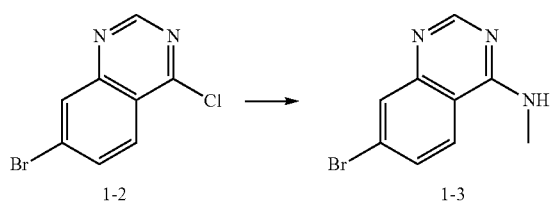

In a microwave tube, Compound 1-2 (150 mg, 616.04 μmol) and a solution of methylamine in ethanol (750 μL, 20-30% purity) were dissolved in tert-butanol (4 mL). The reaction mixture was kept at 90° C. for microwave reaction for 0.5 h, and then concentrated under reduced pressure. The resulting residue was dissolved in 20 mL of ethyl acetate, washed with 10 mL of water and 20 mL of saturated brine respectively, dried over anhydrous sodium sulfate, filtered, and concentrated, to obtain Compound 1-3. $^1$H NMR (400 MHz, CDCl$_3$) δ ppm 8.45 (s, 1H), 7.85 (d, J=3.2 Hz, 2H), 7.67 (s, 1H), 3.07 (s, 3H); LCMS (ESI) m/z: 240 (M+3).

3) Synthesis of Compound 1-5

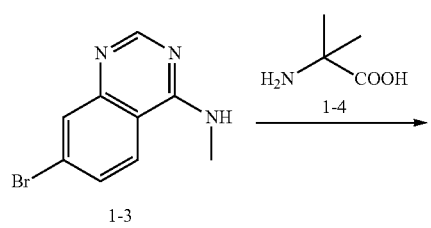

In a microwave tube, Compound 1-3 (250 mg, 961.86 μmol), Compound 1-4 (149 mg, 1.44 mmol), potassium carbonate (332 mg, 2.40 mmol), cuprous chloride (19 mg, 192.37 μmol) and 2-acetylcyclohexanone (27 mg, 192.37 μmol) were dissolved in a mixed solution of DMF (5 mL) and water (0.5 mL), and the resulting mixture was kept at 130° C. for microwave reaction for 1.5 h. The reaction mixture was cooled, and then filtered. 12 mL of water was added to the filtrate, and the resulting mixture was then extracted with ethyl acetate (20 mL×3), and the aqueous phase was concentrated under reduced pressure to obtain Compound 1-5. LCMS (ESI) m/z: 261 (M+1).

4) Synthesis of Compound 1-6

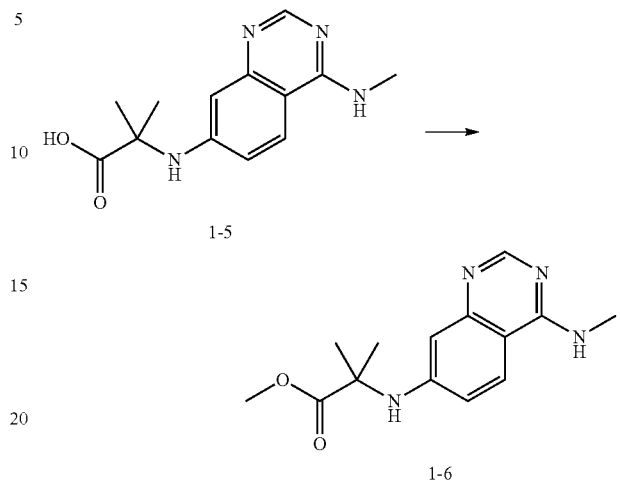

Dichlorosulfoxide (500 μL) was added dropwise to a solution of Compound 1-5 (300 mg, 1.15 mmol) in methanol (4 mL) in an ice bath. Then, the resulting mixture was heated to 26° C., and stirred at this temperature for 6 h. The reaction mixture was concentrated under reduced pressure, and 10 mL of water was added to the residue. The resulting mixture was extracted with ethyl acetate (15 mL×3), and the aqueous phase was adjusted to pH=10 with a saturated sodium bicarbonate solution. A brown solid precipitated, and was filtered. The filter cake was collected to obtain Compound 1-6. $^1$H NMR (400 MHz, CDCl$_3$) δ ppm 8.22 (s, 1H), 7.80-7.78 (dd, J=4.4, 8.8 Hz, 2H), 6.78-6.76 (d, J=9.2 Hz, 1H), 6.71 (s, 1H), 6.25 (s, 1H), 3.59 (s, 3H), 2.91 (s, 3H), 1.49 (s, 6H).

5) Synthesis of Compound 1

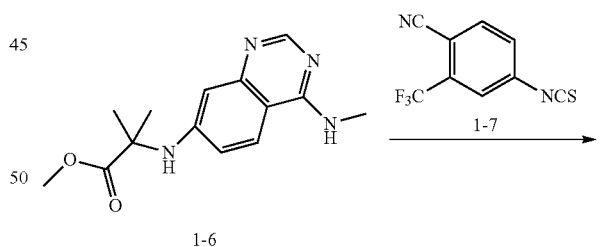

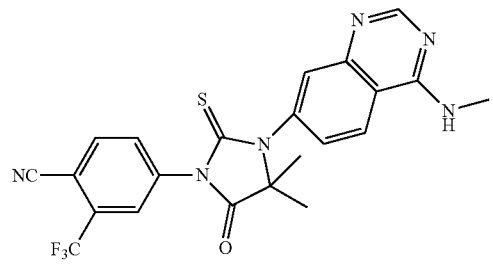

Compound 1-6 (150 mg, 546.81 μmol) and Compound 1-7 (250 mg, 1.09 mmol) were dissolved in a mixed solution of DMF (500 μL) and methylbenzene (2 mL), and the resulting mixture was heated to 90° C., and stirred at this temperature in a nitrogen atmosphere for 48 h. 3 mL of methanol was added dropwise to the reaction mixture, and the resulting mixture was stirred at room temperature for 0.5 h. Then, the reaction mixture was spin-dried under reduced pressure. The resulting solid was dissolved in 15 mL of ethyl acetate, then washed with 15 mL of water and 30 mL of saturated brine respectively, dried over anhydrous sodium sulfate, filtered, and spin-dried. The crude product was purified by a preparative TLC plate and preparative HPLC method to obtain Compound 1. $^1$H NMR (400 MHz, CDCl$_3$) δ ppm 8.76 (s, 1H), 8.02 (d, J=8 Hz, 2H), 7.83-7.91 (m, 3H), 7.44 (dd, J=2, 2.2 Hz, 1H), 5.89 (d, J=4.4 Hz, 1H), 3.27 (d, J=4.8 Hz, 3H), 1.70 (s, 6H); LCMS (ESI) m/z: 471 (M+1).

Example 2 Synthesis of Compound 2

1) Synthesis of Compound 2-2

Dichlorosulfoxide (1.96 g, 16.44 mmol) was added dropwise to a solution of Compound 2-1 (850 mg, 5.48 mmol) in methanol (10 mL) at 0° C. After the completion of the dropwise addition, the resulting mixture was stirred at 25° C. for 12 h. The reaction mixture was concentrated, and the resulting residue was basified with a saturated sodium bicarbonate solution (30 mL), and extracted with dichloromethane (20 mL×2). The combined organic phase was washed with water (50 mL), dried over anhydrous sodium sulfate, filtered, and concentrated to obtain Compound 2-2. LCMS (ESI) m/z: 170 (M+1).

2) Synthesis of Compound 2-4

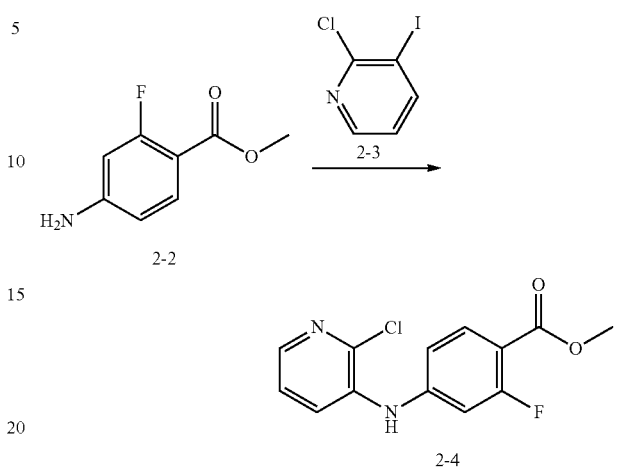

Compound 2-2 (300 mg, 1.77 mmol), Compound 2-3 (637 mg, 2.66 mmol), 4,5-bis(diphenylphosphino)-9,9-dimethylxanthene (103 mg, 177.36 μmol), bis(dibenzylideneacetone) palladium (102 mg, 177.36 μmol), and cesium carbonate (1.16 g, 3.55 mmol) were added to a microwave tube filled with methylbenzene (5 mL). Then, the resulting mixture was kept at 120° C. for microwave reaction for 2 h. The reaction mixture was diluted with dichloromethane (5 mL), and filtered. The filtrate was concentrated. The resulting crude product was purified by a chromatographic column to obtain Compound 2-4. LCMS (ESI) m/z: 281 (M+1).

3) Synthesis of Compound 2-6

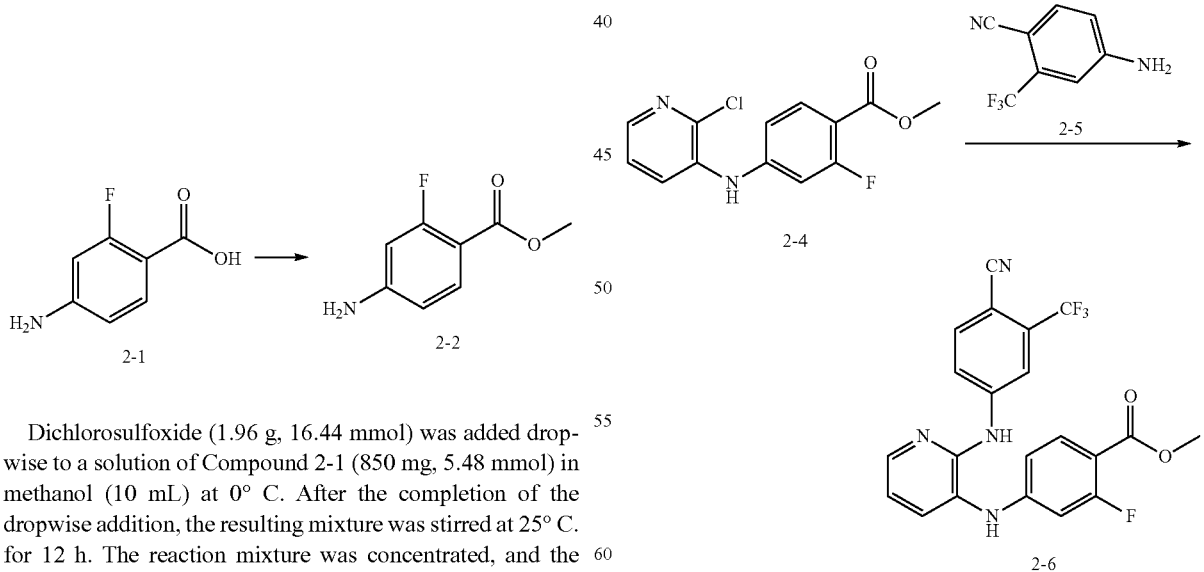

Compound 2-4 (200 mg, 712.56 μmol), Compound 2-5 (159 mg, 855.07 μmol), 4,5-bis(diphenylphosphino)-9,9-dimethylxanthene (41 mg, 71.26 μmol), cesium carbonate (464 mg, 1.43 mmol), and bis(dibenzylideneacetone)palladium (41 mg, 71.26 μmol) were added to a microwave tube filled with methylbenzene (5 mL). Then, the resulting mixture was kept at 120° C. for microwave reaction for 2 h. The reaction mixture was diluted with dichloromethane (20 mL), and filtered. The filtrate was concentrated. The resulting crude product was purified by a preparative chromatoplate to obtain Compound 2-6. LCMS (ESI) m/z: 431 (M+1).

4) Synthesis of Compound 2-7

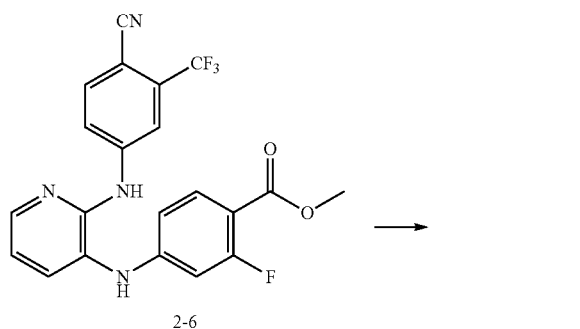

Thiophosgene (107 mg, 929.48 µmol) was added dropwise to a solution of Compound 2-6 (200 mg, 464.74 µmol) and sodium tert-butoxide (223 mg, 2.32 mmol) in tetrahydrofuran (2 mL) at 0° C. After the completion of the dropwise addition, the resulting mixture was stirred at 60° C. for 12 h. The reaction mixture was cooled to 20° C. and then water (10 mL) was added to quench the reaction. The resulting mixture was diluted with dichloromethane (10 mL), and extracted with dichloromethane (10 mL×2). The combined organic phase was washed with saturated brine (20 mL), dried over anhydrous sodium sulfate, filtered, and concentrated. The resulting crude product was purified by a preparative chromatoplate to obtain Compound 2-7. LCMS (ESI) m/z: 473 (M+1).

5) Synthesis of Compound 2-8

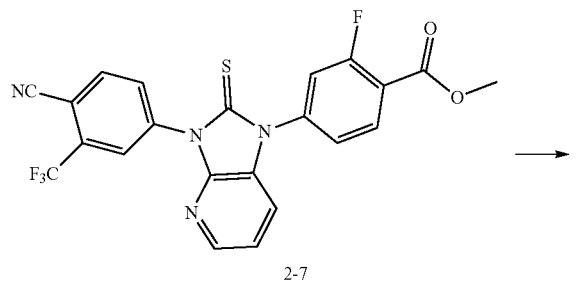

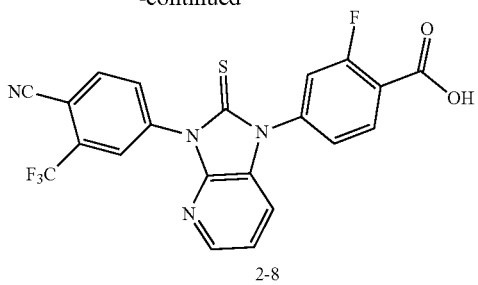

An aqueous solution of lithium hydroxide (1 M, 1 mL) was added dropwise to a solution of Compound 2-7 (40 mg, 84.67 µmol) in tetrahydrofuran (4 mL) at room temperature (20° C.). After the completion of the dropwise addition, the resulting mixture was heated to 80° C., and stirred for 2 h. The reaction mixture was acidified to pH=5-6 with 1M dilute hydrochloric acid, and extracted with dichloromethane (10 mL×3). The combined organic phase was washed with saturated brine (20 mL), dried over anhydrous sodium sulfate, filtered, and concentrated to obtain Compound 2-8. LCMS (ESI) m/z: 459 (M+1).

6) Synthesis of Compound 2

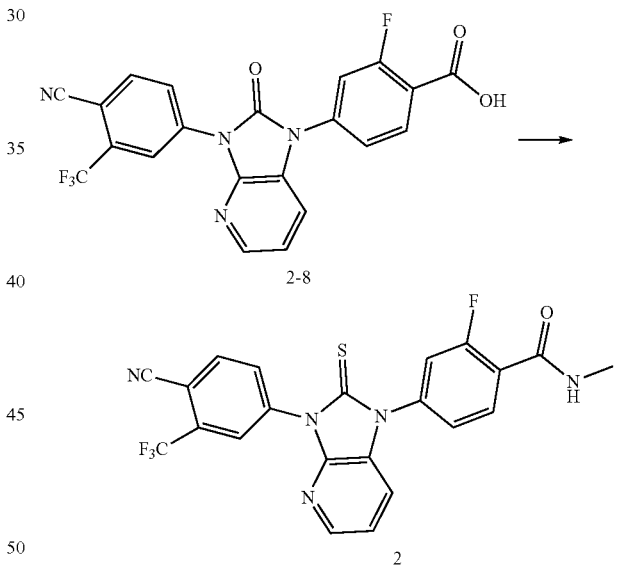

At room temperature (20° C.), methylamine hydrochloride (5 mg, 78.54 µmol), triethylamine (20 mg, 196.35 µmol), and O-(7-azabenzotriazol-1-yl)-N,N,N',N'-tetramethyluronium hexafluorophosphate (30 mg, 78.54 µmol) were added to a solution of Compound 2-8 (30 mg, 65.45 µmol) in dichloromethane (2 mL). The resulting mixture was stirred at 20° C. for 1 h. Water (10 mL) was added to the reaction mixture, and then the resulting mixture was diluted with dichloromethane (10 mL), and extracted with dichloromethane (10 mL×2). The combined organic phase was washed with saturated brine (20 mL), dried over anhydrous sodium sulfate, filtered, and concentrated. The resulting crude product was purified by a preparative TLC plate and preparative HPLC method to obtain Compound 2. $^1$H NMR (400 MHz, CDCl$_3$) δ ppm 8.40-8.38 (m, 1H), 8.27-8.24 (m, 2H), 8.18-8.16 (m, 1H), 8.10-8.09 (m, 1H), 7.53-7.49 (m, 2H), 7.38-7.36 (m, 1H), 7.28-7.27 (m, 1H), 3.11 (d, J=4.8 Hz, 3H); LCMS (ESI) m/z: 472 (M+1).

Example 3 Synthesis of Compound 3

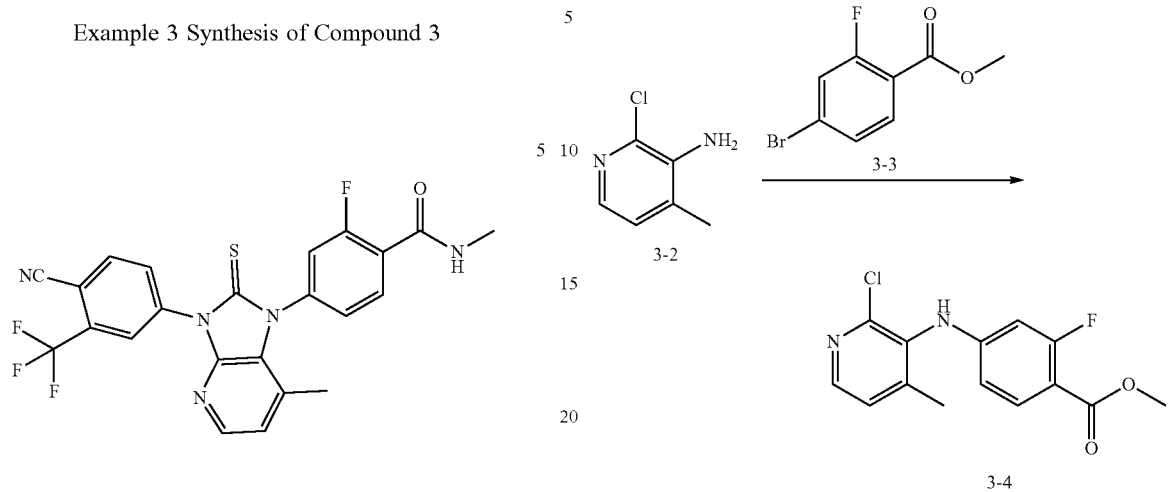

1) Synthesis of Compound 3-2

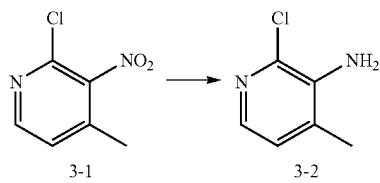

Zinc powder (3.98 g, 60.84 mmol) and ammonium chloride (3.25 g, 60.84 mmol) were added to a solution of Compound 3-1 (2.10 g, 12.17 mmol) in methanol (20 mL) and dichloromethane (10 mL). The resulting reaction mixture was stirred at 15° C. for 24 h. The reaction mixture was filtered, and the filter cake was washed with dichloromethane (40 mL). The resulting filtrate was concentrated under reduced pressure to obtain Compound 3-2. LCMS (ESI) m/z: 143 (M+1).

2) Synthesis of Compound 3-3

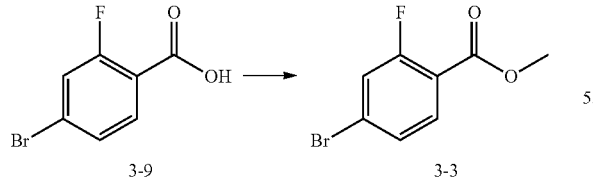

Dichlorosulfoxide (13.12 g, 110.31 mmol) was added to a solution of Compound 3-9 (4.00 g, 18.26 mmol) in anhydrous methanol (40 mL) at 0° C. The resulting reaction mixture was stirred at 15° C. for 16 h. The reaction mixture was concentrated under reduced pressure, and the residue obtained from the concentration was purified by a silica gel column to obtain Compound 3-3.

3) Synthesis of Compound 3-4

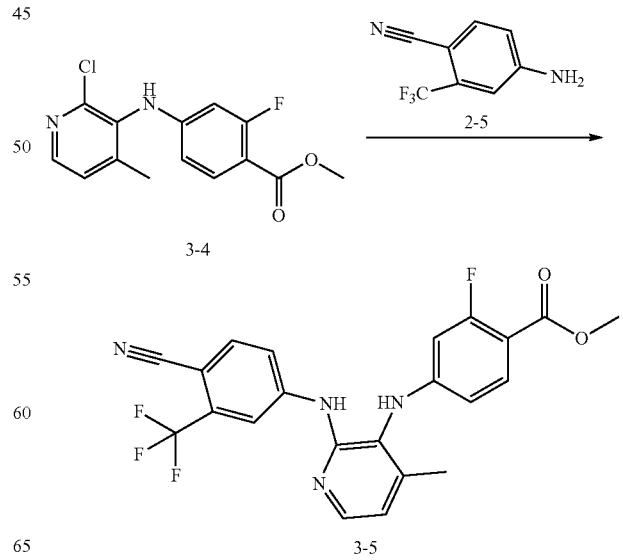

A mixture of Compound 3-3 (1.08 g, 4.63 mmol), Compound 3-2 (600 mg, 4.21 mmol), bis(dibenzylideneacetone) palladium (242 mg, 420.79 μmol), 4,5-bis(diphenylphosphino)-9,9-dimethylxanthene (244 mg, 420.79 μmol), cesium carbonate (2.74 g, 8.42 mmol), and methylbenzene (15 mL) was added to a microwave tube. The microwave tube was sealed, and then heated to 130° C. for microwave reaction for 2 h. The reaction mixture was filtered and concentrated under reduced pressure. The residue obtained from the concentration was purified by a silica gel column to obtain Compound 3-4. $^1$H NMR (400 MHz, CDCl$_3$) δ ppm 8.23 (d, J=5.0 Hz, 1H), 7.85 (t, J=8.4 Hz, 1H), 7.22 (d, J=5.0 Hz, 1H), 6.42 (dd, J=2.3, 8.5 Hz, 1H), 6.21 (dd, J=2.3, 12.8 Hz, 1H), 5.94 (s, 1H), 3.90 (s, 3H), 2.28 (s, 3H); LCMS (ESI) m/z: 295 (M+1).

4) Synthesis of Compound 3-5

Compound 3-4 (500 mg, 1.70 mmol), Compound 2-5 (348 mg, 1.87 mmol), bis(dibenzylideneacetone)palladium (98 mg, 170.00 μmol), 4,5-bis(diphenylphosphino)-9,9-dimethylxanthene (98 mg, 170.00 μmol), cesium carbonate (1.11 g, 3.40 mmol), and methylbenzene (8 mL) were added to a microwave tube. The microwave tube was sealed, and then heated to 130° C. for microwave reaction for 2 h. The reaction mixture was filtered and concentrated under reduced pressure. The residue obtained from the concentration was purified by a silica gel column to obtain Compound 3-5. LCMS (ESI) m/z: 445 (M+1).

5) Synthesis of Compound 3-6

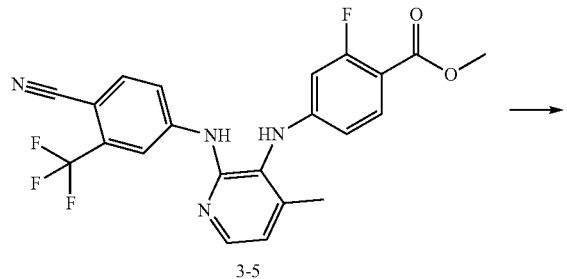

3-5

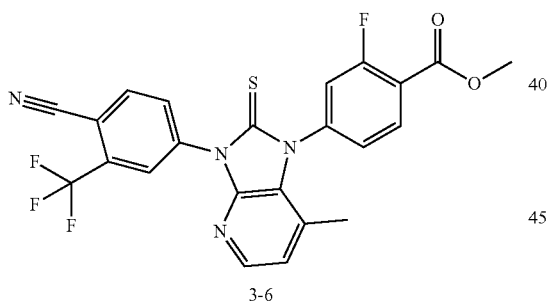

3-6

Potassium tert-butoxide (216 mg, 2.25 mmol) and thiophosgene (104 mg, 900.12 μmol) were added to a solution of Compound 3-5 (100 mg, 225.03 μmol) in tetrahydrofuran (2 mL) and methylbenzene (2 mL). The resulting reaction mixture was heated to 100° C., and stirred for 16 h. Ethyl acetate (20 mL) and water (20 mL) were added to the reaction mixture for liquid separation. The organic phase was washed with saturated brine (20 mL), dried over anhydrous sodium sulfate, filtered, and concentrated under reduced pressure. The residue obtained from the concentration was purified by a preparative TLC plate to obtain Compound 3-6. $^1$H NMR (400 MHz, CDCl$_3$) δ ppm 8.27 (d, J=1.5 Hz, 1H), 8.21 (t, J=7.9 Hz, 1H), 8.17-8.10 (m, 2H), 8.09-8.04 (m, 1H), 7.43-7.32 (m, 2H), 7.02 (d, J=5.0 Hz, 1H), 4.01 (s, 3H), 1.98 (s, 3H); LCMS (ESI) m/z: 487 (M+1)

6) Synthesis of Compound 3-7

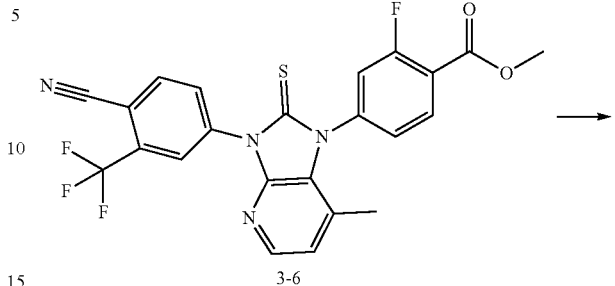

3-6

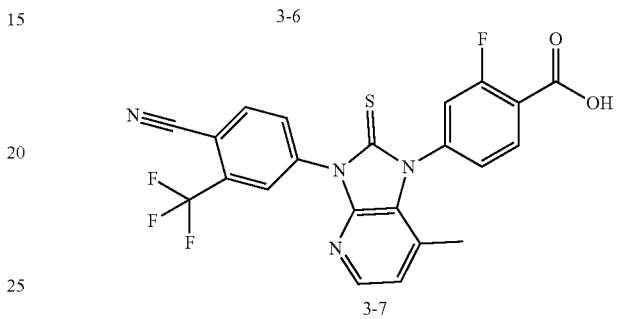

3-7

Lithium hydroxide (9 mg, 205.58 μmol) was added to a solution of Compound 3-6 (50 mg, 102.79 μmol) in tetrahydrofuran (1.2 mL) and water (0.3 mL). The resulting reaction mixture was stirred at 5° C. for 16 h. 1M hydrochloric acid solution (10 mL) and ethyl acetate (20 mL) were added to the reaction mixture for liquid separation. The organic phase was washed with saturated brine (15 mL), dried over anhydrous sodium sulfate, filtered, and concentrated under reduced pressure to obtain the target compound 3-7. LCMS (ESI) m/z: 473 (M+1).

7) Synthesis of Compound 3

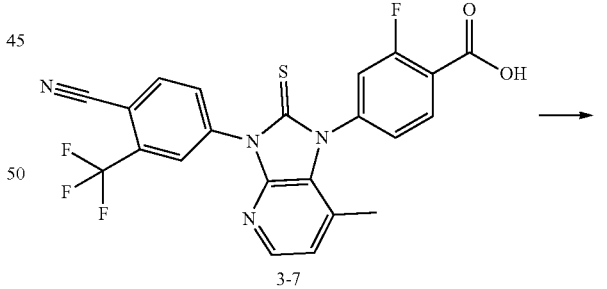

3-7

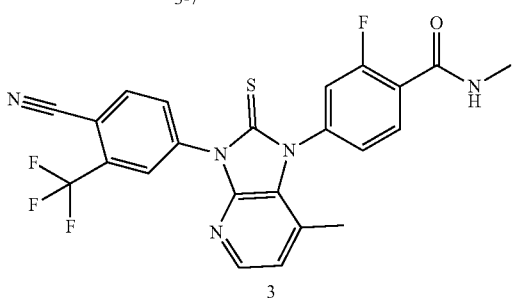

3

O-(7-azabenzotriazol-1-yl)-N,N,N',N'-tetramethyluronium hexafluorophosphate (39 mg, 101.60 μmol), triethylamine (26 mg, 254.01 μmol), and methylamine hydrochloride (9 mg, 127.01 μmol) were added to a solution of Compound 3-7 (40 mg, 84.67 μmol) in dichloromethane (1 mL). The resulting reaction mixture was stirred at 5° C. for 16 h. Dichloromethane (15 mL) and water (10 mL) were added to the reaction mixture for liquid separation. The organic phase was washed with saturated brine (10 mL), dried over anhydrous sodium sulfate, filtered, and concentrated under reduced pressure. The residue obtained from the concentration was purified by preparative HPLC to obtain the Compound 3. $^1$H NMR (400 MHz, CDCl$_3$) δ ppm 8.37 (t, J=8.3 Hz, 1H), 8.27 (s, 1H), 8.18-8.10 (m, 2H), 8.10-8.04 (m, 1H), 7.45-7.33 (m, 2H), 7.01 (d, J=5.0 Hz, 1H), 6.76 (br s, 1H), 3.10 (d, J=4.5 Hz, 3H), 1.97 (s, 3H); LCMS (ESI) m/z: 486 (M+1).

Example 4 Synthesis of Compound 4

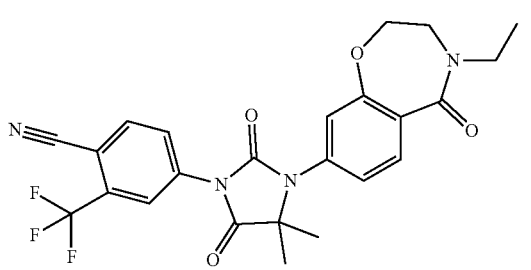

1) Synthesis of Compound 4-2

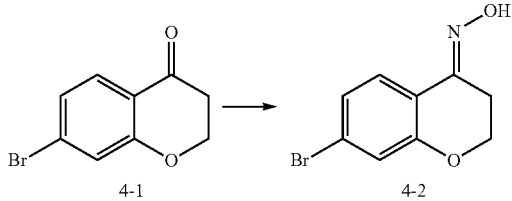 [SMILES: O=C1CCOc2cc(Br)ccc21 ; O/N=C1\CCOc2cc(Br)ccc21]

Triethylamine (1.34 g, 13.22 mmol) and hydroxylamine hydrochloride (918 mg, 13.22 mmol) were added to a solution of Compound 4-1 (2.00 g, 8.81 mmol) in methanol (30 mL). The resulting reaction mixture was stirred at 10° C. for 16 h, heated to 30° C. and stirred for 16 h. The reaction mixture was concentrated under reduced pressure, and then ethyl acetate (50 mL) and water (40 mL) were added. The organic phase was washed with saturated brine (40 mL), dried over anhydrous sodium sulfate, and concentrated under reduced pressure to obtain Compound 4-2. LCMS (ESI) m/z: 242 (M+1).

2) Synthesis of Compound 4-3

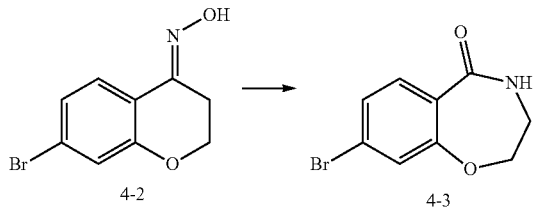 [SMILES: O/N=C1\CCOc2cc(Br)ccc21 ; O=C1NCCOc2cc(Br)ccc21]

A mixture of Compound 4-2 (2.00 g, 8.26 mmol) and polyphosphoric acid (20 mL) was heated to 95° C. and stirred for 3 h. 150 mL of water was added to the reaction mixture, and then the resulting mixture was stirred for 30 min, and extracted with ethyl acetate (100 mL×3). The organic phase was washed with saturated brine (150 mL), dried over anhydrous sodium sulfate, and concentrated under reduced pressure. The residue obtained from the concentration was purified by a preparative TLC plate to obtain Compound 4-3. LCMS (ESI) m/z: 242 (M+1).

3) Synthesis of Compound 4-4

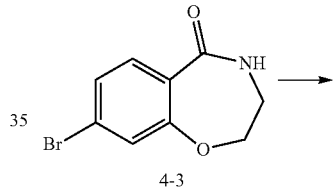

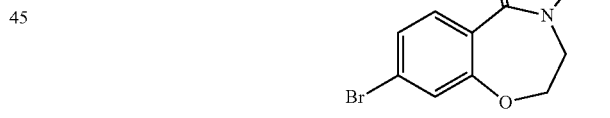

60% Sodium hydride (50 mg, 1.25 mmol) was added to a solution of Compound 4-3 (200 mg, 826.21 μmol) in DMF (4 mL), and the resulting mixture was stirred at 10° C. for 10 min. Then, iodoethane (155 mg, 993.78 μmol) was added. The resulting reaction mixture was stirred at 10° C. for 30 min. The reaction mixture was slowly poured into water (30 mL), and extracted with ethyl acetate (20 mL×3). The organic phase was washed with saturated brine (40 mL), dried over anhydrous sodium sulfate, and concentrated under reduced pressure. The residue obtained from the concentration was purified by preparative TLC to obtain Compound 4-4. $^1$H NMR (400 MHz, CDCl$_3$) δ ppm 7.70 (d, J=8.3 Hz, 1H), 7.26 (dd, J=1.8, 8.3 Hz, 1H), 7.16 (d, J=1.8 Hz, 1H), 4.38 (t, J=5.0 Hz, 2H), 3.64 (q, J=7.3 Hz, 2H), 3.50 (t, J=5.0 Hz, 2H), 1.23 (t, J=7.2 Hz, 3H).

4) Synthesis of Compound 4-5

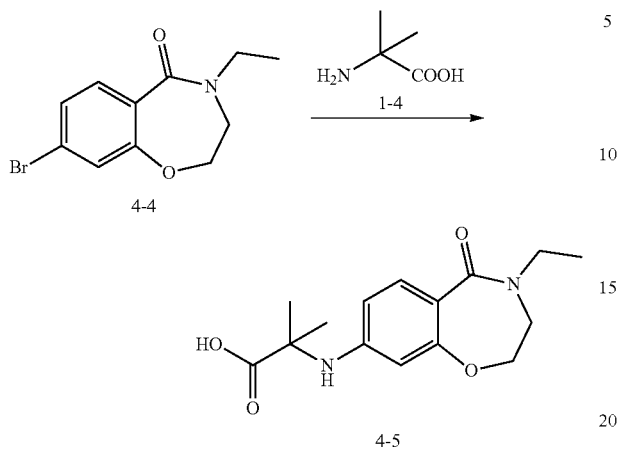

A turbid liquid of Compound 4-4 (100 mg, 370.21 µmol), Compound 1-4 (57 mg, 555.32 µmol), cuprous chloride (7 mg, 74.04 µmol), 2-acetylcyclohexanone (10 mg, 74.04 µmol), and potassium carbonate (128 mg, 925.53 µmol) in DMF (1.5 mL) and water (0.08 mL) was added to a microwave tube, and kept at 130° C. for microwave reaction for 1 h. The reaction mixture was filtered through Celite, washed with ethyl acetate (5 mL), and concentrated under reduced pressure. The residue obtained from the concentration was dissolved in water (10 mL), and extracted with ethyl acetate (5 mL). Concentrated hydrochloric acid (0.5 mL) was added to the aqueous phase, and the resulting turbid aqueous solution was concentrated under reduced pressure. The residue obtained from the concentration was slurried with dichloromethane/methanol (10/1, 20 mL), and filtered. The filtrate was concentrated under reduced pressure to obtain Compound 4-5. LCMS (ESI) m/z: 293 (M+1).

5) Synthesis of Compound 4-6

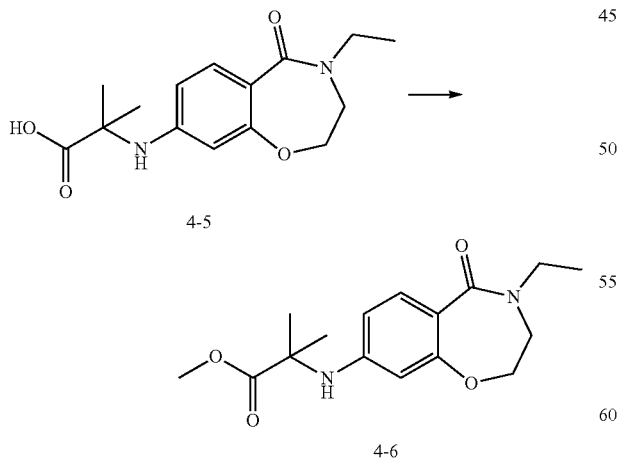

Dichlorosulfoxide (407 mg, 3.42 mmol) was carefully added dropwise (exothermic) to a turbid liquid of Compound 4-5 (100 mg, 342.08 µmol) in methanol (4 mL). The resulting yellow clear solution was stirred at 40° C. for 16 h. The reaction mixture was concentrated under reduced pressure. The residue obtained from the concentration was purified by a preparative TLC plate to obtain Compound 4-6. LCMS (ESI) m/z: 307 (M+1).

6) Synthesis of Compound 4

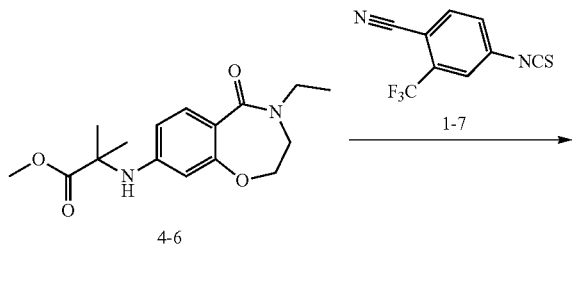

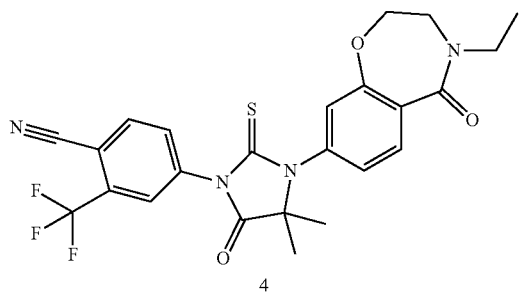

Compound 1-7 (186 mg, 816.05 µmol) was added to a solution of Compound 4-6 (50 mg, 163.21 µmol) in methylbenzene (1 mL) and DMF (0.02 mL). The resulting reaction mixture was heated to 100° C., and stirred for 24 h. Methanol (2 mL) was added to the reaction mixture, and the resulting mixture was stirred for 5 min, and then concentrated under reduced pressure. The residue obtained from the concentration was purified by a preparative TLC plate, and then purified by preparative HPLC to obtain Compound 4. $^1$H NMR (400 MHz, CDCl$_3$) δ ppm 7.98 (d, J=8.3 Hz, 1H), 7.95-7.84 (m, 2H), 7.77 (dd, J=1.9, 8.2 Hz, 1H), 7.01 (dd, J=2.0, 8.5 Hz, 1H), 6.89 (d, J=2.0 Hz, 1H), 4.40 (t, J=4.8 Hz, 2H), 3.62 (q, J=7.2 Hz, 2H), 3.56 (t, J=4.9 Hz, 2H), 1.52 (s, 6H), 1.20 (t, J=7.2 Hz, 3H); LCMS (ESI) m/z: 503 (M+1).

Example 5 Synthesis of Compound 5

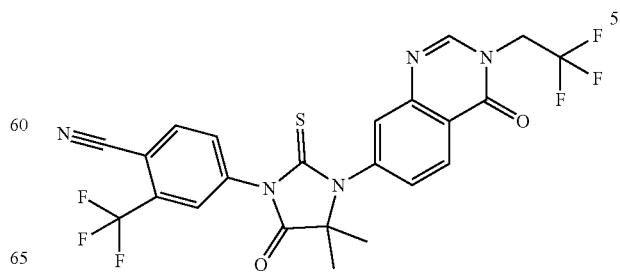

1) Synthesis of Compound 5-1

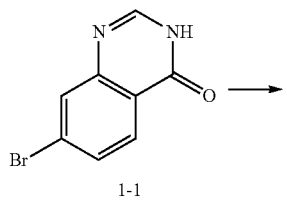

1-1

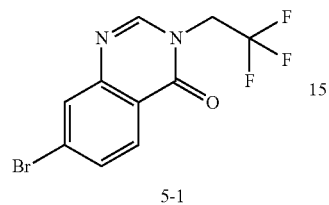

5-1

Cesium carbonate (869 mg, 2.66 mmol) and 1,1,1-trifluoro-2-iodoethane (933 mg, 4.44 mmol) were added to a solution of Compound 1-1 (500 mg, 2.22 mmol) in DMF (10 mL). The resulting reaction mixture was stirred at 100° C. for 16 h. The reaction mixture was cooled, and then filtered to remove cesium carbonate. The filtrate was poured into water (40 mL), and extracted with ethyl acetate (30 mL×3). The organic phase was washed with saturated brine (50 mL), dried over anhydrous sodium sulfate, and concentrated under reduced pressure. The residue obtained from the concentration was slurried with petroleum ether/ethyl acetate (10 mL, 10/1), and filtered to obtain Compound 5-1. $^{1}$H NMR (400 MHz, CDCl$_3$) δ ppm 8.11 (d, J=8.5 Hz, 1H), 7.96 (s, 1H), 7.85 (d, J=1.8 Hz, 1H), 7.60 (dd, J=1.8, 8.5 Hz, 1H), 4.59 (q, J=8.4 Hz, 2H).

2) Synthesis of Compound 5-2

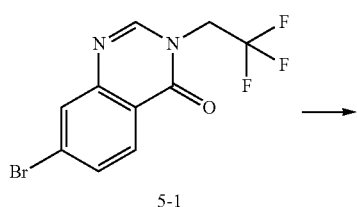

5-1

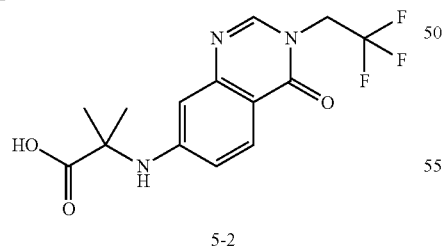

5-2

A turbid liquid of Compound 5-1 (300 mg, 976.98 μmol), Compound 1-4 (151 mg, 1.47 mmol), cuprous chloride (19 mg, 195.40 μmol), 2-acetylcyclohexanone (27 mg, 195.40 μmol), and potassium carbonate (338 mg, 2.44 mmol) in DMF (3 mL) and water (0.15 mL) was added to a microwave tube, and kept at 130° C. for microwave reaction for 1 h. The reaction mixture was filtered through Celite, washed with ethyl acetate (10 mL), and concentrated under reduced pressure. The residue obtained from the concentration was dissolved in water (30 mL), and extracted with ethyl acetate (5 mL). Concentrated hydrochloric acid (1 mL) was added to the aqueous phase, and the resulting turbid aqueous solution was concentrated under reduced pressure. The residue obtained from the concentration was slurried with dichloromethane/methanol (10/1, 20 mL), and filtered. The filtrate was concentrated under reduced pressure to obtain Compound 5-2. LCMS (ESI) m/z: 330 (M+1).

3) Synthesis of Compound 5-3

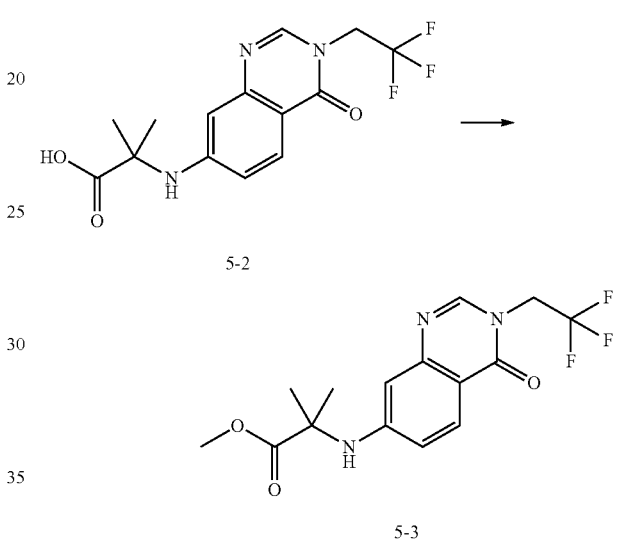

Dichlorosulfoxide (1.15 g, 9.65 mmol, 0.7 mL) was carefully added dropwise (exothermic) to a turbid liquid of Compound 5-2 (500 mg, 945.42 μmol) in methanol (5 mL). The resulting yellow clear solution was stirred at 40° C. for 16 h. The reaction mixture was concentrated under reduced pressure. The residue obtained from the concentration was purified by a preparative TLC plate to obtain Compound 5-3. LCMS (ESI) m/z: 344 (M+1).

4) Synthesis of Compound 5

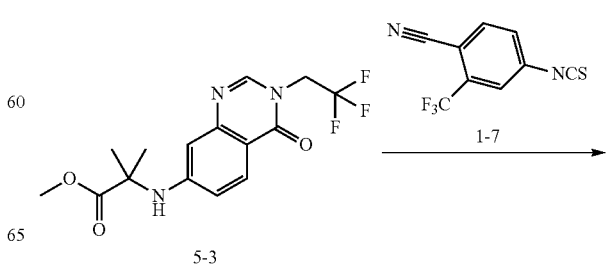

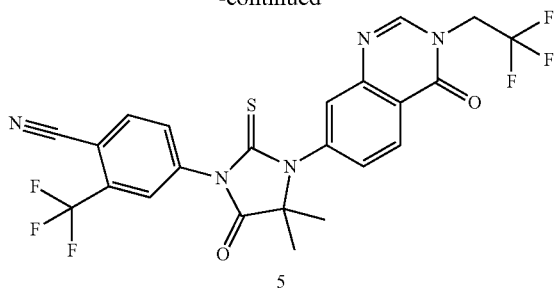

5

Compound 1-7 (166 mg, 728.25 μmol) was added to a solution of Compound 5-3 (50 mg, 145.65 μmol) in methylbenzene (1 mL) and DMF (0.05 mL). The resulting reaction mixture was heated to 120° C., and stirred for 48 h. Methanol (2 mL) was added to the reaction mixture, and the resulting mixture was stirred for 5 min, and then concentrated under reduced pressure. The residue obtained from the concentration was purified by preparative HPLC to obtain Compound 5. $^1$H NMR (400 MHz, CDCl$_3$) δ ppm 8.42 (d, J=8.5 Hz, 1H), 8.03 (s, 1H), 7.95-7.89 (m, 2H), 7.79 (dd, J=2.0, 8.3 Hz, 1H), 7.65 (d, J=1.8 Hz, 1H), 7.43 (dd, J=2.0, 8.5 Hz, 1H), 4.64 (q, J=8.3 Hz, 2H), 1.58 (s, 6H); LCMS (ESI) m/z: 540 (M+1).

Example 6 Synthesis of Compound 6

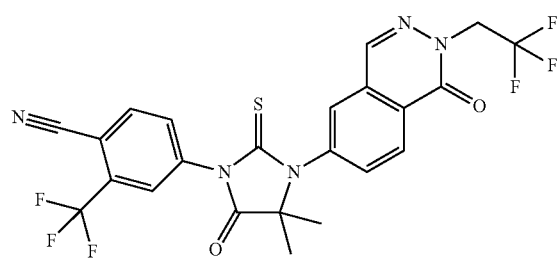

6

1) Synthesis of Compound 6-2

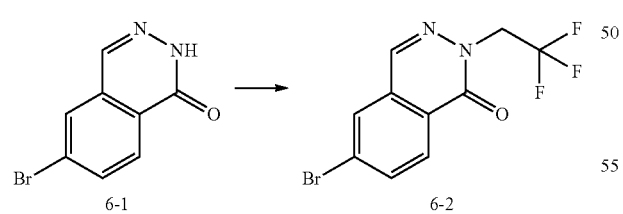

1,1,1-Trifluoro-2-iodoethane (933 mg, 4.44 mmol) was added to a solution of Compound 6-1 (500 mg, 2.22 mmol) and cesium carbonate (869 mg, 2.66 mmol) in DMF (8 mL). The reaction mixture was stirred at 100° C. for 16 h. The reaction mixture was cooled, and then filtered to remove cesium carbonate. The filtrate was poured into water (10 mL), and extracted with ethyl acetate (10 mL×3). The organic phase was washed with saturated brine (15 mL), dried over anhydrous sodium sulfate, and concentrated under reduced pressure. The residue obtained from the concentration was slurried with petroleum ether/ethyl acetate (10 mL, 10/1), and filtered to obtain Compound 6-2. $^1$H NMR (400 MHz, CDCl$_3$) δ ppm 8.32 (d, J=8.3 Hz, 1H), 8.14 (s, 1H), 7.95-7.89 (m, 2H), 4.87 (q, J=8.3 Hz, 2H).

2) Synthesis of Compound 6-3

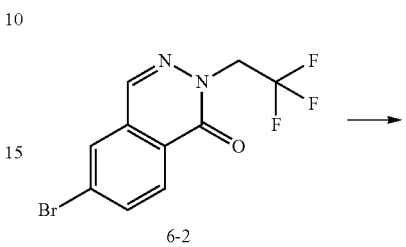

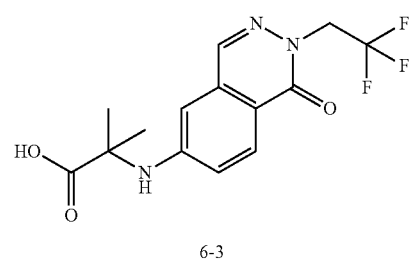

A turbid liquid of Compound 6-2 (300 mg, 976.98 μmol), Compound 1-4 (151 mg, 1.47 mmol), cuprous chloride (19 mg, 195.40 μmol), 2-acetylcyclohexanone (27 mg, 195.40 μmol), and potassium carbonate (338 mg, 2.44 mmol) in DMF (3 mL) and water (0.15 mL) was added to a microwave tube, and kept at 130° C. for microwave reaction for 1 h. The reaction mixture was filtered through Celite, washed with ethyl acetate (10 mL), and concentrated under reduced pressure. The residue obtained from the concentration was dissolved in water (10 mL), and extracted with ethyl acetate (5 mL). Concentrated hydrochloric acid (0.5 mL) was added to the aqueous phase, and the resulting turbid aqueous solution was concentrated under reduced pressure. The residue obtained from the concentration was slurried with dichloromethane/methanol (10/1, 40 mL), and filtered. The filtrate was concentrated under reduced pressure to obtain Compound 6-3. LCMS (ESI) m/z: 330 (M+1).

3) Synthesis of Compound 6-4

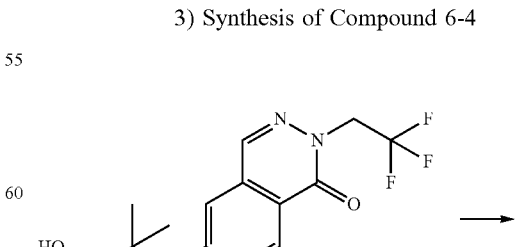

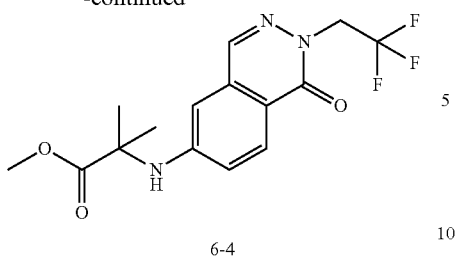

6-4

Dichlorosulfoxide (1.31 g, 11.03 mmol, 0.8 mL) was carefully added dropwise (exothermic) to a turbid liquid of Compound 6-3 (500 mg, 1.17 mmol) in methanol (5 mL). The resulting yellow clear solution was stirred at 40° C. for 16 h. The reaction mixture was concentrated under reduced pressure. The residue obtained from the concentration was purified by a preparative TLC plate to obtain Compound 6-4. LCMS (ESI) m/z: 344 (M+1).

4) Synthesis of Compound 6

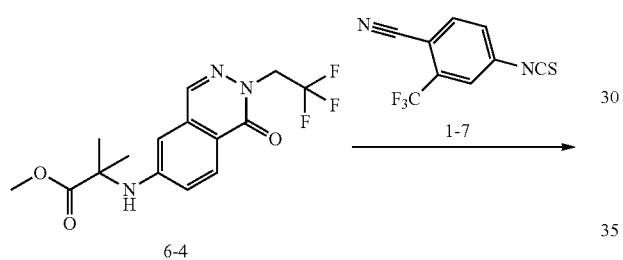

Compound 1-7 (299 mg, 1.31 mmol) was added to a solution of Compound 6-4 (90 mg, 262.16 μmol) in methylbenzene (2 mL) and DMF (0.1 mL). The resulting reaction mixture was heated to 120° C., and stirred for 48 h. Methanol (2 mL) was added to the reaction mixture, and the resulting mixture was stirred for 5 min, and then concentrated under reduced pressure. The residue obtained from the concentration was purified by a preparative TLC plate, and then purified by preparative HPLC to obtain Compound 6. $^1$H NMR (400 MHz, CDCl$_3$) δ ppm 8.56 (d, J=8.3 Hz, 1H), 8.17 (s, 1H), 7.94 (d, J=8.3 Hz, 1H), 7.90 (s, 1H), 7.77 (dd, J=1.8, 8.3 Hz, 1H), 7.69-7.62 (m, 2H), 4.82 (q, J=8.5 Hz, 2H), 1.59 (s, 6H); LCMS (ESI) m/z: 540 (M+1).

Example 7 Synthesis of Compound 7 and Compound 8

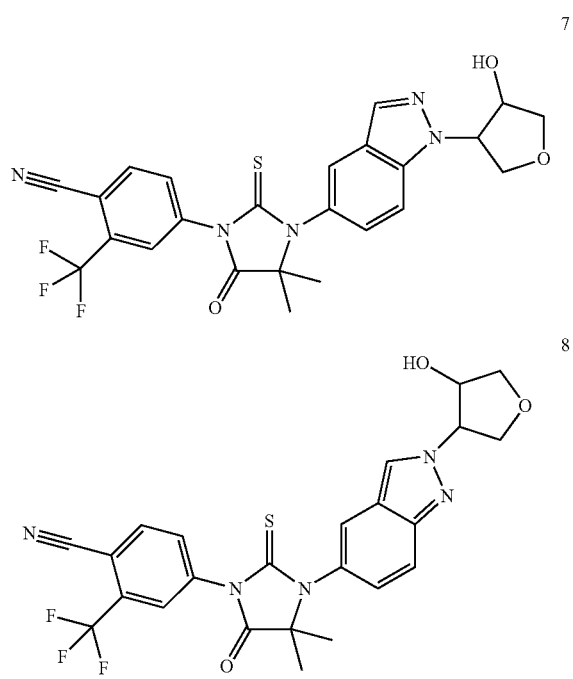

1) Synthesis of Compound 7-2

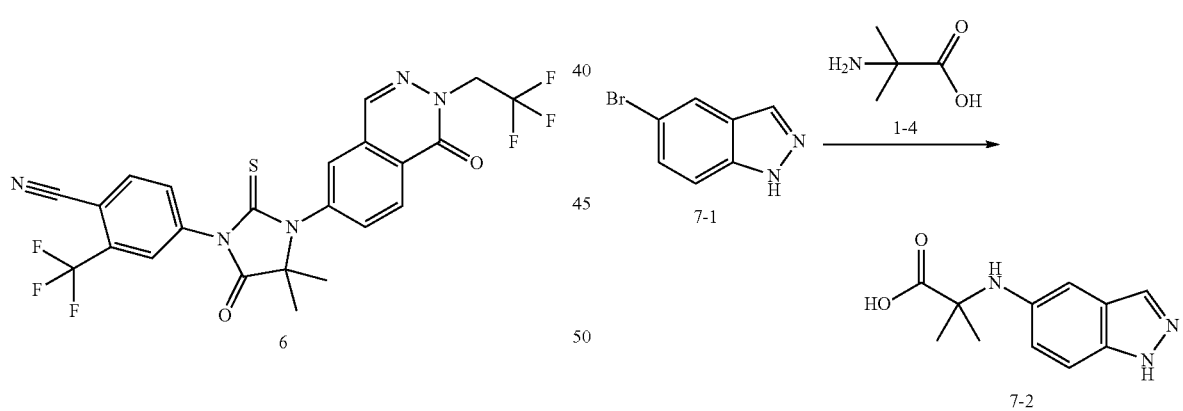

In a microwave tube, Compound 7-1 (1.00 g, 5.08 mmol), Compound 1-4 (785 mg, 7.61 mmol), 2-acetylcyclohexanone (142 mg, 1.02 mmol), cuprous chloride (100 mg, 1.02 mmol), and potassium carbonate (1.75 g, 12.69 mmol) were dissolved in DMF (5 mL) and water (90 μL) at 15° C. Then, the resulting mixture was microwave-heated to 130° C., and stirred at this temperature for 1.2 h. The reaction mixture was directly filtered, and spin-dried. 15 mL of water was added, and then the resulting mixture was extracted with ethyl acetate (15 mL×2). Then, the aqueous phase was concentrated to obtain Compound 7-2. LCMS (ESI) m/z: 220 (M+1).

2) Synthesis of Compound 7-3

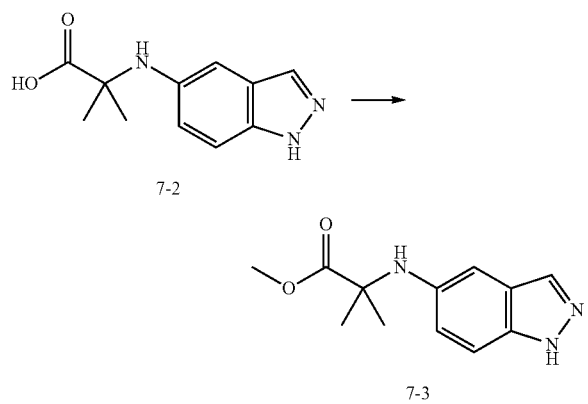 [SMILES: CC(C)(Nc1ccc2[nH]ncc2c1)C(=O)O ; COC(=O)C(C)(C)Nc1ccc2[nH]ncc2c1]

Dichlorosulfoxide (5.84 g, 49.08 mmol) was added dropwise to a solution of Compound 7-2 (800 mg, 3.65 mmol) in methanol (10 mL) in an ice water bath. After the completion of the dropwise addition, the resulting mixture was stirred at 50° C. for 12 h. The reaction mixture was directly concentrated to obtain Compound 7-3. LCMS (ESI) m/z: 234 (M+1).

3) Synthesis of Compound 7-4

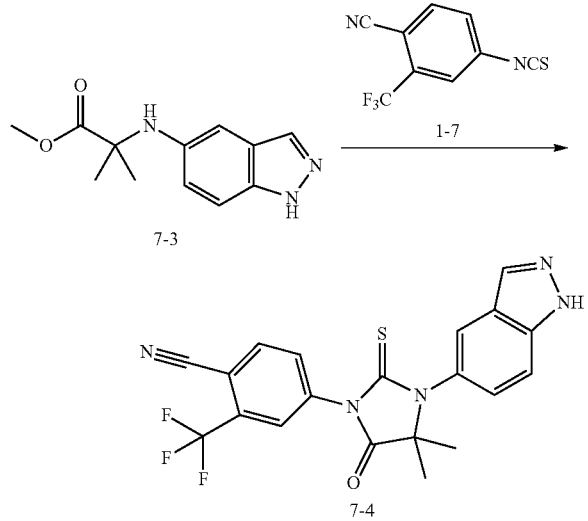

Compound 7-3 (400 mg, 1.71 mmol) and Compound 1-7 (1.17 g, 5.14 mmol) were dissolved in DMF (1.5 mL) and methylbenzene (6 mL) at 15° C. After three times of nitrogen displacement, the mixture was heated to 100° C. and stirred for 12 h under nitrogen protection. 5 mL of methanol was added to the reaction mixture, and then the resulting mixture was stirred for 20 min, and concentrated under reduced pressure. The crude product was purified by flash column chromatography to obtain Compound 7-4. LCMS (ESI) m/z: 430 (M+1).

4) Synthesis of Compound 7 and Compound 8

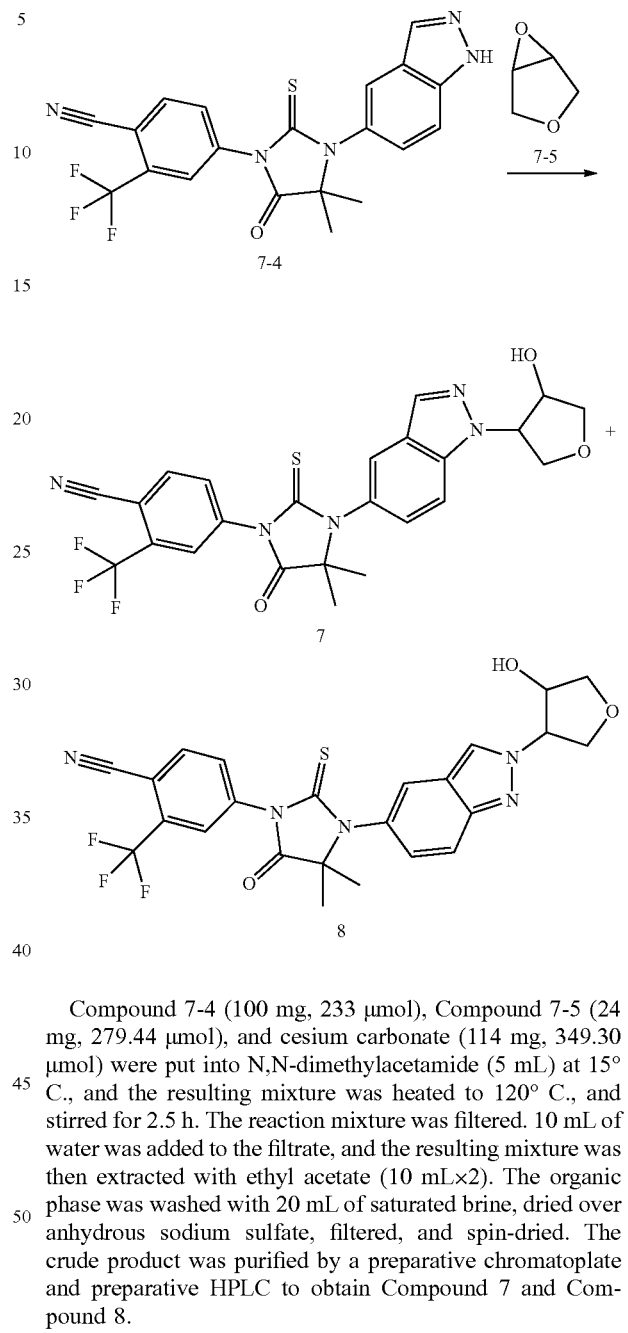

Compound 7-4 (100 mg, 233 μmol), Compound 7-5 (24 mg, 279.44 μmol), and cesium carbonate (114 mg, 349.30 μmol) were put into N,N-dimethylacetamide (5 mL) at 15° C., and the resulting mixture was heated to 120° C., and stirred for 2.5 h. The reaction mixture was filtered. 10 mL of water was added to the filtrate, and the resulting mixture was then extracted with ethyl acetate (10 mL×2). The organic phase was washed with 20 mL of saturated brine, dried over anhydrous sodium sulfate, filtered, and spin-dried. The crude product was purified by a preparative chromatoplate and preparative HPLC to obtain Compound 7 and Compound 8.

$^1$H NMR (400 MHz, CDCl$_3$) δ ppm 8.14 (s, 1H), 8.04-7.99 (m, 2H), 7.89 (br d, J=8.28 Hz, 1H), 7.74-7.69 (m, 2H), 7.34 (br d, J=8.78 Hz, 1H), 5.14 (br s, 1H), 4.81 (br s, 1H), 4.55-4.49 (m, 1H), 4.40-4.29 (m, 2H), 3.97 (br d, J=7.03 Hz, 1H), 2.15 (br d, J=5.27 Hz, 1H), 1.65 (s, 6H); LCMS (ESI) m/z: 516 (M+1) (Compound 7).

$^1$H NMR (400 MHz, CDCl$_3$) δ ppm 8.17 (s, 1H), 7.97-8.02 (m, 2H), 7.89-7.83 (m, 2H) 7.64 (s, 1H), 7.16 (dd, J=9.03, 2.01 Hz, 1H), 5.09 (br s, 1H), 4.75 (br s, 1H), 4.48 (dd, J=10.16, 6.15 Hz, 1H), 4.39-4.31 (m, 2H), 4.00-3.86 (m, 1H), 2.51 (br s, 1H), 1.63 (s, 6H); LCMS (ESI) m/z: 516 (M+1) (Compound 8).

Example 8 Synthesis of Compound 9

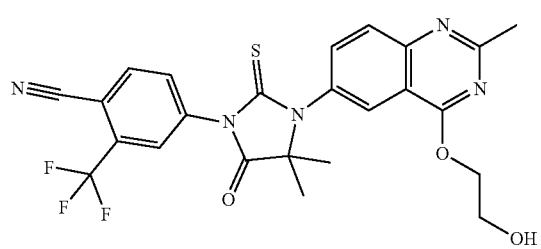

1) Synthesis of Compound 9-2

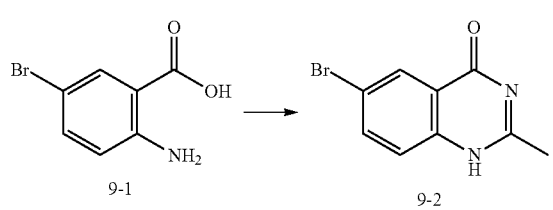

A mixture of Compound 9-1 (2.00 g, 9.26 mmol), triethyl orthoacetate (3.00 g, 25.00 mmol), and aminomethanol (20 mL) (15% wt.) was added to an airtight jar, and stirred at 110° C. for 4 h. The reaction mixture was concentrated under reduced pressure. The residue obtained from the concentration was slurried with methanol (30 mL), and filtered to obtain a white solid. The filtrate was concentrated under reduced pressure, re-slurried with methanol (15 mL), and filtered to obtain a white solid. The two batches of white solids were combined to obtain Compound 9-2. $^1$H NMR (400 MHz, DMSO-d6) δ ppm 12.38 (br s, 1H), 8.14 (d, J=2.3 Hz, 1H), 7.91 (dd, J=2.4, 8.7 Hz, 1H), 7.53 (d, J=8.8 Hz, 1H), 2.34 (s, 3H).

2) Synthesis of Compound 9-3

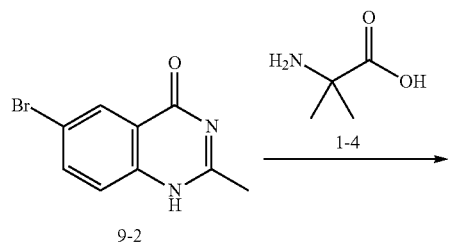

Compound 9-2 (600 mg, 2.51 mmol), Compound 1-4 (388 mg, 3.76 mmol), potassium carbonate (867 mg, 6.28 mmol), cuprous chloride (50 mg, 502.00 μmol), 2-acetylcyclohexanone (70 mg, 502.00 μmol), DMF (7 mL), and water (350 μL) were added to a 20 mL microwave tube. The resulting mixture was kept at 130° C. for microwave reaction for 1 h. The reaction mixture was filtered, and the filtrate was concentrated to dryness under reduced pressure. The residue obtained from the concentration was dissolved in water (50 mL), and washed with dichloromethane (30 mL×3). Concentrated hydrochloric acid (1.5 mL) was added to the aqueous phase, such that the aqueous phase was acidic (pH about 6), and then the aqueous phase was concentrated under reduced pressure. The residue obtained from the concentration was slurried with dichloromethane/methanol (30 mL/30 mL) at 29° C. for 2 min, filtered, and concentrated under reduced pressure to obtain Compound 9-3. LCMS (ESI) m/z: 262 (M+1).

3) Synthesis of Compound 9-4

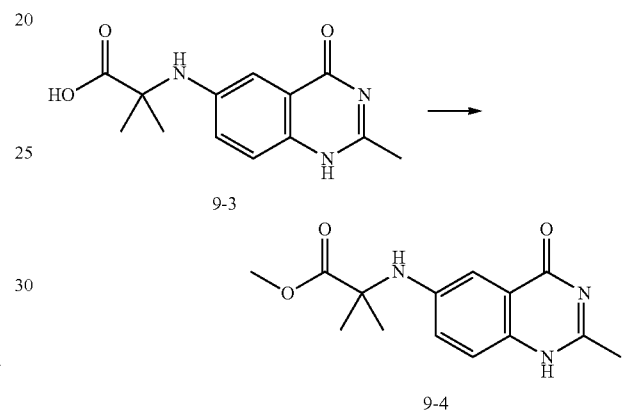

Compound 9-3 (1.18 g, 2.58 mmol) was dissolved in anhydrous methanol (20 mL), and dichlorosulfoxide (3.28 g, 27.58 mmol, 2.00 mL) was added dropwise at 0° C. The resulting mixture was heated to 50° C., and stirred for 18 h. The reaction mixture was concentrated under reduced pressure, a saturated sodium bicarbonate solution (50 mL) was added, and the resulting mixture was extracted with dichloromethane (30 mL×3). The organic phases were combined, washed with saturated brine (50 mL), dried over anhydrous sodium sulfate, and filtered. The filtrate was concentrated to dryness under reduced pressure. The residue obtained from the concentration was slurried with dichloromethane/ethyl acetate (10 mL/10 mL) at 29° C. for 0.5 h, and filtered. The resulting filter cake was Compound 9-4. $^1$H NMR (400 MHz, CDCl$_3$) δ ppm 10.94 (s, 1H), 7.52-7.50 (d, J=9.2 Hz, 1H), 7.30-7.29 (d, J=2.8 Hz, 1H), 7.06-7.04 (m, 1H), 4.45 (s, 1H), 3.76 (s, 3H), 2.52 (s, 3H), 1.65 (s, 6H); LCMS (ESI) m/z: 276 (M+1).

4) Synthesis of Compound 9-5

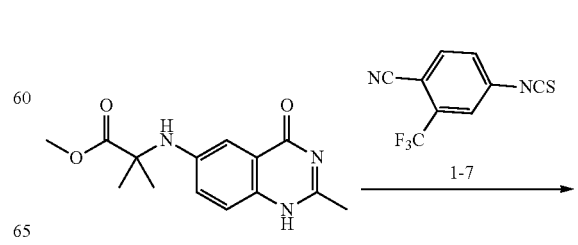

-continued

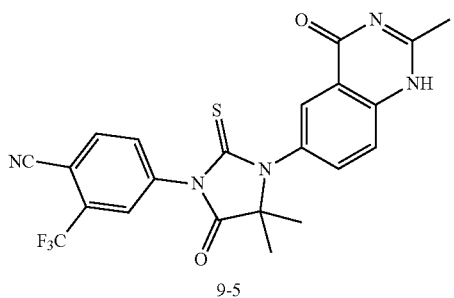

9-5

Compound 9-4 (300 mg, 933.89 μmol) and Compound 1-7 (864 mg, 3.79 mmol) were dissolved in DMF (1.5 mL) and methylbenzene (6 mL). The resulting mixture was heated to 120° C., and stirred for 18 h. The reaction mixture was concentrated to dryness under reduced pressure. The residue obtained from the concentration was purified by a preparative chromatoplate to obtain Compound 9-5. LCMS (ESI) m/z: 472 (M+1).

5) Synthesis of Compound 9

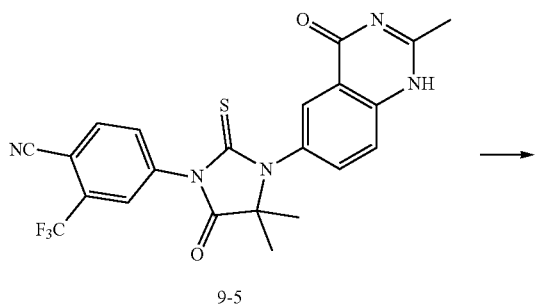

9-5

→

9

A turbid liquid of Compound 9-5 (130 mg, 275.74 μmol), 2-bromoethanol (83 mg, 661.78 μmol), and potassium carbonate (100 mg, 722.44 μmol) in DMF (3 mL) was stirred at 29° C. for 67 h. The reaction mixture was filtered directly. The filtrate was separated and purified by preparative HPLC to obtain Compound 9. $^1$HNMR (400 MHz, CDCl$_3$) δ ppm 8.04 (d, J=2.4 Hz, 1H), 7.96-7.92 (m, 3H), 7.91-7.80 (dd, J=45.6 Hz, 1H), 7.65-7.64 (dd, J=2.8 Hz, 1H), 4.721-4.71 (m, 2H), 4.70 (s, 2H), 2.69 (s, 3H), 1.59 (s, 6H); LCMS (ESI) m/z: 516 (M+1).

Example 9 Synthesis of Compound 10

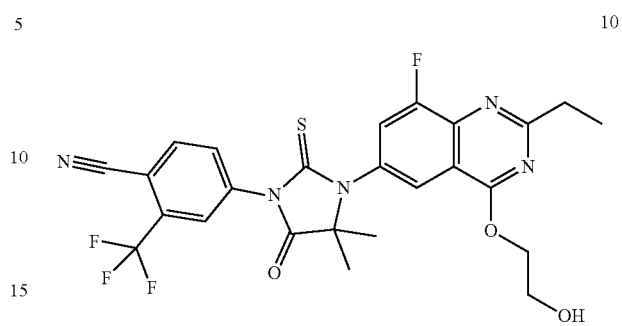

10

1) Synthesis of Compound 10-2

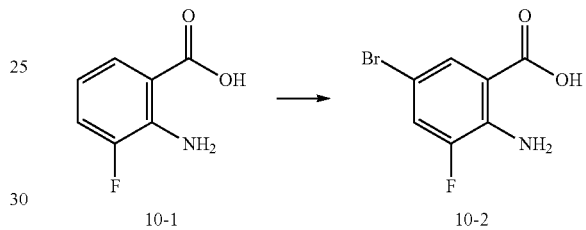

10-1    10-2

Compound 10-1 (20.00 g, 128.92 mmol) was dissolved in dichloromethane (200 mL), and NBS (22.95 g, 128.92 mmol) was added. The resulting mixture was stirred at 20° C. for 2 h. The reaction mixture was filtered, and the filter cake was washed with dichloromethane (75 mL×3). The resulting filter cake was dried under reduced pressure to obtain Compound 10-2. $^1$H NMR (400 MHz, DMSO-d6) δ ppm 7.66-7.61 (m, 1H), 7.52 (dd, J=2.3, 10.8 Hz, 1H); LCMS (ESI) m/z: 234 (M+1).

2) Synthesis of Compound 10-3

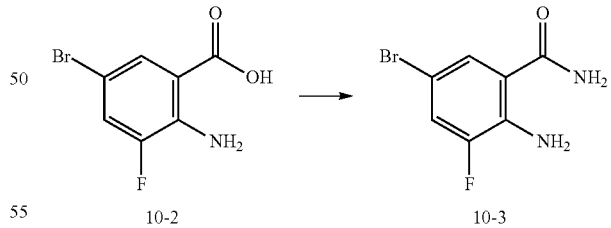

10-2    10-3

Ammonia water (51.52 g, 396.90 mmol) (purity: 27%) was added to a solution of Compound 10-2 (30.96 g, 132.30 mmol), O-(7-azabenzotriazol-1-yl)-N,N,N',N'-tetramethyl-uronium hexafluorophosphate (70.42 g, 185.22 mmol), and triethylamine (26.77 g, 264.60 mmol) in DMF (500 mL). The resulting mixture was stirred at 20° C. for 4 h. 2000 mL of water was added to the reaction mixture, and the resulting mixture was stirred for 1 h, and filtered. The filter cake was washed with water (50 mL×3), and the resulting white solid was dried in an infrared oven. The filtrate was extracted with dichloromethane (100 mL×3). The resulting organic phase was concentrated under reduced pressure. The residue obtained from the concentration was slurried with water (500 mL) at 20° C. for 20 min, and filtered. The filter cake was dried in the infrared oven. The two dried white solids were combined to obtain Compound 10-3. ¹H NMR (400 MHz, CDCl₃) δ ppm 7.35 (br d, J=7.0 Hz, 1H), 7.18-7.08 (m, 1H); LCMS (ESI) m/z: 235 (M+3).

3) Synthesis of Compound 10-4

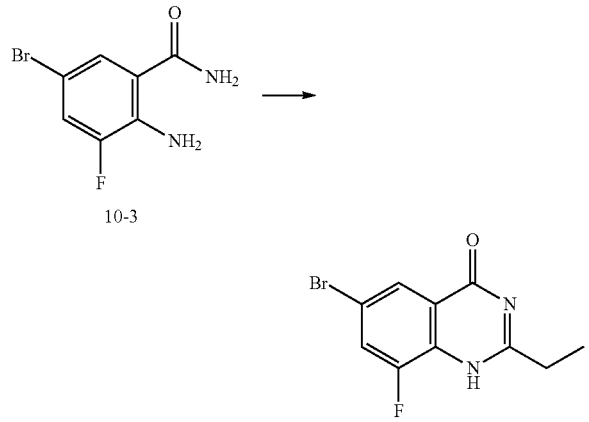

Propionyl chloride (28.39 g, 306.80 mmol) was added to a turbid liquid of Compound 10-3 (14.30 g, 61.36 mmol) in trichloromethane (200 mL). The resulting mixture was stirred at 70° C. for 16 h. The reaction mixture was cooled to 15° C., methanol (5 mL) was added, and then the resulting mixture was concentrated to dryness under reduced pressure. The residue obtained from the concentration was dissolved in a saturated sodium bicarbonate solution (100 mL), and extracted with dichloromethane/methanol (10/1, 200 mL×3). The organic phases were combined, washed with saturated brine (100 mL), dried over anhydrous sodium sulfate, and filtered. The filtrate was concentrated to dryness under reduced pressure. The residue obtained from the concentration was slurried with ethyl acetate (100 mL) at 15° C. for 30 min, and filtered. The filter cake was washed with ethyl acetate (10 mL×3), and then dried in an infrared oven to obtain Compound 10-4. ¹H NMR (400 MHz, CDCl₃) δ ppm 8.00 (br d, J=1.3 Hz, 1H), 7.57-7.48 (m, 1H), 2.95 (s, 1H), 2.62 (q, J=7.5 Hz, 2H), 1.33-1.22 (m, 3H); LCMS (ESI) m/z: 273 (M+3).

4) Synthesis of Compound 10-5

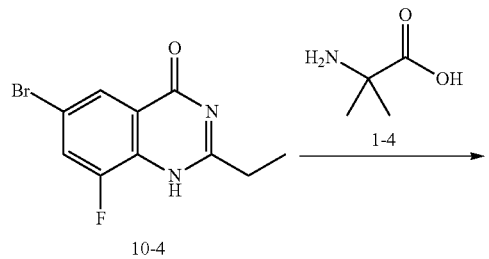

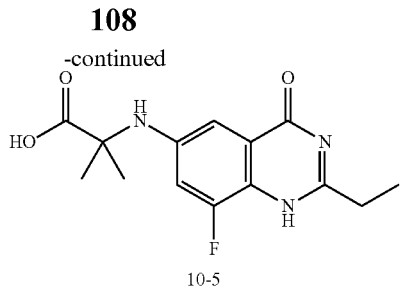

Compound 10-4 (1.50 g, 5.53 mmol), Compound 1-4 (855 mg, 8.30 mmol), cuprous chloride (220 mg, 2.22 mmol), 2-acetylcyclohexanone (310 mg, 2.22 mmol), potassium carbonate (1.91 g, 13.83 mmol), DMF (10 mL), and water (500 μL) were added to a 30 mL microwave tube, respectively. The resulting mixture was kept at 130° C. for microwave reaction for 80 min. The reaction mixture was filtered, and the filter cake was washed with DMF (10 mL×3). The resulting aqueous phase was acidified to a pH of about 6 with dilute hydrochloric acid (2 mol/L). The aqueous phase was concentrated to dryness under reduced pressure. The residue obtained from the concentration was slurried with dichloromethane/methanol (10/1, 30 mL) at 15° C. for 2 min, and filtered. The filtrate was concentrated under reduced pressure to obtain Compound 10-5. LCMS (ESI) m/z: 294 (M+1).

5) Synthesis of Compound 10-6

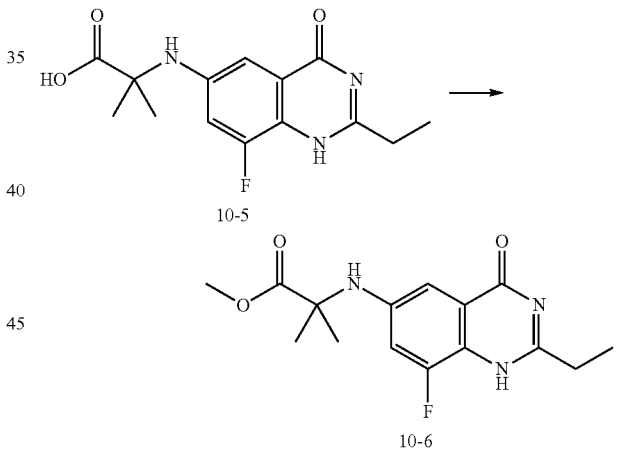

Dichlorosulfoxide (29.94 g, 251.64 mmol) was added dropwise to a solution of Compound 10-5 (7.30 g, 24.89 mmol) in methanol (80 mL) at 0° C. After the completion of the dropwise addition, the resulting mixture was heated to 50° C., and stirred for 18 h. The reaction mixture was cooled to 15° C., and concentrated to dryness under reduced pressure. The residue obtained from the concentration was dissolved in a saturated sodium bicarbonate solution (40 mL), and extracted with dichloromethane/methanol (10/1, 60 mL×4). The organic phases were combined, washed with saturated brine (50 mL), dried over anhydrous sodium sulfate, and filtered. The filtrate was concentrated to dryness under reduced pressure. The residue obtained from the concentration was purified by a silica gel column to obtain Compound 10-6. ¹H NMR (400 MHz, CDCl₃) δ ppm 7.01 (d, J=2.5 Hz, 1H), 6.72 (dd, J=2.5, 12.3 Hz, 1H), 3.68 (s, 3H), 2.72 (q, J=7.6 Hz, 2H), 1.56 (s, 6H), 1.36-1.31 (m, 3H); LCMS (ESI) m/z: 308 (M+1).

6) Synthesis of Compound 10-7

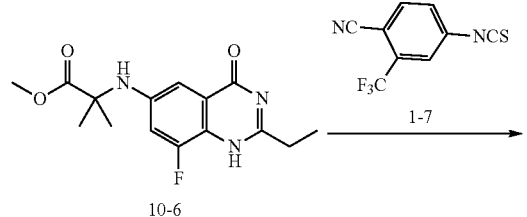

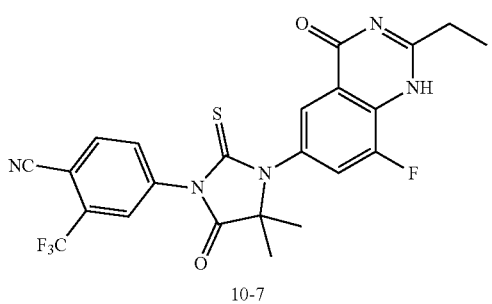

Under nitrogen protection, Compound 10-6 (2.10 g, 6.83 mmol) and Compound 1-7 (6.23 g, 27.32 mmol) were dissolved in DMF (5 mL) and methylbenzene (50 mL), and the resulting mixture was heated to 120° C., and stirred for 18 h. The reaction mixture was concentrated to dryness under reduced pressure. The residue obtained from the concentration was purified by a silica gel column to obtain Compound 10-7. $^1$H NMR (400 MHz, CDCl$_3$) δ ppm 7.99-7.93 (m, 2H), 7.78 (dd, J=1.6, 8.2 Hz, 1H), 7.58 (d, J=8.3 Hz, 1H), 7.40 (dd, J=2.1, 9.9 Hz, 1H), 2.86-2.77 (m, 3H), 1.59 (s, 6H), 1.44-1.33 (m, 3H); LCMS (ESI) m/z: 504 (M+1).

7) Synthesis of Compound 10

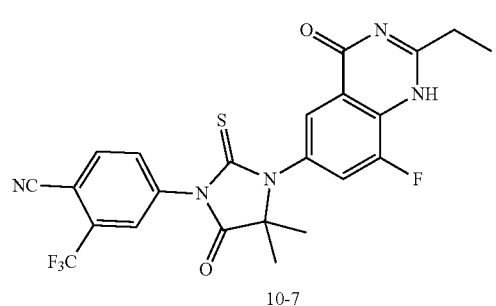

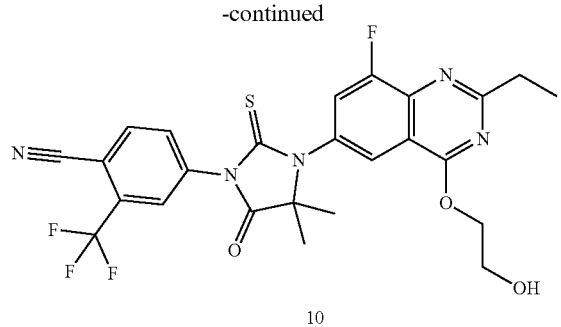

Under nitrogen protection, a turbid liquid of Compound 10-7 (1.32 g, 2.62 mmol), 2-bromoethanol (4.10 g, 32.75 mmol), potassium carbonate (1.45 g, 10.48 mmol), and DMF (50 mL) was stirred at 40° C. for 78 h. The reaction mixture was filtered directly. The filtrate was separated and purified by preparative HPLC and preparative chromatography to obtain Compound 10. $^1$H NMR (400 MHz, CDCl$_3$) δ ppm 7.94 (d, J=8.0 Hz, 1H), 7.90 (d, J=1.5 Hz, 1H), 7.85 (s, 1H), 7.78 (dd, J=1.8, 8.3 Hz, 1H), 7.39 (dd, J=2.1, 9.9 Hz, 1H), 4.76-4.71 (m, 2H), 4.03 (br d, J=3.8 Hz, 2H), 2.98 (q, J=7.5 Hz, 2H), 2.72 (br s, 1H), 1.60 (s, 6H), 1.35 (t, J=7.7 Hz, 3H); LCMS (ESI) m/z: 548 (M+1).

Example 10 Synthesis of Compound 11

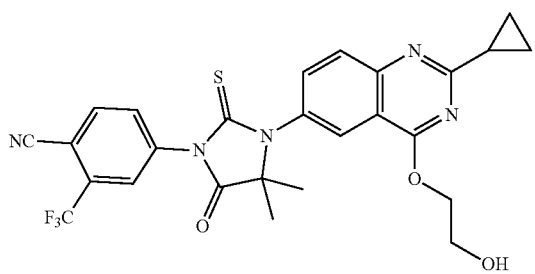

1) Synthesis of Compound 11-2

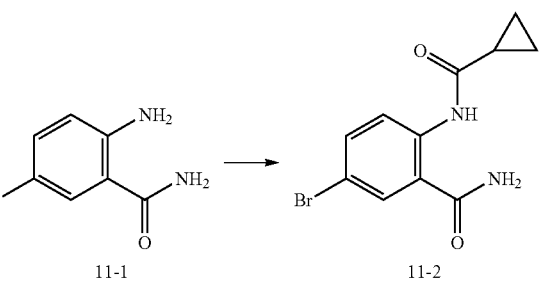

Cyclopropylformyl chloride (8.55 g, 81.84 mmol) was added dropwise to a solution of Compound 11-1 (4.40 g, 20.46 mmol) in trichloromethane (100 mL) at 20° C. The reaction mixture was heated to 65° C. and reacted for 12 h. The reaction mixture was cooled to room temperature, and concentrated to obtain Compound 11-2. LCMS (ESI) m/z: 285 (M+3).

2) Synthesis of Compound 11-3

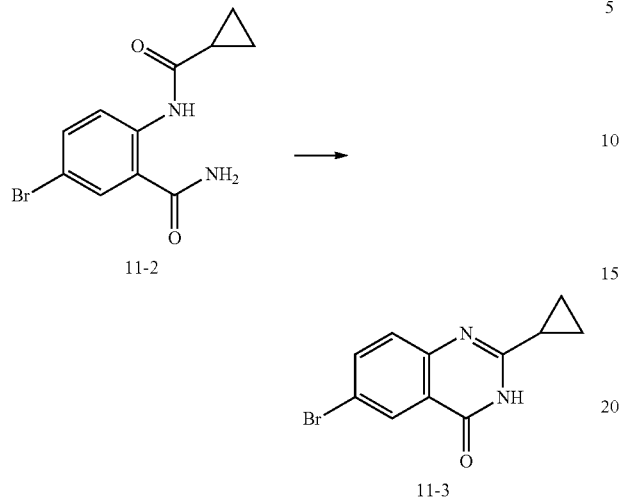

Sodium methoxide (4.12 g, 76.28 mmol) was added to a solution of Compound 11-2 (5.40 g, 19.07 mmol) in methanol (100 mL) at 20° C. The reaction mixture reacted at 20° C. for 12 h. The reaction mixture was cooled to room temperature, and concentrated to obtain a crude product. The crude product was added in water (100 mL), and neutralized with 1M aqueous solution of hydrochloric acid to pH=7. A large amount of gray solids precipitated. After filtration, the filter cake was collected and dried to obtain Compound 11-3. $^1$H NMR (400 MHz, DMSO-d6) δ ppm 8.09 (d, J=2.26 Hz, 1H), 7.68 (d, J=2.26 Hz, 1H), 7.41 (d, J=8.78 Hz, 1H), 7.24 (dd, J=8.78, 2.26 Hz, 1H), 2.00-1.86 (m, 1H), 1.13-0.97 (m, 4H); LCMS (ESI) m/z: 267 (M+3).

3) Synthesis of Compound 11-4

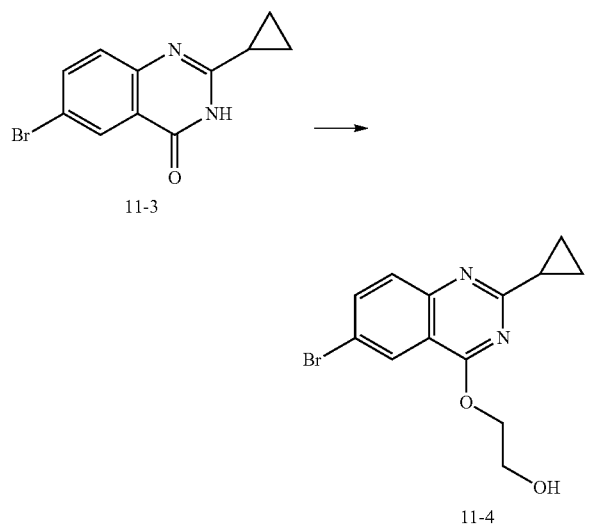

DMF (414 mg, 5.66 mmol) was added dropwise to a solution of Compound 11-3 (1.50 g, 5.66 mmol) and dichlorosulfoxide (20 mL), and the resulting mixture was stirred at 80° C. for 3 h. The reaction mixture was concentrated to dryness under reduced pressure, and the residue was dissolved in ethanediol (20 mL). Triethylamine (344 mg, 3.40 mmol) was added, and the resulting mixture was further stirred at 80° C. for 1 h. The reaction mixture was cooled to ° C. Dichloromethane (80 mL) was added to the resulting mixture, which was washed with water (50 mL×3). The organic phase was dried over anhydrous sodium sulfate, and filtered. The filtrate was concentrated to dryness under reduced pressure. The residue obtained from the concentration was purified by a silica gel column to obtain Compound 11-4. LCMS (ESI) m/z: 309 (M+1).

4) Synthesis of Compound 11-5

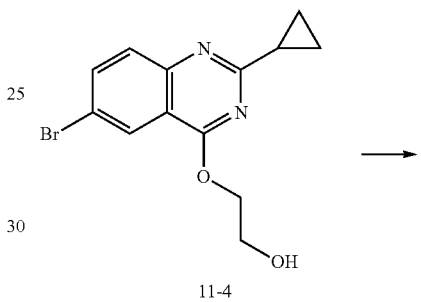

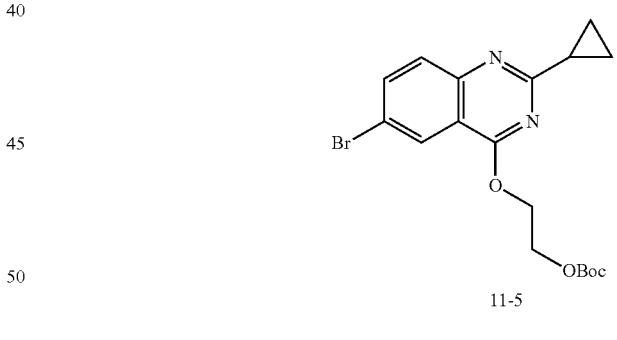

Triethylamine (275 mg, 2.72 mmol), 4-dimethylaminopyridine (22 mg, 181.14 μmol), and diBoc (495 mg, 2.72 mmol) were added dropwise to a solution of Compound 11-4 (280 mg, 905.68 μmol) in dichloromethane (10 mL). The resulting mixture was stirred at 15° C. for 17 h. The reaction mixture was diluted with dichloromethane (20 mL). Water (20 mL) was added to the resulting mixture, then 2 mol/L dilute hydrochloric acid (5 drops) was added dropwise, and the resulting mixture was washed three times. The organic phase was washed with a saturated sodium carbonate solution (20 mL), dried over anhydrous sodium sulfate, and filtered. The filtrate was concentrated under reduced pressure to obtain Compound 11-5. LCMS (ESI) m/z: 411 (M+3).

5) Synthesis of Compound 11-6

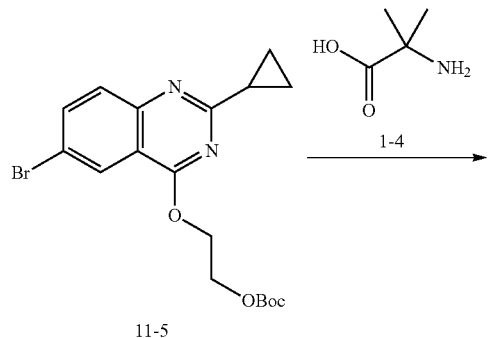

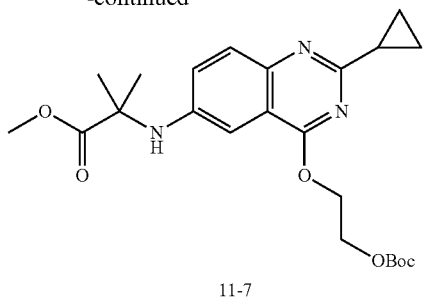

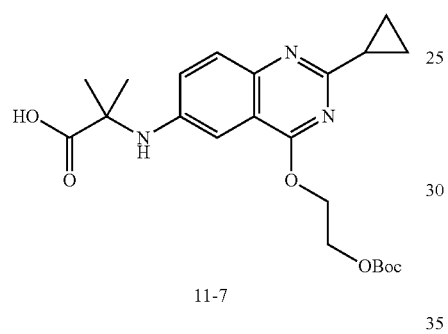

Compound 11-5 (250 mg, 610.84 μmol), Compound 1-4 (95 mg, 916.27 μmol), potassium carbonate (338 mg, 2.44 mmol), cuprous chloride (12 mg, 122.17 μmol), 2-acetylcyclohexanone (17 mg, 122.17 μmol), DMF (5 mL), and water (0.1 mL) were added to a 10 mL microwave tube. The resulting mixture was kept at 130° C. for microwave reaction for 1 h. The reaction mixture was filtered, and the filter cake was washed with DMF (5 mL×2). The filtrate was concentrated to dryness under reduced pressure. The residue obtained from the concentration was slurried with dichloromethane (20 mL) at 15° C. for 2 min, and filtered. The filtrate was concentrated under reduced pressure to obtain Compound 11-6. LCMS (ESI) m/z: 432 (M+1).

6) Synthesis of Compound 11-7

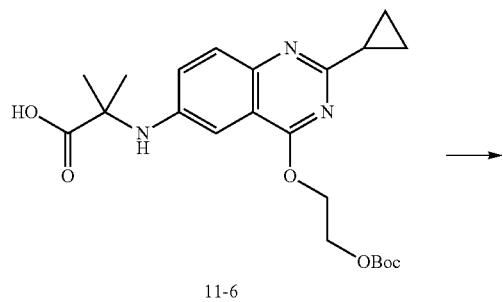

A solution of TMSCHN₂ in n-hexane (2M, 1.74 mL, 3.48 mmol) was added dropwise to a solution of Compound 11-6 (500 mg, 1.16 mmol) in dichloromethane (5 mL) and methanol (500 μL). The resulting mixture was stirred at 20° C. for 1.5 h. The reaction mixture was concentrated to dryness under reduced pressure. The residue obtained from the concentration was purified by a preparative chromatoplate to obtain Compound 11-7. LCMS (ESI) m/z: 446 (M+1).

7) Synthesis of Compound 11-8

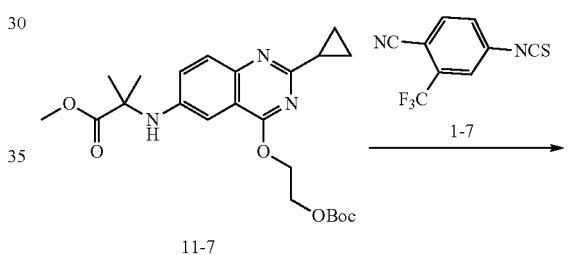

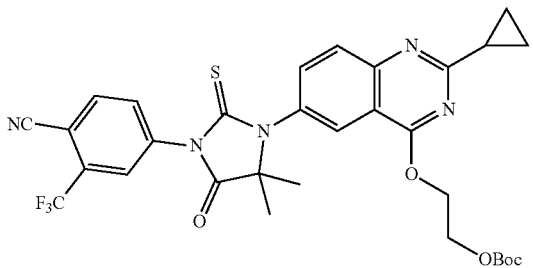

Compound 11-7 (85 mg, 190.79 μmol) and Compound 1-7 (131 mg, 572.38 μmol) were dissolved in DMF (500 μL) and methylbenzene (3 mL). The resulting mixture was stirred at 120° C. for 16 h under nitrogen protection. The reaction mixture was cooled to room temperature, and then concentrated under reduced pressure. The residue obtained from the concentration was purified by a preparative chromatoplate to obtain Compound 11-8. LCMS (ESI) m/z: 642 (M+1).

8) Synthesis of Compound 11

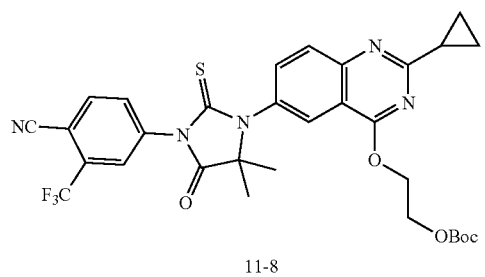

11-8

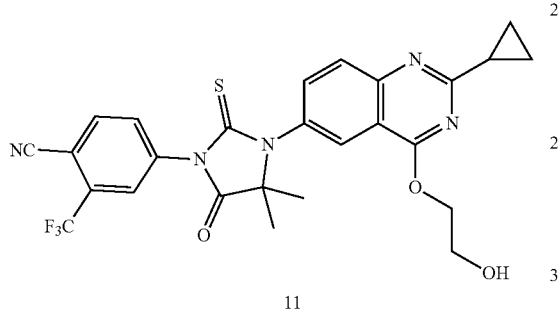

11

Trifluoroacetic acid (2 mL) was added to a solution of Compound 11-8 (50 mg, 77.92 μmol) in dichloromethane (6 mL), and then the resulting mixture was stirred at 15° C. for 3 h. The reaction mixture was diluted with dichloromethane (10 mL), and washed with a saturated aqueous solution of sodium bicarbonate (20 mL×3) and water (20 mL), respectively. The combined organic phase was washed with saturated brine (20 mL), dried over anhydrous sodium sulfate, filtered, and concentrated to obtain a crude product. The crude product was purified by preparative HPLC to obtain Compound 11. $^1$H NMR (400 MHz, CDCl$_3$) δ ppm 8.02-7.97 (m, 1H), 7.95-7.88 (m, 3H), 7.79 (dd, J=8.28, 1.76 Hz, 1H), 7.59 (dd, J=8.91, 2.38 Hz, 11H), 4.66-4.62 (m, 2H), 4.00 (br s, 2H), 2.52 (br s, 1H), 2.26-2.17 (m, 1H), 1.58 (s, 6H), 1.19-1.12 (m, 2H), 1.09-1.01 (m, 2H); LCMS (ESI) m/z: 542 (M+1).

Example 11 Synthesis of Compound 12

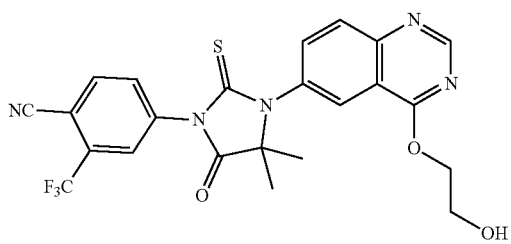

12

1) Synthesis of Compound 12-1

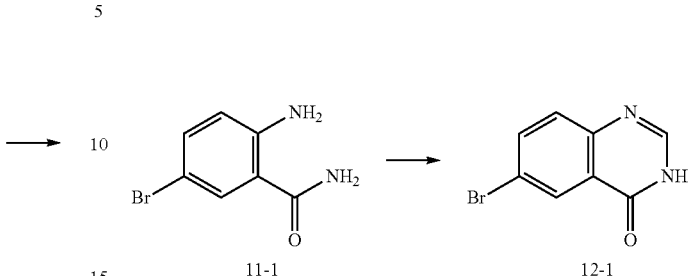

P-methylbenzenesulfonic acid (218 mg, 1.40 mmol) and Compound 11-1 (3.00 g, 13.95 mmol) were added to trimethyl orthoformate (29.10 g, 274.22 mmol) at room temperature (10° C.). The reaction mixture was heated to 110° C., and reacted for 1 h. The reaction mixture was cooled to room temperature, and directly concentrated to obtain Compound 12-1. LCMS (ESI) m/z: 225 (M+1).

2) Synthesis of Compound 12-2

DMF (578 mg, 7.90 mmol) was added to a solution of Compound 12-1 (2.00 g, 8.89 mmol) in dichlorosulfoxide (10 mL) at 20° C. The reaction mixture was heated to 80° C., and reacted for 2 h, and then concentrated. The resulting yellow solid was dissolved in ethanediol (10 mL), triethylamine (4.00 g, 39.50 mmol) was added, and the resulting mixture was stirred at 80° C. for 1 h. The reaction mixture was diluted with water (50 mL), and extracted with dichloromethane (50 mL×3). The organic phase was dried over anhydrous sodium sulfate, filtered, and concentrated to obtain Compound 12-2. LCMS (ESI) m/z: 269 (M+1).

3) Synthesis of Compound 12-3

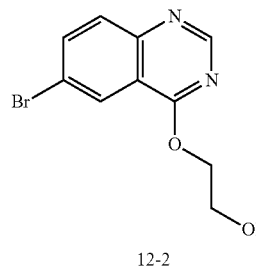 

12-2

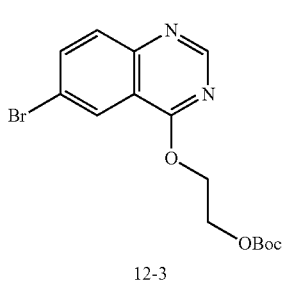

12-3

Triethylamine (4.51 g, 44.58 mmol) and diBoc (8.10 g, 37.15 mmol) were added dropwise to a solution of Compound 12-2 (4.00 g, 14.86 mmol) and 4-dimethylaminopyridine (363 mg, 2.97 mmol) in dichloromethane (30 mL). The resulting mixture was stirred at 15° C. for 3 h. The reaction mixture was diluted with dichloromethane (20 mL). The resulting mixture was washed with dilute hydrochloric acid (30 mL×4) (the dilute hydrochloric acid was obtained by diluting 2 mol/L dilute hydrochloric acid (4 mL) with water (120 mL)). The organic phase was washed with a saturated sodium carbonate solution (30 mL), dried over anhydrous sodium sulfate, and filtered. The filtrate was concentrated to dryness under reduced pressure. The residue obtained from the concentration was purified by a silica gel column to obtain Compound 12-3. $^1$H NMR (400 MHz, CDCl$_3$) δ ppm 8.78 (s, 1H), 8.42-8.20 (m, 1H), 7.98-7.75 (m, 2H), 4.80 (br d, J=3.5 Hz, 2H), 4.63-4.45 (m, 2H), 1.50 (s, 9H); LCMS (ESI) m/z: 369 (M+1).

4) Synthesis of Compound 12-4

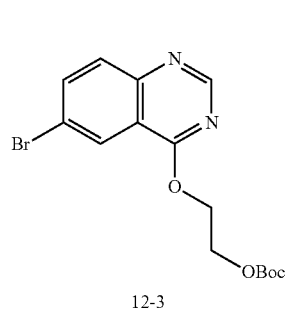 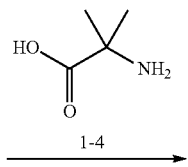

12-3         1-4

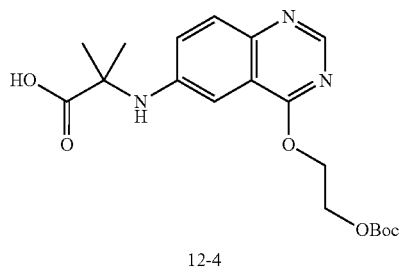

12-4

Compound 12-3 (1.00 g, 2.71 mmol), Compound 1-4 (419 mg, 4.07 mmol), potassium carbonate (562 mg, 4.07 mmol), cuprous chloride (107 mg, 1.08 mmol), 2-acetylcyclohexanone (152 mg, 1.08 mmol), DMF (8 mL), and water (800 μL) were added to a 30 mL microwave tube. The resulting mixture was kept at 130° C. for microwave reaction for 40 min. The reaction mixture was filtered, and the filter cake was washed with DMF (3 mL×3). Dilute hydrochloric acid (2 mol/L) was added dropwise to the filtrate to adjust the pH to about 7, and then the resulting mixture was concentrated to dryness under reduced pressure. The residue obtained from the concentration was slurried with dichloromethane/methanol (10/1, 20 mL) at 15° C. for 2 min, and filtered. The filtrate was concentrated under reduced pressure to obtain Compound 12-4. LCMS (ESI) m/z: 392 (M+1).

5) Synthesis of Compound 12-5

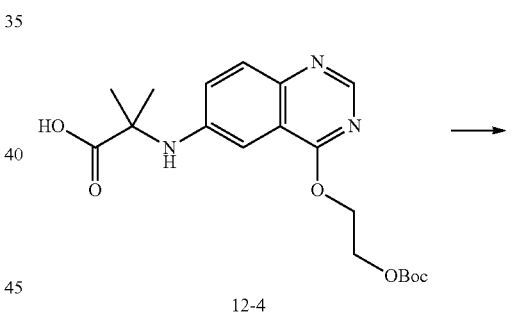

12-4

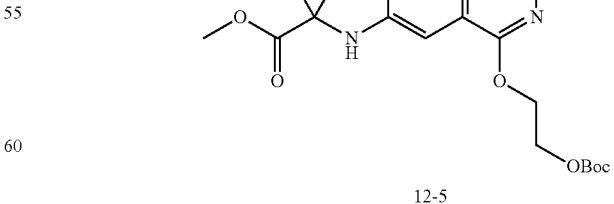

12-5

With reference to the synthesis method of Compound 11-7, Compound 12-5 was prepared with Compound 12-4 as the starting material. LCMS (ESI) m/z: 406 (M+1).

6) Synthesis of Compound 12-6

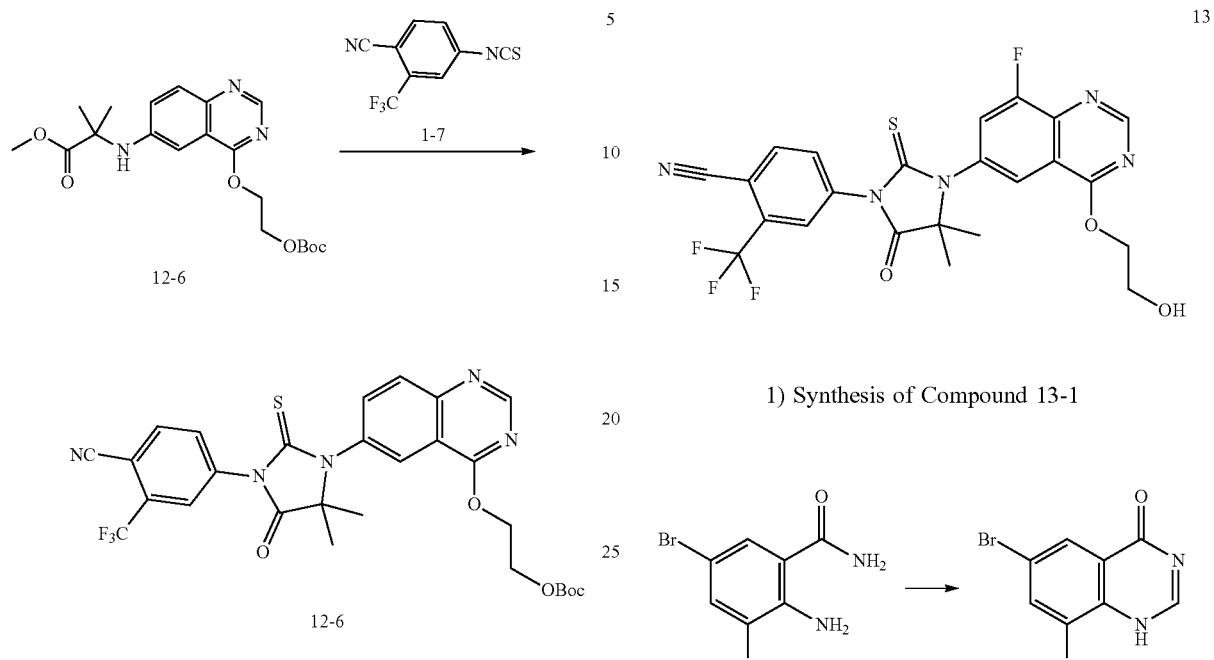

With reference to the synthesis of Compound 11-8, Compound 12-6 was prepared with Compound 12-5 as the starting material. LCMS (ESI) m/z: 602 (M+1).

7) Synthesis of Compound 12

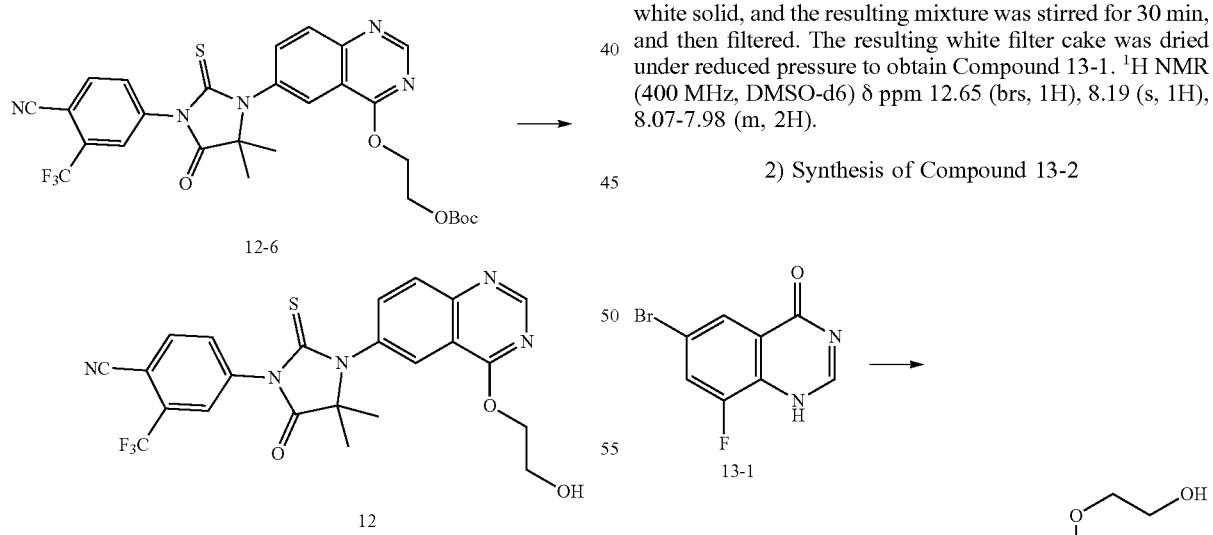

With reference to the synthesis of Compound 11, Compound 12 was prepared with Compound 12-6 as the starting material. $^1$H NMR (400 MHz, CDCl$_3$) δ ppm 8.90 (s, 1H), 8.19 (d, J=2.3 Hz, 1H), 8.15 (d, J=8.8 Hz, 1H), 8.05-7.99 (m, 2H), 7.88 (dd, J=2.0, 8.3 Hz, 1H), 7.79 (dd, J=2.4, 8.9 Hz, 1H), 4.85-4.79 (m, 2H), 4.15-4.08 (m, 2H), 2.74 (br s, 1H), 1.69 (s, 6H); LCMS (ESI) m/z: 502 (M+1).

Example 12 Synthesis of Compound 13

1) Synthesis of Compound 13-1

P-methylbenzenesulfonic acid (245 mg, 1.29 mmol) was added to a solution of Compound 10-3 (3.00 g, 12.87 mmol) and trimethyl orthoformate (30 mL). The resulting white turbid liquid was heated to 110° C., and stirred for 16 h. The reaction mixture was concentrated under reduced pressure to obtain a white solid. Ethyl acetate (50 mL) was added to the white solid, and the resulting mixture was stirred for 30 min, and then filtered. The resulting white filter cake was dried under reduced pressure to obtain Compound 13-1. $^1$H NMR (400 MHz, DMSO-d6) δ ppm 12.65 (brs, 1H), 8.19 (s, 1H), 8.07-7.98 (m, 2H).

2) Synthesis of Compound 13-2

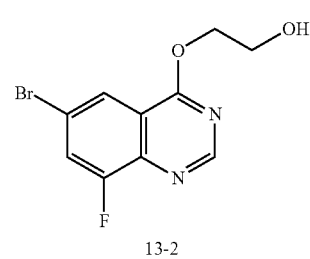

DMF (15 mg, 206.0 µmol) was added to a mixed solution of Compound 13-1 (500 mg, 2.06 mmol) and dichlorosulfoxide (4.92 g, 41.36 mmol, 3 mL). The resulting reaction mixture was heated to 80° C., and stirred for 2 h. The reaction mixture was concentrated under reduced pressure. Dichloromethane (3 mL), ethanediol (1.11 g, 17.88 mmol, 1 mL), and triethylamine (657 mg, 6.49 mmol, 0.9 mL) were added to the residue (light yellow solid) obtained from the concentration. The resulting reaction mixture was heated to 80° C., and stirred for 1 h. The reaction mixture was filtered. The filtrate was poured into water (40 mL), and extracted with ethyl acetate (30 mL). The organic phase was washed with saturated brine (20 mL), dried over anhydrous sodium sulfate, and concentrated under reduced pressure to obtain Compound 13-2. LCMS (ESI) m/z: 289 (M+3).

3) Synthesis of Compound 13-3

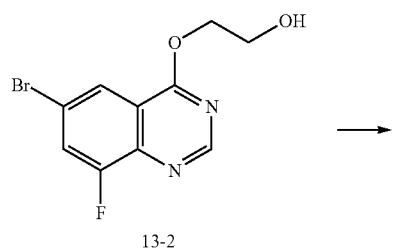

13-2

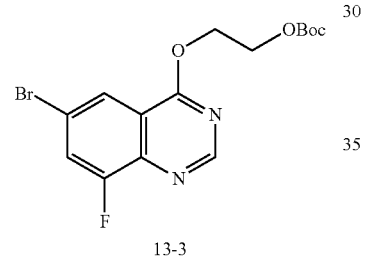

13-3 diBoc (570 mg, 2.61 mmol, 0.6 mL), triethylamine (475 mg, 4.69 mmol, 0.65 mL), and 4-dimethylaminopyridine (27 mg, 221.00 µmol) were added to a mixed solution of Compound 13-2 (630 mg, 2.19 mmol) in dichloromethane (10 mL). The resulting reaction mixture was stirred at 10° C. for 1 h. The reaction mixture was concentrated under reduced pressure, and the residue obtained from the concentration was purified by a silica gel column to obtain Compound 13-3. $^1$H NMR (400 MHz, CDCl$_3$) δ ppm 8.84 (s, 1H), 8.15 (t, J=1.5 Hz, 1H), 7.68 (dd, J=2.0, 9.3 Hz, 1H), 4.86-4.78 (m, 2H), 4.59-4.52 (m, 2H), 1.51 (s, 9H).

4) Synthesis of Compound 13-4

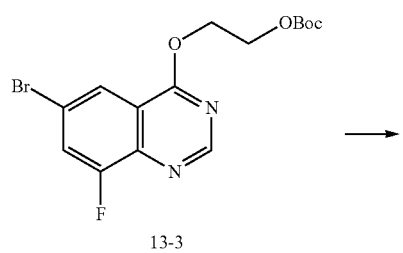

13-3

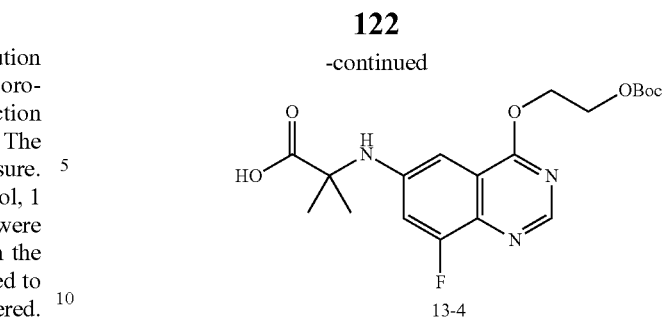

13-4

Compound 13-3 (300 mg, 774.79 µmol), Compound 1-4 (120 mg, 1.16 mmol), potassium carbonate (268 mg, 1.94 mmol), cuprous chloride (15 mg, 151.52 µmol), 2-acetylcyclohexanone (22 mg, 156.94 µmol), DMF (2 mL), and water (0.1 mL) were added to a microwave tube. The microwave tube was sealed, and kept at 130° C. for microwave reaction for 40 min. The reaction mixture was filtered, and washed with ethyl acetate (20 mL). The filtrate was concentrated under reduced pressure. 1M hydrochloric acid was added to the residue obtained from the concentration (pH=6-7), and the resulting mixture was extracted with ethyl acetate (30 mL). The organic phase was washed with saturated brine (30 mL), dried over anhydrous sodium sulfate, and concentrated under reduced pressure to obtain Compound 13-4. LCMS (ESI) m/z: 410 (M+1).

5) Synthesis of Compound 13-5

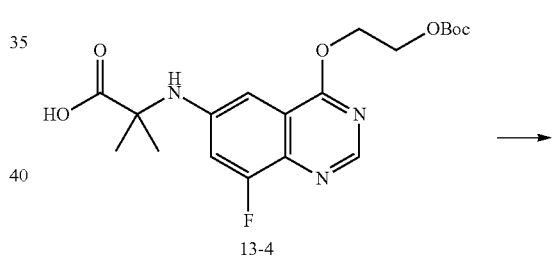

13-4

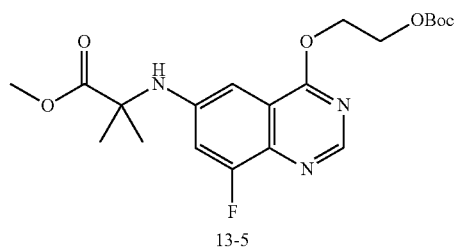

13-5

A solution of TMSCHN$_2$ in n-hexane (2M, 1 mL) was added to a solution of Compound 13-4 (290 mg, 708.34 µmol) in dichloromethane (5 mL) and methanol (0.5 mL). The resulting reaction mixture was stirred at 10° C. for 1 h. The reaction mixture was concentrated under reduced pressure. The residue obtained from the concentration was purified by a preparative TLC plate to obtain Compound 13-5. LCMS (ESI) m/z: 424 (M+1).

6) Synthesis of Compound 13-6

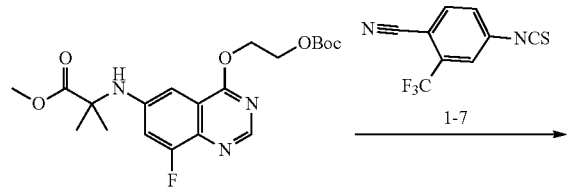

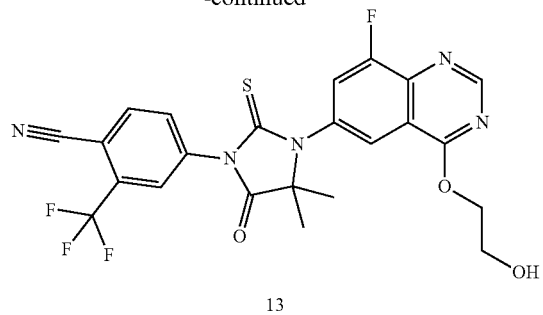

13-5

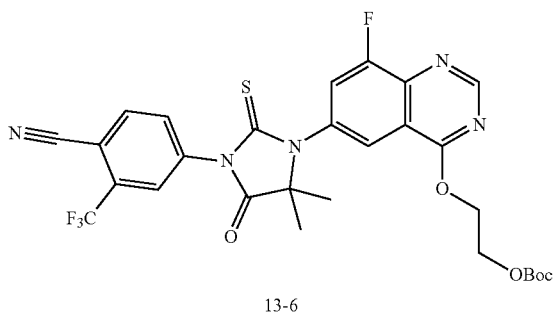

13-6

A mixed solution of Compound 13-5 (100 mg, 236.17 µmol), Compound 1-7 (270 mg, 1.18 mmol), methylbenzene (2 mL), and DMF (0.5 mL) was heated to 110° C., and stirred for 16 h. Compound 1-7 (270 mg, 1.18 mmol) was supplemented to the reaction mixture. The reaction mixture was further stirred at 110° C. for 16 h. Methanol (2 mL) was added to the reaction mixture, which was stirred for 30 min, and then concentrated under reduced pressure. The residue obtained from the concentration was purified by a preparative TLC plate to obtain Compound 13-6. LCMS (ESI) m/z: 620 (M+1).

7) Synthesis of Compound 13

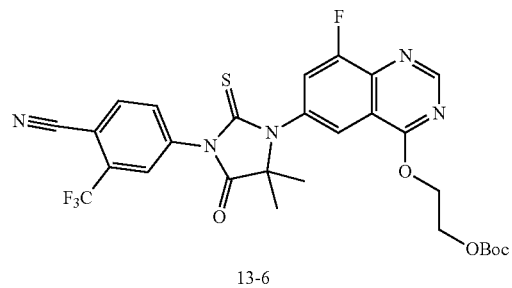

13-6

13

Trifluoroacetic acid (0.4 mL) was added to a solution of Compound 13-6 (100 mg, 161.40 µmol) in dichloromethane (2 mL). The resulting reaction mixture was stirred at 10° C. for 2 h. A saturated aqueous solution of sodium bicarbonate was added to the reaction mixture (pH about 7), which was extracted with dichloromethane (30 mL). The organic phase was washed with saturated brine (30 mL), dried over anhydrous sodium sulfate, and concentrated under reduced pressure. The residue obtained from the concentration was purified by a preparative TLC plate, and then purified by preparative HPLC to obtain Compound 13. $^1$H NMR (400 MHz, CDCl$_3$) δ ppm 8.94 (s, 1H), 8.06-7.94 (m, 3H), 7.86 (dd, J=1.9, 8.2 Hz, 1H), 7.53 (dd, J=2.1, 9.9 Hz, 1H), 4.86-4.76 (m, 2H), 4.17-4.07 (m, 2H), 2.47 (br t, J=5.5 Hz, 1H), 1.69 (s, 6H); LCMS (ESI) m/z: 520 (M+1).

Example 13 Synthesis of Compound 14

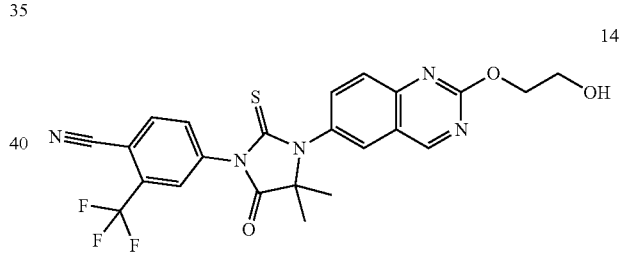

14

1) Synthesis of Compound 14-2

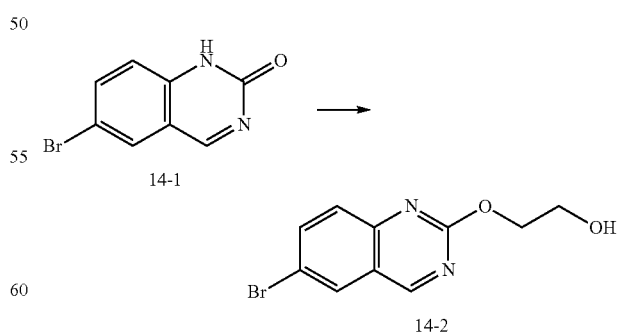

Phosphorus oxychloride (182 mg, 1.18 mmol, 0.11 mL) and N,N-diisopropylethylamine (29 mg, 224.40 µmol) were added to a mixed solution of Compound 14-1 (50 mg, 222.18 µmol) and anhydrous methylbenzene (1 mL). The resulting reaction mixture was stirred at 10° C. for 0.5 h, heated to 110° C., and stirred for 5 h. The reaction mixture was concentrated under reduced pressure. Ethanediol (138 mg, 2.22 mmol) and triethylamine (73 mg, 722.08 μmol, 0.1 mL) were added to the residue obtained from the concentration. The resulting mixed solution was stirred at 110° C. for 16 h. The reaction mixture was concentrated under reduced pressure. The residue obtained from the concentration was diluted with dichloromethane (20 mL), and washed with water (10 mL) and saturated brine (15 mL). The organic phase was dried over anhydrous sodium sulfate, and concentrated under reduced pressure to obtain Compound 14-2. LCMS (ESI) m/z: 269 (M+1).

2) Synthesis of Compound 14-3

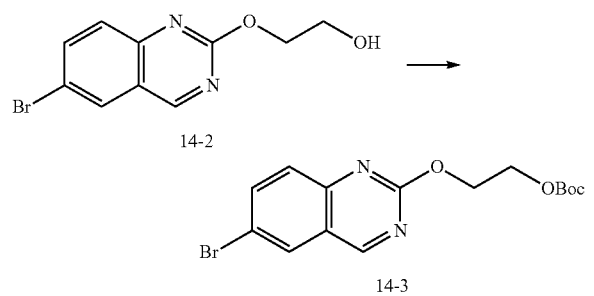

diBoc (30 mg, 137.46 μmol), triethylamine (23 mg, 227.30 μmol), and 4-dimethylaminopyridine (2 mg, 16.37 μmol) were added to a mixed solution of Compound 14-2 (30 mg, 111.49 μmol) in dichloromethane (1 mL). The resulting reaction mixture was stirred at 10° C. for 1 h. The reaction mixture was concentrated under reduced pressure. The residue obtained from the concentration was purified by a preparative TLC plate to obtain Compound 14-3. LCMS (ESI) m/z: 391 (M+23).

3) Synthesis of Compound 14-4

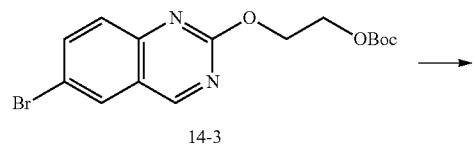

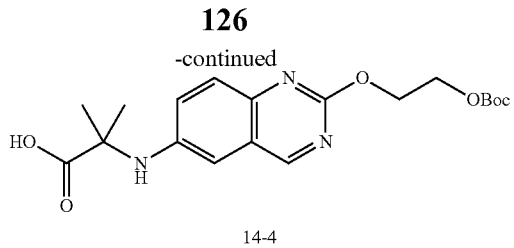

Compound 14-3 (20 mg, 54.17 μmol), Compound 1-4 (9 mg, 87.28 μmol), potassium carbonate (20 mg, 144.63 μmol), cuprous chloride (2 mg, 20.20 μmol), 2-acetylcyclohexanone (2 mg, 14.27 μmol), DMF (1 mL), and water (0.05 mL) were added to a microwave tube. The microwave tube was sealed, and kept at 130° C. for microwave reaction for 30 min. The reaction mixture was filtered, and washed with ethyl acetate (10 mL). The filtrate was concentrated under reduced pressure. 1N hydrochloric acid was added to the residue obtained from the concentration (pH 6-7), which was extracted with ethyl acetate (20 mL). The organic phase was washed with saturated brine (20 mL), dried over anhydrous sodium sulfate, and concentrated under reduced pressure to obtain Compound 14-4. LCMS (ESI) m/z: 392 (M+1).

4) Synthesis of Compound 14-5

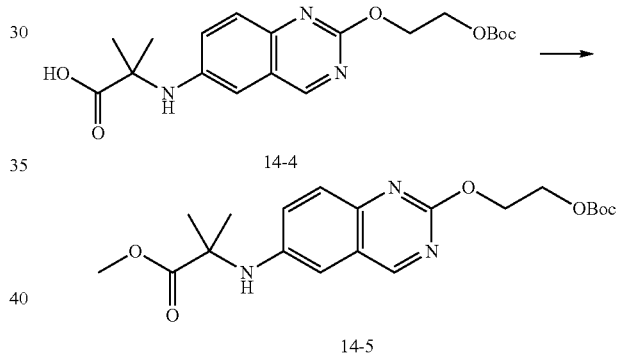

A solution of TMSCHN$_2$ in n-hexane (2M, 0.1 mL) was added to a solution of Compound 14-4 (25 mg, 63.87 μmol) in dichloromethane (1 mL) and methanol (0.1 mL). The resulting reaction mixture was stirred at 10° C. for 1 h. The reaction mixture was concentrated under reduced pressure. The residue obtained from the concentration was purified by a preparative TLC plate to obtain Compound 14-5. LCMS (ESI) m/z: 428 (M+23).

5) Synthesis of Compound 14-6

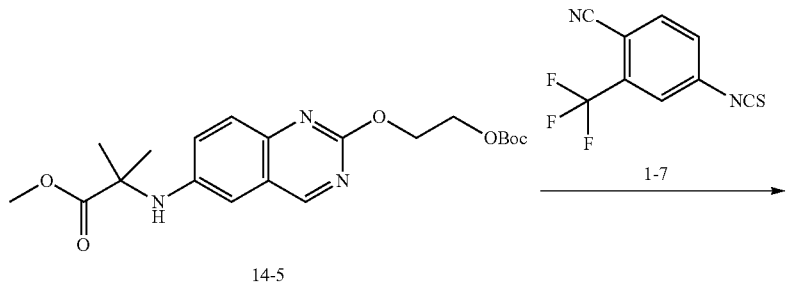

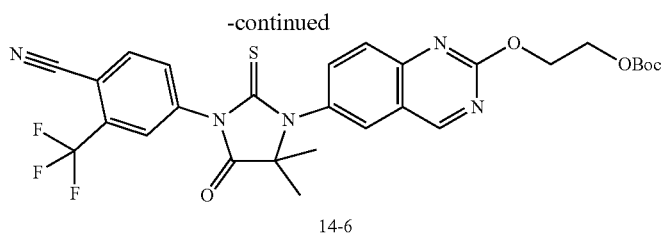

14-6

A mixed solution of Compound 14-5 (10 mg, 24.66 μmol), Compound 1-7 (28 mg, 122.81 μmol), methylbenzene (1 mL), and DMF (0.2 mL) was heated to 110° C., and stirred for 16 h. Compound 1-7 (28 mg, 122.81 μmol) was supplemented to the reaction mixture, and the resulting reaction mixture was further stirred at 110° C. for 8 h. Methanol (1 mL) was added to the reaction mixture, which was stirred for 30 min, and then concentrated under reduced pressure. The residue obtained from the concentration was purified by a preparative TLC plate to obtain Compound 14-6. LCMS (ESI) m/z: 624 (M+23).

6) Synthesis of Compound 14

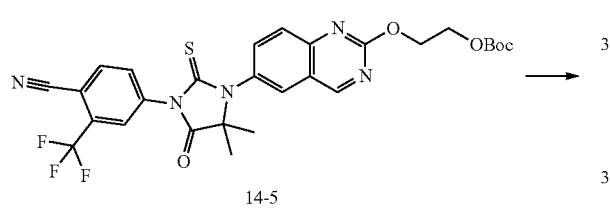

14-5

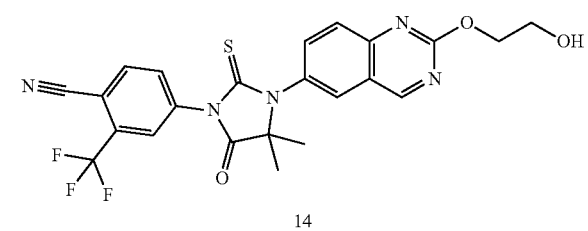

14

Trifluoroacetic acid (0.1 mL) was added to a solution of Compound 14-6 (10 mg, 16.62 μmol) in dichloromethane (1 mL). The resulting reaction mixture was stirred at 15° C. for 1 h. A saturated aqueous solution of sodium bicarbonate was added to the reaction mixture (pH about 8), and the resulting mixture was extracted with dichloromethane (10 mL). The organic phase was washed with saturated brine (10 mL), dried over anhydrous sodium sulfate, and concentrated under reduced pressure. The residue obtained from the concentration was purified by a preparative TLC plate to obtain Compound 14. $^1$H NMR (400 MHz, CDCl$_3$) δ ppm 9.33 (s, 1H), 8.04-7.96 (m, 3H), 7.90-7.83 (m, 2H), 7.76 (dd, J=2.3, 8.8 Hz, 1H), 4.76-4.65 (m, 2H), 4.14-4.02 (m, 2H), 2.67 (br s, 1H), 1.67 (s, 6H); LCMS (ESI) m/z: 502 (M+1).

Example 14 Synthesis of Compound 15

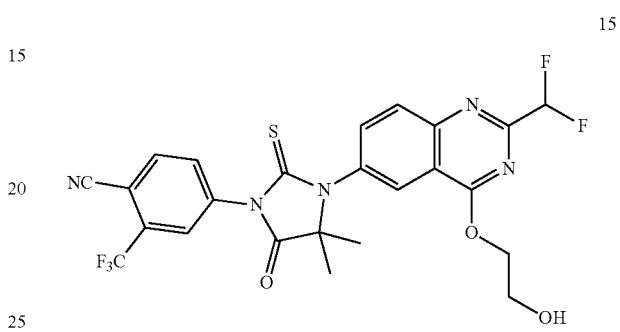

15

1) Synthesis of Compound 15-1

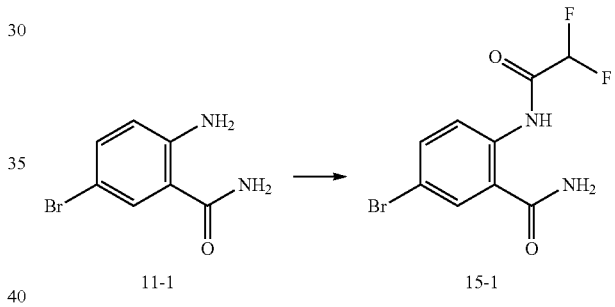

11-1        15-1

At room temperature (10° C.), 0-(7-azabenzotriazol-1-yl)-N,N,N',N'-tetramethyluronium hexafluorophosphate (7.82 g, 20.55 mmol) was added to a solution of Compound 11-1 (3.40 g, 15.81 mmol), 2,2-difluoroacetic acid (3.04 g, 31.62 mmol), and triethylamine (4.80 g, 47.43 mmol) in dichloromethane (50 mL). The reaction mixture reacted at 10° C. for 12 h. The reaction mixture was directly concentrated to obtain a crude product. The crude product was purified by flash column chromatography to obtain Compound 15-1. $^1$H NMR (400 MHz, CDCl$_3$) δ ppm 12.72 (br s, 1H), 8.34 (br d, J=8.78 Hz, 1H), 8.05 (br s, 1H), 7.87 (br s, 1H), 7.41 (br d, J=9.03 Hz, 1H), 6.57 (br s, 1H), 6.01-5.65 (m, 1H).

2) Synthesis of Compound 15-2

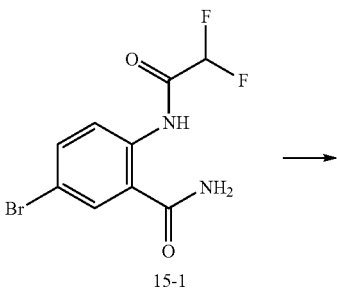

15-1

-continued

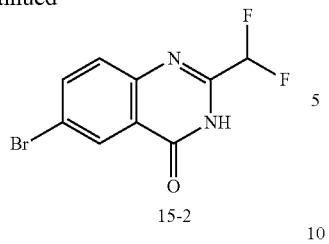

15-2

Sodium methoxide (1.77 g, 32.76 mmol) was added to a solution of Compound 15-1 (3.20 g, 10.92 mmol) in methanol (10 mL) at room temperature (10° C.). The reaction mixture reacted at 30° C. for 12 h. The reaction mixture was cooled to room temperature, and concentrated to obtain a crude product. The crude product was purified by flash column chromatography to obtain Compound 15-2. $^1$H NMR (400 MHz, CDCl$_3$) δ ppm 12.69 (br s, 1H), 8.28 (s, 1H), 7.75 (br d, J=8.78 Hz, 1H), 7.52 (d, J=8.53 Hz, 1H), 6.51-6.18 (m, 1H); LCMS (ESI) m/z: 277 (M+3).

3) Synthesis of Compound 15-3

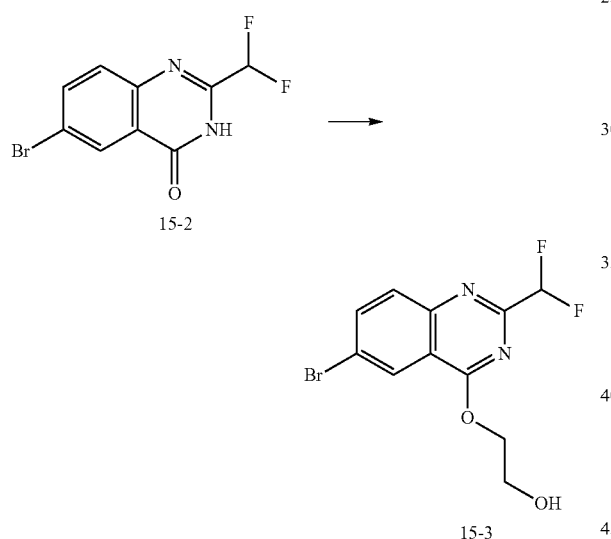

With reference to the synthesis of Compound 11-4, Compound 15-3 was prepared with Compound 15-2 as the starting material. LCMS (ESI) m/z: 321 (M+3).

4) Synthesis of Compound 15-4

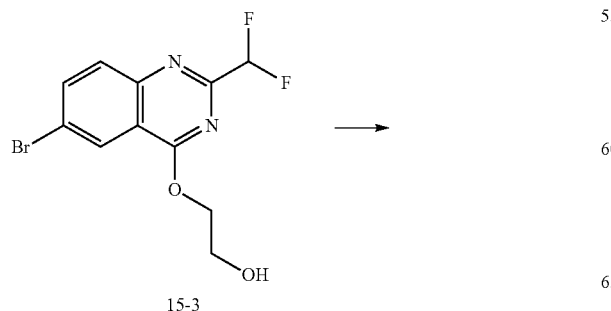

-continued

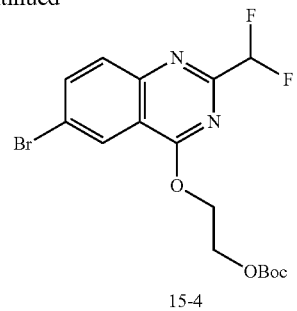

15-4

With reference to the synthesis of Compound 11-5, Compound 15-4 was prepared with Compound 15-3 as the starting material. LCMS (ESI) m/z: 419 (M+1).

5) Synthesis of Compound 15-5

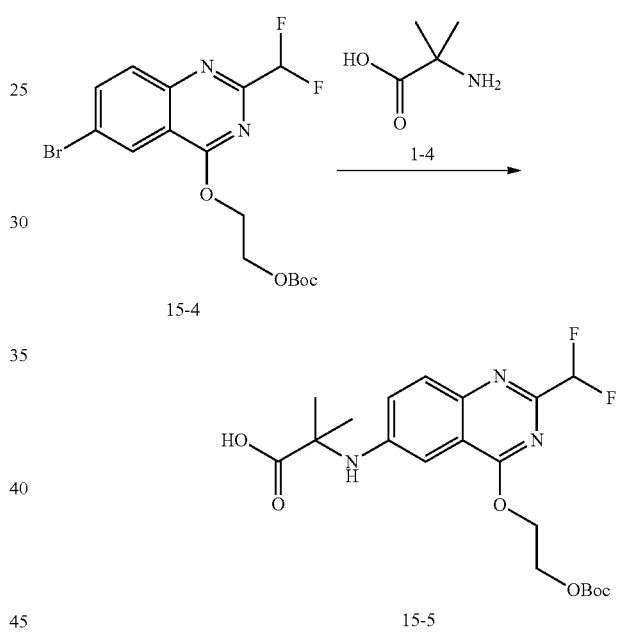

With reference to the synthesis of Compound 11-6, Compound 15-5 was prepared with Compound 15-4 as the starting material. LCMS (ESI) m/z: 442 (M+1).

6) Synthesis of Compound 15-6

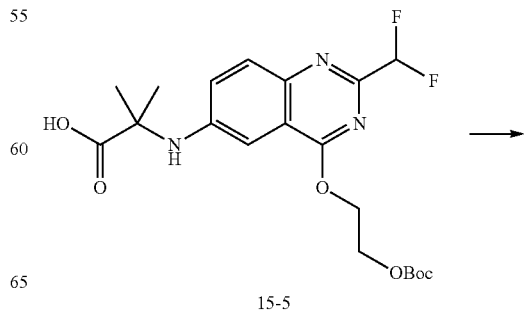

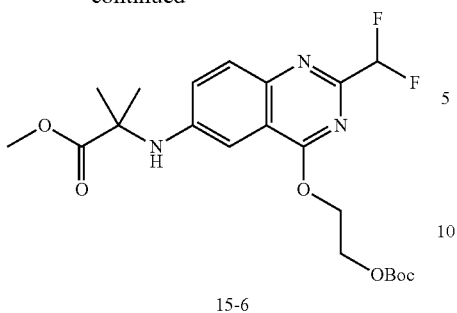

15-6

With reference to the synthesis of Compound 11-7, Compound 15-6 was prepared with Compound 15-5 as the starting material. LCMS (ESI) m/z: 456 (M+1).

7) Synthesis of Compound 15-7

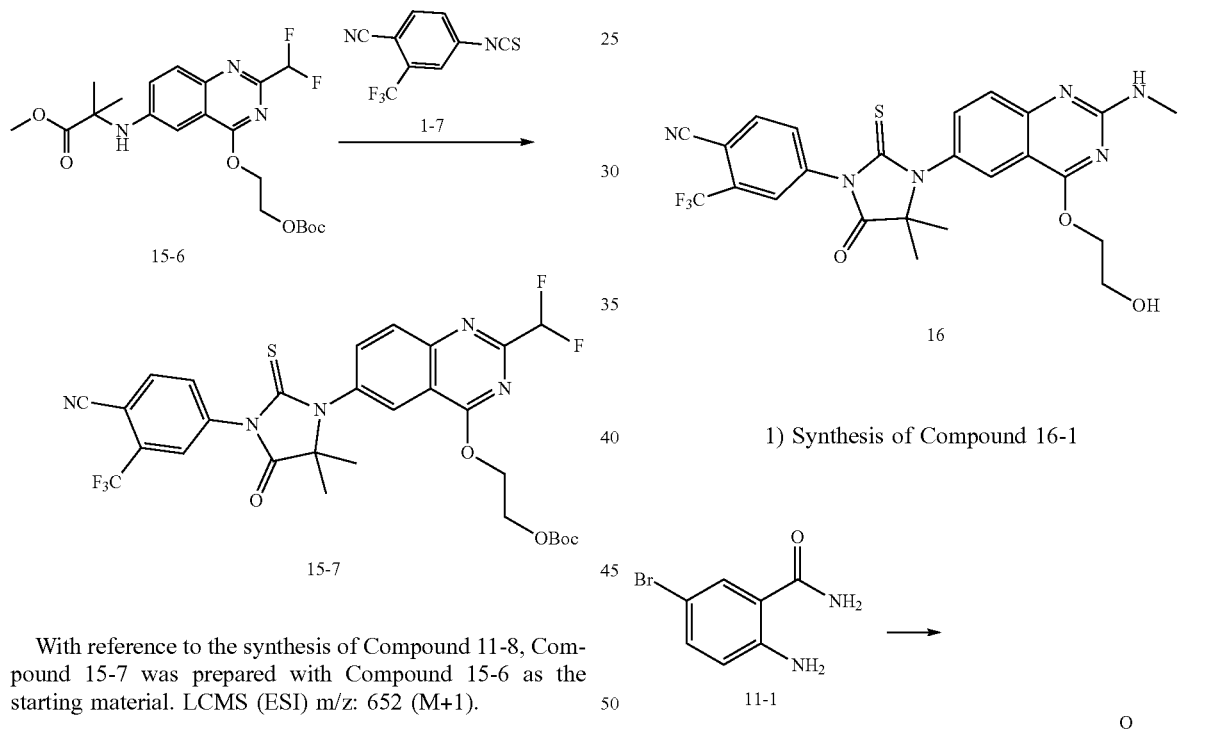

15-7

With reference to the synthesis of Compound 11-8, Compound 15-7 was prepared with Compound 15-6 as the starting material. LCMS (ESI) m/z: 652 (M+1).

8) Synthesis of Compound 15

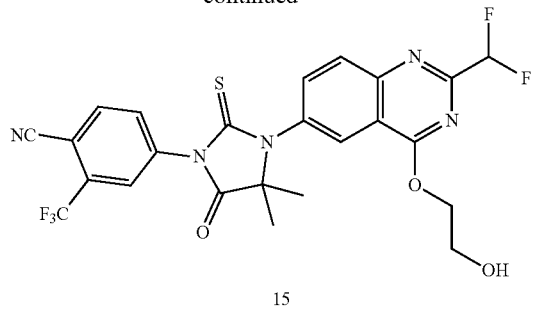

15

With reference to the synthesis of Compound 11, Compound 15 was prepared with Compound 15-7 as the starting material. $^1$H NMR (400 MHz, CDCl$_3$) δ ppm 8.26-8.20 (m, 2H), 8.06-8.00 (m, 2H), 7.91-7.83 (m, 2H), 6.85-6.52 (m, 1H), 4.92-4.87 (m, 2H), 4.15 (br d, J=3.8 Hz, 2H), 2.40 (br s, 1H), 1.70 (s, 6H); LCMS (ESI) m/z: 552 (M+1).

Example 15 Synthesis of Compound 16

16

1) Synthesis of Compound 16-1

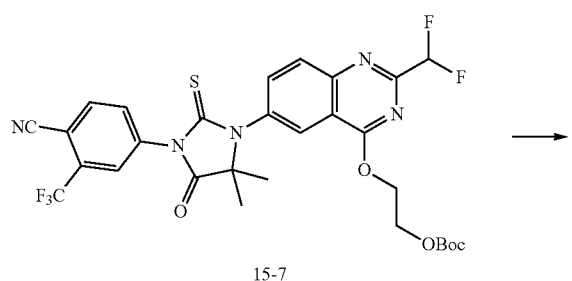

CDI (11.31 g, 69.75 mmol) was added to a turbid liquid of Compound 11-1 (10 g, 46.50 mmol) in tetrahydrofuran (100 mL). The resulting mixture was stirred at 75° C. for 18 h. The reaction mixture was cooled to room temperature, and a solid precipitated, and was filtered. The filter cake was washed with tetrahydrofuran (10 mL×3). The filter cake was concentrated to dryness under reduced-pressure to obtain Compound 16-1. $^1$H NMR (400 MHz, DMSO-d6) δ ppm 11.47-11.16 (m, 2H), 7.92 (d, J=2.3 Hz, 1H), 7.77 (dd, J=2.3, 8.8 Hz, 1H), 7.10 (d, J=8.5 Hz, 1H).

2) Synthesis of Compound 16-2

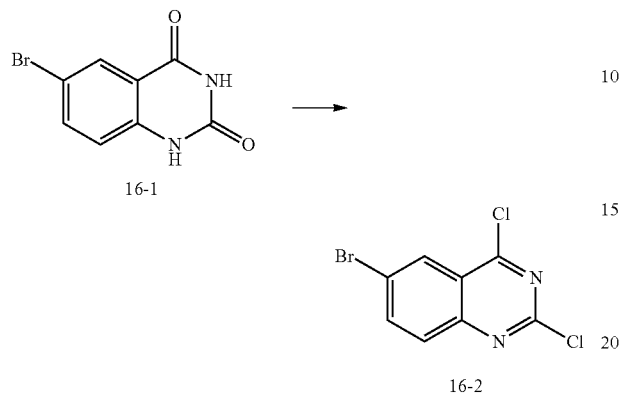

N,N-diisopropylethylamine (5.87 g, 45.43 mmol) was added dropwise to a solution of Compound 16-1 (7.3 g, 30.29 mmol) in phosphorus oxychloride (100 mL). The resulting mixture was stirred at 110° C. for 2 h. The reaction mixture was cooled to room temperature, diluted with dichloromethane (400 mL), slowly added to water (500 mL) under stirring, extracted with dichloromethane (50 mL×3), and washed with saturated brine (50 mL×3). The organic phases were combined, dried over anhydrous sodium sulfate, and filtered. The filtrate was concentrated under reduced pressure to obtain Compound 16-2. LCMS (ESI) m/z: 279 (M+3).

3) Synthesis of Compound 16-3

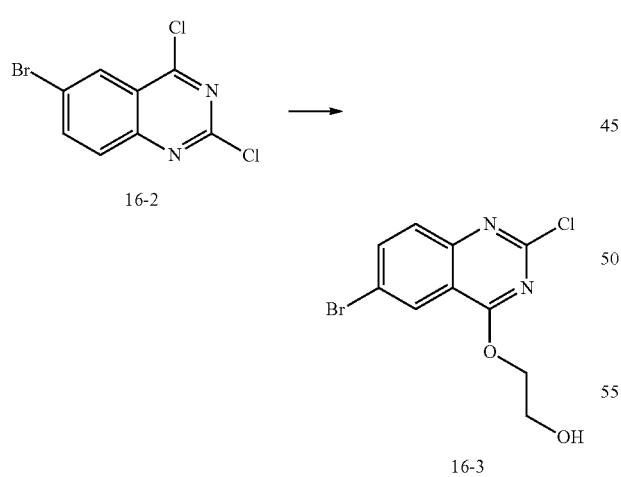

Sodium hydride (173 mg, 4.32 mmol, 60% purity) was added to a solution of Compound 16-2 (1 g, 3.60 mmol) and ethanediol (268 mg, 4.32 mmol) in tetrahydrofuran (50 mL). The mixture was stirred at 10° C. for 1 h. The reaction mixture was quenched with water (20 mL), and the resulting mixture was extracted with dichloromethane (20 mL×3). The combined organic phase was washed with saturated brine (20 mL), dried over anhydrous sodium sulfate, filtered, and concentrated to obtain Compound 16-3. LCMS (ESI) m/z: 305 (M+3).

4) Synthesis of Compound 16-4

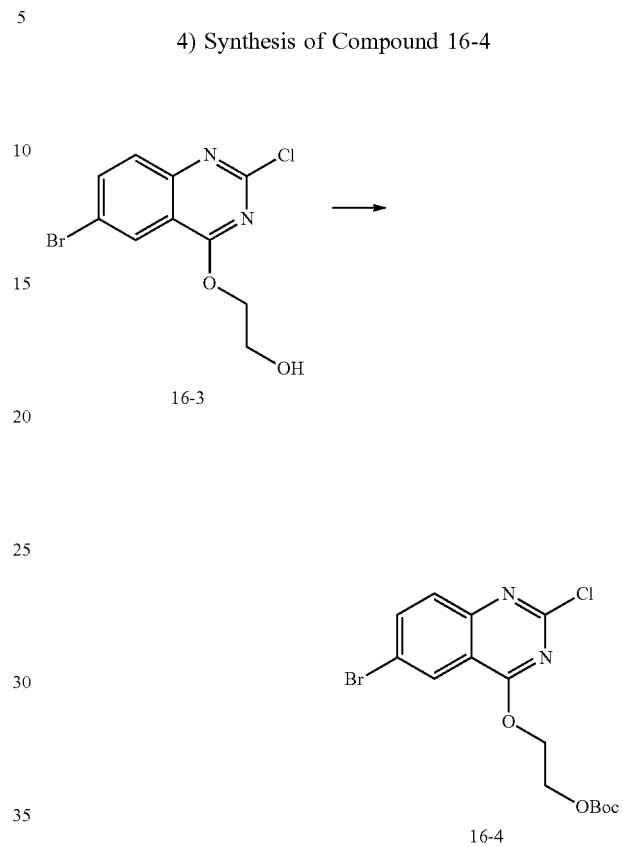

At 10° C., triethylamine (1.10 g, 10.87 mmol) was added to a mixture of Compound 16-3 (1.1 g, 3.62 mmol), diBoc (1.19 g, 5.44 mmol), and 4-dimethylaminopyridine (88.55 mg, 724.78 μmol) in dichloromethane (20 mL). The reaction mixture reacted at 10° C. for 1 h. The reaction mixture was washed with 1M dilute hydrochloric acid (20 mL) and water (20 mL×2) respectively, dried over anhydrous sodium sulfate, filtered, and concentrated to obtain Compound 16-4. ¹HNMR (400 MHz, CDCl₃) δ ppm 8.23 (d, J=2.26 Hz, 1H), 7.66 (d, J=9.03 Hz, 1H), 7.85 (dd, J=8.78, 2.26 Hz, 1H), 4.75 (dt, J=4.27, 2.38 Hz, 2H), 4.48 (dt, J=4.20, 2.29 Hz, 2H), 1.44 (s, 9H).

5) Synthesis of Compound 16-5

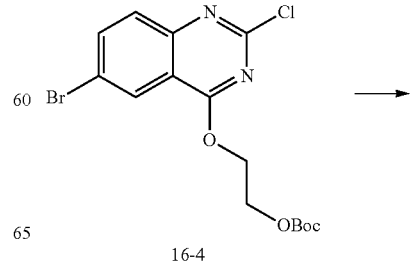

7) Synthesis of Compound 16-7

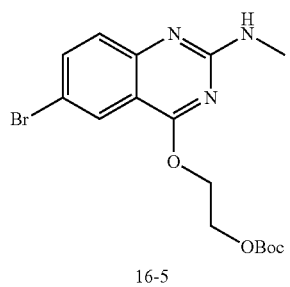

16-5

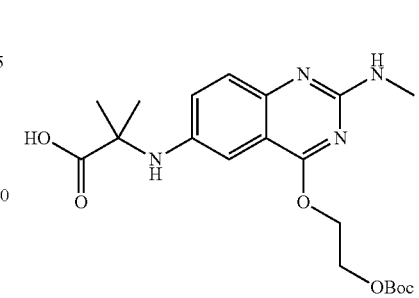

16-6

A solution of methylamine in tetrahydrofuran (2.0 M, 2.5 mL) was added to a solution of Compound 16-4 (1 g, 2.48 mmol) in tetrahydrofuran (3 mL) at 10° C. The reaction mixture was kept at 80° C. for microwave reaction for 0.5 h. The reaction mixture was directly concentrated to obtain a crude product. The crude product was purified by flash column chromatography to obtain Compound 16-5. LCMS (ESI) m/z: 400 (M+3).

6) Synthesis of Compound 16-6

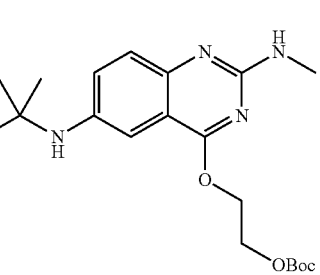

16-7

With reference to the synthesis of Compound 11-7, Compound 16-7 was prepared with Compound 16-6 as the starting material. LCMS (ESI) m/z: 435 (M+1).

8) Synthesis of Compound 16-8

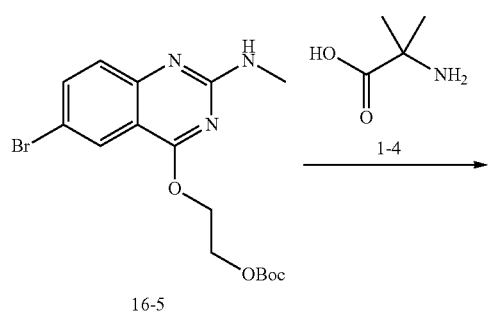

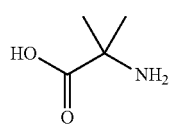

16-5

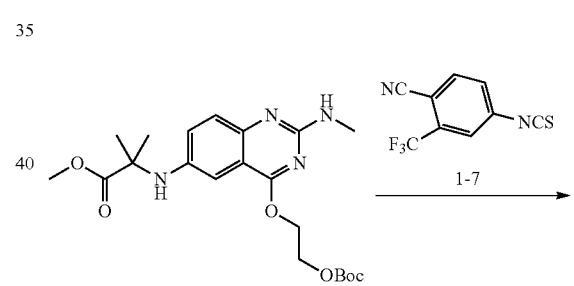

16-7

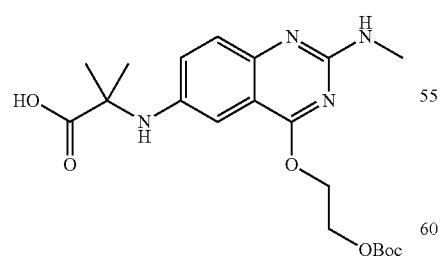

16-6

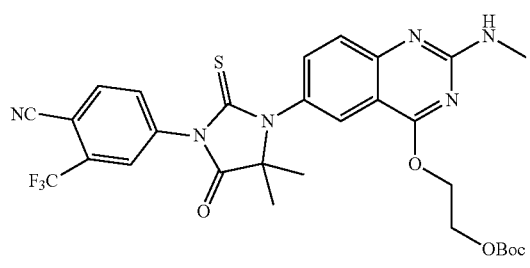

16-8

With reference to the synthesis of Compound 11-6, Compound 16-6 was prepared with Compound 16-5 as the starting material. LCMS (ESI) m/z: 421 (M+1).

With reference to the synthesis of Compound 11-8, Compound 16-8 was prepared with Compound 16-7 as the starting material. LCMS (ESI) m/z: 631 (M+1).

9) Synthesis of Compound 16

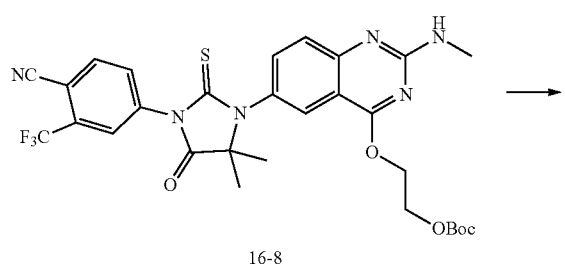

16-8

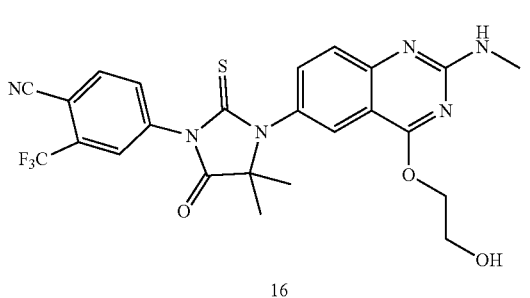 [SMILES: CNc1nc(OCCO)c2cc(N3C(=S)N(c4ccc(C#N)c(C(F)(F)F)c4)C(=O)C3(C)C)ccc2n1]

16

With reference to the synthesis of Compound 11, Compound 16 was prepared with Compound 16-8 as the starting material. $^1$H NMR (400 MHz, CDCl$_3$) δ ppm 7.99-7.87 (m, 2H), 7.85-7.74 (m, 2H), 7.58 (br d, J=8.03 Hz, 1H), 7.42 (dd, J=8.78, 2.26 Hz, 1H), 4.59 (br s, 2H), 4.09-3.85 (m, 2H), 3.08-2.98 (m, 3H), 1.56 (s, 6H); LCMS (ESI) m/z: 531 (M+1).

Example 16 Synthesis of Compound 17

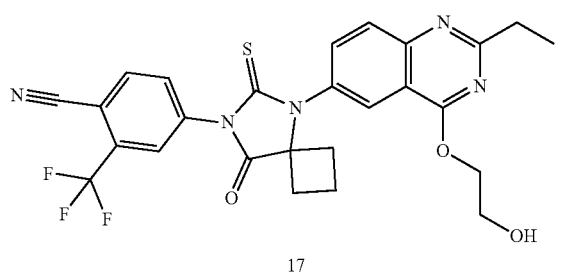 [SMILES: CCc1nc(OCCO)c2cc(N3C(=S)N(c4ccc(C#N)c(C(F)(F)F)c4)C(=O)C34CCC4)ccc2n1]

17

1) Synthesis of Compound 17-1

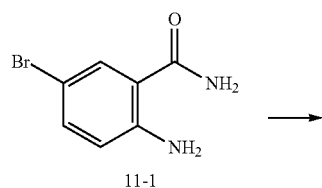

11-1

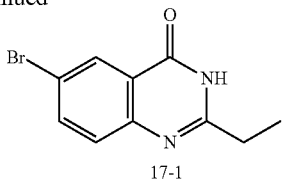

17-1

Propionyl chloride (12.91 g, 139.50 mmol) was added to a solution of Compound 11-1 (10.00 g, 46.50 mmol) in trichloromethane (200 mL) at 20° C. The reaction mixture was heated to 70° C., and reacted for 12 h. The reaction mixture was cooled to room temperature, and concentrated to obtain a crude product. Ethyl acetate (100 mL) was added to the crude product and the resulting mixture was stirred at 25° C. for 0.5 h, and filtered. The collected filter cake was dried in a drying oven to obtain Compound 17-1. LCMS (ESI) m/z: 253 (M+1).

2) Synthesis of Compound 17-2

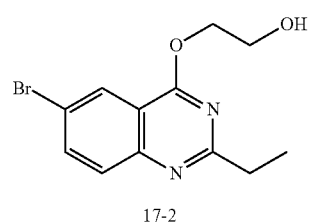

17-1

17-2

2-Bromoethanol (1.24 g, 9.88 mmol, 0.7 mL) was added to a mixed solution of Compound 17-1 (1.00 g, 3.95 mmol), potassium carbonate (1.36 g, 9.88 mmol), benzyltriethylammonium chloride (90 mg, 395.00 μmol), and dimethoxyethane (20 mL). The resulting reaction mixture was heated to 90° C., and stirred for 16 h. 2-Bromoethanol (1.24 g, 9.88 mmol, 0.7 mL) and benzyltriethylammonium chloride (135 mg, 592.70 μmol) were supplemented to the reaction mixture. The resulting reaction mixture was heated to 90° C., and stirred for 16 h. The reaction mixture was filtered, and the filtrate was concentrated under reduced pressure. The residue obtained from the concentration was purified by a silica gel column to obtain Compound 17-2. $^1$H NMR (400 MHz, CDCl$_3$) δ ppm 8.30 (d, J=2.0 Hz, 1H), 7.87 (dd, J=2.3, 8.8 Hz, 1H), 7.75 (d, J=8.8 Hz, 1H), 4.80-4.72 (m, 2H), 4.08 (br d, J=3.5 Hz, 2H), 3.31 (br s, 1H), 2.96 (q, J=7.5 Hz, 2H), 1.40 (t, J=7.7 Hz, 3H).

3) Synthesis of Compound 17-3

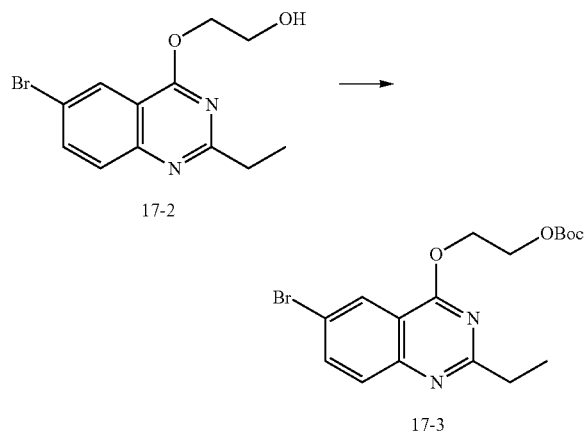

5) Synthesis of Compound 17-5

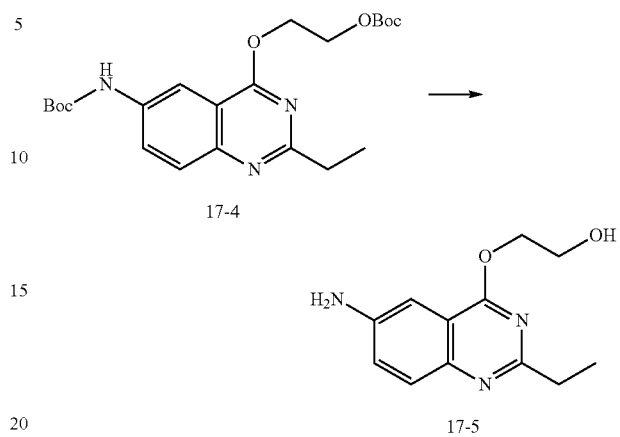

diBoc (171 mg, 783.51 μmol), triethylamine (139 mg, 1.37 mmol, 0.19 mL), and 4-dimethylaminopyridine (10 mg, 81.85 μmol) were added to a mixed solution of Compound 17-2 (200 mg, 673.06 μmol) in dichloromethane (4 mL). The resulting reaction mixture was stirred at 10° C. for 1 h. The reaction mixture was concentrated under reduced pressure. The residue obtained from the concentration was purified by a silica gel column to obtain Compound 17-3. LCMS (ESI) m/z: 397 (M+1).

4) Synthesis of Compound 17-4

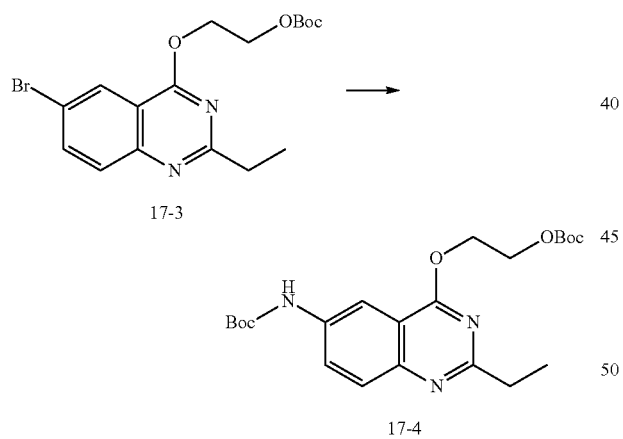

A mixture of Compound 17-3 (130 mg, 327.24 μmol), Boc-NH$_2$ (50 mg, 426.80 μmol), cesium carbonate (266 mg, 816.40 μmol), bis(dibenzylideneacetone)palladium (20 mg, 34.78 μmol), 4,5-bis(diphenylphosphino)-9,9-dimethylxanthene (20 mg, 34.56 μmol), and methylbenzene (2 mL) was added to a microwave tube, and kept at 120° C. for microwave reaction for 0.5 h. The reaction mixture was filtered through Celite. The filtrate was diluted with ethyl acetate (30 mL), washed with water (20 mL) and saturated brine (20 mL), dried over anhydrous sodium sulfate, and concentrated under reduced pressure. The residue obtained from the concentration was purified by a preparative TLC plate to obtain Compound 17-4. LCMS (ESI) m/z: 434 (M+1).

Trifluoroacetic acid (0.2 mL) was added to a solution of Compound 17-4 (85 mg, 196.08 μmol) in dichloromethane (2 mL). The resulting reaction mixture was stirred at 15° C. for 12 h. A saturated aqueous solution of sodium bicarbonate was added to the reaction mixture (pH about 8), which was extracted with dichloromethane (20 mL). The organic phase was washed with saturated brine (20 mL), dried over anhydrous sodium sulfate, and concentrated under reduced pressure. Lithium hydroxide (82 mg, 1.95 mmol) was added to a solution of the resulting yellow oil (64 mg, 194.37 μmol) in tetrahydrofuran (2 mL) and water (0.5 mL). The resulting reaction mixture was stirred at 15° C. for 16 h. The reaction mixture was dried over anhydrous sodium sulfate, and concentrated under reduced pressure to obtain Compound 17-5. LCMS (ESI) m/z: 234 (M+1).

6) Synthesis of Compound 17-6

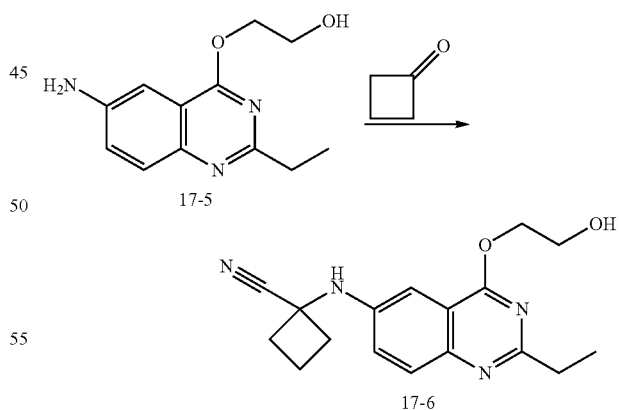

Trimethylsilyl cyanide (25 mg, 252.00 μmol) and zinc chloride (4 mg, 29.32 μmol) were added to a mixed solution of Compound 17-5 (20 mg, 85.74 μmol), cyclobutanone (36 mg, 513.63 μmol), sodium sulfate (50 mg, 352.01 μmol) and tetrahydrofuran (2 mL). The resulting reaction mixture was stirred at 10° C. for 19 h. An aqueous solution of sodium sulfite (5 mL) was added to the reaction mixture, which was extracted with ethyl acetate (5 mL×3). The organic phase was washed with saturated brine (10 mL), dried over anhydrous sodium sulfate, and concentrated under reduced pressure to obtain Compound 17-6. LCMS (ESI) m/z: 313 (M+1).

7) Synthesis of Compound 17-7

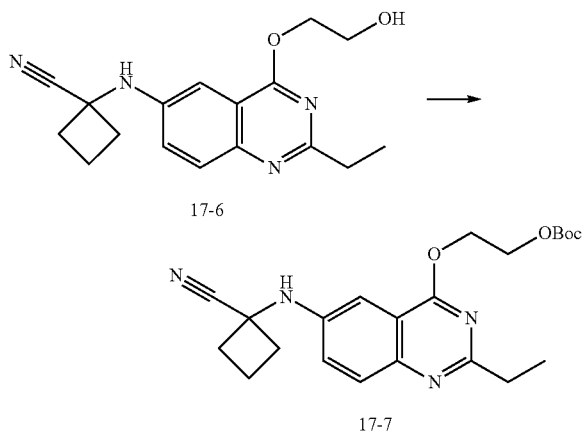

diBoc (23 mg, 105.39 μmol), triethylamine (20 mg, 197.65 μmol), and 4-dimethylaminopyridine (2 mg, 16.37 μmol) were added to a mixed solution of Compound 17-6 (30 mg, 96.04 μmol) in dichloromethane (1 mL). The resulting reaction mixture was stirred at 10° C. for 1 h. The reaction mixture was concentrated under reduced pressure. The residue obtained from the concentration was purified by a preparative TLC plate to obtain Compound 17-7. LCMS (ESI) m/z: 413 (M+1).

8) Synthesis of Compound 17-8

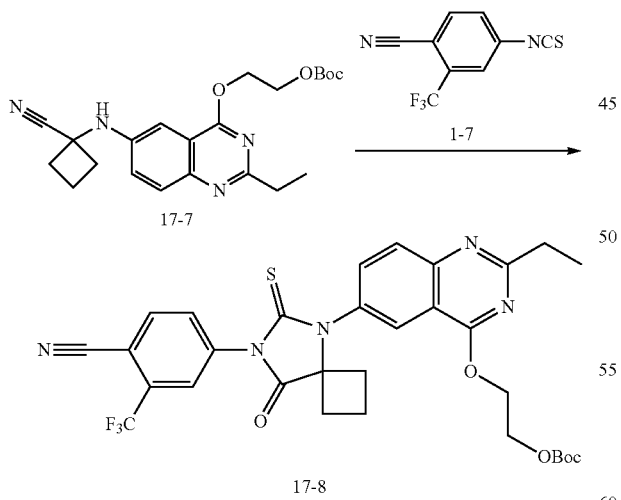

A mixed solution of Compound 17-7 (20 mg, 48.49 μmol), Compound 1-7 (28 mg, 122.70 μmol), methylbenzene (1 mL), and DMF (0.2 mL) was heated to 110° C., and stirred for 16 h. Compound 1-7 (54 mg, 236.64 μmol) was supplemented to the reaction mixture, and the resulting mixture was further stirred at 110° C. for 4 h. Methanol (1 mL) was added to the reaction mixture, which was stirred for 30 min, and then concentrated under reduced pressure. The residue obtained from the concentration was purified by a preparative TLC plate (petroleum ether/ethyl acetate=1/1) to obtain Compound 17-8. LCMS (ESI) m/z: 642 (M+1).

9) Synthesis of Compound 17

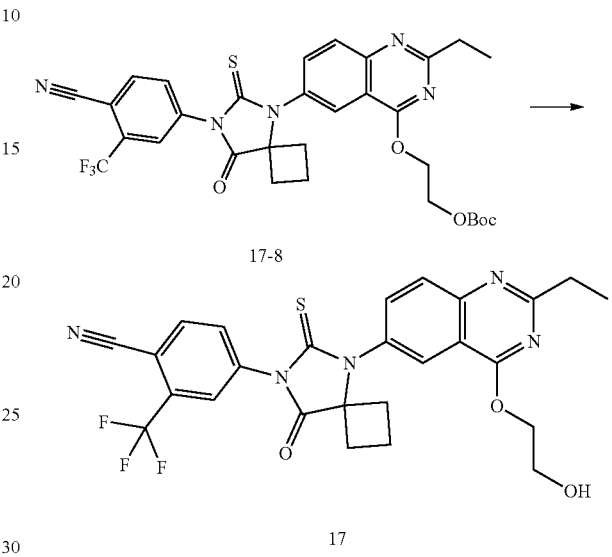

Trifluoroacetic acid (0.2 mL) was added to a solution of Compound 17-8 (30 mg, 46.75 μmol) in dichloromethane (1 mL). The resulting reaction mixture was stirred at 10° C. for 2 h. A saturated aqueous solution of sodium bicarbonate was added to the reaction mixture (pH about 8), which was extracted with dichloromethane (10 mL×3). The organic phase was washed with saturated brine (15 mL), dried over anhydrous sodium sulfate, and concentrated under reduced pressure. The residue obtained from the concentration was purified by a preparative TLC plate to obtain Compound 17. $^1$H NMR (400 MHz, CDCl$_3$) δ ppm 8.09 (d, J=2.3 Hz, 1H), 8.01 (d, J=8.8 Hz, 1H), 7.92 (dd, J=3.1, 5.1 Hz, 2H), 7.80 (dd, J=1.8, 8.3 Hz, 1H), 7.64 (dd, J=2.5, 8.8 Hz, 1H), 4.77-4.69 (m, 2H), 4.07-3.98 (m, 2H), 3.12-2.81 (m, 3H), 2.73-2.62 (m, 2H), 2.59-2.46 (m, 2H), 2.26-2.13 (m, 1H), 1.65-1.55 (m, 1H), 1.38-1.33 (m, 3H); LCMS (ESI) m/z: 542 (M+1).

Example 17 Synthesis of Compound 18

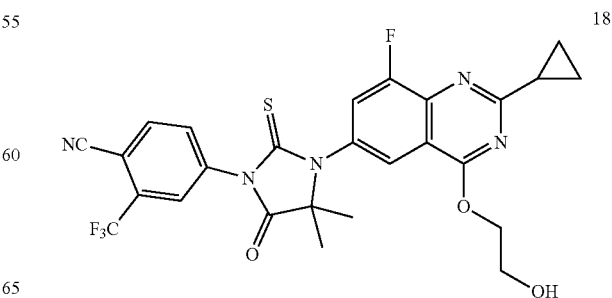

1) Synthesis of Compound 18-1

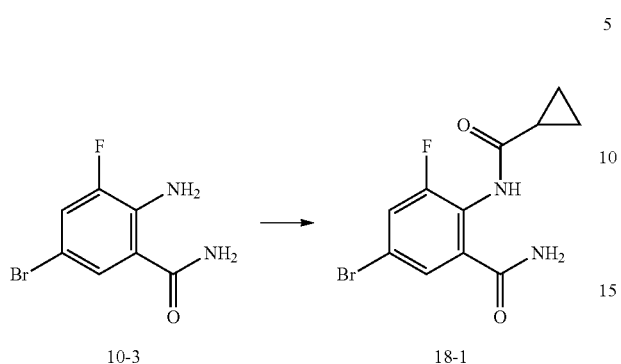

With reference to the synthesis of Compound 11-2, Compound 18-1 was prepared with Compound 10-3 as the starting material. LCMS (ESI) m/z: 301 (M+1).

2) Synthesis of Compound 18-2

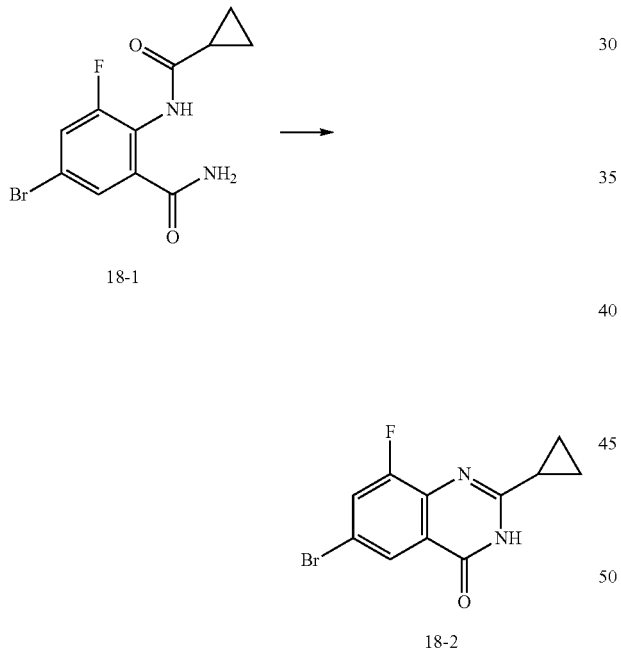

A solution of potassium tert-butoxide in tetrahydrofuran (1M, 81 mL) was added to a solution of Compound 18-1 (8.1 g, 26.90 mmol) in tetrahydrofuran (150 mL). The resulting mixture was stirred at 30° C. for 16 h. The reaction mixture was cooled to room temperature, and concentrated to dryness under reduced pressure. The residue obtained from the concentration was dissolved in water (40 mL), and adjusted to a pH of about 7 with dilute hydrochloric acid (2 mol/L), and a white solid precipitated. The turbid liquid was filtered, and the filter cake was washed with water (10 mL×2). The resulting filter cake was dried in an infrared oven to obtain Compound 18-2. LCMS (ESI) m/z: 285 (M+3).

3) Synthesis of Compound 18-3

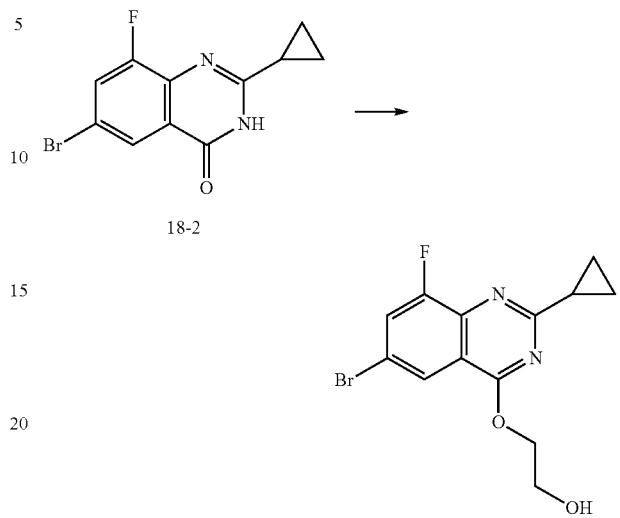

With reference to the synthesis of Compound 11-4, Compound 18-3 was prepared with Compound 18-2 as the starting material. LCMS (ESI) m/z: 329 (M+3).

4) Synthesis of Compound 18-4

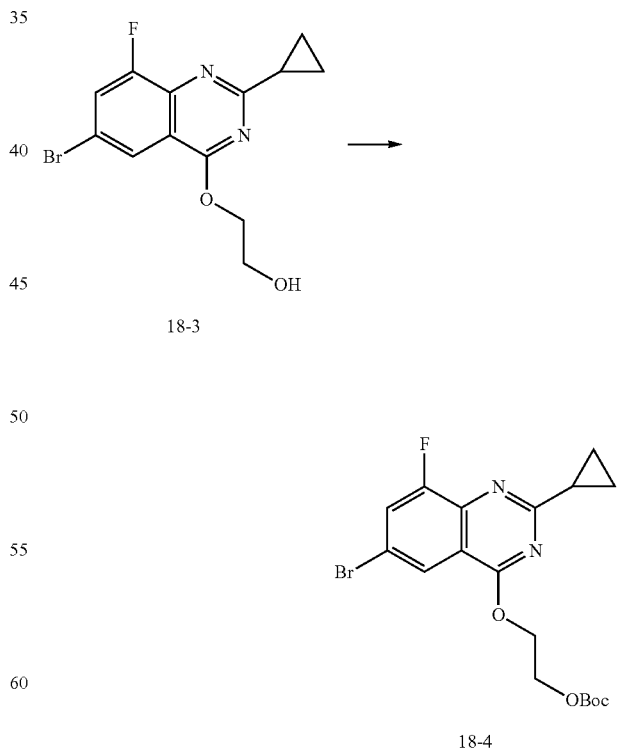

With reference to the synthesis of Compound 11-5, Compound 18-4 was prepared with Compound 18-3 as the starting material. LCMS (ESI) m/z: 429 (M+3).

5) Synthesis of Compound 18-5

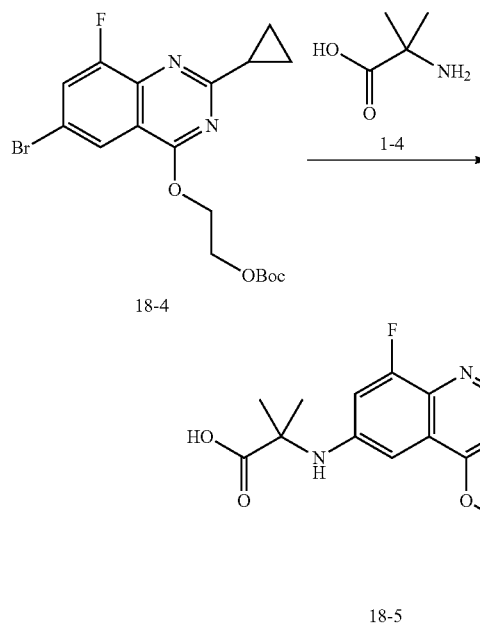

18-4

With reference to the synthesis of Compound 11-6, Compound 18-5 was prepared with Compound 18-4 as the starting material. LCMS (ESI) m/z: 450 (M+1).

6) Synthesis of Compound 18-6

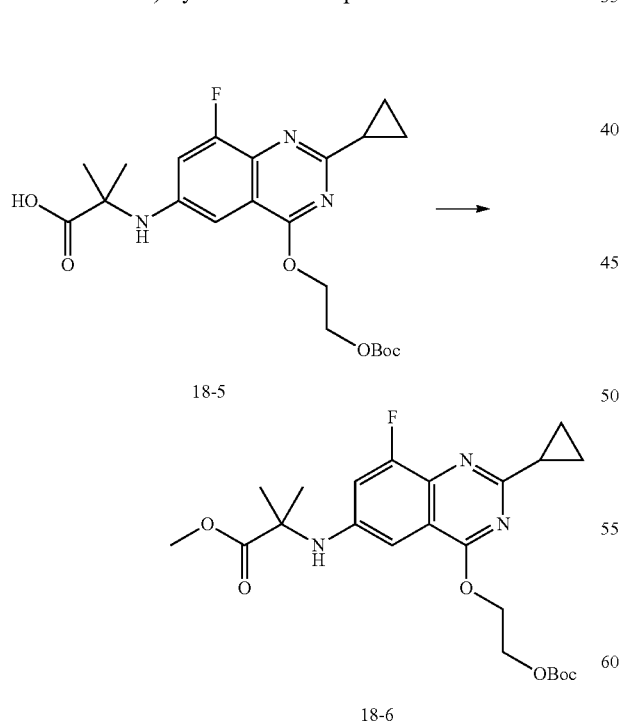

18-5

18-6

With reference to the synthesis of Compound 11-7, Compound 18-6 was prepared with Compound 18-5 as the starting material. LCMS (ESI) m/z: 464 (M+1).

7) Synthesis of Compound 18-7

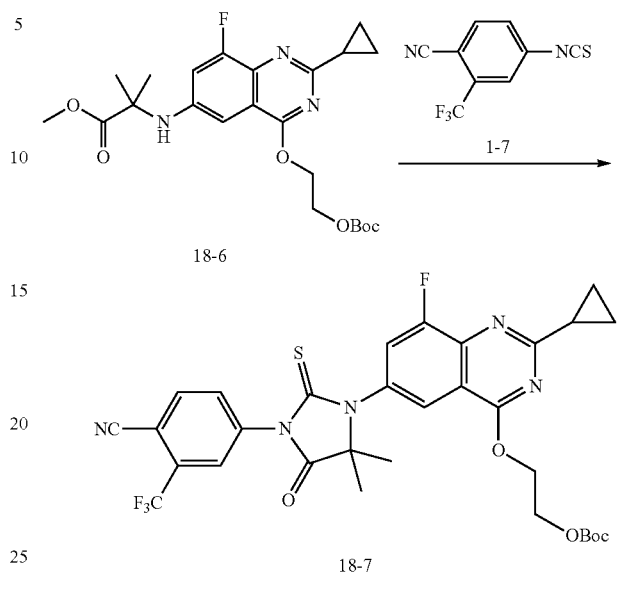

18-6

18-7

With reference to the synthesis of Compound 11-8, Compound 18-7 was prepared with Compound 18-6 as the starting material. LCMS (ESI) m/z: 660 (M+1).

8) Synthesis of Compound 18

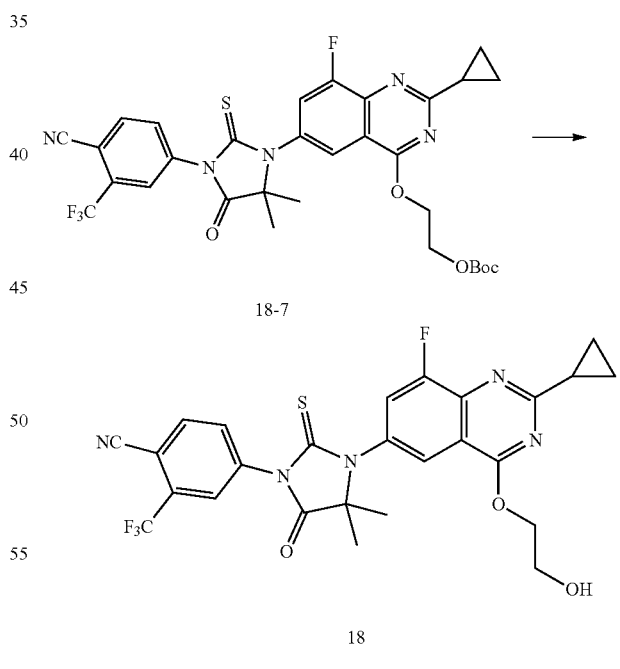

18-7

18

With reference to the synthesis of Compound 11, Compound 18 was prepared with Compound 18-7 as the starting material. $^1$H NMR (400 MHz, CDCl$_3$) δ ppm 8.05-7.96 (m, 2H), 7.90-7.84 (m, 2H), 7.44 (dd, J=2.3, 10.0 Hz, 1H), 4.77-4.70 (m, 2H), 4.10 (br s, 2H), 2.44-2.36 (m, 1H), 2.32 (br s, 1H), 1.68 (s, 6H), 1.31-1.24 (m, 2H), 1.21-1.13 (m, 2H); LCMS (ESI) m/z: 560 (M+1).

Example 18 Synthesis of Compound 19

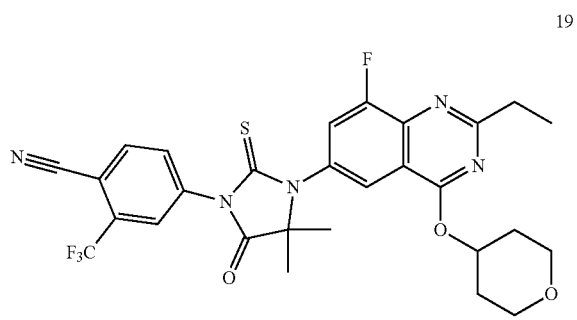 [SMILES: CCc1nc(OC2CCOCC2)c2cc(N3C(=S)N(c4ccc(C#N)c(C(F)(F)F)c4)C(=O)C3(C)C)cc(F)c2n1]

19

1) Synthesis of Compound 19-1

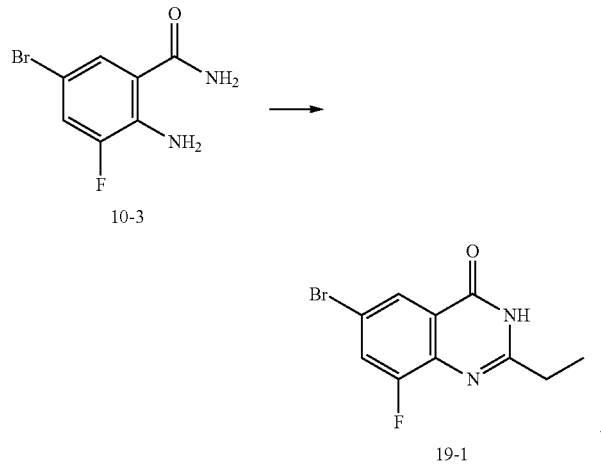

P-methylbenzenesulfonic acid (1 g, 5.26 mmol) was added to a turbid liquid of Compound 10-3 (10 g, 42.44 mmol) and trimethyl orthoformate (60 mL). The resulting turbid liquid was heated to 120° C., and stirred for 32 h. The reaction mixture was concentrated under reduced pressure. The residue obtained from the concentration was purified by a silica gel column to obtain Compound 19-1. LCMS (ESI) m/z: 271 (M+1).

2) Synthesis of Compound 19-2

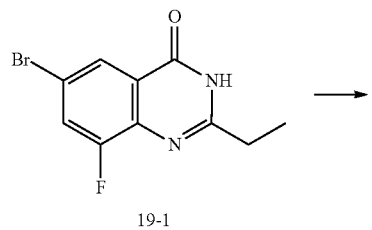

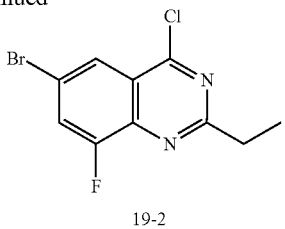

DMF (742 mg, 5.74 mmol, 1 mL) was added to a mixed solution of Compound 19-1 (1 g, 3.69 mmol) and phosphorus oxychloride (19.3 g, 125.87 mmol, 11.7 mL). The resulting reaction mixture was heated to 110° C., and stirred for 4 h. The reaction mixture was concentrated under reduced pressure, diluted with dichloromethane (100 mL), and then slowly poured into water (80 mL). The resulting mixture was extracted with dichloromethane (50 mL×2), and the organic phase was successively washed with a saturated aqueous solution of sodium bicarbonate (pH about 7) and saturated brine (150 mL), dried over anhydrous sodium sulfate, and concentrated under reduced pressure to obtain Compound 19-2. LCMS (ESI) m/z: 289 (M+1).

3) Synthesis of Compound 19-3

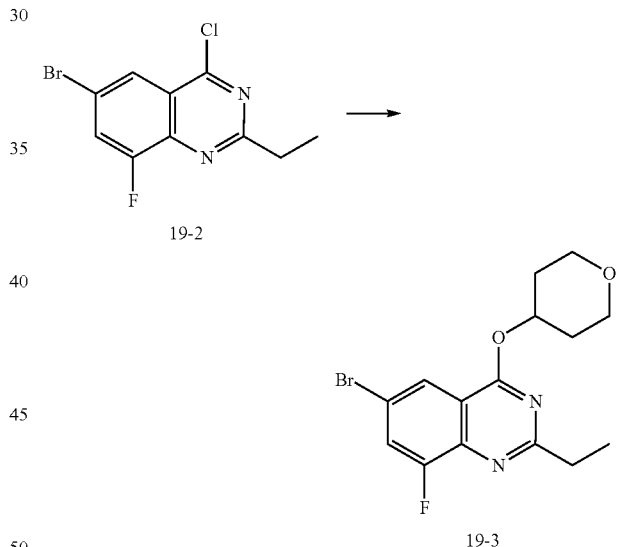

Sodium hydride (166 mg, 4.14 mmol, 60% purity) was added to a solution of Compound 19-2 (1 g, 3.45 mmol) and tetrahydropyran-4-ol (423 mg, 4.14 mmol) in tetrahydrofuran (30 mL). The mixture was stirred at 13° C. for 1 h, and further stirred at 10° C. for 12 h. Tetrahydropyran-4-ol (176 mg, 1.73 mmol) and sodium hydride (69 mg, 1.73 mmol, 60% purity) were supplemented, and the resulting mixture was further stirred at 14° C. for 12 h. The reaction mixture was quenched with water (20 mL), and extracted with dichloromethane (20 mL×3). The combined organic phase was washed with saturated brine (20 mL), dried over anhydrous sodium sulfate, filtered, and concentrated to obtain a crude product. The crude product was purified by flash column chromatography to obtain Compound 19-3. LCMS (ESI) m/z: 355 (M+1).

4) Synthesis of Compound 19-4

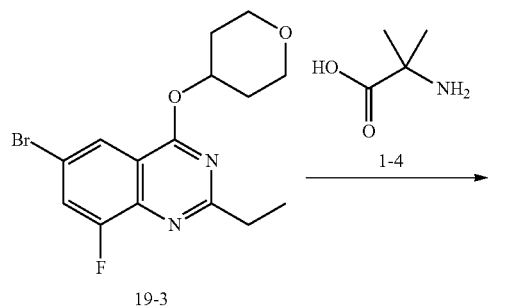

19-3

With reference to the synthesis of Compound 11-6, Compound 19-4 was prepared with Compound 19-3 as the starting material. LCMS (ESI) m/z: 378 (M+1).

5) Synthesis of Compound 19-5

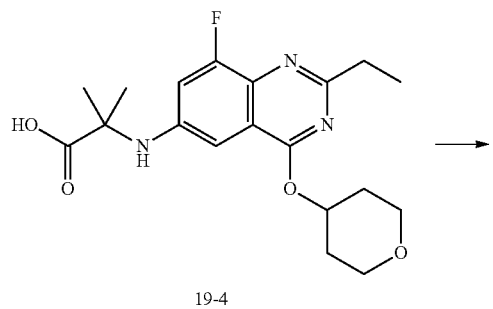

19-4

19-5

With reference to the synthesis of Compound 11-7, Compound 19-5 was prepared with Compound 19-4 as the starting material. LCMS (ESI) m/z: 392 (M+1).

6) Synthesis of Compound 19

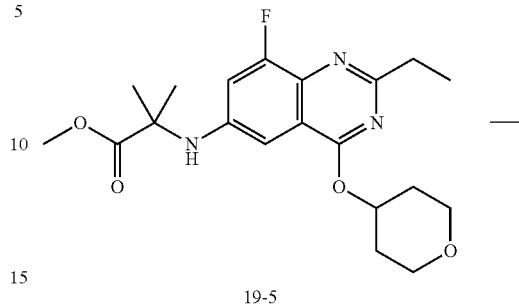

19-5

19

With reference to the synthesis of Compound 11-8, Compound 19 was prepared with Compound 19-5 as the starting material. $^1$H NMR (400 MHz, CDCl$_3$) δ ppm 8.06-7.98 (m, 2H), 7.92-7.83 (m, 2H), 7.47 (dd, J=10.04, 2.26 Hz, 1H), 5.66 (tt, J=8.63, 4.30 Hz, 1H), 4.06 (dt, J=11.80, 4.52 Hz, 2H), 3.70 (ddd, J=11.86, 9.10, 2.89 Hz, 2H), 3.06 (q, J=7.70 Hz, 2H), 2.26-2.16 (m, 2H), 2.02-1.89 (m, 2H), 1.69 (s, 6H), 1.43 (t, J=7.53 Hz, 3H); LCMS (ESI) m/z: 588 (M+1).

Example 19 Synthesis of Compound 20

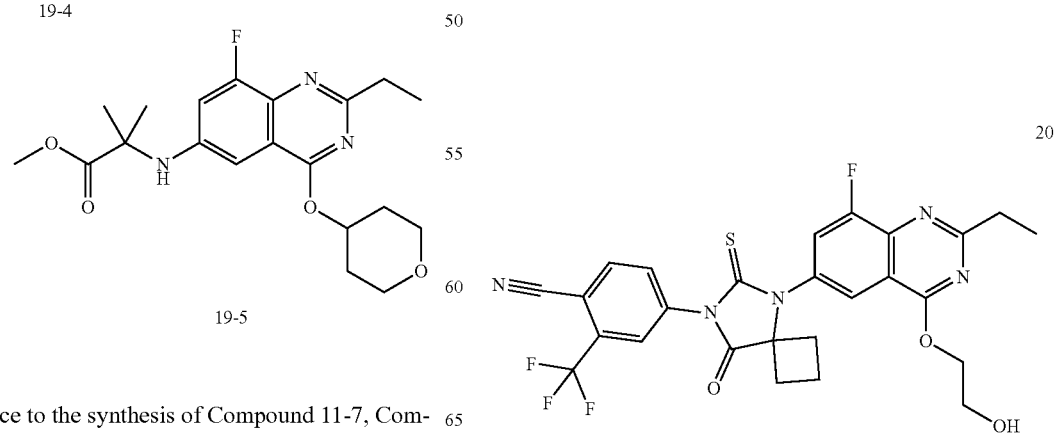

20

1) Synthesis of Compound 20-1

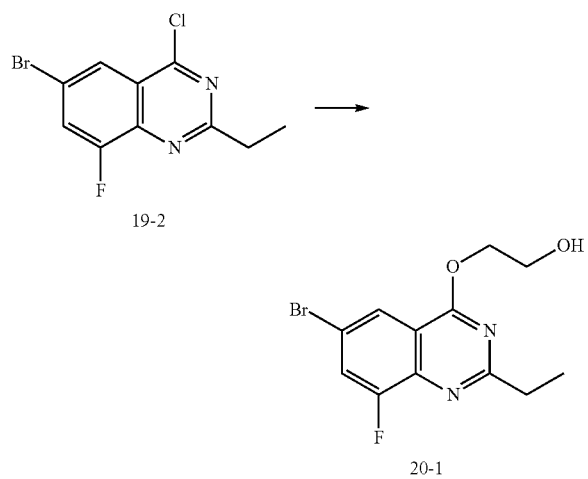

Sodium hydride (170 mg, 4.25 mmol, 60%) was added to a solution of Compound 19-2 (1 g, 3.45 mmol) and ethanediol (266 mg, 4.29 mmol) in tetrahydrofuran (10 mL). The resulting reaction mixture was stirred at 10° C. for 6 h. The reaction mixture was quenched with a saturated aqueous solution of ammonium chloride (100 mL), and then extracted with dichloromethane (100 mL×2). The organic phase was washed with saturated brine (100 mL), dried over anhydrous sodium sulfate, and concentrated under reduced pressure to obtain Compound 20-1. LCMS (ESI) m/z: 315 (M+1).

2) Synthesis of Compound 20-2

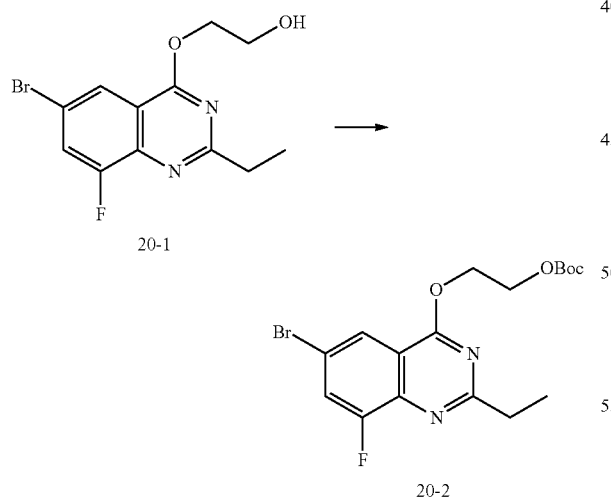

diBoc (835 mg, 3.83 mmol), triethylamine (654 mg, 6.47 mmol, 0.9 mL), and 4-dimethylaminopyridine (46 mg, 376.53 μmol) were added to a mixed solution of Compound 20-1 (1 g, 3.17 mmol) in dichloromethane (10 mL). The resulting reaction mixture was stirred at 10° C. for 1 h. The reaction mixture was concentrated under reduced pressure. The residue obtained from the concentration was purified by a silica gel column to obtain Compound 20-2. $^1$H NMR (400 MHz, CDCl$_3$) δ ppm 8.12-8.06 (m, 1H), 7.62 (dd, J=2.0, 9.5 Hz, 1H), 4.84-4.76 (m, 2H), 4.58-4.51 (m, 2H), 2.99 (q, J=7.5 Hz, 2H), 1.51 (s, 9H), 1.39 (t, J=7.7 Hz, 3H).

3) Synthesis of Compound 20-3

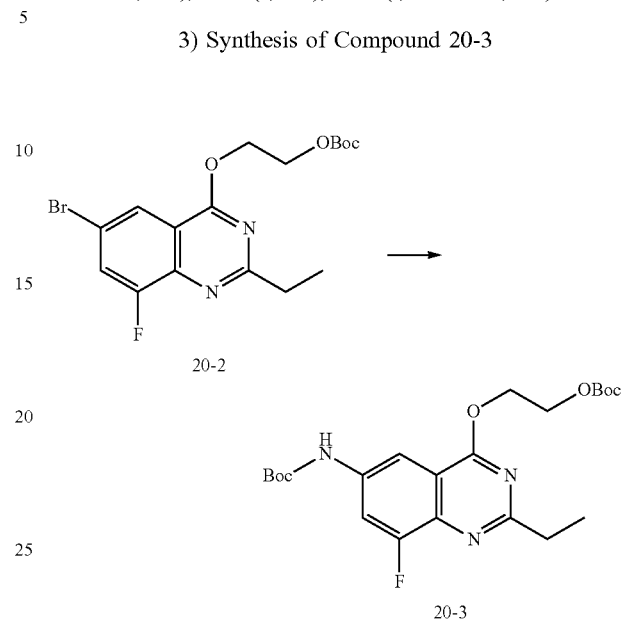

A mixture of Compound 20-2 (800 mg, 1.93 mmol), Boc-NH$_2$ (339 mg, 2.89 mmol), cesium carbonate (1.57 g, 4.82 mmol), bis(dibenzylideneacetone)palladium (111 mg, 193.04 μmol), 4,5-bis(diphenylphosphino)-9,9-dimethylxanthene (112 mg, 193.56 μmol), and methylbenzene (10 mL) was added to a microwave tube, and kept at 120° C. for microwave reaction for 0.5 h. The reaction mixture was filtered through Celite, and the filtrate was concentrated under reduced pressure. The residue obtained from the concentration was purified by a silica gel column to obtain Compound 20-3. LCMS (ESI) m/z: 452 (M+1).

4) Synthesis of Compound 20-4

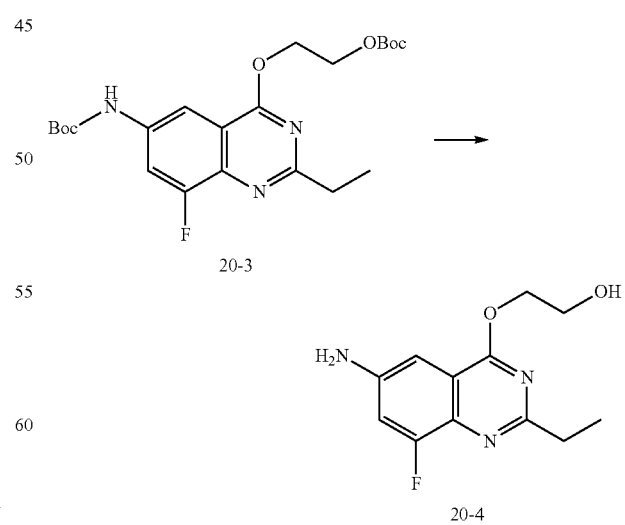

Trifluoroacetic acid (2 mL) was added to a solution of Compound 20-3 (750 mg, 1.66 mmol) in anhydrous dichloromethane (8 mL). The resulting reaction mixture was stirred at 10° C. for 3 h. A saturated aqueous solution of sodium bicarbonate was added to the reaction mixture (pH about 7), which was extracted with dichloromethane (30 mL). The organic phase was washed with saturated brine (20 mL), dried over anhydrous sodium sulfate, and concentrated under reduced pressure. Lithium hydroxide (520 mg, 12.39 mmol) was added to a solution of the resulting yellow oil (430 mg, 1.24 mmol) in tetrahydrofuran (6 mL) and water (1.5 mL). The resulting reaction mixture was stirred at 10° C. for 3 h. The reaction mixture was dried over anhydrous sodium sulfate, and concentrated under reduced pressure to obtain Compound 20-4. LCMS (ESI) m/z: 252 (M+1).

5) Synthesis of Compound 20-5

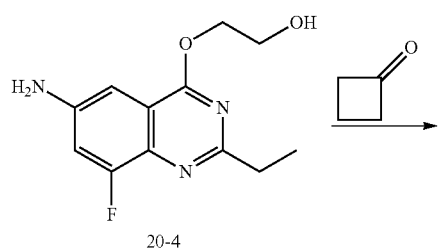

20-4

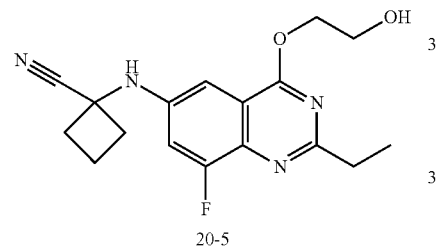

20-5

Trimethylsilyl cyanide (232 mg, 2.34 mmol) and zinc chloride (33 mg, 241.98 µmol) were added to a mixed solution of Compound 20-4 (200 mg, 796.00 µmol), cyclobutanone (334 mg, 4.77 mmol), sodium sulfate (453 mg, 3.19 mmol) and tetrahydrofuran (5 mL). The resulting reaction mixture was stirred at 10° C. for 16 h. An aqueous solution of sodium sulfite (20 mL) was added to the reaction mixture, and the resulting mixture was extracted with ethyl acetate (15 mL×3). The organic phase was washed with saturated brine (20 mL), dried over anhydrous sodium sulfate, and concentrated under reduced pressure to obtain Compound 20-5. LCMS (ESI) m/z: 331 (M+1).

6) Synthesis of Compound 20-6

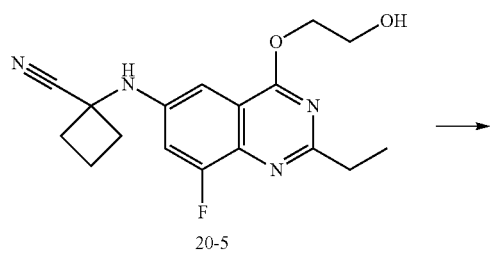

20-5

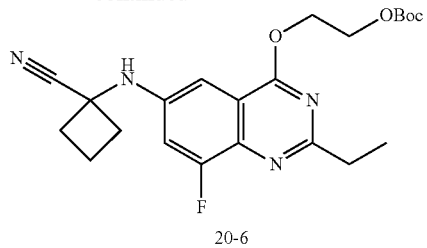

20-6 diBoc (237 mg, 1.09 mmol), triethylamine (189 mg, 1.87 mmol), and 4-dimethylaminopyridine (12 mg, 98.23 µmol) were added to a mixed solution of Compound 20-5 (300 mg, 908.11 µmol) in dichloromethane (4 mL). The resulting reaction mixture was stirred at 10° C. for 16 h. The reaction mixture was concentrated under reduced pressure. The residue obtained from the concentration was purified by a silica gel column to obtain Compound 20-6. LCMS (ESI) m/z: 431 (M+1).

7) Synthesis of Compound 20-7

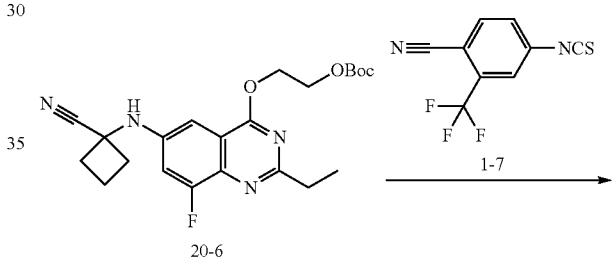

20-6

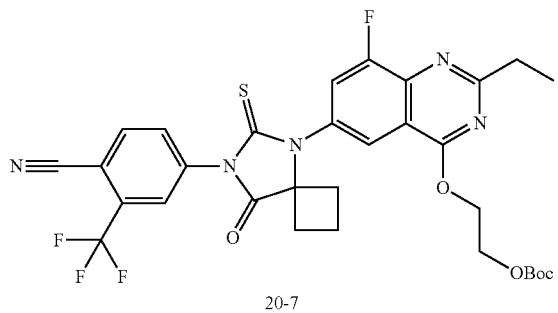

20-7

A mixed solution of Compound 20-6 (80 mg, 185.84 µmol), Compound 1-7 (170 mg, 744.98 µmol), methylbenzene (2 mL), and DMF (0.5 mL) was heated to 110° C., and stirred for 16 h. Methanol (1 mL) was added to the reaction mixture, which was stirred for 30 min, and then concentrated under reduced pressure. The residue obtained from the concentration was purified by a preparative TLC plate to obtain Compound 20-7. LCMS (ESI) m/z: 660 (M+1).

8) Synthesis of Compound 20

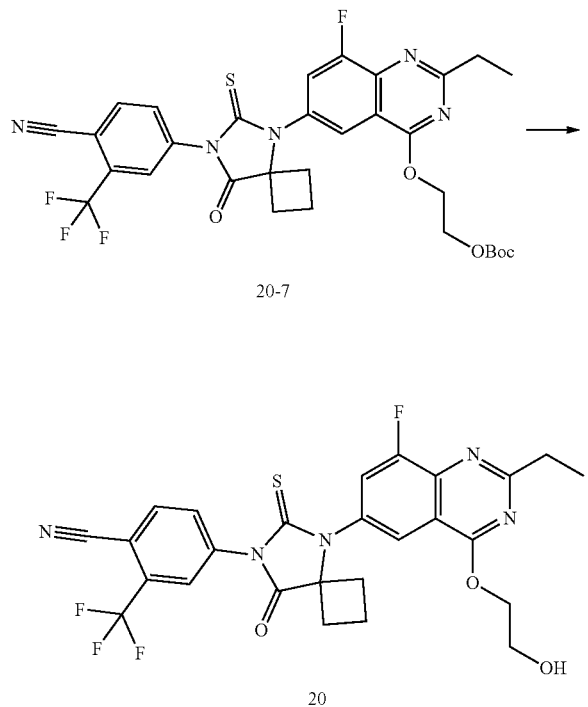

Trifluoroacetic acid (0.4 mL) was added to a solution of Compound 20-7 (70 mg, 106.12 μmol) in anhydrous dichloromethane (2 mL). The resulting reaction mixture was stirred at 10° C. for 1 h. A saturated aqueous solution of sodium bicarbonate was added to the reaction mixture (pH about 8), which was extracted with dichloromethane (10 mL×3). The organic phase was washed with saturated brine (15 mL), dried over anhydrous sodium sulfate, and concentrated under reduced pressure. The residue obtained from the concentration was purified by preparative HPLC to obtain Compound 20. $^1$H NMR (400 MHz, CDCl$_3$) δ ppm 7.98-7.86 (m, 3H), 7.79 (br d, J=8.0 Hz, 1H), 7.40 (br d, J=9.8 Hz, 1H), 4.79-4.68 (m, 2H), 4.03 (br s, 2H), 2.99 (q, J=7.5 Hz, 2H), 2.76-2.60 (m, 3H), 2.59-2.46 (m, 2H), 2.30-2.14 (m, 1H), 1.52 (br s, 1H), 1.36 (t, J=7.5 Hz, 3H); LCMS (ESI) m/z: 560 (M+1).

Example 20 Synthesis of Compound 21

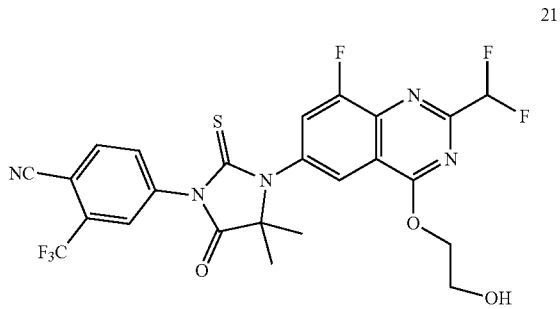 [SMILES: CC1(C)C(=O)N(c2ccc(C#N)c(C(F)(F)F)c2)C(=S)N1c1cc(F)c2nc(C(F)F)nc(OCCO)c2c1]

1) Synthesis of Compound 21-1

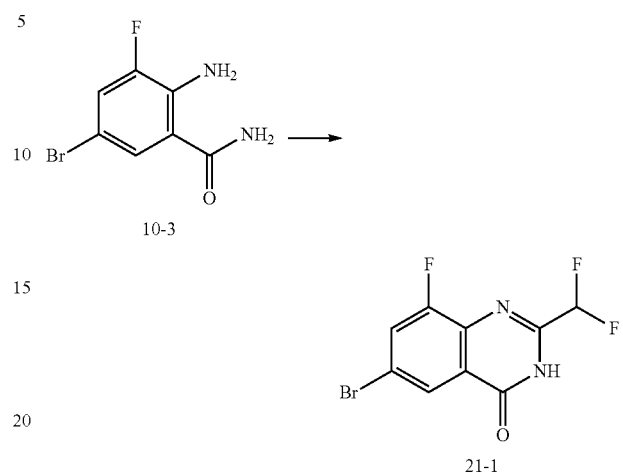

At room temperature (10° C.), O-(7-azabenzotriazol-1-yl)-N,N,N',N'-tetramethyluronium hexafluorophosphate (10.61 g, 27.89 mmol) was added to a solution of Compound 10-3 (5 g, 21.46 mmol), 2,2-difluoroacetic acid (6.18 g, 64.37 mmol), and triethylamine (8.68 g, 85.82 mmol) in dichloromethane (10 mL). The reaction mixture was kept at 10° C. for 13 h. The reaction mixture was concentrated to obtain a crude product. The crude product was purified by flash column chromatography to obtain Compound 21-1. $^1$H NMR (400 MHz, CDCl$_3$) δ ppm 12.90 (br s, 1H), 7.79 (s, 1H), 7.38-7.29 (m, 1H), 6.50-5.96 (m, 1H).

2) Synthesis of Compound 21-2

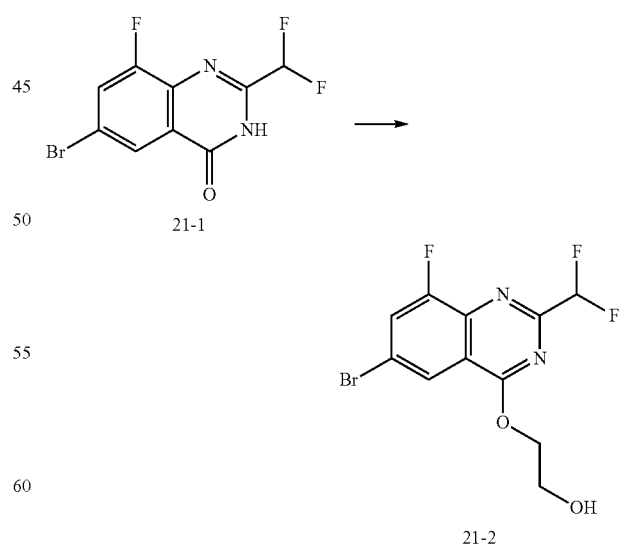

With reference to the synthesis of Compound 11-4, Compound 21-2 was prepared with Compound 21-1 as the starting material. LCMS (ESI) m/z: 337 (M+1).

3) Synthesis of Compound 21-3

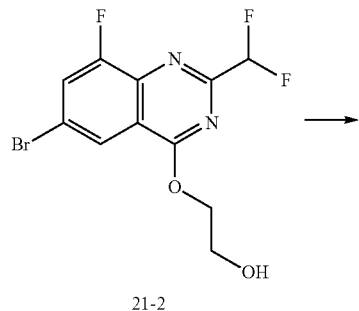

21-2

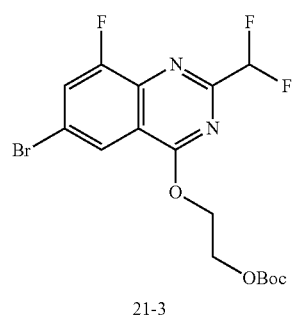

21-3

With reference to the synthesis of Compound 11-5, Compound 21-3 was prepared with Compound 21-2 as the starting material. LCMS (ESI) m/z: 439 (M+3).

4) Synthesis of Compound 21-4

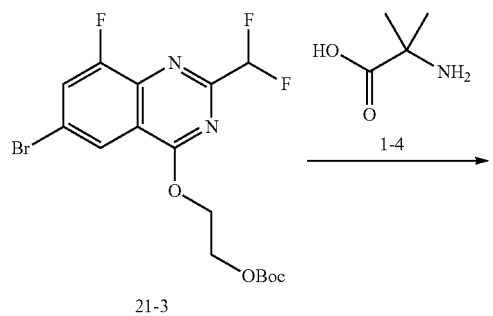

21-3

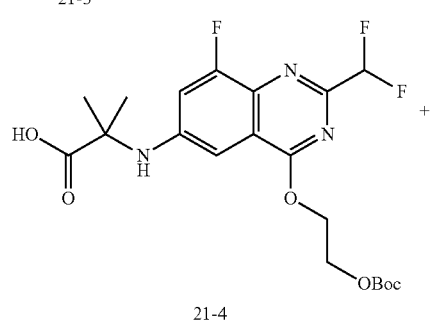

21-4

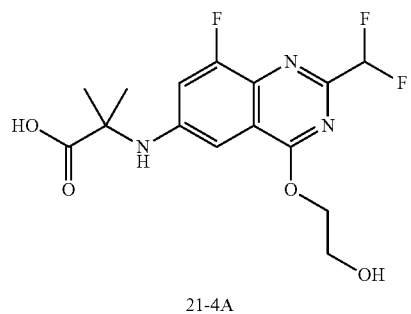

21-4A

Compound 21-3 (1.5 g, 3.43 mmol), Compound 1-4 (531 mg, 5.15 mmol), cuprous chloride (34 mg, 343.09 μmol), 2-acetylcyclohexanone (48 mg, 343.09 μmol), and potassium carbonate (948 mg, 6.86 mmol) were added to a microwave tube filled with DMF (15 mL) and water (1.5 mL). After nitrogen purge for 1 min, the resulting mixture was kept at 130° C. for microwave reaction for 20 min. The reaction mixture was cooled to room temperature, and filtered. The filter cake was washed with DMF (5 mL×2). The filtrates were combined, acidified to pH=6-7 with an aqueous solution of dilute hydrochloric acid (2M), and concentrated. The resulting oil was added to dichloromethane/methanol (30 mL/3 mL), stirred at room temperature (20° C.) for 10 min, and filtered to remove insolubles. The filtrate was concentrated to obtain a mixture of Compound 21-4 and Compound 21-4A. LCMS (ESI) m/z: 360 (M+1); 460 (M+1).

5) Synthesis of Compound 21-5

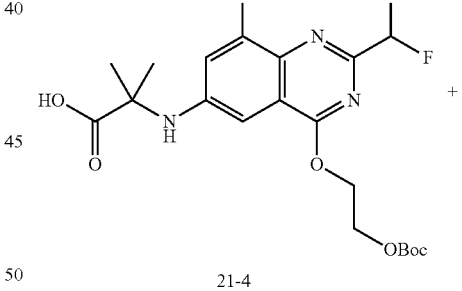

21-4

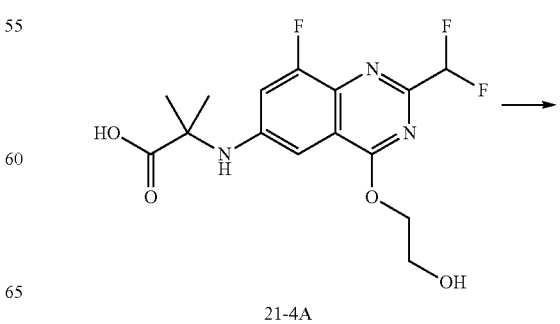

21-4A

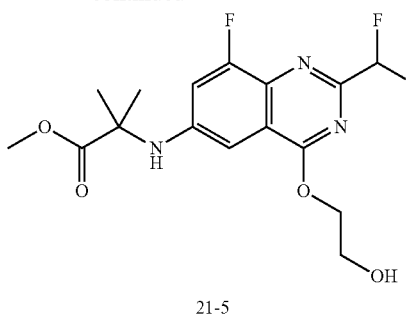

21-5

At 0° C., a solution of TMSCHN₂ in n-hexane (2M, 5 mL) was added dropwise to a solution of Compound 21-4 (2.3 g, 5.01 mmol) (a mixture containing Compound 21-4A) in dichloromethane (20 mL) and methanol (4 mL), and then the resulting mixture was further stirred at 10° C. for 2 h. The reaction mixture was concentrated to obtain a crude product. The crude product was purified by flash column chromatography to obtain Compound 21-5. LCMS (ESI) m/z: 374 (M+1).

6) Synthesis of Compound 21-6

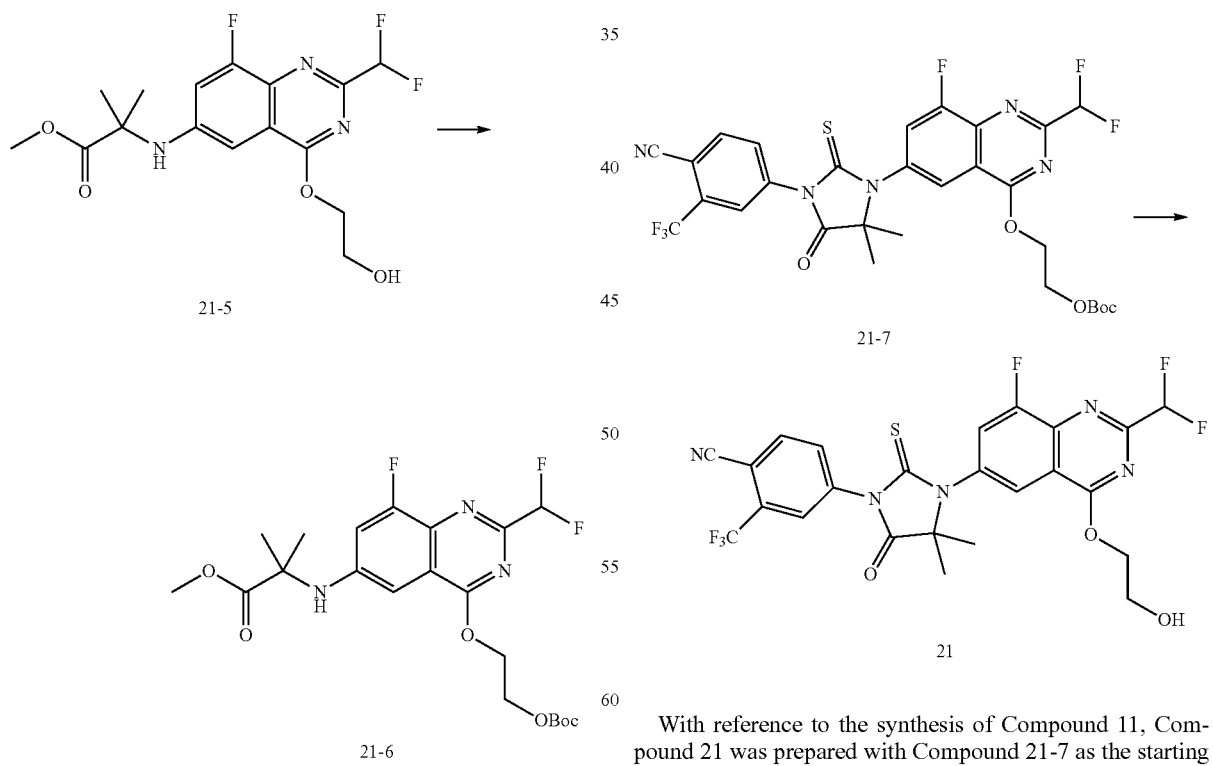

With reference to the synthesis of Compound 11-5, Compound 21-6 was prepared with Compound 21-5 as the starting material. LCMS (ESI) m/z: 474 (M+1).

7) Synthesis of Compound 21-7

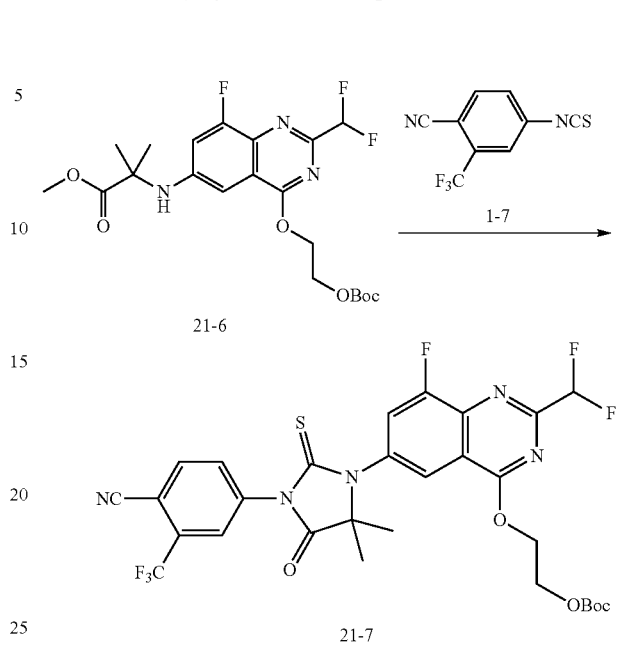

With reference to the synthesis of Compound 11-8, Compound 21-7 was prepared with Compound 21-6 as the starting material. LCMS (ESI) m/z: 670 (M+1).

8) Synthesis of Compound 21

With reference to the synthesis of Compound 11, Compound 21 was prepared with Compound 21-7 as the starting material. ¹H NMR (400 MHz, CDCl₃) δ ppm 7.95 (s, 3H), 7.78 (dd, J=8.28, 2.01 Hz, 1H), 7.52 (dd, J=9.79, 2.01 Hz, 1H), 6.84-6.36 (m, 1H), 4.89-4.75 (m, 2H), 4.17-4.00 (m, 2H), 2.25-2.12 (m, 1H), 1.61 (s, 6H); LCMS (ESI) m/z: 570 (M+1).

Example 21 Synthesis of Compound 22

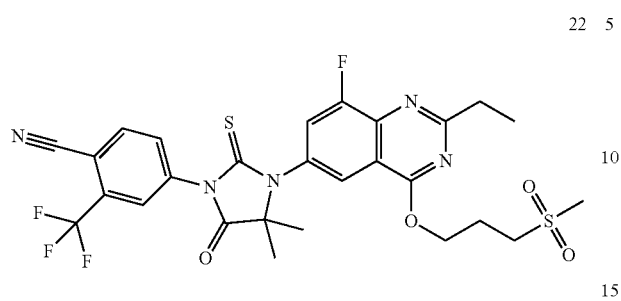
22

1) Synthesis of Compound 22-1

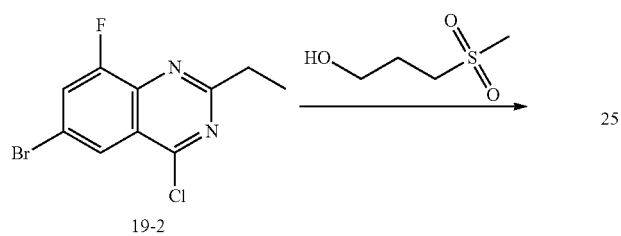
19-2

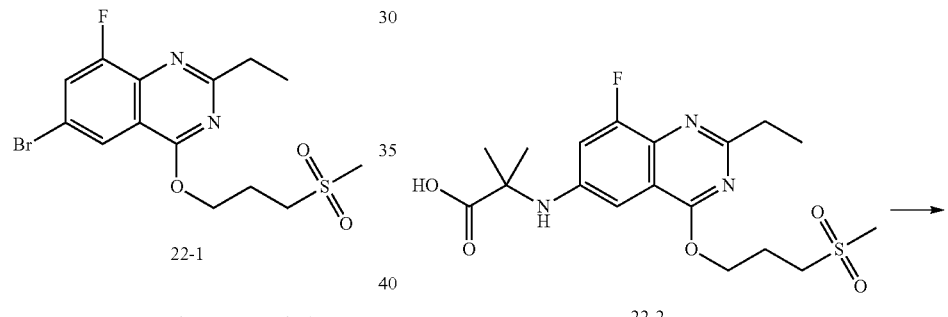
22-1

Sodium hydride (166 mg, 4.14 mmol, 60% purity) was added to a solution of Compound 19-2 (1 g, 3.45 mmol) and 3-(methylsulfonyl)-1-propanol (573 mg, 4.14 mmol) in tetrahydrofuran (20 mL). The mixture was stirred at 16° C. for 1 h. Water (20 mL) was added to the reaction mixture, which was extracted with dichloromethane (20 mL×2). The combined organic phase was washed with saturated brine (20 mL), dried over anhydrous sodium sulfate, filtered, and concentrated to obtain Compound 22-1. LCMS (ESI) m/z: 393 (M+3).

2) Synthesis of Compound 22-2

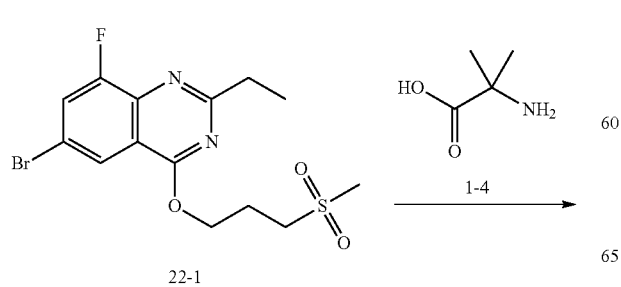
22-1

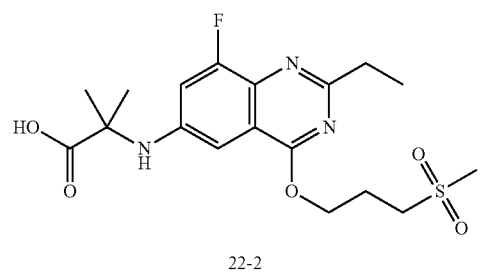
22-2

With reference to the synthesis of Compound 11-6, Compound 22-2 was prepared with Compound 22-1 as the starting material. LCMS (ESI) m/z: 414 (M+1).

3) Synthesis of Compound 22-3

22-2

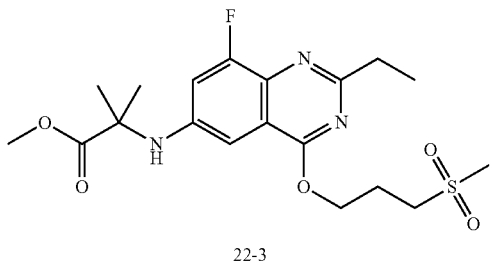
22-3

With reference to the synthesis of Compound 11-7, Compound 22-3 was prepared with Compound 22-2 as the starting material. LCMS (ESI) m/z: 428 (M+1).

4) Synthesis of Compound 22

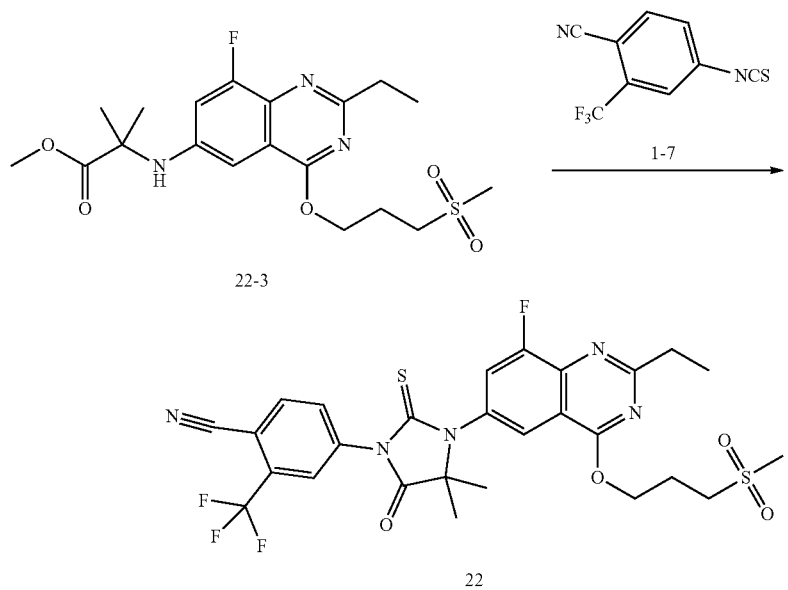

With reference to the synthesis of Compound 11-8, Compound 22 was prepared with Compound 22-3 as the starting material. $^1$H NMR (400 MHz, CDCl$_3$) δ ppm 8.07-7.99 (m, 2H), 7.94-7.83 (m, 2H), 7.48 (dd, J=10.04, 2.26 Hz, 1H), 4.81 (t, J=6.27 Hz, 2H), 3.37-3.23 (m, 2H), 3.07 (q, J=7.53 Hz, 2H), 3.00 (s, 3H), 2.57-2.47 (m, 2H), 1.69 (s, 6H), 1.44 (t, J=7.53 Hz, 3H); LCMS (ESI) m/z: 624 (M+1).

Example 22 Synthesis of Compound 23

23

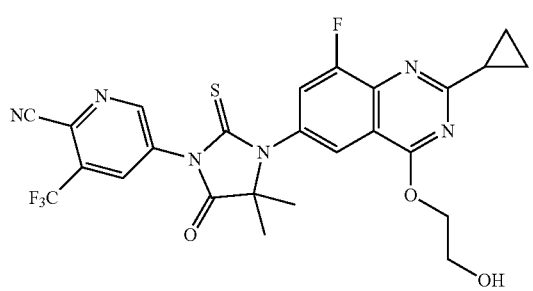

1) Synthesis of Compound 23-2

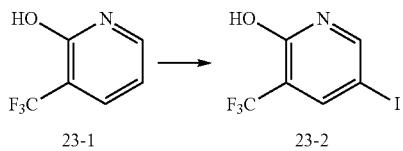 [SMILES: Oc1ncccc1C(F)(F)F ; Oc1ncc(I)cc1C(F)(F)F]

Compound 23-1 (10 g, 61.31 mmol) was dissolved in a mixed solution of acetonitrile (50 mL) and DMF (50 mL), and NBS (13.79 g, 61.31 mmol) was added. The resulting mixture was heated to 80° C., and stirred for 2 h. The reaction mixture was cooled to room temperature. 1 mol/L sodium bicarbonate solution (62 mL) was added to the reaction mixture, and stirred for 5 min. The resulting mixture was concentrated to dryness under reduced pressure. Water (80 mL) was added to the residue obtained from the concentration, and the resulting mixture was extracted with dichloromethane (100 mL×4). The organic phases were combined, dried over anhydrous sodium sulfate, and filtered. The filtrate was concentrated to dryness under reduced pressure. At room temperature, dichloromethane (15 mL) was added to the residue obtained from the concentration. The resulting mixture was stirred for 5 min, and filtered. The filter cake was washed with dichloromethane (5 mL), and the filter cake was dried under reduced pressure to obtain Compound 23-2. $^1$H NMR (400 MHz, DMSO-d6) δ ppm 12.57 (br s, 1H), 8.00 (s, 1H), 7.99-7.97 (m, 1H); LCMS (ESI) m/z: 290 (M+1).

2) Synthesis of Compound 23-3

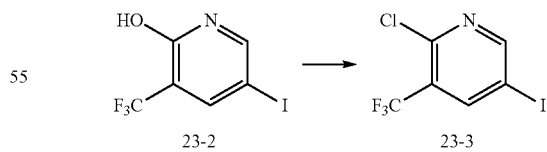

DMF (8 mL) was added to a solution of Compound 23-2 (8.1 g, 28.03 mmol) in phosphorus oxychloride (21.38 g, 139.58 mmol). The resulting mixture was stirred at 110° C. for 80 min. The reaction mixture was cooled to room temperature, and slowly added dropwise to water (150 mL) which was stirred at room temperature. The resulting mixture was adjusted to a pH of about 8 with a saturated sodium bicarbonate solution, and extracted with dichloromethane (40 mL×4). The organic phases were combined, dried over anhydrous sodium sulfate, and filtered. The filtrate was concentrated under reduced pressure to obtain Compound 23-3. $^1$H NMR (400 MHz, CDCl$_3$) δ ppm 8.71 (d, J=1.8 Hz, 1H), 8.21 (d, J=2.0 Hz, 1H).

3) Synthesis of Compound 23-4

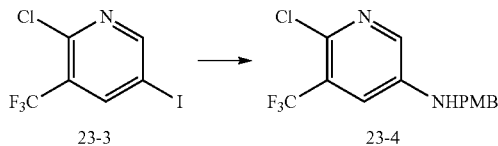

P-methoxybenzylamine (3.25 g, 23.68 mmol), bis(dibenzylideneacetone)palladium (2.72 g, 4.74 mmol), 4,5-bis(diphenylphosphino)-9,9-dimethylxanthene (2.74 g, 4.74 mmol), and sodium tert-butoxide (3.41 g, 35.52 mmol) were added to a solution of Compound 23-3 (7.28 g, 23.68 mmol) in methylbenzene (100 mL). The resulting mixture was subjected to nitrogen displacement four times, heated to 110° C. and stirred for 1 h under nitrogen protection. The reaction mixture was cooled to room temperature, water (100 mL) was added to the reaction mixture, and the resulting mixture was extracted with ethyl acetate (80 mL×3). The organic phases were combined, dried over anhydrous sodium sulfate, and filtered. The filtrate was concentrated to dryness under reduced pressure. The residue obtained from the concentration was purified by a silica gel column to obtain Compound 23-4. $^1$H NMR (400 MHz, CDCl$_3$) δ ppm 7.84 (d, J=2.8 Hz, 1H), 7.18 (d, J=8.0 Hz, 2H), 7.13-7.09 (m, 1H), 6.84-6.80 (m, 2H), 4.20 (d, J=5.5 Hz, 2H), 3.73 (s, 3H); LCMS (ESI) m/z:317 (M+1).

4) Synthesis of Compound 23-5

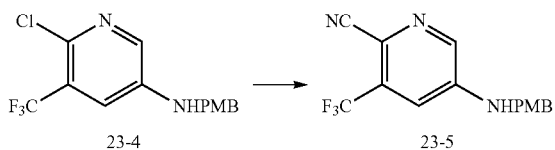

Zinc cyanide (4.16 g, 35.42 mmol) was added to a solution of Compound 23-4 (7.1 g, 22.42 mmol) in DMF (100 mL). 1,1'-Bis(diphenylphosphino)ferrocene (4.53 g, 4.48 mmol) was added after nitrogen displacement three times, and then bis(dibenzylideneacetone)palladium (2.58 g, 4.48 mmol) was added after nitrogen displacement three times. After nitrogen displacement three times, the resulting mixture was heated to 150° C. and stirred for 50 min under nitrogen protection. The reaction mixture was cooled to room temperature, and concentrated to dryness under reduced pressure. The residue obtained from the concentration was purified by a silica gel column to obtain Compound 23-5. $^1$H NMR (400 MHz, CDCl$_3$) δ ppm 8.18 (d, J=2.5 Hz, 1H), 7.27 (d, J=8.5 Hz, 2H), 7.09 (d, J=2.8 Hz, 1H), 6.93 (d, J=8.5 Hz, 2H), 5.07 (br s, 1H), 4.38 (d, J=5.3 Hz, 2H), 3.83 (s, 3H); LCMS (ESI) m/z: 308 (M+1).

5) Synthesis of Compound 23-6

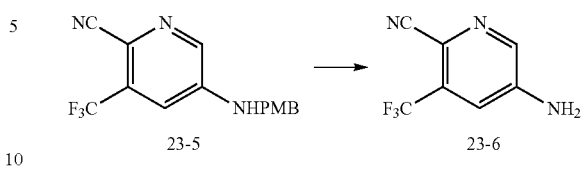

Compound 23-5 (3.4 g, 11.07 mmol) was dissolved in a mixed solution of dichloromethane (4 mL) and trifluoroacetic acid (16 mL). The resulting mixture was stirred at 10° C. for 2 h. The reaction mixture was concentrated to dryness under reduced pressure. The residue obtained from the concentration was diluted with ethyl acetate (50 mL), and washed with a saturated sodium bicarbonate solution (50 mL×3). The resulting organic phase was dried over anhydrous sodium sulfate, and filtered. The filtrate was concentrated to dryness under reduced pressure. The residue obtained from the concentration was slurried with ethyl acetate (20 mL) at room temperature for 20 min, and filtered. The filter cake was concentrated under reduced pressure to obtain Compound 23-6. $^1$H NMR (400 MHz, DMSO-d6) δ ppm 8.19 (d, J=2.3 Hz, 1H), 7.29 (d, J=2.5 Hz, 1H), 7.00 (s, 2H).

6) Synthesis of Compound 23-7

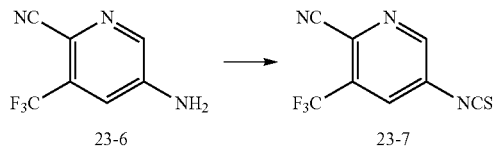

Thiophosgene (1.76 g, 15.28 mmol) was added dropwise to water (50 mL), and the resulting mixture was stirred at 10° C. for 30 min. Then, Compound 23-6 (1.43 g, 7.64 mmol) was added in batches, and the resulting mixture was stirred at 10° C. for 5 h. The reaction mixture was extracted with dichloromethane (40 mL×2). The organic phases were combined, dried over anhydrous sodium sulfate, and filtered. The filtrate was concentrated under reduced pressure to obtain Compound 23-7.

7) Synthesis of Compound 23-8

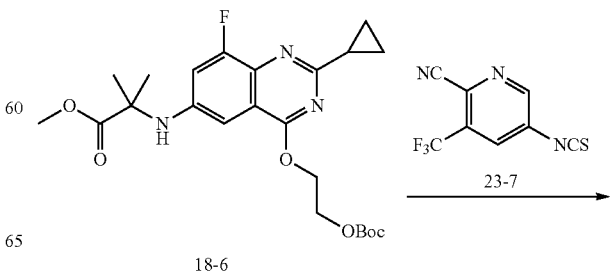

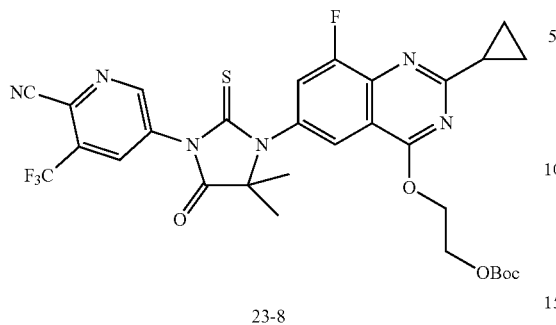

23-8

With reference to the synthesis of Compound 11-8, Compound 23-8 was prepared with Compound 18-6 and Compound 23-7 as the starting materials. LCMS (ESI) m/z: 661 (M+1).

8) Synthesis of Compound 23

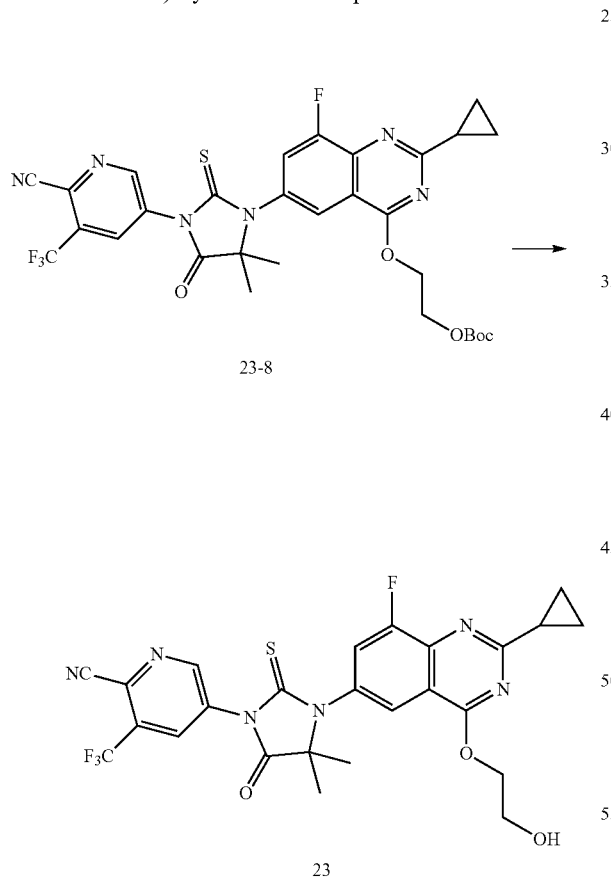

With reference to the synthesis of Compound 11, Compound 23 was prepared with Compound 23-8 as the starting material. $^1$H NMR (400 MHz, CDCl$_3$) δ ppm 9.12 (d, J=2.01 Hz, 1H), 8.39 (d, J=2.26 Hz, 1H), 7.88 (s, 1H), 7.43 (dd, J=9.91, 2.13 Hz, 1H), 4.79-4.68 (m, 2H), 4.15-4.05 (m, 2H), 2.45-2.35 (m, 1H), 2.30 (t, J=5.65 Hz, 1H), 1.75-1.73 (m, 1H), 1.70 (s, 5H), 1.31-1.25 (m, 2H), 1.20-1.15 (m, 2H); LCMS (ESI) m/z: 561 (M+1).

Example 23 Synthesis of Compound 24

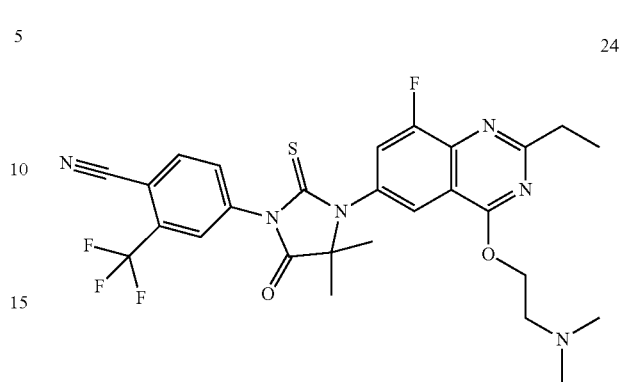

24

1) Synthesis of Compound 24-1

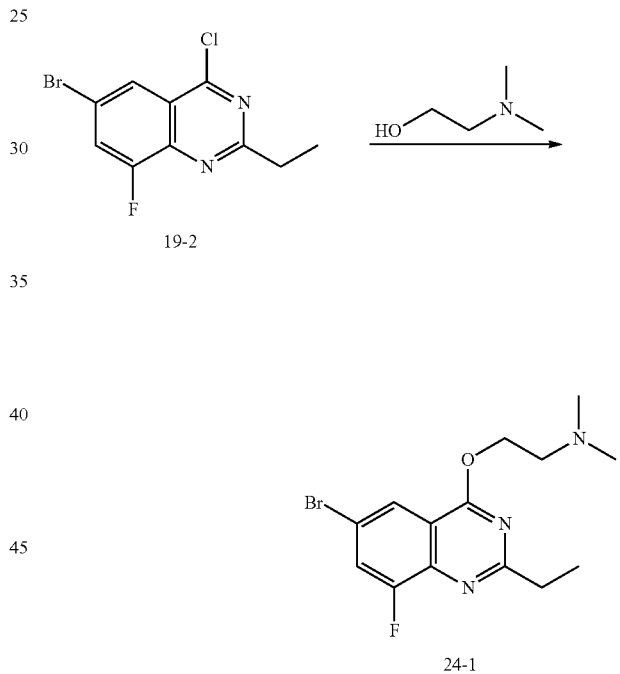

Sodium hydride (166 mg, 4.15 mmol, 60%) was added to a solution of Compound 19-2 (1 g, 3.45 mmol) and N,N-dimethylethanolamine (370 mg, 4.15 mmol) in tetrahydrofuran (20 mL). The resulting reaction mixture was stirred at 10° C. for 1 h. The reaction mixture was quenched with a saturated aqueous solution of ammonium chloride (50 mL), and then extracted with dichloromethane (40 mL×2). The organic phase was washed with saturated brine (50 mL), dried over anhydrous sodium sulfate, and concentrated under reduced pressure. The residue obtained from the concentration was purified by a silica gel column to obtain Compound 24-1. $^1$H NMR (400 MHz, CDCl$_3$) δ ppm 8.10-8.04 (m, 1H), 7.60 (dd, J=2.1, 9.7 Hz, 1H), 4.70 (t, J=5.8 Hz, 2H), 2.99 (q, J=7.5 Hz, 2H), 2.84 (t, J=5.8 Hz, 2H), 2.38 (s, 6H), 1.40 (t, J=7.7 Hz, 3H).

2) Synthesis of Compound 24-2

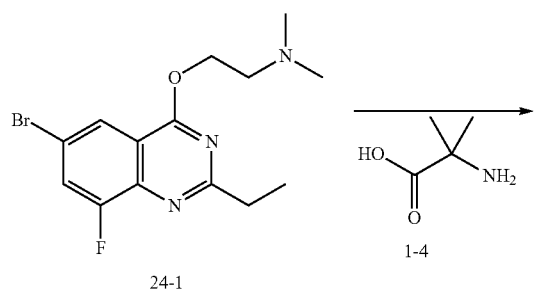

24-1        1-4

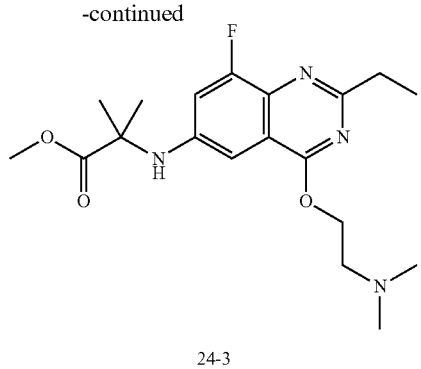

24-3

A solution of TMSCHN$_2$ in n-hexane (2M, 0.4 mL) was added to a solution of Compound 24-2 (0.25 g, 686.03 µmol) in dichloromethane (2 mL) and methanol (0.2 mL). The resulting reaction mixture was stirred at 10° C. for 1 h. Water was poured into the reaction mixture, which was extracted with dichloromethane (20 mL). The organic phase was washed with saturated brine (15 mL), dried over anhydrous sodium sulfate, and concentrated under reduced pressure. The residue obtained from the concentration was purified by a preparative TLC plate to obtain Compound 24-3. LCMS (ESI) m/z: 379 (M+1).

4) Synthesis of Compound 24

Compound 24-1 (400 mg, 1.17 mmol), Compound 1-4 (180 mg, 1.75 mmol), potassium carbonate (404 mg, 2.92 mmol), cuprous chloride (23 mg, 232.32 µmol), 2-acetylcyclohexanone (33 mg, 235.41 µmol), DMF (4 mL), and water (0.2 mL) were added to a microwave tube. The microwave tube was sealed, and kept at 130° C. for microwave reaction for 40 min. The reaction mixture was filtered, and washed with ethyl acetate (20 mL). The filtrate was concentrated under reduced pressure. 1N hydrochloric acid was added to the residue obtained from the concentration (pH 6-7). The resulting mixture was freeze-dried. Dichloromethane/methanol (20 mL, 10/1) were added to the resulting solid, and the resulting mixture was dried over anhydrous sodium sulfate, filtered, and concentrated under reduced pressure to obtain Compound 24-2. LCMS (ESI) m/z: 365 (M+1).

3) Synthesis of Compound 24-3

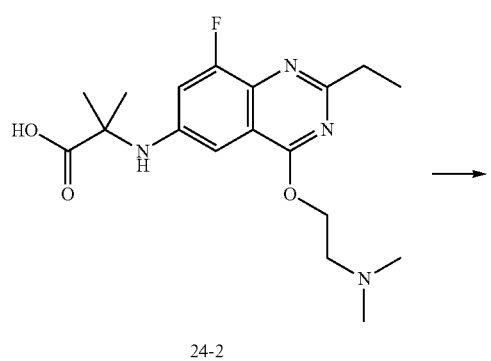

24-2

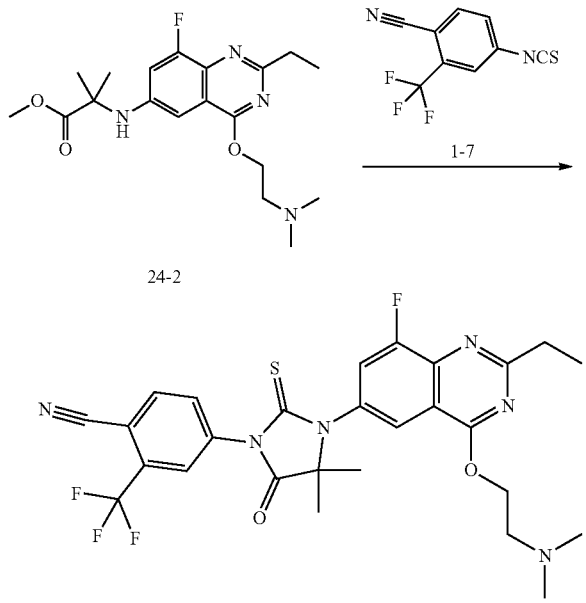

A mixed solution of Compound 24-3 (60 mg, 158.55 µmol), Compound 1-7 (120 mg, 525.87 µmol), methylbenzene (2 mL), and DMF (0.5 mL) was heated to 110° C., and stirred for 16 h. Methanol (1 mL) was added to the reaction mixture, and the resulting mixture was stirred for 30 min, and then concentrated under reduced pressure. The residue obtained from the concentration was purified by a preparative TLC plate, and then purified by preparative HPLC to obtain Compound 24. $^1$H NMR (400 MHz, CDCl$_3$) δ ppm 7.97-7.84 (m, 3H), 7.79 (br d, J=10.0 Hz, 1H), 7.37 (dd, J=2.1, 10.2 Hz, 1H), 4.70 (t, J=5.9 Hz, 2H), 2.98 (q, J=7.5 Hz, 2H), 2.83 (br s, 2H), 2.36 (br s, 6H), 1.59 (s, 6H), 1.35 (t, J=7.5 Hz, 3H); LCMS (ESI) m/z: 575.0 (M+1).

Example 24 Synthesis of Compound 25

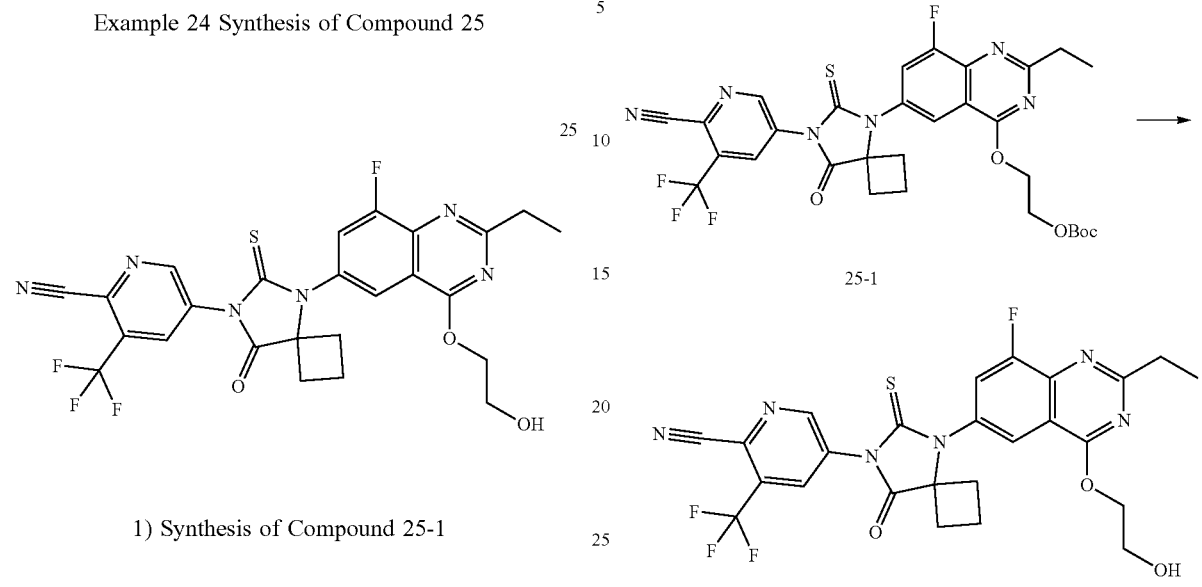

1) Synthesis of Compound 25-1

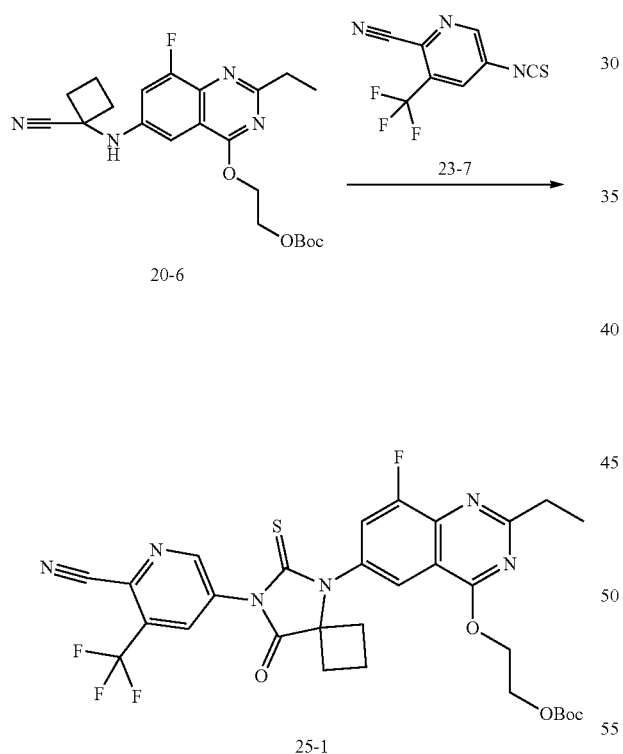

A mixed solution of Compound 20-6 (80 mg, 185.84 μmol), Compound 23-7 (130 mg, 567.24 μmol), methylbenzene (2 mL), and DMF (0.5 mL) was heated to 110° C., and stirred for 16 h. Methanol (1 mL) was added to the reaction mixture, and the resulting mixture was stirred for 30 min, and then concentrated under reduced pressure. The residue obtained from the concentration was purified by a preparative TLC plate to obtain Compound 25-1. LCMS (ESI) m/z: 661 (M+1).

2) Synthesis of Compound 25

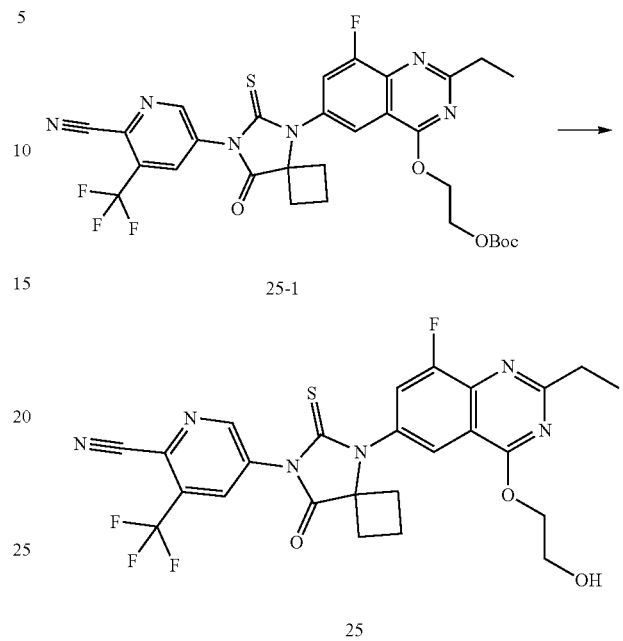

Trifluoroacetic acid (0.4 mL) was added to a solution of Compound 25-1 (90 mg, 136.23 μmol) in dichloromethane (2 mL). The resulting reaction mixture was stirred at 10° C. for 1 h. A saturated aqueous solution of sodium bicarbonate was added to the reaction mixture (pH about 8), which was extracted with dichloromethane (10 mL×3). The organic phase was washed with saturated brine (15 mL), dried over anhydrous sodium sulfate, and concentrated under reduced pressure. The residue obtained from the concentration was purified by preparative HPLC to obtain Compound 25. $^1$H NMR (400 MHz, CDCl$_3$) δ ppm 9.03 (d, J=1.8 Hz, 1H), 8.30 (d, J=1.8 Hz, 1H), 7.91 (s, 1H), 7.39 (dd, J=2.0, 9.8 Hz, 1H), 4.78-4.69 (m, 2H), 4.08-3.97 (m, 2H), 2.99 (q, J=7.5 Hz, 2H), 2.70 (br t, J=9.4 Hz, 2H), 2.61-2.48 (m, 2H), 2.30-2.13 (m, 1H), 1.73-1.55 (m, 2H), 1.36 (t, J=7.7 Hz, 3H); LCMS (ESI) m/z: 561 (M+1).

Example 25 Synthesis of Compound 26

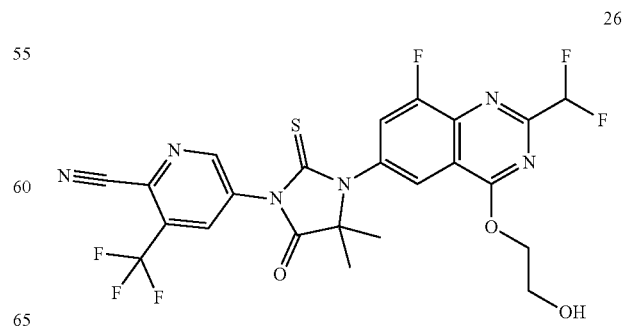

1) Synthesis of Compound 26-1

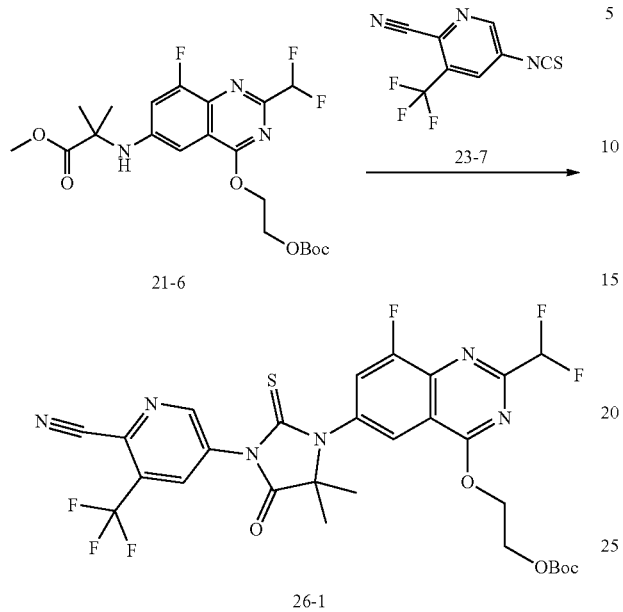

With reference to the synthesis of Compound 11-8, Compound 26-1 was prepared with Compound 21-6 as the starting material. LCMS (ESI) m/z: 671 (M+1).

2) Synthesis of Compound 26

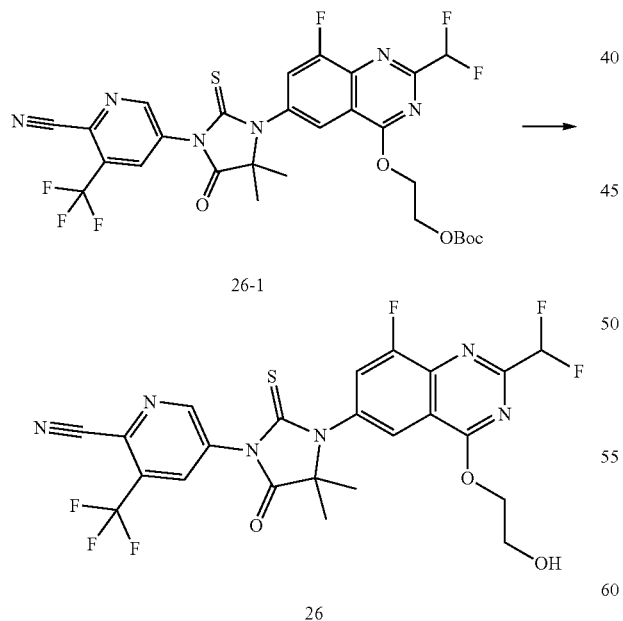

With reference to the synthesis of Compound 11, Compound 26 was prepared with Compound 26-1 as the starting material. $^1$H NMR (400 MHz, CDCl$_3$) δ ppm 9.03 (d, J=1.76 Hz, 1H), 8.29 (d, J=2.01 Hz, 1H), 7.96 (s, 1H), 7.58-7.45 (m, 1H), 6.85-6.44 (m, 1H), 4.89-4.76 (m, 2H), 4.07 (br d, J=3.76 Hz, 2H), 2.16 (br s, 1H), 1.64 (s, 6H); LCMS (ESI) m/z: 571 (M+1).

Example 26 Synthesis of Compound 27

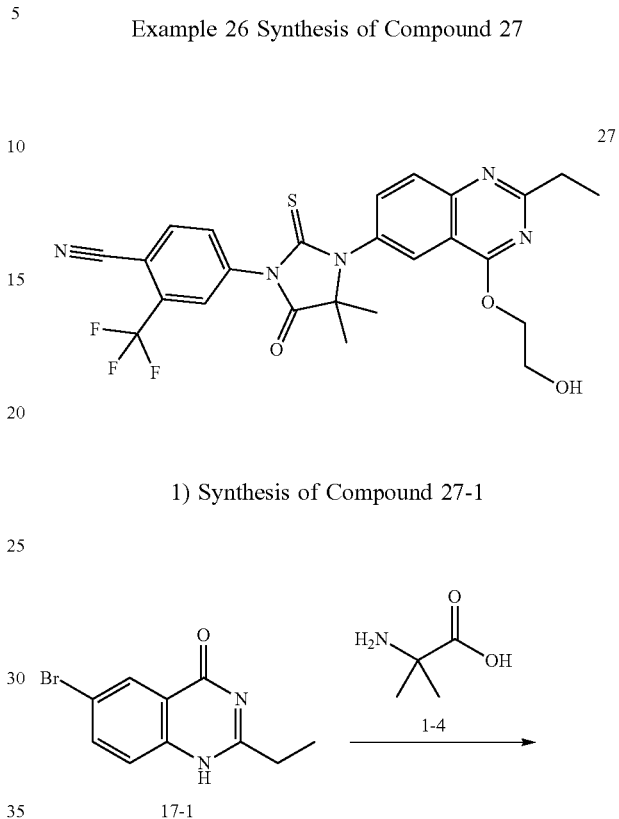

1) Synthesis of Compound 27-1

Compound 17-1 (1.50 g, 5.93 mmol), Compound 1-4 (917 mg, 8.89 mmol), cuprous chloride (117 mg, 1.19 mmol), 2-acetylcyclohexanone (166 mg, 1.19 mmol), potassium carbonate (2.05 g, 14.82 mmol), N,N-dimethylformamide (10 mL), and water (2.5 mL) were added to a 30 mL microwave tube. The resulting mixture was kept at 130° C. for microwave reaction for 1 h. The reaction mixture was filtered, and the filter cake was washed with DMF (10 mL×3). Dilute hydrochloric acid (2 mol/L) was added dropwise to the filtrate, such that the filtrate was weakly acidic (pH about 6). The filtrate was concentrated to dryness under reduced pressure. The residue obtained from the concentration was slurried with dichloromethane/methanol (10/1, 30 mL) at 15° C. for 2 min, and filtered. The filtrate was concentrated to dryness under reduced pressure to obtain Compound 27-1. LCMS (ESI) m/z: 276 (M+1).

2) Synthesis of Compound 27-2

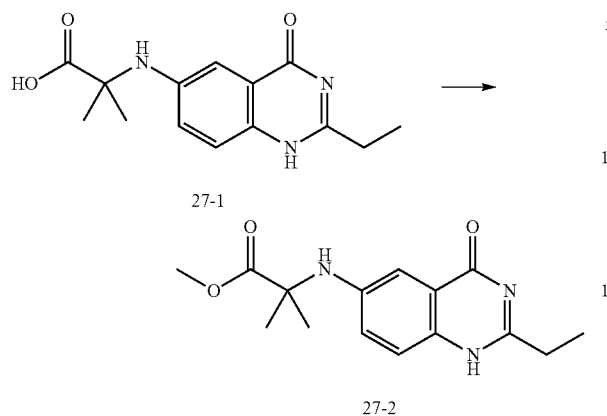

Compound 27-1 (4.40 g, 15.98 mmol) was dissolved in methanol (40 mL), and dichlorosulfoxide (19.01 g, 159.80 mmol, 11.59 mL) was added dropwise at 0° C. The resulting mixture was heated to 50° C., and stirred for 18 h. The reaction mixture was cooled to 15° C., and concentrated to dryness under reduced pressure. The residue obtained from the concentration was dissolved in a saturated sodium bicarbonate solution (50 mL), and extracted with dichloromethane/methanol (10:1, 80 mL×4). The organic phases were combined, washed with saturated brine (50 mL), dried over anhydrous sodium sulfate, and filtered. The filtrate was concentrated to dryness under reduced pressure. The residue obtained from the concentration was purified by a silica gel column to obtain Compound 27-2. LCMS (ESI) m/z: 290 (M+1).

3) Synthesis of Compound 27-3

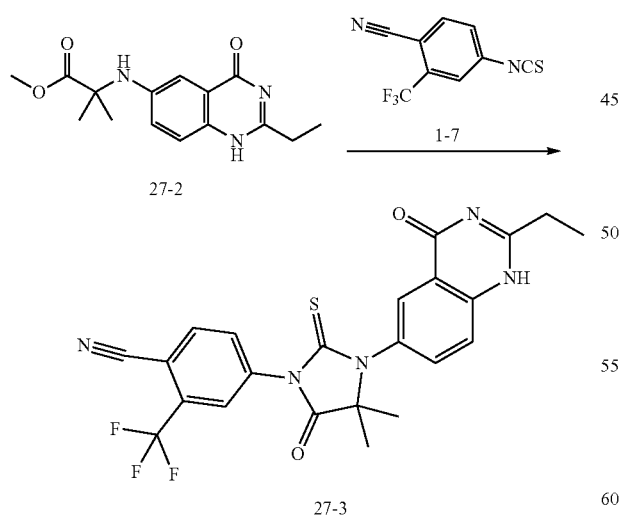

Under nitrogen protection, Compound 27-2 (560 mg, 1.94 mmol) and Compound 1-7 (1.77 g, 7.74 mmol) were dissolved in N,N-dimethylformamide (2 mL) and methylbenzene (20 mL), and the resulting mixture was heated to 120° C., and stirred for 18 h. The reaction mixture was cooled to room temperature, and concentrated to dryness under reduced pressure. The residue obtained from the concentration was purified by a silica gel column to obtain Compound 27-3. LCMS (ESI) m/z: 486 (M+1).

4) Synthesis of Compound 27

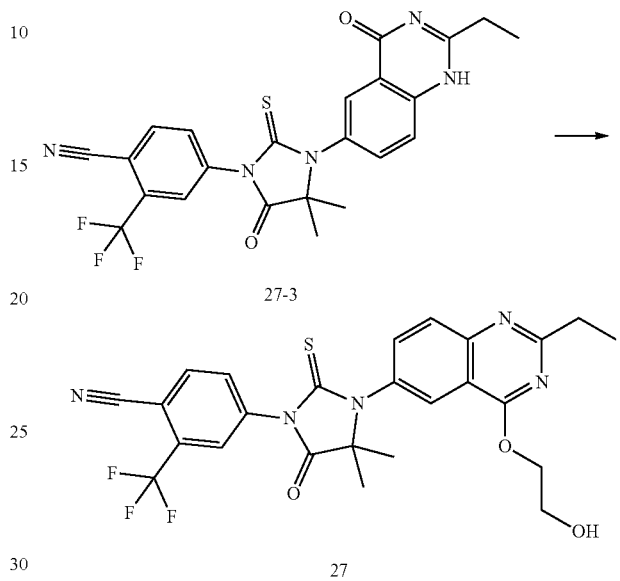

Under nitrogen protection, a turbid liquid of Compound 27-3 (789 mg, 1.63 mmol), 2-bromoethanol (609 mg, 4.88 mmol), potassium carbonate (674 mg, 4.88 mmol), and N,N-dimethylformamide (10 mL) was stirred at 30° C. for 17 h, supplemented with 2-bromoethanol (609 mg, 4.88 mmol) and further stirred at 30° C. for 5 h, and supplemented with 2-bromoethanol (609 mg, 4.88 mmol) and further stirred at 30° C. for 18 h. The reaction mixture was cooled to room temperature, and then directly filtered. The filtrate was separated and purified by preparative HPLC to obtain Compound 27. $^1$HNMR (400 MHz, CDCl$_3$) δ ppm 8.13 (d, J=2.5 Hz, 1H), 8.08-7.99 (m, 3H), 7.88 (dd, J=2.0, 8.3 Hz, 1H), 7.73 (dd, J=2.4, 8.9 Hz, 1H), 4.85-4.78 (m, 2H), 4.14-4.07 (m, 2H), 3.16 (t, J=5.6 Hz, 1H), 3.03 (q, J=7.5 Hz, 2H), 1.68 (s, 6H), 1.44 (t, J=7.5 Hz, 3H); LCMS (ESI) m/z: 530 (M+1).

Example 27 Synthesis of Compound 28

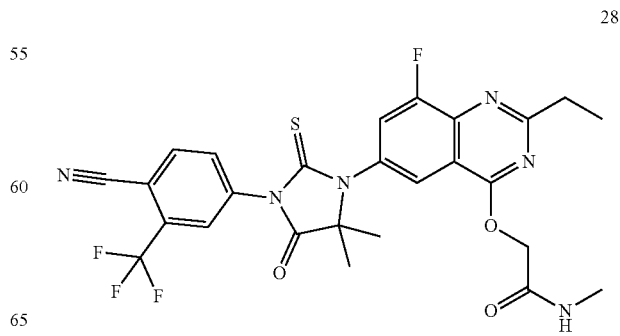

1) Synthesis of Compound 28-1

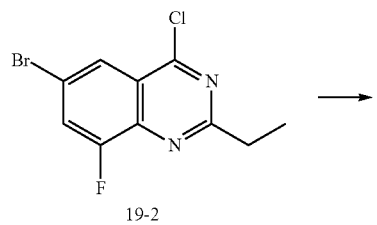

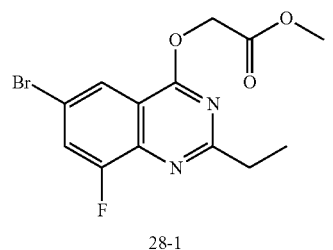

Sodium hydride (166 mg, 60% purity) was added to a solution of Compound 19-2 (1.00 g) and methyl 2-hydroxyacetate (373 mg) in tetrahydrofuran (20 mL). The mixture was stirred at 16° C. for 1 h. The reaction mixture was quenched with water (20 mL), and extracted with dichloromethane (20 mL×3). The combined organic phase was washed with saturated brine (20 mL), dried over anhydrous sodium sulfate, filtered, and concentrated to obtain Compound 28-1. LCMS (ESI) m/z: 345 (M+3).

2) Synthesis of Compound 28-2

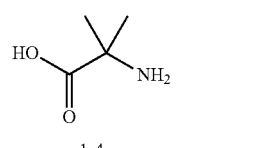

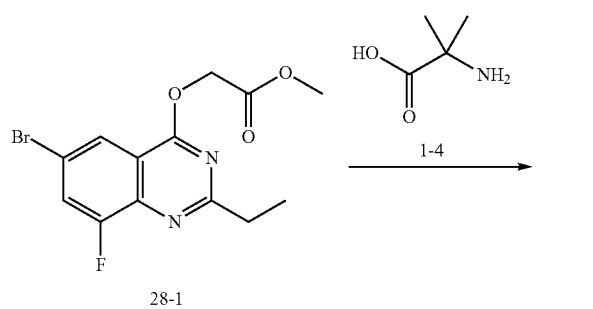

Compound 28-1 (600 mg), Compound 1-4 (270 mg), cuprous chloride (17 mg), 2-acetylcyclohexanone (25 mg), and potassium carbonate (604 mg) were added to a microwave tube filled with DMF (10 mL) and water (2 mL). After nitrogen purge for 1 min, the resulting mixture was kept at 130° C. for microwave reaction for 1 h, and filtered, and the filter cake was washed with DMF (2 mL). The filtrate was adjusted to pH=7 with 2M hydrochloric acid, and then concentrated. Dichloromethane/methanol (10/1, 20 mL) was added to the resulting oil to precipitate a solid. After filtration, the resulting filtrate was concentrated to obtain Compound 28-2. LCMS (ESI) m/z: 352 (M+1).

3) Synthesis of Compound 28-3

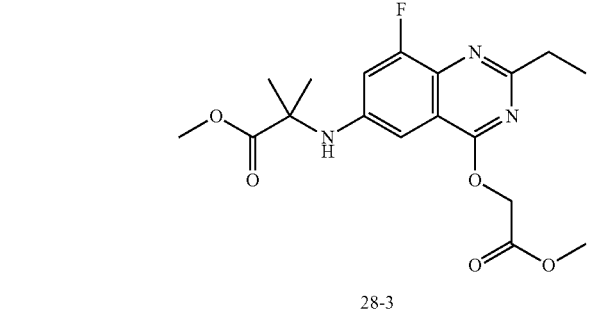

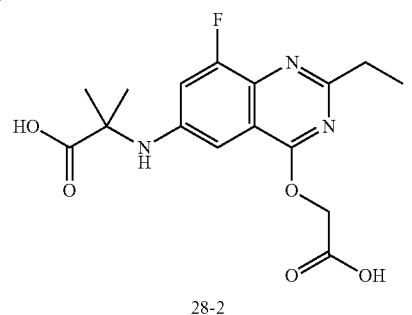

TMSCHN$_2$ (2M, 4.70 mL) was added dropwise to a solution of Compound 28-2 (1.10 g) in dichloromethane (20 mL) and methanol (2 mL). After the completion of the dropwise addition, the mixture reacted at 18° C. for 2 h. The reaction mixture was concentrated, and the concentrate was purified by thin layer chromatography to obtain Compound 28-3. LCMS (ESI) m/z: 380 (M+1).

4) Synthesis of Compound 28-4

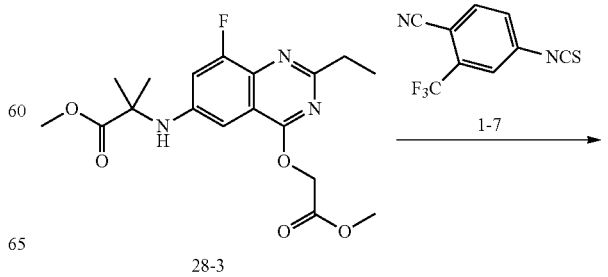

-continued

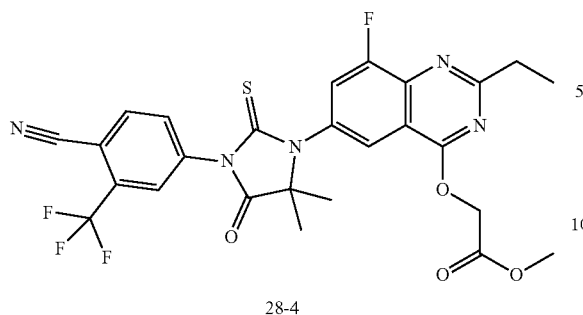

28-4

Compound 1-7 (230 mg) was added to Compound 28-3 (130 mg) in a mixed solvent of methylbenzene (4 mL) and DMF (1 mL), and then the resulting mixture was heated to 120° C., and stirred for 28 h. The reaction mixture was cooled to room temperature, and concentrated. The concentrate was purified by thin layer chromatography to obtain Compound 28-4. LCMS (ESI) m/z: 576 (M+1).

5) Synthesis of Compound 28-5

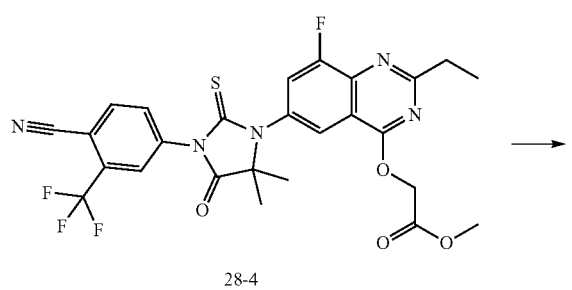

28-4

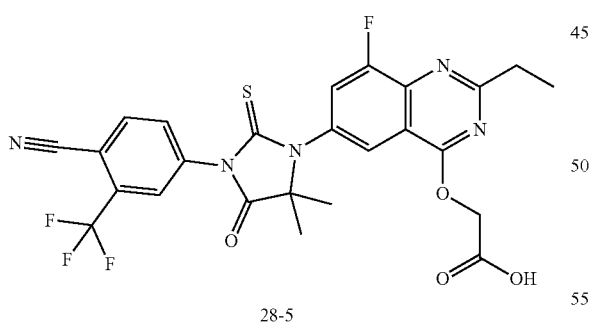

28-5

Lithium hydroxide (1M, 0.5 mL) was added to a solution of Compound 28-4 (90 mg) in tetrahydrofuran (3 mL), and the resulting mixture was stirred at 15° C. for 1 h. Then, the reaction mixture was adjusted to a pH of about 6 with 1M dilute hydrochloric acid, and extracted with dichloromethane (20 mL×2). The combined organic phase was washed with saturated brine (20 mL), dried over anhydrous sodium sulfate, filtered, and concentrated to obtain Compound 28-5. LCMS (ESI) m/z: 562 (M+1).

6) Synthesis of Compound 28

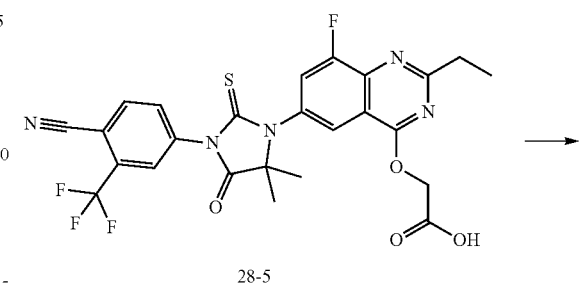

28-5

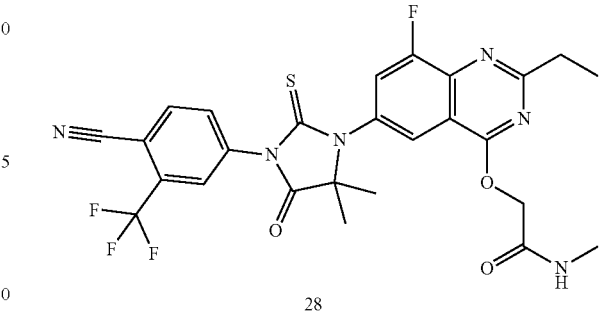

28

HATU (75 mg) was added to a solution of Compound 28-5 (80 mg), methylamine hydrochloride (16 mg), and triethylamine (50 mg) in dichloromethane (5 mL). Then, the resulting mixture was stirred at 15° C. for 1 h. The reaction mixture was concentrated, and the concentrate was purified by thin layer chromatography. The resulting sample was further purified by HPLC (alkaline) to obtain Compound 28. $^1$H NMR (400 MHz, CDCl$_3$) δ ppm 7.97-8.08 (m, 2H), 7.94 (s, 1H), 7.87 (dd, J=8.28, 1.76 Hz, 1H), 7.52 (dd, J=10.04, 2.01 Hz, 1H), 6.12 (br s, 1H), 5.17 (s, 2H), 3.08 (q, J=7.53 Hz, 2H), 2.94 (d, J=4.77 Hz, 3H), 1.70 (s, 6H), 1.42 (t, J=7.53 Hz, 3H); LCMS (ESI) m/z: 575 (M+1).

Example 28 Synthesis of Compound 29

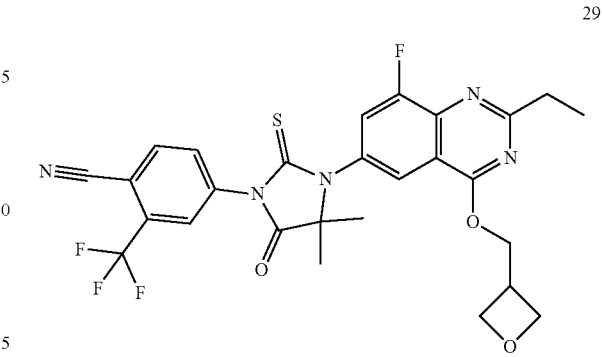

29

1) Synthesis of Compound 29-2

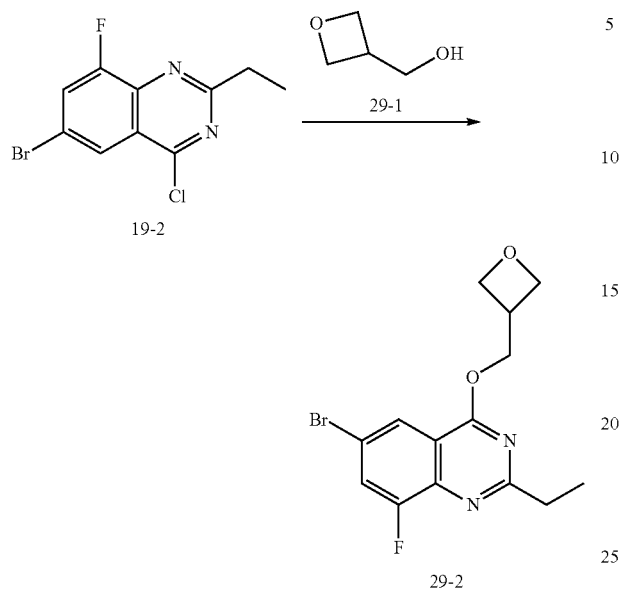

With reference to the synthesis of Compound 28-1, Compound 29-2 was prepared with Compound 19-2 as the starting material. LCMS (ESI) m/z: 343 (M+3).

2) Synthesis of Compound 29-3

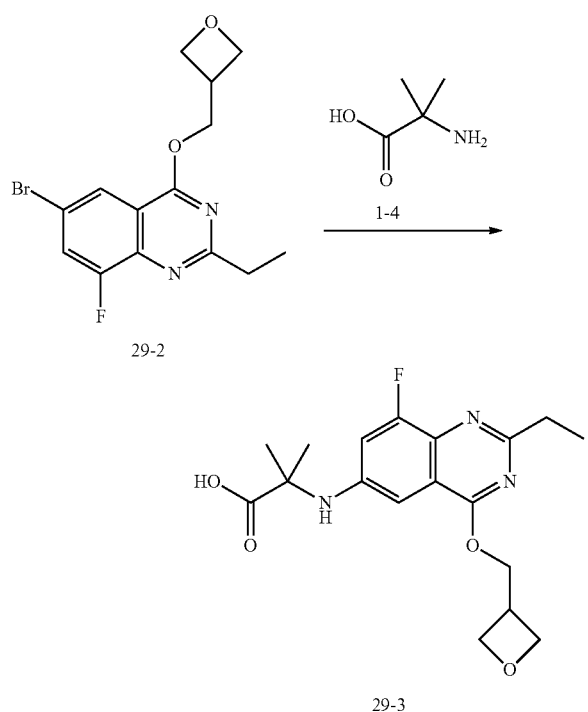

With reference to the synthesis of Compound 28-2, Compound 29-3 was prepared with Compound 29-2 as the starting material. LCMS (ESI) m/z: 364 (M+1).

3) Synthesis of Compound 29-4

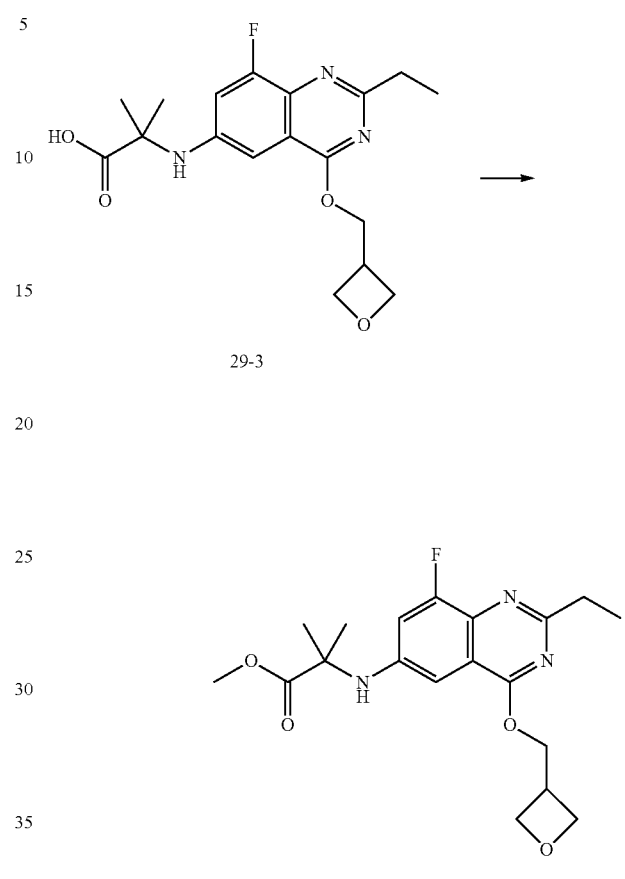

With reference to the synthesis of Compound 28-3, Compound 29-4 was prepared with Compound 29-3 as the starting material. $^1$H NMR (400 MHz, CDCl$^3$) δ ppm 6.71 (dd, J=12.17, 2.64 Hz, 1H), 6.64 (d, J=2.01 Hz, 1H), 4.76 (dd, J=7.78, 6.27 Hz, 2H), 4.62 (d, J=6.27 Hz, 2H), 4.53 (t, J=6.15 Hz, 2H), 4.29 (s, 1H), 3.58 (s, 3H), 3.35-3.45 (m, 1H), 2.79 (q, J=7.53 Hz, 2H), 1.47 (s, 6H), 1.22 (t, J=7.65 Hz, 3H); LCMS (ESI) m/z: 378 (M+1).

4) Synthesis of Compound 29

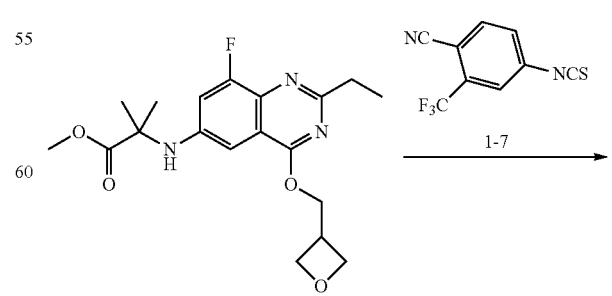

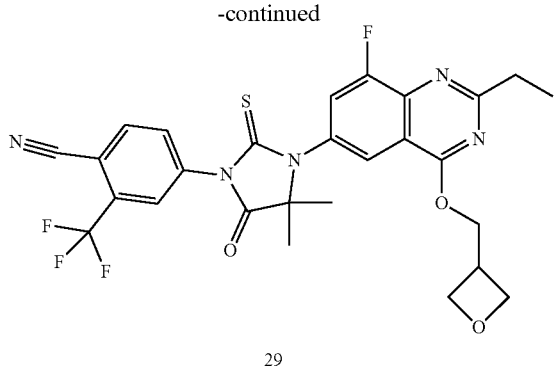

29

With reference to the synthesis of Compound 28-4, Compound 29 was prepared with Compound 29-4 as the starting material. $^1$H NMR (400 MHz, CDCl$_3$) δ ppm 7.88-7.98 (m, 2H), 7.74-7.84 (m, 2H), 7.39 (dd, J=10.04, 2.01 Hz, 1H), 4.85 (dd, J=7.78, 6.27 Hz, 2H), 4.79 (d, J=6.27 Hz, 2H), 4.59 (t, J=6.15 Hz, 2H), 3.44-3.55 (m, 1H), 2.98 (q, J=7.53 Hz, 2H), 1.58 (s, 6H), 1.32-1.40 (m, 3H); LCMS (ESI) m/z: 574 (M+1).

Example 29 Synthesis of Compound 30

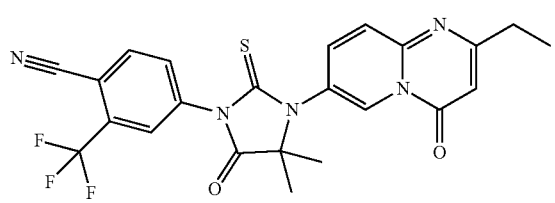

1) Synthesis of Compound 30-3

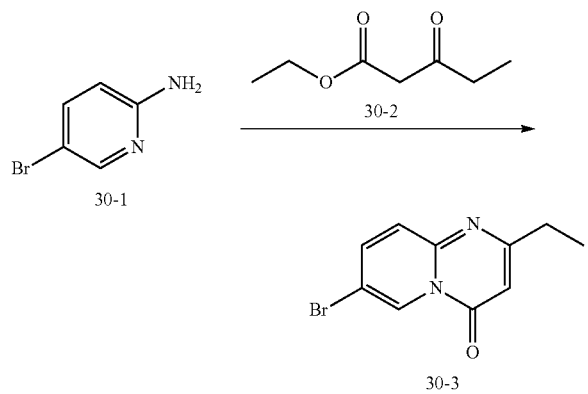

Compound 30-1 (20.00 g) and Compound 30-2 (16.67 g) were added to acetic acid (250 mL). Then, the resulting mixture was heated to 120° C., and stirred at this temperature for 16 h. The reaction mixture was concentrated under reduced pressure, diluted with 200 mL of water, and extracted with ethyl acetate (200 mL×3). After liquid separation, the organic phases were collected, and combined. The combined organic phase was dried over anhydrous sodium sulfate, filtered, and concentrated under reduced pressure. The concentrate was slurried with petroleum ether to obtain Compound 30-3. $^1$H NMR (400 MHz, CDCl$_3$) δ ppm 9.16 (d, J=1.98 Hz, 1H), 7.73 (dd, J=9.48, 2.21 Hz, 1H), 7.48 (d, J=9.48 Hz, 1H), 6.39 (s, 1H), 2.72 (q, J=7.64 Hz, 2H), 1.32 (t, J=7.61 Hz, 3H).

2) Synthesis of Compound 30-4

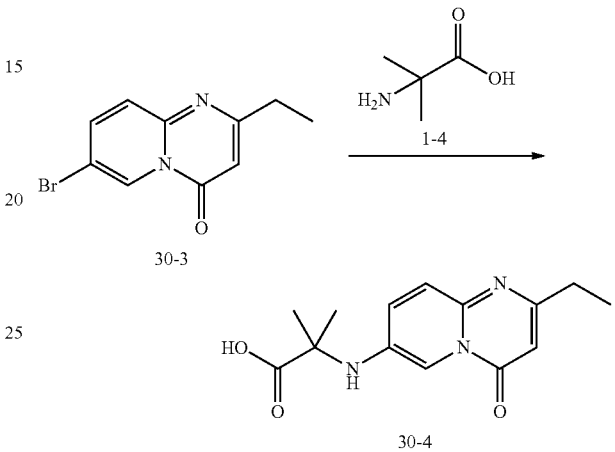

Compound 30-3 (1.50 g), Compound 1-4 (916 mg), cuprous chloride (58 mg), 2-acetylcyclohexanone (83 mg), and potassium carbonate (2.05 g) were added to a microwave reaction tube. Then, the solvent of DMF (15 mL) and water (3 mL) was added, and the resulting mixture was kept at 130° C. for microwave reaction for 1 h. The reaction mixture was filtered, and the filter cake was washed with DMF (10 mL×3). The combined filtrate was concentrated to obtain Compound 30-4. LCMS (ESI) m/z: 276 (M+1).

3) Synthesis of Compound 30-5

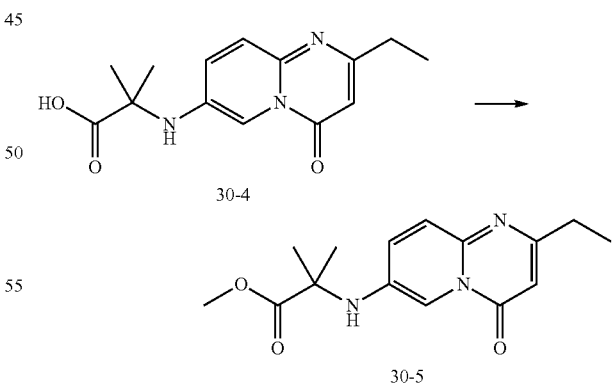

A solution of methanol/hydrochloric acid (100 mL) was added to Compound 30-4 (3.76 g). The resulting mixture was heated to 70° C., and stirred at this temperature for 16 h. The reaction mixture was concentrated, adjusted to pH=7 with a saturated sodium bicarbonate solution, and extracted with ethyl acetate (25 mL×3). The organic phases were combined, and were successively washed with saturated brine (25 mL×3), dried over anhydrous sodium sulfate, filtered, and concentrated. The concentrate was purified by column chromatography to obtain Compound 30-5. LCMS (ESI) m/z: 290 (M+1).

4) Synthesis of Compound 30

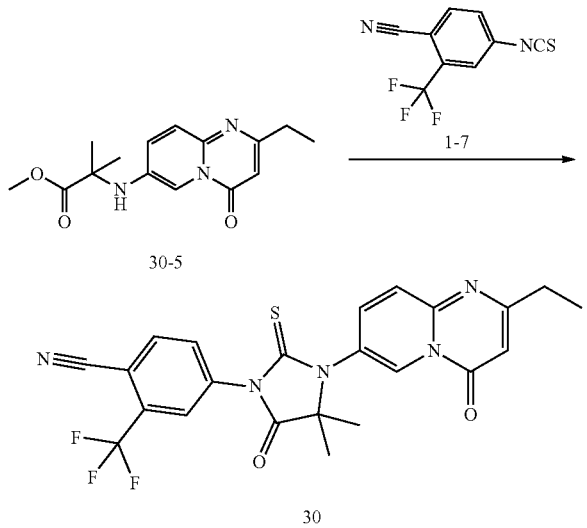

Compound 30-5 (200 mg) and Compound 1-7 (315 mg) were dissolved in a mixed solution of methylbenzene (4 mL) and DMF (1 mL), and the resulting mixture was heated to 120° C., and stirred at this temperature in a nitrogen atmosphere for 16 h. The reaction mixture was concentrated under reduced pressure, dissolved in acetonitrile, and purified by preparative HPLC to obtain Compound 30. $^1$H NMR (400 MHz, CDCl$_3$) δ ppm 9.02 (d, J=1.98 Hz, 1H), 8.02 (d, J=8.38 Hz, 1H), 7.96 (s, 1H), 7.82-7.88 (m, 1H), 7.67-7.73 (m, 1H), 7.60-7.66 (m, 1H), 6.44 (s, 1H), 2.77 (q, J=7.57 Hz, 2H), 1.35 (t, J=7.61 Hz, 3H). LCMS (ESI) m/z: 486 (M+1).

Example 30 Synthesis of Compound 31

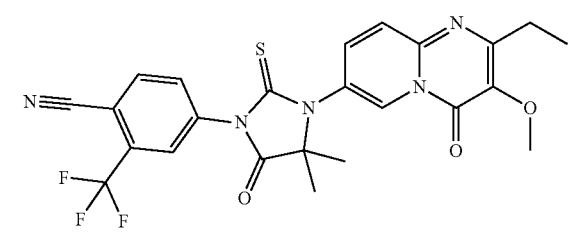

1) Synthesis of Compound 31-1

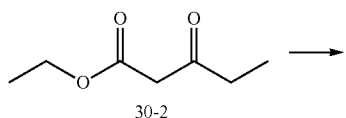

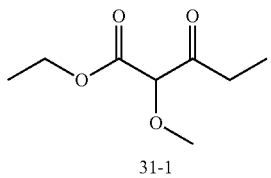

In a dry single-necked flask, iodobenzene diacetate (16.09 g) and methanol (250 mL) were added, then a solution of boron trifluoride diethyl etherate (7.09 g) was added dropwise, and then Compound 30-2 (6.86 g) was added. The resulting mixture was stirred at 25° C. for 28 h. After the completion of the reaction, the reaction mixture was concentrated. 50 mL of a saturated aqueous solution of sodium bicarbonate was added, and the resulting mixture was extracted with ethyl acetate (75 mL×3). After liquid separation, the organic phase was washed with 50 ml of saturated brine, dried over anhydrous sodium sulfate, filtered, and concentrated. The concentrate was purified by a chromatographic column to obtain Compound 31-1. $^1$H NMR (400 MHz, CDCl$_3$) δ ppm 4.27-4.18 (m, 3H), 3.43 (s, 3H), 2.67-2.51 (m, 2H), 1.26 (t, J=7.2 Hz, 3H), 1.02 (t, J=7.3 Hz, 3H), LCMS (ESI) m/z: 175 (M+1).

2) Synthesis of Compound 31-4

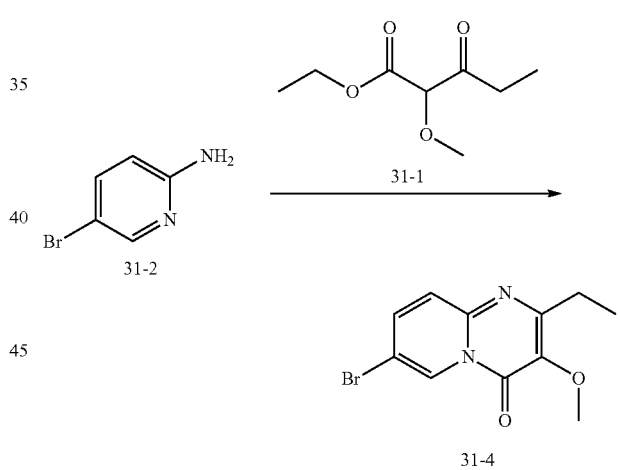

In a dry reaction flask, Compound 31-1 (2.15 g) and Compound 31-2 (2.14 g) were added, and then ethanol (22 mL) and acetic acid (2.2 mL) were added. The resulting mixture was heated to 90° C., stirred for 72 h, and concentrated to dryness to remove the solvent. 50 mL of water was added to the residue, and the resulting mixture was fully stirred, and extracted with ethyl acetate (30 mL×3). The organic phase was dried over anhydrous sodium sulfate, and filtered. The filtrate was concentrated, and the concentrate was purified by a chromatographic column to obtain Compound 31-4. $^1$H NMR (400 MHz, CDCl$_3$) δ ppm 9.08-9.07 (m, 1H), 7.59 (dd, J=2.2, 9.5 Hz, 1H), 7.44 (dd, J=0.7, 9.5 Hz, 1H), 3.97 (s, 3H), 2.81 (q, J=7.7 Hz, 2H), 1.27 (t, J=7.6 Hz, 3H).

3) Synthesis of Compound 31-5

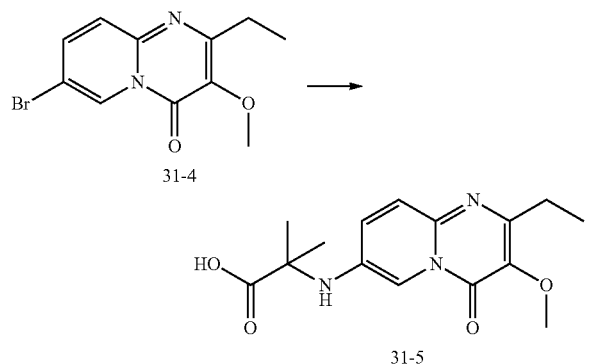

5) Synthesis of Compound 31

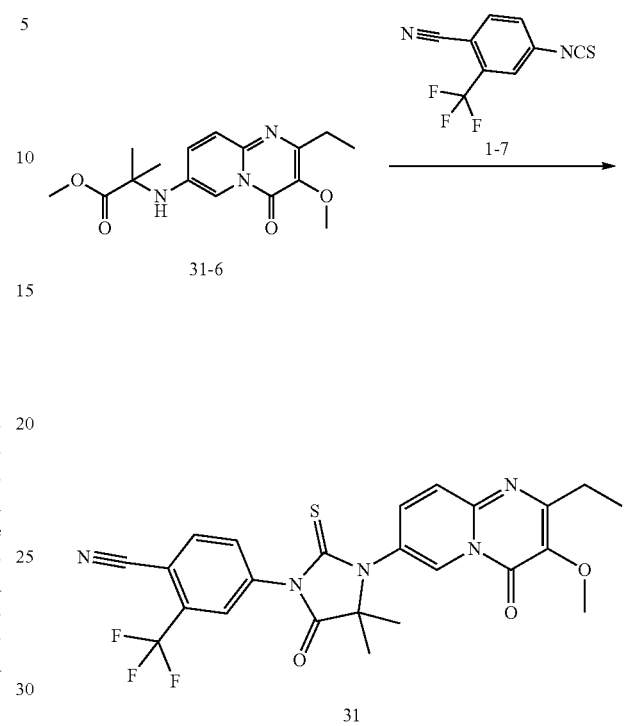

In a microwave tube, Compound 31-4 (250 mg), Compound 2-aminoisobutyric acid (149 mg), potassium carbonate (332 mg), cuprous chloride (19 mg), and 2-acetylcyclohexanone (27 mg, 192 μmol) were dissolved in a mixed solvent of DMF (5 mL) and water (0.5 mL), and the resulting mixture was kept at 130° C. for microwave reaction for 1.5 h. The reaction mixture was cooled, and then filtered. 12 mL of water was added to the filtrate, which was then extracted with ethyl acetate (20 mL×3), and the aqueous phase was concentrated under reduced pressure to obtain Compound 31-5. LCMS (ESI) m/z: 306 (M+1).

4) Synthesis of Compound 31-6

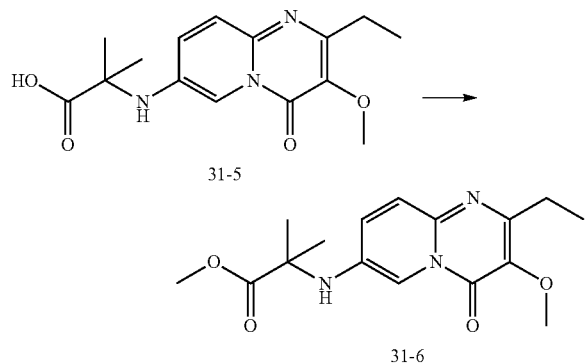

In a pre-dried single-necked flask, Compound 31-5 (5.50 g) and a solution of hydrochloric acid in methanol (4N, 50 mL) were added, and the resulting mixture was heated to 90° C. and stirred for 12 h under nitrogen protection. A solid residue was obtained by concentration under reduced pressure. The solid residue was dissolved in 100 mL of ethyl acetate, and then washed with a saturated aqueous solution of sodium bicarbonate (50 mL×1). After liquid separation, the organic phase was collected, washed with saturated brine (50 mL×1), dried over anhydrous sodium sulfate, and filtered. The filtrate was concentrated, and the resulting concentrate was purified by a chromatographic column to obtain Compound 31-6. $^1$H NMR (400 MHz, CDCl$_3$) δ ppm 8.15 (d, J=2.2 Hz, 1H), 7.44 (d, J=9.5 Hz, 1H), 7.15 (dd, J=2.8, 9.6 Hz, 1H), 4.28 (s, 1H), 3.95 (s, 3H), 3.77 (s, 3H), 2.78 (q, J=7.6 Hz, 2H), 1.62 (s, 6H), 1.26 (t, J=7.6 Hz, 3H). LCMS (ESI) m/z: 320 (M+1).

In a dry single-necked flask, Compound 31-6 (200 mg), DMF (1.5 mL) and methylbenzene (6 mL) were added, and then Compound 1-7 (429 mg) was added. Under nitrogen protection, the resulting mixture was heated to 80° C., and stirred at this temperature for 3 h. After concentration under reduced pressure, the concentrate was purified by preparative HPLC method to obtain Compound 31. $^1$H NMR (400 MHz, CDCl$_3$) δ ppm 8.97 (d, J=2.2 Hz, 1H), 8.02 (d, J=8.2 Hz, 1H), 7.97 (s, 1H), 7.85 (br d, J=8.4 Hz, 1H), 7.68 (d, J=9.5 Hz, 1H), 7.51 (dd, J=2.2, 9.5 Hz, 1H), 4.02 (s, 3H), 2.88 (q, J=7.6 Hz, 2H), 1.69 (s, 6H), 1.32 (t, J=7.6 Hz, 3H). LCMS (ESI) m/z: 516 (M+1).

Example 31 Synthesis of Compound 32

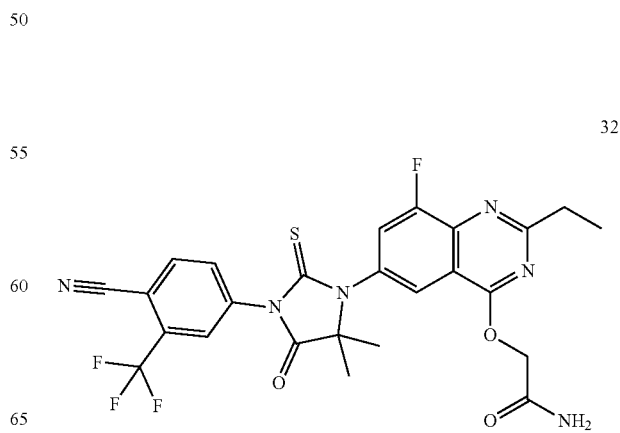

1) Synthesis of Compound 32-1

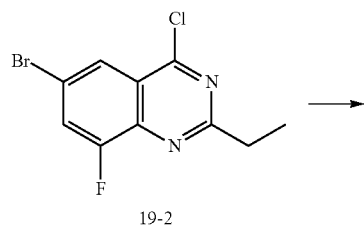

In a dry reaction flask, Compound 19-2 (1.00 g), methyl 2-hydroxyacetate (466 mg) and tetrahydrofuran (10 mL) were added, and then NaH (207 mg, 60% purity) was added in batches. The reaction mixture reacted at 20° C. for 1 h, then was diluted with a saturated aqueous solution of ammonium chloride (50 mL), and extracted with ethyl acetate (30 mL×3). The organic phases were combined, and concentrated. The resulting concentrate was purified by a chromatographic column to obtain Compound 32-1. $^1$H NMR (400 MHz, CDCl$_3$) δ ppm 8.16-8.20 (m, 1H), 7.67 (dd, J=9.54, 2.13 Hz, 1H), 5.15 (s, 2H), 3.82 (s, 3H), 2.99 (q, J=7.57 Hz, 2H), 1.37 (t, J=7.53 Hz, 3H).

2) Synthesis of Compound 32-2

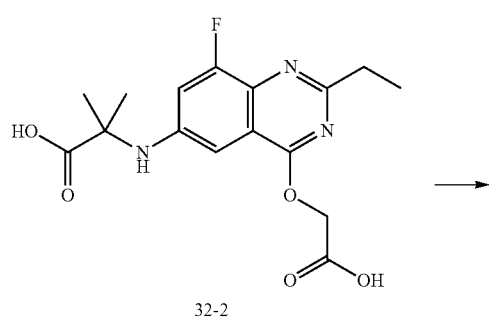

In a microwave tube, Compound 32-1 (500 mg), Compound 1-4 (225 mg), cuprous chloride (14 mg), 2-acetylcyclohexanone (20 mg), and potassium carbonate (402 mg) were added, and then DMF (4 mL) and water (0.5 mL) were added. After nitrogen purge for 1 min, the resulting mixture was kept at 130° C. for microwave reaction for 1 h. The reaction mixture was filtered in the presence of Celite, and the filter cake was washed with DMF (5 mL×2). The filtrate was collected, and concentrated to dryness under reduced pressure, to obtain Compound 32-2. LCMS (ESI) m/z: 352 (M+1).

3) Synthesis of Compound 32-3

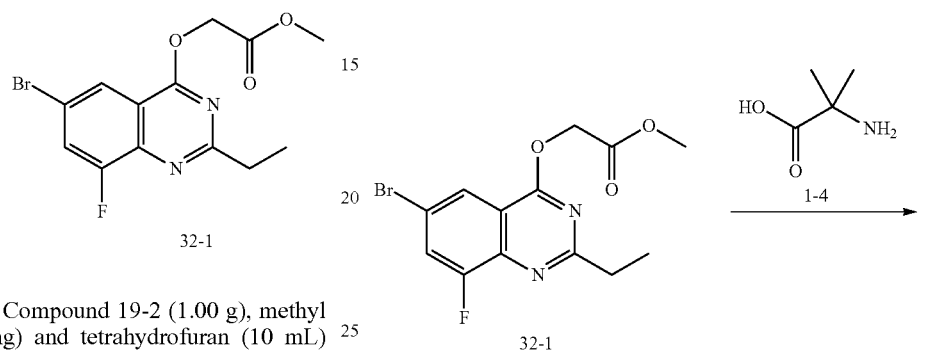

A solution of TMSCHN$_2$ in n-hexane (2M, 4.70 mL) was added dropwise to a solution of Compound 32-2 (1.10 g) in dichloromethane (20 mL) and methanol (2 mL). The resulting mixture reacted at 20° C. for 2 h. TMSCHN$_2$ (2M, 4.70 mL) was supplemented, and then the mixture was stirred for 16 h. The reaction mixture was concentrated to dryness. The residue was purified by a chromatographic column to obtain Compound 32-3. $^1$H NMR (400 MHz, CDCl$_3$) δ ppm 6.84-6.91 (m, 2H) 5.04-5.12 (m, 2H) 4.48 (s, 1H) 3.79 (s, 3H) 3.75 (s, 3H) 2.91 (q, J=7.53 Hz, 2H) 1.64 (s, 6H) 1.32 (t, J=7.59 Hz, 3H).

4) Synthesis of Compound 32-4

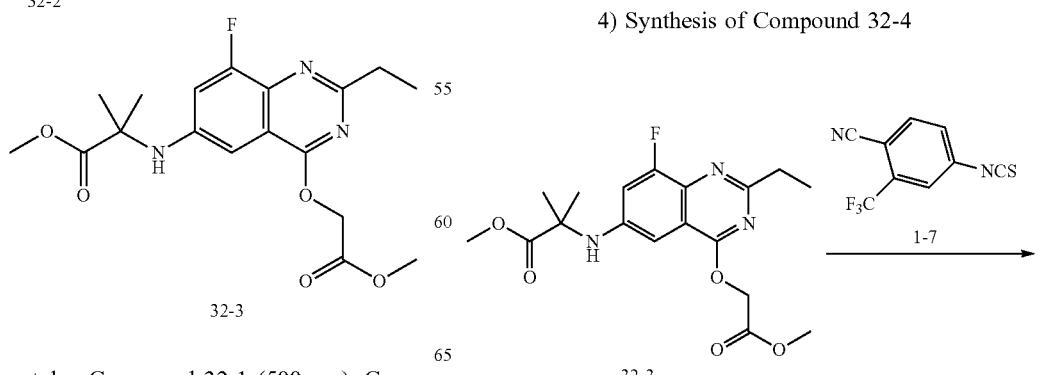

6) Synthesis of Compound 32

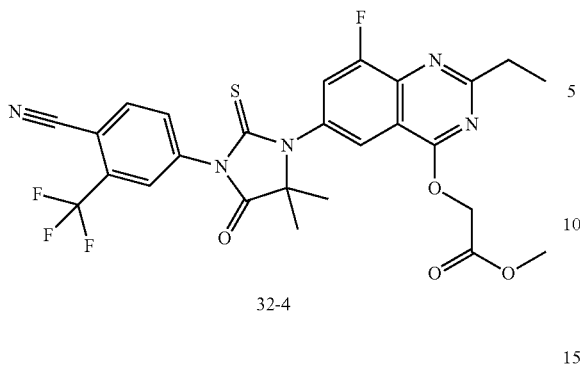

32-4

In a dry single-necked flask, Compound 32-3 (630 mg) and Compound 1-7 (378 mg) were added, and then methylbenzene (4 mL) and DMF (1 mL) were added. The resulting mixture reacted at 120° C. for 24 h. The reaction mixture was concentrated under reduced pressure. The resulting residue was purified by preparative HPLC to obtain Compound 32-4. LCMS (ESI) m/z: 576 (M+1).

5) Synthesis of Compound 32-5

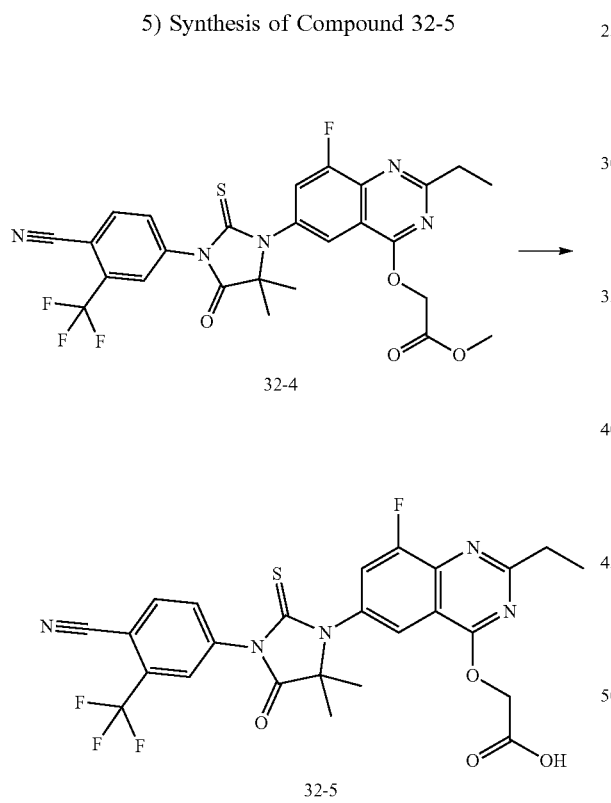

32-4

32-5

In a pre-dried single-necked flask, Compound 32-4 (55 mg) and tetrahydrofuran (4 mL) were added, and then a solution of lithium hydroxide monohydrate (6 mg) in water (1 mL) was added. The resulting mixture was stirred at 25° C. for 2 h. A saturated ammonium chloride solution (5 mL) and ethyl acetate (10 mL) were added to the reaction mixture for liquid separation. The aqueous phase was extracted with ethyl acetate (5 mL×3). The organic phases were combined, dried over sodium sulfate, and concentrated. The resulting residue was purified by preparative TLC to obtain Compound 32-5. LCMS (ESI) m/z: 562 (M+1).

6) Synthesis of Compound 32

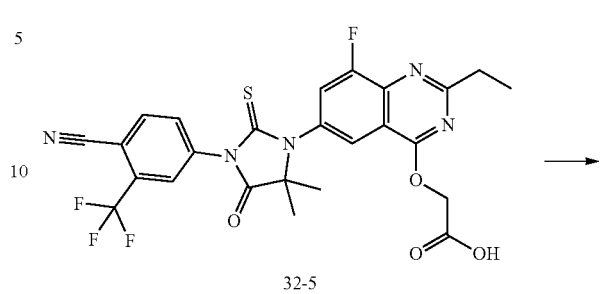

32-5

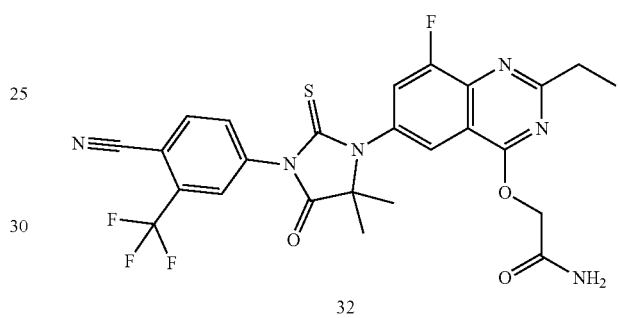

32

In a 10 mL dry reaction flask, Compound 32-5 (37 mg) and dichloromethane (2 mL) were added, and then HATU (30 mg), ammonium chloride (5 mg), and triethylamine (20 mg) were added at 0° C. The resulting mixture was stirred at 25° C. for 16 h, then diluted with 4 mL of water, extracted with dichloromethane (5 mL×3), dried, and concentrated. The resulting residue was separated by preparative HPLC to obtain Compound 32. $^1$H NMR (400 MHz, CDCl$_3$) δ ppm 7.99 (d, J=8.16 Hz, 1H), 7.95 (s, 1H), 7.90 (s, 1H), 7.83 (dd, J=8.27, 1.87 Hz, 1H), 7.48 (dd, J=9.81, 2.09 Hz, 1H), 6.03 (br s, 1H), 5.59 (br s, 1H), 5.13 (s, 2H), 3.05 (q, J=7.57 Hz, 2H), 1.66 (s, 6H), 1.40 (t, J=7.61 Hz, 3H); LCMS (ESI) m/z: 561 (M+1).

Example 32 Synthesis of Compound 33

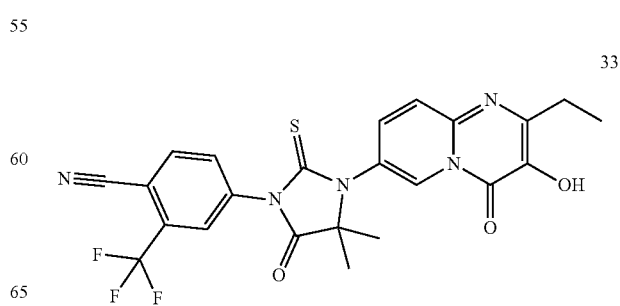

33

193

1) Synthesis of Compound 33

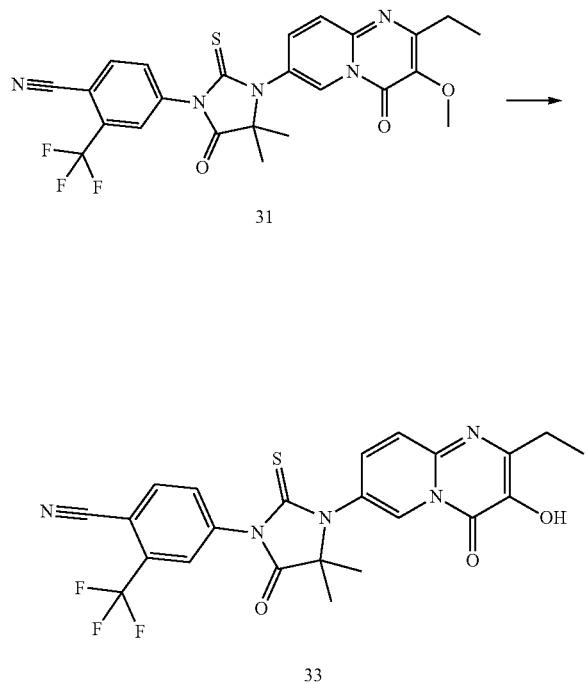

In a dry single-necked flask, Compound 31 (50 mg) and dichloromethane (2 mL) were added, and then boron tribromide (97 mg) was added in an ice bath. The resulting mixture was controlled at a temperature of 0° C., and stirred for 2 h. At 0° C., 0.5 mL of ice water was added to the reaction mixture to quench the reaction, and then a small amount of sodium bicarbonate solids were added to adjust the pH to 7-8. After dichloromethane was removed under reduced pressure at 0° C., 3 mL of DMSO was added to the residue to dissolve the mixture. After filtration, the resulting solution was purified by preparative HPLC method to obtain Compound 33. $^1$H NMR (400 MHz, CDCl$_3$) δ ppm 8.83 (d, J=1.5 Hz, 1H), 8.02 (d, J=8.4 Hz, 1H), 7.97 (d, J=2.0 Hz, 1H), 7.85 (dd, J=2.0, 8.2 Hz, 1H), 7.70-7.67 (m, 1H), 7.40 (dd, J=2.3, 9.6 Hz, 1H), 2.92 (q, J=7.6 Hz, 2H), 1.69 (s, 6H), 1.35 (t, J=7.6 Hz, 3H); LCMS (ESI) m/z: 502 (M+1).

Example 33 Synthesis of Compound 34

194

1) Synthesis of Compound 34-2

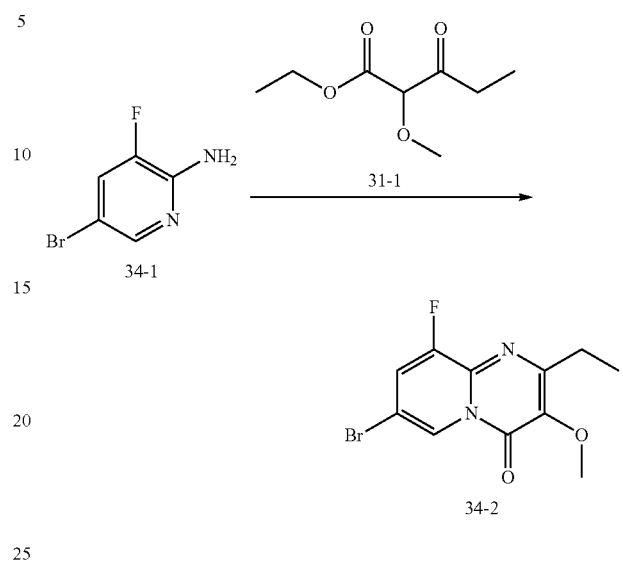

Compound 31-1 (5.03 g) was added to a solution of Compound 34-1 (2.00 g) in acetic acid (20 mL), and the resulting mixture was heated to 110° C., and stirred for 16 h. The reaction mixture was concentrated. The concentrate was diluted with dichloromethane (30 mL), washed with a saturated sodium bicarbonate solution (30 mL×2) and saturated brine (30 mL) respectively, dried over anhydrous sodium sulfate, filtered, and concentrated. The concentrate was purified by flash column chromatography (model: ISCO-RF150) to obtain Compound 34-2. LCMS (ESI) m/z: 301 (M+1).

2) Synthesis of Compound 34-3

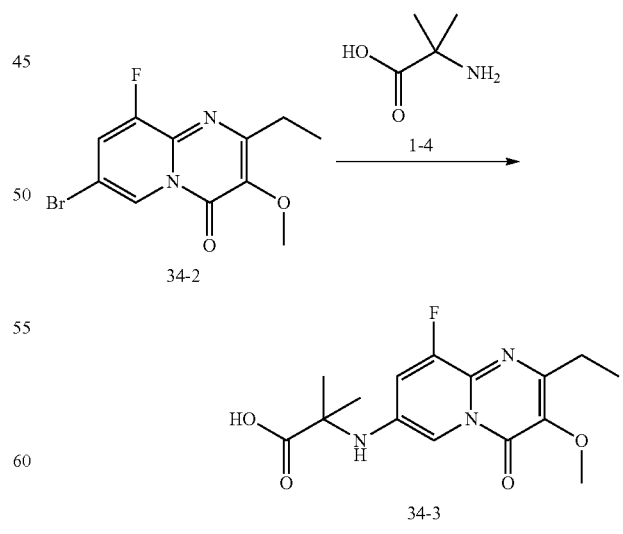

With reference to the synthesis of Compound 31-5, Compound 34-3 was prepared with Compound 34-2 as the starting material. LCMS (ESI) m/z: 324 (M+1).

3) Synthesis of Compound 34-4

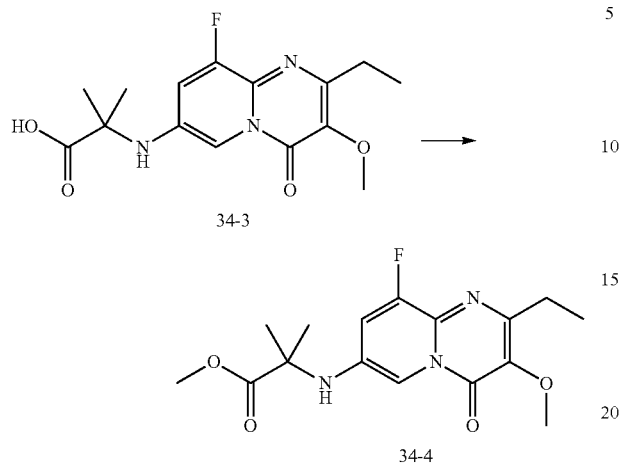

With reference to the synthesis of Compound 31-6, Compound 34-4 was prepared with Compound 34-3 as the starting material. $^1$H NMR (400 MHz, CDCl$_3$) δ ppm 7.92 (dd, J=2.38, 0.88 Hz, 1H), 6.90 (dd, J=10.42, 2.38 Hz, 1H), 3.89-3.94 (m, 1H), 3.91 (s, 2H), 3.73 (s, 3H), 2.77 (q, J=7.70 Hz, 2H), 1.57 (s, 6H), 1.21 (t, J=7.53 Hz, 3H); LCMS (ESI) m/z: 337.9 (M+1).

4) Synthesis of Compound 34

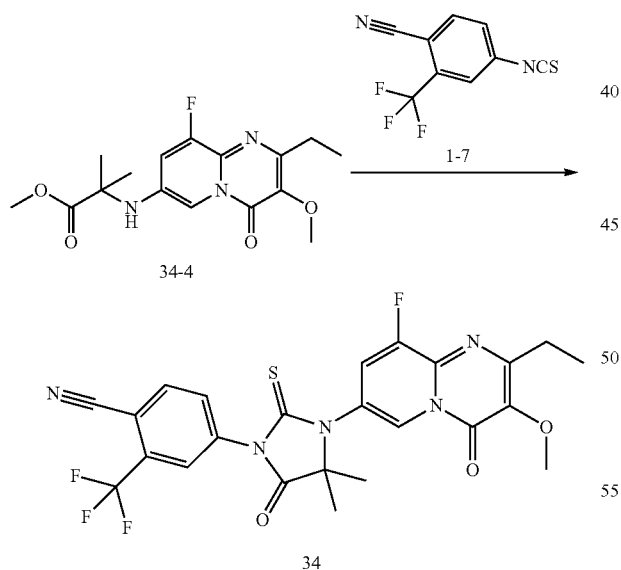

With reference to the synthesis of Compound 31, Compound 34 was prepared with Compound 34-4 as the starting material. $^1$H NMR (400 MHz, CDCl$_3$) δ ppm 8.74-8.85 (m, 1H), 8.02 (d, J=8.28 Hz, 1H), 7.95 (d, J=2.01 Hz, 1H), 7.83 (dd, J=8.28, 2.01 Hz, 1H), 7.27-7.31 (m, 1H), 4.03 (s, 3H), 2.91 (q, J=7.53 Hz, 2H), 1.69 (s, 6H), 1.33 (t, J=7.53 Hz, 3H); LCMS (ESI) m/z: 534 (M+1).

Example 34 Synthesis of Compound 35

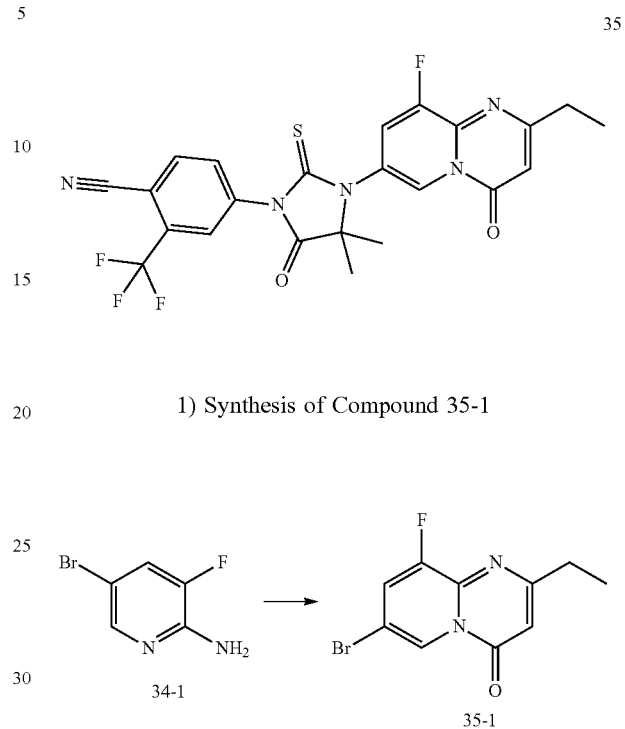

1) Synthesis of Compound 35-1

Methyl propionylacetate (4.00 g) was added to a solution of Compound 34-1 (4.00 g) in acetic acid (40 mL). The resulting mixture was heated to 110° C., and stirred for 94 h. Methyl propionylacetate (8.26 g) was supplemented to the reaction mixture, and the reaction mixture was further stirred for 16 h. The reaction mixture was concentrated. The concentrate was diluted with ethyl acetate (80 mL), and a saturated aqueous solution of sodium bicarbonate (80 mL) was added. After liquid separation, the organic phase was washed with saturated brine (80 mL), dried over anhydrous sodium sulfate, filtered, and concentrated. The residue obtained from the concentration was purified by a silica gel column to obtain Compound 35-1. $^1$H NMR (400 MHz, CDCl$_3$) δ ppm 8.89 (s, 1H), 7.45 (dd, J=2.0, 8.0 Hz, 1H), 6.36 (s, 1H), 2.70 (q, J=7.5 Hz, 2H), 1.25 (t, J=7.5 Hz, 3H).

2) Synthesis of Compound 35-2

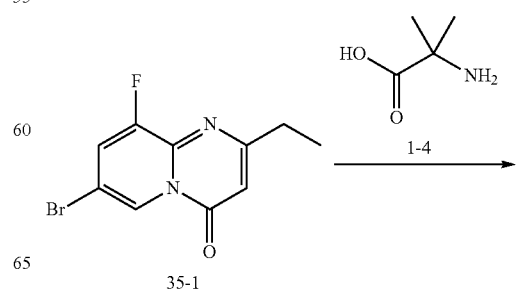

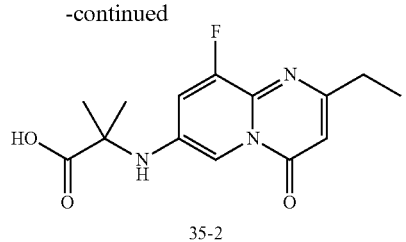

35-2

Compound 35-1 (400 mg), Compound 1-4 (228 mg), potassium carbonate (510 mg), cuprous chloride (30 mg), 2-acetylcyclohexanone (42 mg), N,N-dimethylformamide (4 mL), and water (0.2 mL) were added to a microwave tube. The microwave tube was sealed, and kept at 130° C. for microwave reaction for 30 min. The reaction mixture was filtered, and washed with ethyl acetate (20 mL). The filtrate was concentrated. 1N hydrochloric acid was added to the residue obtained from the concentration (to adjust the pH to 6-7), and the resulting mixture was concentrated. Dichloromethane/methanol (40 mL, 10/1) were added to the residue obtained from the concentration, and the resulting mixture was dried over anhydrous sodium sulfate, and filtered. The filtrate was concentrated under reduced pressure to obtain Compound 35-2. LCMS (ESI) m/z: 294 (M+1).

3) Synthesis of Compound 35-3

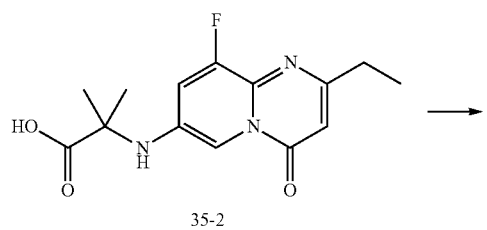

A solution of trimethylsilyldiazomethane in n-hexane (2M, 1.2 mL) was added to a solution of Compound 35-2 (500 mg) in dichloromethane (10 mL) and methanol (1 mL). The resulting mixture was stirred at 15° C. for 2 h. The reaction mixture was concentrated. The residue obtained from the concentration was purified by a silica gel column to obtain Compound 35-3. $^1$H NMR (400 MHz, CDCl$_3$) δ ppm 8.01 (d, J=1.3 Hz, 1H), 7.04 (dd, J=2.4, 10.4 Hz, 1H), 6.26 (s, 1H), 4.43 (br s, 1H), 3.72 (s, 3H), 2.66 (q, J=7.5 Hz, 2H), 1.56 (s, 6H), 1.23 (t, J=7.5 Hz, 3H).

4) Synthesis of Compound 35

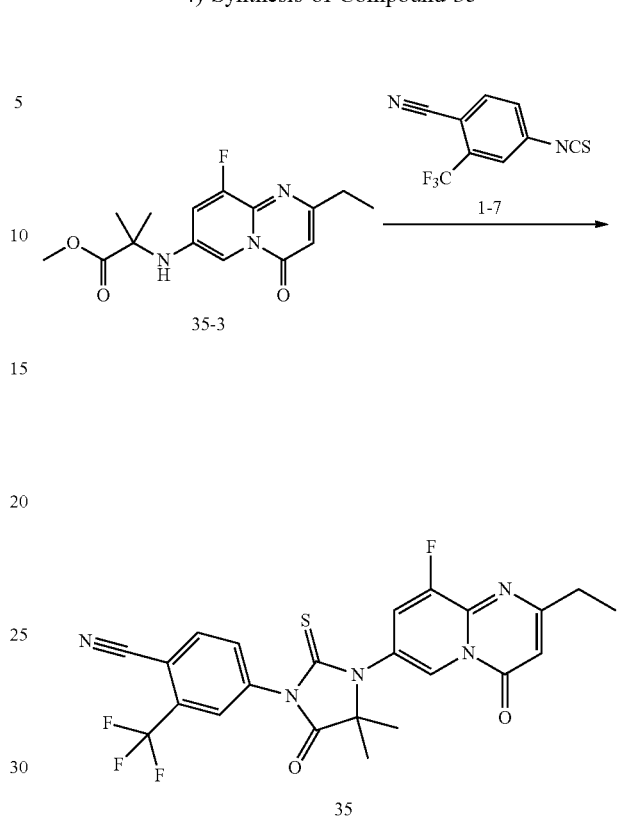

A mixed solution of Compound 35-3 (100 mg) and Compound 1-7 (297 mg) in N,N-dimethylformamide (0.5 mL) and methylbenzene (2 mL) was heated to 120° C., and stirred for 16 h. Methanol (0.5 mL) was added to the reaction mixture, which was stirred for 30 min, and then concentrated under reduced pressure. The residue obtained from the concentration was purified by a preparative chromatoplate to obtain Compound 35. $^1$H NMR (400 MHz, CDCl$_3$) δ ppm 8.76 (d, J=1.8 Hz, 1H), 7.94 (d, J=8.3 Hz, 1H), 7.88 (d, J=2.0 Hz, 1H), 7.76 (dd, J=2.0, 8.3 Hz, 1H), 7.33 (dd, J=2.3, 8.8 Hz, 1H), 6.42 (s, 1H), 2.74 (q, J=7.7 Hz, 2H), 1.62 (s, 6H), 1.28 (t, J=7.5 Hz, 3H); LCMS (ESI) m/z: 504 (M+1).

Example 35 Synthesis of Compound 36

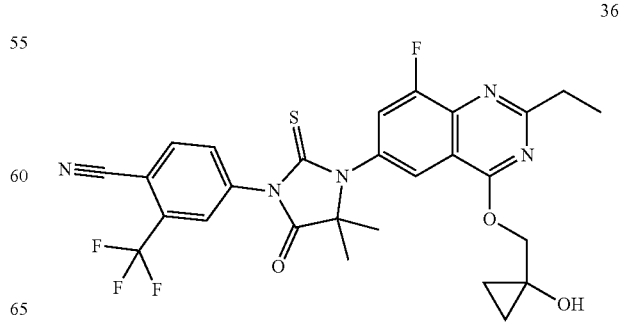

36

1) Synthesis of Compound 36-1

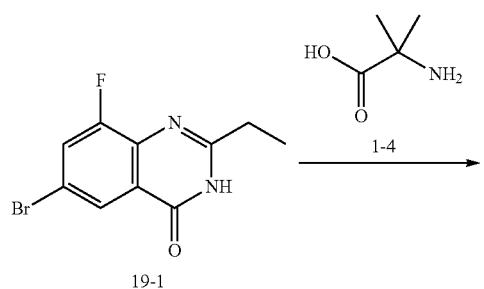

In a 50 mL dry single-necked flask, Compound 19-1 (1.00 g), Compound 1-4 (571 mg), water (2.5 mL) and DMF (10 mL) were added, and then cuprous chloride (36 mg), 2-acetylcyclohexanone (52 mg), and potassium carbonate (1.02 g) were added. The resulting mixture was stirred at 130° C. for 90 min. Water (10 mL) was added, the mixture was adjusted to pH=2-3 with 1M dilute hydrochloric acid, and ethyl acetate (40 mL) was added. The aqueous phase was extracted with ethyl acetate (40 mL×3). The organic phases were combined, and concentrated to remove the solvent. Dichloromethane (5 mL) was added to the concentrate, and stirred for 5 min. Petroleum ether (10 mL) was slowly added dropwise, and the resulting mixture was stirred for 10 min. The mixture was filtered, and the filter cake was dried to obtain Compound 36-1. LCMS (ESI) m/z: 294 (M+1).

2) Synthesis of Compound 36-2

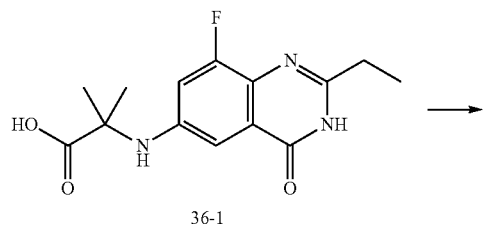

In a 50 mL dry single-necked flask, Compound 36-1 (3.00 g) and a hydrochloric acid/methanol solution (30 mL) were added, and the resulting mixture was stirred at 60° C. for 16 h, and then concentrated. Ethyl acetate (20 mL) and a saturated potassium carbonate solution (20 mL) were added to the residue obtained from the concentration. After liquid separation, the resulting organic phase was dried over anhydrous sodium sulfate, and filtered. The filtrate was concentrated to obtain Compound 36-2. LCMS (ESI) m/z: 308 (M+1).

3) Synthesis of Compound 36-3

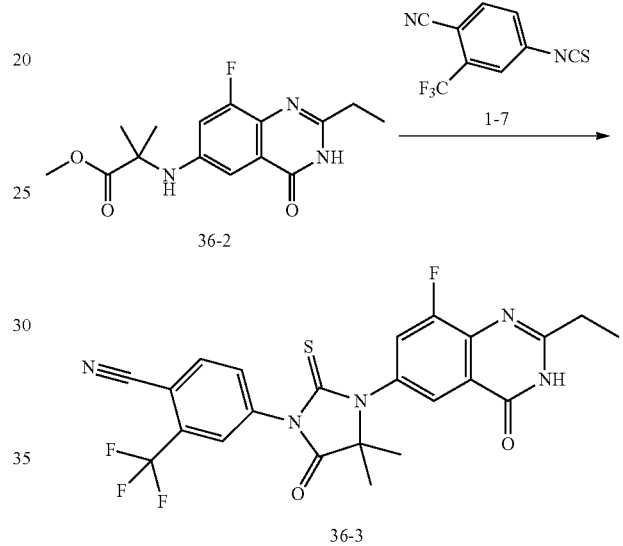

In a single-necked flask, Compound 36-2 (2.10 g), Compound 1-7 (4.68 g), methylbenzene (20 mL), and DMF (5 mL) were added, and the resulting mixture reacted at 120° C. for 16 h under nitrogen protection, and then was concentrated to remove methylbenzene and DMF. The residue obtained from the concentration was purified by column chromatography to obtain Compound 36-3. $^1$H NMR (400 MHz, CDCl$_3$) δ ppm 7.97-8.06 (m, 4H), 7.86 (dd, J=8.22, 1.82 Hz, 1H), 7.48 (dd, J=9.79, 2.26 Hz, 1H), 2.85-2.91 (m, 2H), 1.67 (s, 6H), 1.47 (t, J=7.59 Hz, 3H).

4) Synthesis of Compound 36-4

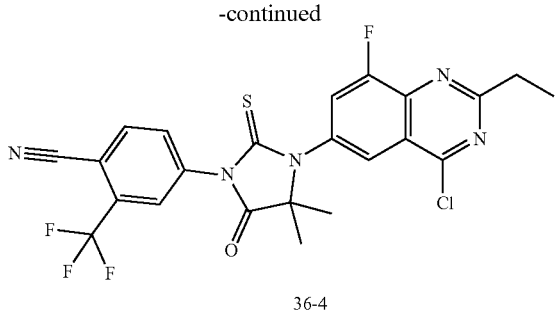

36-4

In a single-necked flask, Compound 36-3 (200 mg) and phosphorus oxychloride (3.30 g) were added. Under nitrogen protection, N,N-diisopropylethylamine (80 mg) was added, and the resulting mixture reacted at 110° C. for 0.5 h. Phosphorus oxychloride was removed from the reaction mixture under reduced pressure. The resulting residue was dissolved in 10 mL of dichloromethane in an ice water bath, and then 30 mL of a saturated sodium bicarbonate solution was added. After liquid separation, the aqueous phase was extracted with dichloromethane (10 mL×3). The organic phases were combined, washed with 10 mL of saturated brine, dried over anhydrous sodium sulfate, and filtered. The filtrate was concentrated under reduced pressure at 45° C. to obtain Compound 36-4. LCMS (ESI) m/z: 522 (M+1).

5) Synthesis of Compound 36

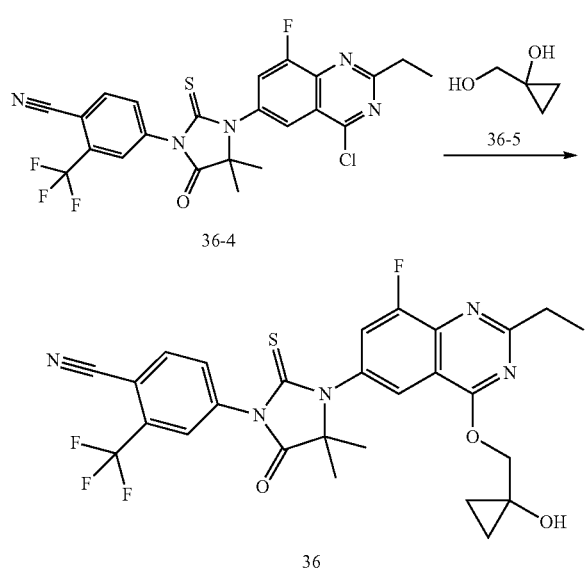

In a reaction flask, Compound 36-4 (100 mg), Compound 36-5 (25 mg), and tetrahydrofuran (1 mL) were added. Under nitrogen protection, sodium hydride (11 mg, 60% purity) was added at 0° C., and the resulting mixture reacted at 20° C. for 0.5 h. The reaction was quenched with a saturated ammonium chloride solution (3 mL). After extraction with ethyl acetate (3 mL×3), the organic phase was washed with saturated brine (1 mL), dried over anhydrous sodium sulfate, and filtered. The filtrate was concentrated at 45° C. The residue obtained from the concentration was purified by preparative HPLC method to obtain Compound 36. $^1$H NMR (400 MHz, CDCl$_3$) δ ppm 8.02 (d, J=8.16 Hz, 1H), 7.99 (s, 1H), 7.94 (s, 1H), 7.86 (br d, J=8.41 Hz, 1H), 7.48 (dd, J=10.04, 2.26 Hz, 1H), 4.76 (s, 2H), 4.05 (s, 1H), 3.06 (q, J=7.49 Hz, 2H), 1.68 (s, 6H), 1.43 (t, J=7.59 Hz, 3H), 0.98-1.02 (m, 2H), 0.82-0.86 (m, 2H). LCMS (ESI) m/z: 574 (M+1).

Example 36 Synthesis of Compound 37

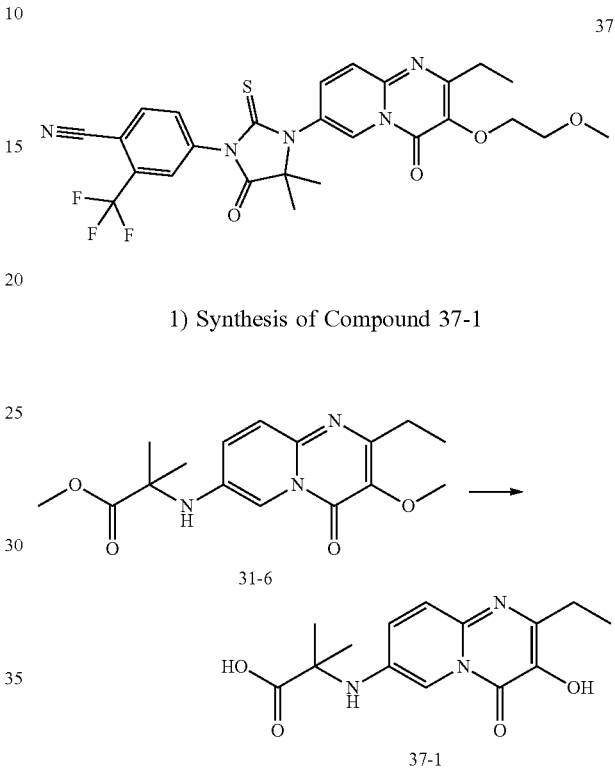

37

1) Synthesis of Compound 37-1

Boron tribromide (2.40 g) was added dropwise to a solution of Compound 31-6 (300 mg) in dichloromethane (8 mL) at 0° C. The resulting mixture was stirred at 0° C. for 2 h. The reaction was quenched with 3 g of ice water, and the reaction mixture was concentrated under reduced pressure to obtain Compound 37-1. LCMS (ESI) m/z: 292 (M+1).

2) Synthesis of Compound 37-2

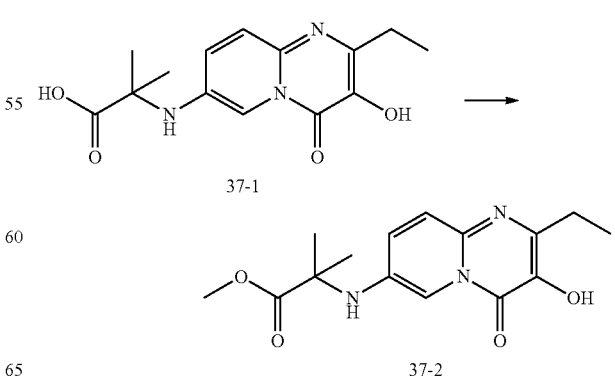

Methanol/hydrochloric acid (4M, 100 mL) as a solvent was added to Compound 37-1 (2.02 g), and the resulting mixture was stirred at 70° C. for 16 h. The reaction mixture was concentrated, the residue obtained from the concentration was neutralized to a neutral pH with a saturated sodium bicarbonate solution, and filtered. The filtrate was freeze-dried to obtain Compound 37-2. LCMS (ESI) m/z: 306 (M+1).

3) Synthesis of Compound 37-3

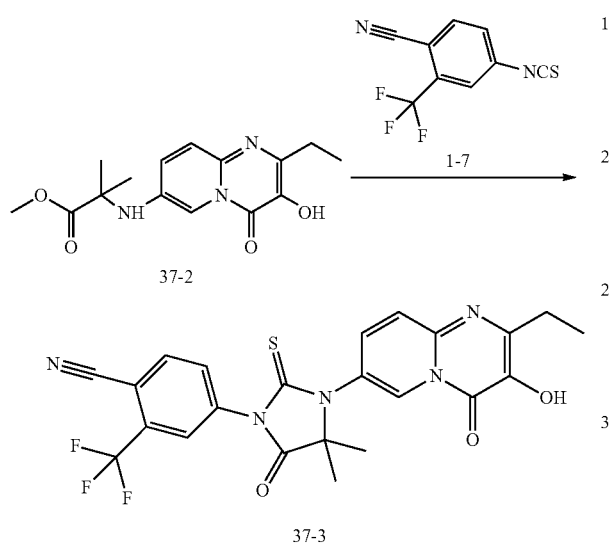

Compound 37-2 (200 mg) and Compound 1-7 (448 mg) were dissolved in a mixed solution of DMF (4 mL) and methylbenzene (1 mL). The resulting mixture was heated to 120° C., and stirred for 16 h. The reaction mixture was concentrated, dissolved in acetonitrile, and purified by preparative HPLC method to obtain Compound 37-3. LCMS (ESI) m/z: 502 (M+1).

4) Synthesis of Compound 37

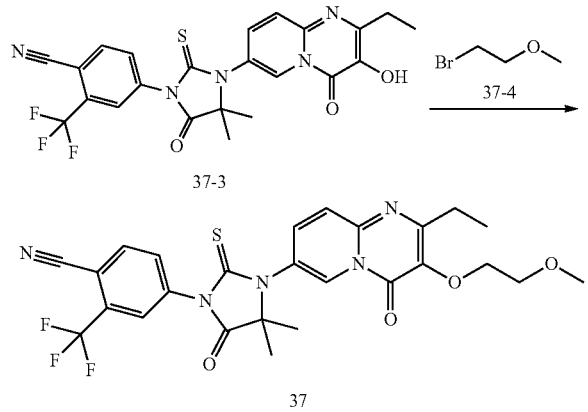

Compound 37-3 (75 mg), Compound 37-4 (25 mg), and potassium carbonate (62 mg) were dissolved in DMF (1 mL). The resulting mixture was heated to 110° C., and stirred at this temperature for 3 h. Compound 37 was obtained by preparative HPLC. $^1$H NMR (400 MHz, CDCl$_3$) δ ppm 8.95 (d, J=2.21 Hz, 1H), 8.02 (d, J=8.16 Hz, 1H), 7.97 (s, 1H), 7.82-7.88 (m, 1H), 7.68 (d, J=9.26 Hz, 1H), 7.51 (dd, J=9.48, 2.43 Hz, 1H), 4.37-4.42 (m, 2H), 3.72-3.77 (m, 2H), 3.46 (s, 3H), 2.93 (q, J=7.50 Hz, 2H), 1.68 (s, 6H), 1.33 (t, J=7.61 Hz, 3H). LCMS (ESI) m/z: 560 (M+1).

Example 37 Synthesis of Compound 38

1) Synthesis of Compound 38

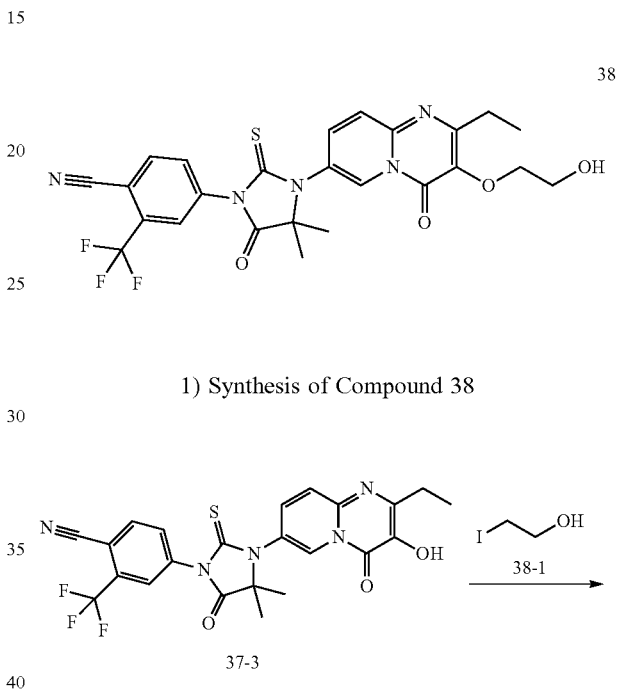

Compound 37-3 (100 mg), Compound 38-1 (41 mg), and potassium carbonate (82 mg) were added to DMF (1 mL), and the resulting mixture was heated to 110° C., and stirred at this temperature for 3 h. Compound 38 was obtained through purification by preparative HPLC method. $^1$H NMR (400 MHz, CDCl$_3$) δ ppm 8.94 (d, J=1.98 Hz, 1H), 8.00 (d, J=8.38 Hz, 1H), 7.94 (s, 1H), 7.83 (br d, J=8.38 Hz, 1H), 7.69 (d, J=9.70 Hz, 1H), 7.54 (dd, J=9.59, 2.32 Hz, 1H), 4.19-4.25 (m, 2H), 4.05-4.12 (m, 1H), 3.87-3.94 (m, 2H), 2.89 (q, J=7.50 Hz, 2H), 1.67 (s, 6H), 1.33 (t, J=7.61 Hz, 3H); LCMS (ESI) m/z: 546 (M+1).

Example 38 Synthesis of Compound 39

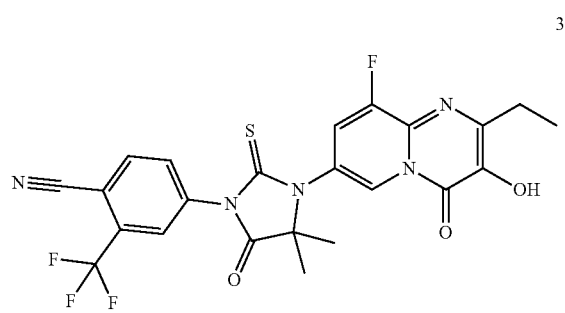

1) Synthesis of Compound 39-1

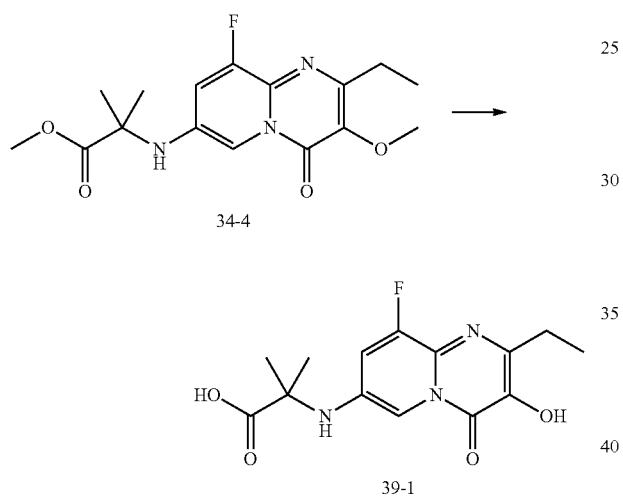

Boron tribromide (0.4 mL) was added to a solution of Compound 34-4 (320 mg) in anhydrous dichloromethane (8 mL) at 0° C. The resulting mixture was stirred at 0° C. for 2 h, diluted with dichloromethane (40 mL), slowly poured into water (20 mL), and extracted with dichloromethane/methanol (10/1, 40 mL). The organic phase was dried over anhydrous sodium sulfate, filtered, and concentrated to obtain Compound 39-1. LCMS (ESI) m/z: 310 (M+1).

2) Synthesis of Compound 39-2

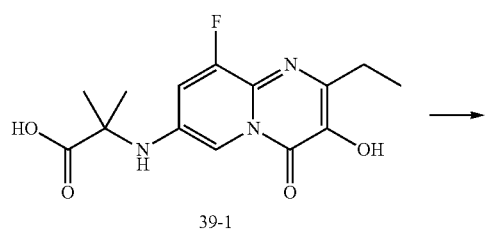

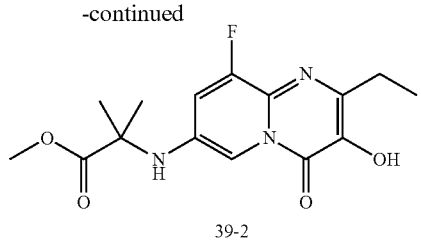

A solution of trimethylsilyldiazomethane in n-hexane (2M, 0.3 mL) was added to a solution of Compound 39-1 (120 mg) in dichloromethane (3 mL) and methanol (0.3 mL). The resulting mixture was stirred at 20° C. for 1 h. The reaction mixture was concentrated under reduced pressure. The residue obtained from the concentration was purified by a preparative chromatoplate to obtain Compound 39-2. $^1$H NMR (400 MHz, CDCl$_3$) δ ppm 7.73 (s, 1H), 6.80 (br d, J=9.5 Hz, 1H), 6.22 (br s, 1H), 4.21 (br s, 1H), 3.73 (s, 3H), 2.81 (q, J=7.5 Hz, 2H), 1.57 (s, 6H), 1.24 (t, J=7.7 Hz, 3H).

3) Synthesis of Compound 39

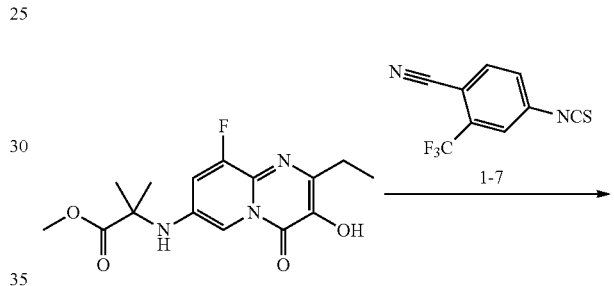

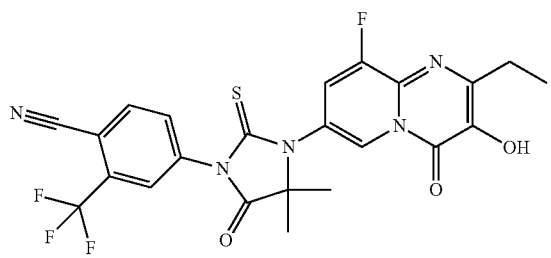

A mixture of Compound 39-2 (30 mg), Compound 1-7 (100 mg), methylbenzene (1 mL), and N,N-dimethylformamide (0.2 mL) was heated to 110° C., and stirred for 16 h. Methanol (1 mL) was added to the reaction mixture, which was stirred for 30 min, and then concentrated under reduced pressure. The residue obtained from the concentration was separated and purified successively by a preparative chromatoplate and preparative HPLC to obtain Compound 39. $^1$H NMR (400 MHz, CDCl$_3$) δ ppm 8.58 (s, 1H), 7.94 (d, J=8.3 Hz, 1H), 7.88 (s, 1H), 7.76 (br d, J=8.0 Hz, 1H), 7.11 (dd, J=2.0, 9.0 Hz, 1H), 2.88 (q, J=7.4 Hz, 2H), 1.62 (s, 6H), 1.28 (t, J=7.7 Hz, 3H); LCMS (ESI) m/z: 520 (M+1).

Example 39 Synthesis of Compound 40

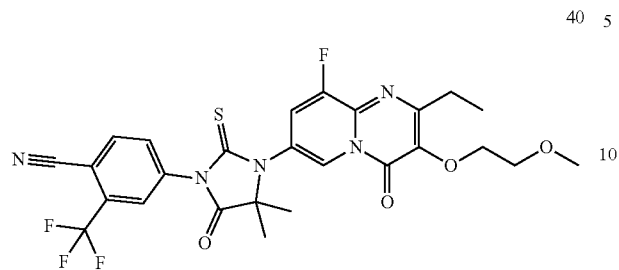
40

1) Synthesis of Compound 40

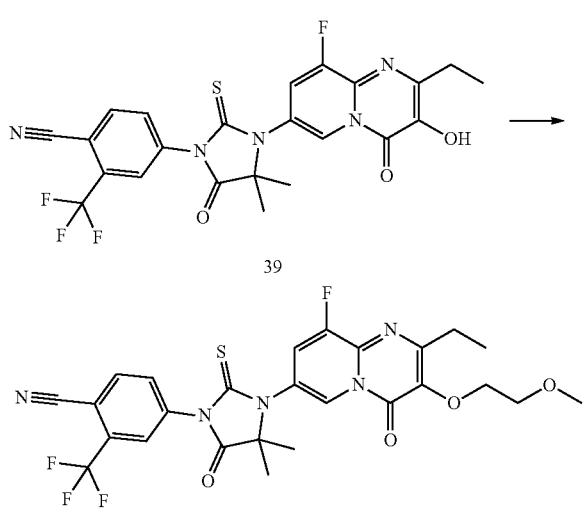
39

40

1-Bromo-2-methoxy-ethane (41 mg) and potassium carbonate (54 mg) were added to a solution of Compound 39 (100 mg) in N,N-dimethylformamide (2 mL). The resulting mixture was stirred at 80° C. for 1 h, and filtered. The filtrate was separated and purified by preparative HPLC to obtain Compound 40. $^1$H NMR (400 MHz, CDCl$_3$) δ ppm 8.69 (br s, 1H), 8.03-7.69 (m, 3H), 7.20 (br s, 1H), 4.33 (br s, 2H), 3.66 (br s, 2H), 3.37 (br s, 3H), 2.88 (br d, J=7.3 Hz, 2H), 1.61 (br s, 6H), 1.26 (br t, J=7.0 Hz, 3H); LCMS (ESI) m/z: 578 (M+1).

Example 40 Synthesis of Compound 41

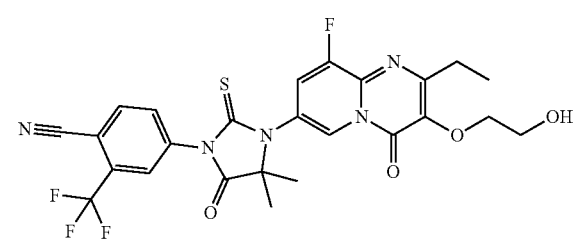
41

1) Synthesis of Compound 41

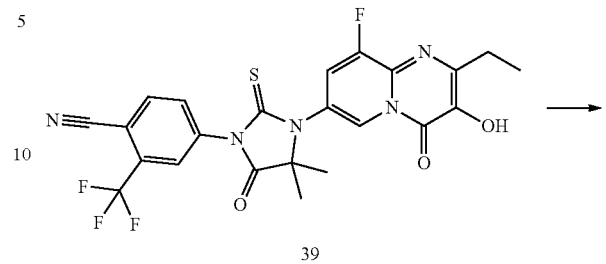
39

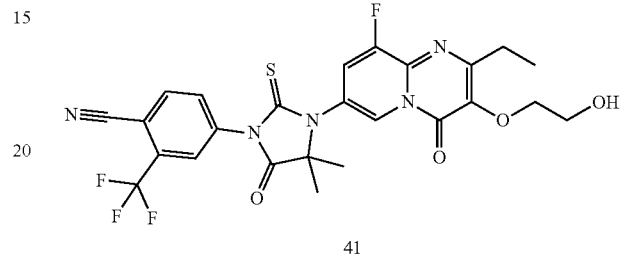
41

Potassium carbonate (60 mg) was added to a solution of Compound 39 (100 mg) and 2-bromoethanol (40 mg) in DMF (2 mL), and the resulting mixture was heated to 100° C. and stirred for 1 h under nitrogen protection. The reaction mixture was cooled to room temperature, and concentrated. The concentrate was purified successively by preparative TLC and preparative HPLC to obtain Compound 41. $^1$H NMR (400 MHz, CDCl$_3$) δ ppm 8.80 (d, J=1.5 Hz, 1H), 8.04 (d, J=8.3 Hz, 1H), 7.97 (s, 1H), 7.85 (dd, J=8.3, 2.0 Hz, 1H), 7.35 (dd, J=8.8, 2.0 Hz, 1H), 4.23-4.35 (m, 2H), 3.95 (br s, 2H), 3.77 (br s, 1H), 2.97 (q, J=7.7 Hz, 2H), 1.71 (s, 6H), 1.38 ppm (t, J=7.5 Hz, 3H); LCMS (ESI) m/z: 564 (M+1).

Example 41 Synthesis of Compound 42

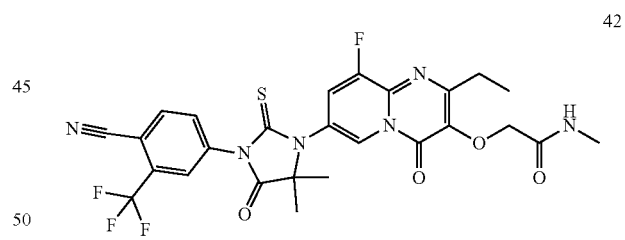
42

1) Synthesis of Compound 42-1

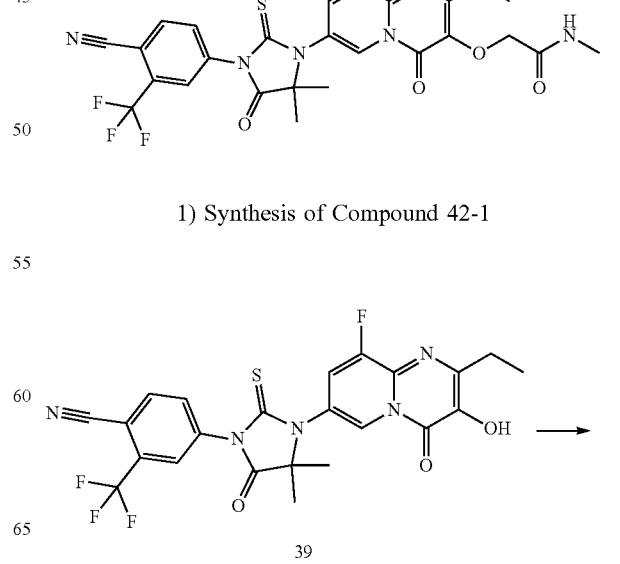
39

3) Synthesis of Compound 42

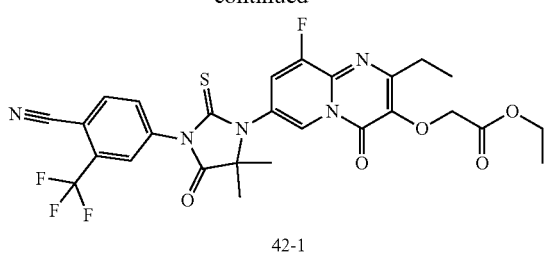

42-1

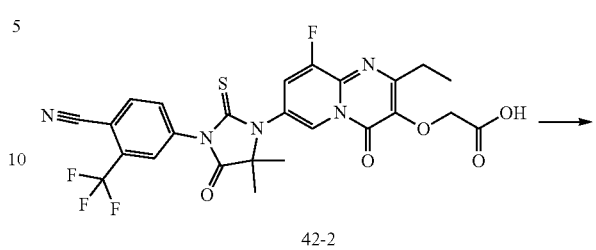

42-2

Potassium carbonate (110 mg) was added to a solution of Compound 39 (200 mg) and ethyl 2-bromoacetate (100 mg) in DMF (5 mL), and the resulting mixture heated to 80° C. and stirred for 1 h under nitrogen protection. The reaction mixture was cooled to room temperature, and filtered. The filter cake was washed with ethyl acetate (2 mL). The filtrate was concentrated to obtain Compound 42-1. LCMS (ESI) m/z: 606 (M+1).

2) Synthesis of Compound 42-2

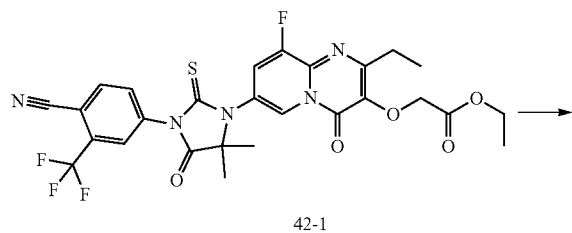

42-1

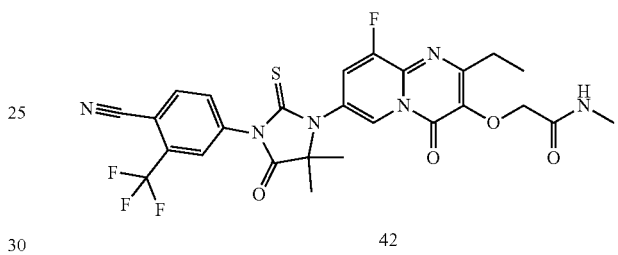

42-2

An aqueous solution of lithium hydroxide monohydrate (1M, 0.7 mL) was added to a solution of Compound 42-1 (200 mg) in tetrahydrofuran (5 mL), and the resulting mixture was stirred at 26° C. for 1 h under nitrogen protection. The reaction mixture was acidified to pH=5-6 with an aqueous solution of dilute hydrochloric acid (1M), and extracted with ethyl acetate (20 mL×3). The combined organic phase was washed with saturated brine (20 mL), dried over anhydrous sodium sulfate, filtered, and concentrated to obtain Compound 42-2. LCMS (ESI) m/z: 578 (M+1).

42

Methylamine hydrochloride (18 mg) was added to a solution of Compound 42-2 (100 mg), HATU (80 mg), and triethylamine (50 mg, 494.12 μmol) in dichloromethane (5 mL), and the resulting mixture was stirred at 26° C. for 1 h. The reaction mixture was acidified to pH=5-6 with an aqueous solution of dilute hydrochloric acid (1M), and extracted with ethyl acetate (20 mL×3). The combined organic phase was washed with saturated brine (20 mL), dried over anhydrous sodium sulfate, filtered, and concentrated. The residue obtained from the concentration was purified by preparative TLC and preparative HPLC to obtain Compound 42. $^1$H NMR (400 MHz, CDCl$_3$) δ ppm 8.68 (s, 1H), 7.95 (d, J=8.3 Hz, 1H), 7.88 (d, J=1.5 Hz, 1H), 7.76 (dd, J=8.3, 1.8 Hz, 1H), 7.31-7.36 (m, 1H), 7.29 (dd, J=8.8, 2.0 Hz, 1H), 4.51 (s, 2H), 2.90 (d, J=5.0 Hz, 3H), 2.84 (q, J=7.7 Hz, 2H), 1.62 (s, 6H), 1.29 ppm (t, J=7.5 Hz, 3H); LCMS (ESI) m/z: 591 (M+1).

Example 42 Synthesis of Compound 43

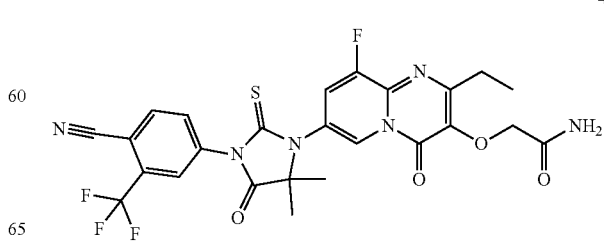

43

1) Synthesis of Compound 43

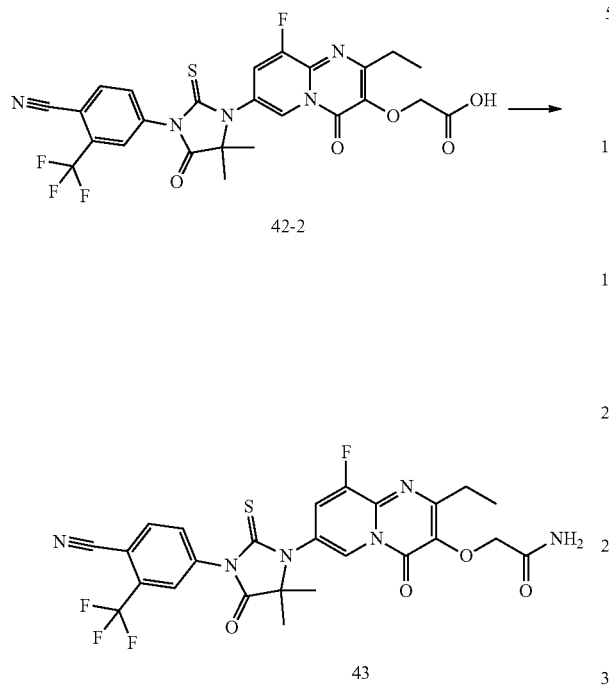

42-2

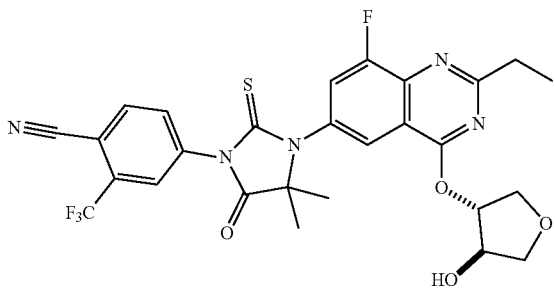

43

Ammonia water (30 mg) was added to a solution of Compound 42-2 (100 mg), HATU (79 mg), and triethylamine (53 mg) in DMF (5 mL), and the resulting mixture was stirred at 26° C. for 1 h. The reaction mixture was acidified to pH=5-6 with an aqueous solution of dilute hydrochloric acid (1M), and extracted with ethyl acetate (20 mL×3). The combined organic phase was washed with saturated brine (20 mL), dried over anhydrous sodium sulfate, filtered, and concentrated. The concentrate was purified by preparative TLC and preparative HPLC to obtain Compound 43. $^1$H NMR (400 MHz, CDCl$_3$) δ ppm 8.69 (s, 1H), 7.91-7.99 (m, 1H), 7.88 (s, 1H), 7.76 (dd, J=8.3, 1.8 Hz, 1H), 7.29 (dd, J=8.8, 2.0 Hz, 2H), 5.62 (br s, 1H), 4.53 (s, 2H), 2.77-2.95 (m, 1H), 1.62 (s, 6H), 1.26-1.34 ppm (m, 3H); LCMS (ESI) m/z: 577.0 (M+1).

Example 43 Synthesis of Compound 44

44

1) Synthesis of Compound 44-2 and Compound 44-3

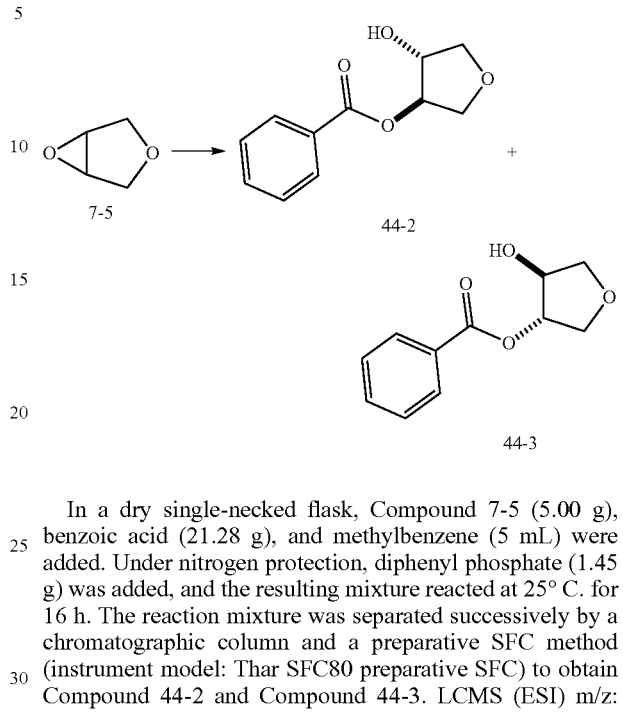

7-5

44-2

44-3

In a dry single-necked flask, Compound 7-5 (5.00 g), benzoic acid (21.28 g), and methylbenzene (5 mL) were added. Under nitrogen protection, diphenyl phosphate (1.45 g) was added, and the resulting mixture reacted at 25° C. for 16 h. The reaction mixture was separated successively by a chromatographic column and a preparative SFC method (instrument model: Thar SFC80 preparative SFC) to obtain Compound 44-2 and Compound 44-3. LCMS (ESI) m/z: 209 (M+1).

2) Synthesis of Compound 44-4

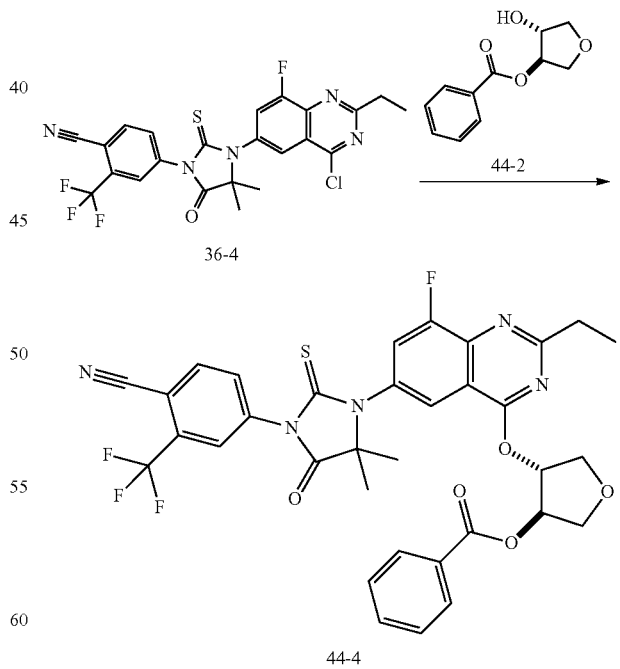

36-4

44-4

In a dry reaction flask, Compound 36-4 (200 mg), Compound 44-2 (120 mg), and tetrahydrofuran (2 mL) were added. Under nitrogen protection, sodium hydride (23 mg, 60% purity) was added, and the resulting mixture reacted at 25° C. for 0.5 h. The reaction was quenched with a saturated ammonium chloride solution (2 mL). After extraction with dichloromethane (3 mL×3), the organic phase was washed with saturated brine (10 mL), dried over anhydrous sodium sulfate, and filtered. The filtrate was concentrated under reduced pressure at 45° C. The residue obtained from the concentration was purified by a preparative TLC plate, to obtain Compound 44-4. LCMS (ESI) m/z: 694 (M+1).

3) Synthesis of Compound 44

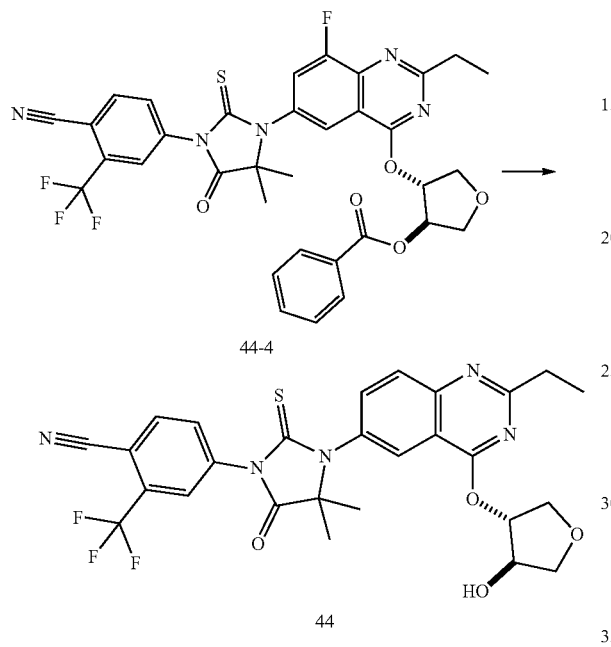

In a dry reaction flask, Compound 44-4 (140 mg), LiOH.H₂O (13 mg), water (0.8 mL), and tetrahydrofuran (1.5 mL) were added, and the resulting mixture reacted at 25° C. for 3 h under nitrogen protection. The reaction mixture was directly spin-dried, and purified by preparative HPLC method to obtain Compound 44. $^1$H NMR (400 MHz, CDCl$_3$) δ ppm 8.02 (d, J=8.38 Hz, 1H), 7.98 (s, 1H), 7.83-7.88 (m, 2H), 7.49 (dd, J=9.92, 2.21 Hz, 1H), 5.46-5.50 (m, 1H), 4.52 (br s, 1H), 4.36 (dd, J=11.03, 5.73 Hz, 1H), 4.23 (dd, J=10.03, 5.84 Hz, 1H), 4.16 (dd, J=10.58, 2.87 Hz, 1H), 3.82 (dd, J=9.81, 4.74 Hz, 1H), 3.40 (d, J=2.65 Hz, 1H), 3.09 (q, J=7.50 Hz, 2H), 1.67 (s, 6H), 1.45 (t, J=7.50 Hz, 3H).

Example 44 Synthesis of Compound 45

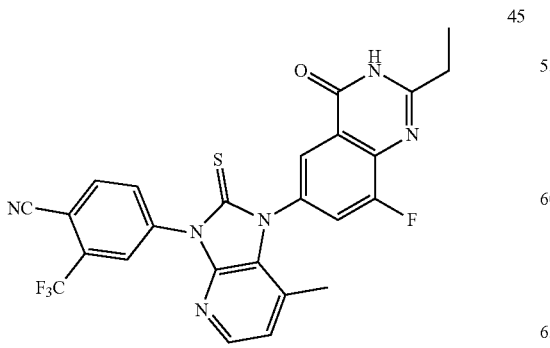

1) Synthesis of Compound 45-1

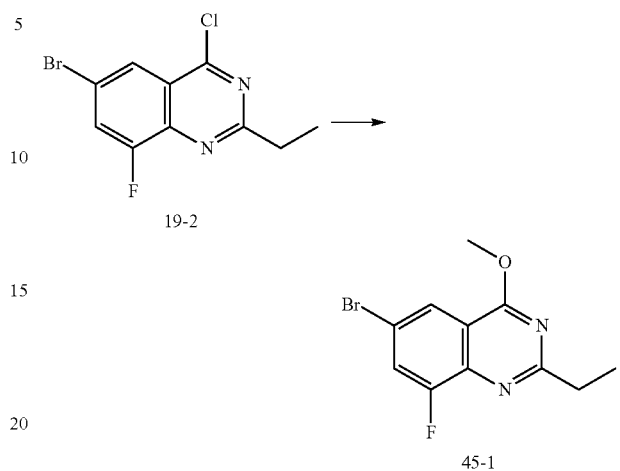

In a dry single-necked flask, methanol (2 mL) and sodium (24 mg) were added, and the resulting mixture was stirred at 25° C. until sodium disappeared. Then, a readily prepared solution of sodium methoxide in methanol was added to a dry single-necked flask filled with Compound 19-2 (300 mg), and the resulting mixture was stirred at 25° C. for 2 h. After filtration, the filter cake was washed with ethyl acetate (10 mL). The filtrate was collected, and concentrated under reduced pressure to obtain Compound 45-1. $^1$H NMR (400 MHz, CDCl$_3$) δ ppm 8.00 (dd, J=1.3, 2.0 Hz, 1H), 7.54 (dd, J=2.1, 9.6 Hz, 1H), 4.12-4.09 (m, 3H), 2.93 (q, J=7.5 Hz, 2H), 1.34 (t, J=7.6 Hz, 3H). LCMS (ESI) m/z: 285 (M+1).

2) Synthesis of Compound 45-2

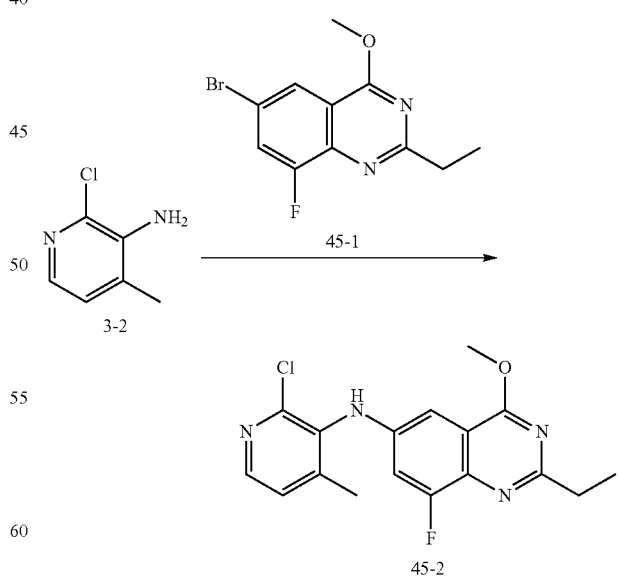

In a dry microwave tube, Compound 45-1 (888 mg), Compound 3-2 (489 mg), cesium carbonate (2.54 g), 4,5-bis(diphenylphosphino)-9,9-dimethylxanthene (180 mg), bis(dibenzylideneacetone)palladium (179 mg), and methylbenzene (18 mL) were added. After nitrogen purge for five min, the resulting mixture was microwaved and stirred at 130° C. for 4 h, and then was concentrated to dryness under reduced pressure to remove the solvent. The residue obtained from the concentration was purified by a chromatographic column to obtain Compound 45-2. ¹H NMR (400 MHz, CDCl₃) δ ppm 8.19 (d, J=4.9 Hz, 1H), 7.20 (d, J=4.9 Hz, 1H), 6.96 (dd, J=2.5, 11.6 Hz, 1H), 6.81-6.77 (m, 1H), 5.79 (s, 1H), 4.09 (s, 3H), 3.00-2.91 (m, 2H), 2.24 (s, 3H), 1.38 (t, J=7.5 Hz, 3H). LCMS (ESI) m/z: 347 (M+1).

3) Synthesis of Compound 45-3

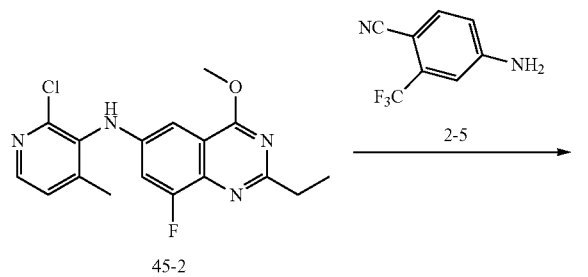

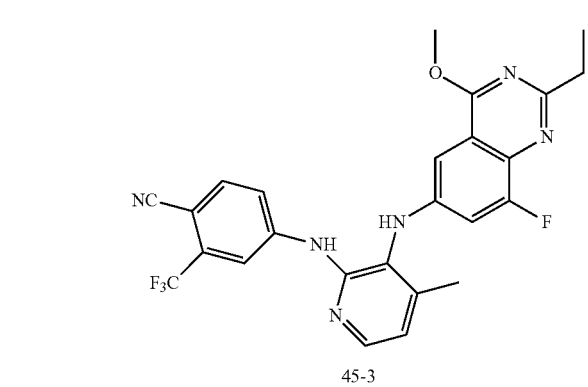

In a dry microwave tube, Compound 45-2 (190 mg), Compound 2-5 (112 mg), 4,5-bis(diphenylphosphino)-9,9-dimethylxanthene (31 mg), bis(dibenzylideneacetone)palladium (31 mg), and cesium carbonate (357 mg) were added, and then methylbenzene (5 mL) was added. After nitrogen purge for 5 min, the microwave tube was sealed. The resulting mixture was microwaved and stirred at 130° C. for 4 h, and then was concentrated to dryness under reduced pressure to remove the solvent. The residue obtained from the concentration was purified by a chromatographic column to obtain a crude product of Compound 45-3. The resulting crude product was slurried with 5 mL of methyl tert-butyl ether to obtain Compound 45-3. ¹H NMR (400 MHz, CDCl₃) δ ppm 8.27 (d, J=2.2 Hz, 1H), 8.15 (d, J=5.1 Hz, 1H), 8.00 (dd, J=2.1, 8.7 Hz, 1H), 7.72 (d, J=8.8 Hz, 1H), 7.14 (dd, J=2.5, 12.5 Hz, 1H), 7.00 (d, J=5.7 Hz, 1H), 6.56-6.53 (m, 1H), 4.02 (s, 3H), 3.19 (s, 3H), 2.85 (q, J=7.5 Hz, 2H), 1.33 (t, J=7.6 Hz, 3H). LCMS (ESI) m/z: 497 (M+1).

4) Synthesis of Compound 45-4

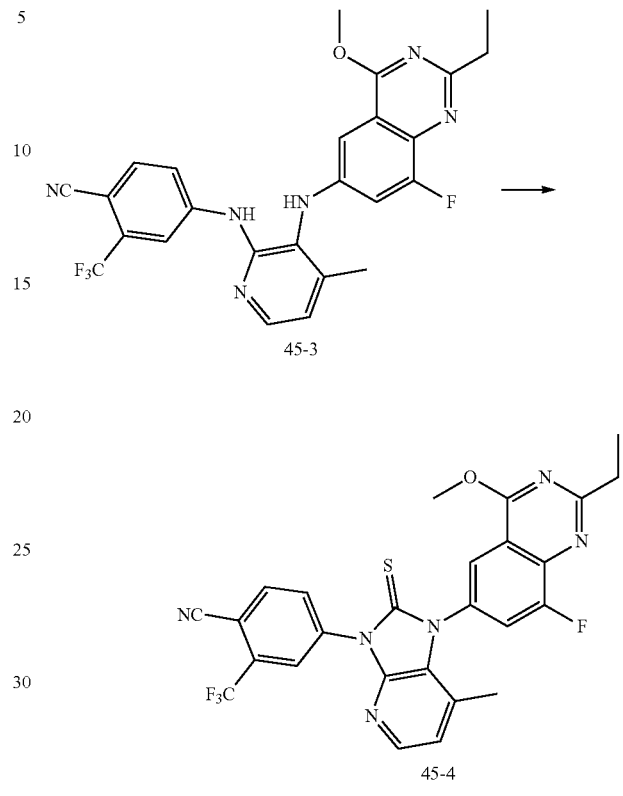

In a dry single-necked flask, Compound 45-3 (65 mg), tetrahydrofuran (0.5 mL), and methylbenzene (0.5 mL) were added, and then sodium tert-butoxide (50 mg) was added. The resulting mixture was stirred at 30° C. for 1 h, and then thiophosgene (45 mg) was added at 30° C. The resulting mixture was stirred at 30° C. for 1 h under nitrogen protection, and then was concentrated to dryness under reduced pressure to remove the solvent. The residue obtained from the concentration was purified by a chromatographic column to obtain Compound 45-4. LCMS (ESI) m/z: 539 (M+1).

5) Synthesis of Compound 45

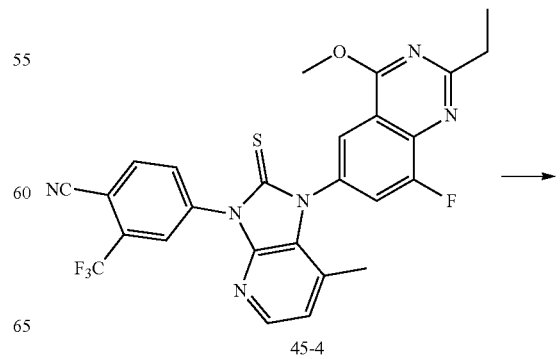

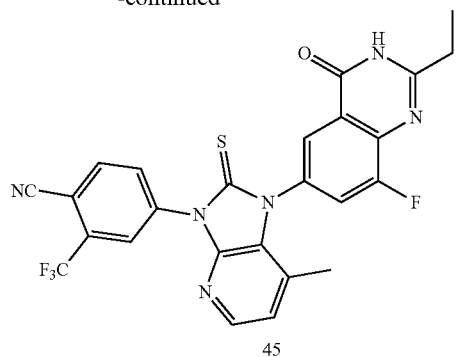

45

In a dry single-necked flask, Compound 45-4 (45 mg), hydrochloric acid (2M, 2 mL), and tetrahydrofuran (2 mL) were added. The resulting mixture was stirred at 30° C. for 1 h under nitrogen protection, and was concentrated to dryness under reduced pressure to remove the solvent. The residue obtained from the concentration was purified by preparative HPLC method to obtain Compound 45. ¹H NMR (400 MHz, CDCl₃) δ ppm 10.55 (br s, 1H), 8.30 (br s, 1H), 8.17 (br d, J=19.6 Hz, 3H), 8.09 (br s, 1H), 7.67 (br s, 1H), 7.03 (br s, 1H), 2.87 (br s, 2H), 1.99 (br s, 3H), 1.47 (br s, 3H). LCMS (ESI) m/z: 525 (M+1).

Example 45 Synthesis of Compound 46

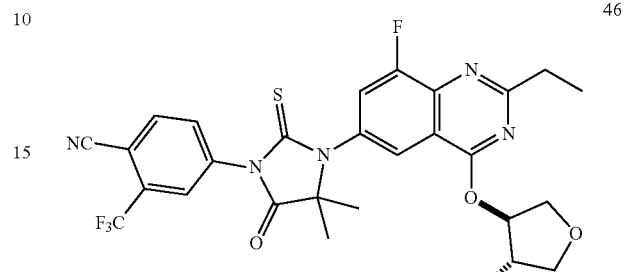

46

1) Synthesis of Compound 46-1

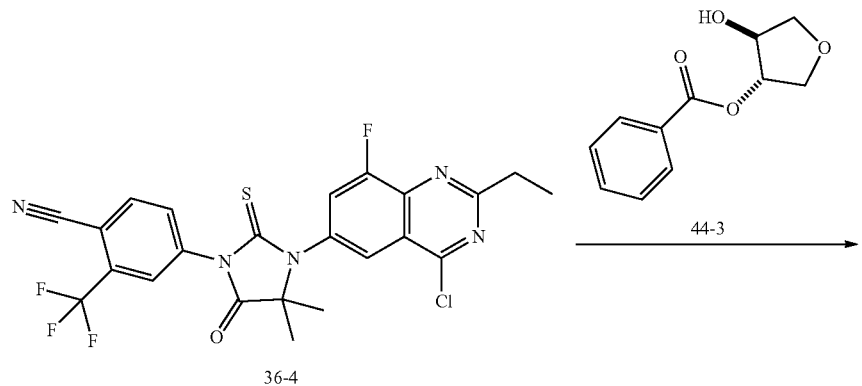

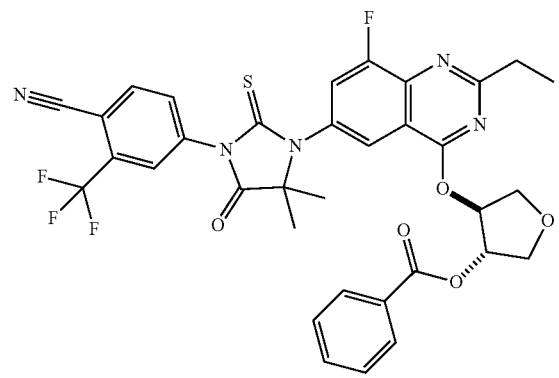

46-1

In a dry reaction flask, Compound 36-4 (200 mg), Compound 44-3 (120 mg), and tetrahydrofuran (2 mL) were added. Under nitrogen protection, sodium hydride (23 mg, 60% purity) was added, and the resulting mixture reacted at 25° C. for 0.5 h. The reaction was quenched with a saturated ammonium chloride solution (5 mL). After extraction with dichloromethane (5 mL×3), the organic phase was washed with saturated brine (10 mL), dried over anhydrous sodium sulfate, and filtered. The filtrate was concentrated under reduced pressure at 45° C. The residue was purified by a preparative TLC plate to obtain Compound 46-1. LCMS (ESI) m/z: 694 (M+1).

2) Synthesis of Compound 46

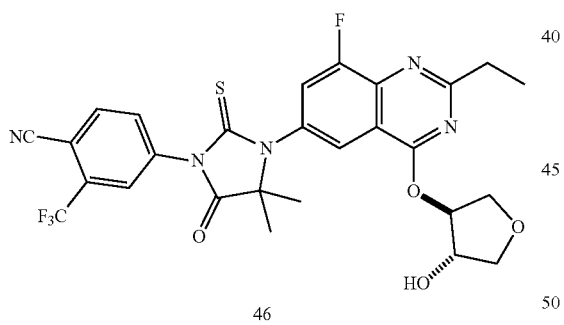

46-1

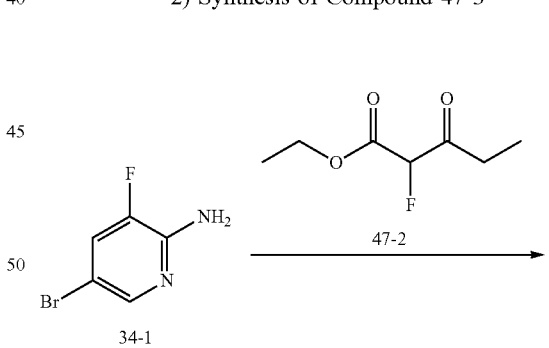

46

In a dry reaction flask, Compound 46-1 (130 mg), lithium hydroxide monohydrate (12 mg), water (0.5 mL), and tetrahydrofuran (1 mL) were added, and the resulting mixture reacted at 25° C. for 4 h under nitrogen protection. The reaction mixture was directly concentrated to dryness, and the residue obtained from the concentration was purified by preparative HPLC method to obtain Compound 46. $^1$H NMR (400 MHz, CDCl$_3$) δ ppm 8.02 (d, J=8.38 Hz, 1H), 7.98 (s, 1H), 7.83-7.89 (m, 2H), 7.49 (dd, J=9.81, 2.09 Hz, 1H), 5.45-5.51 (m, 1H), 4.52 (br s, 1H), 4.36 (dd, J=10.80, 5.95 Hz, 1H), 4.23 (dd, J=9.92, 5.73 Hz, 1H), 4.16 (dd, J=10.80, 3.09 Hz, 1H), 3.82 (dd, J=9.70, 4.85 Hz, 1H), 3.40 (d, J=2.65 Hz, 1H), 3.09 (q, J=7.57 Hz, 2H), 1.67 (s, 6H), 1.45 (t, J=7.61 Hz, 3H). LCMS (ESI) m/z: 590 (M+1).

Example 46 Synthesis of Compound 47

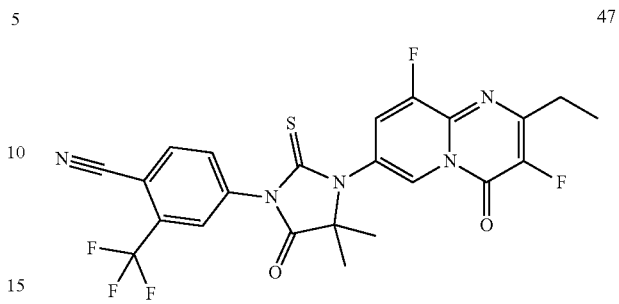

47

1) Synthesis of Compound 47-2

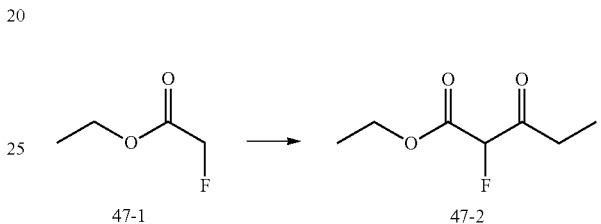

Compound 47-1 (23.00 g) and propionyl chloride (50.14 g) were successively added to a solution of sodium ethoxide (22.13 g) and triethylamine (1.10 g) in tetrahydrofuran (220 mL) at 5° C. After the completion of the addition, the resulting mixture was stirred at 25° C. for 16 h. The reaction mixture was concentrated under reduced pressure, and then distilled under reduced pressure, to obtain Compound 47-2 by collecting fractions at the temperatures of 36° C., 40° C., and 60° C., respectively.

2) Synthesis of Compound 47-3

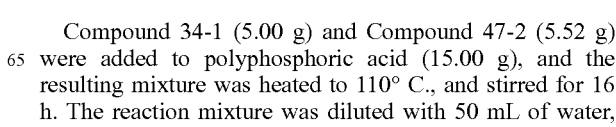

Compound 34-1 (5.00 g) and Compound 47-2 (5.52 g) were added to polyphosphoric acid (15.00 g), and the resulting mixture was heated to 110° C., and stirred for 16 h. The reaction mixture was diluted with 50 mL of water, adjusted to a neutral pH with a saturated sodium hydroxide solution, and extracted with ethyl acetate (30 mL×3). The organic phase was collected, dried, filtered and concentrated. The residue was purified by column chromatography to obtain Compound 47-3. $^1$H NMR (400 MHz, CDCl$_3$) δ ppm 8.93 (t, J=1.65 Hz, 1H), 7.49 (dd, J=8.16, 1.76 Hz, 1H), 2.90 (qd, J=7.61, 2.98 Hz, 2H), 1.35 (t, J=7.61 Hz, 3H).

3) Synthesis of Compound 47-4

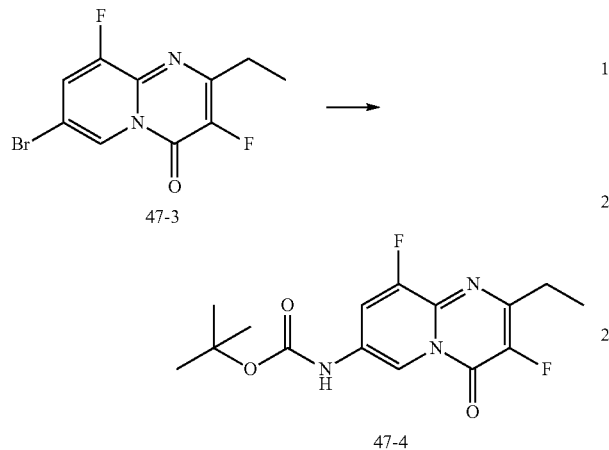

Compound 47-3 (800 mg), tert-butyl carbamate (972 mg), cesium carbonate (2.25 g), 4,5-bis(diphenylphosphino)-9,9-dimethylxanthene (160.13 mg), and bis(dibenzylideneacetone)palladium (159 mg) were added to a microwave tube filled with methylbenzene (8 mL). The resulting mixture reacted at 120° C. for microwave reaction for 50 min. The reaction mixture was concentrated under reduced pressure, and the residue obtained from the concentration was purified by column chromatography to obtain Compound 47-4. $^1$H NMR (400 MHz, CDCl$_3$) δ ppm 9.00 (s, 1H) 7.31-7.37 (m, 1H) 2.92 (qd, J=7.57, 2.87 Hz, 2H) 1.57 (s, 9H) 1.36 (t, J=7.61 Hz, 3H).

4) Synthesis of Compound 47-5

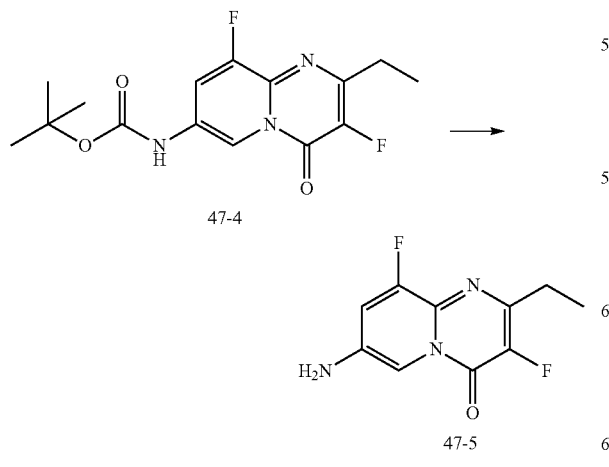

Compound 47-4 (400 mg) was added to a solution of hydrochloric acid-methanol (4M, 20 mL), and the resulting mixture was stirred at 25° C. for 1 h. The reaction mixture was concentrated under reduced pressure. Water (25 mL) was added to the residue obtained from the concentration, and the resulting mixture was extracted with ethyl acetate (30 mL×3). The organic phase was collected, dried, filtered, and concentrated under reduced pressure to obtain Compound 47-5. LCMS (ESI) m/z: 226 (M+1).

5) Synthesis of Compound 47-6

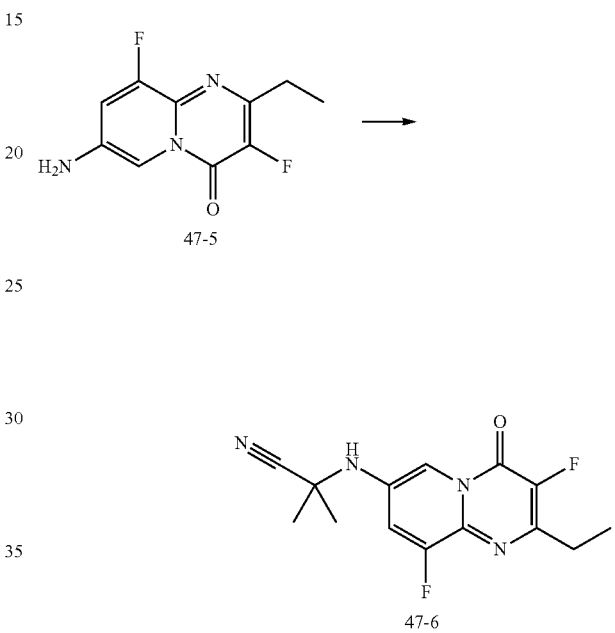

In a reaction flask, Compound 47-5 (200 mg), zinc chloride (36 mg), sodium sulfate (504 mg), acetone (331 mg), TMSCN (264 mg), and tetrahydrofuran (2 mL) were added, and the resulting mixture reacted at 25° C. for 16 h. The reaction mixture was concentrated under reduced pressure, and the residue obtained from the concentration was purified by a preparative chromatoplate to obtain Compound 47-6. $^1$H NMR (400 MHz, CDCl$_3$) δ ppm 8.48 (s, 1H), 7.30 (dd, J=10.03, 2.32 Hz, 1H), 4.28 (s, 1H), 3.50 (s, 1H), 2.90 (qd, J=7.61, 2.98 Hz, 2H), 1.80 (s, 5H), 1.31-1.39 (m, 3H).

6) Synthesis of Compound 47-7

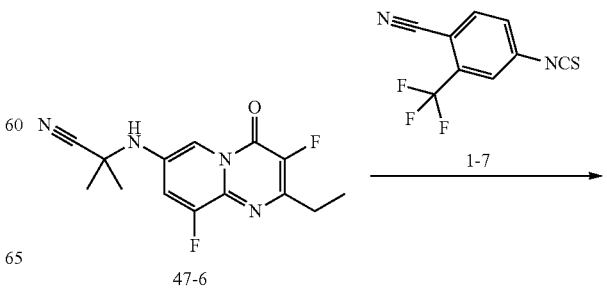

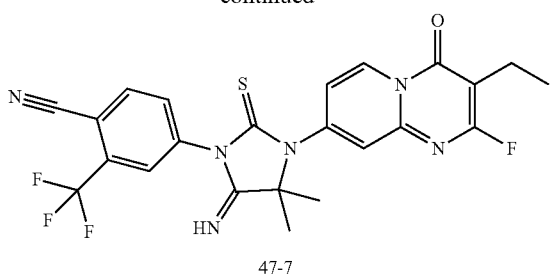

47-7

In a reaction flask, Compound 47-6 (100 mg), Compound 1-7 (312 mg), methylbenzene (2 mL), and DMF (0.5 mL) were added, and the resulting mixture was stirred at 25° C. Then, sodium hydride (21 mg, 60% purity) was added, and the resulting mixture reacted for 4 h under stirring. The reaction mixture was concentrated under reduced pressure, and the residue obtained from the concentration was purified by preparative HPLC to obtain Compound 47-7. LCMS (ESI) m/z: 521 (M+1).

7) Synthesis of Compound 47

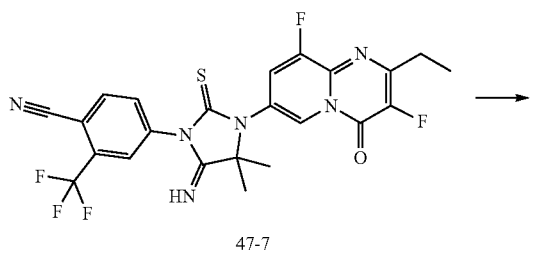

47-7

→

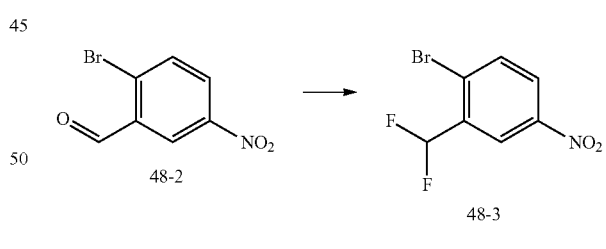

47

In a reaction flask, Compound 47-7 (20 mg), methylbenzene (2 mL), and acetic acid (0.5 mL) were added, and the resulting mixture was refluxed at 120° C. for 16 h. The reaction mixture was concentrated under reduced pressure, and the residue obtained from the concentration was purified by preparative HPLC to obtain Compound 47. $^1$H NMR (400 MHz, CDCl$_3$) δ ppm 8.80 (s, 1H), 8.02 (d, J=8.38 Hz, 1H), 7.95 (s, 1H), 7.83 (d, J=9.04 Hz, 1H), 7.37 (d, J=7.28 Hz, 1H), 2.95 (dd, J=7.72, 3.09 Hz, 2H), 1.70 (s, 6H), 1.38 (t, J=7.61 Hz, 3H). LCMS (ESI) m/z: 522 (M+1).

Example 47 Synthesis of Compound 48

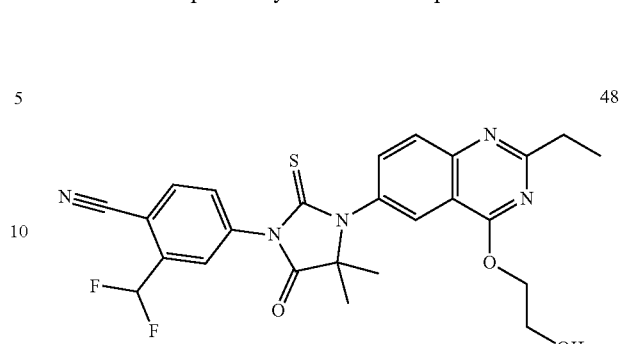

48

1) Synthesis of Compound 48-2

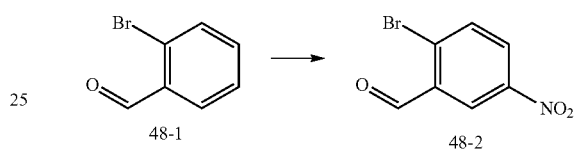

Potassium nitrate (4.10 g) was added to a solution of Compound 48-1 (5.00 g) in concentrated sulfuric acid (40 mL) at 0° C. The resulting mixture was stirred at 0° C. for 1 h. The reaction mixture was slowly poured into ice water (150 mL) which was stirred for dilution, and a solid precipitated. After filtration, the filter cake was washed with water (50 mL), dissolved in ethyl acetate (150 mL), dried over anhydrous sodium sulfate, filtered, and concentrated to obtain Compound 48-2. $^1$H NMR (400 MHz, CDCl$_3$) δ ppm 10.27-10.35 (m, 1H), 8.65 (d, J=2.8 Hz, 1H), 8.23 (dd, J=8.8, 2.8 Hz, 1H), 7.82 ppm (d, J=8.5 Hz, 1H).

2) Synthesis of Compound 48-3

DAST (8.54 g) was added to a solution of Compound 48-2 (6 g) in dichloromethane (100 mL) at 0° C. The resulting mixture was stirred at 0° C. for 1 h, and then cooled to 0° C. A saturated sodium bicarbonate solution (50 mL) was added to quench the reaction. After extraction with dichloromethane (50 mL), the organic phase was washed with saturated brine (50 mL), dried over anhydrous sodium sulfate, filtered, and concentrated. The residue obtained from the concentration was purified by flash column chromatography (model: ISCO-RF150) to obtain Compound 48-3. $^1$H NMR (400 MHz, CDCl$_3$) δ ppm 8.45 (d, J=2.5 Hz, 1H), 8.14 (dd, J=8.8, 2.8 Hz, 1H), 7.77 (d, J=8.8 Hz, 1H), 6.71-7.01 ppm (m, 1H).

3) Synthesis of Compound 48-4

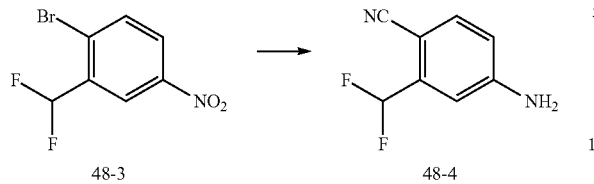

Zinc cyanide (4.00 g), zinc powder (1.60 g, 24.47 mmol), DPPF (1.76 g) and bis(dibenzylideneacetone)palladium (1.83 g) were successively added to a solution of Compound 48-3 (4.00 g) in DMF (15 mL). After nitrogen purge for 30 sec, the resulting mixture was heated to 130° C. for microwave reaction for 1 h, then cooled to room temperature, and filtered. The filtrate was concentrated, and the residue obtained from the concentration was purified by flash column chromatography (ISCO-RF150) to obtain Compound 48-4. $^1$H NMR (400 MHz, CDCl$_3$) δ ppm 7.41 (d, J=8.3 Hz, 1H), 6.58-6.90 (m, 3H), 4.32 ppm (br s, 2H).

4) Synthesis of Compound 48-5

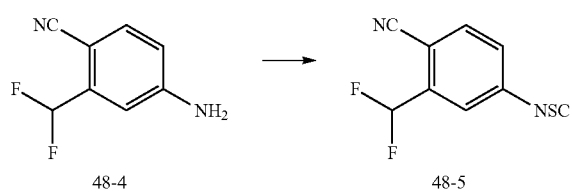

At 29° C., thiophosgene (900 mg) was added to H$_2$O (10 mL) to form a solution, and the resulting mixture was stirred for half an hour. Then, Compound 48-4 (500 mg) was added to the above mixture, and the mixture was further stirred at 29° C. for 2 h. The reaction mixture was extracted with dichloromethane (30 mL×2). The combined organic phase was washed with saturated brine (20 mL), dried over anhydrous sodium sulfate, filtered, and concentrated to obtain Compound 48-5. $^1$H NMR (400 MHz, CDCl$_3$) δ ppm 7.69 (d, J=8.3 Hz, 1H), 7.50 (s, 1H), 7.28-7.39 (m, 1H), 6.64-6.99 ppm (m, 1H).

5) Synthesis of Compound 48-6

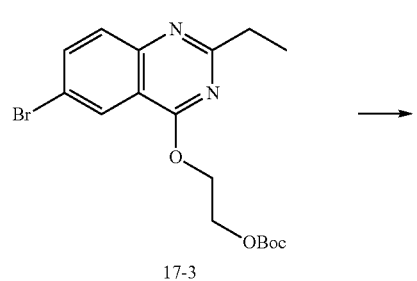

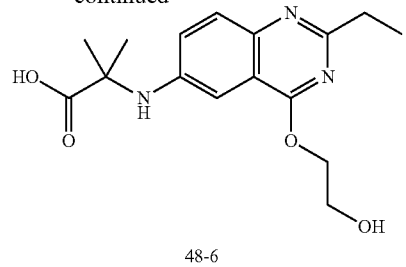

Compound 17-3 (200 mg), Compound 1-4 (100 mg), cuprous chloride (10 mg), 2-acetylcyclohexanone (10 mg), and potassium carbonate (180 mg) were added to a microwave tube filled with DMF (5 mL) and water (1 mL). After nitrogen purge for 1 min, the resulting mixture was kept at 130° C. for microwave reaction for 1.5 h. The reaction mixture was filtered, and the filter cake was washed with DMF (2 mL). The filtrate was neutralized with 1M dilute hydrochloric acid to pH=7, and concentrated. The residue obtained from the concentration was added to DCM/MeOH (20 mL, v/v=10/1) to precipitate a solid, and filtered. The filtrate was concentrated to obtain Compound 48-6. LCMS (ESI) m/z: 320 (M+1).

6) Synthesis of Compound 48-7

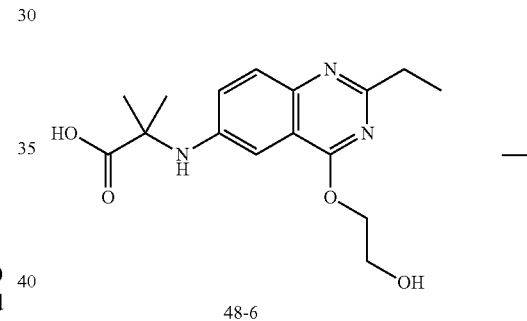

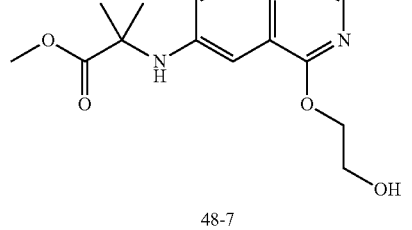

A solution of TMSCHN$_2$ in n-hexane (2M, 0.75 mL) was added dropwise to a solution of Compound 48-6 (320 mg) in dichloromethane (10 mL) and methanol (1 mL) at 29° C. After the completion of the dropwise addition, the resulting mixture reacted at 29° C. for 1 h. The reaction mixture was concentrated, and the residue obtained from the concentration was purified by preparative TLC to obtain Compound 48-7. LCMS (ESI) m/z: 334 (M+1).

7) Synthesis of Compound 48-8

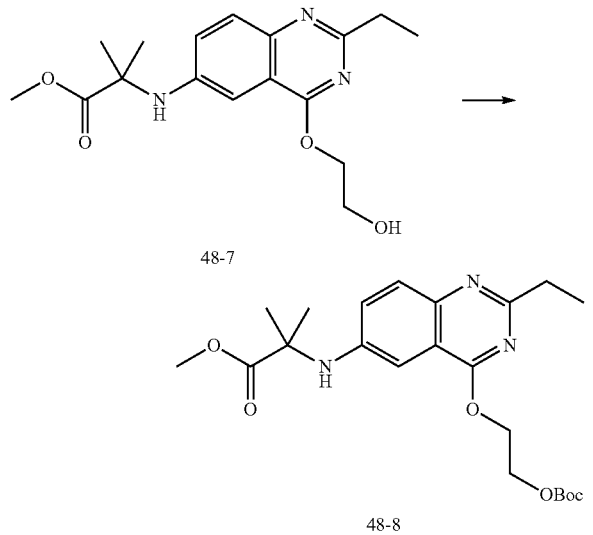

Boc₂O (160 mg) was added to a solution of Compound 48-7 (220 mg), triethylamine (170 mg), and DMAP (20 mg) in dichloromethane (10 mL) at 29° C. After the completion of the dropwise addition, the resulting mixture reacted at 29° C. for 0.5 h. The reaction mixture was concentrated, and the residue obtained from the concentration was purified by preparative TLC to obtain Compound 48-8. LCMS (ESI) m/z: 434 (M+1).

8) Synthesis of Compound 48-9

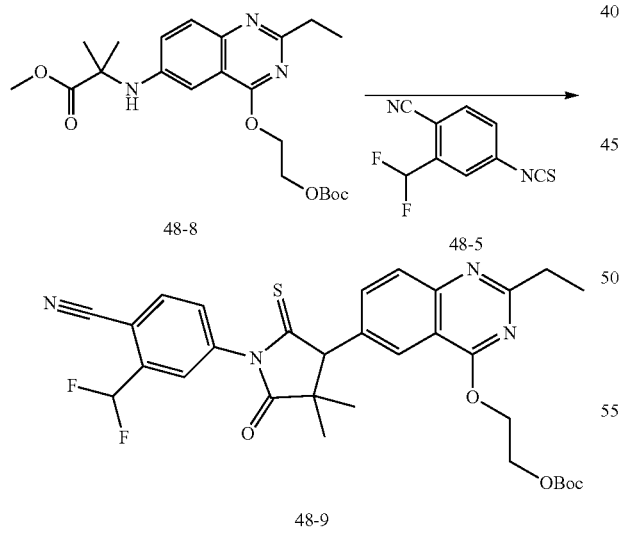

Compound 48-5 (75 mg) was added to Compound 48-8 (50 mg) in a mixed solvent of methylbenzene (15 mL) and DMF (3 mL), and then the resulting mixture was heated to 120° C. and stirred for 12 h under nitrogen protection. The reaction mixture was cooled to room temperature, and concentrated to obtain a crude product. The crude product was purified by preparative TLC to obtain Compound 48-9. LCMS (ESI) m/z: 612 (M+1).

9) Synthesis of Compound 48

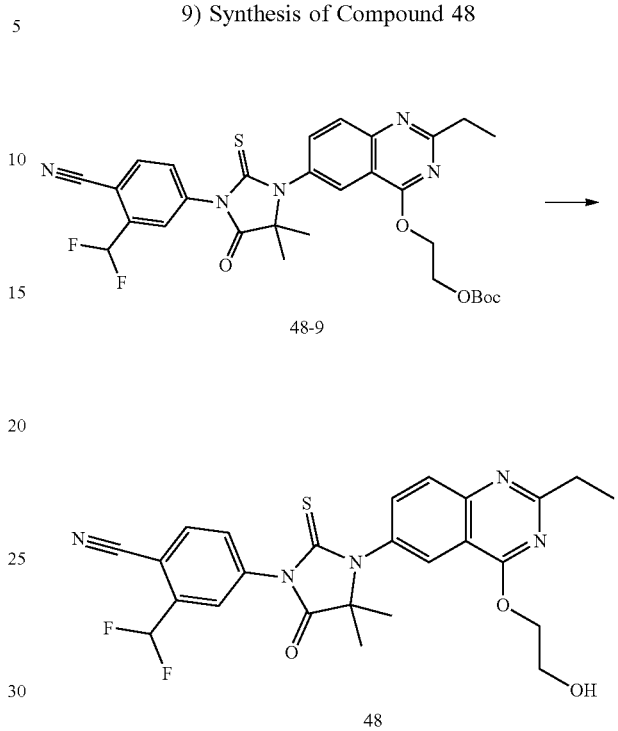

Trifluoroacetic acid (581 mg) was added dropwise to a solution of Compound 48-9 (35 mg) in dichloromethane (5 mL). Then, the resulting mixture was stirred at 28° C. for 0.5 h. The reaction mixture was neutralized with a saturated sodium bicarbonate solution to pH=~7, and extracted with dichloromethane (20 mL×2). The combined organic phase was washed with saturated brine (20 mL), dried over anhydrous sodium sulfate, filtered, and concentrated to obtain a crude product. The crude product was purified by preparative TLC to obtain Compound 48. ¹H NMR (400 MHz, CDCl₃) δ ppm 8.05 (d, J=2.0 Hz, 1H), 7.97 (d, J=9.0 Hz, 1H), 7.86 (br d, J=4.5 Hz, 2H), 7.58-7.73 (m, 2H), 6.75-7.10 (m, 1H), 4.62-4.84 (m, 2H), 4.02 (br s, 2H), 3.10 (br s, 1H), 2.94 (q, J=7.7 Hz, 2H), 1.58 (s, 6H), 1.35 ppm (t, J=7.7 Hz, 3H); LCMS (ESI) m/z: 512 (M+1).

Example 48 Synthesis of Compound 49

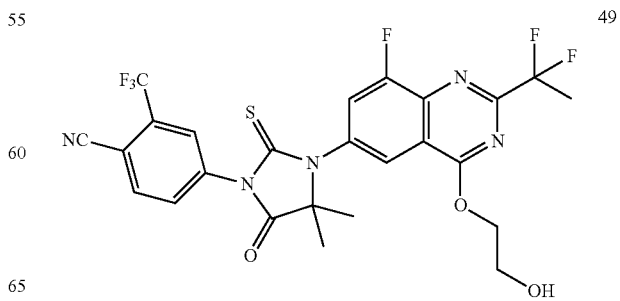

1) Synthesis of Compound 49-2

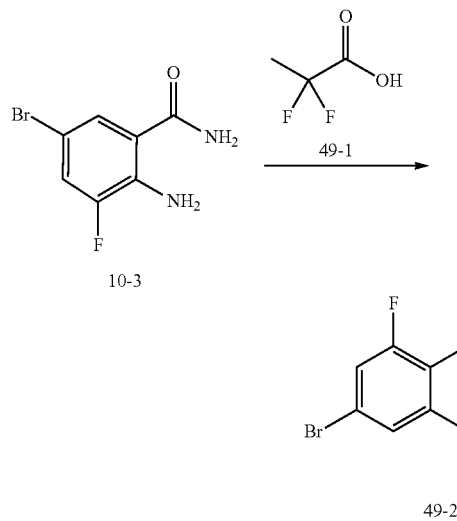

In a dry reaction flask, Compound 10-3 (10.00 g) and Compound 49-1 (5.67 g) were added, and then trimethylsilyl polyphosphate (42.91 mmol) was added. The resulting mixture was heated to 130° C. and stirred for 12 h under nitrogen protection. 100 mL of water and 100 mL of ethyl acetate were added to the reaction mixture. After liquid separation, the organic phase was collected, dried over anhydrous sodium sulfate, filtered, and concentrated. The residue obtained from the concentration was purified by a chromatographic column to obtain a crude product. The resulting crude product was slurried with 20 mL of ethyl acetate and 40 mL of methyl tert-butyl ether to obtain Compound 49-2. $^1$H NMR (400 MHz, CDCl$_3$) δ ppm 8.09-8.00 (m, 2H), 2.00 (t, J=19.3 Hz, 3H). LCMS (ESI) m/z: 307 (M+1).

2) Synthesis of Compound 49-3

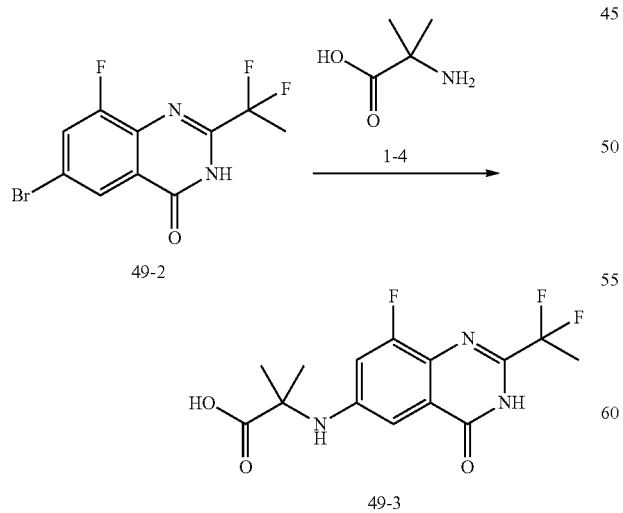

In a dry microwave tube, Compound 49-2 (1.00 g), Compound 1-4 (1.01 g), DMF (20 mL), water (4 mL), potassium carbonate (2.25 g), and 2-acetylcyclohexanone (91 mg) were added, and then cuprous chloride (645 mg) was added. After nitrogen purge for five min, the microwave tube was sealed, and then the resulting mixture was microwaved and stirred at 90° C. for 1 h. The mixture was concentrated under reduced pressure to obtain Compound 49-3. LCMS (ESI) m/z: 330 (M+1).

3) Synthesis of Compound 49-4

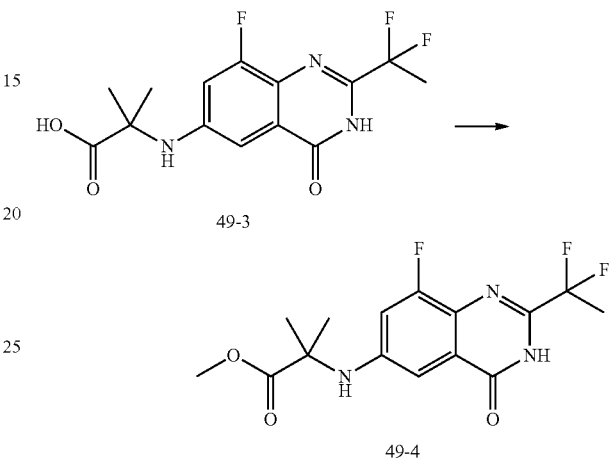

In a dry single-necked flask, Compound 49-3 (8.58 g) and a solution of hydrochloric acid-methanol (4M, 250 mL) were added, and the resulting mixture was stirred at 80° C. for 12 h, and then concentrated to dryness under reduced pressure to remove the solvent and obtain a solid. The solid was purified by a chromatographic column to obtain Compound 49-4. $^1$H NMR (400 MHz, CDCl$_3$) δ ppm 9.33 (br s, 1H), 7.08 (d, J=1.8 Hz, 1H), 6.77 (dd, J=2.8, 12.0 Hz, 1H), 4.68 (s, 1H), 3.75 (s, 3H), 2.09 (t, J=19.0 Hz, 3H), 1.63 (s, 6H). LCMS (ESI) m/z: 344 (M+1).

4) Synthesis of Compound 49-5

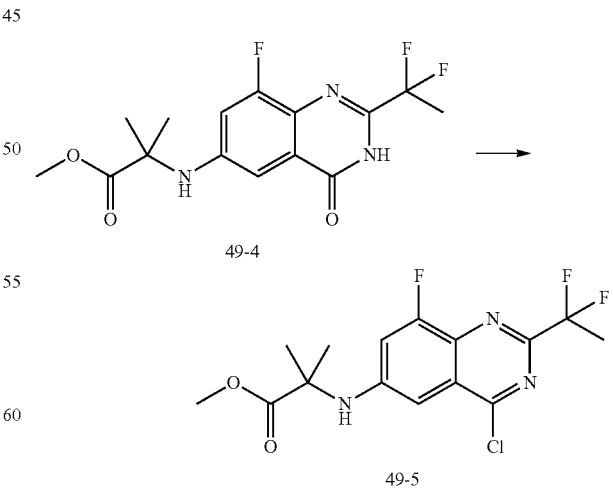

In a dry single-necked flask, Compound 49-4 (2.85 g, 8.30 mmol) and phosphorus oxychloride (43.29 g) were added, and then diisopropylethylamine (1.67 g) was added. The resulting mixture was stirred at 110° C. for 4 h, and then was concentrated under reduced pressure to remove the solvent. The solid obtained from the concentration was dissolved in 26 mL of ethyl acetate, and the resulting solution was slowly added dropwise to a mixed solution of 31 mL of methanol and 110 mL of triethylamine at a controlled temperature of 0-10° C. After the completion of the dropwise addition, the resulting mixture was filtered. The filtrate was collected, and was concentrated to dryness under reduced pressure at 40° C. to remove the solvent. The residue obtained from the concentration was purified by a chromatographic column to obtain Compound 49-5. LCMS (ESI) m/z: 362 (M+1).

5) Synthesis of Compound 49-6

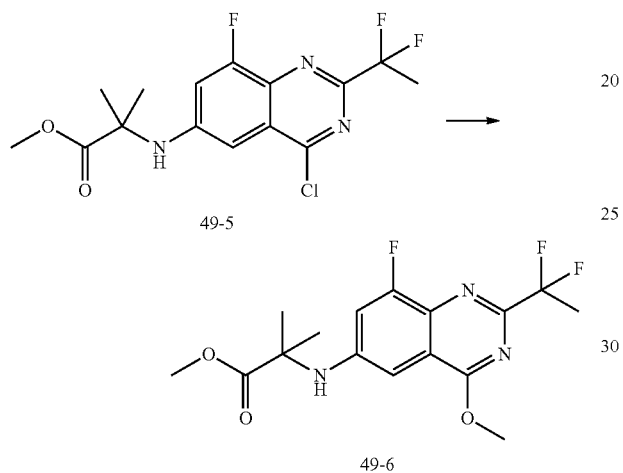

49-5

49-6

In a dry single-necked flask, Compound 49-5 (4.00 g) was added, then methanol (100 mL) was added, and then sodium methoxide (2.99 g) was added. The resulting mixture was stirred at 30° C. for 0.5 h under nitrogen protection. 200 mL of ethyl acetate was added to the reaction mixture, and the resulting mixture was filtered. A solution of hydrochloric acid-methanol (4M, 3 mL) was added to the filtrate. The resulting mixture was concentrated under reduced pressure at 30° C. to 100 mL, and filtered. The filtrate was concentrated to dryness under reduced pressure at 30° C., and the residue obtained from the concentration was purified by a chromatographic column to obtain Compound 49-6. $^1$H NMR (400 MHz, CDCl$_3$) δ ppm 6.89 (dd, J=2.5, 11.8 Hz, 1H), 6.78 (d, J=1.8 Hz, 1H), 4.60 (br s, 1H), 4.18 (s, 3H), 3.73 (s, 3H), 2.09 (t, J=18.5 Hz, 3H), 1.67-1.63 (m, 6H). LCMS (ESI) m/z: 358 (M+1).

6) Synthesis of Compound 49-7

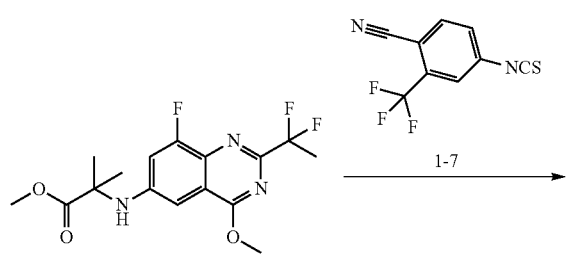

1-7

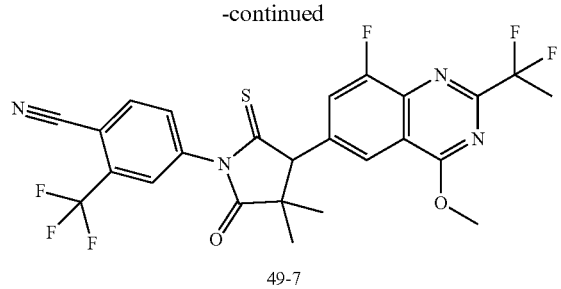

49-7

In a dry single-necked flask, Compound 49-6 (2.66 g), Compound 1-7 (3.40 g), DMF (3.6 mL), and methylbenzene (18 mL) were added. Under nitrogen protection, the resulting mixture was stirred at 90° C. for 48 h, and then was concentrated under reduced pressure to remove the solvent. The residue obtained from the concentration was purified by column chromatography to obtain Compound 49-7. $^1$H NMR (400 MHz, CDCl$_3$) δ ppm 8.00 (d, J=8.4 Hz, 1H), 7.98-7.95 (m, 2H), 7.84 (dd, J=1.9, 8.3 Hz, 1H), 7.54 (dd, J=2.2, 9.7 Hz, 1H), 4.28 (s, 3H), 2.14 (t, J=18.5 Hz, 3H), 1.67 (s, 6H). LCMS (ESI) m/z: 554 (M+1).

7) Synthesis of Compound 49-8

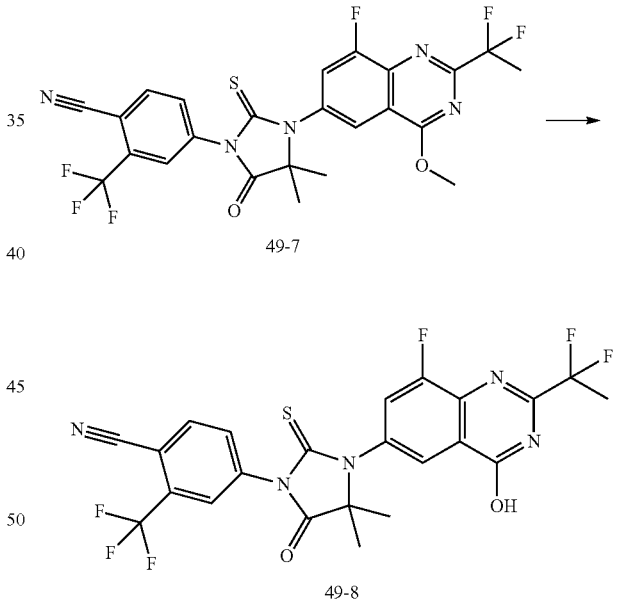

49-7

49-8

In a dry single-necked flask, Compound 49-7 (200 mg) was added, and then tetrahydrofuran (1 mL) and concentrated hydrochloric acid (12M, 1 mL) were added, and the resulting mixture was stirred at 25° C. for 5 min. Dichloromethane (5 mL) was added to the reaction mixture. After liquid separation, the organic phase was dried over anhydrous sodium sulfate, filtered, and concentrated to dryness under reduced pressure to remove the solvent and obtain Compound 49-8. $^1$H NMR (400 MHz, CDCl$_3$) δ ppm 9.73 (br s, 1H), 8.05 (s, 1H), 8.00 (d, J=8.4 Hz, 1H), 7.95 (s, 1H), 7.83 (d, J=8.2 Hz, 1H), 7.53 (dd, J=2.2, 9.5 Hz, 1H), 2.15 (t, J=19.2 Hz, 3H), 1.65 (s, 6H). LCMS (ESI) m/z: 540 (M+1).

8) Synthesis of Compound 49-9

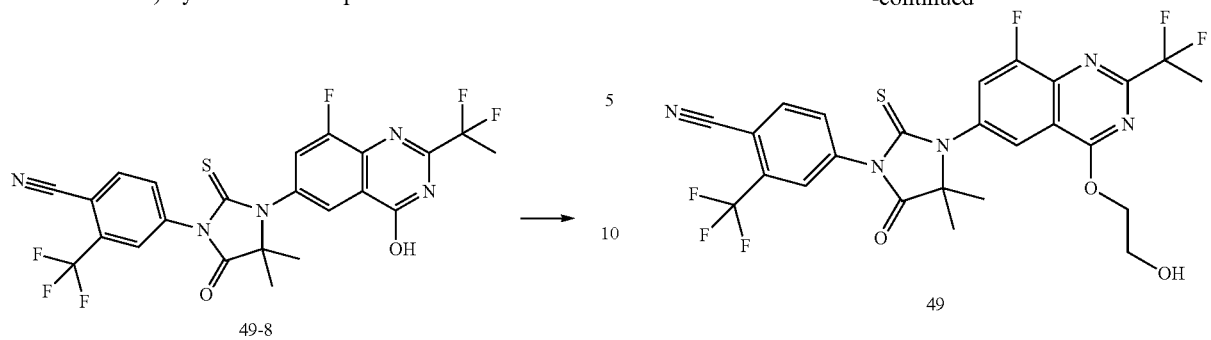

49-8

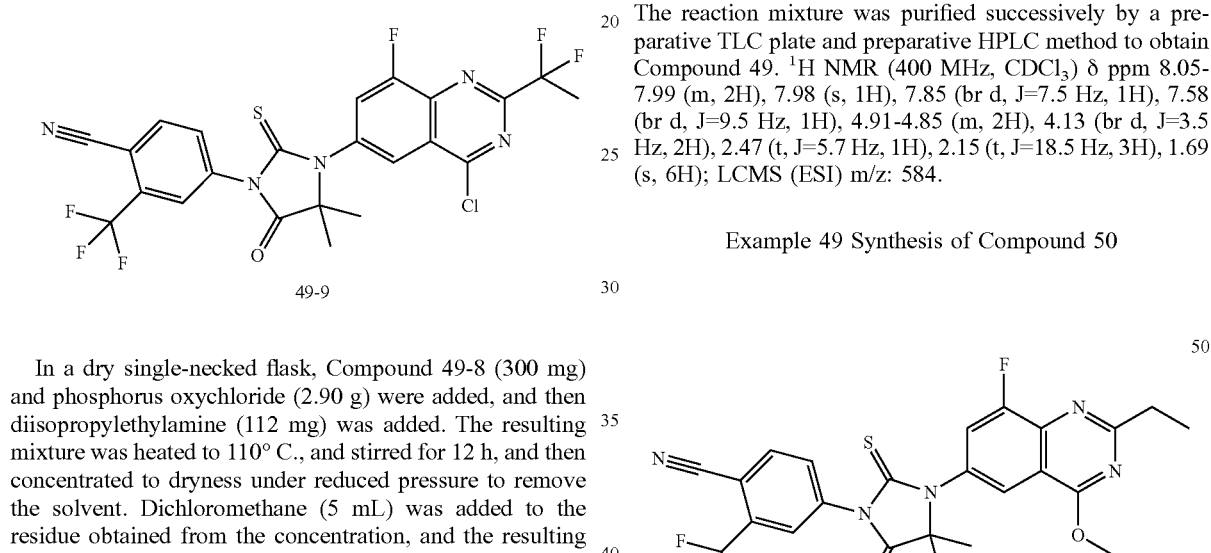

49-9

In a dry single-necked flask, Compound 49-8 (300 mg) and phosphorus oxychloride (2.90 g) were added, and then diisopropylethylamine (112 mg) was added. The resulting mixture was heated to 110° C., and stirred for 12 h, and then concentrated to dryness under reduced pressure to remove the solvent. Dichloromethane (5 mL) was added to the residue obtained from the concentration, and the resulting mixture was washed with 10 mL of an iced saturated sodium bicarbonate solution. After liquid separation, the organic phase was washed with saturated brine, dried over anhydrous sodium sulfate, filtered, and concentrated to dryness under reduced pressure to remove the solvent, and the residue obtained from the concentration was purified by preparative TLC to obtain Compound 49-9. $^1$H NMR (400 MHz, CDCl$_3$) δ ppm 8.11-8.08 (m, 1H), 8.02 (d, J=8.2 Hz, 1H), 7.97 (d, J=2.0 Hz, 1H), 7.84 (dd, J=2.1, 8.3 Hz, 1H), 7.72 (dd, J=2.1, 9.2 Hz, 1H), 2.18 (t, J=18.5 Hz, 3H), 1.70 (s, 6H). LCMS (ESI) m/z: 558 (M+1).

9) Synthesis of Compound 49

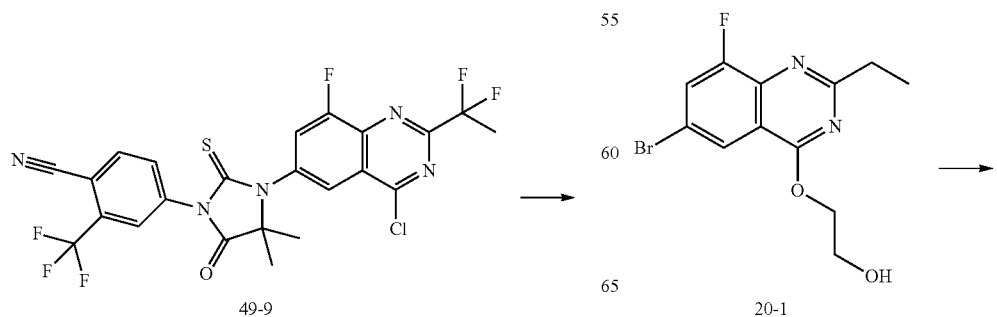

49-9

49

In a dry single-necked flask, Compound 49-9 (44 mg), ethanediol (45 mg), and tetrahydrofuran (0.5 mL) were added, and then sodium hydride (9 mg, 60% purity) was added. The resulting mixture was stirred at 25° C. for 1 h. The reaction mixture was purified successively by a preparative TLC plate and preparative HPLC method to obtain Compound 49. $^1$H NMR (400 MHz, CDCl$_3$) δ ppm 8.05-7.99 (m, 2H), 7.98 (s, 1H), 7.85 (br d, J=7.5 Hz, 1H), 7.58 (br d, J=9.5 Hz, 1H), 4.91-4.85 (m, 2H), 4.13 (br d, J=3.5 Hz, 2H), 2.47 (t, J=5.7 Hz, 1H), 2.15 (t, J=18.5 Hz, 3H), 1.69 (s, 6H); LCMS (ESI) m/z: 584.

Example 49 Synthesis of Compound 50

50

1) Synthesis of Compound 50-1

20-1

-continued

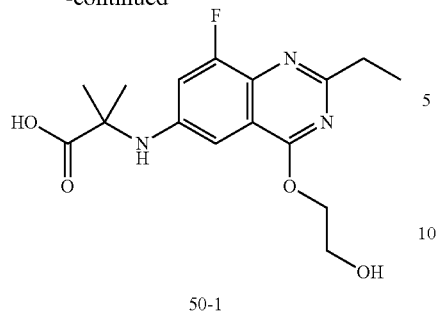

50-1

With reference to the synthesis of Compound 48-6, Compound 50-1 was prepared with Compound 20-1 as the starting material. LCMS (ESI) m/z: 338 (M+1).

2) Synthesis of Compound 50-2

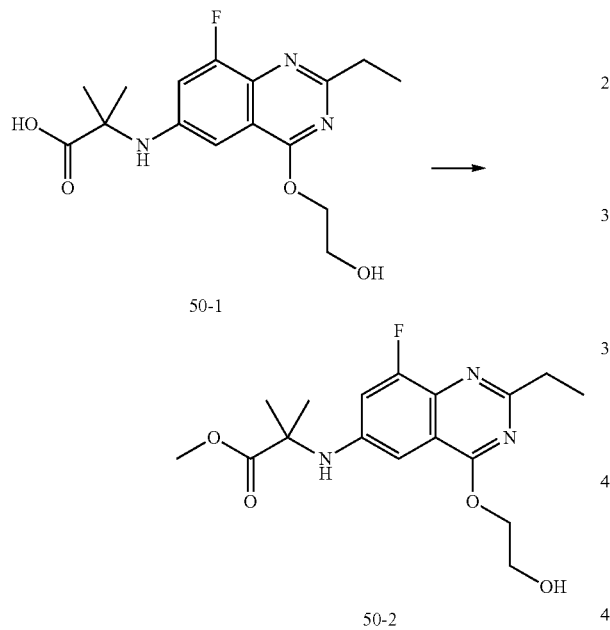

With reference to the synthesis of Compound 48-7, Compound 50-2 was prepared with Compound 50-1 as the starting material. LCMS (ESI) m/z: 352 (M+1).

3) Synthesis of Compound 50-3

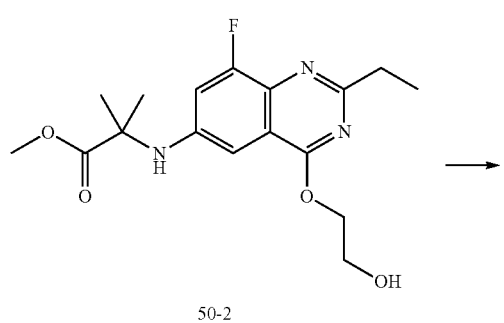

-continued

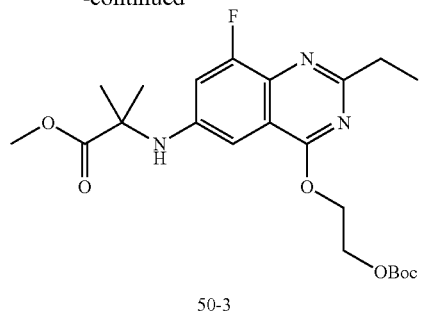

50-3

With reference to the synthesis of Compound 48-8, Compound 50-3 was prepared with Compound 50-2 as the starting material. LCMS (ESI) m/z: 452 (M+1).

4) Synthesis of Compound 50-4

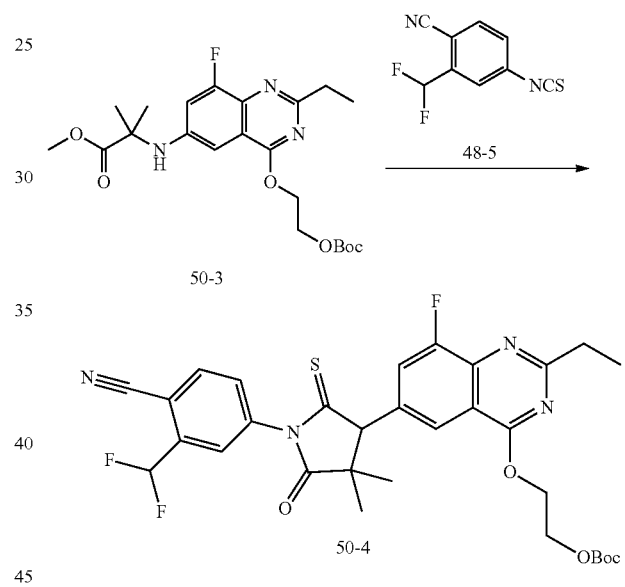

With reference to the synthesis of Compound 48-9, Compound 50-4 was prepared with Compound 50-3 and Compound 48-5 as the starting materials. LCMS (ESI) m/z: 630 (M+1).

5) Synthesis of Compound 50

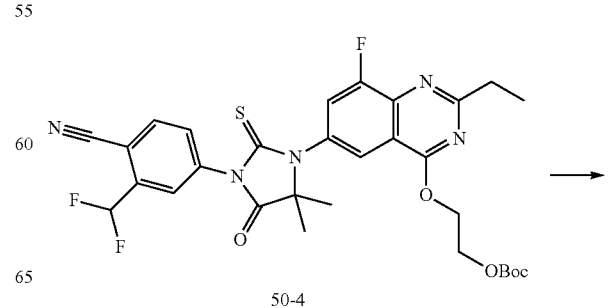

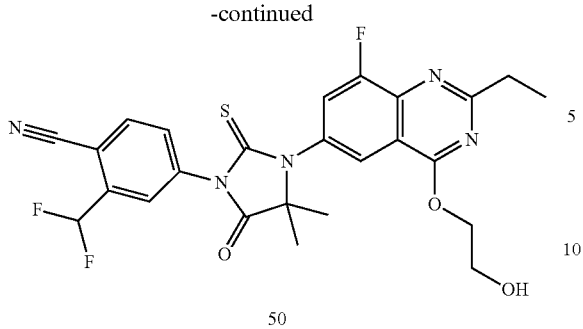
50
With reference to the synthesis of Compound 48, Compound 50 was prepared with Compound 50-4 as the starting material. $^1$H NMR (400 MHz, CDCl$_3$) δ ppm 7.80-7.91 (m, 3H), 7.69 (d, J=8.3 Hz, 1H), 7.40 (dd, J=10.0, 2.0 Hz, 1H), 6.75-7.08 (m, 1H), 4.68-4.78 (m, 2H), 4.02 (br s, 2H), 2.98 (q, J=7.6 Hz, 2H), 2.74 (br s, 1H), 1.59 (s, 6H), 1.35 ppm (t, J=7.5 Hz, 3H); LCMS (ESI) m/z: 530 (M+1).
Example 50 Synthesis of Compound 51
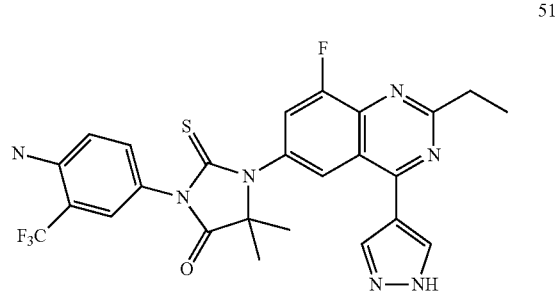 [SMILES: CCc1nc(-c2cn[nH]c2)c2cc(N3C(=S)N(c4ccc(N)c(C(F)(F)F)c4)C(=O)C3(C)C)cc(F)c2n1]
51
1) Synthesis of Compound 51
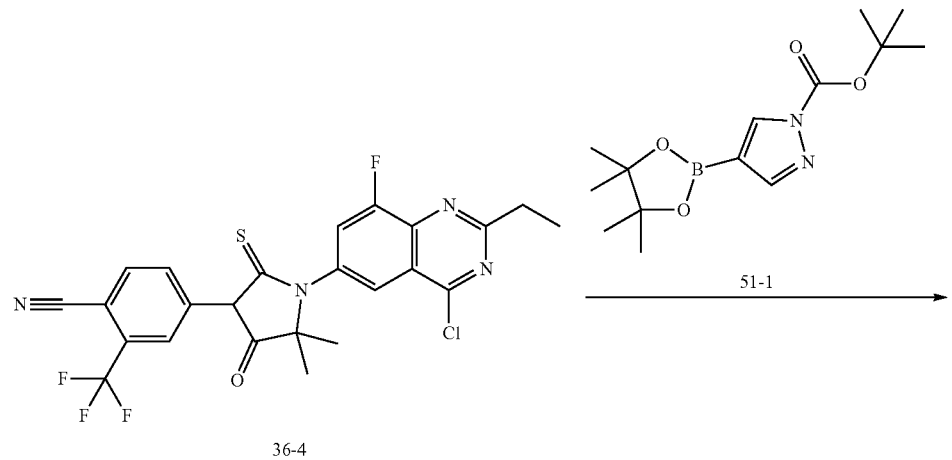
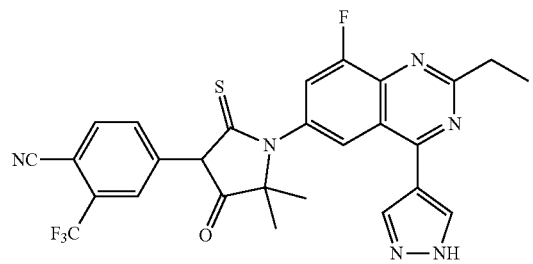
51

In a dry microwave tube, Compound 36-4 (500 mg), Compound 55-1 (564 mg), sodium carbonate (2M, 800 μL, an aqueous solution), 1,2-dichloroethane (7 mL), and water (3 mL) were added. After nitrogen purge, dichlorobis(triphenylphosphine)palladium (67 mg) was added, and the resulting mixture reacted at 140° C. for 10 min. The reaction mixture was concentrated, and the residue obtained from the concentration was purified successively by a preparative TLC plate and preparative HPLC method to obtain Compound 51. ¹H NMR (400 MHz, CDCl₃) δ ppm 8.28 (s, 2H), 8.08 (s, 1H), 8.03 (d, J=8.16 Hz, 1H), 7.99 (s, 1H), 7.86 (d, J=8.16 Hz, 1H), 7.51-7.55 (m, 1H), 3.23 (q, J=7.50 Hz, 2H), 1.69 (s, 6H), 1.51 (t, J=7.72 Hz, 3H). LCMS (ESI) m/z: 554 (M+1).

Example 51 Synthesis of Compound 52

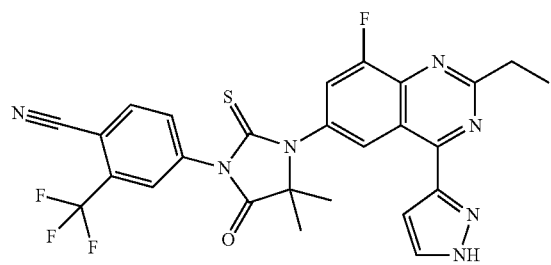

52

1) Synthesis of Compound 52

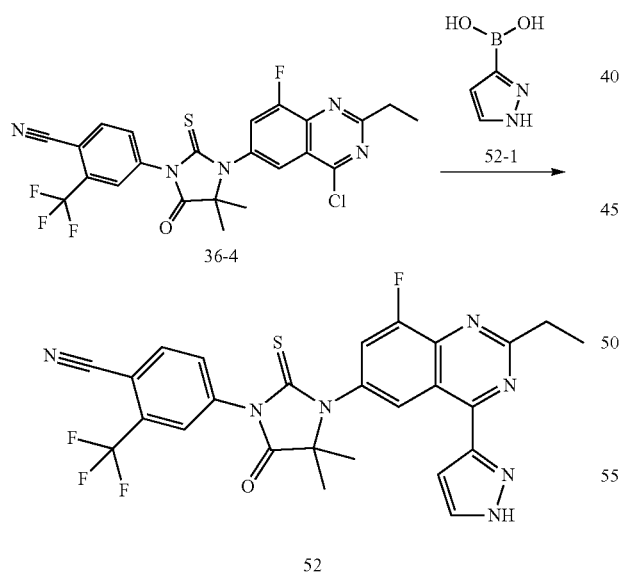

52

In a dry single-necked flask, Compound 36-4 (300 mg), Compound 52-1 (129 mg), sodium carbonate (102 mg), 1,2-dichloroethane (2.1 mL), and water (0.9 mL) were added. After nitrogen purge, dichlorobis(triphenylphosphine)palladium (40 mg) was added, and the resulting mixture was refluxed at 100° C. and reacted for 16 h. The reaction mixture was concentrated, and the residue obtained from the concentration was purified successively by a preparative TLC plate and preparative HPLC method to obtain Compound 52. ¹H NMR (400 MHz, CDCl₃) δ ppm 9.52-9.55 (m, 1H), 8.93 (d, J=2.89 Hz, 1H), 7.98-8.04 (m, 2H), 7.92 (d, J=0.88 Hz, 1H), 7.86-7.91 (m, 1H), 7.59 (dd, J=9.91, 2.13 Hz, 1H), 6.60 (dd, J=2.89, 1.63 Hz, 1H), 3.20 (q, J=7.53 Hz, 2H), 1.73 (s, 5H), 1.67-1.77 (m, 1H), 1.50 (t, J=7.59 Hz, 3H). LCMS (ESI) m/z: 554 (M+1).

Example 52 Synthesis of Compound 53

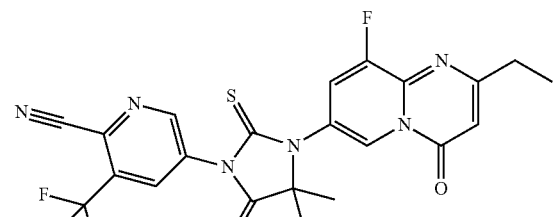

53

1) Synthesis of Compound 53

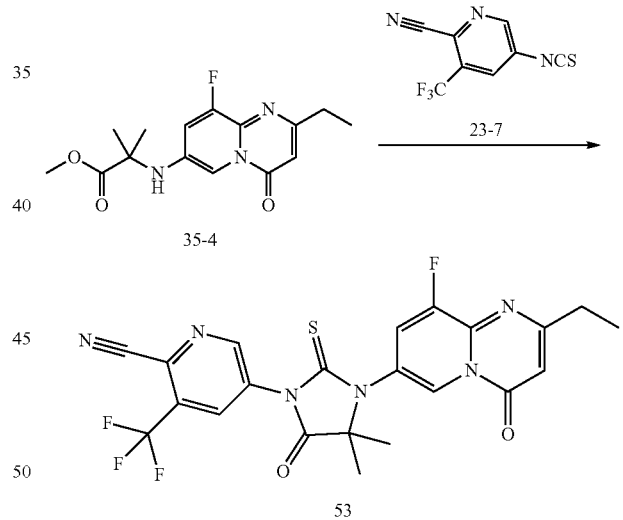

53

A mixed solution of Compound 35-4 (100 mg), Compound 23-7 (299 mg), N,N-dimethylformamide (0.5 mL), and methylbenzene (2 mL) was heated to 120° C., and stirred for 16 h. Methanol (5 mL) was added to the reaction mixture, and the resulting mixture was stirred for 30 min, and then concentrated under reduced pressure. The residue obtained from the concentration was purified successively by a silica gel column and preparative HPLC to obtain Compound 53. ¹H NMR (400 MHz, CDCl₃) δ ppm 9.01 (d, J=1.5 Hz, 1H), 8.76 (s, 1H), 8.28 (d, J=1.8 Hz, 1H), 7.32 (dd, J=1.8, 8.8 Hz, 1H), 6.42 (s, 1H), 2.75 (q, J=7.5 Hz, 2H), 1.64 (s, 6H), 1.29 (t, J=7.5 Hz, 3H); LCMS (ESI) m/z: 505 (M+1).

Example 53 Synthesis of Compound 54

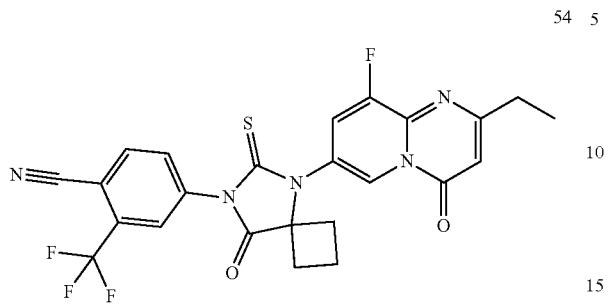

54

1) Synthesis of Compound 54-1

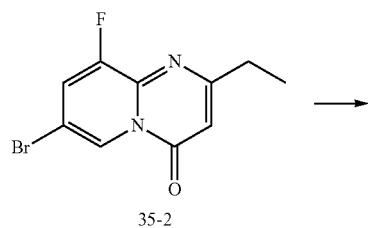

35-2

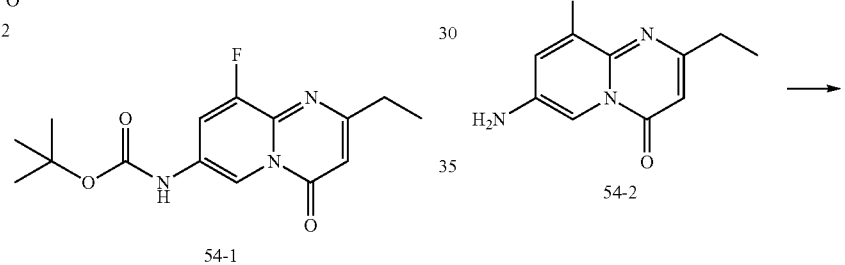

54-1

In a microwave tube, Compound 35-2 (500 mg), tert-butyl carbamate (324 mg), cesium carbonate (1.50 g), 4,5-bis(diphenylphosphino)-9,9-dimethylxanthene (107 mg), bis(dibenzylideneacetone)palladium (170 mg), and methylbenzene (6 mL) were added. The microwave tube was sealed, and the resulting mixture was kept at 120° C. for microwave reaction for 30 min. The reaction mixture was filtered, and washed with ethyl acetate (20 mL). The filtrate was concentrated under reduced pressure. The residue obtained from the concentration was purified by a silica gel column to obtain Compound 54-1. $^1$H NMR (400 MHz, CDCl$_3$) δ ppm 8.90 (s, 1H), 8.15 (br s, 1H), 7.57 (br s, 1H), 6.32 (s, 1H), 2.71 (q, J=7.5 Hz, 2H), 1.49 (s, 9H), 1.26 (t, J=7.5 Hz, 3H).

2) Synthesis of Compound 54-2

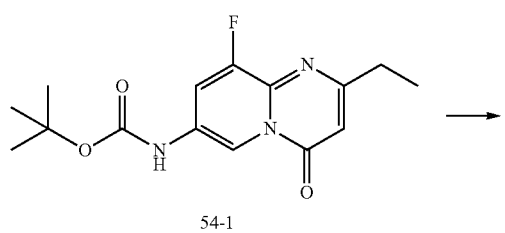

54-1

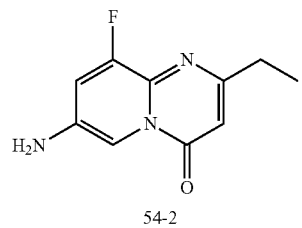

54-2

Trifluoroacetic acid (0.4 mL) was added to a solution of Compound 54-1 (200 mg) in dichloromethane (2 mL). The resulting reaction mixture was stirred at 26° C. for 4 h. A saturated aqueous solution of sodium bicarbonate (pH about 7) was added to the reaction mixture, which was extracted with dichloromethane (20 mL). The organic phase was washed with saturated brine (15 mL), dried over anhydrous sodium sulfate, and concentrated under reduced pressure to obtain Compound 54-2. LCMS (ESI) m/z: 208 (M+1).

3) Synthesis of Compound 54-3

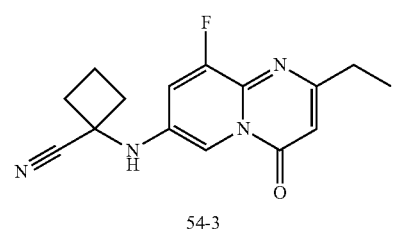

Cyclobutanone (115 mg) and zinc chloride (12 mg) were added to a mixed solution of Compound 54-2 (60 mg), trimethylsilyl cyanide (81 mg), sodium sulfate (154 mg), and tetrahydrofuran (2 mL). The resulting reaction mixture was stirred at 25° C. for 16 h. An aqueous solution of sodium sulfite (10 mL) was added to the reaction mixture, and the resulting mixture was extracted with ethyl acetate (10 mL×3). The organic phase was washed with saturated brine (10 mL), dried over anhydrous sodium sulfate, and concentrated under reduced pressure. The residue obtained from the concentration was purified by a silica gel column to obtain Compound 54-3. LCMS (ESI) m/z: 287 (M+1).

4) Synthesis of Compound 54

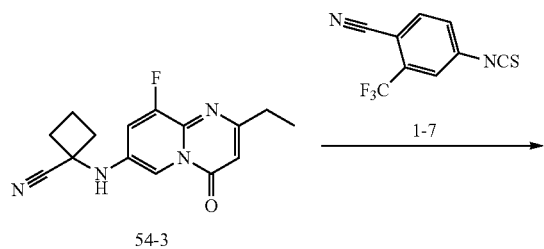

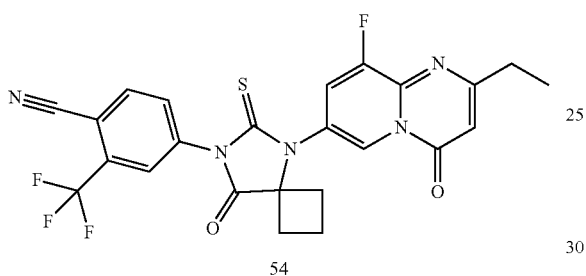

Compound 1-7 (224 mg) was added to a solution of Compound 54-3 (70 mg), N,N-dimethylformamide (0.5 mL), and methylbenzene (2 mL). The resulting mixture was heated to 120° C., and stirred for 16 h. Compound 1-7 (224 mg) was supplemented to the reaction mixture, which was further stirred for 16 h. Methanol (5 mL) was added to the reaction mixture, which was stirred for 30 min, and then concentrated under reduced pressure. The residue obtained from the concentration was purified successively by a silica gel column and preparative HPLC to obtain Compound 54. $^1$H NMR (400 MHz, CDCl$_3$) δ ppm 8.82 (s, 1H), 7.94 (d, J=8.3 Hz, 1H), 7.89 (s, 1H), 7.76 (br d, J=8.3 Hz, 1H), 7.33 (dd, J=1.8, 8.8 Hz, 1H), 6.43 (s, 1H), 2.82-2.63 (m, 4H), 2.58-2.43 (m, 2H), 2.34-2.18 (m, 1H), 1.73 (q, J=10.5 Hz, 1H), 1.29 (t, J=7.5 Hz, 3H); LCMS (ESI) m/z: 516 (M+1).

Example 54 Synthesis of Compound 55

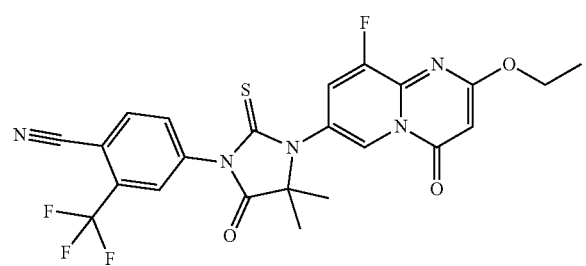

1) Synthesis of Compound 55-1

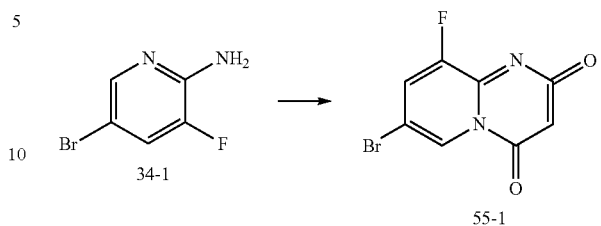

In a dry single-necked flask, Compound 34-1 (15.00 g) and dichloromethane (150 mL) were added, and cooled to −40° C. Then, malonyl dichloride (14.72 g) was added. The resulting mixture was slowly warmed to 25° C., and stirred for 24 h. After filtration, a solid was collected. The resulting solid was slurried with a mixed solvent of 100 mL of methanol and 100 mL of dichloromethane, and filtered to obtain Compound 55-1. $^1$H NMR (400 MHz, DMSO-d6) δ ppm 8.73 (t, J=1.7 Hz, 1H), 8.20 (dd, J=2.0, 9.3 Hz, 1H), 5.54 (s, 1H). LCMS (ESI) m/z: 259 (M+1).

2) Synthesis of Compound 55-2

In a dry single-necked flask, Compound 55-1 (1.00 g), potassium carbonate (1.07 g), iodoethane (682 mg), and NMP (10 mL) were added. Under nitrogen protection, the resulting mixture was heated to 60° C., and stirred for 48 h. Iodoethane (682 mg) was supplemented, and the resulting mixture was heated to 60° C., and refluxed for 12 h. 100 mL of saturated brine and 100 mL of ethyl acetate were successively added to the reaction mixture, which was filtered to remove the solid. After liquid separation of the filtrate, the organic phase was collected, dried over anhydrous sodium sulfate, filtered, and concentrated to dryness under reduced pressure. The residue obtained from the concentration was successively purified by a chromatographic column, and slurried with 20 mL of methyl tert-butyl ether to obtain Compound 55-2. $^1$H NMR (400 MHz, CDCl$_3$) δ ppm 8.98 (t, J=1.7 Hz, 1H), 7.56 (dd, J=2.1, 7.8 Hz, 1H), 5.82 (s, 1H), 4.42 (q, J=7.1 Hz, 2H), 1.42 (t, J=7.1 Hz, 3H). LCMS (ESI) m/z: 287 (M+1).

3) Synthesis of Compound 55-3

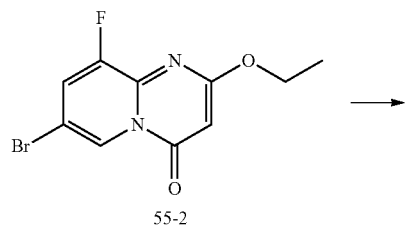

55-2

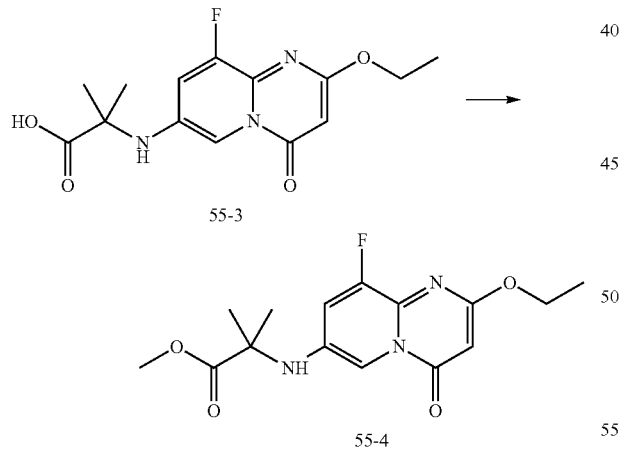

In a dry microwave tube, Compound 55-2 (600 mg), 2-aminoisobutyric acid (646 mg), 2-acetylcyclohexanone (59 mg), potassium carbonate (578 mg), DMF (12 mL), and water (2.4 mL) were added, and then cuprous chloride (41 mg) was added. After nitrogen purge for 5 min, the microwave tube was sealed. The resulting mixture was microwaved and stirred at 90° C. for 2 h. 2-Acetylcyclohexanone (59 mg) and cuprous chloride (41 mg) were supplemented, and the resulting mixture was microwaved and stirred for 1.5 h, and then concentrated under reduced pressure to obtain Compound 55-3. LCMS (ESI) m/z: 310 (M+1).

4) Synthesis of Compound 55-4

In a dry single-necked flask, Compound 55-3 (1.20 g), a solution of TMSCHN$_2$ in n-hexane (2M, 3.88 mL), dichloromethane (20 mL), and methanol (3 mL) were added. Under nitrogen protection, the resulting mixture was stirred at 25° C. for 12 h. A solution of TMSCHN$_2$ in n-hexane (2M, 3.88 mL) was supplemented, and the resulting mixture was stirred at 25° C. for 6 h; a solution of TMSCHN$_2$ in n-hexane (2M, 3.88 mL) was supplemented, and the resulting mixture was stirred at 25° C. for 12 h; a solution of TMSCHN$_2$ in n-hexane (2M, 3.88 mL) was supplemented, and the resulting mixture was stirred at 25° C. for 6 h; and a solution of TMSCHN$_2$ in n-hexane (2M, 7.76 mL) was supplemented, and the resulting mixture was stirred at 25° C. for 12 h. The resulting mixture was concentrated to dryness under reduced pressure to remove the solvent. The resulting crude product was purified by a chromatographic column to obtain Compound 55-4. LCMS (ESI) m/z: 324 (M+1).

5) Synthesis of Compound 55

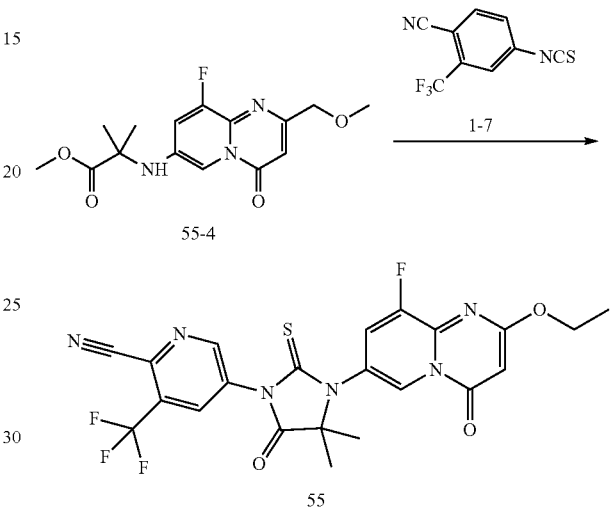

In a dry single-necked flask, Compound 55-4 (80 mg), DMF (0.4 mL), and methylbenzene (2 mL) were added, and then Compound 1-7 (624 mg) was added. Under nitrogen protection, the resulting mixture was heated to 90° C., and stirred for 10 h, and then concentrated to dryness under reduced pressure to remove the solvent. The crude product was purified successively by a preparative TLC plate and preparative HPLC method to obtain Compound 55. $^1$H NMR (400 MHz, CDCl$_3$) δ ppm 8.80 (s, 1H), 7.94 (d, J=8.4 Hz, 1H), 7.87 (s, 1H), 7.75 (br d, J=7.7 Hz, 1H), 7.39 (br d, J=8.6 Hz, 1H), 5.82 (s, 1H), 4.41 (q, J=7.2 Hz, 2H), 1.61 (s, 6H), 1.39 (t, J=7.1 Hz, 3H). LCMS (ESI) m/z: 520 (M+1).

Example 55 Synthesis of Compound 56

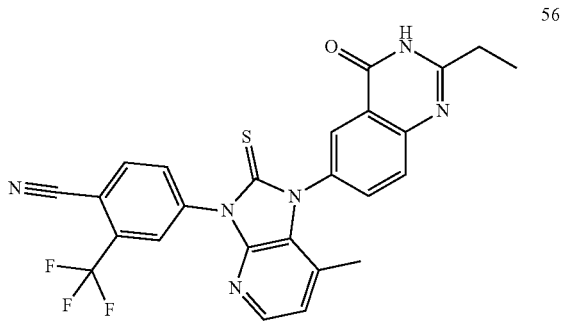 [SMILES: CCc1nc2ccc(-n3c(=S)n(-c4ccc(C#N)c(C(F)(F)F)c4)c4nccc(C)c43)cc2c(=O)[nH]1]

1) Synthesis of Compound 56-1

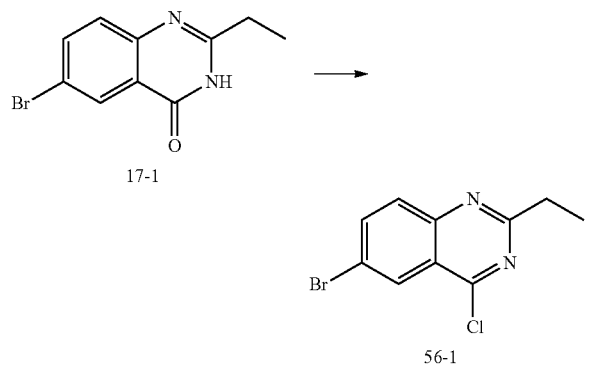

In a reaction flask, phosphorous oxychloride (50 mL) was added, Compound 17-1 (5.00 g) was slowly added, and then N,N-diisopropylethylamine (3.98 g) was added. The resulting mixture reacted at 110° C. for 2 h. The reaction mixture was concentrated under reduced pressure to obtain a crude product. The crude product was dissolved in 80 mL of ethyl acetate, and 20 mL of ice water was added for liquid separation. 40 mL of an iced saturated sodium bicarbonate solution was added to the organic phase. After liquid separation, the organic phase was dried over anhydrous sodium sulfate, filtered, and concentrated under reduced pressure, to obtain Compound 56-1.

2) Synthesis of Compound 56-2

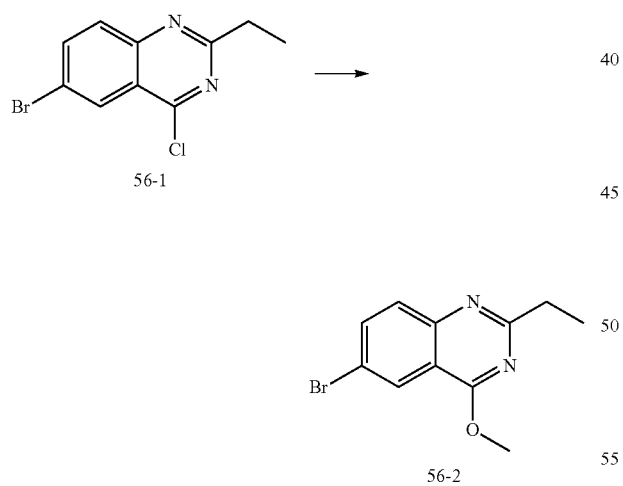

In a round-bottomed flask, Compound 56-1 (4.65 g), sodium methoxide (4.63 g), and methanol (47 mL) were added, and reacted at 25° C. for 60 min. After the completion of the reaction, the resulting mixture was concentrated, and the residue obtained from the concentration was purified by flash column chromatography to obtain Compound 56-2. $^1$H NMR (400 MHz, CDCl$_3$) δ ppm 8.25 (d, J=2.21 Hz, 1H), 7.83 (dd, J=8.93, 2.32 Hz, 1H), 7.70-7.74 (m, 1H), 4.13-4.20 (m, 3H), 2.96 (q, J=7.50 Hz, 2H), 1.41 (t, J=7.50 Hz, 3H).

3) Synthesis of Compound 56-3

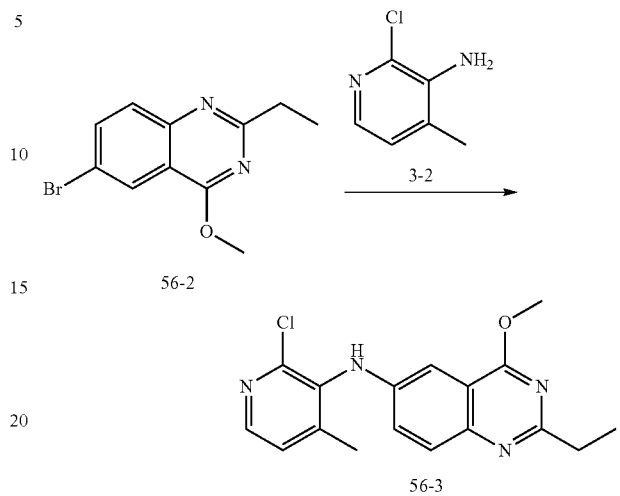

In a reaction flask, Compound 56-2 (500 mg), Compound 3-2 (801 mg), 4,5-bis(diphenylphosphino)-9,9-dimethylxanthene (108 mg), cesium carbonate (1.52 g), and DMF (5 mL) were added. After nitrogen purge for 1 min, bis(dibenzylideneacetone)palladium (107 mg) was added, and the resulting mixture reacted at 80° C. for 16 h. The reaction mixture was concentrated under reduced pressure to obtain a crude product. The crude product was separated and purified by flash column chromatography to obtain Compound 56-3. $^1$H NMR (400 MHz, CDCl$_3$) δ ppm 8.18 (d, J=4.85 Hz, 1H), 7.79 (d, J=9.04 Hz, 1H), 7.29 (d, J=2.87 Hz, 1H), 7.20 (d, J=4.85 Hz, 1H), 6.99 (d, J=2.65 Hz, 1H), 5.84 (s, 1H), 4.10 (s, 3H), 2.90-2.98 (m, 2H), 2.23 (s, 3H), 1.40 (t, J=7.61 Hz, 3H).

4) Synthesis of Compound 56-4

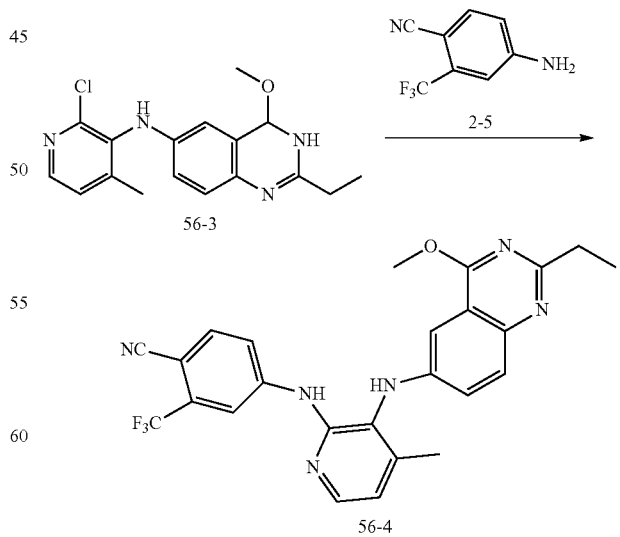

In a microwave tube, Compound 56-3 (500 mg), Compound 2-5 (311 mg), 4,5-bis(diphenylphosphino)-9,9-dimethylxanthene (88 mg), cesium carbonate (991 mg), and methylbenzene (5 mL) were added. Under nitrogen purge, Pd(dba)$_2$ (87 mg) was added, and after nitrogen purge for 1 min, the resulting mixture was kept at 130° C. for microwave reaction for 2 h. The reaction mixture was concentrated under reduced pressure to obtain a crude product. The crude product was purified by column chromatography to obtain Compound 56-4. $^1$H NMR (400 MHz, CDCl$_3$) δ ppm 8.23 (d, J=5.02 Hz, 1H), 8.16 (d, J=2.13 Hz, 1H), 7.98 (dd, J=8.66, 2.26 Hz, 1H), 7.79 (d, J=8.91 Hz, 1H), 7.76 (s, 1H), 7.68 (d, J=8.66 Hz, 1H), 7.00 (d, J=2.64 Hz, 1H), 6.91 (d, J=5.14 Hz, 1H), 5.31 (s, 1H), 5.27 (s, 1H), 4.07 (s, 3H), 2.93 (q, J=7.57 Hz, 2H), 2.21 (s, 3H), 1.39 (t, J=7.59 Hz, 3H).

5) Synthesis of Compound 56-5

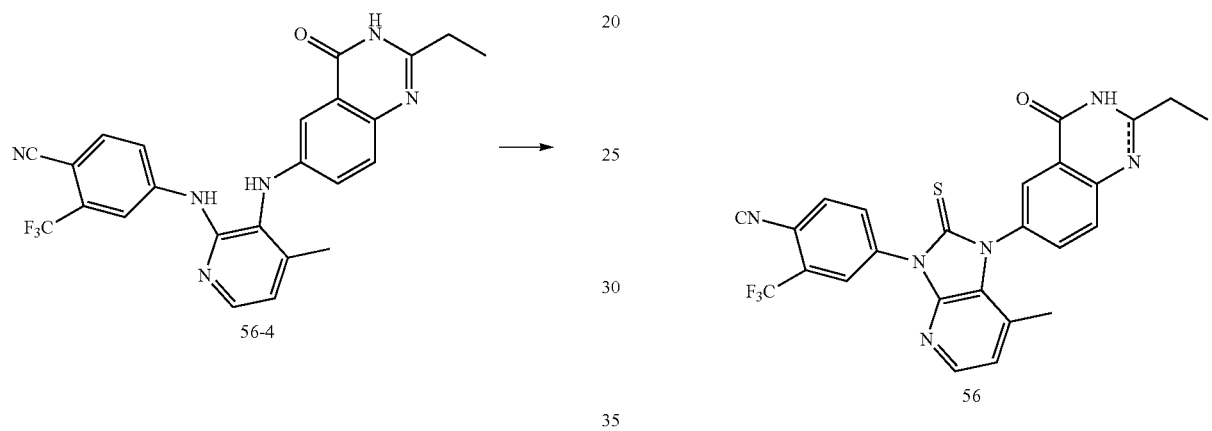

56-4

56-5

At 0° C., in a reaction flask, Compound 56-4 (79 mg) and tetrahydrofuran (0.8 mL) were added, and fully stirred, and then sodium hydride (22 mg, 60% purity) was added. After the resulting mixture reacted for 0.5 h, thiophosgene (30 mg) was added, and the reaction mixture was stirred at 25° C. for 15.5 h. The reaction mixture was concentrated under reduced pressure to obtain a crude product. The crude product was purified by a silica gel plate of thin layer chromatography to obtain Compound 56-5. $^1$H NMR (400 MHz, CDCl$_3$) δ ppm 8.29 (s, 1H), 8.27 (d, J=2.43 Hz, 1H), 8.24-8.28 (m, 1H), 8.08-8.12 (d, J=5.07 Hz, 1H), 8.07 (s, 1H), 8.05 (s, 1H), 7.84 (dd, J=8.82, 2.43 Hz, 1H), 6.97-7.01 (m, 1H), 4.17 (s, 3H), 2.98-3.07 (m, 2H), 1.88 (s, 3H), 1.44 (t, J=7.50 Hz, 3H).

8) Synthesis of Compound 56

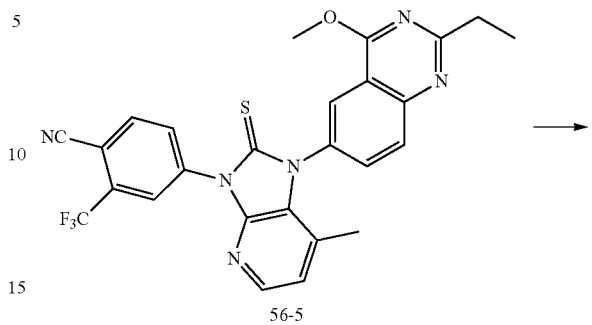

56-5

In a reaction flask, Compound 56-5 (70 mg), an aqueous solution of hydrochloric acid (2M, 1 mL), and tetrahydrofuran (1 mL) were added, and stirred at 30° C. for 16 h. The reaction mixture was concentrated under reduced pressure to obtain a crude product. The crude product was purified by preparative HPLC method to obtain Compound 56. $^1$H NMR (400 MHz, CDCl$_3$) δ ppm 9.28 (br s, 1H), 8.36 (d, J=1.98 Hz, 1H), 8.31 (s, 1H), 8.19 (d, J=8.16 z, 1H), 8.13 (d, J=5.07 Hz, 1H), 8.08 (d, J=8.38 Hz, 1H), 7.91-7.95 (m, 1H), 7.85-7.90 (m, 1H), 6.99-7.02 (m, 1H), 2.81 (q, J=7.64 Hz, 2H), 1.93 (s, 3H), 1.45 (t, J=7.61 Hz, 3H). LCMS (ESI) m/z: 507 (M+1).

Example 56 Synthesis of Compound 57

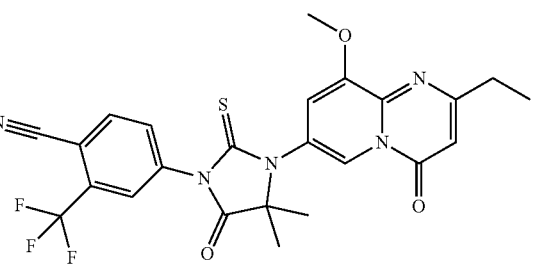

57

1) Synthesis of Compound 57-2

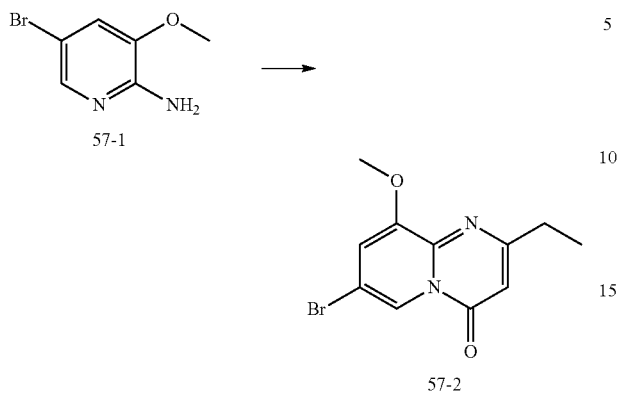

Methyl propionylacetate (2.56 g) was added to a solution of Compound 57-1 (1.00 g) in acetic acid (10 mL). The resulting mixture was heated to 110° C., and stirred for 16 h. The reaction mixture was concentrated under reduced pressure. The residue obtained from the concentration was diluted with ethyl acetate (30 mL), and a saturated aqueous solution of sodium bicarbonate (30 mL) was added. After liquid separation, the organic phase was washed with saturated brine (30 mL), dried over anhydrous sodium sulfate, filtered, and concentrated. The residue obtained from the concentration was purified by a silica gel column to obtain Compound 57-2. $^1$H NMR (400 MHz, CDCl$_3$) δ ppm 8.83 (s, 1H), 7.05 (s, 1H), 6.44 (s, 1H), 4.08 (s, 3H), 2.82 (q, J=7.5 Hz, 2H), 1.34 (t, J=7.7 Hz, 3H).

2) Synthesis of Compound 57-3

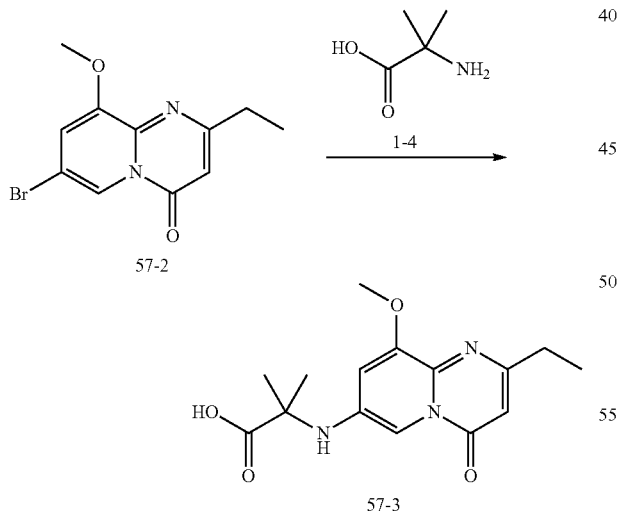

Compound 57-2 (300 mg), Compound 1-4 (165 mg), potassium carbonate (366 mg), 2-acetylcyclohexanone (30 mg), cuprous chloride (21 mg), N,N-dimethylformamide (2 mL), and water (0.1 mL) were added to a microwave tube. The microwave tube was sealed, and the resulting mixture was kept at 130° C. for microwave reaction for 30 min. The reaction mixture was filtered, the filter cake was washed with ethyl acetate (20 mL), and the filtrate was concentrated under reduced pressure. 1N hydrochloric acid was added to the residue obtained from the concentration (pH 6-7). The resulting mixture was extracted with ethyl acetate (20 mL×3), and the organic phase was washed with saturated brine (30 mL), dried over anhydrous sodium sulfate, and filtered. The filtrate was concentrated. Dichloromethane/methanol (10/1, 20 mL) were added to the residue obtained from the concentration. The resulting mixture was filtered, and the filtrate was concentrated under reduced pressure to obtain Compound 57-3. LCMS (ESI) m/z: 306 (M+1).

3) Synthesis of Compound 57-4

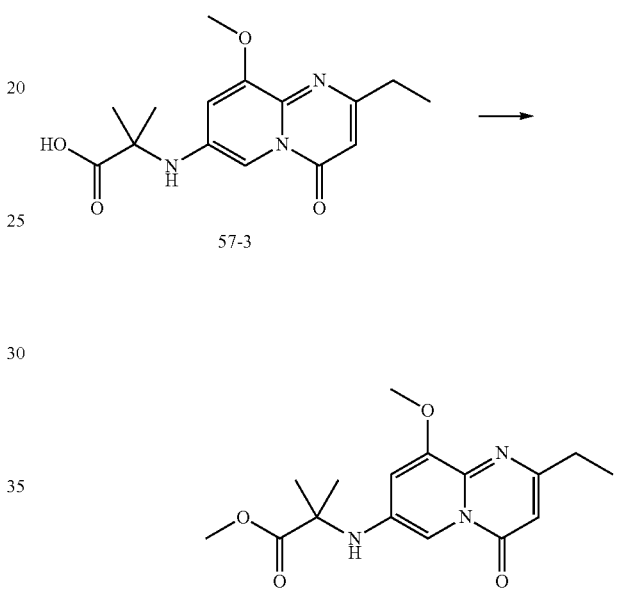

A solution of trimethylsilyldiazomethane in n-hexane (2M, 0.8 mL) was added to a solution of Compound 57-3 (300 mg), dichloromethane (5 mL) and methanol (0.5 mL). The resulting reaction mixture was stirred at 20° C. for 16 h. The reaction mixture was concentrated under reduced pressure. The residue obtained from the concentration was purified by a silica gel column to obtain Compound 57-4. $^1$H NMR (400 MHz, CDCl$_3$) δ ppm 7.88 (d, J=2.3 Hz, 1H), 6.55 (d, J=1.8 Hz, 1H), 6.26 (s, 1H), 3.94 (s, 3H), 3.72 (s, 3H), 2.72 (q, J=7.4 Hz, 2H), 1.57 (s, 6H), 1.24 (t, J=7.5 Hz, 3H).

4) Synthesis of Compound 57

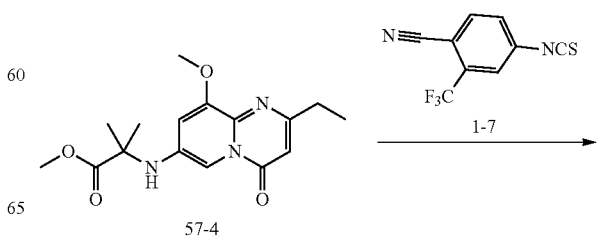

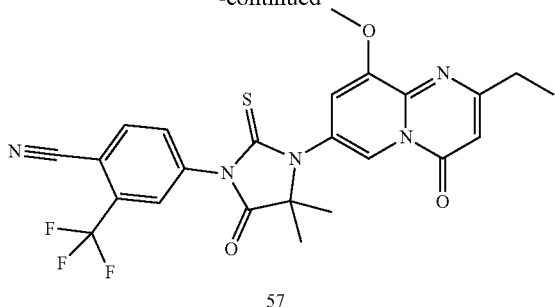

57

A mixed solution of Compound 57-4 (150 mg), Compound 1-7 (430 mg), N,N-dimethylformamide (0.5 mL), and methylbenzene (2 mL) was heated to 120° C., and stirred for 16 h. Methanol (5 mL) was added to the reaction mixture, which was stirred for 30 min, and then concentrated under reduced pressure. The residue obtained from the concentration was purified successively by a silica gel column and preparative HPLC to obtain Compound 57. $^1$H NMR (400 MHz, CDCl$_3$) δ ppm 8.71 (d, J=2.0 Hz, 1H), 8.03 (d, J=8.3 Hz, 1H), 7.98 (d, J=1.5 Hz, 1H), 7.86 (dd, J=2.0, 8.3 Hz, 1H), 6.90 (d, J=2.0 Hz, 1H), 6.49 (s, 1H), 4.09 (s, 3H), 2.86 (q, J=7.5 Hz, 2H), 1.72 (s, 6H), 1.37 (t, J=7.5 Hz, 3H); LCMS (ESI) m/z: 516 (M+1).

Example 57 Synthesis of Compound 58

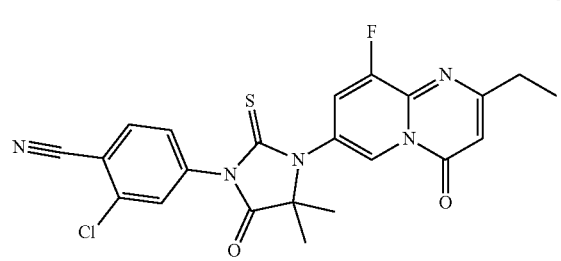

58

1) Synthesis of Compound 58-1

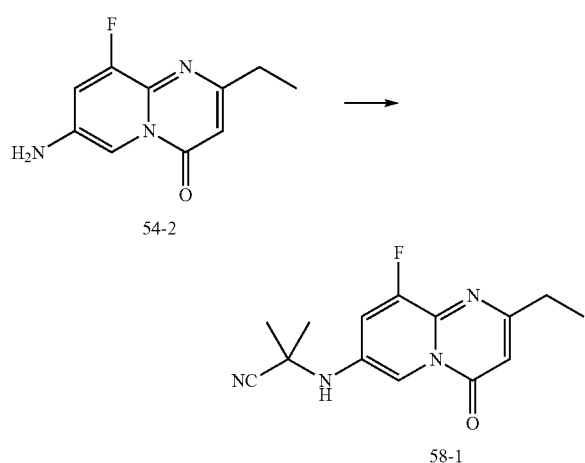

In a dry reaction flask, Compound 54-2 (300 mg), zinc chloride (59 mg), sodium sulfate (823 mg), acetone (505 mg), trimethylsilyl cyanide (431 mg), and tetrahydrofuran (3 mL) were added, and reacted at 25° C. for 4 h under nitrogen protection. The reaction mixture was directly concentrated, and the residue obtained from the concentration was purified by preparative TLC method to obtain Compound 58-1. $^1$H NMR (400 MHz, CDCl$_3$) δ ppm 8.52 (s, 1H), 7.33 (dd, J=9.98, 2.32 Hz, 1H), 6.46 (s, 1H), 2.78 (q, J=7.65 Hz, 2H), 1.78 (s, 6H), 1.33 (t, J=7.59 Hz, 3H).

2) Synthesis of Compound 58-3

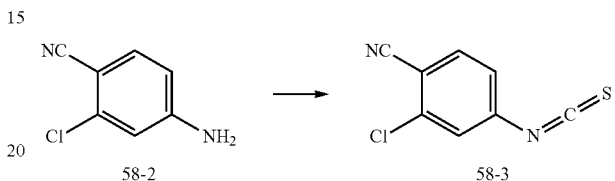

Water (10 mL) was added to a single-necked flask, and then thiophosgene (1.13 g) was added dropwise. After stirring at 25° C. for 0.5 h under nitrogen protection, Compound 58-2 (1.00 g) was added in batches, and the resulting mixture further reacted at 25° C. for 2 h. The reaction mixture was extracted with dichloromethane (10 mL×3). The organic phase was washed with saturated brine (15 mL), dried over anhydrous sodium sulfate, and filtered. The filtrate was concentrated. The residue obtained from the concentration was purified by column chromatography to obtain Compound 58-3. $^1$H NMR (400 MHz, CDCl$_3$) δ ppm 7.67 (d, J=8.38 Hz, 1H), 7.37 (d, J=1.98 Hz, 1H) 7.21 (dd, J=8.38, 1.98 Hz, 1H).

3) Synthesis of Compound 58-4

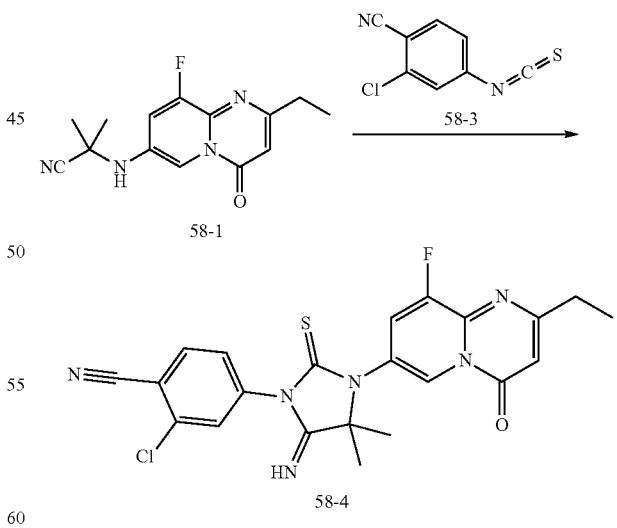

In a dry reaction flask, Compound 58-1 (200 mg), Compound 58-3 (568 mg), methylbenzene (2 mL), and DMF (0.5 mL) were added. Under nitrogen protection, sodium hydride (44 mg, 60% purity) was added, and the resulting mixture reacted at 25° C. for 0.5 h. The reaction mixture was concentrated, and the residue obtained from the concentration was purified by column chromatography to obtain Compound 58-4. LCMS (ESI) m/z: 469 (M+1).

4) Synthesis of Compound 58

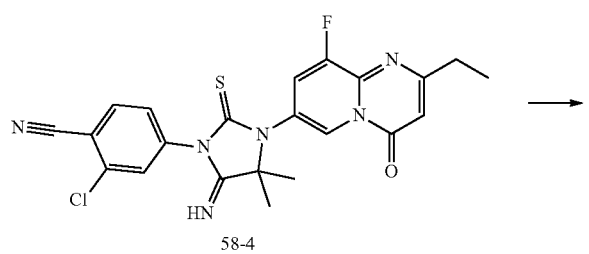
58-4

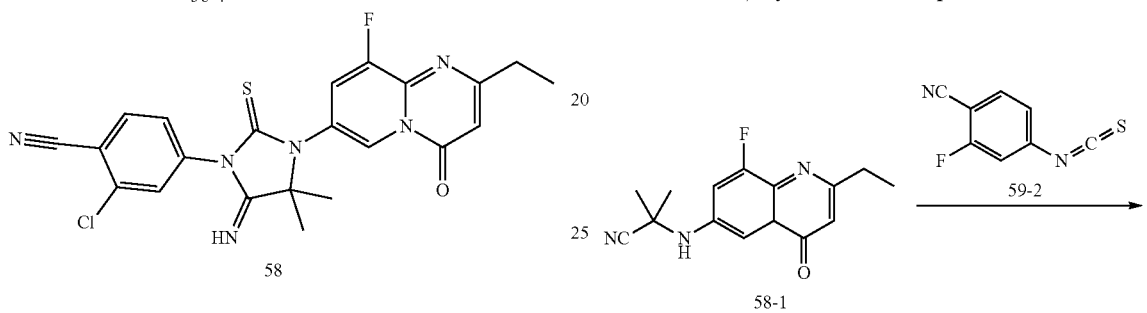
58

In a dry reaction flask, Compound 58-4 (110 mg), methylbenzene (1.1 mL), and glacial acetic acid (1.1 mL) were added, and kept at 110° C. for 16 h under nitrogen protection. The reaction mixture was concentrated, and the residue obtained from the concentration was purified by preparative HPLC to obtain Compound 58. $^1$H NMR (400 MHz, CDCl$_3$) δ ppm 8.83 (s, 1H), 7.84 (d, J=8.16 Hz, 1H), 7.68 (d, J=1.98 Hz, 1H), 7.51 (dd, J=8.27, 2.09 Hz, 1H), 7.41 (dd, J=8.71, 2.09 Hz, 1H), 6.49 (s, 1H), 2.82 (q, J=7.57 Hz, 2H), 1.68 (s, 6H), 1.36 (t, J=7.61 Hz, 3H). LCMS (ESI) m/z: 470 (M+1).

Example 58 Synthesis of Compound 59

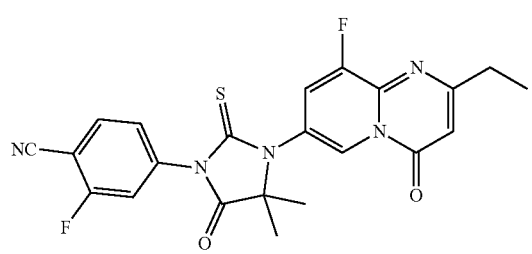
59

1) Synthesis of Compound 59-2

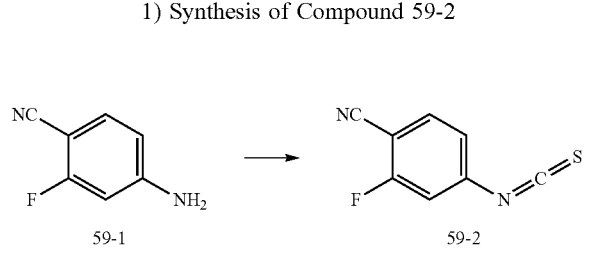
59-1       59-2

Water (10 mL) was added to a single-necked flask, and then thiophosgene (1.27 g) was added dropwise. After stirring at 25° C. for 0.5 h under nitrogen protection, Compound 59-1 (1.00 g) was added in batches, and the resulting mixture further reacted at 25° C. for 2 h. The reaction mixture was extracted with dichloromethane (10 mL×3). The organic phase was washed with saturated brine (15 mL), dried over anhydrous sodium sulfate, and filtered. The filtrate was concentrated. The residue obtained from the concentration was purified by column chromatography to obtain Compound 59-2. $^1$H NMR (400 MHz, CDCl$_3$) δ ppm 7.63 (dd, J=8.38, 7.06 Hz, 1H), 7.10-7.15 (m, 1H), 7.07 (dd, J=9.15, 1.87 Hz, 1H).

2) Synthesis of Compound 59-3

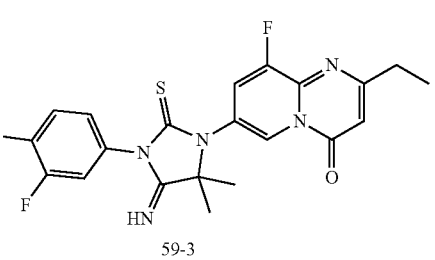
59-3

In a dry reaction flask, Compound 58-1 (200 mg), Compound 59-2 (520 mg), methylbenzene (2 mL), and DMF (0.5 mL) were added. Under nitrogen protection, sodium hydride (44 mg, 60% purity) was added, and the resulting mixture reacted at 25° C. for 0.5 h. The reaction mixture was concentrated, and the residue obtained from the concentration was purified by column chromatography to obtain Compound 59-3. LCMS (ESI) m/z: 453 (M+1).

3) Synthesis of Compound 59

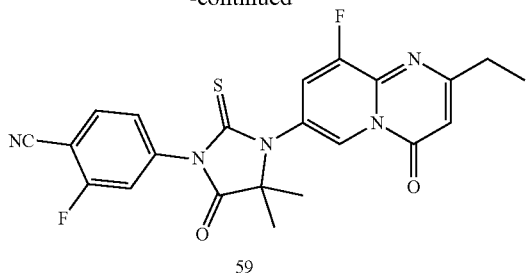

59

In a dry reaction flask, Compound 59-3 (80 mg), methylbenzene (0.8 mL), and glacial acetic acid (0.8 mL) were added, and reacted at 110° C. for 16 h under nitrogen protection. The reaction mixture was concentrated to obtain a crude product, and the crude product was purified by preparative HPLC to obtain Compound 59. $^1$H NMR (400 MHz, CDCl$_3$) δ ppm 8.83 (s, 1H) 7.77-7.84 (m, 1H) 7.38-7.45 (m, 3H) 6.49 (s, 1H) 2.82 (q, J=7.35 Hz, 2H) 1.68 (s, 6H) 1.36 (t, J=7.61 Hz, 3H).

Example 59 Synthesis of Compound 60

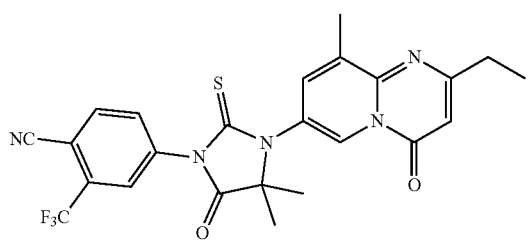

60

1) Synthesis of Compound 60-2

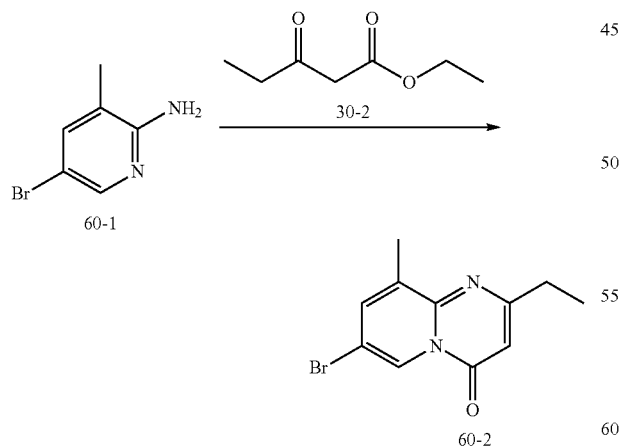

In a dry single-necked flask, Compound 60-1 (10.00 g), Compound 30-2 (10.02 g), and polyphosphoric acid (30 g) were added, heated to 110° C. and stirred for 16 h under nitrogen protection. The reaction mixture was poured to 200 mL of ice water, and then adjusted to pH=7 with a sodium bicarbonate solid. 200 mL of ethyl acetate was added. After liquid separation, the organic phase was collected, dried over anhydrous sodium sulfate, and filtered. The filtrate was concentrated under reduced pressure, and the residue obtained from the concentration was purified by a chromatographic column to obtain Compound 60-2. $^1$H NMR (400 MHz, DMSO-d6) δ ppm 8.81 (d, J=1.8 Hz, 1H), 7.94 (d, J=0.9 Hz, 1H), 6.31 (s, 1H), 2.62 (q, J=7.5 Hz, 2H), 2.44 (s, 3H), 1.21 (t, J=7.5 Hz, 3H). LCMS (ESI) m/z: 267 (M+1).

2) Synthesis of Compound 60-3

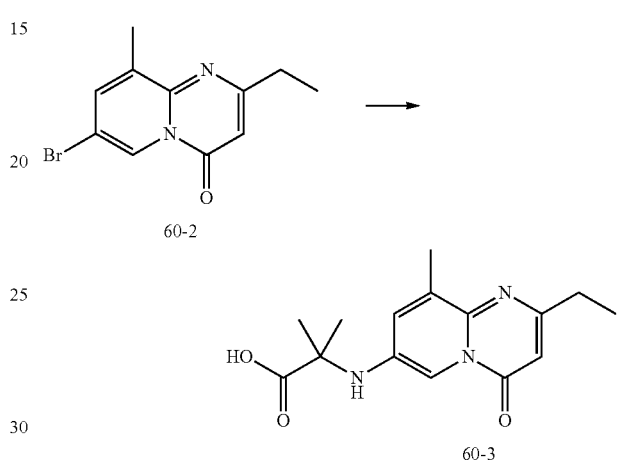

In a dry microwave tube, Compound 60-2 (500 mg), 2-aminoisobutyric acid (579 mg), 2-acetylcyclohexanone (52 mg), potassium carbonate (517 mg), DMF (4 mL), and water (1 mL) were added, and then cuprous chloride (37 mg) was added. After nitrogen purge for 5 min, the microwave tube was sealed, and the resulting mixture was microwaved and stirred at 90° C. for 4 h. The reaction mixture was concentrated under reduced pressure to obtain Compound 60-3. LCMS (ESI) m/z: 290 (M+1).

3) Synthesis of Compound 60-4

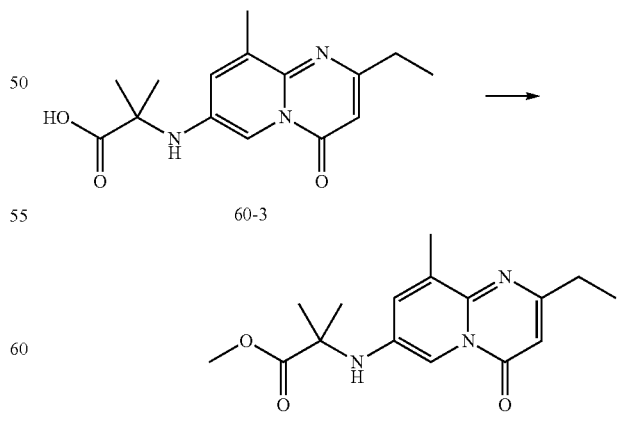

In a dry single-necked flask, Compound 60-3 (800 mg) and a solution of hydrochloric acid-methanol (4M, 25 mL)

were added, heated to 90° C. and refluxed for 2 h under nitrogen protection. The reaction mixture was concentrated, and 20 mL of a saturated sodium bicarbonate solution and 20 mL of ethyl acetate were added to the residue obtained from the concentration. After liquid separation, the organic phase was collected, dried over anhydrous sodium sulfate, filtered, and concentrated under reduced pressure to obtain a crude product, which was purified by a chromatographic column to obtain Compound 60-4. $^1$H NMR (400 MHz, CDCl$_3$) δ ppm 8.18 (d, J=2.6 Hz, 1H), 7.13 (d, J=1.5 Hz, 1H), 7.14-7.11 (m, 1H), 6.49-5.91 (m, 1H), 3.77 (s, 3H), 2.68 (q, J=7.6 Hz, 2H), 2.53 (s, 3H), 1.61 (s, 6H), 1.29 (t, J=7.5 Hz, 3H). LCMS (ESI) m/z: 304 (M+1).

4) Synthesis of Compound 60

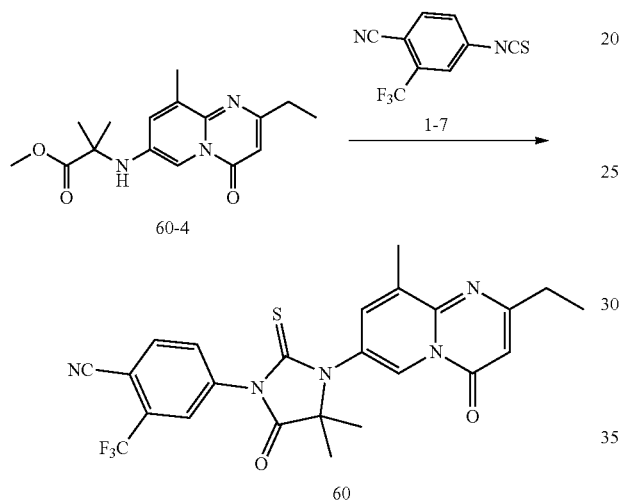

In a dry single-necked flask, Compound 60-4 (110 mg), Compound 1-7 (165 mg), DMF (0.2 mL), and methylbenzene (1 mL) were added, heated to 90° C. and stirred for 48 h under nitrogen protection. The reaction mixture was concentrated to dryness, and the resulting crude product was purified by preparative HPLC to obtain Compound 60. $^1$H NMR (400 MHz, CDCl$_3$) δ ppm 8.95 (d, J=2.0 Hz, 1H), 8.03 (d, J=8.4 Hz, 1H), 7.98 (s, 1H), 7.86 (br d, J=8.2 Hz, 1H), 7.48 (s, 1H), 6.44 (s, 1H), 2.79 (q, J=7.6 Hz, 2H), 2.64 (s, 3H), 1.69 (s, 6H), 1.37 (t, J=7.5 Hz, 3H). LCMS (ESI) m/z: 500 (M+1).

Example 60 Synthesis of Compound 61

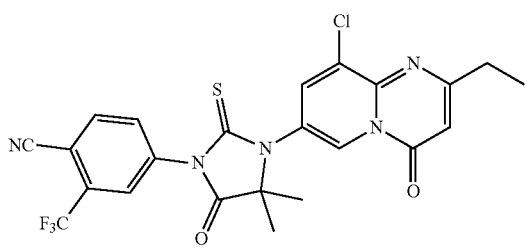

1) Synthesis of Compound 61-2

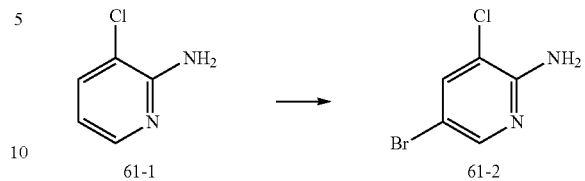

In a dry single-necked flask, Compound 61-1 (5.00 g) and acetonitrile (50 mL) were added, and the temperature was controlled at 0° C., and NBS (6.92 g) dissolved in acetonitrile (50 mL) was slowly added dropwise to the reaction flask and the temperature was controlled to no more than 10° C. After the completion of the dropwise addition, the resulting mixture was stirred at 20° C. for 20 h, and then was concentrated to dryness under reduced pressure to remove the solvent. A solid crude product was obtained, and 200 mL of a saturated sodium bicarbonate solution was added thereto. After ultrasonic processing for 1 h and then filtration, the filter cake was washed with 100 mL of water, to obtain Compound 61-2. $^1$H NMR (400 MHz, CDCl$_3$) δ ppm 8.06 (br s, 1H), 7.63 (d, J=2.0 Hz, 1H), 4.93 (br s, 2H). LCMS (ESI) m/z: 207 (M+1).

2) Synthesis of Compound 61-3

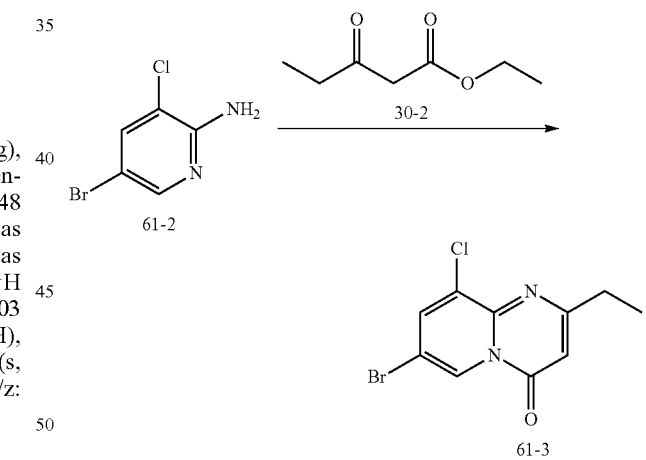

In a dry single-necked flask, Compound 61-2 (5.00 g), Compound 30-2 (4.52 g), and polyphosphoric acid (15 g) were added, and stirred at 110° C. for 16 h under nitrogen protection. 200 mL of water was added to the reaction mixture, and the resulting mixture was stirred until dissolution. 200 mL of ethyl acetate was added for extraction. After liquid separation, the organic phase was dried over anhydrous sodium sulfate, filtered, and concentrated to dryness under reduced pressure to remove the solvent. The obtained crude product was purified by a chromatographic column to obtain Compound 61-3. $^1$H NMR (400 MHz, CDCl$_3$) δ ppm 9.06 (d, J=2.0 Hz, 1H), 7.89 (d, J=2.0 Hz, 1H), 6.40 (s, 1H), 2.76 (q, J=7.6 Hz, 2H), 1.32 (t, J=7.5 Hz, 3H). LCMS (ESI) m/z: 288 (M+1).

3) Synthesis of Compound 61-4

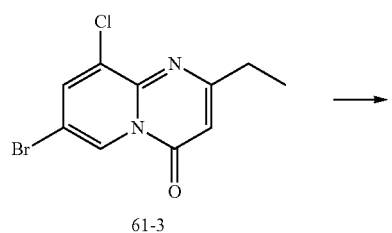

In a dry microwave tube, Compound 61-3 (500 mg), 2-aminoisobutyric acid (538 mg), 2-acetylcyclohexanone (49 mg), potassium carbonate (481 mg), DMF (4 mL), and water (1 mL) were added, and then cuprous chloride (34 mg) was added. After nitrogen purge for 5 min, the microwave tube was sealed, and the resulting mixture was microwaved and stirred at 110° C. for 1 h. The reaction mixture was concentrated under reduced pressure to obtain Compound 61-4. LCMS (ESI) m/z: 310 (M+1).

4) Synthesis of Compound 61-5

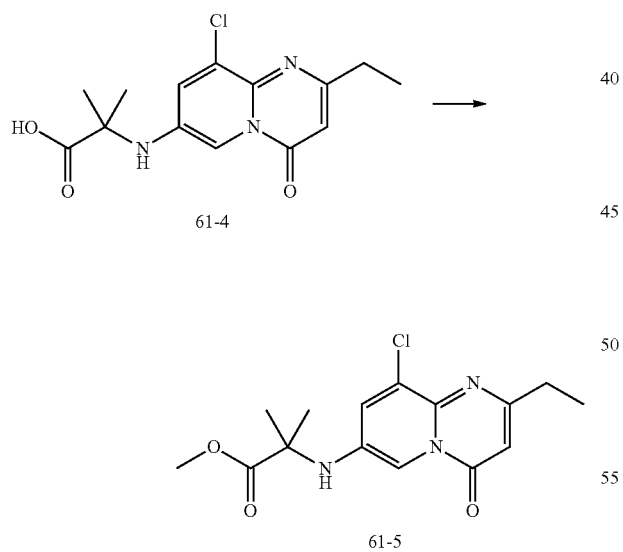

In a dry single-necked flask, Compound 61-4 (300 mg) and a solution of hydrochloric acid-methanol (4M, 8.76 mL) were added, heated to 90° C. and refluxed for 2 h under nitrogen protection. The reaction mixture was concentrated to dryness under reduced pressure. 50 mL of a saturated sodium bicarbonate solution and 50 mL of ethyl acetate were added to the residual solid product. After liquid separation, the organic phase was dried over anhydrous sodium sulfate, filtered, and concentrated to dryness to remove the solvent. The obtained crude product was purified by a chromatographic column to obtain Compound 61-5. $^1$H NMR (400 MHz, CDCl$_3$) δ ppm 8.21 (d, J=2.6 Hz, 1H), 7.48 (d, J=2.6 Hz, 1H), 6.30 (s, 1H), 4.41 (s, 1H), 3.77 (s, 3H), 2.73 (q, J=7.6 Hz, 2H), 1.61 (s, 6H), 1.29 (t, J=7.6 Hz, 3H). LCMS (ESI) m/z: 323.77 (M+1).

5) Synthesis of Compound 61

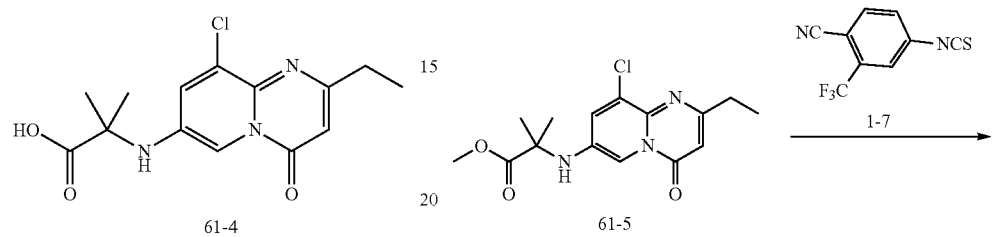

In a dry single-necked flask, Compound 61-5 (110 mg), Compound 1-7 (155 mg), DMF (0.2 mL), and methylbenzene (1 mL) were added, and stirred at 90° C. for 20 h under nitrogen protection. The resulting mixture was concentrated to dryness under reduced pressure, and the obtained crude product was purified by preparative HPLC to obtain Compound 61. $^1$H NMR (400 MHz, CDCl$_3$) δ ppm 8.94 (d, J=2.4 Hz, 1H), 8.00 (d, J=8.4 Hz, 1H), 7.94 (s, 1H), 7.82 (d, J=8.2 Hz, 1H), 7.78 (d, J=2.2 Hz, 1H), 6.46 (s, 1H), 2.81 (q, J=7.4 Hz, 2H), 1.68 (s, 6H), 1.36 (t, J=7.5 Hz, 3H). LCMS (ESI) m/z: 520 (M+1).

Example 61 Synthesis of Compound 62

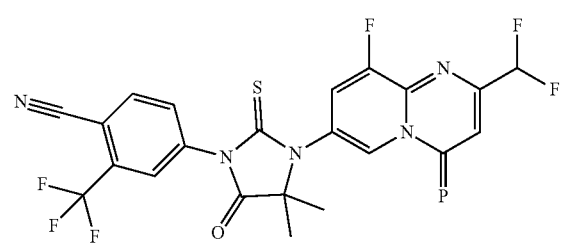

1) Synthesis of Compound 62-2

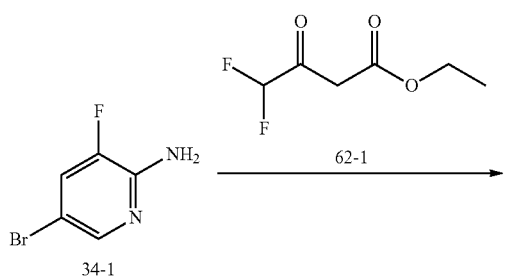

In a dry single-necked flask, Compound 34-1 (5.00 g) and Compound 62-1 (5.65 g) were added, and then polyphosphoric acid (15.00 g) was added. The resulting mixture was heated to 110° C. and stirred at this temperature for 16 h under nitrogen protection. The reaction mixture was slowly added to an iced aqueous solution of sodium bicarbonate (about 500 mL), adjusted to pH=7, and extracted with ethyl acetate (200 mL×4). The organic phases were combined, dried over anhydrous sodium sulfate, filtered, and concentrated. The resulting residue was purified by column chromatography to obtain Compound 62-2. $^1$H NMR (400 MHz, CDCl$_3$) δ ppm 9.04 (t, J=1.57 Hz, 1H), 7.67 (dd, J=7.78, 2.01 Hz, 1H), 6.84 (s, 1H), 6.37-6.70 (m, 1H).

2) Synthesis of Compound 62-3

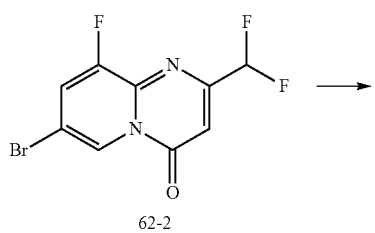

In a dry single-necked flask, Compound 62-2 (1.00 g), tert-butyl carbamate (1.20 g), cesium carbonate (2.78 g), 4,5-bis(diphenylphosphino)-9,9-dimethylxanthene (197 mg), and methylbenzene (20 mL) were added. Under nitrogen protection, bis(dibenzylideneacetone)palladium (196 mg) was added, and the resulting mixture was refluxed at 120° C. for 2 h. The reaction mixture was diluted with water (30 mL), and extracted with ethyl acetate (30 mL×3). The organic phases were combined, dried over anhydrous sodium sulfate, filtered, and concentrated under reduced pressure. The residue obtained from the concentration was purified by column chromatography to obtain Compound 62-3. $^1$H NMR (400 MHz, CDCl$_3$) δ ppm 9.10 (s, 1H), 8.35 (br s, 1H), 7.88 (br s, 1H), 6.77 (s, 1H), 6.40-6.70 (m, 1H), 1.57 (s, 9H).

3) Synthesis of Compound 62-4

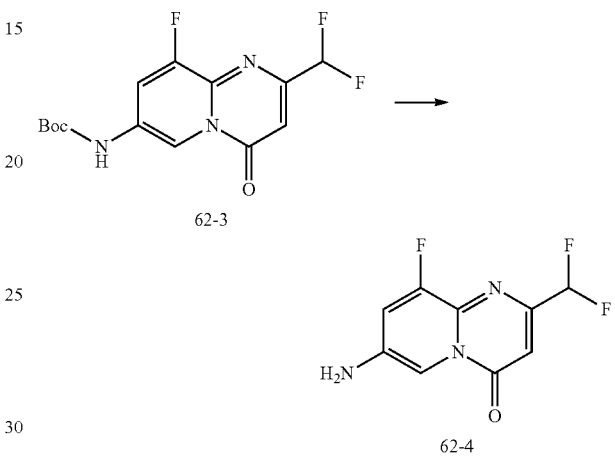

In a dry single-necked flask, Compound 62-3 (1.50 g) and a solution of hydrochloric acid/methanol (4M, 576.92 mL) were added, and stirred at 25° C. for 16 h. The reaction mixture was concentrated to dryness under reduced pressure. The resulting residue was dissolved in 50 mL of water, adjusted to pH=8-9 by adding a saturated sodium bicarbonate solution, extracted with ethyl acetate (50 mL×3), washed with saturated brine (50 mL), dried over anhydrous sodium sulfate, filtered, and concentrated under reduced pressure. The concentrate was purified by column chromatography to obtain Compound 62-4. LCMS (ESI) m/z: 230 (M+1).

4) Synthesis of Compound 62-5

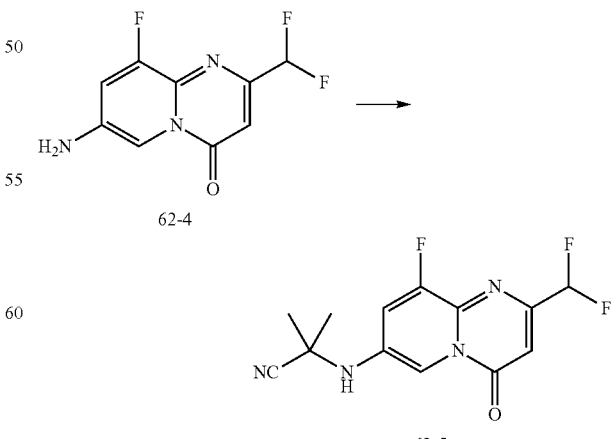

In a dry reaction flask, Compound 62-4 (450 mg), zinc chloride (80 mg), sodium sulfate (1.12 g), acetone (684 mg), trimethylsilyl cyanide (584 mg), and tetrahydrofuran (4.5 mL) were added, and reacted at 30° C. for 4 h under nitrogen protection. The reaction mixture was directly spin-dried, and purified by column chromatography to obtain Compound 62-5. $^1$H NMR (400 MHz, CDCl$_3$) δ ppm 8.55 (s, 1H), 7.38 (dd, J=9.79, 2.51 Hz, 1H), 6.78 (s, 1H), 6.40-6.69 (m, 1H), 2.02-2.21 (m, 1H), 1.82 (s, 6H).

5) Synthesis of Compound 62

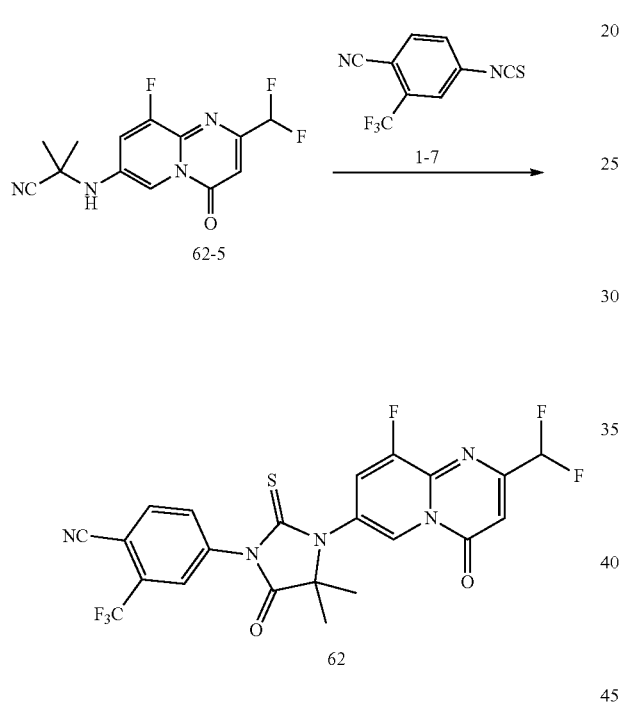

In a dry reaction flask, Compound 62-5 (200 mg), Compound 1-7 (616 mg), methylbenzene (2 mL), and DMF (0.5 mL) were added. Under nitrogen protection, sodium hydride (40 mg, 60% purity) was added, and the resulting mixture reacted at 25° C. for 0.5 h. The reaction mixture was directly spin-dried, and purified by preparative HPLC. After the completion of separation, the product was left to stand still in a separation system (water (0.05% HCl)-acetonitrile) for 16 h, then adjusted to pH=8 with a saturated aqueous solution of sodium bicarbonate, and extracted with dichloromethane (10 mL×3). The combined organic phase was dried over anhydrous sodium sulfate, filtered, and concentrated. The resulting solid was dissolved in water (40 mL) and acetonitrile (8 mL), and the resulting solution was freeze-dried to obtain Compound 62. $^1$H NMR (400 MHz, CDCl$_3$) δ ppm 8.89 (s, 1H), 8.03 (d, J=8.38 Hz, 1H), 7.95 (s, 1H), 7.81-7.85 (m, 11H), 7.56 (dd, J=8.49, 2.09 Hz, 1H), 6.90 (s, 1H), 6.43-6.72 (m, 1H), 1.71 (s, 6H).

Example 62 Synthesis of Compound 63

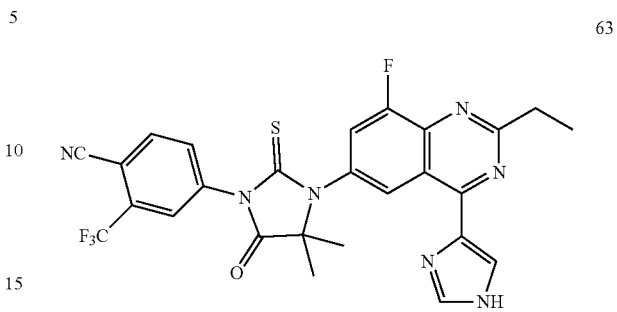

1) Synthesis of Compound 63-3

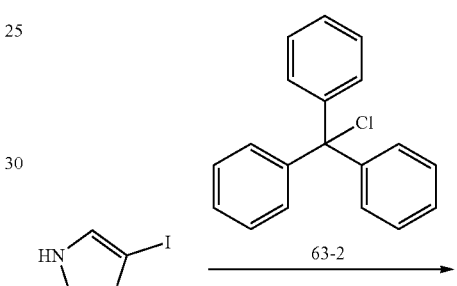

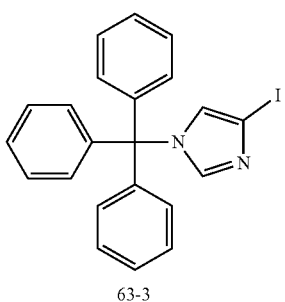

In a dry single-necked flask, Compound 63-1 (1.00 g), DMF (10 mL), and triethylamine (620 mg) were added. Under nitrogen protection, Compound 63-2 (1.44 g) was added, and the resulting mixture reacted at 20° C. for 16 h. The reaction mixture was diluted with 10 mL of ice water, and then filtered. The filter cake was collected, and slurried with 3 mL of methyl tert-butyl ether for purification. The solid was collected to obtain Compound 63-3. $^1$H NMR (400 MHz, CDCl$_3$) δ ppm 7.34-7.38 (m, 9H), 7.33 (d, J=1.38 Hz, 1H), 7.10-7.15 (m, 6H), 6.92 (d, J=1.38 Hz, 1H).

2) Synthesis of Compound 63

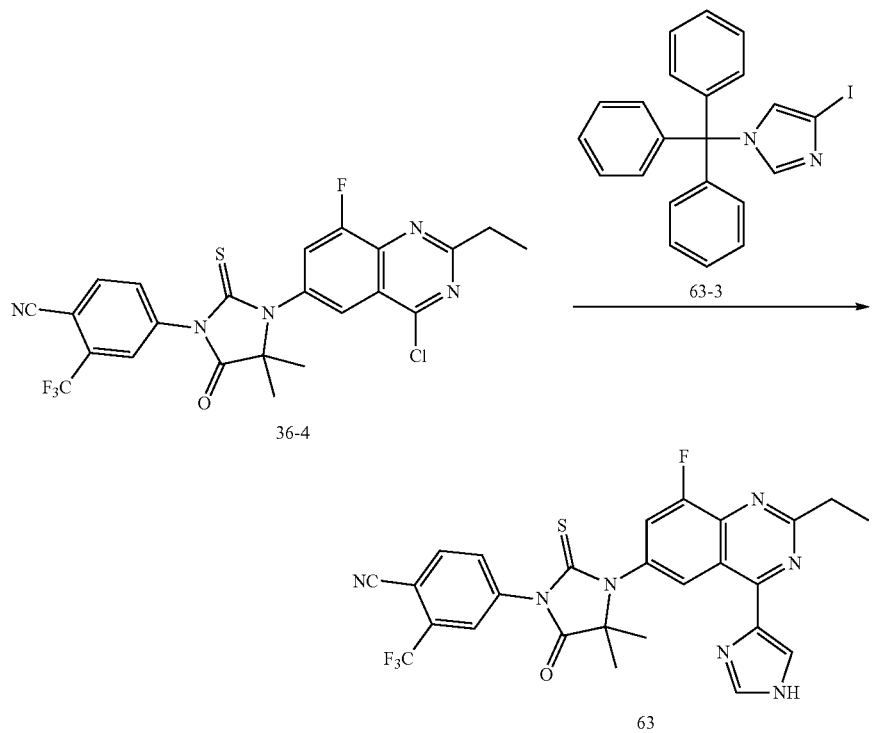

In a dry reaction flask, Compound 63-3 (167 mg) and tetrahydrofuran (1.2 mL) were added. Under nitrogen protection, a solution of ethyl magnesium bromide in tetrahydrofuran (3M, 147 μL) was quickly added, and the resulting mixture reacted at room temperature (15° C.) for 0.17 h. A solution of zinc chloride in diethyl ether (1M, 766 μL) was quickly added to the reaction system, and the resulting mixture further reacted at 15° C. for 2 h. Then, under nitrogen protection, the reaction system was transferred to a dry reaction flask filled with Compound 36-4 (0.10 g) and tetrakis(triphenylphosphine) palladium (22 mg), heated to 95° C., and refluxed for 12 h. The reaction mixture was concentrated, and the obtained crude product was purified successively by a preparative TLC plate and preparative HPLC method to obtain Compound 63. $^1$H NMR (400 MHz, CDCl$_3$) δ ppm 8.29 (s, 1H), 8.02 (d, J=8.16 Hz, 1H), 7.97 (s, 1H), 7.94 (d, J=1.54 Hz, 1H), 7.85 (dd, J=8.27, 1.87 Hz, 1H), 7.69 (t, J=1.43 Hz, 1H), 7.61 (dd, J=9.59, 2.09 Hz, 1H), 7.36 (s, 1H), 3.24 (q, J=7.57 Hz, 2H), 1.68 (s, 6H), 1.51 (t, J=7.61 Hz, 3H).

Example 63 Synthesis of Compound 64

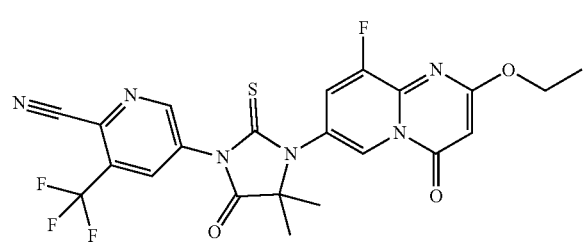

1) Synthesis of Compound 64

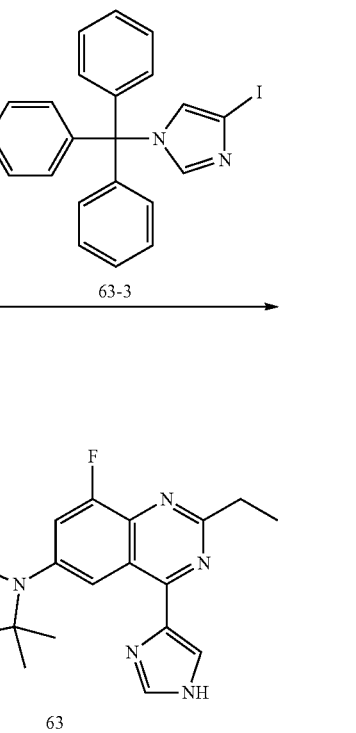

In a dry single-necked flask, Compound 55-4 (5 mg), Compound 23-7 (7 mg), DMF (0.1 mL), and methylbenzene (0.5 mL) were added, heated to 90° C. and stirred for 48 h under nitrogen protection. The reaction mixture was concentrated to dryness to remove the solvent, and the obtained crude product was purified by preparative HPLC method to obtain Compound 64. $^1$H NMR (400 MHz, CDCl$_3$) δ ppm 9.08 (s, 1H), 8.87 (s, 1H), 8.34 (s, 1H), 7.44 (br d, J=8.4 Hz, 1H), 5.89 (s, 1H), 4.48 (q, J=6.9 Hz, 2H), 1.71 (s, 6H), 1.46 (t, J=6.9 Hz, 3H); LCMS (ESI) m/z: 521 (M+1).

Example 64 Synthesis of Compound 65

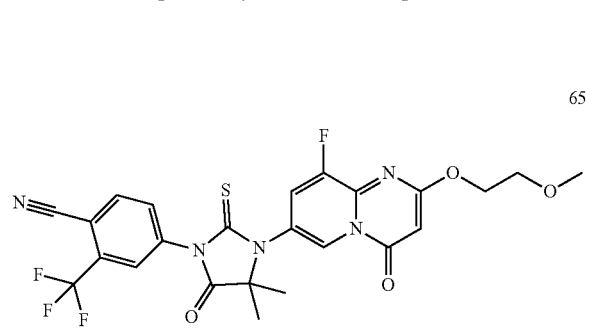 [SMILES: COCCOc1cc(=O)n2cc(N3C(=S)N(c4ccc(C#N)c(C(F)(F)F)c4)C(=O)C3(C)C)cc(F)c2n1]

1) Synthesis of Compound 65-1

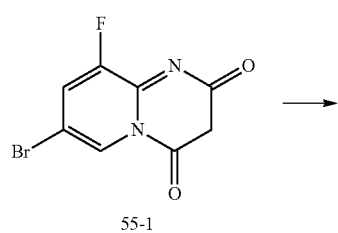

In a dry single-necked flask, Compound 55-1 (500 mg), potassium carbonate (533 mg), 2-bromoethyl methyl ether (606 mg), and NMP (5 mL) were added, heated to 70° C. and stirred for 72 h under nitrogen protection. 100 mL of saturated brine and 100 mL of ethyl acetate were successively added to the reaction mixture. After liquid separation, the organic phase was collected, dried over anhydrous sodium sulfate, and filtered. The filtrate was concentrated under reduced pressure. The obtained crude product was purified by a chromatographic column, slurried with 10 mL of methyl tert-butyl ether, and filtered to obtain Compound 65-1. ¹H NMR (400 MHz, CDCl₃) δ ppm 8.99 (d, J=1.3 Hz, 1H), 7.57 (dd, J=1.8, 7.7 Hz, 1H), 5.90 (s, 1H), 4.56 (dd, J=4.0, 5.3 Hz, 2H), 3.74 (dd, J=4.0, 5.3 Hz, 2H), 3.43 (d, J=1.1 Hz, 3H). LCMS (ESI) m/z: 317 (M+1).

2) Synthesis of Compound 65-2

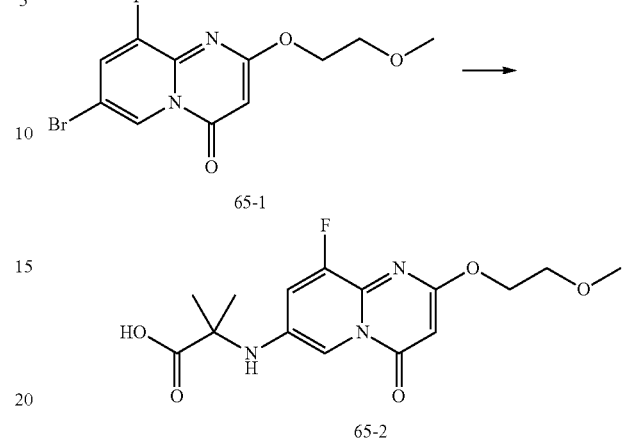

In a dry microwave tube, Compound 65-1 (230 mg), 2-aminoisobutyric acid (224 mg), 2-acetylcyclohexanone (20 mg), potassium carbonate (200 mg), DMF (2 mL), and water (0.4 mL) were added, and then cuprous chloride (14 mg) was added. After nitrogen purge for 5 min, the microwave tube was sealed, and the resulting mixture was microwaved and stirred at 90° C. for 4 h. The reaction mixture was concentrated, and the obtained crude product was purified by a chromatographic column to obtain Compound 65-2. LCMS (ESI) m/z: 340 (M+1).

3) Synthesis of Compound 65-3

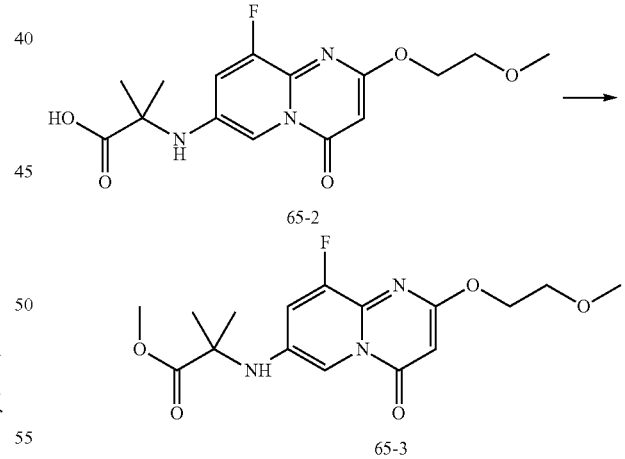

In a dry single-necked flask, Compound 65-2 (320 mg), dichloromethane (6 mL), and methanol (1 mL) were added, and then TMSCHN₂ (2M, 1.89 mL) was added. Under nitrogen protection, the resulting mixture was stirred at 18° C. for 1 h. TMSCHN₂ (2M, 1.89 mL) was supplemented, and the reaction was continued for additional 2 h. The reaction mixture was concentrated to dryness under reduced pressure to remove the solvent, and the obtained crude product was purified by preparative HPLC to obtain Compound 65-3. LCMS (ESI) m/z: 354 (M+1).

4) Synthesis of Compound 65

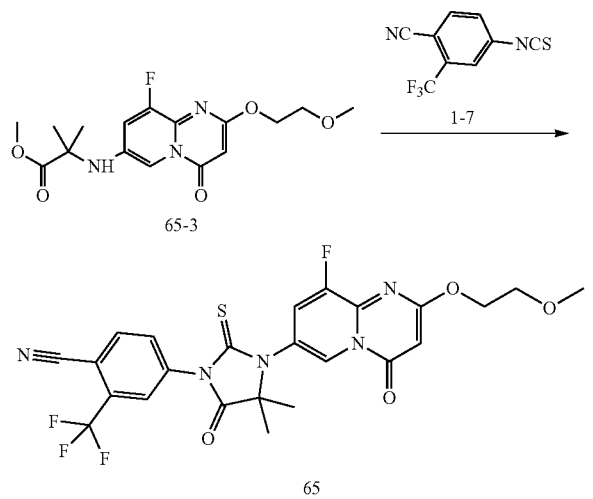

In a dry single-necked flask, Compound 65-3 (30 mg), Compound 1-7 (39 mg), DMF (0.1 mL), and methylbenzene (0.5 mL) were added, kept at 90° C. and stirred for 48 h under nitrogen protection. The reaction mixture was concentrated to dryness under reduced pressure. The resulting crude product was purified by preparative HPLC method to obtain Compound 65. ¹H NMR (400 MHz, CDCl₃) δ ppm 8.88 (s, 1H), 8.01 (d, J=8.4 Hz, 1H), 7.94 (s, 1H), 7.82 (dd, J=2.0, 8.4 Hz, 1H), 7.47 (dd, J=2.1, 8.5 Hz, 1H), 5.96 (s, 1H), 4.64-4.60 (m, 2H), 3.79-3.74 (m, 2H), 3.45 (s, 3H), 1.68 (s, 6H). LCMS (ESI) m/z: 550 (M+1).

Example 65 Synthesis of Compound 66

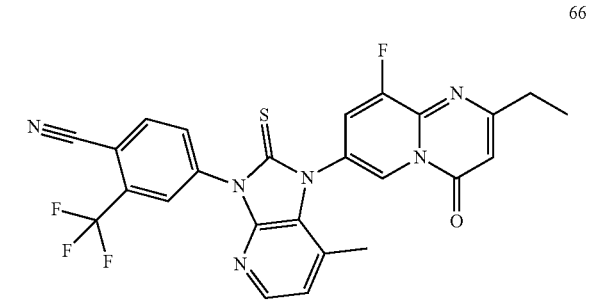 [SMILES: CCc1cc(=O)n2cc(-n3c(=S)n(-c4ccc(C#N)c(C(F)(F)F)c4)c4nccc(C)c43)cc(F)c2n1]

1) Synthesis of Compound 66-1

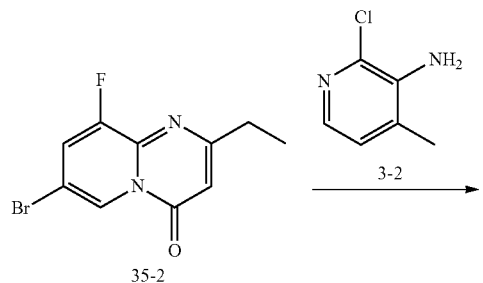

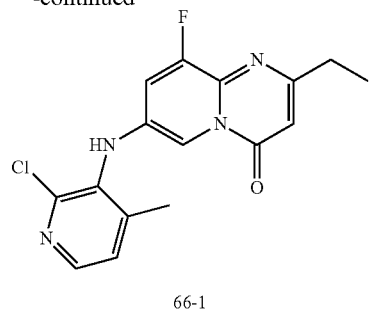

In a reaction flask, Compound 35-2 (500 mg), Compound 3-2 (789 mg), 4,5-bis(diphenylphosphino)-9,9-dimethylxanthene (107 mg), cesium carbonate (1.50 g), and methylbenzene (5 mL) were added. Under nitrogen protection, bis(dibenzylideneacetone)palladium (106 mg) was added, and the resulting mixture reacted at 90° C. for 16 h. The reaction mixture was concentrated under reduced pressure, and the resulting crude product was separated by column chromatography to obtain Compound 66-1. LCMS (ESI) m/z: 333 (M+1).

2) Synthesis of Compound 66-2

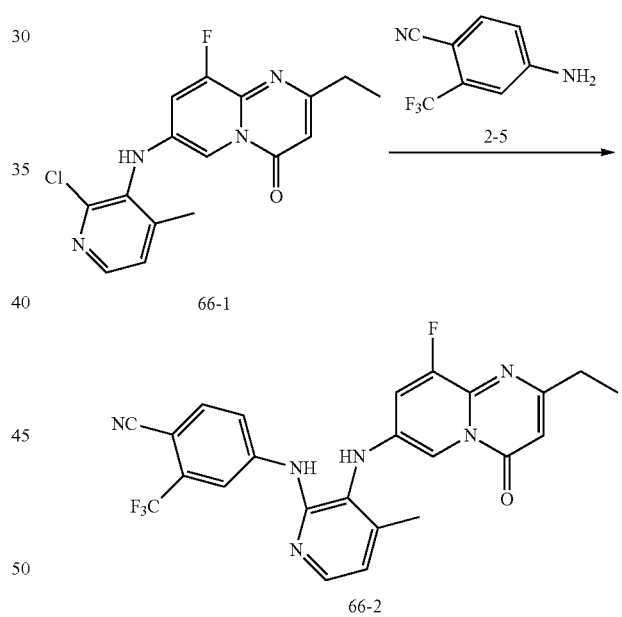

In a microwave tube, Compound 66-1 (200 mg), Compound 2-5 (123 mg), cesium carbonate (392 mg), 4,5-bis(diphenylphosphino)-9,9-dimethylxanthene (35 mg), and methylbenzene (2 mL) were added. Under nitrogen protection, bis(dibenzylideneacetone)palladium (34.56 mg) was added, and the resulting mixture was kept at 130° C. for microwave reaction for 2 h. The reaction mixture was concentrated under reduced pressure to obtain a crude product, which was purified by preparative HPLC to obtain Compound 66-2. ¹H NMR (400 MHz, CDCl₃) δ ppm 8.21-8.26 (m, 2H), 8.07-8.12 (m, 2H), 7.85 (s, 1H), 7.70 (d, J=8.38 Hz, 1H), 7.08 (br d, J=7.50 Hz, 1H), 6.90 (d, J=5.29 Hz, 1H), 6.33 (s, 1H), 5.63 (br s, 1H), 2.74 (q, J=7.64 Hz, 2H), 2.25 (s, 3H), 1.22-1.24 (t, J=7.61 Hz, 3H).

3) Synthesis of Compound 66

1) Synthesis of Compound 67

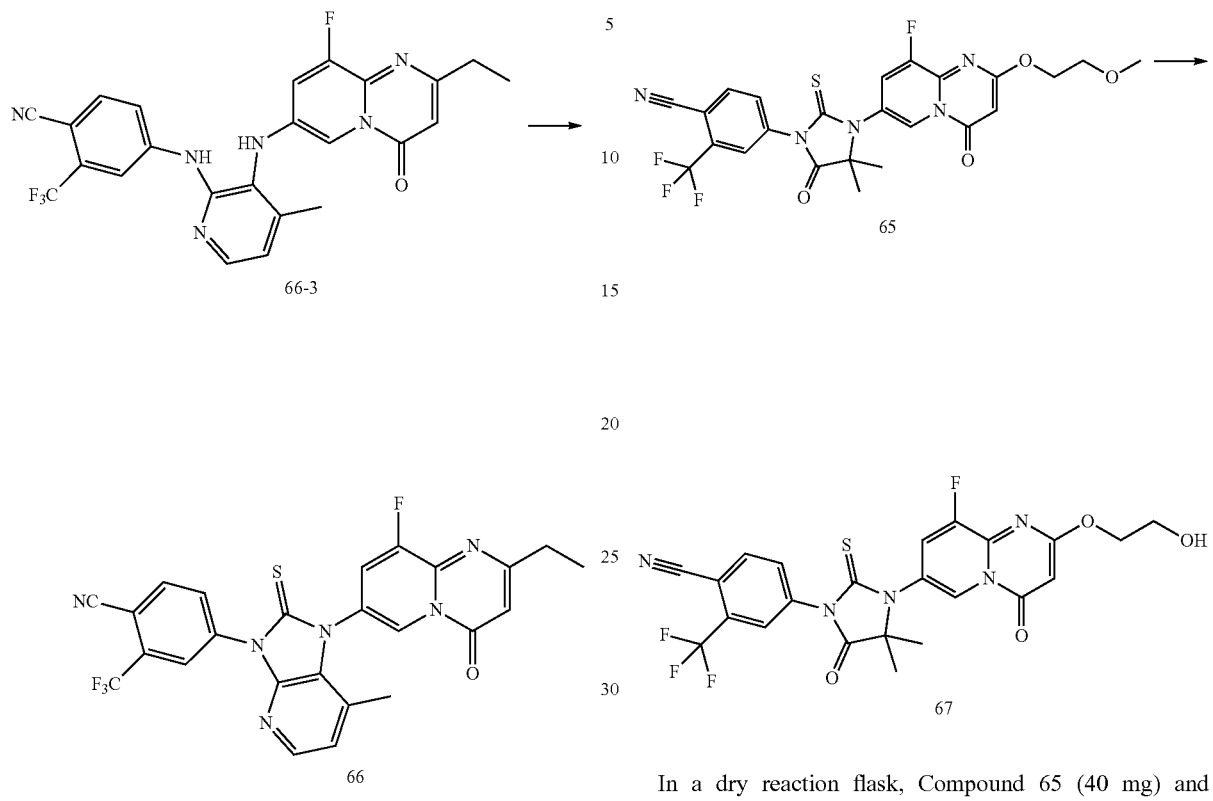

At 0° C., in a reaction flask, Compound 66-3 (40 mg) and tetrahydrofuran (0.4 mL) were added, and fully stirred, and then NaH (11 mg, 60% purity) was added. After reaction for 0.5 h, thiophosgene (19 mg) was added, and the reaction mixture was stirred at 25° C. for 15.5 h. The reaction mixture was concentrated under reduced pressure to obtain a crude product, which was purified successively by a preparative TLC plate and preparative HPLC to obtain Compound 66. $^1$H NMR (400 MHz, CDCl$_3$) δ ppm 9.01 (s, 1H), 8.28 (s, 1H), 8.17 (d, J=5.07 Hz, 1H), 8.15 (d, J=1.98 Hz, 1H), 8.07-8.12 (m, 1H), 7.63 (dd, J=8.49, 2.32 Hz, 1H), 7.07 (d, J=5.29 Hz, 1H), 6.52 (s, 1H), 2.85 (q, J=7.50 Hz, 2H), 2.15 (s, 3H), 1.39 (t, J=7.50 Hz, 3H). LCMS (ESI) m/z: 525 (M+1).

Example 66 Synthesis of Compound 67

In a dry reaction flask, Compound 65 (40 mg) and dichloromethane (0.5 mL) were added. Under nitrogen protection, boron tribromide (73 mg) was added at 0° C., and the resulting mixture was warmed to 15° C. and reacted for 2 h. The reaction was quenched with a saturated sodium bicarbonate solution (15 mL). The resulting mixture was extracted with dichloromethane (10 mL×3), dried over anhydrous sodium sulfate, and filtered. The filtrate was concentrated. The residue obtained from the concentration was purified by preparative HPLC to obtain Compound 67. $^1$H NMR (400 MHz, CDCl$_3$) δ ppm 8.89 (s, 1H), 7.99-8.05 (m, 1H), 7.95 (br s, 1H), 7.83 (br d, J=8.16 Hz, 1H), 7.51 (br d, J=7.72 Hz, 1H), 5.96 (d, J=3.09 Hz, 1H), 4.59 (br d, J=4.41 Hz, 2H), 4.01 (br s, 2H), 2.53 (br s, 1H), 1.69 (d, J=2.87 Hz, 6H). LCMS (ESI) m/z: 536 (M+1).

Example 67 Synthesis of Compound 68

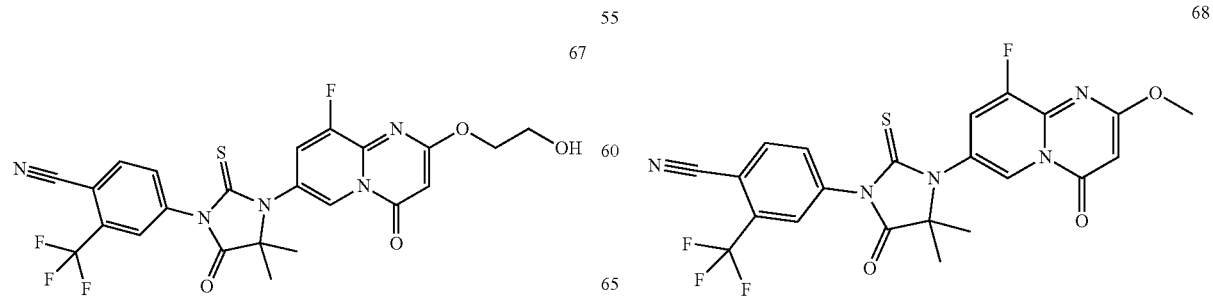

1) Synthesis of Compound 68-1

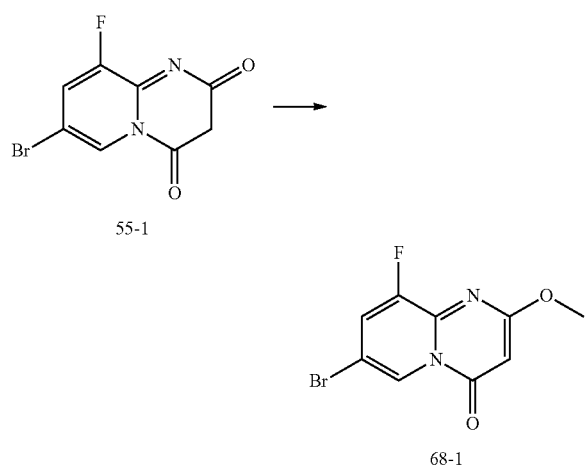

In a dry single-necked flask, Compound 55-1 (1.00 g), N-methylpyrrolidone (10 mL), and potassium carbonate (1.07 g) were added. Under nitrogen protection, iodomethane (1.24 g) was added, and the resulting mixture reacted at 40° C. for 16 h. The reaction mixture was diluted with water (200 mL), and extracted with ethyl acetate (150 mL×2). The organic phases were combined, dried over anhydrous sodium sulfate, and filtered. The filtrate was concentrated to dryness to obtain Compound 68-1. $^1$H NMR (400 MHz, CDCl$_3$) δ ppm 9.01 (s, 1H), 7.60 (dd, J=7.84, 2.07 Hz, 1H), 5.87 (s, 1H), 4.04 (s, 3H).

2) Synthesis of Compound 68-2

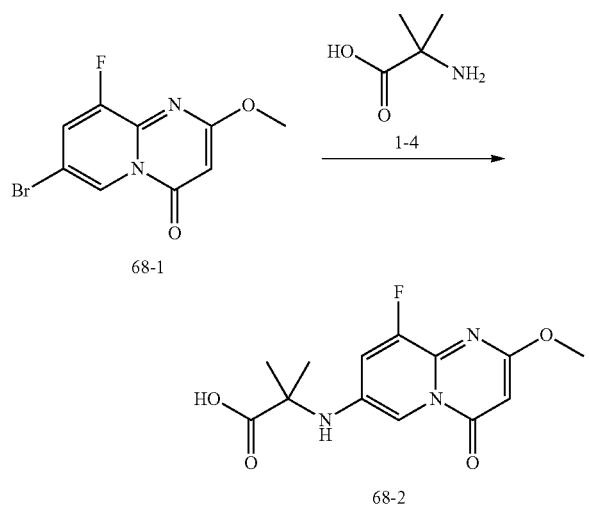

In a microwave tube, Compound 68-1 (600 mg), Compound 1-4 (340 mg), DMF (12 mL), water (2.4 mL), potassium carbonate (607 mg), and 2-acetylcyclohexanone (31 mg) were added. Under nitrogen purge, cuprous chloride (22 mg) was added, and the resulting mixture was kept at 110° C. for microwave reaction for 3 h. The reaction mixture was directly concentrated, and the residue obtained from the concentration was purified by column chromatography to obtain Compound 68-2. $^1$H NMR (400 MHz, CD$_3$OD) δ ppm 7.98 (br s, 1H), 7.40-7.49 (m, 1H), 5.74 (s, 1H), 3.98 (s, 3H), 1.60 (s, 6H), 1.58-1.62 (m, 1H).

3) Synthesis of Compound 68-3

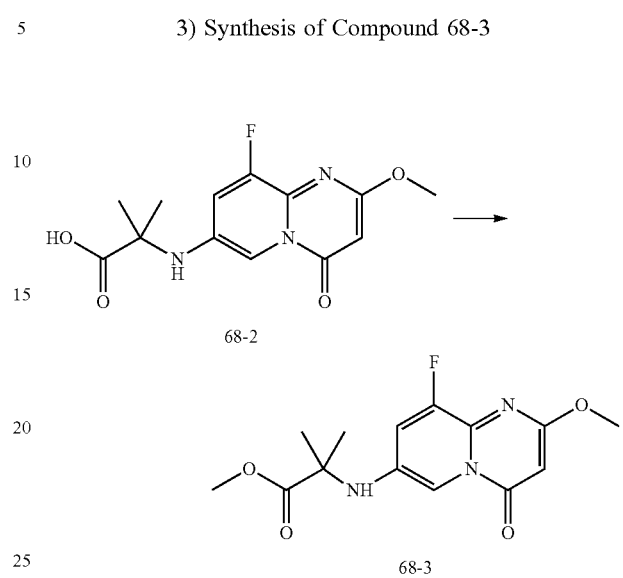

In a dry single-necked flask, Compound 68-2 (530 mg), dichloromethane (10 mL), and methanol (1.7 mL) were added. Under nitrogen protection, a solution of trimethylsilyldiazomethane in n-hexane (2M, 3.59 mL) was added, and the resulting mixture reacted at 15° C. for 16 h. The reaction mixture was concentrated, and the residue obtained from the concentration was purified by column chromatography to obtain Compound 68-3. $^1$H NMR (400 MHz, CDCl$_3$) δ ppm 8.16 (d, J=1.38 Hz, 1H), 7.14 (dd, J=10.16, 2.51 Hz, 1H), 5.80 (s, 1H), 4.32 (br s, 1H), 3.99 (s, 3H), 3.80 (s, 3H), 1.63 (s, 6H).

4) Synthesis of Compound 68

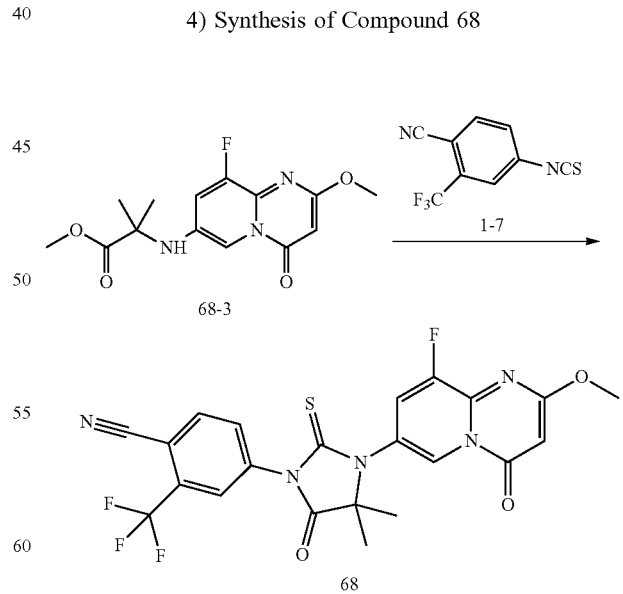

In a dry reaction flask, Compound 68-3 (120 mg), methylbenzene (2.5 mL), and DMF (0.5 mL) were added. Under nitrogen protection, Compound 1-7 (177 mg) was added, and the resulting mixture reacted at 90° C. for 16 h. The reaction mixture was purified by preparative HPLC to obtain Compound 68. $^1$H NMR (400 MHz, CDCl$_3$) δ ppm 8.89 (s, 1H), 8.02 (d, J=8.38 Hz, 1H), 7.95 (s, 1H), 7.83 (d, J=7.72 Hz, 1H), 7.48 (br d, J=8.16 Hz, 1H), 5.92 (s, 1H), 4.08 (s, 3H), 1.69 (s, 6H). LCMS (ESI) m/z: 506 (M+1).

Example 68 Synthesis of Compound 69

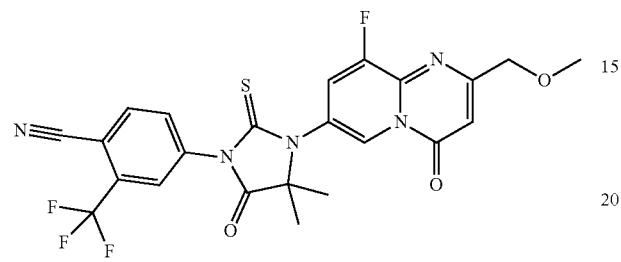

69

1) Synthesis of Compound 69-2

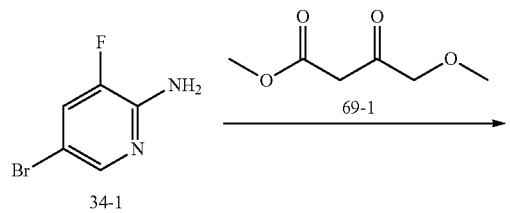

In a dry single-necked flask, Compound 34-1 (3.00 g) and polyphosphoric acid (20 mL) were added, and then Compound 69-1 (4.59 g, 31.41 mmol) was added. Under nitrogen protection, the resulting mixture was heated to 110° C. and stirred for 16 h. 200 mL of water was added to the reaction mixture, and then 200 mL of ethyl acetate was added. The resulting mixture was filtered to remove insolubles. The filtrate was left to stand still for stratification. The organic phase was collected, dried over anhydrous sodium sulfate, and filtered. The filtrate was concentrated to dryness under reduced pressure to remove the solvent. The resulting crude product was purified by a chromatographic column to obtain Compound 69-2. $^1$H NMR (400 MHz, CDCl$_3$) δ ppm 9.01 (t, J=1.6 Hz, 1H), 7.57 (dd, J=2.0, 8.0 Hz, 1H), 6.74 (s, 1H), 4.53 (s, 2H), 3.56-3.53 (m, 3H). LCMS (ESI) m/z: 287 (M+1).

2) Synthesis of Compound 69-3

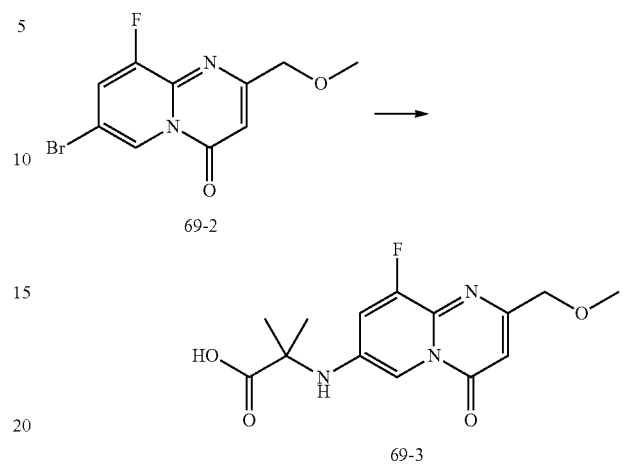

In a dry single-necked flask, Compound 69-2 (200 mg), 2-aminoisobutyric acid (216 mg), potassium carbonate (193 mg), DMF (4 mL), water (1 mL), and 2-acetylcyclohexanone (19 mg) were added, and then cuprous chloride (14 mg) was added. After nitrogen purge for 5 min, the single-necked flask was sealed, and then the resulting mixture was microwaved and stirred at 90° C. for 3 h. The reaction mixture was concentrated to dryness under reduced pressure to remove the solvent, and the resulting crude product was purified by a chromatographic column to obtain Compound 69-3. LCMS (ESI) m/z: 310 (M+1).

3) Synthesis of Compound 69-4

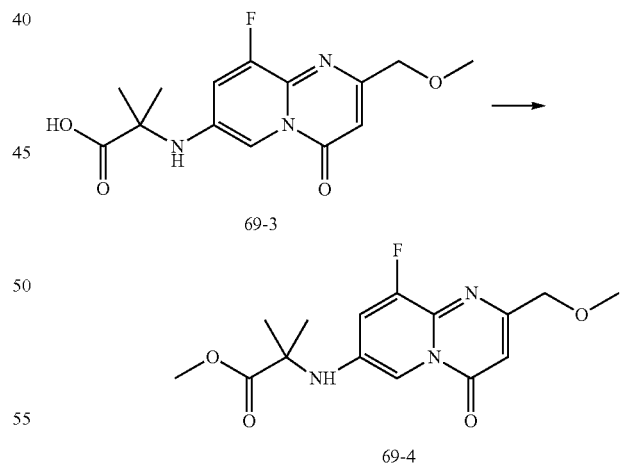

In a dry single-necked flask, Compound 69-3 (150 mg), dichloromethane (3 mL), and methanol (0.45 mL) were added, and then a solution of TMSCHN$_2$ in n-hexane (2M, 1.94 mL) was added. Under nitrogen protection, the resulting mixture was stirred at 18° C. for 2 h. The reaction mixture was concentrated to dryness under reduced pressure to remove the solvent, and the resulting crude product was purified by a chromatographic column to obtain Compound 69-4. LCMS (ESI) m/z: 324 (M+1).

4) Synthesis of Compound 69

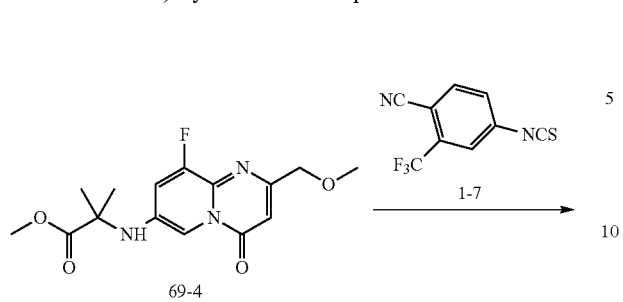

In a dry single-necked flask, Compound 69-4 (130 mg), DMF (0.2 mL), and methylbenzene (1.5 mL) were added, and then Compound 1-7 (276 mg) was added. Under nitrogen protection, the resulting mixture was heated to 90° C., and stirred for 16 h. The reaction mixture was concentrated to dryness under reduced pressure. The resulting crude product was purified by preparative HPLC to obtain Compound 69. ¹H NMR (400 MHz, CDCl₃) δ ppm 8.87 (s, 1H), 8.04 (d, J=8.3 Hz, 1H), 7.97 (s, 1H), 7.85 (dd, J=1.9, 8.3 Hz, 1H), 7.45 (dd, J=2.2, 8.7 Hz, 1H), 6.81 (s, 1H), 4.58 (s, 2H), 3.57 (s, 3H), 1.72 (s, 6H). LCMS (ESI) m/z: 520 (M+1).

Example 69 Synthesis of Compound 70

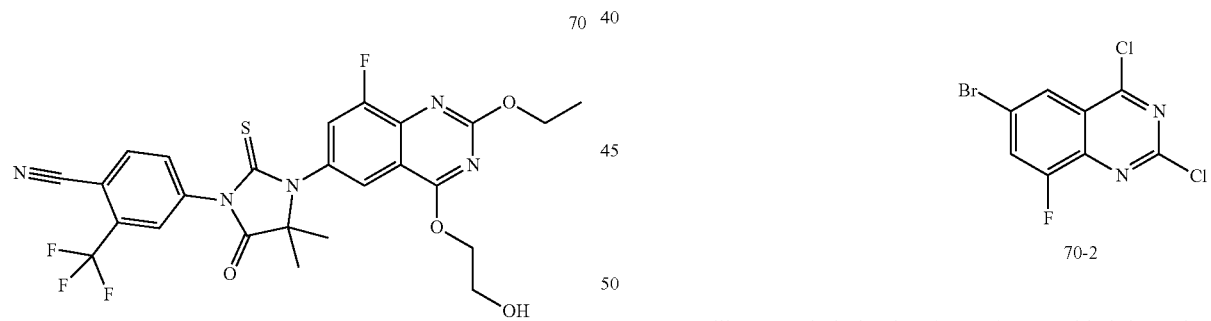

1) Synthesis of Compound 70-1

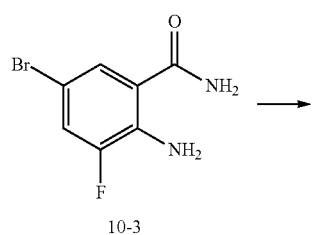

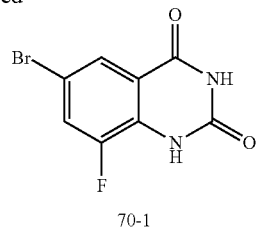

1,1'-Carbonyldiimidazole (1.04 g) was added to a solution of Compound 10-3 (1.00 g) in tetrahydrofuran (10 mL). The resulting mixture was stirred at 70° C. for 16 h. The reaction mixture was filtered, and the filter cake was dried under reduced pressure to obtain Compound 70-1. ¹H NMR (400 MHz, DMSO-d6) δ ppm 11.59 (br s, 2H), 7.91 (dd, J=2.0, 10.0 Hz, 1H), 7.80 (s, 1H).

2) Synthesis of Compound 70-2

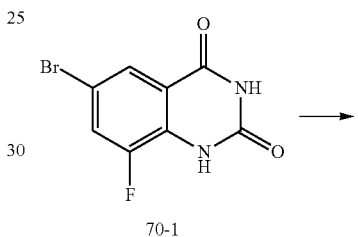

N,N-diisopropylethylamine (7.18 g) was added dropwise to a solution of Compound 70-1 (9.60 g) in phosphorus oxychloride (50 mL). The resulting mixture was stirred at 110° C. for 2 h. The reaction mixture was concentrated under reduced pressure, diluted with heated dichloromethane (200 mL), and then slowly poured into ice water (150 mL). After liquid separation, the aqueous layer was extracted with dichloromethane (100 mL×2), and the organic phases were combined, successively washed with a saturated aqueous solution of sodium bicarbonate (200 mL) and saturated brine (200 mL), dried over anhydrous sodium sulfate, filtered, and concentrated. The residue obtained from the concentration was purified by a silica gel column to obtain Compound 70-2. ¹H NMR (400 MHz, CDCl₃) δ ppm 8.17 (t, J=1.6 Hz, 1H), 7.76 (dd, J=1.9, 8.7 Hz, 1H); LCMS (ESI) m/z: 297 (M+1).

3) Synthesis of Compound 70-3

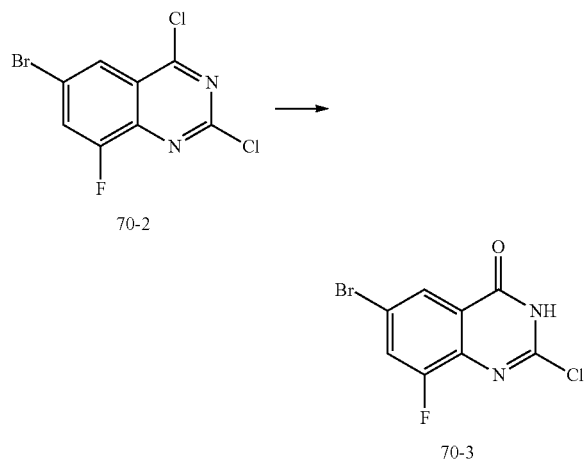

An aqueous solution of sodium hydroxide (1M, 40 mL) was added to a solution of Compound 70-2 (4.00 g) in tetrahydrofuran (50 mL), and the resulting mixture was further stirred at 10° C. for 3 h. The reaction mixture was poured into an aqueous solution of hydrochloric acid (1N) (pH about 7), and extracted with ethyl acetate (100 mL×3). The organic phase was washed with saturated brine (150 mL), dried over anhydrous sodium sulfate, filtered, and concentrated to obtain Compound 70-3. LCMS (ESI) m/z: 279 (M+1).

4) Synthesis of Compound 70-4

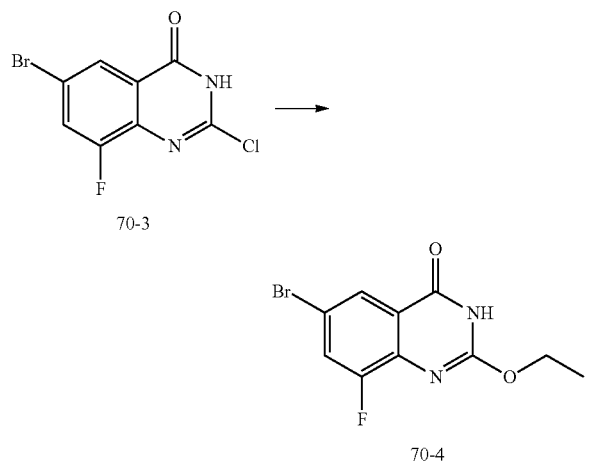

In a microwave tube, sodium ethoxide (660 mg) was added to a mixed solution of Compound 70-3 (900 mg) and ethanol (12 mL). The resulting mixture was kept at 110° C. for microwave reaction for 1 h. The reaction mixture was concentrated under reduced pressure. The residue obtained from the concentration was dissolved in water (30 mL), and extracted with ethyl acetate (30 mL×3). Then, the aqueous phase was extracted with dichloromethane/methanol (v/v=10/1, 30 mL×3). The organic phases were combined, dried over anhydrous sodium sulfate, filtered, and concentrated to obtain Compound 70-4. $^1$H NMR (400 MHz, DMSO-d6) δ ppm 7.84 (s, 1H), 7.69 (dd, J=2.0, 10.3 Hz, 1H), 4.35 (q, J=7.0 Hz, 2H), 1.30 (t, J=7.0 Hz, 3H).

5) Synthesis of Compound 70-5

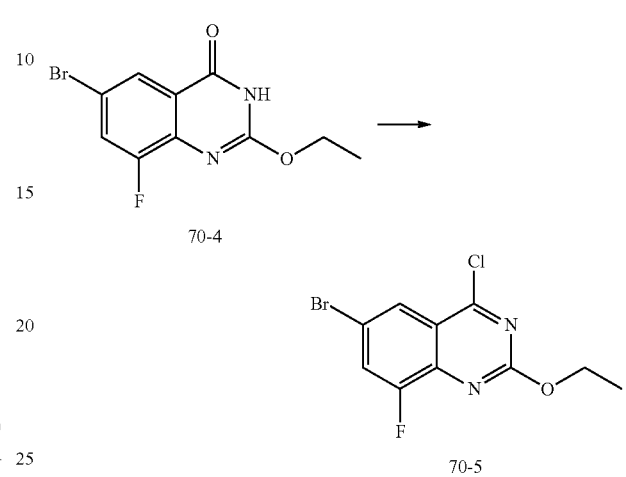

N,N-diisopropylethylamine (742 mg) was added dropwise to a solution of Compound 70-4 (1.10 g) in phosphorus oxychloride (8 mL), and the resulting mixture was stirred at 110° C. for 3 h. The reaction mixture was concentrated under reduced pressure. The residue obtained from the concentration was diluted with dichloromethane (150 mL), and poured into ice water. After liquid separation, the organic phase was successively washed with a saturated aqueous solution of sodium bicarbonate (150 mL) and saturated brine (150 mL), dried over anhydrous sodium sulfate, and filtered. The filtrate was concentrated to obtain Compound 70-5. LCMS (ESI) m/z: 307 (M+3).

6) Synthesis of Compound 70-6

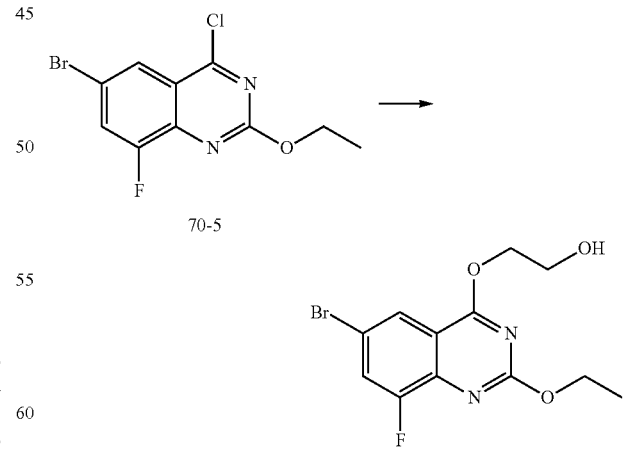

Sodium hydride (190 mg, 60% purity) was added to a solution of Compound 70-5 (1.20 g) and ethanediol (360 mg) in tetrahydrofuran (20 mL), and the resulting mixture was stirred at 10° C. for 24 h. The reaction mixture was poured into a saturated aqueous solution of ammonium chloride (50 mL), and extracted with ethyl acetate (50 mL×3). The organic phase was washed with saturated brine (50 mL), dried over anhydrous sodium sulfate, and filtered. The filtrate was concentrated to obtain Compound 70-6. LCMS (ESI) m/z: 333 (M+3).

7) Synthesis of Compound 70-7

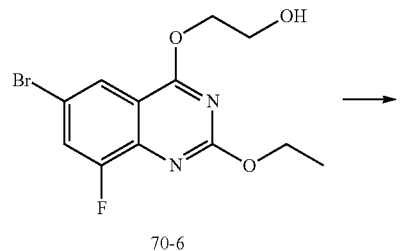

70-6

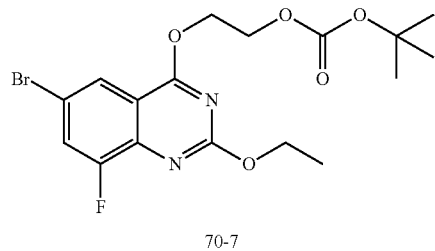

70-7

Triethylamine (1.19 g) and 4-dimethylaminopyridine (48 mg) were added to a mixed solution of Compound 70-6 (1.30 g), di-tert-butyl dicarbonate (1.03 g), and dichloromethane (20 mL), and the resulting mixture was stirred at 15° C. for 1 h. The reaction mixture was concentrated under reduced pressure. The residue obtained from the concentration was purified by a silica gel column to obtain Compound 70-7. $^1$H NMR (400 MHz, CDCl$_3$) δ ppm 7.96-7.92 (m, 1H), 7.49 (dd, J=2.1, 9.7 Hz, 1H), 4.73-4.69 (m, 2H), 4.52-4.44 (m, 4H), 1.44 (s, 9H), 1.40 (t, J=7.0 Hz, 3H).

8) Synthesis of Compound 70-8

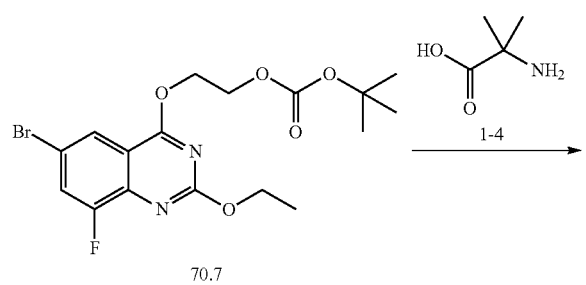

70.7   1-4

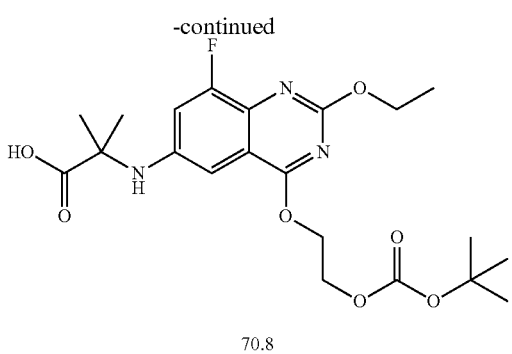

70.8

Compound 70-7 (600 mg), Compound 1-4 (215 mg), potassium carbonate (480 mg), cuprous chloride (28 mg), 2-acetylcyclohexanone (39 mg), N,N-dimethylformamide (6 mL), and water (0.3 mL) were added to a microwave tube. The microwave tube was sealed, and the resulting mixture was kept at 120° C. for microwave reaction for 1 h. The reaction mixture was filtered, and washed with ethyl acetate (10 mL). The filtrate was concentrated under reduced pressure. 1N hydrochloric acid was added to the residue obtained from the concentration (pH=6-7), and the resulting mixture was extracted with tetrahydrofuran/ethyl acetate (1/3, 20 mL×3) for liquid separation. The organic phase was washed with saturated brine (30 mL), dried over anhydrous sodium sulfate, and filtered. The filtrate was concentrated under reduced pressure to obtain Compound 70-8. LCMS (ESI) m/z: 454 (M+1).

9) Synthesis of Compound 70-9

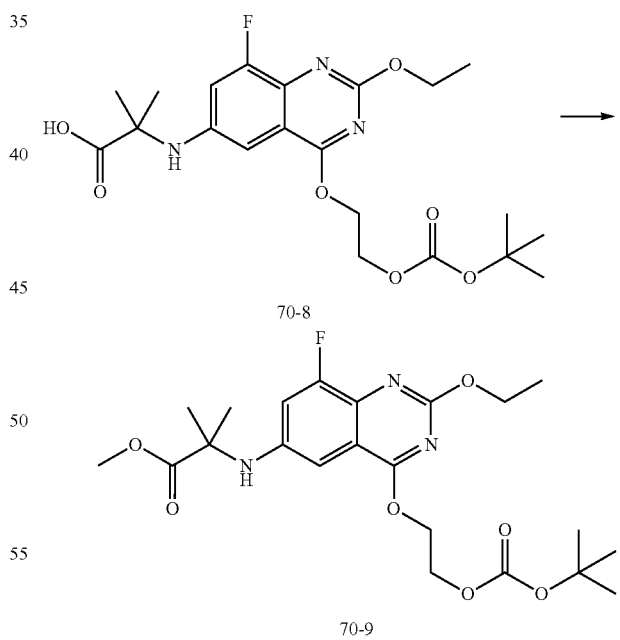

A solution of trimethylsilyldiazomethane in n-hexane (2M, 1.1 mL) was added to a solution of Compound 70-8 (650 mg), dichloromethane (10 mL), and methanol (1 mL), and the resulting mixture was stirred at 10° C. for 2 h. The reaction mixture was concentrated under reduced pressure. The residue obtained from the concentration was purified by a silica gel column to obtain Compound 70-9. LCMS (ESI) m/z: 468 (M+3).

10) Synthesis of Compound 70-10

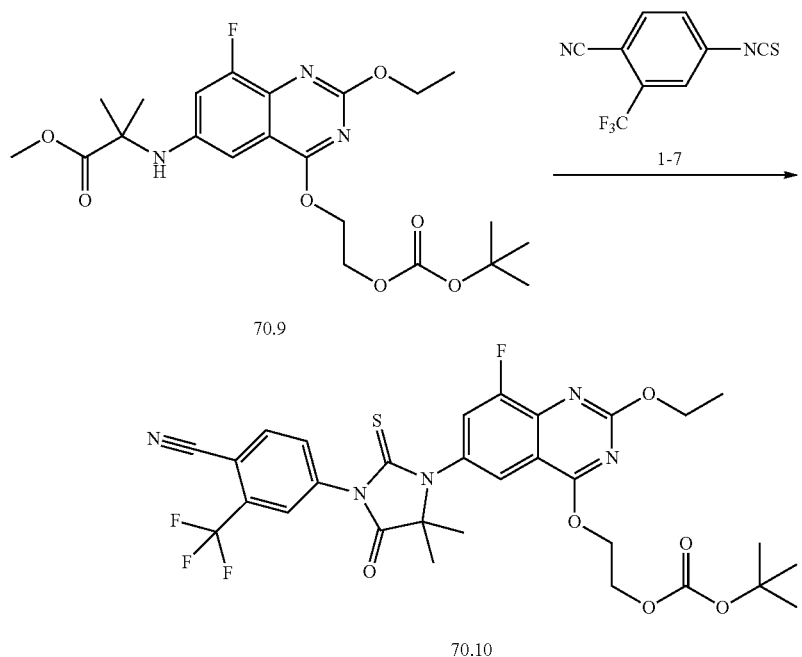

70.9

70.10

A mixed solution of Compound 70-9 (100 mg), Compound 1-7 (196 mg), N,N-dimethylformamide (0.5 mL), and methylbenzene (2 mL) was heated to 120° C., and stirred for 16 h. Methanol (2 mL) was added to the reaction mixture, which was stirred for 30 min, and then concentrated under reduced pressure. The residue obtained from the concentration was purified by a preparative chromatoplate to obtain Compound 70-10. LCMS (ESI) m/z: 664 (M+1).

11) Synthesis of Compound 70

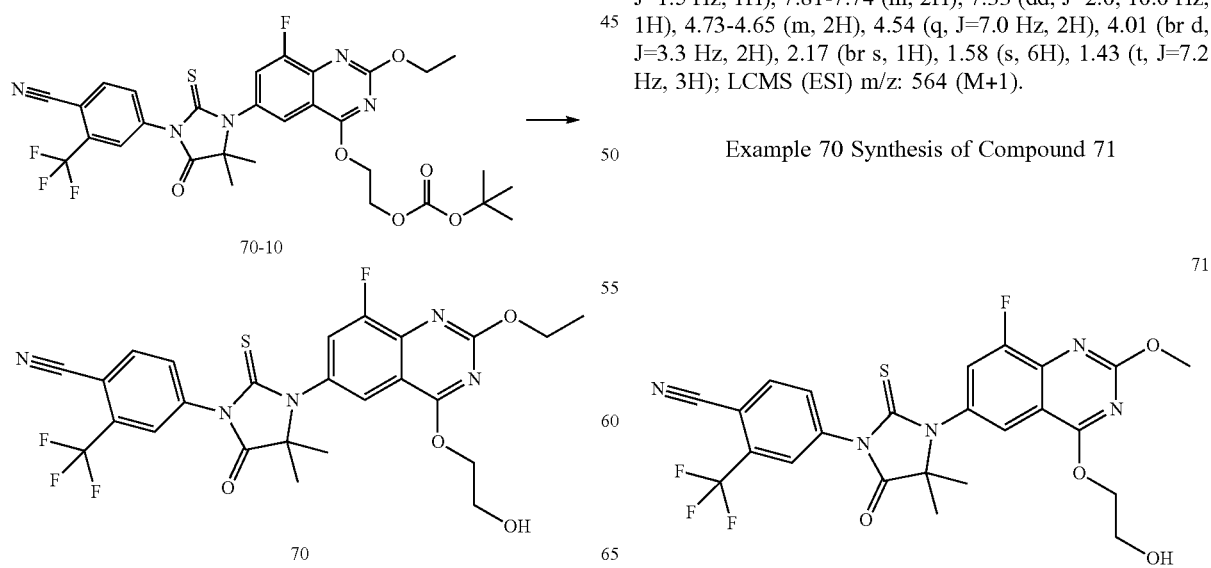

70-10

70

71

Trifluoroacetic acid (1 mL) was added to a solution of Compound 70-10 (180 mg) in dichloromethane (4 mL), and the resulting mixture was stirred at 10° C. for 2 h. A saturated aqueous solution of sodium bicarbonate was added to the reaction mixture (pH about 8), which was extracted with dichloromethane (10 mL×3). The organic phase was washed with saturated brine (15 mL), dried over anhydrous sodium sulfate, and concentrated under reduced pressure. The residue obtained from the concentration was separated and purified successively by a preparative chromatoplate and preparative HPLC to obtain Compound 70. $^1$H NMR (400 MHz, CDCl$_3$) δ ppm 7.93 (d, J=8.3 Hz, 1H), 7.90 (d, J=1.5 Hz, 1H), 7.81-7.74 (m, 2H), 7.33 (dd, J=2.0, 10.0 Hz, 1H), 4.73-4.65 (m, 2H), 4.54 (q, J=7.0 Hz, 2H), 4.01 (br d, J=3.3 Hz, 2H), 2.17 (br s, 1H), 1.58 (s, 6H), 1.43 (t, J=7.2 Hz, 3H); LCMS (ESI) m/z: 564 (M+1).

Example 70 Synthesis of Compound 71

1) Synthesis of Compound 71-1

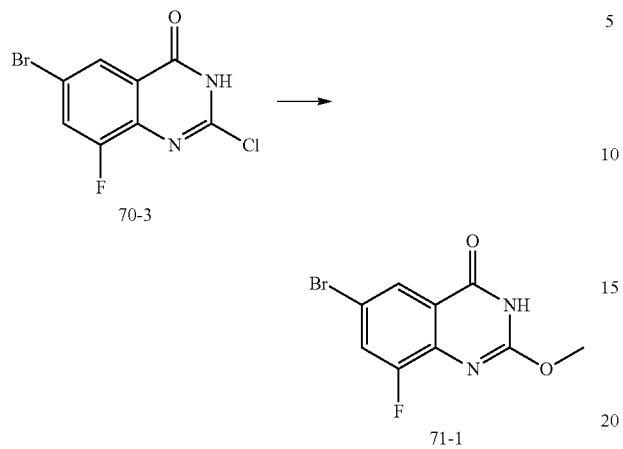

In a microwave tube, sodium methoxide (520 mg) was added to a solution of Compound 70-3 (900 mg) in methanol (10 mL). The resulting mixture was kept at 100° C. for microwave reaction for 1.5 h. The reaction mixture was concentrated under reduced pressure. Tetrahydrofuran (100 mL) was added to the residue obtained from the concentration. The resulting mixture was stirred for 20 min, and then filtered. The filtrate was concentrated under reduced pressure to obtain Compound 71-1. $^1$H NMR (400 MHz, DMSO-d6) δ ppm 7.78-7.73 (m, 1H), 7.42 (dd, J=2.3, 10.3 Hz, 1H), 3.72 (s, 3H).

2) Synthesis of Compound 71-2

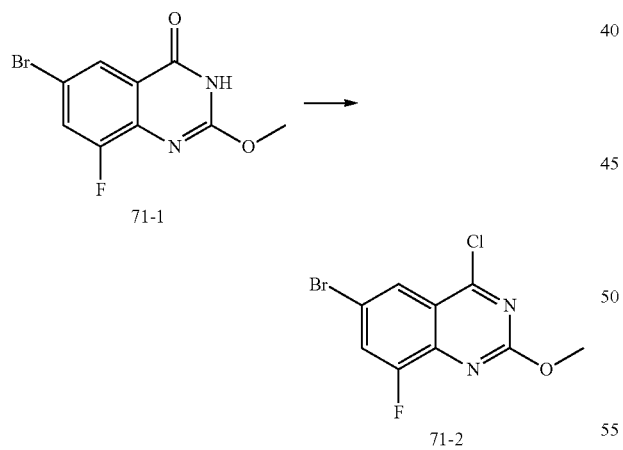

N,N-diisopropylethylamine (618 mg) was added dropwise to a solution of Compound 71-1 (870 mg) in phosphorus oxychloride (6 mL), and the resulting mixture was stirred at 110° C. for 4 h. The reaction mixture was concentrated under reduced pressure. The residue obtained from the concentration was diluted with dichloromethane (20 mL), and poured into ice water. After liquid separation, the organic phase was successively washed with a saturated aqueous solution of sodium bicarbonate (15 mL) and saturated brine (15 mL), dried over anhydrous sodium sulfate, and filtered. The filtrate was concentrated under reduced pressure to obtain Compound 71-2. LCMS (ESI) m/z: 293 (M+3).

3) Synthesis of Compound 71-3

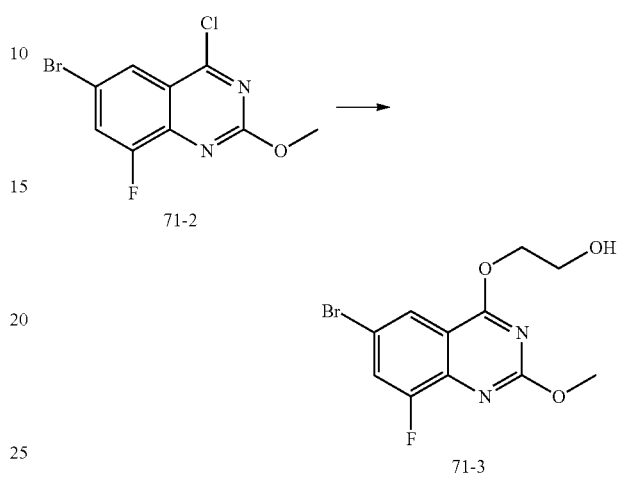

Sodium hydride (165 mg, 60% purity) was added to a solution of Compound 71-2 (1.00 g) and ethanediol (320 mg) in tetrahydrofuran (20 mL), and the resulting mixture was stirred at 10° C. for 4 h. The reaction mixture was poured into a saturated aqueous solution of ammonium chloride (40 mL), and extracted with ethyl acetate (50 mL×3). The organic phase was washed with saturated brine (50 mL), dried over anhydrous sodium sulfate, and filtered. The filtrate was concentrated under reduced pressure to obtain Compound 71-3. LCMS (ESI) m/z: 319 (M+3).

4) Synthesis of Compound 71-4

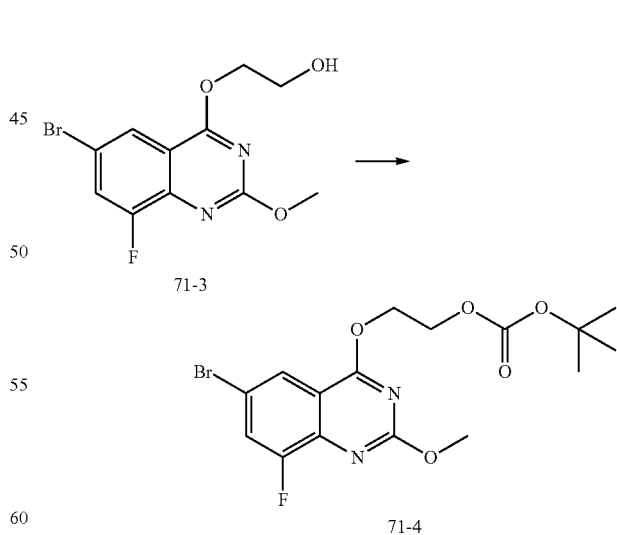

Triethylamine (1.05 g) and 4-dimethylaminopyridine (43 mg) were added to a mixed solution of Compound 71-3 (1.10 g), di-tert-butyl dicarbonate (908 mg), and dichloromethane (20 mL), and the resulting mixture was stirred at 15° C. for 1 h. The reaction mixture was concentrated under reduced pressure. The residue obtained from the concentration was purified by a silica gel column to obtain Compound 71-4. ¹H NMR (400 MHz, CDCl₃) δ ppm 7.98-7.93 (m, 1H), 7.51 (dd, J=2.0, 9.5 Hz, 1H), 4.75-4.67 (m, 2H), 4.49-4.43 (m, 2H), 4.05 (s, 3H), 1.44 (s, 9H).

5) Synthesis of Compound 71-5

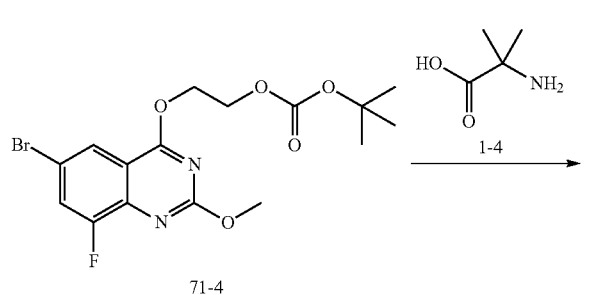

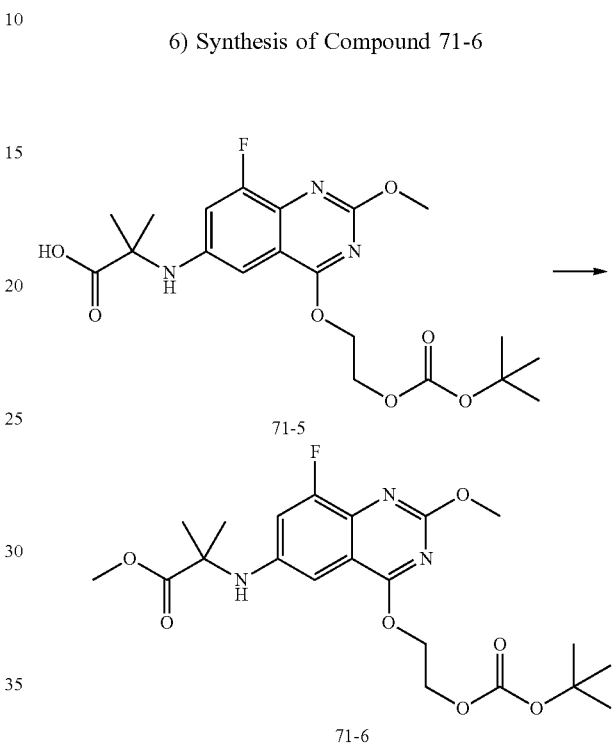

Compound 71-4 (500 mg), Compound 1-4 (185 mg), potassium carbonate (414 mg), cuprous chloride (24 mg), 2-acetylcyclohexanone (34 mg), N,N-dimethylformamide (4 mL), and water (0.2 mL) were added to a microwave tube. The microwave tube was sealed, and the resulting mixture was kept at 120° C. for microwave reaction for 1 h. The reaction mixture was filtered, and washed with ethyl acetate (10 mL). The filtrate was concentrated under reduced pressure. 1N hydrochloric acid was added to the residue obtained from the concentration (pH 6-7), and the resulting mixture was extracted with tetrahydrofuran/ethyl acetate (1/3, 20 mL×3) for liquid separation. The organic phase was washed with saturated brine (30 mL), dried over anhydrous sodium sulfate, and filtered. The filtrate was concentrated under reduced pressure to obtain Compound 71-5. LCMS (ESI) m/z: 440 (M+1).

6) Synthesis of Compound 71-6

A solution of trimethylsilyldiazomethane in n-hexane (2M, 1.1 mL) was added to a solution of Compound 71-5 (470 mg) in dichloromethane (5 mL) and methanol (1 mL), and the resulting mixture was stirred at 10° C. for 4 h. The reaction mixture was concentrated under reduced pressure. The residue obtained from the concentration was purified by a silica gel column to obtain Compound 71-6. LCMS (ESI) m/z: 454 (M+1).

7) Synthesis of Compound 71-7

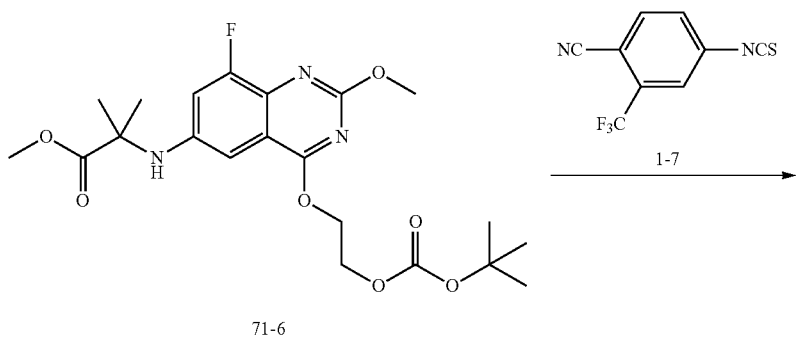

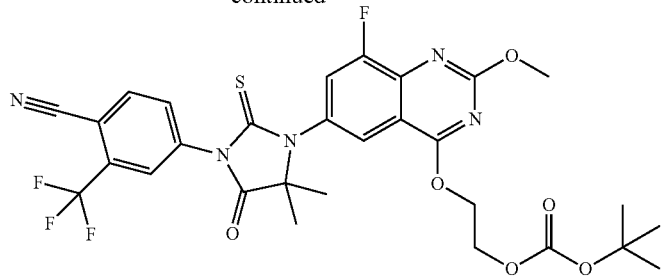

71-7

A mixed solution of Compound 71-6 (100 mg), Compound 1-7 (202 mg), N,N-dimethylformamide (0.5 mL), and methylbenzene (2 mL) was heated to 120° C., and stirred for 16 h. Methanol (2 mL) was added to the reaction mixture, which was stirred for 30 min, and then concentrated under reduced pressure. The residue obtained from the concentration was purified by a preparative chromatoplate to obtain Compound 71-7. LCMS (ESI) m/z: 650 (M+1).

8) Synthesis of Compound 71

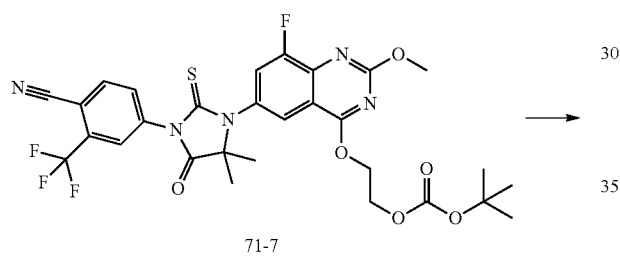

Trifluoroacetic acid (0.5 mL) was added to a solution of Compound 71-7 (100 mg) in dichloromethane (2 mL), and the resulting mixture was stirred at 10° C. for 2 h. A saturated aqueous solution of sodium bicarbonate was added to the reaction mixture (pH about 8), and the resulting mixture was extracted with dichloromethane (10 mL×3). The organic phase was washed with saturated brine (15 mL), dried over anhydrous sodium sulfate, and concentrated under reduced pressure. The residue obtained from the concentration was purified successively by a preparative chromatoplate and preparative HPLC to obtain Compound 71. $^1$H NMR (400 MHz, CDCl$_3$) δ ppm 7.97-7.87 (m, 2H), 7.83-7.73 (m, 2H), 7.35 (dd, J=2.3, 10.0 Hz, 1H), 4.73-4.65 (m, 2H), 4.09 (s, 3H), 4.02 (br d, J=3.5 Hz, 2H), 2.21 (br t, J=5.4 Hz, 1H), 1.59 (s, 6H); LCMS (ESI) m/z: 550 (M+1).

Example 71 Synthesis of Compound 72

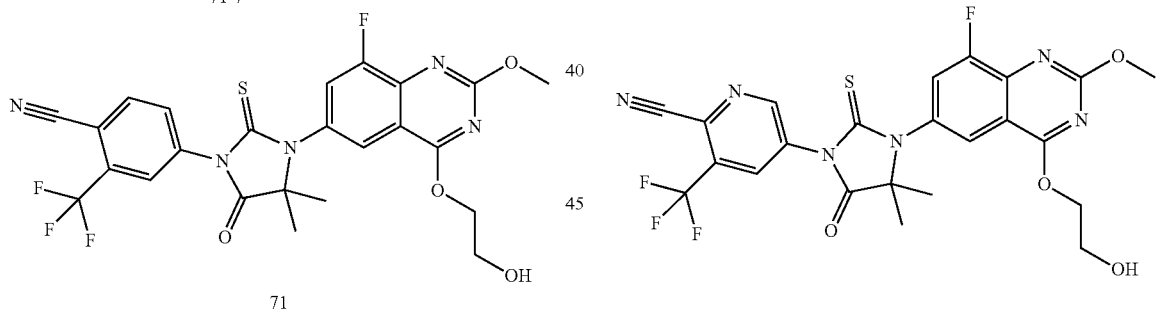

1) Synthesis of Compound 72-1

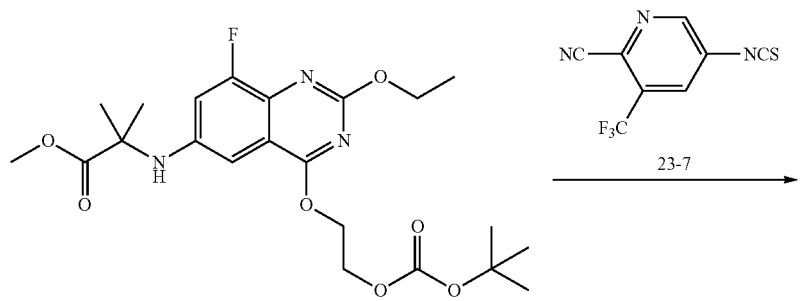

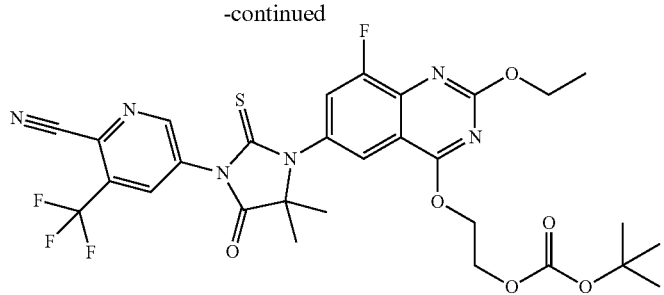

72-1

A mixed solution of Compound 70-9 (60 mg), Compound 23-7 (118 mg), N,N-dimethylformamide (0.5 mL), and methylbenzene (2 mL) was heated to 120° C., and stirred for 16 h. Methanol (2 mL) was added to the reaction mixture, which was stirred for 30 min, and then concentrated under reduced pressure. The residue obtained from the concentration was purified by a preparative chromatoplate to obtain Compound 72-1. LCMS (ESI) m/z: 665 (M+1).

2) Synthesis of Compound 72

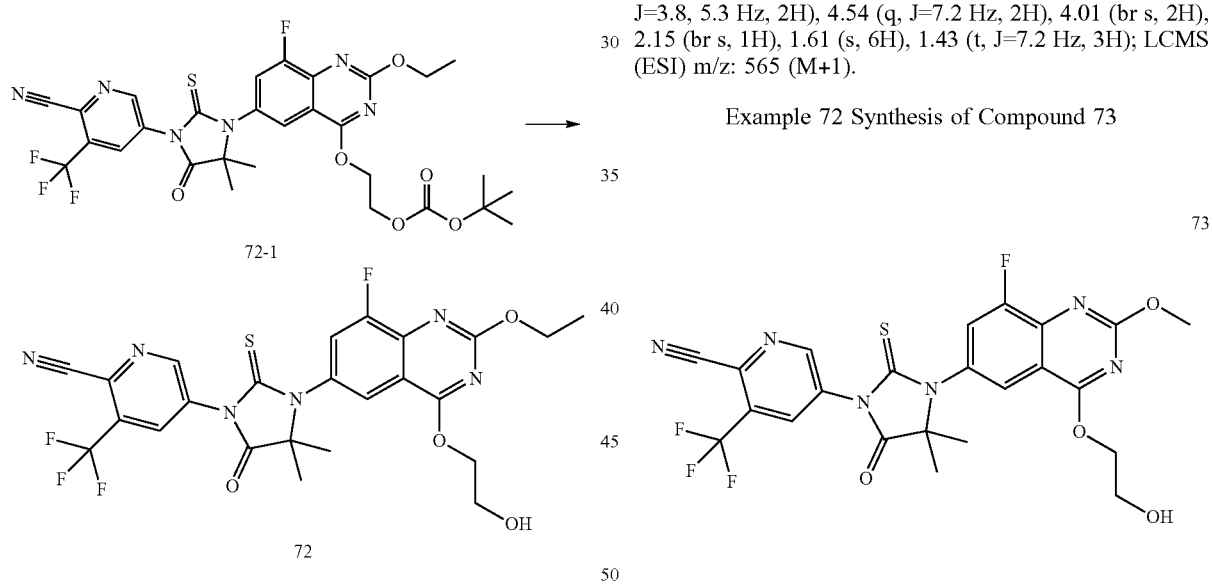

Trifluoroacetic acid (0.2 mL) was added to a solution of Compound 72-1 (45 mg) in dichloromethane (1 mL). The resulting reaction mixture was stirred at 10° C. for 2 h. A saturated aqueous solution of sodium bicarbonate was added to the reaction mixture (pH about 8), and the resulting mixture was extracted with dichloromethane (10 mL×3). The organic phase was washed with saturated brine (15 mL), dried over anhydrous sodium sulfate, and concentrated under reduced pressure. The residue obtained from the concentration was separated and purified by preparative HPLC to obtain Compound 72. $^1$H NMR (400 MHz, CDCl$_3$) δ ppm 9.03 (d, J=2.3 Hz, 1H), 8.29 (d, J=2.3 Hz, 1H), 7.77 (d, J=1.5 Hz, 1H), 7.32 (dd, J=2.3, 10.0 Hz, 1H), 4.70 (dd, J=3.8, 5.3 Hz, 2H), 4.54 (q, J=7.2 Hz, 2H), 4.01 (br s, 2H), 2.15 (br s, 1H), 1.61 (s, 6H), 1.43 (t, J=7.2 Hz, 3H); LCMS (ESI) m/z: 565 (M+1).

Example 72 Synthesis of Compound 73

1) Synthesis of Compound 73-1

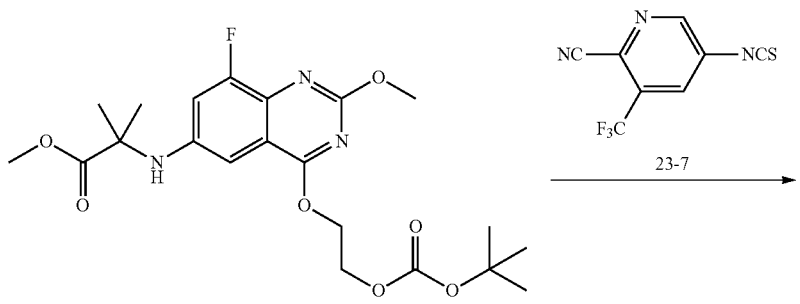

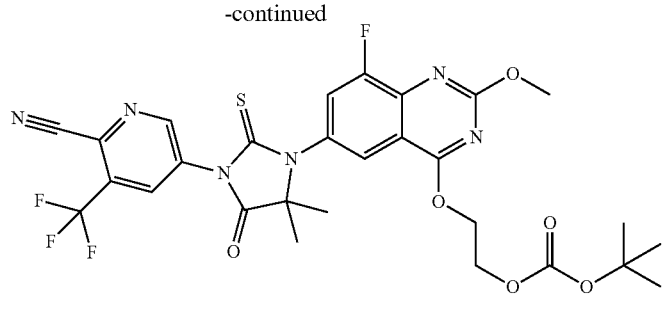

73-1

A mixed solution of Compound 71-6 (55 mg), Compound 23-7 (112 mg), N,N-dimethylformamide (0.5 mL), and methylbenzene (2 mL) was heated to 120° C., and stirred for 16 h. Methanol (2 mL) was added to the reaction mixture, which was stirred for 30 min, and then concentrated under reduced pressure. The residue obtained from the concentration was purified by a preparative chromatoplate to obtain Compound 73-1. LCMS (ESI) m/z: 651 (M+1).

2) Synthesis of Compound 73

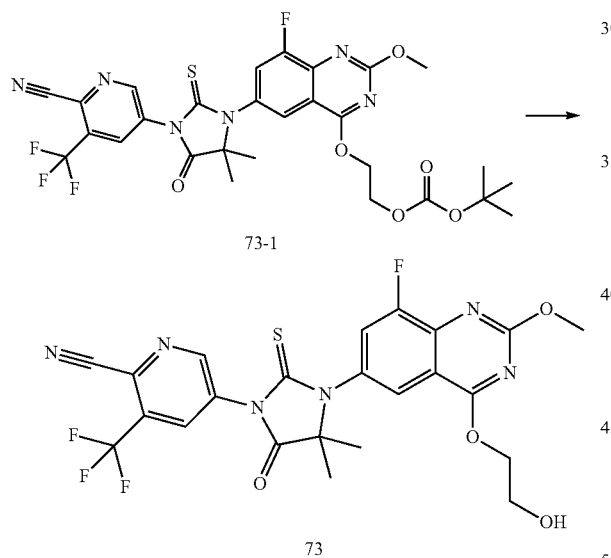

Trifluoroacetic acid (0.2 mL) was added to a solution of Compound 73-1 (50 mg) in dichloromethane (1 mL). The resulting reaction mixture was stirred at 10° C. for 2 h. A saturated aqueous solution of sodium bicarbonate was added to the reaction mixture (pH about 8), and the resulting mixture was extracted with dichloromethane (10 mL×3). The organic phase was washed with saturated brine (15 mL), dried over anhydrous sodium sulfate, and concentrated under reduced pressure. The residue obtained from the concentration was separated and purified by preparative HPLC to obtain Compound 73. $^1$H NMR (400 MHz, CDCl$_3$) δ ppm 9.02 (d, J=2.0 Hz, 1H), 8.29 (d, J=2.0 Hz, 1H), 7.78 (s, 1H), 7.33 (dd, J=2.3, 10.0 Hz, 1H), 4.73-4.65 (m, 2H), 4.10 (s, 3H), 4.02 (br s, 2H), 2.21 (br s, 1H), 1.61 (s, 6H); LCMS (ESI) m/z: 551 (M+1).

Example 73 Synthesis of Compound 74

1) Synthesis of Compound 74

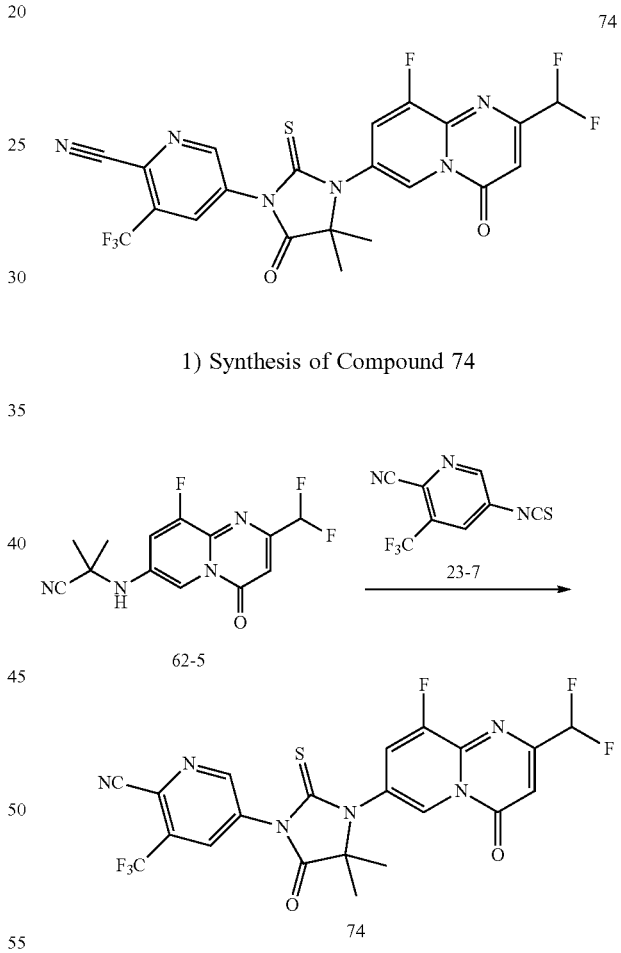

In a dry reaction flask, Compound 62-5 (100 mg), Compound 23-7 (309 mg), DMF (0.25 mL), and methylbenzene (1 mL) were added. Under nitrogen protection, sodium hydride (20 mg, 60% purity) was added, and the resulting mixture reacted at 25° C. for 0.5 h. The reaction mixture was concentrated. The residue obtained from the concentration was purified by acidic preparative HPLC method. Then, the product was left to stand still in a separation eluent (water (0.05% HCl)-acetonitrile), then adjusted to pH=8 with a saturated aqueous solution of sodium bicarbonate, and extracted with dichloromethane (10 mL×3). The combined organic phase was dried over anhydrous sodium sulfate, filtered, and concentrated. The resulting concentrate was dissolved in water (20 mL) and acetonitrile (8 mL), and then freeze-dried to obtain Compound 74. $^1$H NMR (400 MHz, CDCl$_3$) δ ppm 9.09 (d, J=2.13 Hz, 1H), 8.89 (s, 1H), 8.35 (d, J=2.01 Hz, 1H), 7.54 (dd, J=8.34, 2.07 Hz, 1H), 6.91 (s, 1H), 6.42-6.75 (m, 1H), 1.74 (s, 6H). LCMS (ESI) m/z: 527 (M+1).

Example 74 Synthesis of Compound 75

75

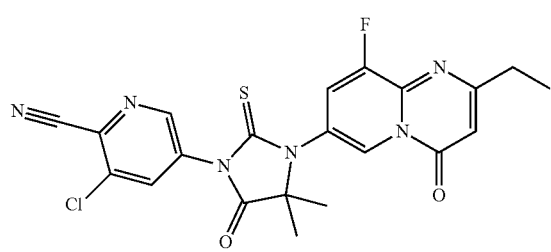

1) Synthesis of Compound 75-2

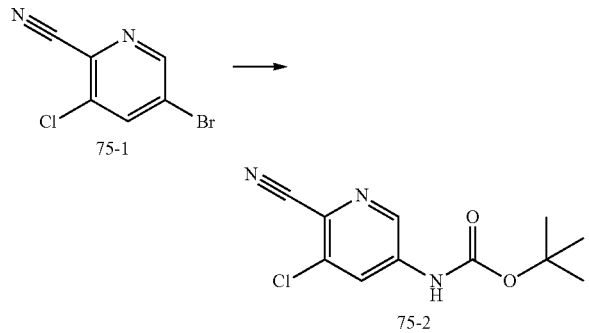

Tris(dibenzylideneacetone)dipalladium (421 mg) and 4,5-bis(diphenylphosphino)-9,9-dimethylxanthene (532 mg) were added to a mixed solution of Compound 75-1 (2.00 g), tert-butyl carbamate (1.08 g), sodium tert-butoxide (2.21 g), and methylbenzene (40 mL). Under nitrogen protection, the resulting mixture was stirred at 100° C. for 3 h. The reaction mixture was filtered through Celite, and the filtrate was concentrated under reduced pressure. The residue obtained from the concentration was purified by a silica gel column to obtain Compound 75-2. $^1$H NMR (400 MHz, CDCl$_3$) δ ppm 8.40 (s, 1H), 8.33 (d, J=2.3 Hz, 1H), 6.98 (br s, 1H), 1.55 (s, 9H).

2) Synthesis of Compound 75-3

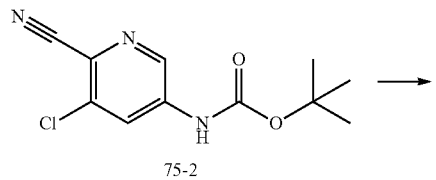

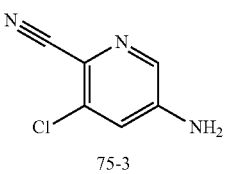

Trifluoroacetic acid (8 mL) was added to a mixed solution of Compound 75-2 (1.70 g) and dichloromethane (20 mL). The resulting reaction mixture was stirred at 10° C. for 3 h. The reaction mixture was concentrated under reduced pressure. The residue obtained from the concentration was diluted with ethyl acetate (60 mL), and washed with a saturated sodium bicarbonate solution (50 mL×3). The resulting organic phase was washed with saturated brine (50 mL), dried over anhydrous sodium sulfate, and filtered. The filtrate was concentrated under reduced pressure. The residue obtained from the concentration was purified by a silica gel column to obtain Compound 75-3. LCMS (ESI) m/z: 154 (M+1).

3) Synthesis of Compound 75-4

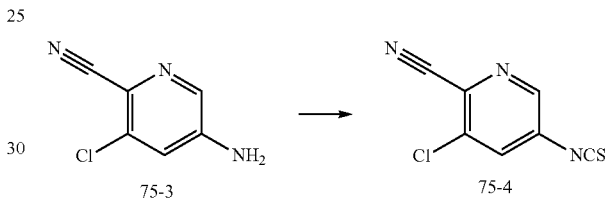

At 10° C., thiophosgene (900 mg) was added dropwise to water (20 mL), and then Compound 75-3 (920 mg) was added in batches. The resulting mixture was stirred at 10° C. for 1 h. The reaction mixture was extracted with dichloromethane (30 mL×2). The organic phases were combined, dried over anhydrous sodium sulfate, and filtered. The filtrate was concentrated to dryness under reduced pressure to obtain Compound 75-4.

4) Synthesis of Compound 75

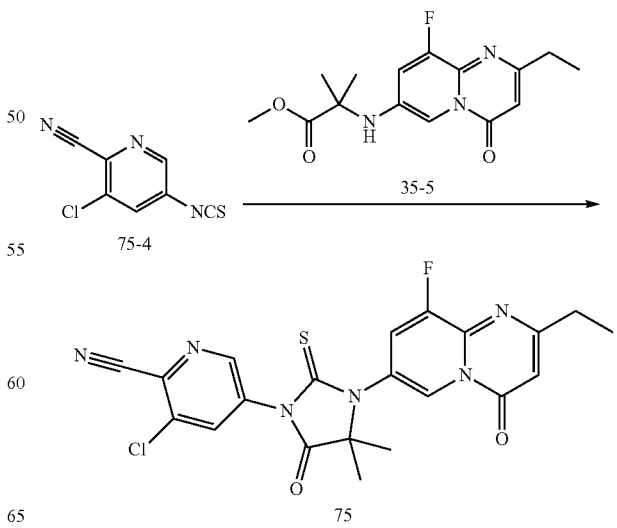

A mixed solution of Compound 35-5 (300 mg) and Compound 75-4 (764 mg) in N,N-dimethylformamide (1.5 mL) and methylbenzene (6 mL) was heated to 120° C., and stirred for 16 h. Methanol (5 mL) was added to the reaction mixture, which was stirred for 30 min, and then concentrated under reduced pressure. The residue obtained from the concentration was purified successively by a silica gel column and preparative HPLC to obtain Compound 75. $^1$H NMR (400 MHz, CDCl$_3$) δ ppm 8.82 (s, 1H), 8.78 (d, J=2.0 Hz, 1H), 8.10 (d, J=2.0 Hz, 1H), 7.39 (dd, J=2.1, 8.7 Hz, 1H), 6.49 (s, 1H), 2.82 (q, J=7.5 Hz, 2H), 1.69 (s, 6H), 1.36 (t, J=7.5 Hz, 3H); LCMS (ESI) m/z: 471 (M+1).

Example 75 Test of Antagonism of Compounds on Nuclear Translocation of Androgen Receptor (AR)

1. PathHunter NHR cell lines were recovered and cultured for amplification.
2. The cells were inoculated onto a 384-well plate prior to testing, and incubated at 37° C. The serum for culture was filtered with charcoal-dextran to reduce the hormone level therein.
3. In the detection of the antagonistic function, a compound was added to the cells and incubated for 60 min. The working concentration of the test compound was diluted from 10 μM at a 3-fold concentration gradient, respectively including: 10000, 3333.3, 1111.1, 370.4, 123.5, 41.2, 13.7, and 4.67 nM. Then, an agonist 6a-Fluorotestosterone 0.06 μM (concentration: EC80, i.e., 80% agonistic compound concentration) was added, and the mixture was incubated at 37° C. or at room temperature for 3-16 h.
4. Signal detection: 12.5 μL or 15 μL (50%, v/v) PathHunter detection mixed solution (kit: DiscoverX product catalog number: 93-0001 series) was added, and incubated at room temperature for 1 h. The chemiluminescent signal was read with a PerkinElmer Envision™ instrument.
5. Data analysis: The compound activity was analyzed with CBIS data analysis software (Cheminnovation, CA). The calculation formula of the inhibition percent of the antagonist is as follows: IC50 inhibition ratio (%)=100%× (1−(average RLU value of the test compound−average RLU value of the blank control group)/(average RLU value of EC80 control group−average RLU value of the blank control group)).

Test results of the antagonism of the compounds on nuclear translocation of the androgen receptor (AR) are as shown in Table 1 below.

TABLE 1

Test Results of Antagonism of Compounds on Nuclear Translocation of Androgen Receptor

| Compound No. | IC50 |
|---|---|
| 1 | >10 μM |
| 2 | >10 μM |
| 3 | 1.40 μM |
| 4 | 2.19 μM |
| 5 | 3.65 μM |
| 6 | 3.07 μM |
| 7 | 4.26 μM |
| 8 | 4.27 μM |
| 9 | 5.35 μM |
| 10 | 1.71 μM |
| 11 | 1.14 μM |
| 12 | 3.26 μM |
| 13 | 6.02 μM |
| 14 | 4.90 μM |
| 15 | 1.12 μM |

TABLE 1-continued

Test Results of Antagonism of Compounds on Nuclear Translocation of Androgen Receptor

| Compound No. | IC50 |
|---|---|
| 16 | 3.91 μM |
| 17 | 0.65 μM |
| 18 | 2.84 μM |
| 19 | 1.86 μM |
| 20 | 1.56 μM |
| 21 | 1.89 μM |
| 22 | 2.36 μM |
| 23 | 1.15 μM |
| 24 | 3.10 μM |
| 25 | 1.22 μM |
| 26 | 1.71 μM |
| 27 | 2.21 μM |
| 28 | 8.88 μM |
| 29 | 0.83 μM |
| 30 | 2.54 μM |
| 31 | 3.80 μM |
| 32 | 6.76 μM |
| 33 | 9.58 μM |
| 34 | 3.23 μM |
| 35 | 2.31 μM |
| 36 | 5.65 μM |
| 37 | 4.47 μM |
| 38 | 3.58 μM |
| 39 | 5.95 μM |
| 40 | 2.15 μM |
| 41 | 2.75 μM |
| 42 | 2.20 μM |
| 43 | 3.50 μM |
| 44 | 3.76 μM |
| 45 | 2.64 μM |
| 46 | 3.08 μM |
| 47 | 2.57 μM |
| 48 | 3.67 μM |
| 49 | 1.43 μM |
| 50 | 3.45 μM |
| 51 | 0.64 μM |
| 52 | 1.23 μM |
| 53 | 2.11 μM |
| 54 | 2.50 μM |
| 55 | 1.40 μM |
| 56 | 2.86 μM |
| 57 | 5.47 μM |
| 58 | 0.95 μM |
| 59 | 8.92 μM |
| 60 | 1.83 μM |
| 61 | 1.45 μM |
| 62 | 1.69 μM |
| 63 | 1.34 μM |
| 64 | 2.81 μM |
| 65 | 2.09 μM |
| 66 | 7.12 μM |
| 67 | 2.30 μM |
| 68 | 1.91 μM |
| 69 | 4.00 μM |
| 70 | 4.27 μM |
| 71 | 2.76 μM |
| 72 | 2.41 μM |
| 73 | 2.13 μM |
| 74 | 2.96 μM |
| 75 | 0.92 μM |

Example 76 Pharmacokinetic Test of Compound 10

1. Abstract

Taking male CD-1 mice as test animals, drug concentrations in plasma at different moments after intravenous and intragastric administration of Compound 10 to the mice were determined by the LC/MS/MS method. The pharmacokinetic behavior of Compound 10 in mice was investigated and its pharmacokinetic profile was evaluated.

2. Experimental Protocol 2.1 Test Drug: Compound 10

2.2 Test Animals:

Four healthy adult male CD-1 mice were divided into 2 groups, with 2 mice in each group, according to the principle of similar body weight. The animals were purchased from Shanghai Super-BK Laboratory Animal Co., Ltd., with Animal Production License No.: SCXK (Shanghai) 2013-0016.

2.3 Drug Preparation

An appropriate amount of sample was weighed, and an appropriate amount of DMSO, PEG400 and water were added successively at a volume ratio of 10:40:50. After stirring and ultrasonic processing, the resulting mixture reached a clear solution state of 0.4 mg/mL for intravenous administration.

An appropriate amount of sample was weighed, and dissolved in a solution of 0.5% CMC+0.2% Tween 80. After stirring and ultrasonic processing, the resulting mixture reached a uniform suspension state of 0.4 mg/mL for intragastric administration.

2.4 Administration

Four male CD-1 mice were divided into 2 groups, and fasted overnight. The first group was intravenously administered at an administration volume of 2.5 mL/kg in a dose of 1 mg/kg; and the second group was intragastrically administered at an administration volume of 5 mL/kg in a dose of 2 mg/kg.

3. Operations

After Compound 10 was intravenously administered to the male CD-1 mice, 30 µL of blood was collected at 0.0833, 0.25, 0.5, 1, 2, 4, 8, and 24 h respectively, and placed in test tubes containing 2 µL of EDTA-$K_2$. After Compound 10 was administered to the intragastric administration group, 30 µL of blood was collected at 0.25, 0.5, 1, 2, 4, 8, and 24 h respectively, and placed in test tubes containing 2 µL of EDTA-$K_2$. The test tubes were centrifuged at 3000 g for 15 min to separate the plasma, which was stored at −60° C. The animals were allowed to eat 2 hours after administration.

After intravenous and intragastric administration to the mice, the content of the test compound in plasma was determined by the LC/MS/MS method. The linear range of the method was 2.00-6000 nmol/L; and the plasma samples were analyzed after the treatment with acetonitrile precipitated protein. Pharmacokinetic test results of Compound 10 are shown in Table 2 below.

TABLE 2

Pharmacokinetic Test Results of Compound 10

| Mode of Administration | Administration Dose | Plasma Concentration $C_{max}$ (nM) | Time to Peak $T_{max}$ (h) | Half Life T1/2 (h) | Apparent Volume of Distribution $V_{dss}$ (L/kg) | Clearance Rate CI (mL/min/kg) | Curve Area (0-t) $AUC_{0-last}$ (nM·h) | Curve Area (0-inf) $AUC_{0-inf}$ (nM·h) | Bioavailability Bioavailability (%) |
|---|---|---|---|---|---|---|---|---|---|
| Intravenous Administration | 1 mg/kg | — | — | 4.88 | 0.384 | 0.912 | 32316 | 33486 | — |
| Intragastric Administration | 2 mg/kg | 2765 | 4.00 | 5.50 | — | — | 26261 | 27935 | 41.7 |

Note:

"—" means that the item does not need to be tested.

Example 77 Pharmacokinetic Test of Compound 35 and Compound 58

1. Abstract

With reference to Example 76, the pharmacokinetic behaviors of Compound 35 and Compound 58 in mice were investigated and their pharmacokinetic profiles were evaluated.

2. Experimental Protocol Refers to Example 76

3. Operations

After Compound 35 and Compound 58 were intravenously administered to the male CD-1 mice, 30 μL of blood was cross-collected at 0.0833, 0.25, 0.5, 1, 2, 4, 8, 24, and 48 h respectively, and placed in test tubes containing 2 μL of EDTA-$K_2$. After Compound 35 and Compound 58 were administered to the intragastric administration group, 30 μL of blood was cross-collected at 0.25, 0.5, 1, 2, 4, 8, 24, and 48 h respectively, and placed in test tubes containing 2 μL of EDTA-$K_2$. The test tubes was centrifuged at 3000 g for 15 min to separate the plasma, which was stored at −60° C. The animals were allowed to eat 4 hours after administration.

After intravenous and intragastric administration to the mice, the content of the test compound in plasma was determined by the LC/MS/MS method. The linear range of the method was 2.00-6000 nmol/L; and the plasma samples were analyzed after the treatment with acetonitrile precipitated protein.

Pharmacokinetic test results of Compound 35 and Compound 58 are shown in Table 3 below.

TABLE 3

Pharmacokinetic Test Results of Compound 35 and Compound 58

| Test Compound | Mode of Administration | Administration Dose | Plasma Concentration $C_{max}$ (nM) | Time to Peak $T_{max}$ (h) | Half Life T1/2 (h) | Apparent Volume of Distribution $V_{dss}$ (L/kg) | Clearance Rate Cl (mL/min/kg) | Curve Area (0-t) $AUC_{0-last}$ (nM · h) | Curve Area (0-inf) $AUC_{0-inf}$ (nM · h) | Bioavailability (%) |
|---|---|---|---|---|---|---|---|---|---|---|
| Compound 35 | Intravenous Administration | 1 mg/kg | — | — | 45.1 | 0.667 | 0.189 | 58694 | 194448 | — |
| | Intragastric Administration | 2 mg/kg | 5775 | 6.00 | ND | — | — | 110377 | ND | 94 |
| Compound 58 | Intravenous Administration | 1 mg/kg | — | — | 36.6 | 0.248 | 0.0794 | 271453 | 447238 | — |
| | Intragastric Administration | 2 mg/kg | 12850 | 8.00 | ND | — | — | 369659 | ND | 68.1 |

Note:
"—" means that the item does not need to be tested; and "ND" means that the data are not detected.

Example 78 Tissue Distribution Test of Compound 27 and Compound 10

1. Abstract

Taking male CD-1 mice as test animals, drug concentrations in plasma and brain after intragastric administration of Compound 27 and Compound 10 to the mice were determined by the LC/MS/MS method, respectively.

2. Experimental Protocol 2.1 Test Drug: Compound 27 and Compound 10
2.2 Test Animals:
Six healthy adult male CD-1 mice were divided into 2 groups, with 3 mice in each group, according to the principle of similar body weight. The animals were purchased from Shanghai Super-BK Laboratory Animal Co., Ltd., with Animal Production License No.: SCXK (Shanghai) 2013-0016.

2.3 Drug Preparation

An appropriate amount of sample was weighed, and an appropriate amount of DMSO, PEG400 and water were added successively at a volume ratio of 10:40:50. After stirring and ultrasonic processing, the resulting mixture reached a clear solution state of 0.4 mg/mL.

2.4 Administration

Six male CD-1 mice were divided into 2 groups, fasted overnight, and intragastrically administered at an administration volume of 5 mL/kg in a dose of 2 mg/kg.

3. Operations

After Compound 27 and Compound 10 were intragastrically administered to the male CD-1 mice, 100 μL of blood was collected by cardiac puncture at 2 h, placed in a test tube containing 2 μl of EDTA-$K_2$, and centrifuged at 3000 g for 15 min to separate 50 μL of plasma, which was stored at −60° C. Meanwhile, brain tissues were collected, washed, then homogenized with 5-fold 15 mM PBS/MeOH (v:v, 2:1), and stored at −60° C. The animals were allowed to eat 2 hours after administration.

After intragastric administration to the mice, the content of the test compound in plasma and brain was determined by the LC/MS/MS method. The linear range of the method was 2.00-6000 nmol/L; and the plasma samples were analyzed after the treatment with acetonitrile precipitated protein.

The results of tissue distribution parameters are shown in Table 4.

TABLE 4

Results of Tissue Distribution Parameters

| Compound | Plasma Concentration (nM) | Concentration in Brain (nmol/kg) | Brain to Blood Ratio |
|---|---|---|---|
| Compound 27 | 9250 ± 2112 | 85.2 ± 21.9 | 0.00917 ± 0.0004 |
| compound 10 | 5000 ± 3156 | 67.38 ± 44.5 | 0.0133 ± 0.0006 |

Example 79 Tissue Distribution Test of Compound 35 and Compound 58

1. Abstract

Taking male CD-1 mice as test animals, drug concentrations in plasma and brain after intragastric administration of Compound 35 and Compound 58 to the mice were determined by the LC/MS/MS method, respectively.

2. Experimental Protocol 2.1 Test Drug: Compound 35 and Compound 58
2.2 Test Animals:
Two healthy adult male CD-1 mice. The animals were purchased from Shanghai Sippr-BK Laboratory Animal Co., Ltd.

2.3 Drug Preparation
An appropriate amount of sample was weighed, and added in a solution of 0.5% CMC+0.2% Tween in water. After stirring and ultrasonic processing, the resulting mixture reached a suspension state of 0.4 mg/mL.

2.4 Drug Administration
Two male CD-1 mice were fasted overnight, and intragastrically administered at an administration volume of 5 mL/kg in a dose of 2 mg/kg.

3. Operations

After Compound 35 and Compound 58 were intragastrically administered to the male CD-1 mice, 100 μL of blood was collected by cardiac puncture at 4 h, placed in a test tube containing 2 μl of EDTA-$K_2$, and centrifuged at 3000 g for 15 min to separate 30 μL of plasma, which was stored at −60° C. Meanwhile, brain tissues were collected, washed, then homogenized with 9-fold 15 mM PBS/MeOH (v:v, 2:1), and stored at −60° C. The animals were allowed to eat 4 hours after administration.

After intragastric administration to the mice, the content of the test compound in plasma and brain was determined by the LC/MS/MS method. The linear range of the method was 2.00-6000 nmol/L; and the plasma samples were analyzed after the treatment with acetonitrile precipitated protein.

The tissue distribution test results are shown in Table 5.

TABLE 5

Tissue Distribution Test Results

| Compound | Plasma Concentration (nM) | Concentration in Brain (mnol/kg) | Brain to Blood Ratio |
|---|---|---|---|
| Compound 35 | 4125 | 281 | 0.0742 |
| Compound 58 | 8260 | 265 | 0.0322 |

Example 80 In Vivo Pharmacodynamic Study of Compound 27 and Compound 10 on Subcutaneous Xenograft Tumor Model of Human Prostate Cancer LNCaP-FGC Cells

1. Experimental Design

TABLE 6

Preparation Method of Test Compound

| Compound | Preparation Method | Concentration (mg/mL) | Storage Condition |
|---|---|---|---|
| Vehicle | 5% DMSO + 40% PEG400 + 10% Solutol + 45% $H_2O$ | — | 4° C. |
| Compound 27 50 mg/kg | 9.15 mg of Compound 27 was weighed, and added to a brown bottle. 90 μL of DMSO was added, and fully vortex-mixed. Then, 0.72 mL of PEG400 and 180 μL of Solutol were added, and fully vortex-mixed. Finally, 0.81 mL of $H_2O$ was added, and fully vortex-mixed to obtain Compound 27 at 5 mg/mL. | 5 | 4° C. |
| Compound 10 50 mg/kg | 9.05 mg of Compound 10 was weighed, and added to a brown bottle. 90 μL of DMSO was added, and fully vortex-mixed. Then, 0.72 mL of PEG400 and 180 μL of Solutol were added, and fully vortex-mixed. Finally, 0.81 mL of $H_2O$ was added, and fully vortex-mixed to obtain Compound 10 at 5 mg/mL. | 5 | 4° C. |
| Compound 35 10 mg/kg | 12.64 mg of Compound 35 was weighed, 0.63 mL of DMSO was added, and vortexed until dissolution. 5.04 mL of PEG400, 1.26 mL of Solutol, and 5.67 mL of $H_2O$ were added, and fully vortexed to obtain a homogeneous solution. | 1 | 4° C. |

TABLE 6-continued

Preparation Method of Test Compound

| Compound | Preparation Method | Concentration (mg/mL) | Storage Condition |
|---|---|---|---|
| Compound 35 20 mg/kg | 25.27 mg of Compound 35 was weighed, 0.63 mL of DMSO was added, and vortexed until dissolution. 5.04 mL of PEG400, 1.26 mL of Solutol, and 5.67 mL of H$_2$O were added, and fully vortexed to obtain a homogeneous solution. | 2 | 4° C. |
| Compound 58 10 mg/kg | 12.6 mg of Compound 58 was weighed, 0.63 mL of DMSO was added, and vortexed until dissolution. 5.04 mL of PEG400, 1.26 mL of Solutol, and 5.67 mL of H$_2$O were added, and fully vortexed to obtain a homogeneous solution. | 1 | 4° C. |
| Compound 58 20 mg/kg | 25.2 mg of Compound 58 was weighed, 0.63 mL of DMSO was added, and vortexed until dissolution. 5.04 mL of PEG400, 1.26 mL of Solutol, and 5.67 mL of H$_2$O were added, and fully vortexed to obtain a homogeneous solution. | 2 | 4° C. |

Note:
The drug needs to be thoroughly mixed gently right before administration to the animals.

TABLE 7

Animal Grouping and Administration Regimen of in vivo Pharmacodynamic Experiment

| Group | Number of Animals | Compound Therapy | Dose (mg/kg) | Administration Volume Parameters (μL/g) | Route of Administration | Administration Frequency |
|---|---|---|---|---|---|---|
| 1 | 6 | Vehicle | — | 10 | PO | QD × 21 days |
| 2 | 6 | Compound 27 | 50 | 10 | PO | QD × 21 days |
| 3 | 6 | Compound 10 | 50 | 10 | PO | QD × 21 days |
| 4 | 6 | Compound 35 | 10 | 10 | PO | QD × 21 days |
| 5 | 6 | Compound 35 | 20 | 10 | PO | QD × 21 days |
| 6 | 6 | Compound 58 | 10 | 10 | PO | QD × 21 days |
| 7 | 6 | Compound 58 | 20 | 10 | PO | QD × 21 days |

2. Experimental Materials 2.1 Experimental Animals
Species: Mice
Strain: CB-17 SCID mice
Week age and body weight: 6-8 weeks old, 18-22 g body weight
Gender: male
Supplier: Beijing Vital River Laboratory Animal Technology Co., Ltd
Animal Certificate No.: 11400700184227

3. Experimental Method and Steps 3.1 Cell Culture
Human prostate cancer LNCaP-FGC cells (ATCC, Manassas, Va.) were cultured in vitro monolayers under the culture conditions of RPMI1640 medium supplemented with 10% fetal bovine serum at 37° C. with 5% $CO_2$. Routine digestion treatment with trypsin-EDTA was performed twice a week for passage. When the cell saturation was 80%-90%, the cells were collected, counted, and inoculated.

3.2 Tumor Cell Inoculation
0.2 mL (10×10$^6$) of LNCaP-FGC cells (10×10$^6$+Matrigel, 1:1) was inoculated subcutaneously to the right back of each CB-17 SCID mouse. When the average tumor volume reached 100-150 mm$^3$, administration in groups was started.

3.3 Tumor Measurement
The tumor diameters were measured with a vernier caliper twice a week. The calculation formula of the tumor volume is: $V=0.5 \times a \times b^2$, wherein a and b represent the long diameter and the short diameter of the tumor, respectively. The antitumor efficacy of the compounds were evaluated by TGI (%) or a relative tumor proliferation rate T/C (%). TGI (%)=[(1−(average tumor volume of a treatment group at the end of drug administration−average tumor volume of the treatment group at the beginning of drug administration))/ (average tumor volume of the vehicle control group at the end of treatment−average tumor volume of the vehicle control group at the beginning of treatment)]×100%. The calculation formula of the relative tumor proliferation rate T/C (%) is as follows: T/C %=$T_{RTV}$/$C_{RTV}$×100% ($T_{RTV}$: RTV of a treatment group; $C_{RTV}$: RTV of a negative control group). The relative tumor volume (RTV) is calculated based on the tumor measurement results, and the calculation formula is RTV=$V_t$/$V_0$, wherein $V_0$ is the average tumor volume measured at the time of administration in groups (i.e., $d_0$), $V_t$ is the average tumor volume at one measurement, and $T_{RTV}$ and $C_{RTV}$ are the data obtained on the same day.

3.4 Statistical Analysis
The statistical analysis includes mean and standard error of mean (SEM) of the tumor volume at each time point for each group. The treatment group showed the best therapeutic effect on the 21st day after administration at the end of the test, and therefore statistical analysis was performed to evaluate the differences between the groups based on the data. The comparison between two groups was analyzed by T-test, and the comparison between three or more groups was analyzed by one-way ANOVA. If there was a significant difference in the F value, the Games-Howell method was used for testing. If there was no significant difference in the F value, the Dunnet (2-sided) method was used for analysis. All data analysis was performed by using SPSS 17.0. "p<0.05" was considered a significant difference.

4. Experimental Results

After 21 days of administration, the test Compound 10 had a significant antitumor effect in the 50 mg/kg group compared with the solvent control group (T/C=23.8%, TGI=83.0%, p≤0.001); and the test Compound 27 had a significant antitumor effect in the 50 mg/kg group compared with the solvent control group (T/C=53.1%, TGI=51.0%, p=0.002). At the same time, the animals had good tolerances to the above test compounds.

After 21 days of administration, the test Compound 35 had significant antitumor effects in the 10 mg/kg group and the 20 mg/kg group compared with the solvent control group (T/C=47.39% and 32.47%, respectively; TGI=59.36% and 76.00%, respectively; p=0.006 and p<0.001, respectively); and Compound 58 had significant antitumor effects in the 10 mg/kg group and the 20 mg/kg group compared with the solvent control group (T/C=43.93% and 32.37%, respectively; TGI=62.75% and 76.16%, respectively; p=0.003 and p<0.001, respectively). At the same time, the animals had good tolerances to the above test compounds.

What is claimed is:

1. A compound of Formula (I) or a pharmaceutically acceptable salt thereof,

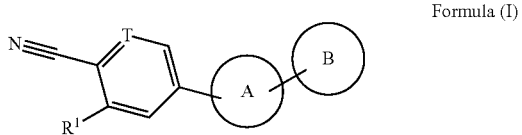

Formula (I)

wherein,

T is selected from the group consisting of CH and N;

$R^1$ is selected from the group consisting of hydrogen, halogen, $C_{1-12}$ alkyl, and halogen-substituted $C_{1-12}$ alkyl;

the ring A is

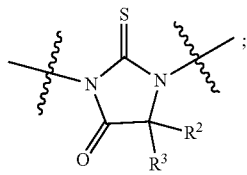

$R^2$ and $R^3$ are each independently selected from $C_{1-12}$ alkyl;

the ring B is

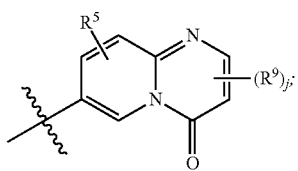

$R^5$ is selected from the group consisting of hydrogen, $C_{1-12}$ alkyl, $C_{1-12}$ alkoxy, and halogen;

j is 0, 1, or 2;

each $R^9$ is independently selected from the group consisting of halogen, $C_{1-12}$ alkyl, $C_{1-12}$ alkoxy, and hydroxyl, wherein the $C_{1-12}$ alkyl is optionally substituted by halogen or $C_{1-12}$ alkoxy, and wherein the hydroxyl is optionally substituted by: —$C_{1-12}$ alkyl-O—$C_{1-12}$ alkyl, —$C_{1-12}$ alkyl-OH, or —$C_{1-12}$ alkyl-C(=O)NR$^f$R$^g$;

$R^f$, and $R^g$ are each independently selected from the group consisting of hydrogen, $C_{1-12}$ alkyl, 3- to 10-membered cycloalkyl, $C_{1-12}$ alkoxy, hydroxyl, and amino.

2. The compound of Formula (I) or a pharmaceutically acceptable salt thereof according to claim 1, wherein $R^2$ and $R^3$ are each independently selected from $C_{1-6}$ alkyl.

3. The compound of Formula (I) or a pharmaceutically acceptable salt thereof according to claim 1, wherein $R^1$ is selected from the group consisting of hydrogen, halogen, $C_{1-6}$ alkyl, and halogen-substituted $C_{1-6}$ alkyl.

4. The compound of Formula (I) or a pharmaceutically acceptable salt thereof according to claim 1, wherein $R^5$ is selected from the group consisting of hydrogen, $C_{1-6}$ alkyl, $C_{1-6}$ alkoxy, and halogen.

5. The compound of Formula (I) or a pharmaceutically acceptable salt thereof according to claim 1, wherein $R^f$, and $R^g$ are each independently selected from the group consisting of hydrogen, $C_{1-6}$ alkyl, 3- to 6-membered cycloalkyl, $C_{1-6}$ alkoxy, hydroxyl, and amino.

6. The compound of Formula (I) or a pharmaceutically acceptable salt thereof according to claim 1, wherein each $R^9$ is independently selected from the group consisting of halogen, $C_{1-6}$ alkyl, $C_{1-6}$ alkoxy, and hydroxyl, wherein the $C_{1-6}$ alkyl is optionally substituted by halogen or $C_{1-6}$ alkoxy, and wherein the hydroxyl is optionally substituted by: —$C_{1-6}$ alkyl-O—$C_{1-6}$ alkyl, —$C_{1-6}$ alkyl-OH, or —$C_{1-6}$ alkyl-C(=O)NR$^f$R$^g$.

7. The compound of Formula (I) or a pharmaceutically acceptable salt thereof according to claim 6, wherein each $R^9$ is independently selected from the group consisting of halogen, methyl, ethyl, methoxy, ethoxy, and hydroxyl, wherein the methyl or ethyl is optionally substituted by halogen or methoxy, and wherein the hydroxyl is optionally substituted by: -ethyl-O-methyl, -ethyl-OH, or -methyl-C(=O)NR$^f$R$^g$.

8. The compound of Formula (I) or a pharmaceutically acceptable salt thereof according to claim 1, wherein the structural unit

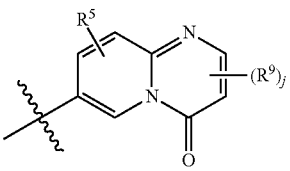

is selected from the group consisting of

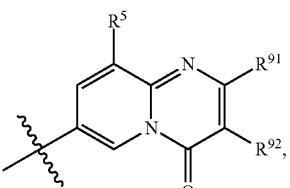

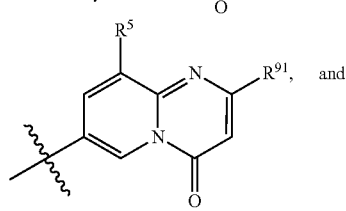

and

-continued

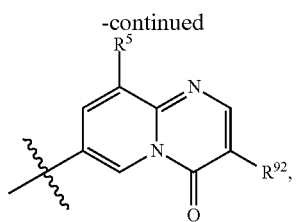

wherein each $R^{91}$ is independently selected from the group consisting of $C_{1-12}$ alkyl, $C_{1-12}$ alkoxy, and hydroxyl, wherein the $C_{1-12}$ alkyl is optionally substituted by $C_{1-12}$ alkoxy or halogen, and wherein the hydroxyl is optionally substituted by —$C_{1-12}$ alkyl-OH, or —$C_{1-12}$ alkyl-O—$C_{1-12}$ alkyl; wherein each $R^{92}$ is independently selected from the group consisting of hydroxyl, —$C_{1-12}$ alkoxy, and halogen, wherein the hydroxyl is optionally substituted by —$C_{1-12}$ alkyl-OH, —$C_{1-12}$ alkyl-O—$C_{1-12}$ alkyl, or —$C_{1-12}$ alkyl-C(=O)NR$^f$R$^g$.

9. The compound of Formula (I) or a pharmaceutically acceptable salt thereof according to claim 1, wherein the structural unit

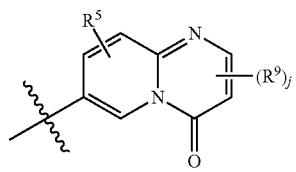

is selected from the group consisting of

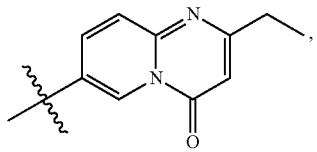

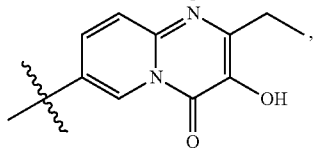

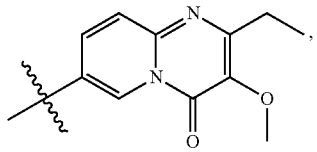

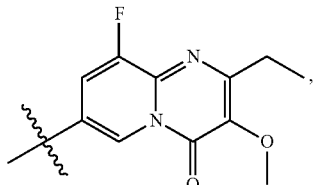

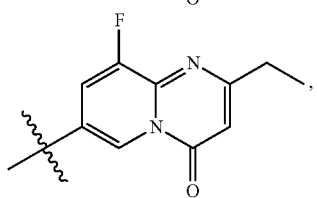

-continued

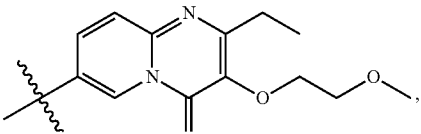

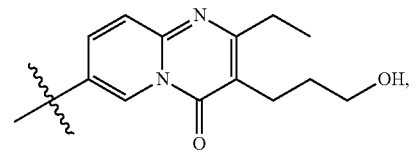

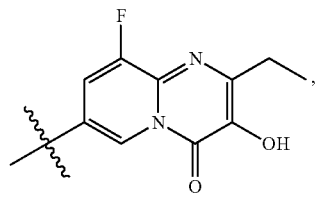

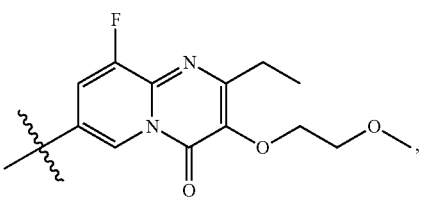

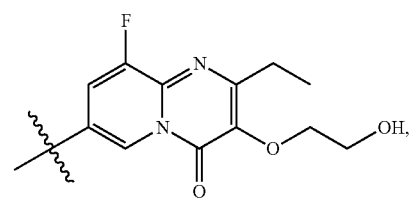

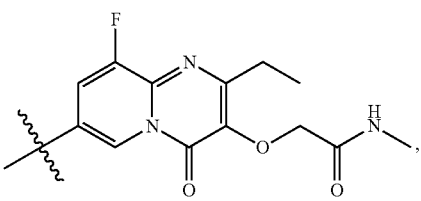

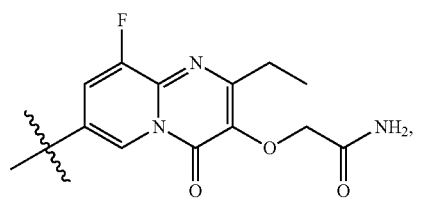

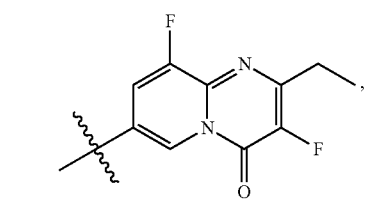

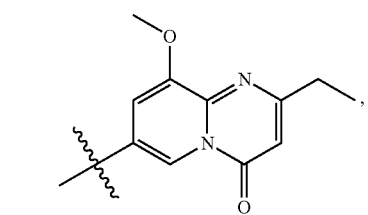

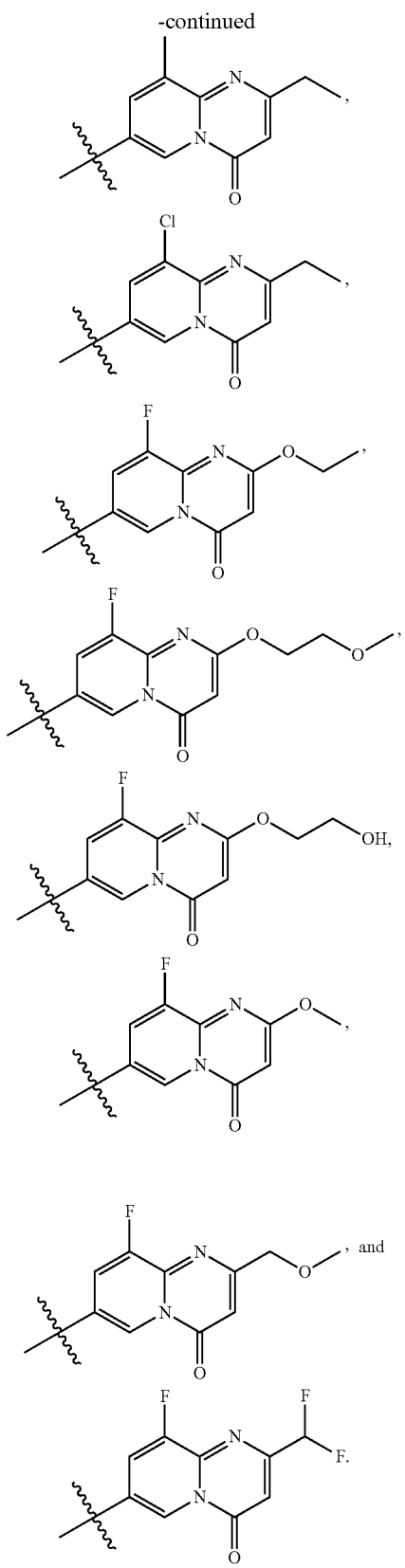

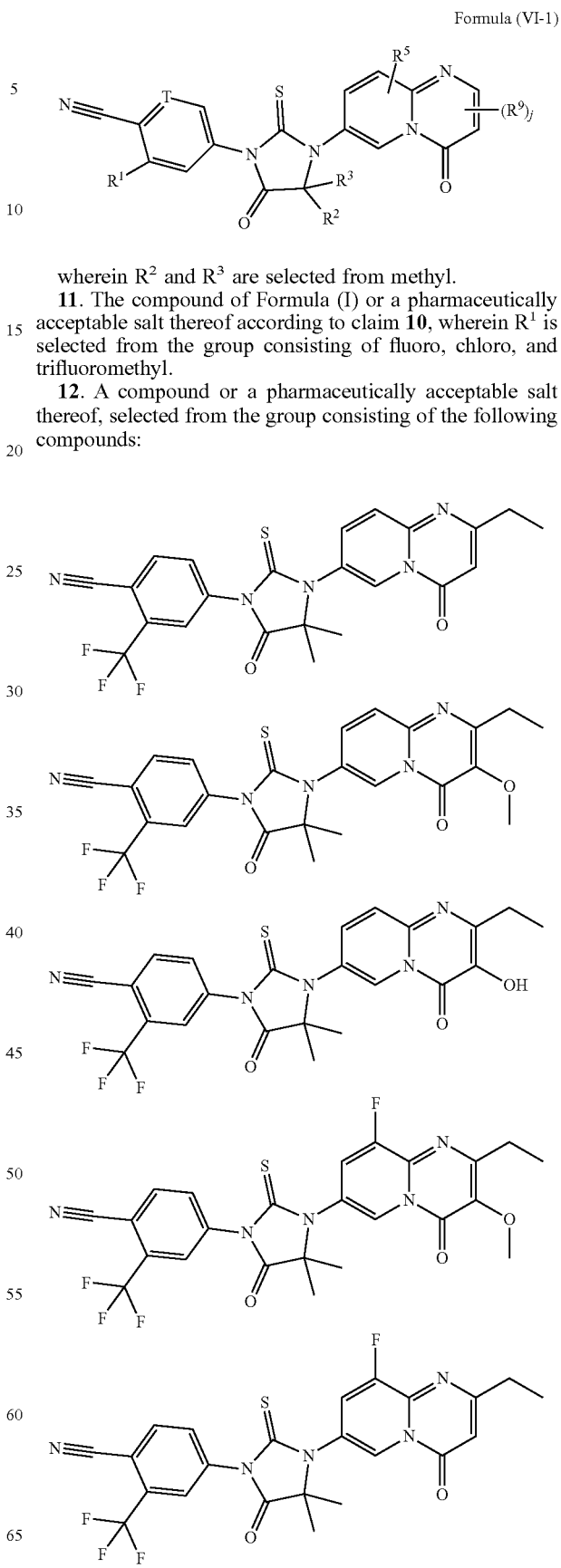

wherein $R^2$ and $R^3$ are selected from methyl.

11. The compound of Formula (I) or a pharmaceutically acceptable salt thereof according to claim 10, wherein $R^1$ is selected from the group consisting of fluoro, chloro, and trifluoromethyl.

12. A compound or a pharmaceutically acceptable salt thereof, selected from the group consisting of the following compounds:

10. The compound of Formula (I) or a pharmaceutically acceptable salt thereof according to claim 1, wherein the compound of Formula (I) is a compound of Formula (VI-1):

315
-continued
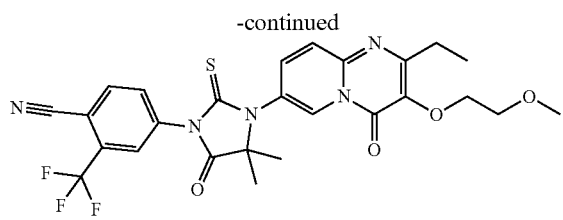
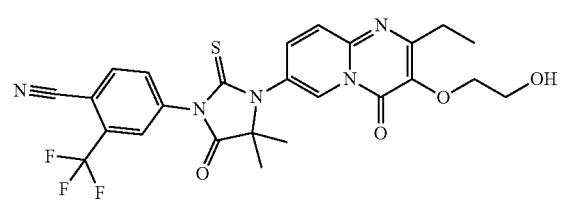
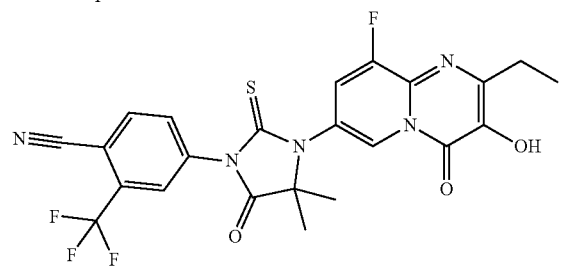
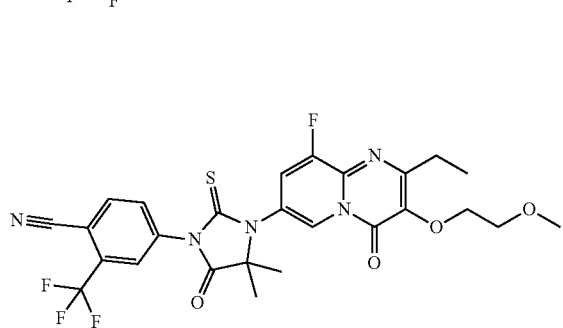
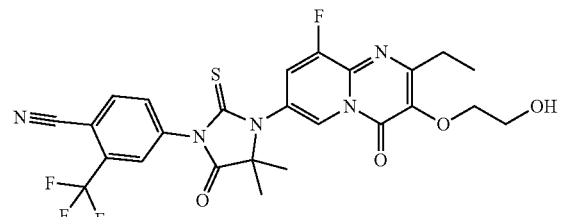
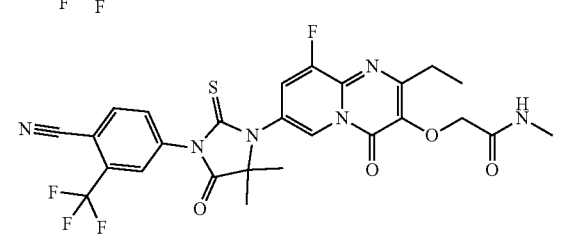
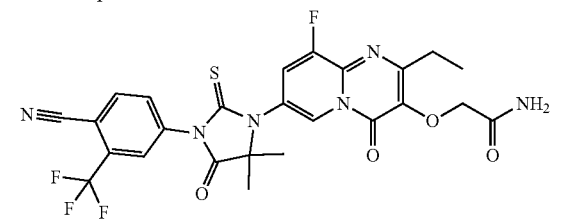
316
-continued
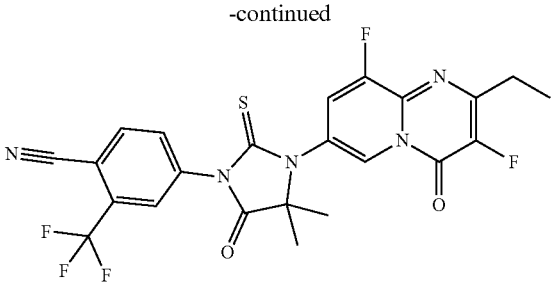
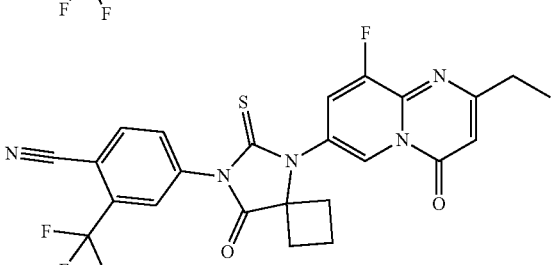
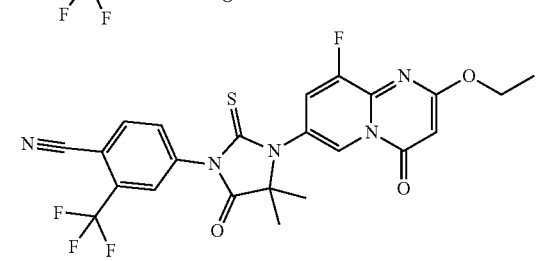
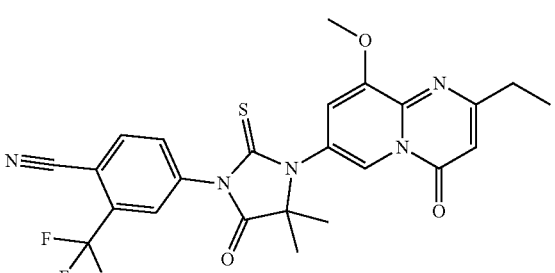
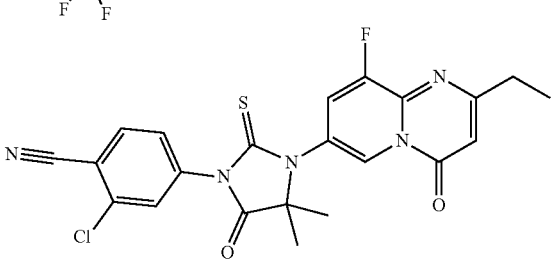

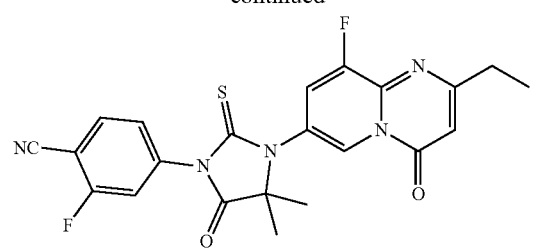

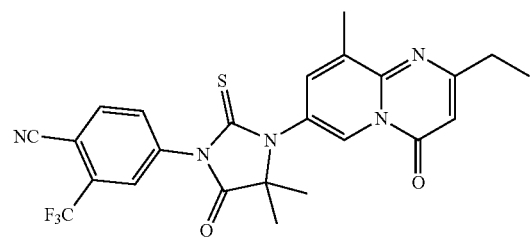

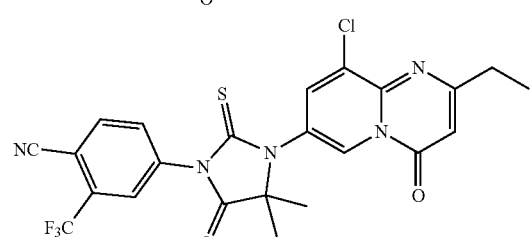

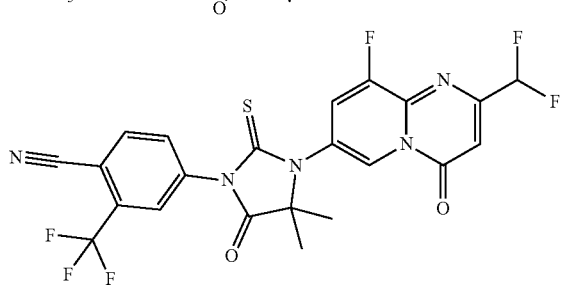

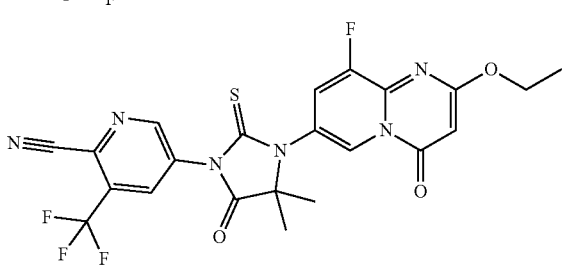

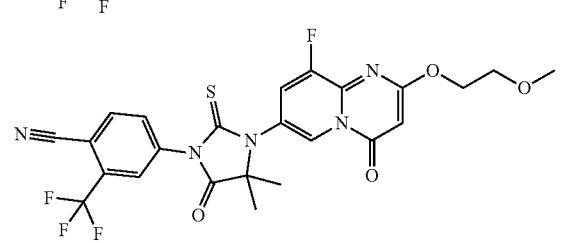

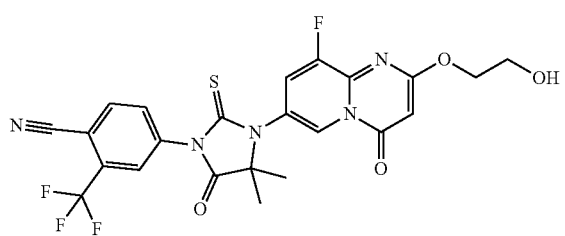

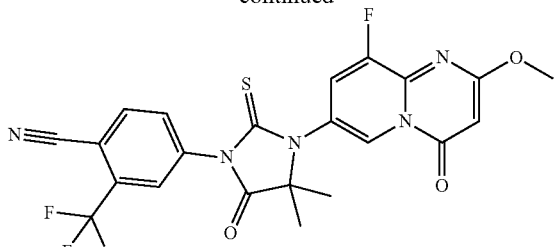

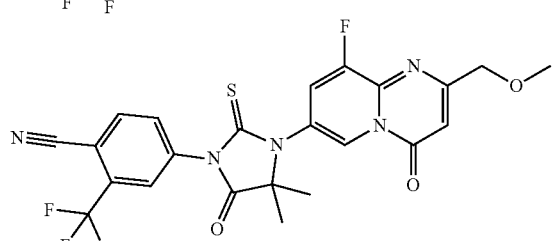

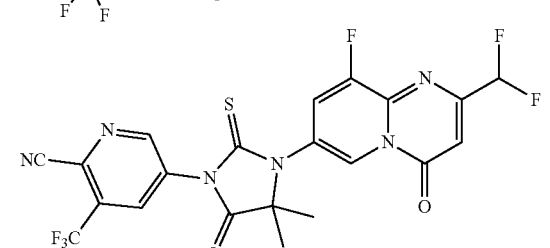

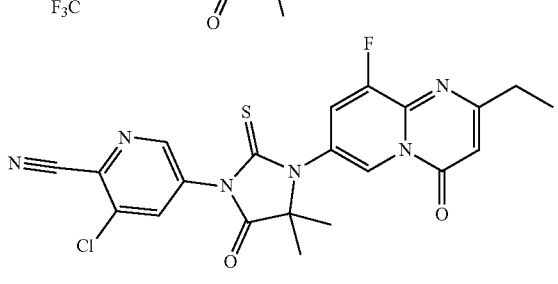

or a pharmaceutically acceptable salt thereof.

13. A pharmaceutical composition, comprising the compound of Formula (I) or a pharmaceutically acceptable salt thereof according to claim 1 and a pharmaceutically acceptable excipient.

14. A method for treating an androgen-mediated disease in a mammal, comprising administering to a mammal in need of the treatment a therapeutically effective amount of the compound of Formula (I) or a pharmaceutically acceptable salt thereof according to claim 1, wherein the androgen-mediated disease is prostate cancer.

15. The compound of Formula (I) or a pharmaceutically acceptable salt thereof according to claim 1, the compound of Formula (I) is

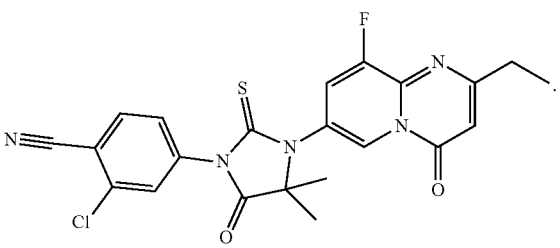 [SMILES: CCc1cc(=O)n2cc(N3C(=S)N(c4ccc(C#N)c(Cl)c4)C(=O)C3(C)C)cc(F)c2n1]

16. The compound of Formula (I) or a pharmaceutically acceptable salt thereof according to claim 8, wherein each $R^{91}$ is independently selected from the group consisting of $C_{1-6}$ alkyl, $C_{1-6}$ alkoxy, and hydroxyl, wherein the $C_{1-6}$ alkyl is optionally substituted by $C_{1-6}$ alkoxy or halogen, and wherein the hydroxyl is optionally substituted by —$C_{1-6}$ alkyl-OH or —$C_{1-6}$ alkyl-O—$C_{1-6}$ alkyl, each $R^{92}$ is independently selected from the group consisting of hydroxyl, —$C_{1-6}$ alkoxy, and halogen, wherein the hydroxyl is optionally substituted by —$C_{1-6}$ alkyl-OH, —$C_{1-6}$ alkyl-O—$C_{1-6}$ alkyl, or —$C_{1-6}$ alkyl-C(=O)NR$^f$R$^g$.

17. The compound of Formula (I) or a pharmaceutically acceptable salt thereof according to claim 2, wherein $R^2$ and $R^3$ are each independently selected from the group consisting of methyl and ethyl.

18. The compound of Formula (I) or a pharmaceutically acceptable salt thereof according to claim 3, wherein $R^1$ is selected from the group consisting of fluoro, chloro, difluoromethyl, and trifluoromethyl.

19. The compound of Formula (I) or a pharmaceutically acceptable salt thereof according to claim 4, wherein $R^5$ is selected from the group consisting of hydrogen, methyl, methoxy, fluoro, chloro, bromo, and iodo.

20. The compound of Formula (I) or a pharmaceutically acceptable salt thereof according to claim 7, wherein each $R^9$ is independently selected from the group consisting of halogen, methyl, ethyl, methoxy, ethoxy, and hydroxyl, wherein the methyl or ethyl is optionally substituted by fluoro or methoxy, and wherein the hydroxyl is optionally substituted by: -ethyl-O-methyl, -ethyl-OH, —$CH_2C$(=O)NHCH$_3$, or —$CH_2C$(=O)NH$_2$.

\* \* \* \* \*